US006716987B1

(12) United States Patent
Ohshima et al.

(10) Patent No.: US 6,716,987 B1
(45) Date of Patent: Apr. 6, 2004

(54) DERIVATIVES OF BENZOFURAN OR BENZODIOXAZOLE COMPOUNDS

(75) Inventors: Etsuo Ohshima, Sunto-gun (JP); Takashi Kawakita, Sunto-gun (JP); Koji Yanagawa, Sunto-gun (JP); Kyoichiro Iida, Sunto-gun (JP); Rie Koike, Sunto-gun (JP); Yoshisuke Nakasato, Sunto-gun (JP); Tohru Matsuzaki, Sunto-gun (JP); Kenji Ohmori, Mishima (JP); Soichiro Sato, Mishima (JP); Hidee Ishii, Tagata-gun (JP); Haruhiko Manabe, Sunto-gun (JP); Michio Ichimura, Mishima (JP); Fumio Suzuki, Mishima (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 10/023,091

(22) Filed: Dec. 20, 2001

Related U.S. Application Data

(60) Division of application No. 08/974,739, filed on Nov. 19, 1997, now Pat. No. 6,514,996, which is a continuation-in-part of application No. 08/784,187, filed on Jan. 15, 1997, now abandoned, which is a continuation-in-part of application No. PCT/JP96/01327, filed on May 20, 1996.

(30) Foreign Application Priority Data

| | | |
|---|---|---|
| May 19, 1995 | (JP) | 7-121537 |
| Oct. 5, 1995 | (JP) | 7-258651 |
| Nov. 19, 1996 | (JP) | 8-307781 |
| Nov. 19, 1996 | (JP) | 8-307782 |
| Nov. 19, 1996 | (JP) | 8-307783 |
| Oct. 1, 1997 | (JP) | 9-268399 |
| Oct. 1, 1997 | (JP) | 9-268400 |

(51) Int. Cl.[7] .................... C07D 413/00; C07D 307/00; C07D 405/00; A61K 31/44; A61K 31/36

(52) U.S. Cl. ................................ 546/271.4; 546/271.4; 546/271.7; 546/281.7; 546/283.4; 546/268.1; 546/284.4; 546/184; 546/190; 549/345; 549/462; 549/466; 549/467; 549/429; 549/456; 548/517; 548/525; 544/106; 544/162; 544/359; 544/374; 544/375; 544/376; 514/514; 514/277; 514/278

(58) Field of Search ........................... 546/268.1, 271.7, 546/281.7, 283.4, 284.1; 514/277, 278; 549/466, 345, 462; 544/375, 106, 376, 162, 358; 548/517, 525

(56) References Cited

U.S. PATENT DOCUMENTS

| | | | | |
|---|---|---|---|---|
| 4,186,135 | A | 1/1980 | Thominet et al. | 260/326.34 |
| 4,888,353 | A | 12/1989 | Lednicer et al. | 514/422 |
| 4,910,193 | A | 3/1990 | Buchheit | 514/216 |
| 5,175,173 | A | * 12/1992 | Sun | 514/305 |
| 5,366,986 | A | 11/1994 | Sindeler et al. | 514/374 |
| 5,506,247 | A | 4/1996 | Sindeler et al. | 514/374 |
| 5,902,824 | A | 5/1999 | Ulrich | 514/462 |
| 6,218,414 | B1 | * 4/2001 | Nisato | 514/382 |
| 6,395,738 | B1 | * 5/2002 | Oshima et al. | 514/252 |

FOREIGN PATENT DOCUMENTS

| | | | |
|---|---|---|---|
| EP | 0147044 | 7/1985 | |
| EP | 0 285 267 | 10/1988 | |
| EP | 0 307 172 | 3/1989 | |
| EP | 0 640 609 | 3/1995 | C07D/521/00 |
| EP | 0 685 479 | 12/1995 | |
| FR | 2 396 757 | 2/1979 | C07D/325/00 |
| FR | 2 438 044 | 4/1980 | C07D/319/18 |
| FR | 2 449 088 | 9/1980 | C07D/405/12 |
| FR | 2 507 604 | 12/1982 | |
| GB | 1 486 356 | 9/1977 | C07D/319/18 |
| GB | 2 057 433 | 4/1981 | C07D/295/18 |
| WO | 93/25517 | 12/1993 | |
| WO | 96/03399 | 2/1996 | |
| WO | 96/36625 | 11/1996 | |

OTHER PUBLICATIONS

Dallacker, F. et al., "Synthese von Apiolanaloga, II[1])", Chemische Berichte, vol. 105, 1972, pp. 3301–3305, XP–001055615.

(List continued on next page.)

*Primary Examiner*—Sabiha Qazi
(74) *Attorney, Agent, or Firm*—Fitzpatrick, Cella, Harper, Scinto

(57) ABSTRACT

An oxygen-containing heterocyclic compound represented by following Formula (I):

(I)

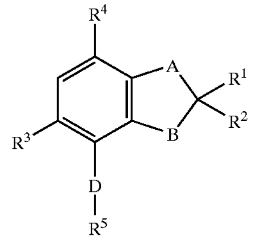

wherein $R^1$ and $R^2$ independently represent hydrogen, lower alkyl, cyano, $-(CH_2)_n-E^1-CO-G^1$ (wherein $E^1$ represents a bond, O, or NH; and $G^1$ represents hydrogen, substituted or unsubstituted lower alkyl, $OR^6$, or $NR^7R^8$; and n represents an integer of 0 to 4), or the like; $R^1$ and $R^2$ are combined to represent a saturated carbon ring together with a carbon atom adjacent thereto; or $R^2$, and $R^{11}$ or $R^{13}$ described below are combined to form a single bond; $R^3$ represents hydrogen, phenyl, or halogen; $R^4$ represents hydroxy, lower alkoxy, or the like; A represents $-C(R^9)(R^{10})-$ or O; B represents O, $NR^{11}$, $-C(R^{12})(R^{13})-$, or $-C(R^{14})(R^{15})-C(R^{16})(R^{17})-$; D represents (i) $-C(R^{18})(R^{19})-X-$ (wherein X represents $-C(R^{21})(R^{22})-$, S, or $NR^{23}$), (ii) $-C(R^{19a})=Y-$ [Y represents $-C(R^{24})-Z-$ (wherein Z represents CONH, $CONHCH_2$, or a bond), or N], or (iii) a bond; and $R^5$ represents aryl, an aromatic heterocyclic group, cycloalkyl, pyridine-N-oxide, cyano, or lower alkoxycarbonyl; or pharmaceutically acceptable salts thereof.

7 Claims, No Drawings

OTHER PUBLICATIONS

Daukshas, V.K. et al., "Acylation of 0–Methoxybenzodioxa-heterocycles and Synthesis of Beta–Amino Ketones from Acetyl Derivatives", Chem. Heterocycl. Comp. (English Translation), vol. 18, No. 12, 1982, pp. 1243–1246, XP–001026984.

Daukshas, V.K. et al., "Synthesis of 5–(Beta–Alkylamino-ethoxy)–Benzo–1,4–Dioxanes Containing Ethyl Groups in the Aromatic Ring", J. Org. Chem. USSR (English Translation), vol. 2, 1966, pp. 293–298, XP–001055301.

Philip et al., Heterocycles, vol. 22, No. 1(1984), pp. 9–12.

Ochuda, et al., CA 122:314550,1994, Abstract of EP 640609).

Hasbun, et al., CA 114:12040, abstract of Fitotrapia (1990) 61 (1) 88).

Judr, L., of Heterocyclic Chem., vol. 34, (2) (1997) pp. 601–604.

Dallacker et al.,(CA 55:24632, abstract of Monassh. 91, (1960), pp. 1089–102.

Shankaran, et al., J. Org. Chem., vol. 49 (1984), pp. 5022–5023.

Cannon et al., "Structures of Nin Quinones Isolated from Two . . . ", Tetrahedron Letters No. 32 (1975), 2795–2798.

Banerjee et al., "Sesebrinic Acid, A Cinnamic Acid Derivative from Seseli", Phytochemistry, vol. 26, No. 6 (1987) 1817–1820.

Jingxi et al., "Studies on Antihepatitic Drugs", Sci. Sin., Ser. B, vol. 26, No. 12 (1983) pp. 1291–1303.

Bishop et al., 3–Aminoalkylldene–3H–indoles . . . , J. Chem. Res., Synop., vol. 6 (1982) p. 159.

Dallacker, Z. Naturforsch., C: Biosci., vol. 33C, No. 7–8 (1978) pp. 465–471.

Berry et al., "Extractives of Australian Timbers . . . ", Aust. J. Chem., vol. 30, No. 8 (1977), pp. 1827–1835.

Guiotto et al., "Coumarins From Unripe Fruits of *Poncirus trifoliate*", Phytochemistry, vol. 16, No. 8 (1977), pp. 1257–1260.

Venturella et al., Ann. Chim. (Rome), vol. 59. No. 5 (1969), pp. 428–433.

Dallacker, "Derivative des Methylendioxybenzols", Chem. Bar., vol. 102, No. 8 (1969), pp. 2663–2676.

Kawase et al., "The Synthesis of 4–Hydroxyfuro[2',3':7,8] coumarins and . . . ", Bull. Chem. Soc. Jap., vol. 41, No. 5 (1968), pp. 1201–1208.

Dyke et al., "Synthesis of Isoflavones", J. Chem. Soc., C. Org., No. 8 (1966), pp. 749–753.

Miyano et al., "Syntheses and Configurational Analysis of Rotenoids, XIX. . . ", Agr. Biol. Chem., vol. 25, No. 9 11961), pp. 673–677.

Seshadri et al., "Polyphenols of the Stem Bark of *Psidium guava*", Phytochemistry, vol. 4, No. 2 (1965), pp. 317–326.

Kaufman et al., "The Desin, Synthesis and Evaluation of . . . ", Bioorg. Med. Chem. Lett., vol. 5, No. 5 11995), pp. 501–506.

Stafford et al., "Structure–Activity Relationships Involving the Cateschol Subunit of Rolipram", Bioorg. Med. Chem. Lett., vol. 4. No. 15 (1994) 1855–59.

Crich et al., "Inhibition of Reararrangments in Stannane–Medicated Radical . . . ", J. Org. Chem., vol. 60, No. 1 (1995), pp. 84–88.

Wade et al., "Chemical and Chemotaxonomical Studies of Ferns, LXXXI", Chem. Pharm. Bull., vol. 40, No. 8 (1992), pp. 2099–2101.

Tanaka et al., "Magnesium and Ammonium–Potassium Lithospermates B, . . . ", Chem. Pharm. Bull., vol. 37, No. 2 (1989), pp. 340–344.

Chun–bo Ai., et al., "Stereostructure of Salvianolic Acid B and Isolation . . . ", J. Nat. Prod., vol. 51, No. 1 (1988), pp. 145–149.

Parker et al., "Aryl Radical–Initiated Cyclizations: Effect of Aryl . . . ", Tetrahedron Lett., vol. 27, No. 25 (1986), pp. 2833–2836.

Akashi et al., "Syntheses of Ring–Hydroxylated Nipradilols . . . ", Chem. Pharm. Bull., vol. 34, No. 5 (1986), pp. 2024–2036.

Crombie et al., J. Chem. Soc., Perkin Trans., vol. 1, No. 7 (1982) 1467–75.

Crombie et al., "Natural Products of Thailand High . . . ", J. Chem. Soc., Perkin Trans., vol. 1, No. 7 (1982), pp. 1455–1466.

Lee, "Synthesis of the Mangostins", Chem. Soc., Perkin Trans., vol. 1, No. 12 (1981), pp. 3205–3213.

Crombie et al., "Isolation of Cannabispiradienone and . . . ", Tetrahedron Letters No. 7 (1979), pp. 661–664.

Crombie et al., "Dihydrostilbenes of Thailand Cannabis", Tetrahedron Letters No. 47 (1978), pp. 4711–4714.

Dallacker et al., (CA 35:24632d).

Monatsh. 91, pp. 1089–102, 1960.

* cited by examiner

DERIVATIVES OF BENZOFURAN OR BENZODIOXAZOLE COMPOUNDS

CROSS REFERENCE TO RELATED APPLICATION

This application is a division of application Ser. No. 08/974,739 filed Nov. 19, 19971 now U.S. Pat. No. 6,514, 996 which in turn is a continuation-in-part of application Ser. No. 08/784,187 filed Jan. 15, 1997 (now abandoned), which is a continuation-in-part of PCT/JP96/01327, filed May 20, 1996.

TECHNICAL FIELD

The present invention relates to oxygen-containing heterocyclic compounds which exhibit phosphodiesterase (PDE) IV inhibitory activity and which are useful as therapeutic agents for inflammatory allergic diseases such as bronchial asthma, allergic rhinitis, and nephritis; autoimmune diseases such as rheumatoid arthritis, multiple sclerosis, Crohn's disease, psoriasis, and systemic lupus erythematosus; diseases of the central nervous system such as depression, amnesia, and dementia; organopathy associated with ischemic reflux caused by cardiac failure, shock, and cerebrovascular diseases, and the like; insulin-resistant diabetes; wounds; AIDS, and the like.

BACKGROUND ART

Heretofore, it is known that the functions of numerous hormones and neurotransmitters are expressed by an increase in the concentration of adenosine 3',5'-cyclic monophosphate (cAMP) or guanosine 3',5'-cyclic monophosphate (cGMP), both of which are the secondary messengers in cells. The cellular concentrations of cAMP and cGMP are controlled by the generation and decomposition thereof, and their decomposition is carried out by PDE. Therefore, when PDE is inhibited, the concentrations of these secondary cellular messengers increase. Up to the present, 7 kinds of PDE isozymes have been found, and the isozyme-selective PDE inhibitors are expected to exhibit pharmacological effect based on their physiological significance and distribution in vivo (TiPS, 1990, 11, 150, TiPS, 1991, 12, 19).

It is known that the activation of inflammatory leukocytes can be suppressed by increasing the concentration of the cellular cAMP. The activation of leukocytes causes secretion of inflammatory cytokines such as tumor necrosis factor (TNF), and expression of the cellular adhesion molecules such as intercellular adhesion molecules (ICAM), followed by cellular infiltration [J. Mol. Cell. Cardiol., 1989, 12, (Suppl. II), S61].

It is known that the contraction of a respiratory smooth muscle can be suppressed by increasing the concentration of the cellular cAMP (T. J. Torphy in Directions for New Anti-Asthma Drugs, eds S. R. O'Donell and C. G. A. Persson, 1988, 37, Birkhauser-Verlag). The contraction of a respiratory smooth muscle is a main symptom of bronchial asthma. Inflammatory-leukocyte infiltration of neutrophils and the like is observed in lesions of organopathy associated with ischemic reflux such as myocardial ischemia. It has been found that the IV type PDE (PDE IV) mainly participates in the decomposition of cAMP in these inflammatory cells and tracheal smooth muscle cells. Therefore, the inhibitors selective for PDE IV are expected to have therapeutic and/or preventive effect on inflammatory diseases, respiratory obstructive diseases, and ischemic diseases.

Further, the PDE IV inhibitors are expected to prevent the progress and spread of the inflammatory reaction transmitted by inflammatory cytokines such as TNFa and interleukin (IL)-8α, because the PDE IV inhibitors suppress the secretion of these cytokines by increasing the concentration of cAMP. For example, TNFα is reported to be a factor of insulin-resistant diabetes because it declines the phosphorylating mechanism of insulin receptors of muscle and fat cells (J. Clin. Invest., 1994, 94, 1543–1549). Similarly, it is suggested that TNFα participates in the onset and progress of autoimmune diseases such as rheumatoid arthritis, multiple sclerosis, and Crohn's disease, and that the PDE IV inhibitors are useful for these diseases (Nature Medicine, 1995, 1, 211–214 and 244–248).

Drugs which increase cAMP are reported to enhance the healing of wounds [Nippon Yakuri-gakkai, the 68th annual meeting (Nagoya), P3-116, 1995].

PDE IV-selective inhibitors having catechol structures are disclosed in WO96-00218, WO96-00215, WO95-35285, WO95-35284, WO95-35283, WO95-35281, WO95-28926, WO95-27692, WO95-24381, WO95-22520, WO95-20578, WO95-17399, WO95-17392, WO95-14681, WO95-14680, WO95-14667, WO95-09837, WO95-09836, WO95-09627, WO95-09624, WO95-09623, WO95-08534, WO95-04046, WO95-04045, WO95-03794, WO95-01338, WO95-00516, WO95-00139, U.S. Pat. No. 5,461,056, EP0685479, EP0685475, EP0685474, EP0671389, WO93-25517, WO94-25437, EP623607, WO94-20446, WO94-20455, WO94-14800, WO94-14742, WO94-12461, WO94-10118, WO94-02465, WO93-19751, WO93-19750, WO93-19749, WO93-19748, WO93-19747, WO93-18024, WO93-15048, WO93-07141, Japanese Published Unexamined Patent Application No. 117239/93, WO92-19594, and EP497564.

Further compounds which have a benzofuran structure and PDE IV-inhibitory activity are reported (Bioorganic Med. Chem. Lett., 1994, 14, 1855–1860, EP685479, WO96-03399).

Heretofore, benzofuran derivatives are industrially useful and are disclosed in patents of intermediates of product materials, light emitting elements, agricultural chemicals, anthelminthics, drugs, and the like.

Benzofuran, benzopyran, and benzodioxole derivatives which have a carboxyl group or a tetrazolyl group are disclosed in J. Med. Chem., 1988, 31, 84–91, and Japanese Published Unexamined Patent Application Nos. 50977/86, 126061/86, 143371/86, and 230760/87, and are described to exhibit leukotriene antagonism, phospholipase inhibitory activity, 5α reductase inhibitory activity, aldose-reductase inhibitory activity, and the like.

WO92-01681 and WO92-12144 disclose benzofuran and benzopyran derivatives which exhibit acyl-CoA acetyltransferase (ACAT) inhibitory activity.

WO93-01169 discloses benzofuran derivatives which exhibit tachykinin antagonism.

EP307172 and U.S. Pat. No. 4,910,193 disclose benzofuran derivatives which exhibit antagonistic activity against serotonin $(5HT)_3$ receptors.

DISCLOSURE OF THE INVENTION

The present invention relates to oxygen-containing heterocyclic compounds represented by following Formula (I):

(I)

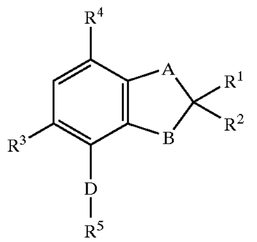

wherein $R^1$ and $R^2$ independently represent hydrogen, substituted or unsubstituted lower alkyl, cycloalkyl, polycycloalkyl, lower alkenyl, cycloalkenyl, substituted or unsubstituted aryl, a substituted or unsubstituted aromatic heterocyclic group, aralkyl, cyano, or $—(CH_2)_n—E^1—$CO—G[wherein $E^1$ represents a bond, O, or NH; and $G^1$ represents hydrogen, substituted or unsubstituted lower alkyl, cycloalkyl, polycycloalkyl, substituted or unsubstituted aryl, a substituted or unsubstituted aromatic heterocyclic group, aralkyl, $OR^6$ (wherein $R^6$ represents hydrogen, lower alkyl, cycloalkyl, polycycloalkyl, substituted or unsubstituted aryl, a substituted or unsubstituted aromatic heterocyclic group, or aralkyl), or $NR^7R^8$ (wherein $R^7$ represents hydrogen, substituted or unsubstituted lower alkyl, cycloalkyl, polycycloalkyl, substituted or unsubstituted aryl, a substituted or unsubstituted aromatic heterocyclic group, substituted or unsubstituted aralkyl, or substituted or unsubstituted heteroarylalkyl; and $R^8$ represents substituted or unsubstituted lower alkyl, cycloalkyl, polycycloalkyl, substituted or unsubstituted aryl, a substituted or unsubstituted aromatic heterocyclic group, substituted or unsubstituted aralkyl, or substituted or unsubstituted heteroarylalkyl; or $R^7$ and $R^8$ are combined to represent a substituted or unsubstituted heterocyclic group containing at least one nitrogen atom); and n represents an integer of 0 to 4]; $R^1$ and $R^2$ are combined to represent a saturated carbon ring together with a carbon atom adjacent thereto; or $R^2$, and $R^{11}$ or $R^{13}$ described below are combined to form a single bond; $R^3$ represents hydrogen, phenyl, or halogen; $R^4$ represents hydroxy or substituted or unsubstituted lower alkoxy; A represents $—C(R^9)(R^{10})—$ (wherein $R^9$ and $R^{10}$ independently represent hydrogen, substituted or unsubstituted lower alkyl, cycloalkyl, or polycycloalkyl) or O; B represents O, $NR^{11}$ [wherein $R^{11}$ represents hydrogen, lower alkyl, cycloalkyl, polycycloalkyl, lower alkenyl, cycloalkenyl, substituted or unsubstituted aryl, a substituted or unsubstituted aromatic heterocyclic group, aralkyl, or —(CH2)$_m$—$E^2$—CO—$G^2$ (wherein $E^2$, $G^2$, and m have the same meanings as the above-described $E^1$, $G^1$, and n, respectively); or $R^{11}$ and $R^2$ are combined to form a single bond], $—C(R^{12})(R^{13})—$ or $—C(R^{12})(R^{13})—O—$ [wherein $R^{12}$ and $R^{13}$ independently represent hydrogen, substituted or unsubstituted lower alkyl, hydroxy, substituted or unsubstituted lower alkoxy, lower alkanoyloxy, substituted or unsubstituted lower alkanoyl, substituted or unsubstituted cycloalkylcarbonyl, lower alkoxycarbonyl, cycloalkyl, polycycloalkyl, lower alkenyl, cycloalkenyl, substituted or unsubstituted aryl, a substituted or unsubstituted aromatic heterocyclic group, substituted or unsubstituted aralkyl, halogen, cyano, or $—(CH_2)_p—E^3—CO—G^3$ (wherein $E^3$, $G^3$, and p have the same meanings as the above-described $E^1$, $G^1$, and n, respectively); $R^{13}$ and $R^2$ are combined to form a single bond; or $R^{13}$ and $R^2$ are combined to form a saturated carbon ring together with two carbon atoms adjacent thereto];

$$—C(R^{14})(R^{15})—C(R^{16})(R^{17})— \text{ or } —C(R^{14})(R^{15})—C(R^{16})(R^{17})—O—$$

[wherein $R^{14}$ and $R^{15}$ independently represent hydrogen, substituted or unsubstituted lower alkyl, hydroxy, substituted or unsubstituted lower alkoxy, lower alkanoyloxy, substituted or unsubstituted lower alkanoyl, substituted or unsubstituted cycloalkylcarbonyl, lower alkoxycarbonyl, cycloalkyl, polycycloalkyl, lower alkenyl, cycloalkenyl, substituted or unsubstituted aryl, a substituted or unsubstituted aromatic heterocyclic group, substituted or unsubstituted aralkyl, halogen, or cyano; or $R^{14}$ and $R^{15}$ are combined to form O; and $R^{16}$ and $R^{17}$ independently represent hydrogen, substituted or unsubstituted lower alkyl, hydroxy, substituted or unsubstituted lower alkoxy, lower alkanoyloxy, substituted or unsubstituted lower alkanoyl, substituted or unsubstituted cycloalkylcarbonyl, lower alkoxycarbonyl, cycloalkyl, polycycloalkyl, lower alkenyl, cycloalkenyl, substituted or unsubstituted aryl, a substituted or unsubstituted aromatic heterocyclic group, substituted or unsubstituted aralkyl, halogen, or cyano; $R^{17}$ and $R^{15}$ are combined to form a single bond; or $R^{17}$ and $R^{15}$ are combined to form a saturated carbon ring together with two carbon atoms adjacent thereto]; or $—C(R^{12'})(R^{13'})—C(R^{14'})(R^{15'})—C(R^{16'})(R^{17'})$ or $—C(R^{12'})(R^{13'})—C(R^{14'})(R^{15'})—C(R^{16'})(R^{17'})—O—$ [wherein $R^{12'}$ and $R^{13'}$ independently represent hydrogen, substituted or unsubstituted lower alkyl, hydroxy, substituted or unsubstituted lower alkoxy, lower alkanoyloxy, substituted or unsubstituted lower alkanoyl, substituted or unsubstituted cycloalkylcarbonyl, lower alkoxycarbonyl, cycloalkyl, polycycloalkyl, lower alkenyl, cycloalkenyl, substituted or unsubstituted aryl, a substituted or unsubstituted aromatic heterocyclic group, substituted or unsubstituted aralkyl, halogen, or cyano; or $R^{12'}$ and $R^{13'}$ are combined to form O; $R^{14'}$ and $R^{15'}$ independently represent hydrogen, substituted or unsubstituted lower alkyl, hydroxy, substituted or unsubstituted lower alkoxy, lower alkanoyloxy, substituted or unsubstituted lower alkanoyl, substituted or unsubstituted cycloalkylcarbonyl, lower alkoxycarbonyl, cycloalkyl, polycycloalkyl, lower alkenyl, cycloalkenyl, substituted or unsubstituted aryl, a substituted or unsubstituted aromatic heterocyclic group, substituted or unsubstituted aralkyl, halogen, or cyano; $R^{13'}$ and $R^{15'}$ are combined to form a single bond; or $R^{13'}$ and $R^{15'}$ form a saturated carbon ring together with two adjacent carbon atoms; and $R^{16'}$ and $R^{17'}$ independently represent hydrogen, substituted or unsubstituted lower alkyl, hydroxy, substituted or unsubstituted lower alkoxy, lower alkanoyloxy, substituted or unsubstituted lower alkanoyl, substituted or unsubstituted cycloalkylcarbonyl, lower alkoxycarbonyl, cycloalkyl, polycycloalkyl, lower alkenyl, cycloalkenyl, substituted or unsubstituted aryl, a substituted or unsubstituted aromatic heterocyclic group, substituted or unsubstituted aralkyl, halogen, or cyano; $R^{15'}$ and $R^{17'}$ are combined to form a single bond; or $R^{15'}$ and $R^{17'}$ form a saturated carbon ring together with two adjacent carbon atoms]. D represents (i) $—C(R^{18})(R^{19})—X—$ [wherein $R^{18}$ represents hydrogen, substituted or unsubstituted lower alkyl, cycloalkyl, polycycloalkyl, lower alkenyl, cycloalkenyl, substituted or unsubstituted aryl, a substituted or unsubstituted aromatic heterocyclic group, hydroxy, substituted or unsubstituted lower alkoxy, or lower alkanoyloxy; and $R^{19}$ represents hydrogen, substituted or unsubstituted lower alkyl, cycloalkyl, polycycloalkyl, lower alkenyl, cycloalkenyl, substituted or unsubstituted aryl, a substituted or unsubstituted aromatic heterocyclic group, hydroxy, substituted or unsubstituted lower alkoxy, lower alkanoyloxy, lower alkanoyl, cycloalkylcarbonyl, lower alkoxycarbonyl, or cyano; or $R^{18}$ and $R^{19}$ are combined to form O, S, or $NR^{20}$ (wherein $R^{20}$ represents hydrogen, substituted or unsubstituted lower alkyl, cycloalkyl, polycycloalkyl, lower alkenyl, cycloalkenyl, substituted or unsubstituted aryl, a substituted or unsubstituted aromatic heterocyclic group, hydroxy, substituted or unsubstituted lower alkoxy, or lower alkanoyloxy); X represents —$C(R^{21})(R^{22})$— (wherein $R^{21}$ and $R^{22}$ independently represent hydrogen, substituted or unsubstituted lower alkyl, cycloalkyl, polycycloalkyl, lower alkenyl, cycloalkenyl, substituted or unsubstituted aryl, a substituted or unsubstituted aromatic heterocyclic group, lower alkanoyl, cycloalkylcarbonyl, lower alkoxycarbonyl, or cyano) or S; or X represents $NR^{23}$ (wherein $R^{23}$ represents hydrogen, substituted or unsubstituted lower alkyl, cycloalkyl, substituted or unsubstituted aryl, a substituted or unsubstituted aromatic heterocyclic group, or substituted or unsubstituted aralkyl, or $R^{23}$ and $R^5$ are combined to form a substituted or unsubstituted heterocyclic group containing at least one nitrogen atom) unless $R^1$ and $R^2$ simultaneously represent substituted or unsubstituted lower alkyl, cycloalkyl, polycycloalkyl, lower alkenyl, or cycloalkenyl included in the above definition, A represents oxygen, and B represents $CH_2$], (ii) —$C(R^{19a})$=Y— [wherein $R^{19a}$ represents hydrogen, substituted or unsubstituted lower alkyl, cycloalkyl, polycycloalkyl, lower alkenyl, cycloalkenyl, substituted or unsubstituted aryl, a substituted or unsubstituted aromatic heterocyclic group, hydroxy, substituted or unsubstituted lower alkoxy, lower alkanoyloxy, lower alkanoyl, cycloalkylcarbonyl, lower alkoxycarbonyl, or cyano; and Y represents —$C(R^{24})$—Z— (wherein $R^{24}$ represents hydrogen, substituted or unsubstituted lower alkyl, cycloalkyl, polycycloalkyl, lower alkenyl, cycloalkenyl, substituted or unsubstituted aryl, a substituted or unsubstituted aromatic heterocyclic group, lower alkanoyl, cycloalkylcarbonyl, lower alkoxycarbonyl, or cyano; or $R^{24}$ and $R^{19a}$ are combined to form a single bond; and Z represents CONH, $CONHCH_2$, or a bond) or N], or (iii) a bond; and $R^5$ represents hydrogen, substituted or unsubstituted lower alkyl, substituted or unsubstituted aralkyl, substituted or unsubstituted aryl, a substituted or unsubstituted aromatic heterocyclic group, cycloalkyl, pyridine-N-oxide, cyano, or lower alkoxycarbonyl, or $R^5$ and $R^{23}$ are combined to form a substituted or unsubstituted heterocyclic group containing at least one nitrogen atom; or pharmaceutically acceptable salts thereof.

Hereinafter, the compounds represented by Formula (I) are referred to as Compounds (I). The same applies to the compounds of other formula numbers.

In the definitions of the groups in Formula (I), the lower alkyl and the lower alkyl moiety of the lower alkoxy, the lower alkanoyloxy, the lower alkanoyl, the lower alkoxycarbonyl, and the heteroarylalkyl include straight-chain or branched alkyl groups having 1 to 8 carbon atoms, such as methyl, ethyl, propyl, isopropyl, butyl, isobutyl, sec-butyl, tert-butyl, pentyl, hexyl, heptyl, and octyl; the cycloalkyl and the cycloalkyl moiety of the cycloalkylcarbonyl include cycloalkyl groups having 3 to 10 carbon atoms, such as cyclopropyl, cyclobutyl, cyclopentyl, cyclohexyl, cycloheptyl, cyclooctyl, cyclononyl, and cyclodecyl; and the polycycloalkyl includes polycycloalkyl groups having 4 to 12 carbon atoms, such as bicyclo[3.2.1]octyl, bicyclo[4.3.2]undecyl, adamantyl, and noradamantyl. The lower alkenyl includes straight-chain or branched alkenyl groups having 2 to 8 carbon atoms, such as vinyl, 1-propenyl, allyl, methacryl, 1-butenyl, crotyl, pentenyl, isoprenyl, hexenyl, heptenyl, and octenyl; and the cycloalkenyl includes cycloalkenyl groups having 4 to 10 carbon atoms, such as cyclobutenyl, cyclopentenyl, cyclohexenyl, cycloheptenyl, cyclooctenyl, cyclononenyl, and cyclodecenyl. The aryl includes phenyl and naphthyl; and the aralkyl includes aralkyl groups having 7 to 15 carbon atoms, such as benzyl, phenethyl, benzhydryl, and naphthylmethyl. The aromatic heterocyclic group and the heteroaryl moiety of the heteroarylalkyl include pyridyl, pyrazinyl, pyrimidinyl, pyridazinyl, quinolinyl, isoquinolinyl, phthalazinyl, quinazolinyl, quinoxalinyl, naphthyridinyl, pyrrolyl, pyrazolyl, imidazolyl, triazolyl, tetrazolyl, thienyl, furyl, thiazolyl, oxazolyl, indolyl, indazolyl, benzimidazolyl, benzotriazolyl, and purinyl. The heterocyclic group containing at least one nitrogen atom includes pyrrolidinyl, piperidino, piperazinyl, morpholino, thiomorpholino, homopiperidino, homopiperazinyl, tetrahydropyridinyl, tetrahydroquinolinyl, tetrahydroisoquinolinyl, pyrrolinyl, indolinyl, benzimidazolin-2-on-1-yl, imidazolin-2-on-1-yl, piperazin-2-on-4-yl, piperazine-2,3-dion-1-yl, piperazine-2,5-dion-1-yl, and imidazolidyl; and the saturated carbon ring together with two adjacent carbon atoms includes groups having 3 to 10 carbon atoms, such as cyclopropane, cyclobutane, cyclopentane, cyclohexane, cycloheptane, cyclooctane, cyclononane, and cyclodecane. The halogen includes a fluorine, chlorine, bromine, and iodine atom.

The substituted lower alkyl has the same or different 1 to 2 substituents such as hydroxy, cycloalkyl, which has the same meaning as defined above, a substituted or unsubstituted aromatic heterocyclic group containing at least one nitrogen atom, and a substituted or unsubstituted heterocyclic group containing at least one nitrogen atom.

The substituted aryl, substituted aromatic heterocyclic group, and substituted aralkyl each has the same or different 1 to 3 substituents such as lower alkyl, hydroxy, lower alkoxy, lower alkanoyl, lower alkoxycarbonyl, carboxyl, aminocarbonyl, trifluoromethyl, amino, cyano, nitro, and halogen. The lower alkyl, lower alkoxy, lower alkanoyl, lower alkoxycarbonyl, and halogen each has the same meaning as defined above.

The substituted heterocyclic group containing at least one nitrogen atom has the same or different 1 to 3 substituents such as substituted or unsubstituted lower alkyl, cycloalkyl, aryl, and aralkyl. However, substituted or unsubstituted lower alkyl here has 1 to 3 substituents such as hydroxy and lower alkoxy. The lower alkyl, cycloalkyl, aryl, alkoxy, and aralkyl each has the same meaning as defined above.

The substituted aromatic heterocyclic group containing at least one nitrogen atom has the same or different 1 to 3 substituents such as substituted or unsubstituted lower alkyl, cycloalkyl, aryl, and aralkyl. However, substituted or unsubstituted lower alkyl here has 1 to 3 substituents such as hydroxy and lower alkoxy. The lower alkyl, cycloalkyl, aryl, alkoxy, and aralkyl each has the same meaning as defined above.

The substituted lower alkoxy has the same or different 1 to 3 substituents such as halogen, which has the same meaning as defined above.

The pharmaceutically acceptable salts of Compounds (I) include pharmaceutically acceptable acid addition salts, metal salts, ammonium salts, and organic amine addition salts.

The pharmaceutically acceptable acid addition salts of Compounds (I) include inorganic acid addition salts such as hydrochloride, sulfate, nitrate, and phosphate, and organic acid addition salts such as acetate, maleate, fumarate, and citrate; the pharmaceutically acceptable metal salts include alkali metal salts such as sodium salt and potassium salt, alkaline earth metal salts such as magnesium salt and calcium salt, aluminium salt; and zinc salt; the pharmaceutically acceptable ammonium salts include ammonium and tetramethylammonium; and the pharmaceutically acceptable organic amine addition salts include addition salts with morpholine and piperidine.

Processes for preparing Compound (I) are described below.

Manufacturing method 1:

Compound (Ia), which is Compound (I) in which D is (i) —C($R^{18}$)($R^{19}$)—X— and $R^5$ is substituted or unsubstituted aryl or a substituted or unsubstituted aromatic heterocyclic group, can be obtained according to the following Processes 1-1 to 1-13.

Process 1-1:

Compound (Iaa), which is Compound (Ia) in which X is —C($R^{21}$)($R^{22}$)—, and $R^{18}$ and $R^{19}$ are not combined to form O, S, or $NR^{20}$, can be prepared according to the following reaction steps:

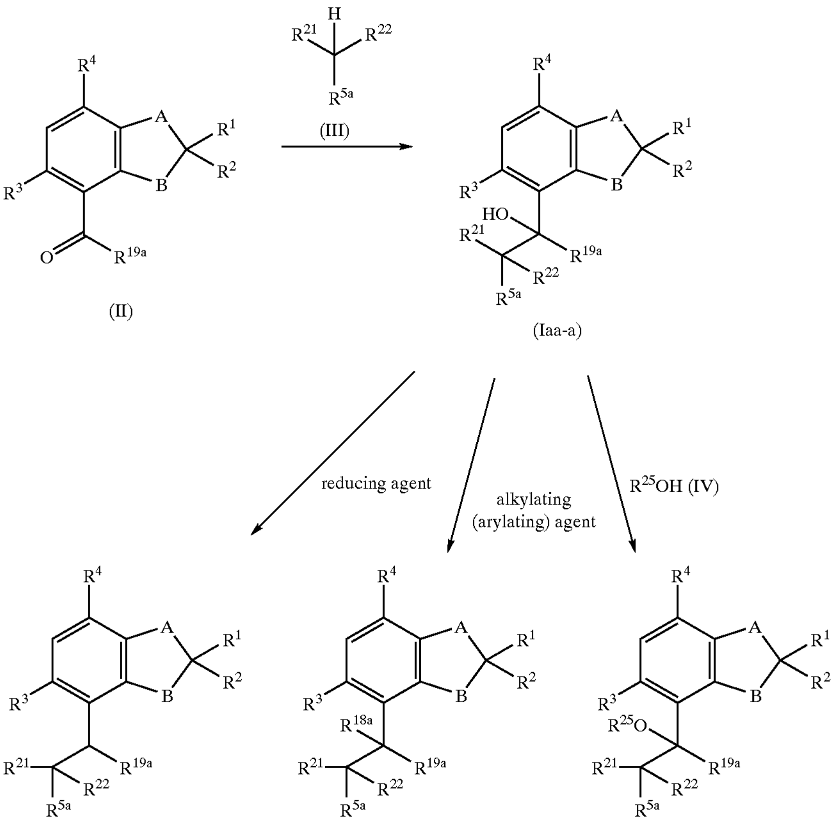

(II) (Iaa-a) (Iaa-b) (Iaa-c) (Iaa-d)

(In the formulae, $R^{5a}$ is substituted or unsubstituted aryl or a substituted or unsubstituted aromatic heterocyclic group in the definition of $R^5$; $R^{18a}$ is a group other than hydrogen, hydroxy, substituted or unsubstituted lower alkoxy, and lower alkanoyloxy in the definition of $R^{18}$, and $R^{18a}$ and $R^{19}$ are not combined to form O, S, or $NR^{20}$; $R^{25}$ is substituted or unsubstituted lower alkyl or lower alkanoyl; and A, B, $R^1$, $R^2$, $R^3$, $R^4$, $R^{19a}$, $R^{21}$, and $R^{22}$ each has the same meaning as defined above.)

The substituted or unsubstituted lower alkyl and lower alkanoyloxy in the definition of $R^{25}$ each has the same meaning as defined above.

The starting Compound (II) Can be obtained according to the known methods (J. Org. Chem., 1987, 52, 4072, Org. Prep. Proced. Int., 1989, 21, 763, Synthesis, 1978, 886, Arzneim.-Forsch., 1971, 21, 204, WO93/18024, WO94/12461) or the methods described in Reference Examples. In addition, the starting Compound (III) is commercially available, or, if the starting Compound (III) is a picoline derivative, it can be obtained according to a known method (WO94/20455) or a similar method thereto.

Compound (Iaa-a), which is Compound (Iaa) in which $R^{18}$ is hydroxy, can be obtained by treating Compound (III) with a base in an inert solvent at the temperature between −100° C. and room temperature for 5 minutes to 10 hours, followed by reaction with a starting Compound (II) at the temperature between −100° C. and the boiling point of the employed solvent for 5 minutes to 30 hours.

Examples of the base are sodium hydroxide, potassium hydroxide, sodium methoxide, potassium ethoxide, sodium hydride, potassium hydride, butyl lithium, lithium dilsopropylamide (LDA), potassium tert-butoxide, triethylamine, diisopropylethylamine, tributylamine, dicyclohexylmethylamine, N-methylmorphorine, N-methylpiperidine, diazabicycloundecene (DBU), and diazabicyclononene (DBN).

Examples of inert solvent are tetrahydrofuran (THF), dioxane, diethyl ether, ethylene glycol, triethylene glycol, glyme, diglyme, methanol, ethanol, butanol, isopropanol, dichloromethane, chloroform, benzene, toluene, dimethylformamide (DMF), and dimethyl sulfoxide (DMSO).

Compound (Iaa-b), which is Compound (Iaa) in which $R^{18}$ is hydrogen, can be obtained by treating Compound (Iaa-a) with a reducing agent in the presence or absence of a catalytic amount to a largely excess amount of an acid catalyst in an inert solvent at the temperature between −100°

C. and the boiling point of the employed solvent for 5 minutes to 48 hours.

Examples of the acid catalyst are p-toluene-sulfonic acid, methanesulfonic acid, hydrochloric acid, trifluoroacetic acid, boron trifluoride, aluminium chloride, stannic chloride, titanium tetrachloride, zinc chloride, and ferric chloride.

Examples of the reducing agent are triethylsilane, tributylsilane, dimethylphenylsilane, and trichlorosilane.

Examples of the inert solvent are THF, dioxane, diethyl ether, ethylene glycol, triethylene glycol, glyme, diglyme, dichloromethane, chloroform, benzene, and toluene.

Compound (Iaa-ba), which is Compound (Iaa-b) in which $R^{22}$ is hydrogen, can also be obtained by treating a corresponding Compound (Iba) prepared by the method described below (Process 2-2) with a reducing agent in an inert solvent at the temperature between −100° C. and the boiling point of the employed solvent for 5 minutes to 30 hours, or by subjecting Compound (Iba) to hydrogenation in the presence of a catalyst in an inert solvent at the temperature between room temperature and the boiling point of the employed solvent for 5 minutes to 30 hours. An example of the reducing agent is sodium borohydride; examples of the catalyst for the hydrogenation are palladium/carbon, palladium, platinum dioxide, and Raney nickel; and examples of the inert solvent are THF, dioxane, metanol, ethanol, butanol, and isopropanol.

Compound (Iaa-c), which is Compound (Iaa) in which $R^{18}$ is a group other than hydrogen, hydroxy, substituted or unsubstituted lower alkoxy, and lower alkanoyloxy in the definition of $R^{18}$, and $R^{18}$ and $R^{19}$ are not combined to form O, S, or $NR^{20}$, can be obtained by reacting Compound (Iaa-a) with an alkylating (arylating) agent in the presence of an acid catalyst in an inert solvent at the temperature between −100° C. and the boiling point of the employed solvent for 5 minutes to 30 hours.

Examples of the alkylating (arylating) agent are various kinds of alkyl- or arylmagnesium bromides, alkyl- or arylmagnesium chlorides, alkyl- or arylmagnesium iodides, trialkylaluminium, tetraalkyltitanium, dialkyltitanium chloride, Tebbe reagent, and trialkylsilylnitrile.

Examples of the acid catalyst are boron trifluoride, aluminium chloride, stannic chloride, titanium tetrachloride, zinc chloride, and ferric chloride.

Examples of the inert solvent are THF, dioxane, diethyl ether, glyme, diglyme, dichloromethane, chloroform, benzene, and toluene.

Compound (Iaa-d), which is Compound (Iaa) in which $R^{18}$ is substituted or unsubstituted lower alkoxy or lower alkanoyloxy, can be obtained by reacting Compound (Iaa-a) with Compound (IV) in the presence of an acid catalyst in an inert solvent or without a solvent at the temperature between −100° C. and the boiling point of the employed solvent for 5 minutes to 48 hours.

Examples of the acid catalyst are p-toluene-sulfonic acid, methanesulfonic acid, hydrochloric acid, sulfuric acid, and trifluoroacetic acid.

Examples of the inert solvent are THF, dioxane, diethyl ether, glyme, diglyme, dichloromethane, chloroform, benzene, toluene, DMF, and DMSO.

Process 1-2:

Compound (Iab), which is Compound (Ia) in which X is S, and $R^{18}$ and $R^{19}$ are not combined to form O, S, or $NR^{20}$, can be prepared by the following reaction steps:

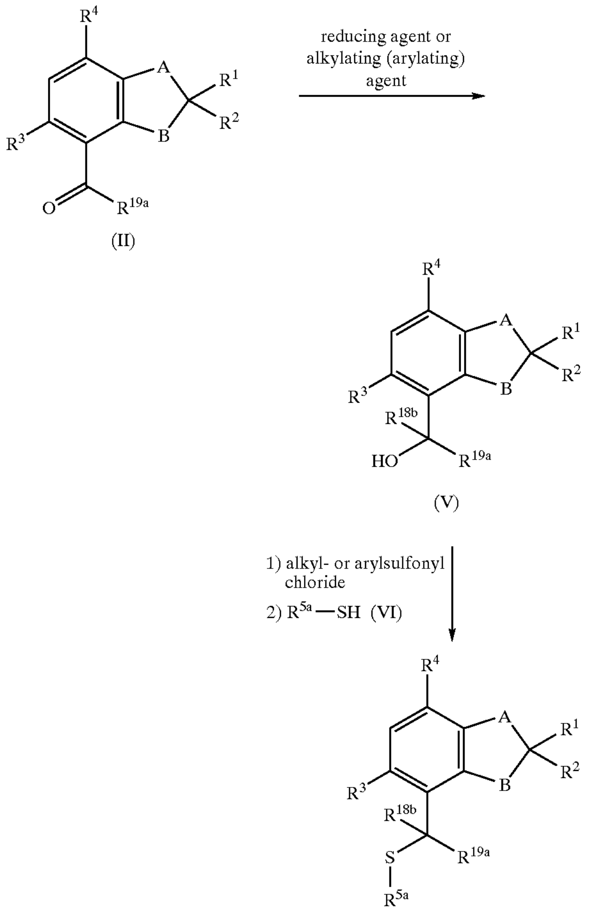

(II)

(V)

(Iab)

(In the formulae, $R^{18b}$ is a group other than hydroxy, substituted or unsubstituted lower alkoxy, and lower alkanoyloxy in the definition of $R^{18}$, and $R^{18b}$ and $R^{19}$ are not combined to form O, S, or $NR^{20}$; and A, B, $R^1$, $R^2$, $R^3$, $R^4$, $R^{5a}$, and $R^{19a}$ each has the same meaning as defined above.)

Compound (Va), which is Compound (V) in which $R^{18b}$ is hydrogen, can be obtained by treating Compound (II) with a reducing agent in an inert solvent at the temperature between −100° C. and the boiling point of the employed solvent for 5 minutes to 30 hours.

Examples of the reducing agent are lithium aluminium hydride and sodium borohydride.

Examples of the inert solvent are THF, dioxane, diethyl ether, ethylene glycol, triethylene glycol, glyme, diglyme, methanol, ethanol, butanol, isopropanol, dichloromethane, chloroform, benzene, and toluene.

Compound (Vb), which is Compound (V) in which $R^{18b}$ is a group other than hydrogen in the definition of $R^{18b}$, can be obtained by reacting Compound (II) with an alkylating (arylating) agent in an inert solvent at the temperature between −100° C. and the boiling point of the employed solvent for 5 minutes to 30 hours.

Examples of the alkylating (arylating) agent are various kinds of alkyl- or arylmagnesium bromides, alkyl- or arylmagnesium chlorides, alkyl- or arylmagnesium iodides, and various kinds of alkyl or aryl lithiums.

Examples of the inert solvent are THF, dioxane, diethyl ether, glyme, diglyme, methanol, ethanol, butanol, isopropanol, dichloromethane, chloroform, benzene, and toluene.

Compound (Iab) can be obtained by reacting Compound (V) with, for example, alkyl- or arylsulfonyl chloride, in the presence of a base in an inert solvent at the temperature between −20° C. and 0° C. for 5 minutes to 5 hours, followed by reaction with Compound (VI) at the temperature between 0° C. and the boiling point of the employed solvent for 5 minutes to 48 hours.

Examples of the base are sodium hydride, potassium hydride, butyl lithium, LDA, potassium tert-butoxide, triethylamine, diisopropylethylamine, tributylamine, dicyclohexylmethylamine, N-methylmorphorine, N-methylpiperidine, DBU, and DBN.

Examples of the alkyl- or arylsulfonyl chloride are methanesulfonyl chloride, benzenesulfonyl chloride, and p-toluenesulfonyl chloride.

Examples of the inert solvent are THF, dioxane, diethyl ether, glyme, diglyme, dichloromethane, chloroform, benzene, toluene, DMF, and DMSO.

Alternatively, Compound (Iab) can also be obtained by reacting Compound (V) with Compound (VI) in the presence of an acid catalyst in an inert solvent at the temperature between −100° C. and the boiling point of the employed solvent for 5 minutes to 48 hours.

Examples of the acid catalyst are p-toluene-sulfonic acid, methanesulfonic acid, hydrochloric acid, trifluoroacetic acid, boron trifluoride, aluminium chloride, stannic chloride, titanium tetrachloride, zinc chloride, and ferric chloride.

Examples of the inert solvent are THF, dioxane, diethyl ether, glyme, diglyme, dichloromethane, chloroform, benzene, and toluene.

Process 1-3:

Compound (Iac), which is Compound (Ia) in which X is $NR^{23}$, and $R^{18}$ and $R^{19}$ are not combined to form O, S, or $NR^{20}$, can be prepared by the following reaction step:

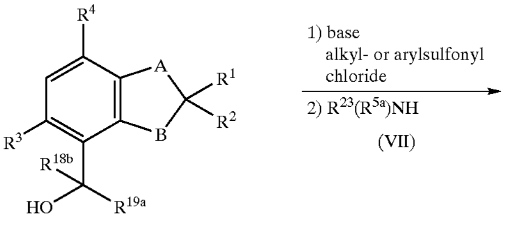

(V)

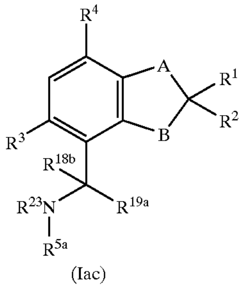

(Iac)

(In the formulae, A, B, $R^1$, $R^2$, $R^3$, $R^4$, $R^{5a}$, $R^{18b}$, $R^{19a}$, and $R^{23}$ each has the same meaning as defined above.)

Compound (Iac) can be obtained according to the method described in Process 1-2 in which Compound (Iab) is obtained from Compound (V) and Compound (VI), using Compound (VII) instead of Compound (VI).

Process 1-4:

Compound (Iad), which is Compound (Ia) in which D is —C(═O)—C($R^{21}$)($R^{22}$)—, can be prepared by the following reaction step:

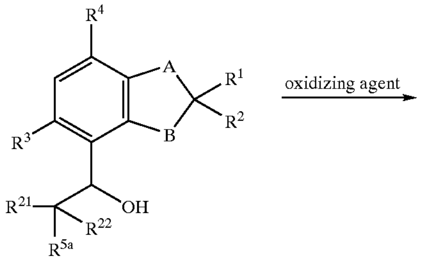

(Iaa-aa)

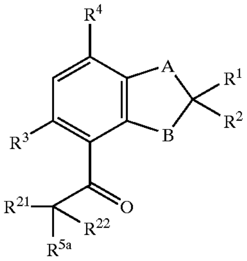

(Iad)

(In the formulae, $R^1$, $R^2$, $R^3$, $R^4$, $R^{5a}$, $R^{21}$, and $R^{22}$ each has the same meaning as defined above.)

Compound (Iad) can be obtained by treating Compound (Iaa-aa), which is Compound (Iaa-a) in which $R^{19a}$ is hydrogen, with an oxidizing agent in an inert solvent containing water at the temperature between 0° C. and the boiling point of the employed solvent for 5 minutes to 72 hours.

Examples of the oxidizing agent are manganese dioxide, potassium permanganate, pyridinium chlorochromate (PCC), and pyridinium dichromate (PDC).

Examples of the inert solvent are THF, dioxane, diethyl ether, ethylene glycol, triethylene glycol, glyme, diglyme, acetone, methyl vinyl ketone, dichloromethane, chloroform, benzene, toluene, DMF, and DMSO.

Process 1-5:

Compound (Iad) can also be prepared according to the following reaction step:

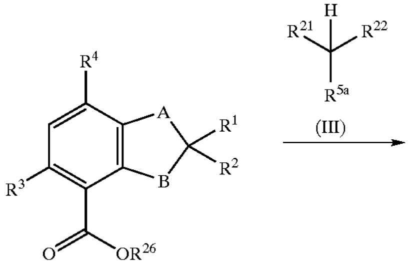

(IIa)

-continued

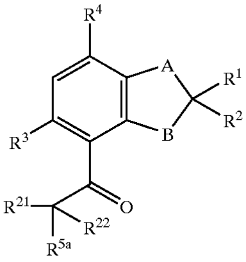

(Iad)

(In the formulae, $R^{26}$ is substituted or unsubstituted lower alkyl; and A, B, $R^1$, $R^2$, $R^3$, $R^4$, $R^{5a}$, $R^{21}$ and $R^{22}$ each has the same meaning as defined above.)

Compound (Iad) can be obtained according to the method described in Process 1-1 in which Compound (Iaa-a) is obtained from Compound (II) and Compound (III), using Compound (IIa), which is a starting Compound (II) in which $R^{19a}$ is substituted or unsubstituted lower alkoxy.

Process 1-6:

Compound (Iad) can also be prepared by the following reaction step:

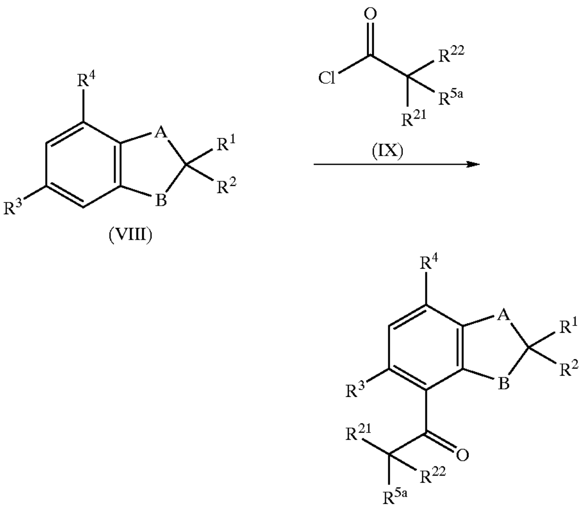

(VIII) (IX) (Iad)

(In the formulae, A, B, $R^1$, $R^2$, $R^3$, $R^4$, $R^{5a}$, $R^{21}$, and $R^{22}$ each has the same meaning as defined above.)

The starting Compound (VIII) can be obtained according to the methods described in Reference Examples or similar methods thereto.

Compound (Iad) can be obtained by reacting Compound (VIII) with Compound (IX) in the presence of an acid catalyst in an inert solvent at the temperature between −100° C. and the boiling point of the employed solvent for 5 minutes to 30 hours.

Examples of the acid catalyst are boron trifluoride, aluminium chloride, stannic chloride, titanium tetrachloride, zinc chloride, and ferric chloride.

Examples of the inert solvent are THF, dioxane, diethyl ether, glyme, diglyme, dichloromethane, 1,2,-dichloroethane, chloroform, benzene, nitrobenzene, and toluene.

Process 1-7:

Compound (Iae), which is Compound (Ia) in which D is —C(=O)—$NR^{23}$—, can be prepared by the following reaction step:

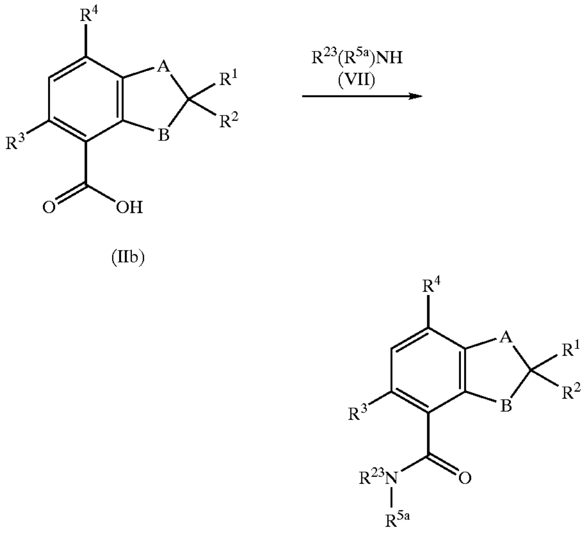

(IIb) (Iae)

(In the formulae, A, B, $R^1$, $R^2$, $R^3$, $R^4$, $R^{5a}$, and $R^{23}$ each has the same meaning as defined above.)

The desired Compound (Iae) can be obtained by dehydrative condensation of Compound (IIb), which is a starting Compound (II) in which $R^{19a}$ is hydroxy, and Compound (VII). For the above condensation, numerous methods are known and applicable, as described in Jikken Kagaku Koza, 22, 137–172, the 4th edition (Nippon Kagakb-Kai, 1992). For example, Compound (IIb) is treated with one equivalent to a largely excess amount of thionyl chloride, phosphorus pentachloride, oxalyl chloride, or the like, if necessary in the presence of a catalytic amount to 20 equivalents of a base, in an inert solvent at the temperature between 0° C. and the boiling point of the employed solvent for 0.1 to 48 hours to give a corresponding acid chloride. Then, the desired Compound (Iae) can be obtained by reacting the obtained acid chloride with 0.5 to 50 equivalents of Compound (VII), if necessary in the presence of 0.5 equivalent to a largely excess amount of a base, in an inert solvent at the temperature between 0° C. and the boiling point of the employed solvent for 0.1 to 48 hours.

Examples of the base are those which are used in the manufacturing method for Compound (Iaa-a) described in Process 1-1.

Examples of the inert solvents are dichloromethane, chloroform, benzene, toluene, THF, dioxane, DMF, and DMSO.

Process 1-8:

Compound (Iaf), which is Compound (Ia) in which D is —C (=O)—S—, can be prepared by the following reaction step:

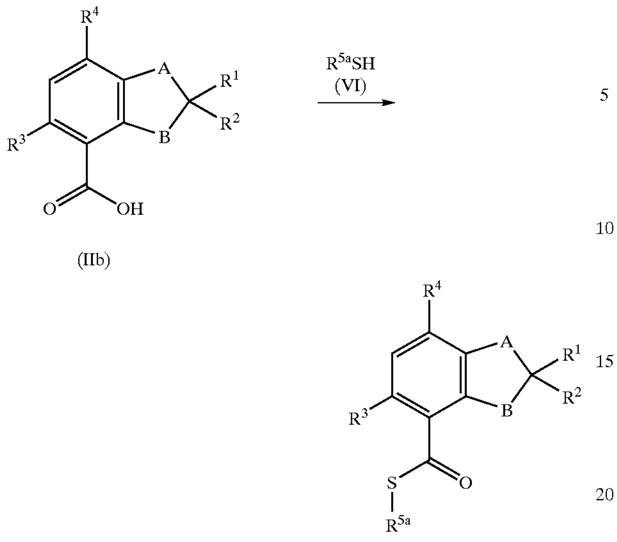

(IIb)

(Iaf)

(In the formulae, A, B, $R^1$, $R^2$, $R^3$, $R^4$, and $R^{5a}$ each has the same meaning as defined above.)

Compound (Iaf) can be obtained according to the method described in Process 1-7 in which Compound (Iae) is obtained from Compound (IIc) and Compound (VII), using Compound (VI) instead of Compound (VII).

Process 1-9:

Compound (Iae-a), which is Compound (Iae) in which one of $R^1$ and $R^{11}$ (or $R^{13}$) is —$(CH_2)_n$—CO—$G^1$ or —$(CH_2)_m$—CO—$G^2$, can be prepared by the following reaction steps:

[In the formulae, $G^a$ is $OR^6$ (with the proviso that $R^6$ is not hydrogen) or $NR^7R^8$ in the definition of $G^1$ (or $G^2$); $R^{27}$ is a protective group of a carboxyl group; and A, B, $R^2$, $R^3$, $R^4$, $R^{5a}$, $R^{23}$, n, and m each has the same meaning as defined above.]

A protective group for a carboxyl group is generally required to be deprotected selectively compared with an amide bond for converting a protected carboxyl group to a carboxyl group, and those which are described in the fifth chapter of Protective Group in Organic Synthesis (the second edition, Green and Watt, Jon Weary and Suns Incorporated, 1991) can be applied. Examples of these are esters of substituted or unsubstituted lower alkyl including methyl, ethyl, and tert-butyl, benzyl, allyl, and 2-(trimethylsilyl)ethyl.

The starting Compound (IIb-a) can be obtained according to the methods described in Reference Examples or similar methods thereto.

Compound (X) can be obtained according to the method described in Process 1-7, using Compound (IIb-a) and Compound (VII).

Compound (Iae-aa), which is Compound (Iae-a) in which $G^1$ (or $G^2$) is hydroxy, can be obtained by treating Compound (X) in the presence of a catalytic to largely excess amount of a base in an inert solvent containing water at the temperature between room temperature and the boiling point of the employed solvent for 0.1 to 48 hours.

Examples of the base are those which are used in the manufacturing method for Compound (Iaa-a) described in Process 1-1; and examples of the inert solvent are THF, dioxane, ethylene glycol, triethylene glycol, glyme, diglyme, methanol, ethanol, butanol, and isopropanol.

Compound (Iae-ab), which is Compound (Iae-a) in which $G^1$ (or $G^2$) is $OR^6$ (with the proviso that $R^6$ is not hydrogen) or $NR^7R^8$, can be obtained according to the method

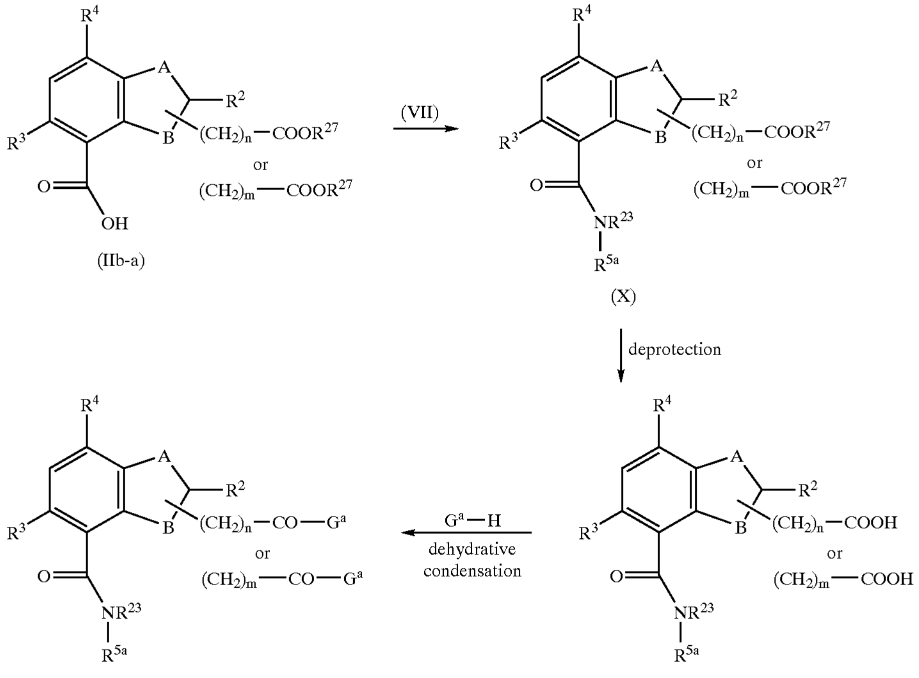

(IIb-a)

(X)

(Iae-ab)

(Iae-aa)

described in Process 1-7, using Compound (Iae-aa) and Compound Ga-H.

Process 1-10:

Compound (Iae-ac), which is Compound (Iae-a) in which $G^1$ (or $G^2$) is substituted or unsubstituted lower alkyl, cycloalkyl, polycycloalkyl, substituted or unsubstituted aryl, a substituted or unsubstituted aromatic heterocyclic group, or aralkyl, can be prepared by the following reaction step:

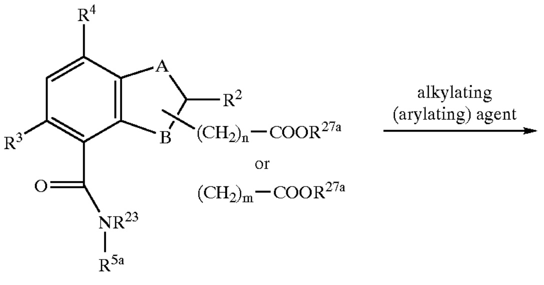

(Xa)

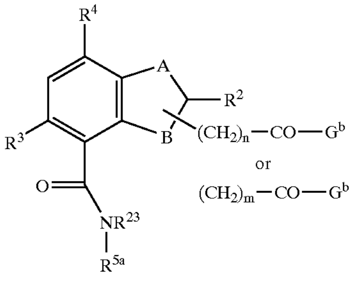

(Iae-ac)

[In the formulae, $R^{27a}$ is substituted or unsubstituted lower alkyl; $G^b$ is substituted or unsubstituted lower alkyl, cycloalkyl, polycycloalkyl, substituted or unsubstituted aryl, a substituted or unsubstituted aromatic heterocyclic group, or aralkyl in the definition of $G^1$ (or $G^2$); and A, B, $R^2$, $R^3$, $R^4$, $R^{5a}$, $R^{23}$, n, and m each has the same meaning as defined above.]

The substituted or unsubstituted lower alkyl in the definition of $R^{27a}$ has the same meaning as defined above.

Compound (Iae-ac) can be obtained by reacting Compound (Xa), which is Compound (X) in which $R^{27}$ is substituted or unsubstituted lower alkyl, with an alkylating (arylating) agent (X) in an inert solvent at the temperature between −100° C. and the boiling point of the employed solvent for 5 minutes to 30 hours.

Examples of the alkylating (arylating) agent are various kinds of alkyl- or arylmagnesium bromides, alkyl- or arylmagnesium chlorides, alkyl- or arylmagnesium iodides, and various kinds of alkyl or aryl lithium.

Examples of the inert solvent are THF, dioxane, diethyl ether, glyme, diglyme, methanol, ethanol, butanol, isopropanol, dichloromethane, chloroform, benzene, and toluene.

Process 1-11:

Compound (Iae-aca), which is Compound (Iae-ac) in which one of $R^1$ and $R^{11}$ (or $R^{13}$) is —CO—$G^b$, can also be prepared by the following reaction step:

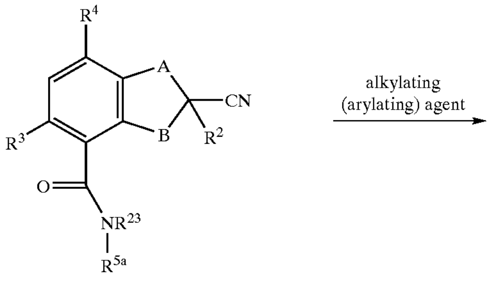

(Iae-b)

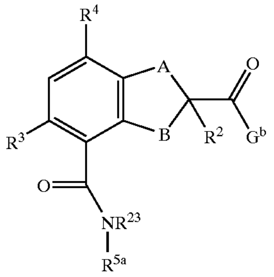

(Iae-aca)

(In the formulae, A, B, $R^2$, $R^3$, $R^4$, $R^{5a}$, $R^{23}$, and $G^b$ each has the same meaning as defined above.)

Compound (Iae-aca) can be obtained according to the method described in Process 1-10 from Compound (Iae-b), which is Compound (Iae) in which $R^1$ is cyano.

Process 1-12:

Compound (Iag), which is Compound (Ia) in which D is —C(═S)—X—, can be prepared by the following reaction step:

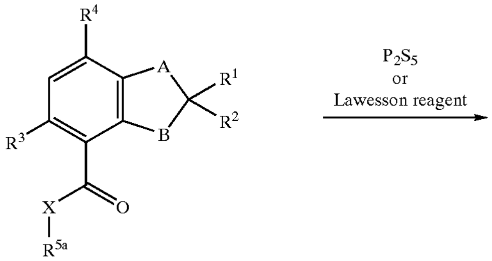

(Iad), (Iae) or (Iaf)

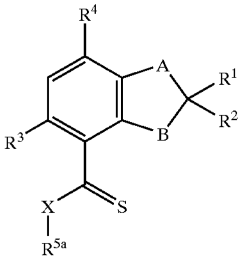

(Iag)

(In the formulae, A, B, $R^1$, $R^2$, $R^3$, $R^4$, $R^{5a}$, and X each has the same meaning as defined above.)

Compound (Iag) can be obtained by treating Compound (Iad), Compound (Iae), or Compound (Iaf) with phosphorus pentasulfide or Lawesson's reagent in an inert solvent at the temperature between room temperature and the boiling point of the employed solvent for 5 minutes to 72 hours.

Examples of inert solvent are pyridine, THF, dioxane, diethyl ether, ethylene glycol, triethylene glycol, glyme, diglyme, dichloromethane, chloroform, benzene, toluene, xylene, DMF, and DMSO.

Process 1-13:

Compound (Iah), which is Compound (Ia) in which D is $—C(=NR^{20})—CR^{21}R^{22}—$, can be prepared by the following reaction step:

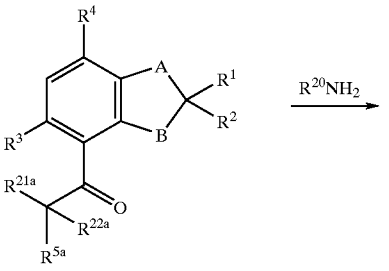

(Iad-a)

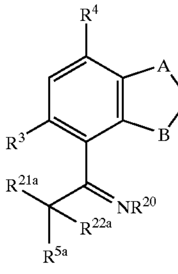

(Iah-a)

(In the formulae, $R^{21a}$ and $R^{22a}$ are groups other than lower alkanoyl, cycloalkanoyl, lower alkoxycarbonyl, and cyano in the definition of $R^{21}$ and $R^{22}$; and A, B, $R^1$, $R^2$, $R^3$, $R^4$, $R^{5a}$, and $R^{20}$ each has the same meaning as defined above.)

Compound (Iah-a), which is Compound (Iah) in which $R^{21a}$ and $R^{22a}$ are groups other than lower alkanoyl, cycloalkanoyl, lower alkoxycarbonyl, and cyano in the definition of $R^{21}$ and $R^{22}$, can be obtained by reacting Compound (Iad-a) with $R^{20}NH_2$ in the presence or absence of an acid catalyst in an inert solvent or without solvent at the temperature between room temperature and the boiling point of the employed solvent for 5 minutes to 48 hours.

Examples of the acid catalyst are p-toluene-sulfonic acid, methanesulfonic acid, hydrochloric acid, sulfuric acid, acetic acid, and trifluoroacetic acid.

Examples of the inert solvent are THF, dioxane, diethyl ether, ethylene glycol, triethylene glycol, glyme, diglyme, methanol, ethanol, isopropanol, tert-butanol, dichloromethane, chloroform, benzene, toluene, DMF, DMSO, and pyridine.

Process 1-14:

Compound (Ia'), which is Compound (I) in which D is (i) $—C(R^{18})(R^{19})—X—$ and $R^5$ is pyridine-N-oxide, can be prepared by the following reaction step:

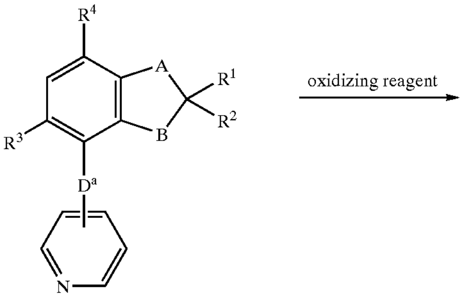

(Iaa), (Iad) or (Iae)

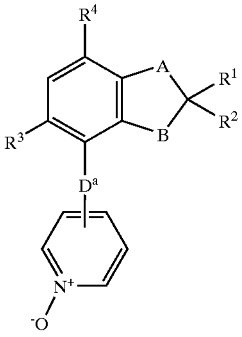

(Ia'a)

[In the formulae, $D^a$ is D in Compound (Iaa), (Iad), and (Iae) and A, B, $R^1$, $R^2$, $R^3$, and $R^4$ each has the same meaning as defined above.]

Compound (Ia'a), which is Compound (Ia') in which D is D in Compound (Iaa), (Iad), and (Iae), can be obtained by treating Compound (Iaa), (Iad), or (Iae) with an oxidizing agent in an inert solvent at the temperature between room temperature and the boiling point of the employed solvent for 5 minutes to 72 hours.

Examples of inert solvent are dichloromethane, chloroform, benzene, toluene, xylene, DMF, DMSO, and acetic acid.

Examples of the oxidizing agent are peracetic acid, trifluoroperacetic acid, metachloroperbenzoic acid, hydrogen peroxide, benzoyl peroxide, tert-butyl hydroperoxide, and tert-amyl hydroperoxide.

Manufacturing method 2:

Compound (Ib), which is Compound (I) in which D is (ii) $—C(R^{19a})=Y—$, can be obtained by the following Processes 2-1 to 2-5.

Process 2-1:

Compound (Iba-a), which is Compound (Ib) in which Y is $—CR^{24}$, $R^5$ is substituted or unsubstituted aryl, or a substituted or unsubstituted aromatic heterocyclic group, $R^{19a}$ is a group other than hydroxy, substituted or unsubstituted lower alkoxy, and lower alkanoyloxy in the definition of $R^{19a}$, and $R^{24}$ and $R^{19a}$ are not combined to form a single bond, can be prepared by the following reaction steps:

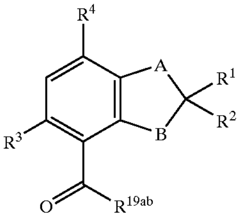

(IIc)

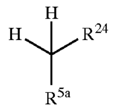

(IIIa)

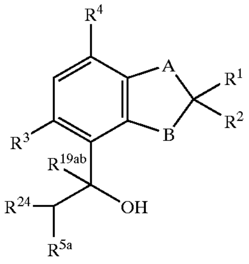

(Iaa-aa)

acid catalyst

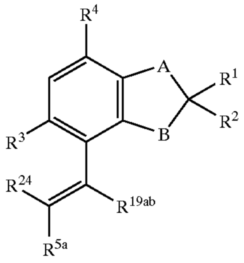

(Iba-a)

(In the formulae, $R^{19ab}$ is a group other than hydroxy, substituted or unsubstituted lower alkoxy, and lower alkanoyloxy in the definition as $R^{19a}$, and $R^{19a}$ and $R^{24}$ are not combined to form a single bond; and A, B, $R^1$, $R^2$, $R^3$, $R^4$, $R^{5a}$, $R^{19a}$, and $R^{24}$ each has the same meaning as defined above.)

Compound (Iaa-aa), which is Compound (Iaa-a) in which $R^{22}$ is hydrogen, can be obtained according to the method similar to the manufacturing method for Compound (Iaa-a) described in Process 1-1, using Compound (IIc) and Compound (IIIa), which is Compound (III) in which $R^{22}$ is hydrogen. Compound (Iaa-aa) is directly converted to Compound (Iba) without isolation when $R^{24}$ is lower alkanoyl, cycloalkanoyl, lower alkoxycarbonyl, or cyano.

Compound (Iba) can be obtained by treating Compound (Iaa-aa) in the presence an acid catalyst in an inert solvent at the temperature between room temperature and the boiling point of the employed solvent for 5 minutes to 48 hours.

Examples of the acid catalyst are p-toluene-sulfonic acid, methanesulfonic acid, hydrochloric acid, sulfuric acid, acetic acid, and trifluoroacetic acid.

Examples of the inert solvent are THF, dioxane, diethyl ether, ethylene glycol, triethylene glycol, glyme, diglyme, dichloromethane, chloroform, benzene, toluene, DMF, and DMSO.

Process 2-2:

Compound (Iba), which is Compound (Ib) in which Y is —$CR^{24}$, $R^{19a}$ iS a group other than hydroxy, substituted or unsubstituted lower alkoyy, and lower alkanoyloxy in the definition of $R^{19a}$, and $R^{24}$ and $R^{19a}$ are not combined to form a single bond, can be prepared by the following reaction step:

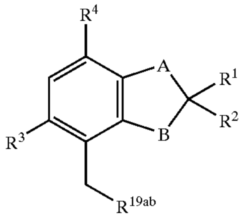

(XI)

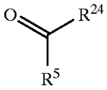

(XII)

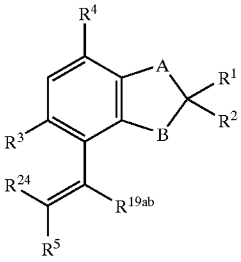

(Iba)

(In the formulae, A, B, $R^1$, $R^2$, $R^3$, $R^4$, $R^5$, $R^{19ab}$, and $R^{24}$ each has the same meaning as defined above.)

The starting compound (XI) can be obtained according to the methods described in Reference Examples or similar methods thereto.

Compound (Iba) can be obtained by treating starting Compound (XI) with a base in an inert solvent at the temperature between −100° C. and the boiling point of the employed solvent for 5 minutes to 10 hours, followed by reaction with Compound (XII) at the temperature between −100° C. and the boiling point of the employed solvent for 5 minutes to 30 hours.

Examples of the base and the inert solvent are those used in the manufacturing method for Compound (Iaa-a) described in Process 1-1.

Process 2-3:

Compound (Ibb), which is Compound (Ib) in which Y is N, $R^{19a}$ is a group other than hydroxy, substituted or unsubstituted lower alkoxy, and lower alkanoyloxy in the definition of $R^{19a}$, and $R^5$ is substituted or unsubstituted aryl or a substituted or unsubstituted aromatic heterocyclic group, can be prepared by the following reaction step:

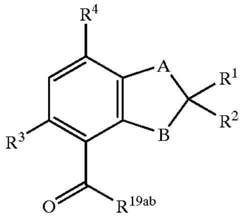

(IIe)

$R^{5a}NH_2$
(VIIa)

-continued

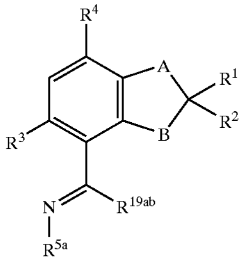

(Ibb)

(In the formulae, A, B, $R^1$, $R^2$, $R^3$, $R^4$, $R^{5a}$, and $R^{19ab}$ each has the same meaning as defined above.)

Compound (Ibb) can be obtained by reacting Compound (IIe) with Compound (VIIa), which is Compound (VII) in which $R^{23}$ is hydrogen, in the presence of an acid catalyst in an inert solvent or without solvent at the temperature between room temperature and the boiling point of the employed solvent for 5 minutes to 48 hours.

Examples of the acid catalyst are p-toluene-sulfonic acid, methanesulfonic acid, hydrochloric acid, sulfuric acid, acetic acid, and trifluoroacetic acid.

Examples of the inert solvent are THF, dioxane, diethyl ether, ethylene glycol, triethylene glycol, glyme, diglyme, methanol, ethanol, isopropanol, tert-butanol, dichloromethane, chloroform, benzene, toluene, DMF, and DMSO.

Process 2-4:

Compound (Ibc), which is Compound (Ib) in which Y is —$CR^{24}$—CONH—, $R^{19a}$ is a group other than hydroxy, substituted or unsubstituted lower alkoxy, and lower alkanoyloxy in the definition of $R^{19a}$, and $R^5$ is substituted or unsubstituted lower aryl or a substituted or unsubstituted aromatic heterocyclic group, can be prepared by the following reaction steps:

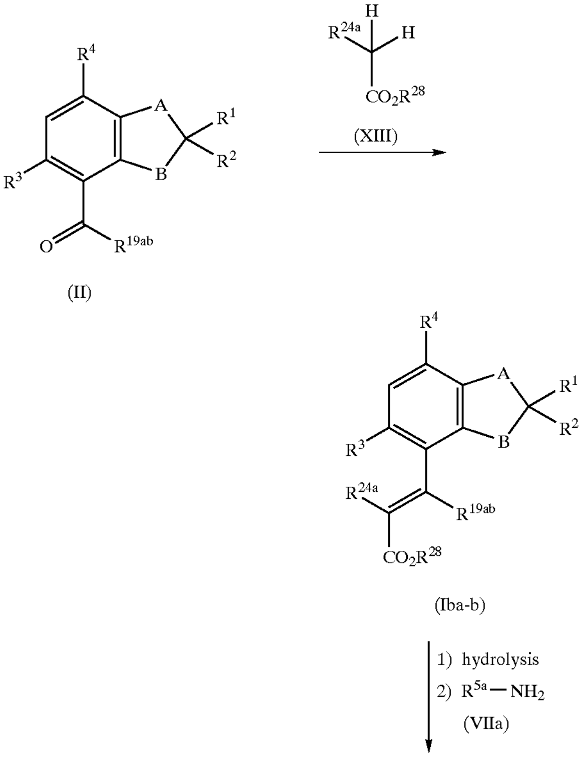

(II) (XIII) (Iba-b)

-continued

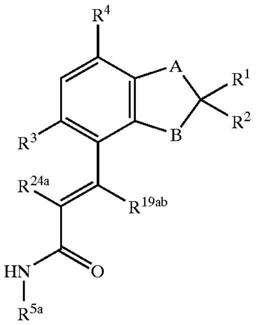

(Ibc-a)

(In the formulae, $R^{28}$ is lower alkyl. $R^{24a}$ is a group other than lower alkanoyl, cycloalkanoyl, lower alkoxycarbonyl, and cyano in the definition as $R^{24}$; and A, B, $R^1$, $R^2$, $R^3$, $R^4$, $R^{5a}$, and $R^{19a}$ each has the same meaning as defined above.)

The lower alkoxy in the definition of $R^{28}$ has the same meaning as defined above.

Compound (Iba-b), which is Compound (Iba) in which $R^5$ is lower alkoxycarbonyl and $R^{24}$ is a group other than lower alkanoyl, cycloalkanoyl, lower alkoxycarbonyl, and cyano, can be obtained according to the method similar to the manufacturing method for Compound (Iba-a) described in Process 2-1, using Compound (II) and Compound (XIII). Further, Compound (Iba-b) can be obtained by reacting Compound (II) with a corresponding diester of phosphorous acid treated with a base in an inert solvent at the temperature between −100° C. and the boiling point of the employed solvent for 5 minutes to 48 hours.

Examples of the inert solvent are THF, dioxane, diethyl ether, ethylene glycol, triethylene glycol, glyme, diglyme, methanol, ethanol, butanol, isopropanol, dichloromethane, chloroform, benzene, toluene, DMF, and DMSO.

Examples of the base are sodium hydroxide, potassium hydroxide, sodium methoxide, potassium ethoxide, sodium hydride, potassium hydride, butyl lithium, LDA, potassium tert-butoxide, triethylamine, diisopropyl-ethylamine, tributylamine, dicyclohexylmethylamine, N-methylmorphorine, N-methylpiperidine, DBU, and DBN.

Compound (Ibc-a), which is Compound (Ibc) in which $R^{24}$ is a group other than lower alkanoyl, cycloalkanoyl, lower alkoxycarbonyl, and cyano, can be obtained according to the method described in Process 1-9 in which Compound (Iae-ab) is obtained from Compound (X), using Compound (Iba-b) and Compound (VIIa).

Process 2-5:

Compound (Ibd), which is Compound (Ib) in which Y is —$CR^{24}$, $R^{24}$ and $R^{19a}$ are combined to form a single bond, and $R^5$ is substituted or unsubstituted aryl, or a substituted or unsubstituted aromatic heterocyclic group, can be prepared by the following reaction steps:

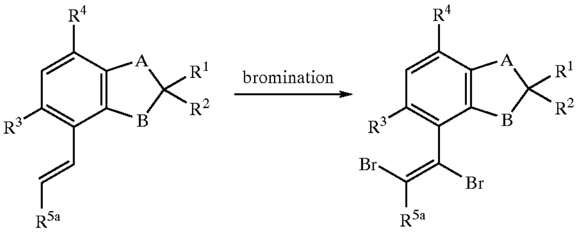

(Iba-aa)

(XIV)

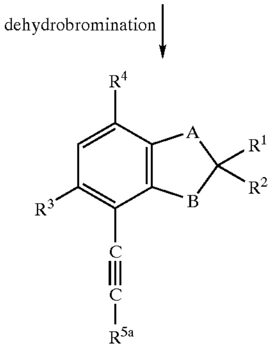

(Ibd)

(In the formulae, A, B, $R^1$, $R^2$, $R^3$, $R^4$, and $R^{5a}$ each has the same meaning as defined above.)

Compound (XIV) can be obtained by treating Compound (Iba-aa), which is Compound (Iba-a) in which $R^{19a}$ and $R^{24}$ are both hydrogen, with a brominating agent in an inert solvent at the temperature between −100° C. and the boiling point of the employed solvent for 5 minutes to 10 hours.

Examples of the inert solvent are THF, dioxane, diethyl ether, ethylene glycol, triethylene glycol, glyme, diglyme, methanol, ethanol, isopropanol, tert-butanol, dichloromethane, chloroform, benzene, toluene, DMF, and DMSO.

Examples of the brominating agent are bromine, tetrabutylammonium tribromide, tetramethylammonium tribromide, pyridinium tribromide, NBS, and copper bromide.

Compound (Ibd) can be obtained by treating Compound (XIV) with a base in an inert solvent at the temperature between −100° C. and the boiling point of the employed solvent for 5 minutes to 10 hours.

Examples of the inert solvent are THF, dioxane, diethyl ether, ethylene glycol, triethylene glycol, glyme, diglyme, methanol, ethanol, isopropanol, tert-butanol, dichloromethane, chloroform, benzene, toluene, DMF, and DMSO.

Examples of the base are potassium hydroxide, sodium ethoxide, sodium methoxide, potassium tert-butoxide, and sodium amide.

Manufacturing method 3:

Compound (Ic), which is Compound (I) in which D is (iii) a bond, and $R^5$ is substituted or unsubstituted aryl, or a substituted or unsubstituted aromatic heterocyclic group, can be obtained by the following process:

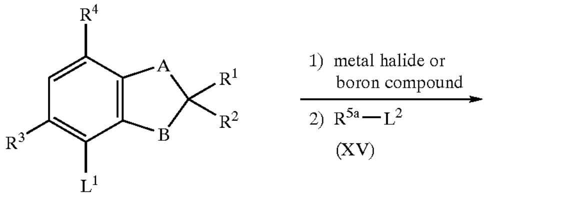

(IIf)

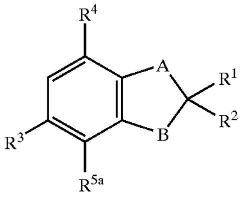

(Ic)

(In the formulae, $L^1$ and $L^2$ independently represent iodine, bromine, or chlorine; and A, B, $R^1$, $R^2$, $R^3$, $R^4$, and $R^{5a}$ each has the same meaning as defined above.)

Examples of the metal halide are alkyltin halides such as tributyltin chloride and trimethyltin chloride, and zinc halides such as zinc chloride, zinc bromide, and zinc iodide; and examples of the boron compound are trimethoxy boron, phenylboric acid, and boric acid.

Compound (Ic) can be obtained by treating Compound (IIf) with a base in an inert solvent. at the temperature between −100° C. and room temperature for 5 minutes to 10 hours, followed by reaction with a metal halide or a boron compound at the temperature between −100° C. and the boiling point of the employed solvent for 5 minutes to 30 hours, and then reacting the obtained product with Compound (xv) in the presence of a catalytic to largely excess amount of a palladium complex in an inert solvent at the temperature between room temperature and the boiling point of the employed solvent for 5 minutes to 30 hours. Moreover, if necessary, a salt such as lithium chloride, or an oxidizing agent such as silver oxide may be added in case of the latter reaction.

Examples of the palladium complex are tetrakis (triphenylphosphine)palladium, bis(triphenyl-phosphine) palladium chloride, bis(acetonitrile)palladium chloride, and palladium acetate.

Examples of the base are sodium hydroxide, potassium hydroxide, sodium methoxide, potassium ethoxide, sodium hydride, potassium hydride, butyl lithium, LDA, potassium tert-butoxide, triethylamine, diisopropyl-ethylamine, tributylamine, dicyclohexylmethylamine, N-methylmorphorine, N-metylpiperidine, DBU, and DBN.

Examples of the inert solvent employed in the treatment with a base followed by reaction with a metal halide or a boron compound are THF, dioxane, diethyl ether, ethylene glycol, triethylene glycol, glyme, diglyme, methanol, ethanol, butanol, isopropanol, dichloromethane, chloroform, benzene, toluene, DMF and DMSO.

Examples of the inert solvent employed in the reaction with Compound (XV) ire THF, dioxane, diethyl ether, dichloromethane, chloroform, benzene, toluene, dimethylacetamide (DMA), DMF, and DMSO.

The intermediates and the desired compounds in the processes described above can be isolated and purified by purification methods conventionally used in organic synthetic chemistry, for example, filtration, extraction, washing, drying, concentration, recrystallization, and various kinds of chromatography. The intermediates may also be subjected to the subsequent reaction without isolation.

Compounds (I) can exist in the form of stereoisomers such as geometrical isomers and optical isomers, and the present invention covers all isomers including these isomers and mixtures thereof.

In the case where a salt of Compound (I) is desired and it is produced in the form of the desired salt, it can be subjected to purification as such. In the case where Compound (I) is produced in the free form and its salt is desired, Compound (I) is dissolved or suspended in a suitable solvent, followed by addition of an acid or a base to form a salt, which may be isolated and purified.

Compounds (I) and pharmaceutically acceptable salts thereof may be in the form of adducts with water or various solvents, which are also within the scope of the present invention.

Examples of Compound (I) obtained in the present invention are shown in Tables 1 to 20.

TABLE 1

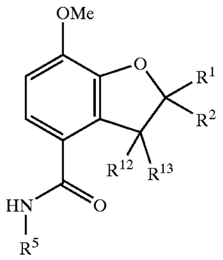

| Compd. No. | $R^1$ | $R^2$ | $R^{13}$ | $R^{12}$ | $R^5$ |
|---|---|---|---|---|---|
| 1 | H | H | H | H | 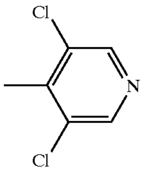 |
| 2 | H | H | H | Me | 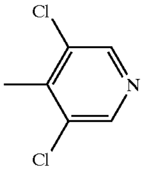 |
| 3 | H | H | H | Et | 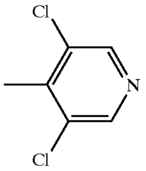 |
| 4 | H | H | H | i-Pr | 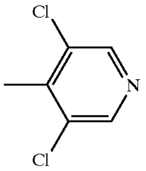 |
| 5 | H | H | H | $CH_2CO_2Et$ | 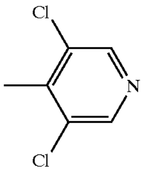 |
| 6 | H | H | H | $CH_2CO_2Et$ | 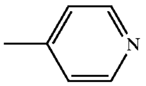 |

TABLE 1-continued

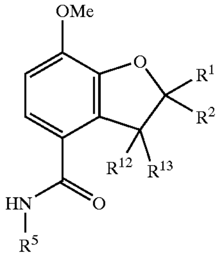

| Compd. No. | $R^1$ | $R^2$ | $R^{13}$ | $R^{12}$ | $R^5$ |
|---|---|---|---|---|---|

*In the Table, Me represents $CH_3$, Et represents $C_2H_5$, and i-Pr represents $(CH_3)_2CH$, respectively.

| Compd. No. | $R^1$ | $R^2$ | $R^{13}$ | $R^{12}$ | $R^5$ |
|---|---|---|---|---|---|
| 7 | H | H | H | $CH_2CO_2Et$ | 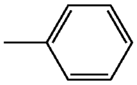 |
| 8 | H | H | H | $CH_2CO_2Et$ | 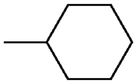 |
| 9 | H | H | H | $CH_2CO_2H$ | 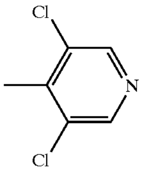 |
| 10 | H | H | H | $CH_2CO_2H$ | 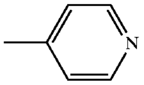 |
| 11 | H | H | H | $CH_2CO_2H$ | 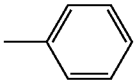 |
| 12 | H | H | H | $CH_2CO_2H$ | 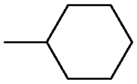 |
| 13 | H | H | H | $CH_2CO_2CH_2C_6H_5$ | 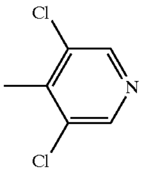 |
| 14 | H | H | H | $CH_2CO_2CH_2C_6H_5$ | 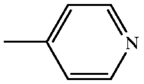 |

*In the Table, Et represents $C_2H_5$.

| Compd. No. | $R^1$ | $R^2$ | $R^{13}$ | $R^{12}$ | $R^5$ |
|---|---|---|---|---|---|
| 15 | H | H | H | $CH_2CO_2CH_2C_6H_5$ | 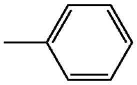 |
| 16 | H | H | H | $CH_2CO_2CH_2C_6H_5$ | 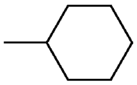 |

TABLE 1-continued
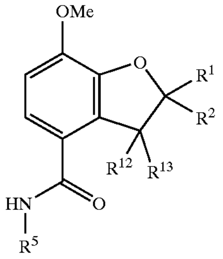
| Compd. No. | $R^1$ | $R^2$ | $R^{13}$ | $R^{12}$ | $R^5$ |
|---|---|---|---|---|---|
| 17 | H | H | H | 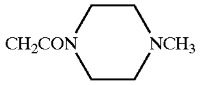 | 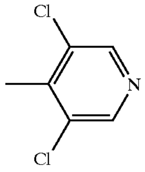 |
| 18 | H | H | H | 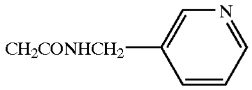 | 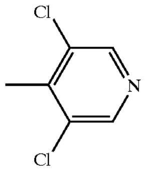 |
| 19 | H | H | H | 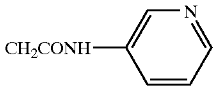 | 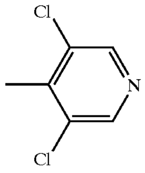 |
| 20 | H | H | H | 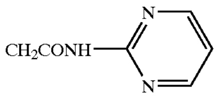 | 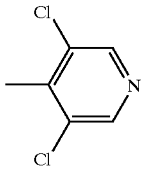 |
| 21 | H | H | H | 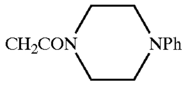 | 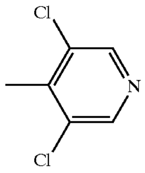 |
| 22 | H | H | H | 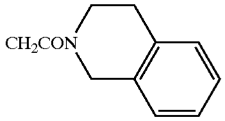 | 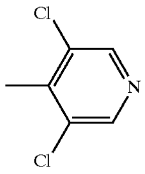 |
In the Table, Ph represents $C_6H_5$.

TABLE 1-continued
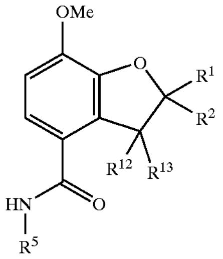
| Compd. No. | $R^1$ | $R^2$ | $R^{13}$ | $R^{12}$ | $R^5$ |
|---|---|---|---|---|---|
| 23 | H | H | H | $CH_2CO_2CH_2CH_2C_6H_5$ | 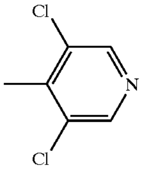 |
| 24 | H | H | H | $CH_2CONHCH_2$— 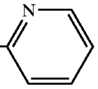 | 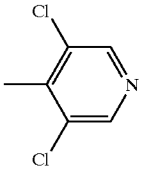 |
| 25 | H | H | H | $CH_2CONHCH_2C_6H_5$ | 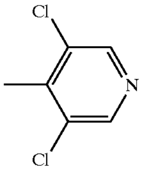 |
| 26 | H | H | H | $CH_2CONHCH_2$— 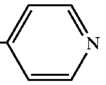 | 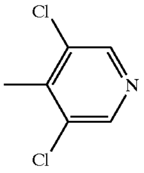 |
| 27 | H | H | 14 | $CH_2CONHC_6H_5$ | 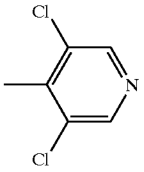 |
| 28 | H | H | H | $CH_2CONHCH_2$— 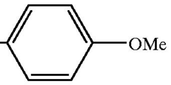 | 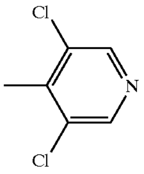 |
| 29 | H | H | H | $CH_2CONHCH_2$— 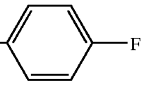 | 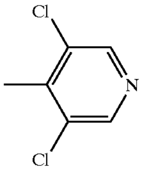 |

TABLE 1-continued
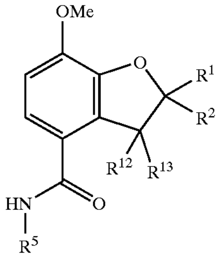
| Compd. No. | $R^1$ | $R^2$ | $R^{13}$ | $R^{12}$ | $R^5$ |
|---|---|---|---|---|---|
| 30 | H | H | H | $CH_2CONHCH_2$— 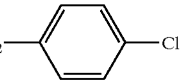 | 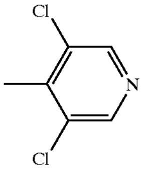 |
*In the Table, Me represents $CH_3$.
| | | | | | |
|---|---|---|---|---|---|
| 31 | H | H | H | $CH_2CONHCH_2$— 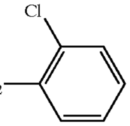 | 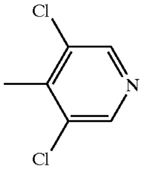 |
| 32 | H | H | H | $CH_2CONH$— 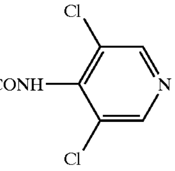 | 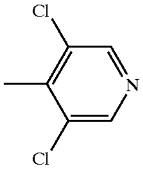 |
| 33 | H | single bond | | H | 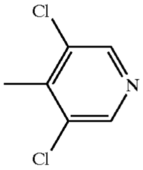 |
| 34 | CN | single bond | | H | 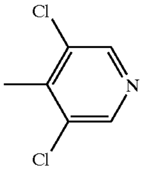 |
| 35 | $COC_6H_5$ | single bond | | H | 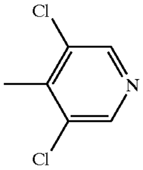 |

TABLE 1-continued
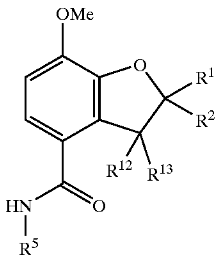
| Compd. No. | $R^1$ | $R^2$ | $R^{13}$ | $R^{12}$ | $R^5$ |
|---|---|---|---|---|---|
| 36 | n-Bu | single bond | | H | 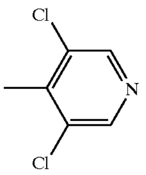 |
| 37 | $CH_2C_6H_5$ | single bond | | H | 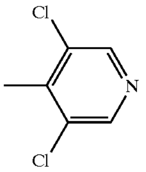 |
| 38 | 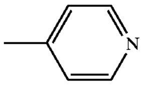 | single bond | | H | 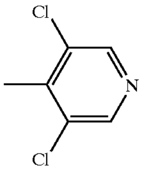 |
| 39 | 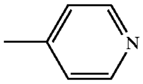 | single bond | | H | 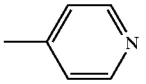 |
| 40 | 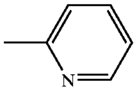 | single bond | | H | 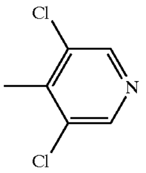 |
| 41 | 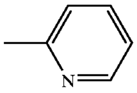 | single bond | | H | 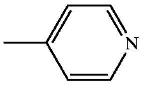 |
*In the Table, n-Bu represents $(CH_2)_3CH_3$.
| | | | | | |
|---|---|---|---|---|---|
| 42 | H | single bond | | $C_6H_5$ | 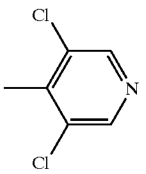 |

TABLE 1-continued
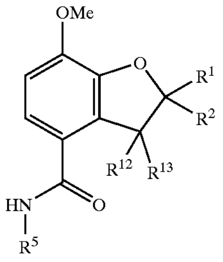
| Compd. No. | $R^1$ | $R^2$ $R^{13}$ | $R^{12}$ | $R^5$ |
|---|---|---|---|---|
| 43 | H | single bond | $CH_2CO_2Et$ | 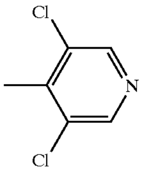 |
| 44 | H | single bond | $CH_2CO_2H$ | 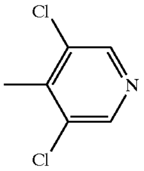 |
| 148 | H | single bond | $CH_2CO_2CH_2C_6H_5$ | 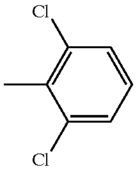 |
| 149 | H | single bond | $CH_2CO_2CH_2C_6H_5$ | 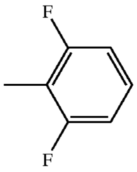 |
| 150 | H | single bond | $CH_2CO_2CH_2C_6H_5$ | 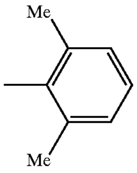 |
*In the Table, Me represents $CH_3$ and Et represents $C_2H_5$, respectively.

TABLE 2
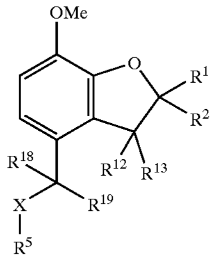
| Compd. No. | $R^1$ | $R^2$ | $R^{13}$ | $R^{12}$ | X | $R^{18}$ | $R^{19}$ | $R^5$ |
|---|---|---|---|---|---|---|---|---|
| 45 | Me | Me | H | H | $CH_2$ | H | H | 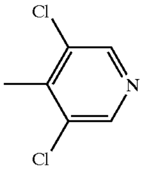 |
| 46 | Me | Me | H | H | $CH_2$ | H | H | 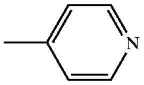 |
| 47 | Me | Me | H | H | $CH_2$ | H | Ph | 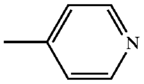 |
| 48 | Me | Me | H | H | S | H | H | 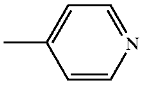 |
| 49 | Me | Me | H | H | S | H | Ph | 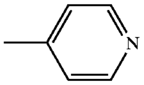 |
| 50 | Et | Et | H | H | $CH_2$ | H | H | 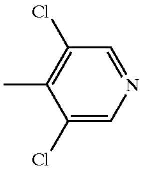 |
| 51 | Et | Et | H | H | $CH_2$ | H | H | 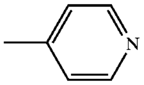 |
| 52 | $-(CH_2)_4-$ | | H | H | $CH_2$ | H | H | 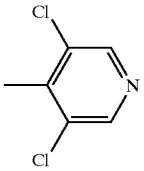 |
*In the Table, Me represents $CH_3$, Et represents $C_2H_5$, and Ph represents $C_6H_5$, respectively.
| | | | | | | | | |
|---|---|---|---|---|---|---|---|---|
| 53 | $-(CH_2)_4-$ | | H | H | $CH_2$ | H | H | 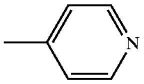 |

TABLE 2-continued
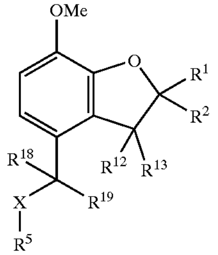
| Compd. No. | $R^1$ | $R^2$ | $R^{13}$ | $R^{12}$ | X | $R^{18}$ | $R^{19}$ | $R^5$ |
|---|---|---|---|---|---|---|---|---|
| 54 | $-(CH_2)_5-$ | | H | H | $CH_2$ | H | H | 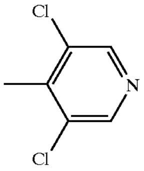 |
| 55 | $-(CH_2)_5-$ | | H | H | $CH_2$ | H | H | 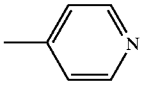 |
| 56 | H | H | H | Me | $CH_2$ | H | H | 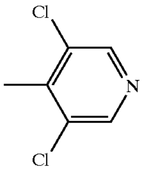 |
| 57 | H | H | H | Me | $CH_2$ | H | H | 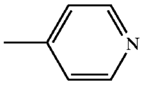 |
| 58 | H | H | H | Me | $CH_2$ | H | Ph | 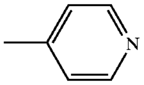 |
| 59 | H | H | H | Me | S | H | H | 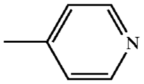 |
| 60A | H | H | H | Me | S | H | Ph | 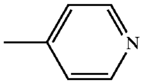 |
| 60B | H | H | H | Me | S | H | Ph | 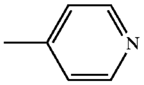 |
| 61 | H | H | H | Me | NH | H | H | 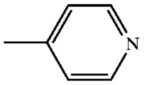 |
| 62 | Me | Me | H | H | $CH_2$ | H | OMe | 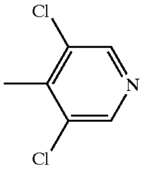 |
*In the Table, Me represents $CH_3$ and Ph represents $C_6H_5$, respectively.

TABLE 2-continued
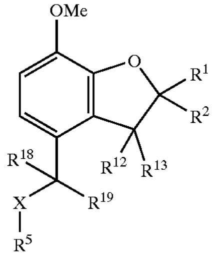
| Compd. No. | $R^1$ | $R^2$ | $R^{13}$ | $R^{12}$ | X | $R^{18}$ | $R^{19}$ | $R^5$ |
|---|---|---|---|---|---|---|---|---|
| 63 | Me | Me | H | H | $CH_2$ | H | CN | 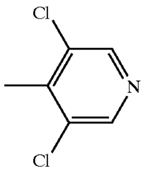 |
| 64 | $—(CH_2)_4—$ | | H | H | $CH_2$ | H | CN | 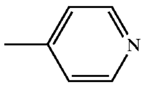 |
| 65 | $—(CH_2)_4—$ | | H | H | $CH_2$ | Me | CN | 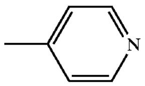 |
| 66 | 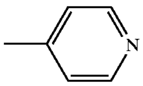 | single bond | | H | $CH_2$ | H | Ph | 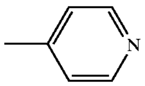 |
*In the Table, Me represents $CH_3$ and Ph represents $C_6H_5$, respectively.
TABLE 3
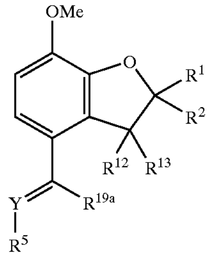
| Compd. No. | $R^1$ | $R^2$ | $R^{13}$ | $R^{12}$ | Y | $R^{19a}$ | $R^5$ |
|---|---|---|---|---|---|---|---|
| 67 | Me | Me | H | H | CH | H | 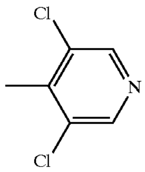 |
| 68 | Me | Me | H | H | CH | H | 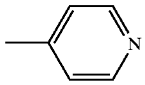 |
| 69 | Me | Me | H | H | CH | Me | 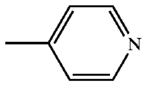 |

TABLE 3-continued
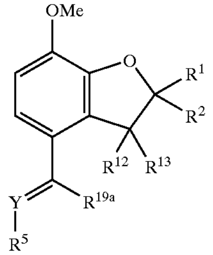
| Compd. No. | $R^1$ | $R^2$ | $R^{13}$ | $R^{12}$ | Y | $R^{19a}$ | $R^5$ |
|---|---|---|---|---|---|---|---|
| 70 | Me | Me | H | H | CH | Ph | 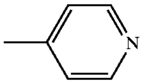 |
| 71 | Et | Et | H | H | CH | H | 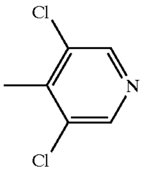 |
| 72 | Et | Et | H | H | CH | H | 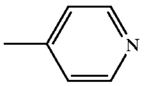 |
| 73 | $-(CH_2)_4-$ | | H | H | CH | H | 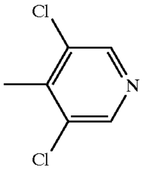 |
| 74 | $-(CH_2)_4-$ | | H | H | CH | H | 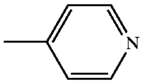 |
*In the Table Me represents $CH_3$, Et represents $C_2H_5$, and Ph represents $C_6H_5$, respectively.
| Compd. No. | $R^1$ | $R^2$ | $R^{13}$ | $R^{12}$ | Y | $R^{19a}$ | $R^5$ |
|---|---|---|---|---|---|---|---|
| 75 | $-(CH_2)_4-$ | | H | H | CH | Me | 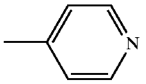 |
| 76 | $-(CH_2)_5-$ | | H | H | CH | H | 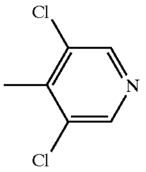 |
| 77 | $-(CH_2)_5-$ | | H | H | CH | H | 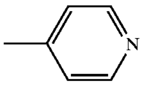 |
| 78 | H | H | H | Me | CH | H | 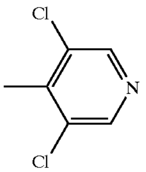 |

TABLE 3-continued
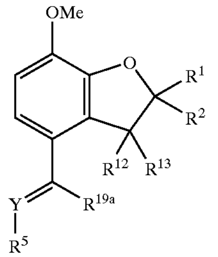
| Compd. No. | $R^1$ | $R^2$ | $R^{13}$ | $R^{12}$ | Y | $R^{19a}$ | $R^5$ |
|---|---|---|---|---|---|---|---|
| 79 | H | H | H | Me | CH | H | 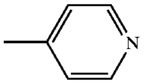 |
| 80 | H | H | H | Me | CH | Ph | 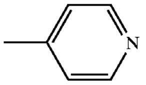 |
| 81 | Ph | single bond | | H | CH | H | 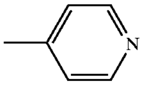 |
| 82 | 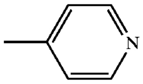 | single bond | | H | CH | H | 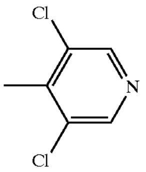 |
| 83 | 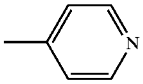 | single bond | | H | CH | H | 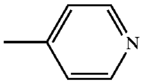 |
| 84 | 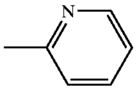 | single bond | | H | CH | H | 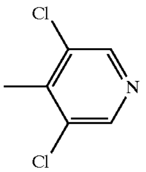 |
| 85 | 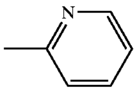 | single bond | | H | CH | H | 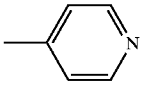 |
| 86 | Me | Me | H | H | CCN | H | 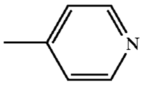 |
| 87 | Me | Me | H | H | $CCO_2Et$ | H | 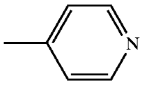 |
| 88 | Me | Me | H | H | CCN | H | CN |
| 89 | Me | Me | H | H | CCN | H | $CO_2Et$ |
| 90 | $—(CH_2)_4—$ | | H | H | CHCONH | H | 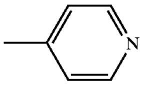 |
*In the Table, Me represents $CH_3$ and Ph represents $C_6H_5$, respectively.

TABLE 3-continued
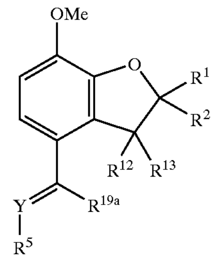
| Compd. No. | $R^1$ | $R^2$ | $R^{13}$ | $R^{12}$ | Y | $R^{19a}$ | $R^5$ |
|---|---|---|---|---|---|---|---|
| 91 | $-(CH_2)_4-$ | | H | H | CHCONH | H | 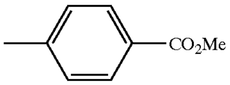 |
| 92 | $-(CH_2)_4-$ | | H | H | CHCONH | H | 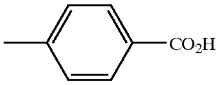 |
| 93 | $-(CH_2)_4-$ | | H | H | CHCONH | H | 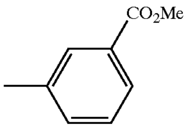 |
| 94 | $-(CH_2)_4-$ | | H | H | CHCONH | H | 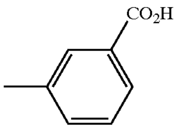 |
*In the Table, Me represents $CH_3$ and Et represents $C_2H_5$, respectively.
TABLE 4
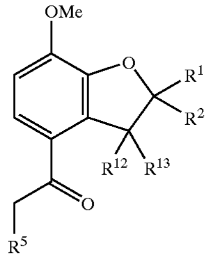
| Compd. No. | $R^1$ | $R^2$ | $R^{13}$ | $R^{12}$ | $R^5$ |
|---|---|---|---|---|---|
| 95 | Me | Me | H | H | 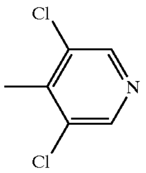 |
| 96 | Me | Me | H | H | 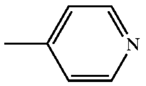 |

TABLE 4-continued
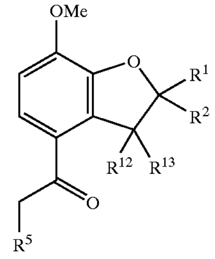
| Compd. No. | $R^1$ | $R^2$ | $R^{13}$ | $R^{12}$ | $R^5$ |
|---|---|---|---|---|---|
| 97 | Et | Et | H | H | 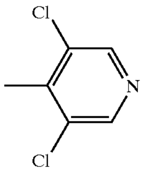 |
| 98 | Et | Et | H | H | 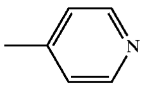 |
| 99 | $-(CH_2)_4-$ | | H | H | 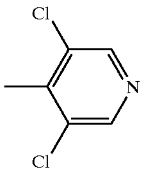 |
| 100 | $-(CH_2)_4-$ | | H | H | 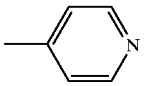 |
| 101 | $-(CH_2)_5-$ | | H | H | 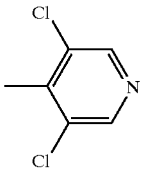 |
| 102 | $-(CH_2)_5-$ | | H | H | 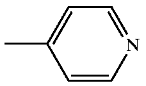 |
*In the Table, Me represents $CH_3$ and Et represents $C_2H_5$, respectively.
| | | | | | |
|---|---|---|---|---|---|
| 103 | H | H | H | Me | 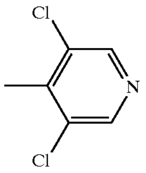 |
| 104 | H | H | H | Me | 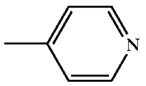 |
| 105 | H | $-(CH_2)_4-$ | | H | 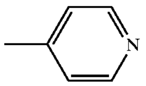 |

TABLE 4-continued
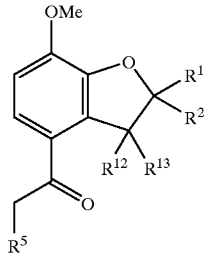
| Compd. No. | $R^1$ | $R^2$ $R^{13}$ | $R^{12}$ | $R^5$ |
|---|---|---|---|---|
| 106 | CN | single bond | H | 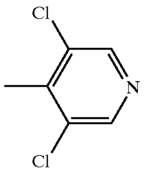 |
| 107 | $COC_6H_5$ | single bond | H | 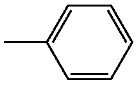 |
| 108 | $COC_6H_5$ | single bond | H | 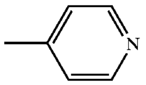 |
| 109 | n-Bu | single bond | H | 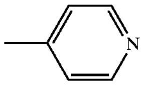 |
| 110 | i-Bu | single bond | H | 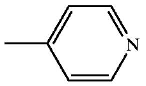 |
| 111 | Ph | single bond | H | 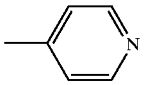 |
| 112 | 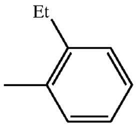 | single bond | H | 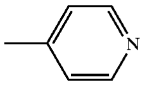 |
| 113 | 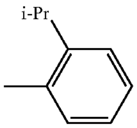 | single bond | H | 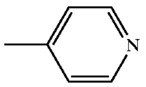 |
*In the Table, Me represents $CH_3$, Et represents $C_2H_5$, n-Bu represents $(CH_2)_3CH_3$, i-Bu represents $(CH_3)_2CHCH_2$, and Ph represents $C_6H_5$, respectively.
| | | | | |
|---|---|---|---|---|
| 114 | 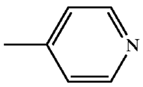 | single bond | H | 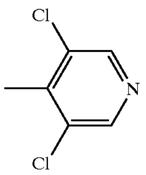 |
| 115 | 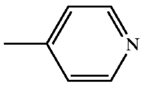 | single bond | H | 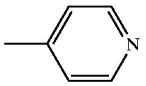 |

TABLE 4-continued
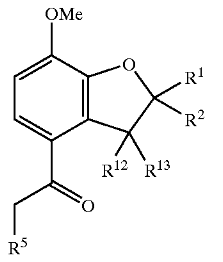
| Compd. No. | $R^1$ | $R^2$ | $R^{13}$ | $R^{12}$ | $R^5$ |
|---|---|---|---|---|---|
| 116 | 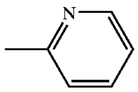 | single bond | | H | 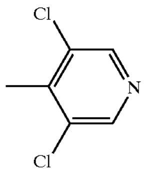 |
| 117 | 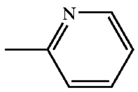 | single bond | | H | 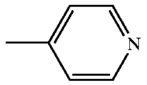 |
| 118 | H | single bond | | Ph | 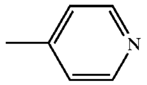 |
| 119 | H | single bond | | $CH_2CO_2Et$ | 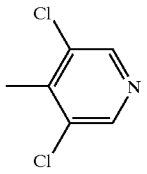 |
| 120 | H | single bond | | $CH_2CO_2Et$ | 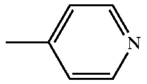 |
*In the Table, Et represents $C_2H_5$ and Ph represents $C_6H_5$, respectively.
| | | | | | |
|---|---|---|---|---|---|
| 151 | H | single bond | | $CH_2CO_2H$ | 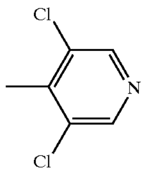 |
| 152 | H | single bond | | $CH_2CO_2CH_2C_6H_5$ | 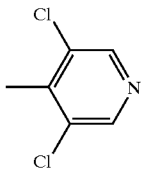 |
| 153 | H | single bond | | $CH_2CO_2CH_2CH_2C_6H_5$ | 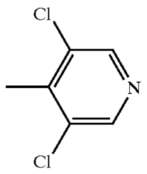 |

TABLE 4-continued
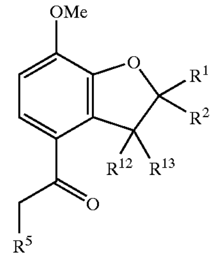
| Compd. No. | $R^1$ | $R^2$ | $R^{13}$ | $R^{12}$ | $R^5$ |
|---|---|---|---|---|---|
| 154 | H | single bond | | 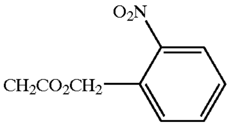 | 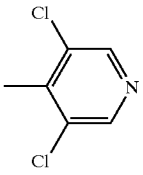 |
| 155 | H | single bond | | $CH_2CONHCH_2C_6H_5$ | 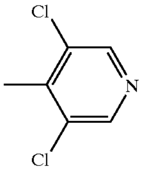 |
| 156 | H | single bond | | 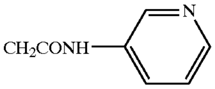 | 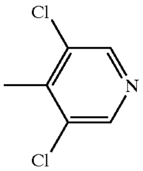 |
| 157 | H | single bond | | 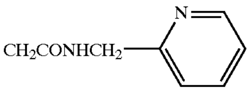 | 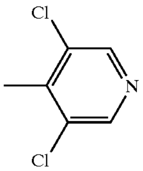 |
| 158 | H | single bond | | $CH_2CO_2Et$ | 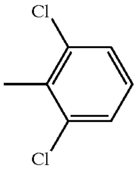 |
| 159 | H | single bond | | $CO_2Et$ | 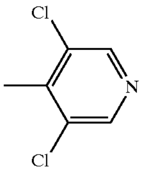 |
*In the Table, Et represents $C_2H_5$.
| | | | | | |
|---|---|---|---|---|---|
| 160 | 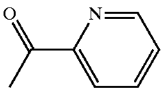 | single bond | | H | 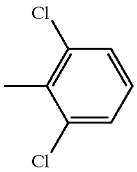 |

TABLE 4-continued
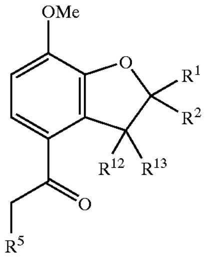
| Compd. No. | $R^1$ | $R^2$ | $R^{13}$ | $R^{12}$ | $R^5$ |
|---|---|---|---|---|---|
| 161 | 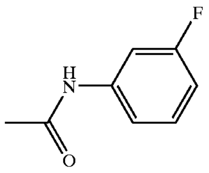 | single bond | | H | 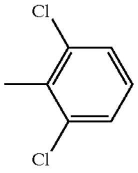 |
| 162 | 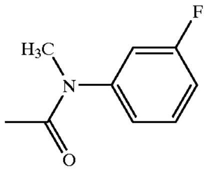 | single bond | | H | 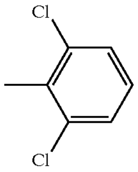 |
| 163 | $COC_6H_5$ | single bond | | H | 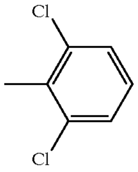 |
| 164 | $COC_6H_5$ | single bond | | H | 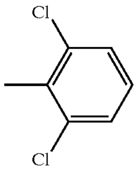 |
| 165 | $CONHC_6H_5$ | single bond | | H | 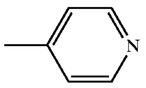 |
| 170 | H | H | H | $CH_2COCH_2$— 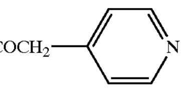 | 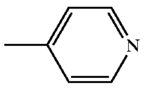 |
| 171 | H | H | H | $CH_2CO_2Et$ | 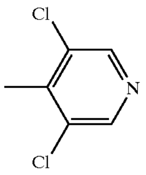 |
| 172 | H | H | H | $CH_2CO_2H$ | 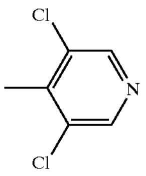 |

TABLE 4-continued
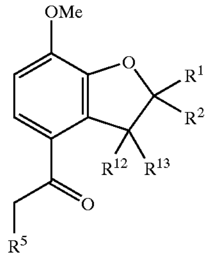
| Compd. No. | $R^1$ | $R^2$ | $R^{13}$ | $R^{12}$ | $R^5$ |
|---|---|---|---|---|---|
| 173 | H | H | H | $CH_2CO_2CH_2C_6H_5$ | 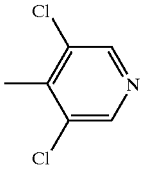 |
*In the Table, Et represents $C_2H_5$.
TABLE 5
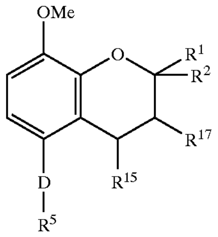
| Compd. No. | $R^1$ | $R^2$ | $R^{15}$ | $R^{17}$ | D | $R^5$ |
|---|---|---|---|---|---|---|
| 121 | Me | Me | single bond | | CONH | 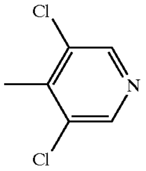 |
| 122 | Me | Me | H | H | CONH | 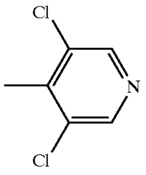 |
| 123 | $—(CH_2)_4—$ | | single bond | | CONH | 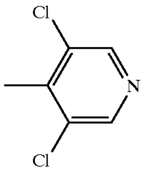 |
TABLE 5-continued
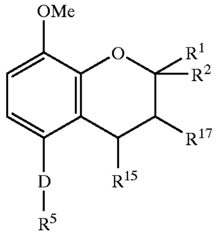
| Compd. No. | $R^1$ | $R^2$ | $R^{15}$ | $R^{17}$ | D | $R^5$ |
|---|---|---|---|---|---|---|
| 124 | $—(CH_2)_4—$ | | H | H | CONH | 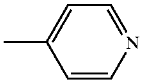 |
| 125 | $—(CH_2)_4—$ | | H | H | CH═CH | 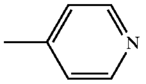 |
| 126 | $—(CH_2)_5—$ | | H | H | CH═CH | 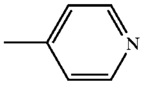 |

TABLE 5-continued
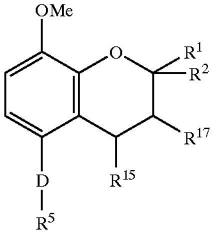
| Compd. No. | $R^1$ | $R^2$ | $R^{15}$ | $R^{17}$ | D | $R^5$ |
|---|---|---|---|---|---|---|
| 127 | $-(CH_2)_4-$ | | H | H | $COCH_2$ | 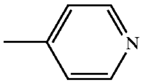 |
| 128 | $-(CH_2)_5-$ | | H | H | $COCH_2$ | 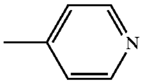 |
*In the Table, Me represents $CH_3$.
TABLE 6
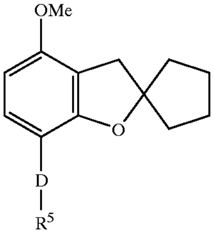
| Compd. No. | D | $R^5$ |
|---|---|---|
| 129 | CONH | 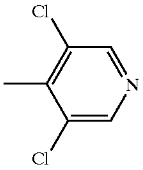 |
| 130 | CONH | 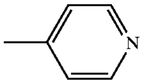 |
| 131 | CH═CH | 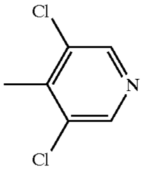 |
TABLE 6-continued
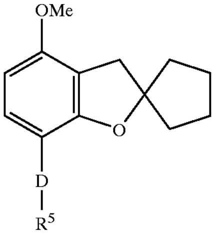
| Compd. No. | D | $R^5$ |
|---|---|---|
| 132 | $COCH_2$ | 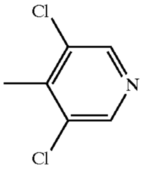 |
| 133 | $COCH_2$ | 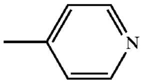 |
*In the Table, Me represents $CH_3$.
TABLE 7
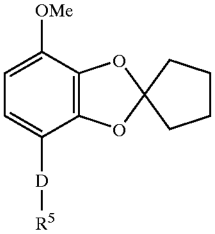
| Compd. No. | D | $R^5$ |
|---|---|---|
| 134 | CONH | 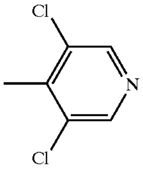 |
| 135 | CONH | 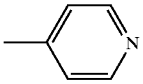 |
| 136 | $CH_2CH_2$ | 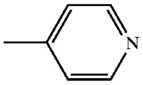 |
| 137 | $CHPhCH_2$ | 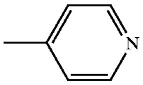 |
| 138 | CH═CH | 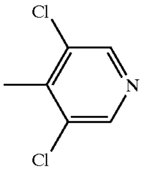 |

TABLE 7-continued
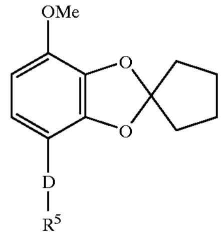
| Compd. No. | D | $R^5$ |
|---|---|---|
| 139 | CPh═CH | 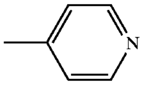 |
| 140 | $COCH_2$ | 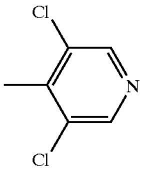 |
| 141 | $COCH_2$ | 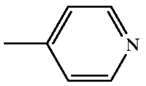 |
*In the Table, Me represents $CH_3$ and Ph represents $C_6H_5$, respectively.
TABLE 8
| Compd. No. | W |
|---|---|
| | 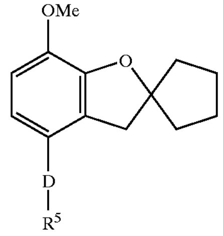 |
| 142 | 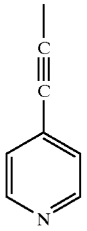 |
| 143 | 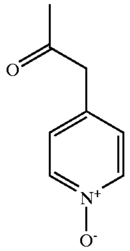 |
*In the Table, Me represents $CH_3$.
TABLE 8-continued
| Compd. No. | W |
|---|---|
| | 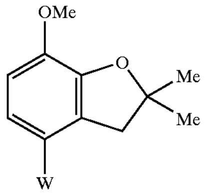 |
| 144 | 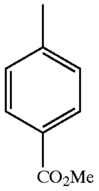 |
| 145 | 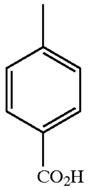 |
| 146 | 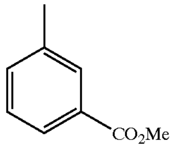 |
| 147 | 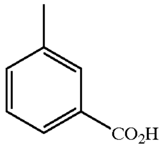 |
*In the Table, Me represents $CH_3$.
TABLE 9
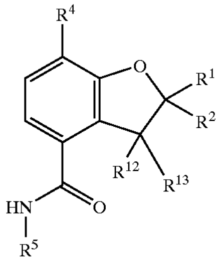
| Compd. No. | $R^1$ | $R^2$ | $R^{13}$ | $R^{12}$ | $R^4$ | $R^5$ |
|---|---|---|---|---|---|---|
| 166 | $COC_6H_5$ | single bond | | H | OMe | 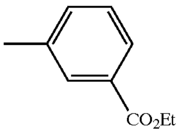 |

TABLE 9-continued

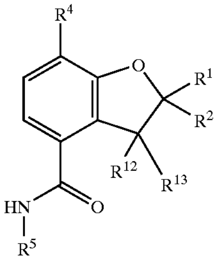

| Compd. No. | $R^1$ | $R^2$ | $R^{13}$ | $R^{12}$ | $R^4$ | $R^5$ |
|---|---|---|---|---|---|---|
| 167 | $COC_6H_5$ | single bond | | H | OMe | 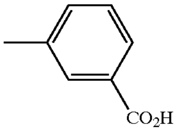 |
| 168 | $COC_6H_5$ | single bond | | H | OMe | 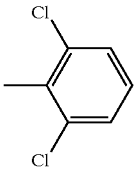 |
| 169 | $COC_6H_5$ | single bond | | H | OH | 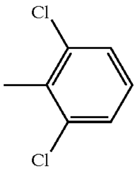 |

*In the Table, Me represents $CH_3$ and Et represents $C_2H_5$, respectively.

TABLE 10

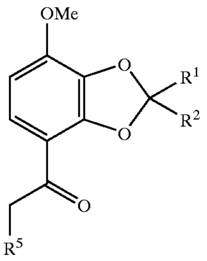

| Compd. No. | $R^1$ | $R^2$ | $R^5$ |
|---|---|---|---|
| 174 | H | H | 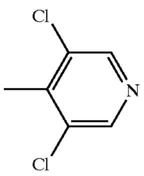 |

TABLE 10-continued

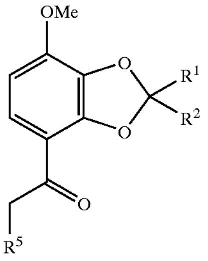

| Compd. No. | $R^1$ | $R^2$ | $R^5$ |
|---|---|---|---|
| 175 | Me | Me | 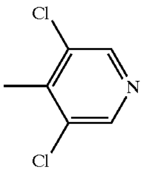 |
| 176 | Ph | Ph | 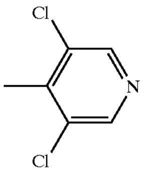 |
| 177 | $—(CH_2)_6—$ | | 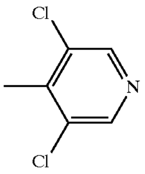 |

*In the Table, Me represents $CH_3$ and Ph represents $C_6H_5$, respectively.

TABLE 11

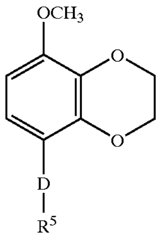

| Compd. No. | D | $R^5$ |
|---|---|---|
| 178 | $COCH_2$ | 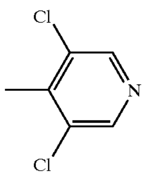 |

TABLE 11-continued
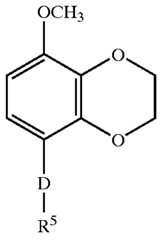
| Compd. No. | D | $R^5$ |
| --- | --- | --- |
| 179 | $COCH_2$ | 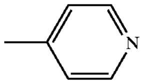 |
| 180 | $COCH_2$ | 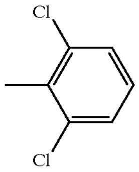 |
| 181 | CH=CH | 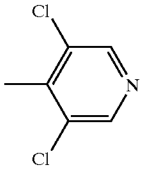 |
| 182 | $CH_2CH_2$ | 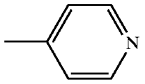 |
| 183 | CONH | 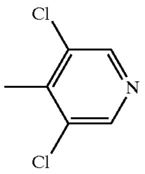 |
TABLE 11-continued
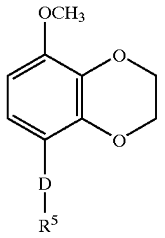
| Compd. No. | D | $R^5$ |
| --- | --- | --- |
| 184 | CONH | 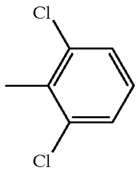 |
| 185 | CONH | 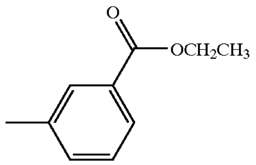 |
| 186 | CONH | 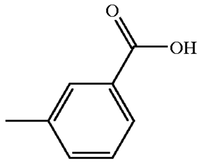 |
| 187 | single bond | 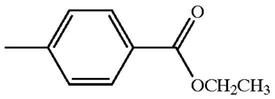 |
| 188 | single bond | 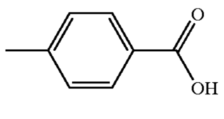 |

TABLE 12
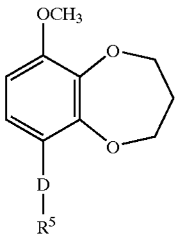
| Compd. No. | D | $R^5$ |
|---|---|---|
| 189 | $COCH_2$ | 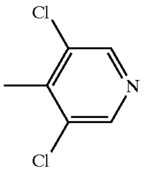 |
| 190 | $COCH_2$ | 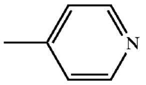 |
| 191 | CH=CH | 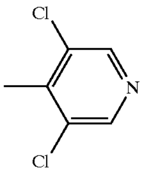 |
| 192 | $CH_2CH_2$ | 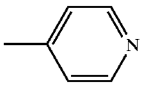 |
| 193 | CONH | 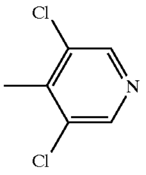 |
TABLE 13
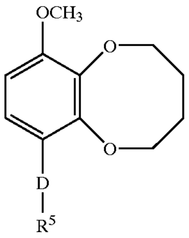
| Compd. No. | D | $R^5$ |
|---|---|---|
| 194 | $COCH_2$ | 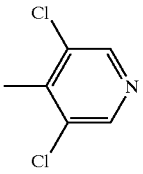 |
| 195 | $COCH_2$ | 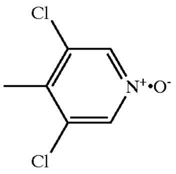 |
| 196 | CONH | 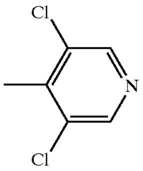 |
TABLE 14
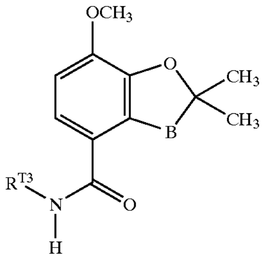
| Compound. No. | B | $R^{T3}$ |
|---|---|---|
| 197 | CH=CH | 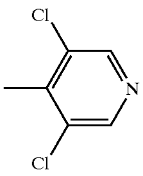 |

TABLE 14-continued
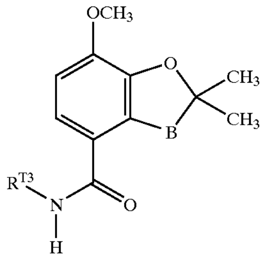
| Compound. No. | B | $R^{T3}$ |
|---|---|---|
| 198 | $(CH_2)_2$ | 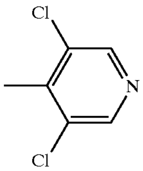 |
| 199 | O | 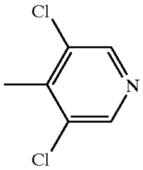 |
| 200 | O | 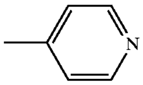 |
TABLE 15
(I)
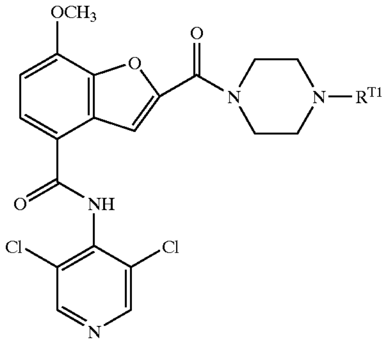
| Compd. No. | $R^{T1}$ |
|---|---|
| 201 | $CH_3$ |
| 202 | $CH_2CH_2OH$ |
TABLE 16
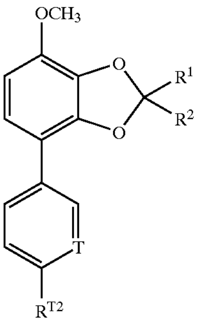
| Compd. No. | $R^1$ | $R^2$ | $R^{T2}$ | T |
|---|---|---|---|---|
| 203 | $-(CH_2)_4-$ | | COOH | N |
| 204 | $CH_3$ | $CH_3$ | COOH | CH |
| 205 | $-(CH_2)_4-$ | | $CH_3$ | N |
TABLE 17
(I)
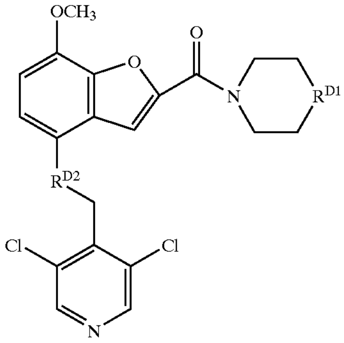
| Compd. No. | $R^{D2}$ | $R^{D1}$ |
|---|---|---|
| 206 | C=O | $N-CH_3$ |
| 207 | C=O | $N-CH_2CH_2OH$ |
| 208 | C=O | $N-CH_2CH_3$ |
| 209 | C=O | $N-CH(CH_3)CH_3$ |
| 210 | C=O | $N-CH_2CH_2OCH_2CH_3$ |
| 211 | $CH_2$ | $N-CH_3$ |
| 212 | $CH_2$ | $N-CH_2CH_2OH$ |

TABLE 18
(I)
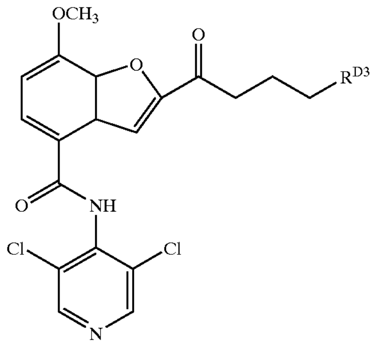
| Compd. No. | $R^{D3}$ |
|---|---|
| 213 | 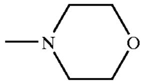 |
| 214 | 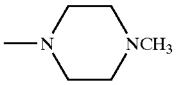 |
| 215 | —OH |
TABLE 19
(I)
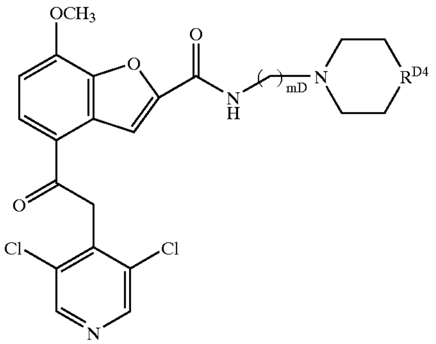
| Compd. No. | $R^{D4}$ | mD |
|---|---|---|
| 216 | O | 2 |
| 217 | $CH_2$ | 2 |
| 218 | N—$CH_3$ | 3 |
TABLE 20
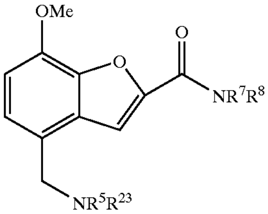
| Compd. No. | $NR^7R^8$ | $NR^5R^{23}$ |
|---|---|---|
| 219 | 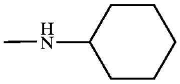 | 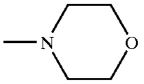 |
| 220 | 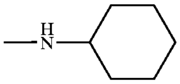 | 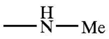 |
| 221 | 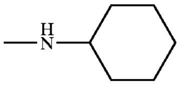 | 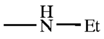 |
| 222 | 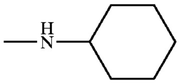 | 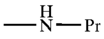 |
| 223 | 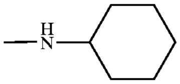 | 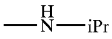 |

TABLE 20-continued
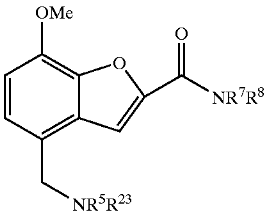
| Compd. No. | $NR^7R^8$ | $NR^5R^{23}$ |
|---|---|---|
| 224 | 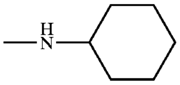 | 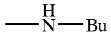 |
| 225 | 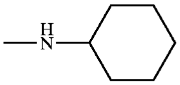 | 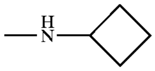 |
| 226 | 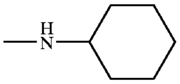 | 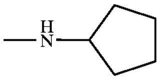 |
| 227 | 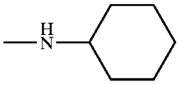 | 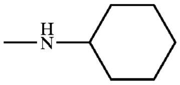 |
| 228 | 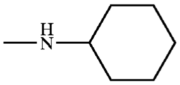 | 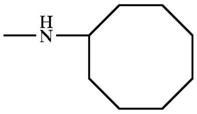 |
| 229 | 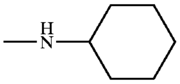 | 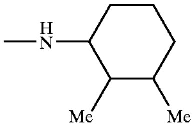 |
| 230 | 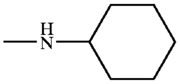 | 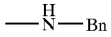 |
| 231 | 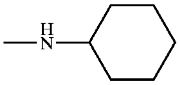 | 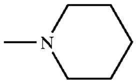 |
| 232 | 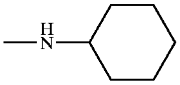 | 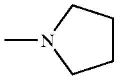 |
| 233 | 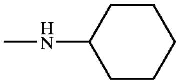 | 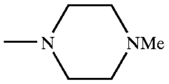 |
| 234 | 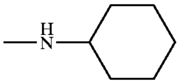 | 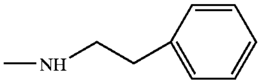 |
| 235 | 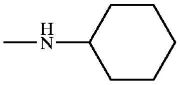 | 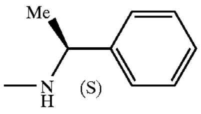 |

TABLE 20-continued
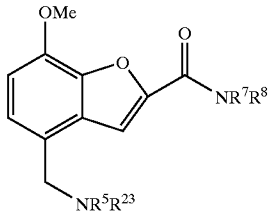
| Compd. No. | $NR^7R^8$ | $NR^5R^{23}$ |
| --- | --- | --- |
| 236 | 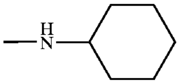 | 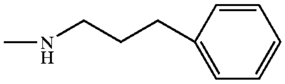 |
| 237 | 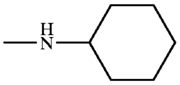 | 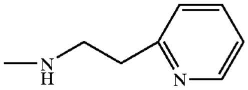 |
| 238 | 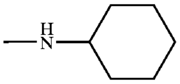 | 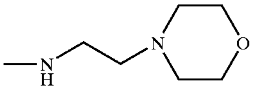 |
| 239 | 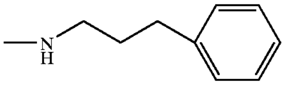 | 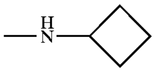 |
| 240 | 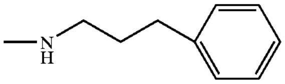 | 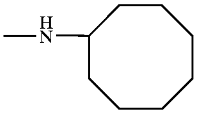 |
| 241 | 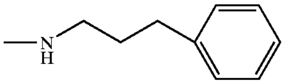 | 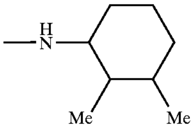 |
| 242 | 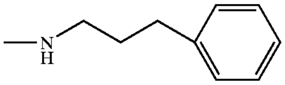 | 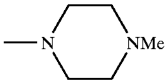 |
| 243 | 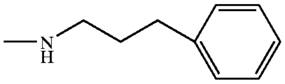 | 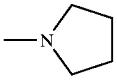 |
| 244 | 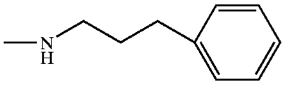 | 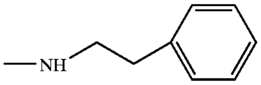 |
| 245 | 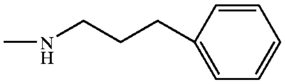 | 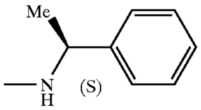 |
| 246 | 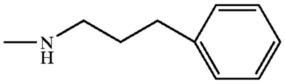 | 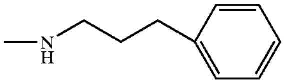 |
| 247 | 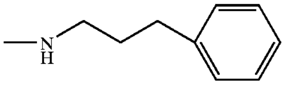 | 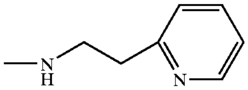 |

TABLE 20-continued
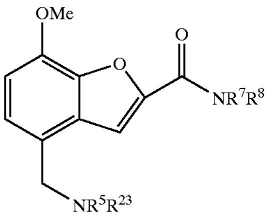
| Compd. No. | $NR^7R^8$ | $NR^5R^{23}$ |
|---|---|---|
| 248 | 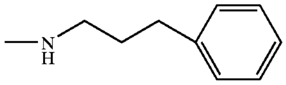 | 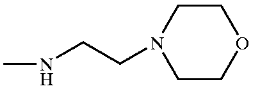 |
| 249 | 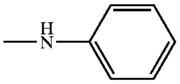 | 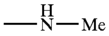 |
| 250 | 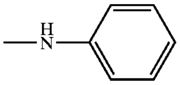 | 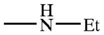 |
| 251 | 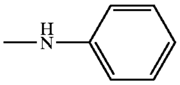 | 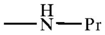 |
| 252 | 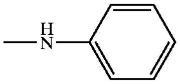 | 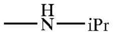 |
| 253 | 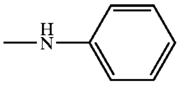 | 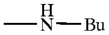 |
| 254 | 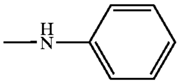 | 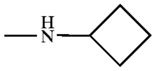 |
| 255 | 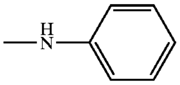 | 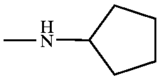 |
| 256 | 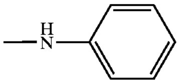 | 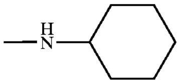 |
| 257 | 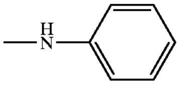 | 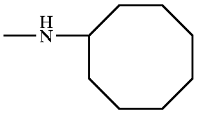 |
| 258 | 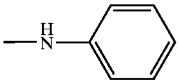 | 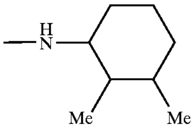 |
| 259 | 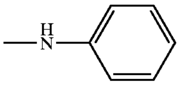 | 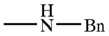 |

TABLE 20-continued
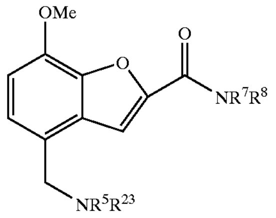
| Compd. No. | $NR^7R^8$ | $NR^5R^{23}$ |
|---|---|---|
| 260 | 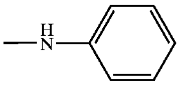 | 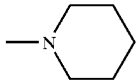 |
| 261 | 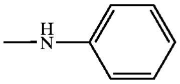 | 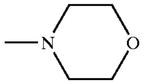 |
| 262 | 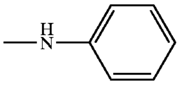 | 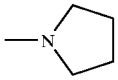 |
| 263 | 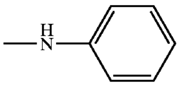 | 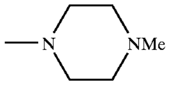 |
| 264 | 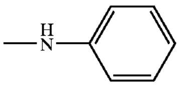 | 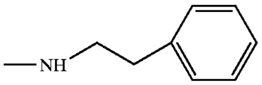 |
| 265 | 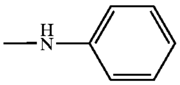 | 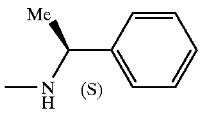 |
| 266 | 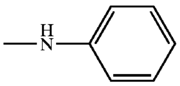 | 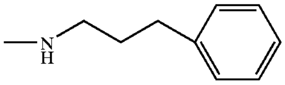 |
| 267 | 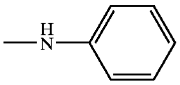 | 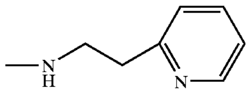 |
| 268 | 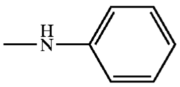 | 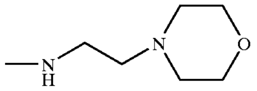 |
| 269 | —Bn | —NH—Me |
| 270 | —Bn | —NH—Et |
| 271 | —Bn | —NH—Pr |
| 272 | —Bn | —NH—iPr |
| 273 | —Bn | —NH—Bu |
| 274 | —Bn | 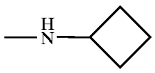 |

TABLE 20-continued
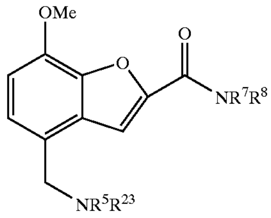
| Compd. No. | $NR^7R^8$ | $NR^5R^{23}$ |
|---|---|---|
| 275 | —Bn | 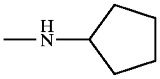 |
| 276 | —Bn | 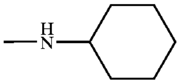 |
| 277 | —Bn | 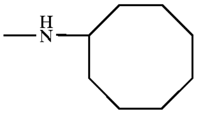 |
| 278 | —Bn | 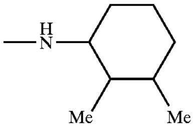 |
| 279 | —Bn | 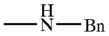 |
| 280 | —Bn | 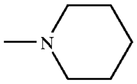 |
| 281 | —Bn | 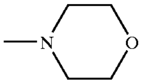 |
| 282 | —Bn | 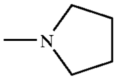 |
| 283 | —Bn | 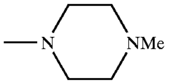 |
| 384 | —Bn | 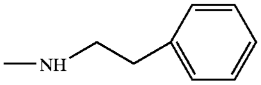 |
| 285 | —Bn | 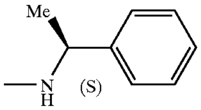 |
| 286 | —Bn | 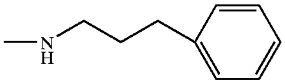 |
| 287 | —Bn | 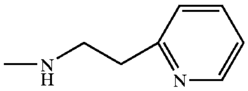 |

TABLE 20-continued
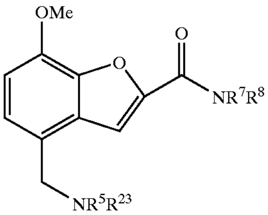
| Compd. No. | $NR^7R^8$ | $NR^5R^{23}$ |
|---|---|---|
| 288 | —Bn | 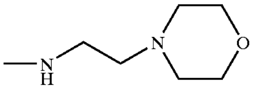 |
| 289 | 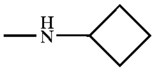 | 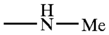 |
| 290 | 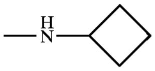 | 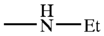 |
| 291 | 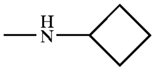 | 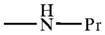 |
| 292 | 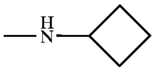 | 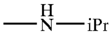 |
| 293 | 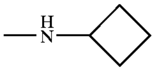 | 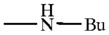 |
| 294 | 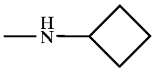 | 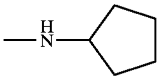 |
| 295 | 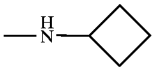 | 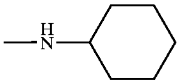 |
| 296 | 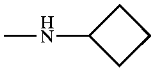 | 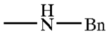 |
| 297 | 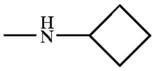 | 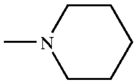 |
| 298 | 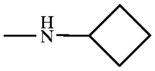 | 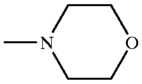 |
| 299 | 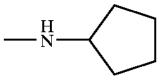 | 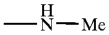 |
| 300 | 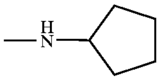 | 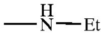 |
| 301 | 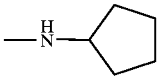 | 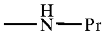 |

TABLE 20-continued
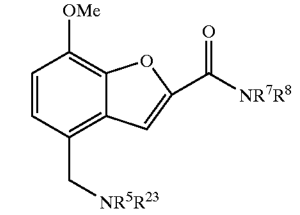
| Compd. No. | $NR^7R^8$ | $NR^5R^{23}$ |
|---|---|---|
| 302 | 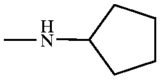 | 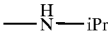 |
| 303 | 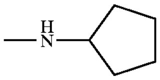 | 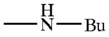 |
| 304 | 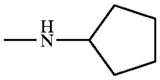 | 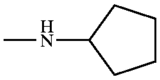 |
| 305 | 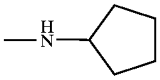 | 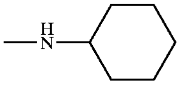 |
| 306 | 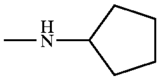 | 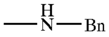 |
| 307 | 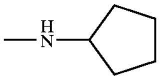 | 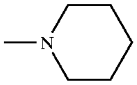 |
| 308 | 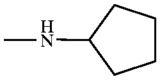 | 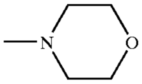 |
| 309 | 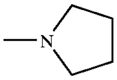 | 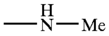 |
| 310 | 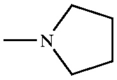 | 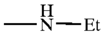 |
| 311 | 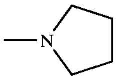 | 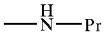 |
| 312 | 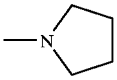 | 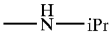 |
| 313 | 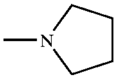 | 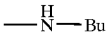 |
| 314 | 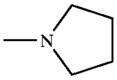 | 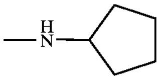 |

TABLE 20-continued
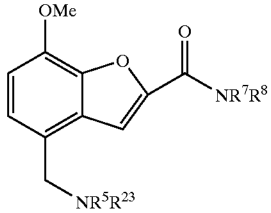
| Compd. No. | $NR^7R^8$ | $NR^5R^{23}$ |
|---|---|---|
| 315 | 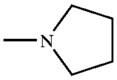 | 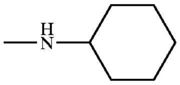 |
| 316 | 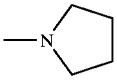 | 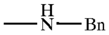 |
| 317 | 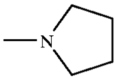 | 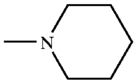 |
| 318 | 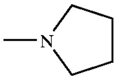 | 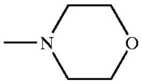 |
| 319 | 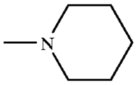 | 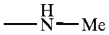 |
| 320 | 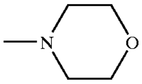 | 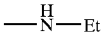 |
| 321 | 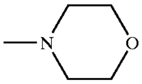 | 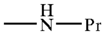 |
| 322 | 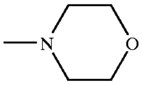 | 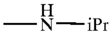 |
| 323 | 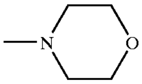 | 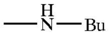 |
| 324 | 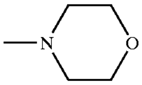 | 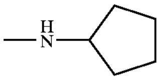 |
| 325 | 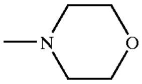 | 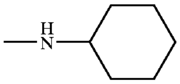 |
| 326 | 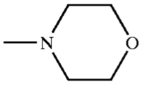 | 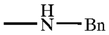 |
| 327 | 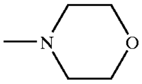 | 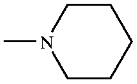 |

TABLE 20-continued
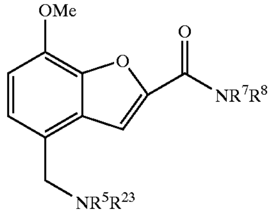
| Compd. No. | $NR^7R^8$ | $NR^5R^{23}$ |
|---|---|---|
| 328 | 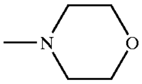 | 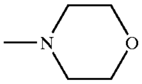 |
| 329 | 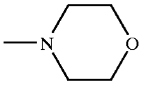 | 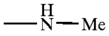 |
| 330 | 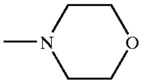 | 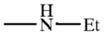 |
| 331 | 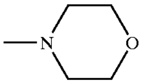 | 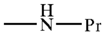 |
| 332 | 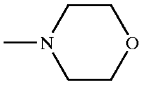 | 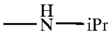 |
| 333 | 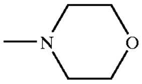 | 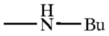 |
| 334 | 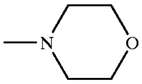 | 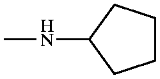 |
| 335 | 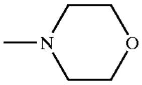 | 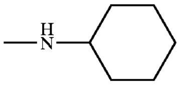 |
| 336 | 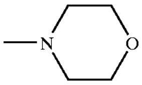 | 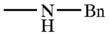 |
| 337 | 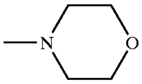 | 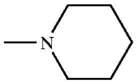 |
| 338 | 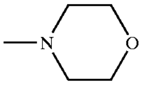 | 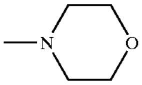 |
| 339 | 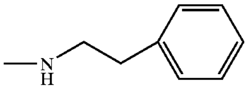 | 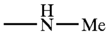 |
| 340 | 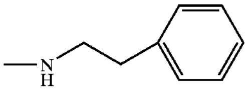 | 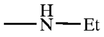 |

TABLE 20-continued
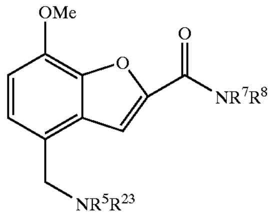
| Compd. No. | $NR^7R^8$ | $NR^5R^{23}$ |
|---|---|---|
| 341 | 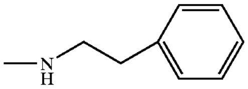 | 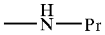 |
| 342 | 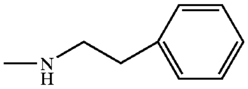 | 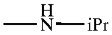 |
| 343 | 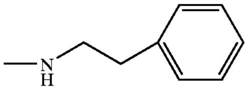 | 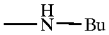 |
| 344 | 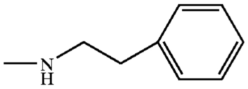 | 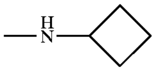 |
| 345 | 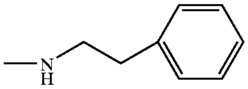 | 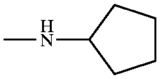 |
| 346 | 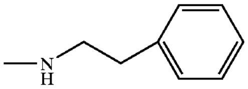 | 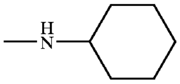 |
| 347 | 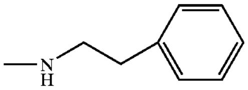 | 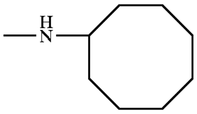 |
| 348 | 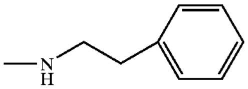 | 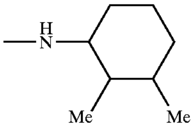 |
| 349 | 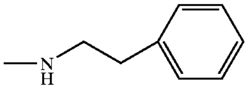 | 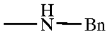 |
| 350 | 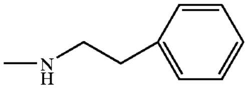 | 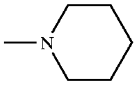 |
| 351 | 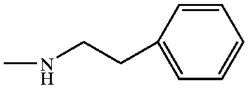 | 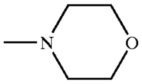 |
| 352 | 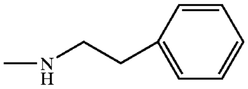 | 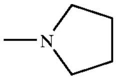 |

TABLE 20-continued
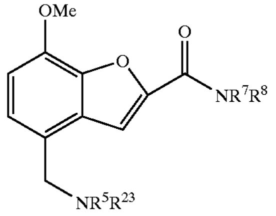
| Compd. No. | $NR^7R^8$ | $NR^5R^{23}$ |
|---|---|---|
| 353 | 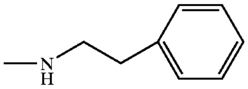 | 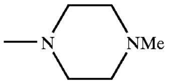 |
| 354 | 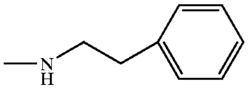 | 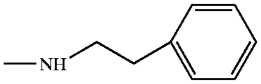 |
| 355 | 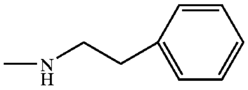 | 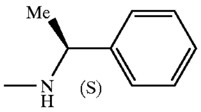 |
| 356 | 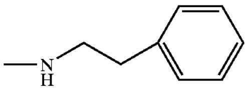 | 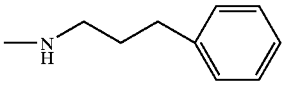 |
| 357 | 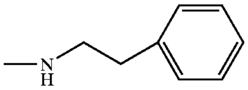 | 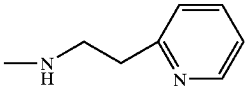 |
| 358 | 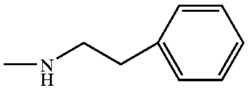 | 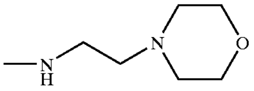 |
| 359 | 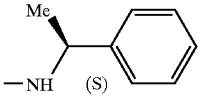 | 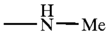 |
| 360 | 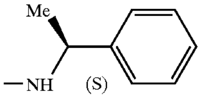 | 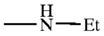 |
| 361 | 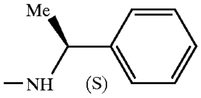 | 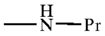 |
| 362 | 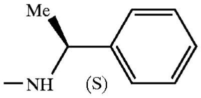 | 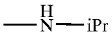 |
| 363 | 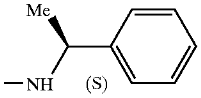 | 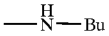 |

TABLE 20-continued
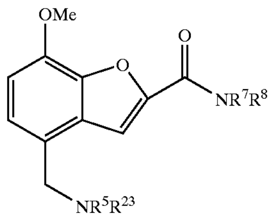
| Compd. No. | $NR^7R^8$ | $NR^5R^{23}$ |
|---|---|---|
| 364 | 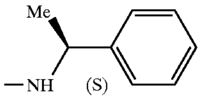 | 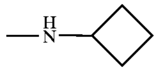 |
| 365 | 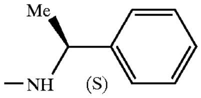 | 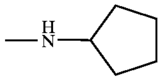 |
| 366 | 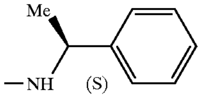 | 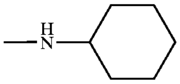 |
| 367 | 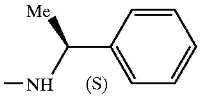 | 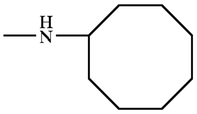 |
| 368 | 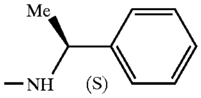 | 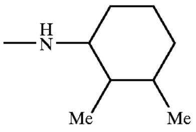 |
| 369 | 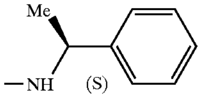 | 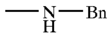 |
| 370 | 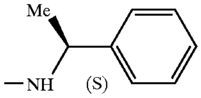 | 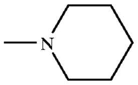 |
| 371 | 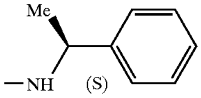 | 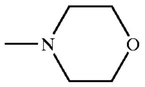 |
| 372 | 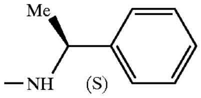 | 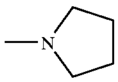 |
| 373 | 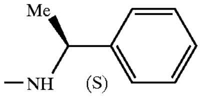 | 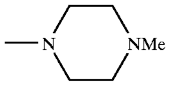 |
| 374 | 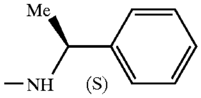 | 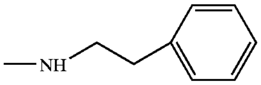 |

TABLE 20-continued
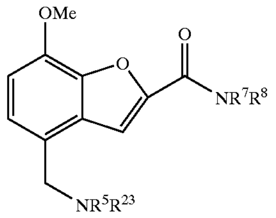
| Compd. No. | $NR^7R^8$ | $NR^5R^{23}$ |
| --- | --- | --- |
| 375 | 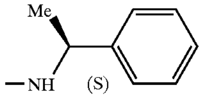 | 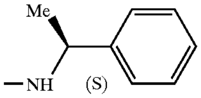 |
| 376 | 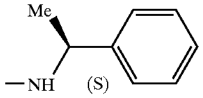 | 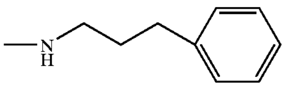 |
| 377 | 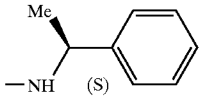 | 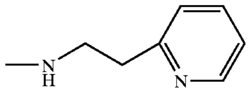 |
| 378 | 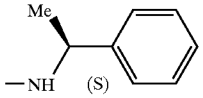 | 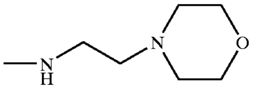 |
| 379 | 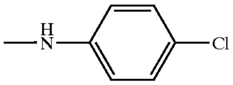 | 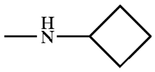 |
| 380 | 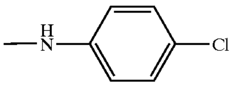 | 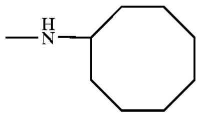 |
| 381 | 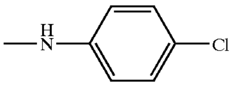 | 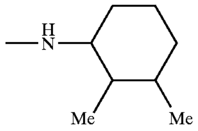 |
| 382 | 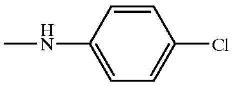 | 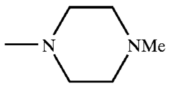 |
| 383 | 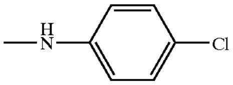 | 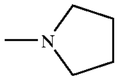 |
| 384 | 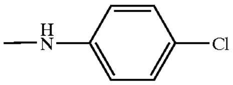 | 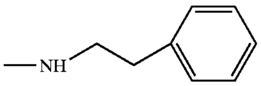 |
| 385 | 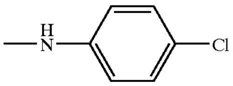 | 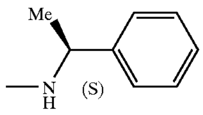 |

TABLE 20-continued
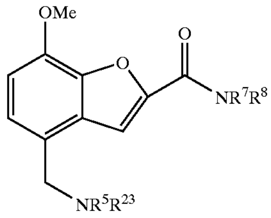
| Compd. No. | $NR^7R^8$ | $NR^5R^{23}$ |
|---|---|---|
| 386 | 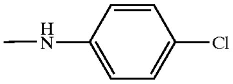 | 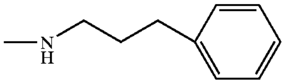 |
| 387 | 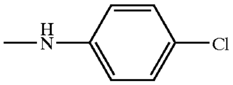 | 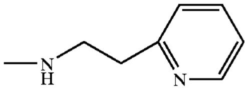 |
| 388 | 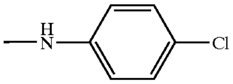 | 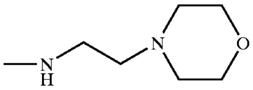 |
| 389 | 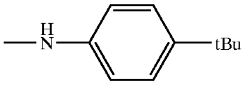 | 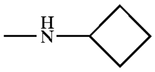 |
| 390 | 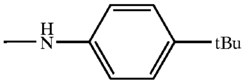 | 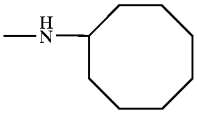 |
| 391 | 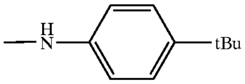 | 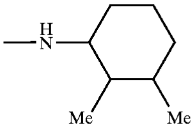 |
| 392 | 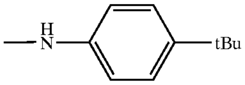 | 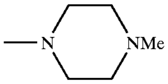 |
| 393 | 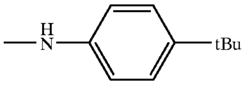 | 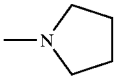 |
| 394 | 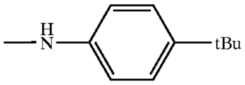 | 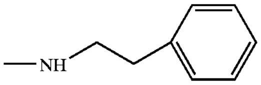 |
| 395 | 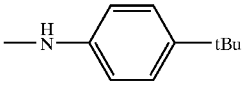 | 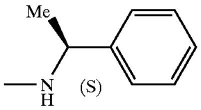 |
| 396 | 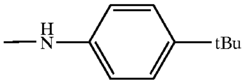 | 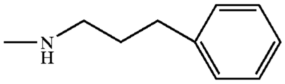 |
| 397 | 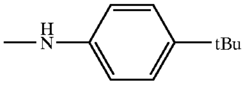 | 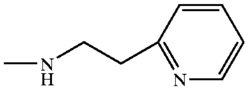 |

TABLE 20-continued
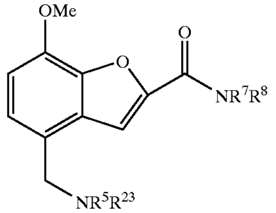
| Compd. No. | $NR^7R^8$ | $NR^5R^{23}$ |
|---|---|---|
| 398 | 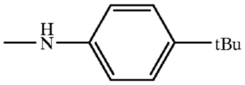 | 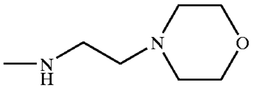 |
| 399 | 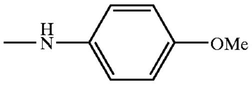 | 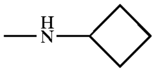 |
| 400 | 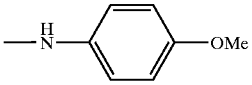 | 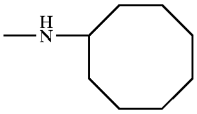 |
| 401 | 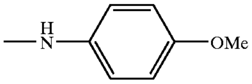 | 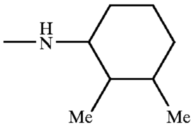 |
| 402 | 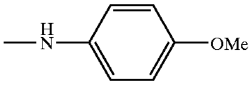 | 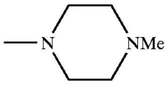 |
| 403 | 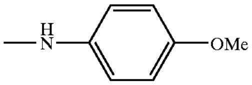 | 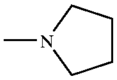 |
| 404 | 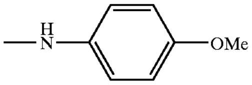 | 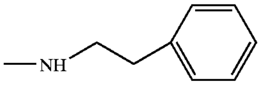 |
| 405 | 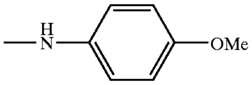 | 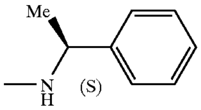 |
| 406 | 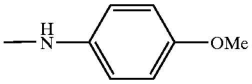 | 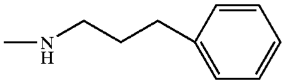 |
| 407 | 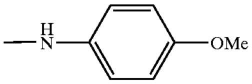 | 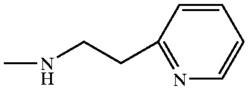 |
| 408 | 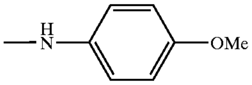 | 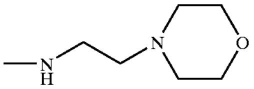 |

TABLE 20-continued
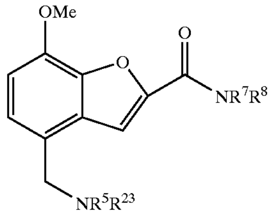
| Compd. No. | $NR^7R^8$ | $NR^5R^{23}$ |
|---|---|---|
| 409 | 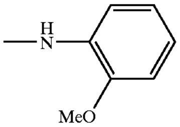 | 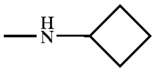 |
| 410 | 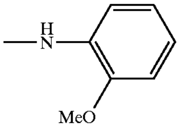 | 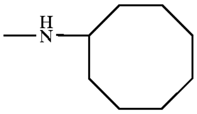 |
| 411 | 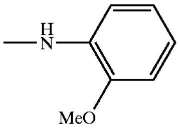 | 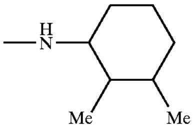 |
| 412 | 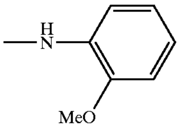 | 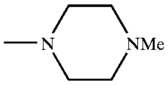 |
| 413 | 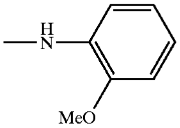 | 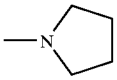 |
| 414 | 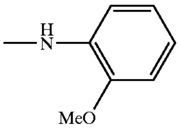 | 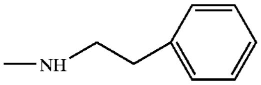 |
| 415 | 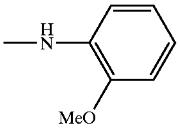 | 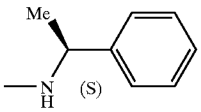 |
| 416 | 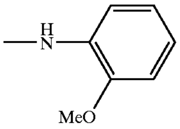 | 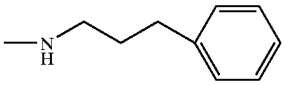 |
| 417 | 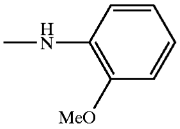 | 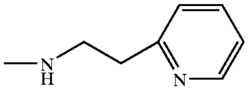 |

TABLE 20-continued

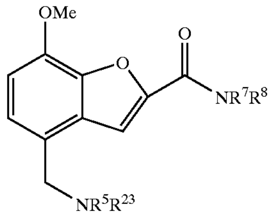

| Compd. No. | $NR^7R^8$ | $NR^5R^{23}$ |
|---|---|---|
| 418 | 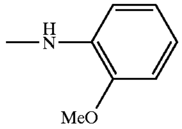 | 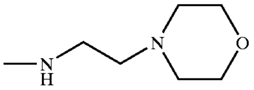 |

*In the Table, Me represents $CH_3$, Et represents $C_2H_5$, Pr represents $C_3H_7$, iPr represents $(CH_3)_2CH$, Bu represents $C_5H_{11}$, Bn represents $C_6H_5CH_2$.

The pharmacological activities of the representative Compounds (I) are described in more detail by Test Examples.

Test Example 1

Inhibition of the PDE IV Enzyme Derived from a Dog Trachea cAMP-specific phosphodiesterase (PDE IV) was purified from a dog tracheal smooth muscle according to the method of Torphy et al. [Molecular Pharmacol., 37, 206–214 (1990)]. The PDE activity was measured by the following two steps according to the method of Kincaid and Manganiello et al. [Method in Enzymology (J. D. Corbin and R. A. Jonson, Eds.), 199, 457–470 (1988)]. Using $[^3]$cAMP (at a final concentration of 1 $\mu$M) as a substrate, the reaction was carried out in a standard mixture containing N,N-bis(2-hydroxyethyl)-2-aminoethanesulfonic acid (50 mM, pH=7.2), $MgCl_2$ (1 mM), and soybean trypsin inhibitor (0.1 mg/ml). The reaction was initiated by adding the enzyme, followed by incubation at 30° C. for 10 to 30 minutes. After stopping the reaction with hydrochloric acid, the generated 5'-cAMP was completely converted to adenosine by 5'-nucleotidase.

The resultant was subjected to chromatography on DEAE-Sephadex A-25, and radio activity of the eluted $[^3H]$ adenosine was counted using a scintillation counter. Each of the test drugs was dissolved in DMSO (final concentration 1.7%) and then added to the mixture.

The results are shown in Table 21.

TABLE 21

| Compound No. | Enzyme Inhibitory Activity (%, $10^{-6}$ M) |
|---|---|
| 2 | 77 |
| 3 | 75 |
| 4 | 53 |
| 5 | 85 |
| 6 | 66 |
| 7 | 37 |
| 8 | 5 |
| 9 | 22 |
| 11 | 6 |
| 12 | 8 |
| 13 | 94 |
| 15 | 75 |
| 16 | 24 |
| 17 | 63 |
| 18 | 81 |
| 19 | 87 |
| 20 | 80 |
| 21 | 84 |
| 22 | 85 |
| 24 | 80 |
| 25 | 84 |
| 26 | 79 |
| 27 | 75 |
| 28 | 83 |
| 29 | 85 |
| 30 | 85 |
| 31 | 89 |
| 32 | 81 |
| 33 | 71 |
| 34 | 100 |
| 36 | 87 |
| 38 | 89 |
| 39 | 77 |
| 40 | 89 |
| 41 | 58 |
| 42 | 73 |
| 43 | 62 |
| 45 | 74 |
| 47 | 68 |
| 48 | 41 |
| 49 | 40 |
| 50 | 69 |
| 51 | 67 |
| 52 | 86 |
| 53 | 84 |
| 54 | 81 |
| 55 | 86 |
| 59 | 24 |
| 60A | 15 |
| 60B | 4 |
| 62 | 63 |
| 63 | 85 |
| 64 | 78 |
| 65 | 74 |
| 66 | 49 |
| 68 | 80 |
| 70 | 68 |
| 71 | 87 |
| 74 | 73 |
| 75 | 72 |
| 76 | 93 |

TABLE 21-continued

| Compound No. | Enzyme Inhibitory Activity (%, $10^{-6}$ M) |
|---|---|
| 77 | 87 |
| 79 | 45 |
| 80 | 17 |
| 81 | 56 |
| 83 | 89 |
| 85 | 69 |
| 87 | 61 |
| 89 | 33 |
| 93 | 23 |
| 97 | 92 |
| 98 | 85 |
| 99 | 91 |
| 103 | 88 |
| 104 | 48 |
| 105 | 66 |
| 107 | 63 |
| 109 | 68 |
| 110 | 80 |
| 111 | 69 |
| 115 | 85 |
| 117 | 87 |
| 118 | 80 |
| 121 | 85 |
| 122 | 92 |
| 124 | 57 |
| 125 | 71 |
| 126 | 58 |
| 127 | 70 |
| 128 | 62 |
| 131 | 51 |
| 132 | 66 |
| 136 | 75 |
| 137 | 61 |
| 139 | 54 |
| 142 | 76 |

Test Example 2

Recombinant Human PDE4A Assay

The CDNA encoding phosphodiesterase 4A was isolated from human testis CDNA library. It predicts a truncated protein lacking 223 amino acids at the N-terminus from the sequence previously reported by Bolger, G., et.al. [Mol. Cell. Biol. 13, 6558–6571 (1993)]. The *E. coli* expression plasmid expressing this recombinant protein was constructed, and the expressed protein was partially purified. PDE activity was measured by the two-step procedure as previously described by Kincaid, R., L. and Manganiello, V., C. [Method. Enzymol. 159, 457–470 (1988)]. The reaction mixture contained (final concentrations) 50 mmol/L N, N-bis(2-hydroxyethyl)-2-aminoethansulfonic acid (pH 7.2), 1 mmol/L $MgCl_2$, 0.1 mg/mL Soybean trypsin inhibitor, and 1 mmol/L [$^3$H]cAMP. The reactions were initiated by addition of the enzymes, incubated at 30° C. for 10 to 30 minutes, depending on the activity of the enzymes, and terminated by addition of hydrochloric acid. The product, [$^3$H]5'-AMP was completely converted by snake venom 5'-nucleotidase, and resulted [$^3$H]adenosine was separeted by DEAE-Sephadex A-25 column. Radioacitivity of eluted adenosine was measured using scintillation counter. All compounds tested were dissolved in DMSO at several different concentrations, and added to reaction mixtures at 1.7 v/v %.

In this study, PDE4A activity was reduced by more than 50% by addition of 10 mmol/L of the compounds tested.

The results are shown in Table 22.

TABLE 22

| Compound No. | Enzyme Inhibitory Activity (%, $10^{-7}$ M) |
|---|---|
| 35 | 100 |
| 84 | 98 |
| 100 | 99 |
| 101 | 100 |
| 102 | 95 |
| 114 | 100 |
| 123 | 87 |
| 134 | 100 |
| 138 | 100 |
| 140 | 100 |
| 141 | 76 |
| 153 | 94 |
| 154 | 92 |
| 155 | 96 |
| 156 | 90 |
| 157 | 89 |
| 159 | 99 |
| 160 | 91 |
| 161 | 87 |
| 163 | 96 |
| 165 | 64 |
| 168 | 96 |
| 177 | 93 |
| 189 | 84 |
| 191 | 84 |
| 194 | 92 |
| 195 | 93 |
| 199 | 57 |

Test Example 3

Suppression of Passive Suhults-Dale Response in Guinea Pig Bronchial Smooth Muscle.

For passive sensitization, rabbit anti-ovalbumin serum prepared by the method of Kohda et al. [Nichiyakurishi, 66, 237 (1970)] was peritoneally administered to male Hartley guinea pigs weighing 350 to 500 g, and 24 hours later the tracheae thereof were removed to be used for the experiment. Zig-zag strips were prepared from the tracheae in accordance with the method of Emmerson and Mackay [J. Pharm. Pharmacol., 31, 798 (1979)], and they were suspended in a Krebs-Henseleit solution with aeration of a mixture of 95% oxygen and 5% carbon dioxide at 37° C. After stabilizing for approximately one hour, ovalbumin, as the antigen, was added to the mixture (at a final concentration of 1 $\mu$m/ml), and the constriction of the muscle was recorded by a recorder (TYPE 3066; Yokokawa Hokushin Denki) via an isotonic transducer (TD-112S; Nippon Koden). A test compound was cumulatively added to the mixture after the constriction had reached the plateau, and the relaxation ratio was determined. The concentration ($IC_{50}$) causing 50% relaxation was calculated by linear regression analysis. The $IC_{50}$ value of Compound 68 of the present invention was 1.6 $\mu$M.

Test Example 4

Suppression of Histamine-Induced Bronchoconstriction Response in Guinea Pig

This test was carried out by a modified Konzett and Rossler method. Under anesthesia with urethane (1.2 g/kg, ip), male Hartley guinea pigs (body weight: 500 to 600 g) were fixed on plates by strings. After undertaking a tracheotomy, cannulae were inserted to the tracheae, right carotid arteries, and left cervical veins. The spontaneous respiration of the guinea pigs was stopped by the administration of gallamie (10 mg/kg) from the left cervical veins via the cannulae. The cannulae inserted into the tracheae were connected to a bronchospasm transducer (Ugo Basile) and a respirator (TB-101, Takashima-shoten, 60 to 70 strokes/minutes, output: 5 cc) and the air overflow volume was recorded by a polygraph (RM-45, Nippon Koden) to measure the amount of bronchoconstriction. For measuring blood pressure, the cannulae inserted in the right carotid arteries were connected to a blood-pressure transducer. Constant bronchoconstriction occurred when histamine (10 $\mu$g/kg, iv) was administered at 3 minutes intervals, and the induced bronchoconstriction was used as the control. A test compound was intravenously administered, and one minute later histamine (10 $\mu$g/kg, iv) was administered. The test compound was cumulatively administered at 5 minutes intervals, and the bronchoconstriction in control and that after the administration of the test compound was compared.

In this test, the $ID_{50}$ value (50% inhibitory dose) of Compound 68 was 0.076 mg/kg in the case of intravenous administration.

Test Example 5

Effect on Anaphylactic Bronchoconstriction Response

For passive sensitization, 1 ml of rabbit anti-ovalbumine serum was peritoneally administered to male Hartley guinea pigs, and 16 to 24 hours later, ovalbumine was intravenously administered as the antigen. The induced anaphylactic bronchoconstriction was measured by the modified Konzett and Rossler method. Each of the tracheal cannulae was completely closed at the end of the measurement and the measured constriction was defined as the maximum constriction. Changes in the constriction were measured as percentage in the maximum constriction. The area under the curve (AUC) indicating the strength of the response was calculated by an image analyzer (MCID system, Imaging Research Company). The test compound was orally administered one hour before the antigen administration, and the $ID_{50}$ value of each drug was calculated from the AUC suppression ratio by linear regression analysis.

In this test, the $ID_{50}$ value (50% inhibitory dose) of Compound 100 was 0.53 mg/kg by oral administration.

Test Example 6

Suppression effect on TNF α production in the LPS induced mouse sepsis model Lipopolysaccharide (LPS, DIFCO Laboratories) was dissolved in physiological saline to make a final concentration of 0.2 mg/ml. The resulting solution was administered intravenously to the tail of Balb/c male mice (7-week-old) (Charls River Japan Co.) at 200 $\mu$l per 20 g body weight of 5 to 6 mice/group. One hour after administration, blood was drawn from a fundus oculi vein of each mouse to obtain serum. Each sample of the test compound was dissolved or suspended in a 0.5% methyl cellulose solution to make a final concentration of 1 mg/ml, and then, administered orally to the mice at 200 $\mu$l per 20 g body weight 90 min. before the administration of LPS. The concentration of TNF a in serum was measured by enzyme-linked immunosorbent assay (ELISA method) as follows: 4 mg/ml anti-mouse TNF a monoclonal antibody (Pharmingen Inc.) diluted with a phosphate buffer solution (PBS) was added to a 96-well microtiter plate (Nalge Nunc International immuno-plate <MaxiSorp=) at 50 ml/well; allowed to stand at 4° C. for 12 hours for coating; mixed with 200 ml/well of a phosphate buffer solution containing 1% bovine serum albumin (BSA) (1% BSA-PBS); allowed to stand at room temperature for 1 hour to block the non-specific binding; washed with phosphate buffer solution; mixed with 100 ml/well of the subject serum diluted two-fold with 1% BSA-PBS; and allowed to stand at room temperature for 2 hours. Furthermore, recombinant mouse TNF α (Genzyme Corp.) diluted with 1% BSA-PBS was similarly treated and used as a standard substance. These plates were washed three times with PBS (0.05% Tween-PBS) containing 0.05% polyoxyethylenesorbitan monolaurate (Tween 20, Wako Pure Chemical Industries, Ltd.), mixed with 50 ml/well of biotin-labelled anti-mouse TNF α monoclonal antibody (Method A: Pharmingen Inc.; Method B: Genzyme Corp) diluted with 1% BSA-PBS to make a concentration of 1 mg/ml, allowed to stand at room temperature for 1 hour, washed three times with 0.05% Tween-PBS, mixed with 100 ml/well of horseradish peroxidase avidin D (Vector Laboratories Inc.) diluted four-thousand-fold with 1% BSA-PBS, and allowed to stand at room temperature for 30 min. Finally, these plates were washed three times with 0.05% Tween-PBS, and mixed with 100 ml/well of 3,3',5,5'-tetramethylbenzidine. After color development, the reaction was stopped by adding 100 ml/well of 10% sulfuric acid solution, and then, the absorbance at 450 nm was measured. The concentration of TNF α in serum was calculated from a calibration curve.

The rate of suppression of each test compound on TNF α production was obtained from the following formula:

$$\text{Suppression rate}=(A-B)/A,$$

wherein A is the TNF α concentration of the control group and B is the TNF α concentration of the experimental group.

In the above formula, the TNF α concentration of the control group is defined as the value obtained in the absence of the test compound (0.5% methyl cellulose solution alone).

Employed as the reference compounds were 7-methoxy-4-[1-oxo-2-(4-pyridyl)ethyl]-spiro[2,3-dihydrobenzofuran-2,1'-cyclopentane] hydrochloride (disclosed in Example 100 of Japanese Patent Laid-Open No. 8-836624 and hereinafter referred to as Compound RA) having the formula (RA) and 2-benzoyl-4-(3,5-dichloro-4-pyridyl)aminocarbonyl)-7-methoxybenzofuran (disclosed in Example 35 of Japanese Patent Laid-Open No. 8-534708 and hereinafter referred to as Compound RB) having the formula (RB):

(RA)

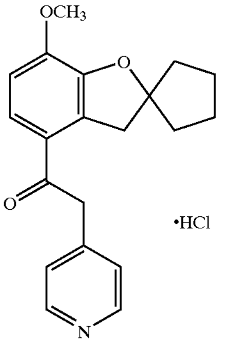

-continued

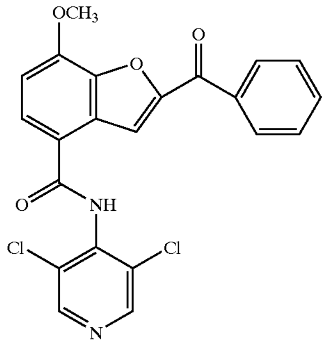

(RB)

Table 23 shows the results.

TABLE 23

| Compound | dose (mg/kg) | Suppression rate (%) |
|---|---|---|
| (Method A) | | |
| 201 | 10 | 70 |
| 202 | 10 | 92 |
| RA | 10 | 81 |
| RB | 10 | 48 |
| 203 | 10 | 100 |
| 204 | 10 | 79 |
| 205 | 10 | 79 |
| RA | 10 | 81 |
| (Method B) | | |
| 206 | 30 | 65 |
| 207 | 30 | 65 |
| RA | 30 | 81 |
| RB | 30 | 30 |
| 213 | 30 | 65 |
| 214 | 30 | 65 |
| (Method A) | | |
| 216 | 10 | 75 |

Test Example 7

Effect on vomiting induction in male Sunkus murinus

Five to fifteen male Sunkus murinus per group weighing approximately 60 g were used for the test. According to the method of Matsumoto, et. al. [Japan J. Pharmacol., 48, 303 (1988)], Sunkus murinus were placed separately into metal wire cages (width 15 cm×length 21 cm×height 15 cm). Each sample of the test compound was suspened in a 0.5% Tween 80 physiological saline solution and administered intraperitoneally (i.p.) at a dose of 10 ml/kg. The animals were observed for 1 hour after administration of the test compound to count the vomiting number. In the group that was administered the test-compound, the results are represented as the number of vomiting animals/the number of experimental animals. Compound RA was employed as a reference compound. Table 24 shows the results.

TABLE 24

| Compound | dose (mg/kg) | Number of vomiting animals/ Number of experimental animals |
|---|---|---|
| 201 | 10 | 0/5 |
| 202 | 10 | 0/5 |
| RA | 10 | 5/5 |
| RB | 10 | 0/5 |
| 203 | 10 | 1/5 |
| 204 | 10 | 2/5 |
| 205 | 10 | 0/5 |
| RA | 10 | 5/5 |
| 206 | 10 | 0/5 |
| 207 | 10 | 0/5 |
| RA | 10 | 5/5 |
| RB | 10 | 0/5 |
| 213 | 10 | 0/5 |
| 214 | 10 | 3/5 |
| 216 | 10 | 0/5 |

As is shown in Tables 23 and 24, the suppression effect of Compounds 201 to 205 of the present invention on the production of TNF α, which activates the inflammatory leukocytes, is stronger than that of Compound RB. In addition, Compounds of the present invention are superior to Compound RA in that they reduce vomiting which is a general side effect of PDE IV inhibitor.

Test Example 8

Effect on neutrophil and Eosinophil Accumulation in BN Rats

The Howell et al's method (Pulmonary Pharmacology, 8, 83–59 (1995)) was partly modified and used for the active sensitization and the antigen exposure.

Oval albumin (OA) (1 mg) and aluminium hydroxide (200 mg) were subcutaneously injected into male Brown-Norway rats (6 week-age, Nippon Charles River), to which were intra abdominally administered dead cells of *Bordetella pertussis* for the active sensitization of the rats. After 14 days, the rats were put into a plastic chamber (30×50×30 cm), and left to inspire a 1% (w/v) OA solution for 10 minutes for antigen induction. For the inspiration, used was an ultrasonic nebulizer (NE-U12, by Omron, Tokyo).

The test compound was suspended in 0.5% methyl cellulose, and orally administered (p.o.) to the rats one hour prior to the antigen challenge. The group of the rats to which 0.5% methyl cellulose was administered and which were left to inspire OA was referred to as OA Group, while the group of the rats which were left to inspire a physiological saline solution in place of OA was referred to as Saline Group.

After 24 hours from the antigen induction, bronchoalveolar lavage (BAL) was performed. Briefly, the rats were anesthetized with pentobarbital (100 mg/kg, i.p.), to which was applied a physiological saline solution (37° C., 4 ml) via a tracheal cannula, using a disposable syringe (5 ml Terumo Syringe, by Terumo, Tokyo), and recovered after about 15 seconds. This operation was repeated two times to obtain bronchoalveolar lavage fluid (BALF). This BALF was centrifuged at 950 rpm for 10 minutes at 4° C., and the precipitated cells were suspended in a physiological saline solution (1 ml). Then, the number of all leukocytes existing in the resulting suspension was counted, using an automatic leukocyte counter (Celltac α MEK-6158, by Nippon Koden, Tokyo). On the other hand, smears of the cells were prepared, using Cytospin 3 (by Shandon, Pittsburgh, USA), and stained with Wright-Giemsa. Those cells of 500 were observed with an optical microscope to count eosinophils (Eos), neutrophiles (Neu), lymphocytes (Lym), macrophages (Mac) and other cells (Oth), from which were obtained the proportions of those cells. The data were multiplied by the number of all leukocytes to obtain the actual numbers of those cells in BALF.

In this experiment, Compound 216 exhibited 100% inhibiting activity against eosinophils and 92% inhibiting activity against neutrophils, at a dose of 30 mg/kg.

Although Compound (I) or pharmaceutically acceptable salts thereof may be administered as they are, it is usually desirable to provide them in the form of various pharmaceutical preparations. Such pharmaceutical preparations may be used for animals and human beings.

The pharmaceutical preparations in accordance with the present invention may contain Compound (I) or a pharmaceutically acceptable salt thereof, as an active ingredient, either solely or as a mixture with other therapeutically effective components. The pharmaceutical preparations may be prepared by any means which are well known in the technical field of pharmaceutics after mixing the active ingredient with one or more pharmaceutically acceptable carriers.

It is desired to use the administration route which is the most effective in therapy such as oral route or parenteral route which includes intrabuccal, intratracheal, intrarectal, subcutaneous, intramuscular, and intravenous administrations.

Examples of the dosage form are nebulae, capsules, tablets, granules, syrups, emulsions, suppositories, injections, ointments, and tapes.

Liquid preparations suitable for oral administration such as emulsions and syrups can be prepared using water; sugars such as sucrose, sorbitol, and fructose; glycols such as polyethylene glycol and propylene glycol; oils such as sesame oil, olive oil, and soybean oil; preservatives such as p-hydroxybenzoate; flavors such as strawberry and peppermint; and the like. Capsules, tablets, powders, granules, and the like can be prepared using excipients such as lactose, glucose, sucrose, and mannitol; disintegrators such as starch and sodium alginate; lubricants such as magnesium stearate and talc; binders such as polyvinyl alcohol, hydroxypropyl cellulose, and gelatin; surfactants such as fatty acid esters; plasticizers such as glycerin; and the like.

Preparations suitable for parenteral administration comprise sterilized aqueous preparations of the active compound which are preferably isotonic to the blood of the patient. For example, a solution for injection is prepared using a carrier such as a salt solution, a glucose solution, or a mixture of a salt solution and a glucose solution. Preparations for intrarectal administration are prepared using a carrier such as cacao fat, hydrogenated fat, or a hydrogenated carboxylic acid, and provided as suppositories. Nebulae are prepared using an active compound per se or with carriers which can disperse the active compound as fine particles to facilitate absorption without stimulating oral or respiratory mucosa. Practical examples of the carrier are lactose and glycerin. Preparations such as aerosols and dry powders can be used depending upon the properties of the active compound and the employed carriers.

These parenteral preparations may also contain one or more auxiliary components selected from diluents, flavors, preservatives, excipients, disintegrators, lubricants, binders, surfactants, and plasticizers, all of which are mentioned in the above oral preparations.

The effective dose and the administration schedule of Compounds (I) or pharmaceutically acceptable salts thereof may vary depending upon the administration route, age and body weight of a patient, and the type or degree of the disease to be treated, but usually, in the case of oral administration, the effective compound is administered in a dose of 0.01 mg to 1 g, preferably, 0.05 to 50 mg/person/day at one time or in several parts. In the case of parenteral administration such as intravenous injection, the effective compound is administered in a dose of 0.001 to 100 mg, preferably, 0.01 to 10 mg/person/day at one time or in several parts. These doses should, however, vary depending upon various conditions as given above.

Certain embodiments of the present invention are illustrated in the following examples and reference examples.

BEST MODE FOR CARRYING OUT THE INVENTION

EXAMPLE 1

4-[(3,5-Dichloro-4-pyridyl)aminocarbonyl]-7-methoxy-2,3-dihydrobenzofuran (Compound 1)

A mixture of Compound IIw (0.61 g) obtained in Reference Example 23, thionyl chloride (3.6 ml), and dichloromethane (3.6 ml) was heated under reflux for 40 minutes. After being allowed to stand for cooling, the solvent was distilled off and the residue was dissolved in dry toluene. The sovent was distilled off under reduced pressure for removal of the residual thionyl chloride to give a crude acid chloride.

4-Amino-3,5-dichloropyridine (0.73 g) was dissolved in THF (7 ml) and sodium hydride (360 mg) was added thereto under ice-cooling, followed by stirring at room temperature for 15 minutes, and then the mixture was again cooled with ice. A solution of the crude acid chloride obtained above in THF (5 ml) was dropwise added to the mixture under ice-cooling, followed by stirring for one hour under ice-cooling. The reaction mixture was extracted with ether. The organic layer was washed with a saturated saline and dried over anhydrous magnesium sulfate, and the solvent was distilled off under reduced pressure. The residue was recrystallized from ethyl acetate to give Compound 1 (0.60 g, 48.0%) as a white solid.

Melting point: 196–197° C.

NMR(DMSO-$d_6$, δ, ppm): 3.43(t, J=9.3 Hz, 2H), 3.86(s, 3H), 4.57(t, J=9.3 Hz, 2H), 7.00(d, J=8.8 Hz, 1H), 7.49(d, J=8.8 Hz, 1H), 8.72(s, 2H), 10.3(s, 1H)

MASS(m/e): 338($M^+$)

IR(KBr, $cm^{-1}$): 1650, 1490, 1280

Elemental analysis: $C_{15}H_{12}N_2O_3Cl_2$

Found (%) C,53.14; H,3.50; N,8.06. Calcd. (%) C,53.12; H,3.57; N,8.26.

EXAMPLE 2

(±)-4-[(3,5-Dichloro-4-pyridyl)aminocarbonyl]-7-methoxy-3-methyl-2,3-dihydrobenzofuran (Compound 2)

Substantially the same procedure as in Example 1 was repeated using Compound IIx (0.116 g) obtained in Reference Example 24 to give Compound 2 (0.145 g, 74%) as a white solid.

Melting point: 198–200° C. (solidified by water)

NMR($CDCl_3$, δ, ppm): 1.32(d, J=8.4 Hz, 3H), 3.96(s, 3H), 3.98–4.12(m, 1H), 4.38(dd, J=9.3, 3.4 Hz, 1H), 4.62–4.77(m, 1H), 6.84(d, J=9.7 Hz, 1H), 7.35(d, J=9.7 Hz, 1H), 7.57–7.68(broad s, 1H), 8.57(s, 2H)

IR(KBr, $cm^{-1}$): 1670, 1490, 1283

MASS(m/z): 353($M^+$)

Elemental analysis: $C_{16}H_{14}Cl_2N_2O_3$

Found (%) C,54.53; H,3.89; N,7.83. Calcd. (%) C,54.41; H,4.00; N,7.93.

EXAMPLE 3

(±)-4-[(3,5-Dichloro-4-pyridyl)aminocarbonyl]-3-ethyl-7-methoxy-2,3-dihydrobenzofuran (Compound 3)

Substantially the same procedure as in Example 1 was repeated using Compound IIy (0.222 g) obtained in Reference Example 25 to give Compound 3 (0.170 g, 46.3%) as a white solid.

Melting point: 202–204° C. (ethanol)

NMR($CDCl_3$, δ, ppm): 0.91(t, J=8.0 Hz, 3H), 1.47–1.88 (m, 2H), 3.85–4.05(m, 1H), 3.95(s, 3H), 4.47–4.72(m, 2H), 6.85(d, J=9.7 Hz, 1H), 7.35(d, J=9.7 Hz, 1H), 7.50–7.69 (broad s, 1H), 8.59(s, 2H)

IR(KBr, $cm^{-1}$): 1668, 1488, 1280

MASS(m/z): 367($M^+$)

Elemental analysis: $C_{17}H_{16}Cl_2N_2O_3$

Found (%) C,55.58; H,4.34; N,7.56. Calcd. (%) C,55.60; H,4.39; N,7.63.

EXAMPLE 4

(±)-4-[(3,5-Dichloro-4-pyridyl)aminocarbonyl]-7-methoxy-3-(2-propyl)-2,3-dihydrobenzofuran (Compound 4)

Substantially the same procedure as in Example 1 was repeated using Compound IIz (0.160 g) obtained in Reference Example 26 to give Compound 4 (0.15 g, 58%) as a white solid.

Melting point: 239–241° C.

NMR(DMSO-$d_6$, δ, ppm): 0.60(d, J=7.5 Hz, 3H), 0.89(d, J=7.1 Hz, 3H), 1.98–2.15(m, 1H), 3.80–3.91(m, 1H), 3.85(s, 3H), 4.36–4.60(m, 2H), 7.01(d, J=9.4 Hz, 1H), 7.40(d, J=9.4 Hz, 1H), 8.75(s, 2H), 10.48(s, 1H)

IR(KBr, $cm^{-1}$): 1650, 1490, 1280

MASS(m/z): 381($M^+$)

Elemental analysis: $C_{18}H_{18}Cl_2N_2O_3$

Found (%) C,56.56; H,4.80; N,7.26. Calcd. (%) C,56.71; H,4.76; N,7.35.

EXAMPLE 5

(±)-4-[(3,5-Dichloro-4-pyridyl)aminocarbonyl]-3-ethoxycarbonylmethyl-7-methoxy-2,3-dihydrobenzofuran (Compound 5)

Substantially the same procedure as in Example 1 was repeated using Compound IIaa (0.172 g) obtained in Reference Example 27 to give Compound 5 (0.131 g, 52%) as a white solid.

Melting point: 186–188° C. (ethanol)

NMR($CDCl_3$, δ, ppm): 1.22(t, J=7.6 Hz, 3H), 2.52(dd, J=16.9 Hz, 11.8 Hz, 1H), 2.94–3.12(m, 1H), 3.97(s, 3H), 4.11(q, J=7.6 Hz, 2H), 4.24–4.41(m, 1H), 4.59(dd, J=10.1 Hz, 4.2 Hz, 1H), 4.70–4.83(m, 1H), 6.88(d, J=9.3 Hz, 1H), 7.37(d, J=9.3 Hz, 1H), 7.58–7.72(broad s, 1H), 8.58(s, 2H)

IR(KBr, $cm^{-1}$): 1722, 1662, 1493, 1285

MASS(m/z): 425($M^+$)

Elemental analysis: $C_{19}H_{18}Cl_2N_2O_5$

Found (%) C,53.65; H,4.11; N,6.59. Calcd. (%) C,53.66; H,4.27; N,6.59.

EXAMPLE 6

(±)-3-Ethoxycarbonylmethyl-7-methoxy-4-pyridylaminocarbonyl-2,3-dihydrobenzofuran (Compound 6)

Substantially the same procedure as in Example 1 was repeated using 4-aminopyridine instead of 4-amino-3,5-dichloropyridine and using Compound IIaa (4.00 g) obtained in Reference Example 27 to give Compound 6 (4.77 g, 94%) as white crystals.

Melting point: 177° C.

NMR(DMSO-$d_6$, δ, ppm): 1.14(t, 3H, J=7 Hz), 2.46–2.56 (m, 1H), 2.79(dd, 1H, J=3 Hz, 16 Hz), 3.88(s, 3H), 4.04(q, 2H, J=7 Hz), 4.16–4.36(m, 1H)4.47(dd, 1H, J=4 Hz, 9 Hz), 4.64(t, 1H, J=9 Hz), 7.08(d, 1H, J=9 Hz), 7.65(d, 1H, J=9 Hz), 8.35(d, 2H, J=8 Hz), 8.74(d, 2H, J=7 Hz), 11.64(s, 1H)

IR(KBr, $cm^{-1}$): 1697, 1614, 1506, 1471, 1269

MASS(m/e): 401($M^+$)

Elemental analysis: $C_{19}H_{20}N_2O_5.1HCl.0.5H_2O$

Found (%) C,56.79; H,5.52; N,6.97. Calcd. (%) C,57.05; H,5.50; N,6.99.

EXAMPLE 7

(±)-3-Ethoxycarbonylmethyl-7-methoxy-4-phenylaminocarbonyl-2,3-dihydrobenzofuran (Compound 7)

Substantially the same procedure as in Example 1 was repeated using aniline instead of 4-amino-3,5-dichloropyridine and using Compound IIaa (0.50 g) obtained in Reference Example 27 to give Compound 7 (0.59 g, 92%) as a white solid.

Melting point: 169–170° C.

NMR($CDCl_3$, δ, ppm): 2.22(t, 3H, J=7 Hz), 2.51(dd, 1H, J=11 Hz, 17 Hz), 3.08(dd, 1H, J=3 Hz, 17 Hz), 3.93(s, 3H), 4.11(q, 2H, J=7 Hz), 4.29–4.39(m, 1H), 4.55 (dd, 1H, J=3 Hz, 9 Hz), 4.75(t, 1H, J=9 Hz), 6.82(d, 1H, J=9 Hz), 7.12–7.20 (m, 3H), 7.36(d, 1H, J=9 Hz), 7.40(s, 1H), 7.58(d, 2H, J=8 Hz), 7.72(s, 1H)

IR(KBr, $cm^{-1}$): 3305, 1722, 1645, 1286, 1194

MASS(m/e): 355($M^+$)

Elemental analysis: $C_{20}H_{21}NO_5$

Found (%) C,67.59; H,5.96; N,3.94. Calcd. (%) C,67.72; H,5.98; N,3.95.

EXAMPLE 8

(±)-4-Cyclohexylaminocarbonyl-3-ethoxycarbonylmethyl-7-methoxy-2,3-dihydrobenzofuran (Compound 8)

Substantially the same procedure as in Example 1 was repeated using cyclohexylamine instead of 4-amino-3,5-dichloropyridine and using Compound IIaa (0.60 g) obtained in Reference Example 27 to give Compound 8 (0.68 g, 87%) as a white solid.

Melting point: 197–199° C.

NMR($CDCl_3$, δ, ppm): 1.24(t, 3H, J=7 Hz), 1.29–1.49(m, 5H), 2.17–2.00(m, 5H), 2.47(dd, 1H, J=11 Hz, 17 Hz), 3.07(dd, 1H, J=3 Hz, 17 Hz), 3.90(s, 3H), 4.13(q, 2H, J=7

Hz), 4.23–4.31(m, 1H), 4.53(dd, 1H, J=3 Hz, 9 Hz), 4.72(t, 1H, J=9 Hz), 5.87 (d, 1H, J=8 Hz), 6.75(d, 1H, J=8 Hz), 7.01(d, 1H, J=8 Hz), 7.27(s, 1H)

IR(KBr, $cm^{-1}$): 3284, 1726, 1718, 1624, 1541, 1524, 1284

MASS (m/e): 361 ($M^+$)

Elemental analysis: $C_{20}H_{27}NO_5$

Found (%) C,66.46; H,7.53; N,3.88. Calcd. (%) C,66.38; H,7.75; N,4.00.

EXAMPLE 9

(±)-3-Carboxymethyl-4-(3,5-dichloro-4-pyridylaminocarbonyl)-7-methoxy-2,3-dihydrobenzofuran (Compound 9)

Compound 5 (0.329 g) obtained in Example 5 was mixed with a 2N aqueous solution of sodium hydroxide (6.6 ml), followed by stirring at room temperature for one hour. Under ice-cooling, the reaction mixture was adjusted to pH 2 by adding hydrochloric acid, and then the precipitated solid was collected by filtration. The obtained crude product was recrystallized from ethanol to give Compound 9 (0.302 g, 98%) as a white solid.

Melting point: 259–263° C.

NMR(DMSO-$d_6$, δ, ppm): 2.40(dd, J=14.5 Hz, 8.9 Hz, 1H), 2.70–2.89(m, 1H), 3.86(s, 3H), 4.03–4.21(m, 1H), 4.34–4.49(m, 1H), 4.55–4.74(m, 1H), 7.04(d, J=8.4 Hz, 1H), 7.49(d, J=8.4 Hz, 1H), 8.75(s, 2H), 10.51(s, 1H), 12.17–12.49(broad s, 1H)

IR(KBr, $cm^{-1}$): 1713, 1663, 1490, 1288

MASS (m/z): 397($M^+$)

Elemental analysis: $C_{17}H_{14}Cl_2N_2O_5.0.5C_2H_6O.0.5H_2O$

Found (%) C,50.49; H,4.37; N,6.31. Calcd. (%) C,50.37; H,4.23; N,6.53.

EXAMPLE 10

(±)-3-Carboxymethyl-7-methoxy-4-pyridylaminocarbonyl-2,3-dihydrobenzofuran (Compound 10)

Substantially the same procedure as in Example 9 was repeated using Compound 6 (4.00 g) obtained in Example 6 to give Compound 10 (2.79 g, 76%) as a white solid.

Melting point: 227–233° C.

NMR(DMSO-$d_6$, δ, ppm): 2.41(dd, 1H, J=6 Hz, 17 Hz), 2.72(dd, 1H, J=3 Hz, 17 Hz), 3.88(s, 3H), 4.10–4.20(m, 1H), 4.45(dd, 1H, J=4 Hz, 9 Hz), 4.64(t, 1H, J=9 Hz), 7.08(d, 1H, J=9 Hz), 7.42(d, 1H, J=9 Hz), 8.30(d, 2H, J=7 Hz), 8.72(d, 2H, J=7 Hz), 11.53(s, 1H), 12.35(broad s, 1H)

IR(KBr, $cm^{-1}$): 3300(br), 2770(br), 1716, 1693, 1614, 1508, 1477, 1271

MASS(m/e): 390($M^+$)

Elemental analysis: $C_{17}H_{16}N_2O_5.HCl.0.2C_2H_6O.H_2O$

Found (%) C,53.56; H,5.17; N,7.18. Calcd. (%) C,53.63; H,5.11; N,7.11.

EXAMPLE 11

(±)-3-Carboxymethyl-7-methoxy-4-phenylaminocarbonyl-2,3-dihydrobenzofuran (Compound 11)

Substantially the same procedure as in Example 9 was repeated using Compound 7 (0.43 g) obtained in Example 7 to give Compound 11 (0.37 g, 94%) as a white solid.

Melting point: 248–251° C.

NMR(DMSO-$d_6$, δ, ppm): 2.38(dd, 1H, J=11 Hz, 17 Hz), 2.78(dd, 1H, J=2 Hz, 17 Hz), 3.84(s, 3H), 4.11–4.18(m, 1H), 4.40(dd, 1H, J=4 Hz, 9 Hz), 4.64(t, 1H, J=9 Hz), 6.99(d, 1H, J=8 Hz), 7.09(t, 1H, J=7 Hz), 7.30–7.36(m, 3H), 7.72(d, 2H, J=8 Hz), 10.15(s, 1H), 12.31(broad s, 1H)

IR(KBr, $cm^{-1}$): 2900(br), 1709, 1645, 1595, 1506, 1442, 1286

MASS(m/e): 327($M^+$)

Elemental analysis: $C_{18}H_{17}NO_5$

Found (%) C,66.05; H,5.23; N,4.28. Calcd. (%) C,65.82; H,5.20; N,4.22.

EXAMPLE 12

(±)-3-Carboxymethyl-4-cyclohexylaminocarbonyl-7-methoxy-2,3-dihydrobenzofuran (Compound 12)

Substantially the same procedure as in Example 9 was repeated using Compound 8 (0.47 g) obtained in Example 8 to give Compound 12 (0.40 g, 95%) as a white solid.

Melting point: 246–247° C.

NMR(DMSO-$d_6$, δ, ppm): 1.06–1.36(m, 5H), 1.53–1.80 (m, 5H), 2.31(dd, 1H, J=11 Hz, 17 Hz), 2.76(dd, 1H, J=2 Hz, 17 Hz), 3.69–3.75(m, 1H), 3.80(s, 3H), 4.13–4.06(m, 1H), 4.36(dd, 1H, J=4 Hz, 9 Hz), 4.59 (t, 1H, J=9 Hz), 6.89(d, 1H, J=9 Hz), 7.13(d, 1H, J=9 Hz), 8.06(d, 1H, J=8 Hz), 12.31 (broad s, 1H)

IR(KBr, $cm^{-1}$): 3410, 3134(br), 1727, 1546, 1282

MASS(m/e): 333($M^+$+1)

Elemental analysis: $C_{18}H_{23}NO_5$

Found (%) C,64.85; H,6.95; N,4.20. Calcd. (%) C,64.99; H,7.08; N,4.28.

EXAMPLE 13

(±)-3-Benzyloxycarbonylmethyl-4-[(3,5-Dichloro-4-pyridyl)aminocarbonyl]-7-methoxy-2,3-dihydrobenzofuran (Compound 13)

Compound 9 (0.291 g) obtained in Example 9 was dissolved in dichloromethane (2.9 ml) and thionyl chloride (1.5 ml) was added thereto, followed by stirring at room temperature for one hour. The solvent was distilled off under reduced pressure, the residue was again dissolved in toluene, and the solvent was distilled off under reduced pressure. Benzyl alcohol (2 ml) was added to the residue followed by heating under reflux for 30 minutes. The reaction solution was concentrated and the residue was recrystallized from ethanol to give Compound 13 (0.304 g, 85.2%) as a white solid.

Melting point: 198–205° C.

NMR(DMSO-$d_6$, δ, ppm): 2.43–2.68(m, 1H), 2.80–3.01 (m, 1H), 3.85(s, 3H), 4.10–4.27(m, 1H), 4.39–4.75(m, 2H), 5.08(s, 2H), 7.05(d, J=9.5 Hz, 1H), 7.24–7.43(m, 5H), 7.50(d, J=9.5 Hz, 1H), 8.77(s, 2H), 10.50(s, 1H)

IR(KBr, $cm^{-1}$): 1722, 1668, 1490, 1288

MASS(m/z): 487($M^+$)

Elemental analysis: $C_{24}H_{20}Cl_2N_2O_5$

Found (%) C,59.32; H,4.00; N,5.72. Calcd. (%) C,59.15; H,4.14; N,5.75.

EXAMPLE 14

(±)-3-Benzyloxycarbonylmethyl-7-methoxy-4-pyridylaminocarbonyl-2,3-dihydrobenzofuran (Compound 14)

Substantially the same procedure as in Example 13 was repeated using Compound 10 (0.12 g) obtained in Example 10 to give Compound 14 (0.07 g, 53%) as a white solid.

Melting point: 165–166° C.

NMR($CDCl_3$, δ, ppm): 2.60(dd, 1H, J=10 Hz, 17 Hz), 3.06 (dd, 1H, J=3 Hz, 17 Hz), 3.94(s, 3H), 4.33–4.40(m, 1H), 4.57(dd, 1H, J=4 Hz, 10 Hz), 4.74(t, 1H, J=9 Hz), 5.10(s, 2H), 6.82(d, 1H, J=9 Hz), 7.16(d, 2H, J=9 Hz), 7.28–7.38(m, 5H), 7.52(dd, 1H, J=1 Hz, 5 Hz), 7.77(broad s, 1H), 8.53(dd, 2H, J=1 Hz, 5 Hz)

IR(KBr, $cm^{-1}$): 3317, 1720, 1653, 1585, 1504, 1284

MASS(m/e): 418($M^+$)

Elemental analysis: $C_{24}H_{22}N_2O_5.0.1C_2H_6O.0.4H_2O$

Found (%) C,67.56; H,5.48; N,6.51. Calcd. (%) C,67.54; H,5.40; N,6.47.

EXAMPLE 15

(±)-3-Benzyloxycarbonylmethyl-7-methoxy-4-phenylaminocarbonyl-2,3-dihydrobenzofuran (Compound 15)

Substantially the same procedure as in Example 13 was repeated using Compound 11 (0.17 g) obtained in Example 11 to give Compound 15 (0.17 g, 76%) as a white solid.

Melting point: 179–180° C.

NMR($CDCl_3$, δ, ppm): 2.59(dd, 1H, J=11 Hz, 17 Hz), 3.13 (dd, 1H, J=3 Hz, 17 Hz), 3.93(s, 3H), 4.32–4.42(m, 1H), 4.55(dd, 1H, J=4 Hz, 9 Hz), 4.74(t, 1H, J=9 Hz), 5.08(d, 1H, J=3 Hz), 6.81(d, 1H, J=9 Hz), 7.16(d, 1H, J=9 Hz), 7.26–7.39(m, 8H), 7.55(dd, 2H, J=1 Hz, 8 Hz), 7.66(s, 1H)

IR(KBr, $cm^{-1}$): 3307, 1722, 1645, 1529, 1506, 1444, 1288

MASS(m/e): 417($M^+$)

Elemental analysis: $C_{25}H_{23}NO_5$

Found (%) C,71.93; H,5.55; N,3.36. Calcd. (%) C,71.82; H,5.51; N,3.36.

EXAMPLE 16

(±)-3-Benzyloxycarbonyl-4-cyclohexylaminocarbonyl-7-methoxy-2,3-dihydrobenzofuran (Compound 16)

Substantially the same procedure as in Example 13 was repeated using Compound 12 (0.20 g) obtained in Example 12 to give Compound 16 (0.20 g, 76%) as a white solid.

Melting point: 178–179° C.

NMR(DMSO-$d_6$, δ, ppm): 1.00–1.34(m, 5H), 1.66–1.86 (m, 5H), 2.46–2.56(m, 1H), 2.88(dd, 1H, J=3 Hz, 17 Hz), 3.76–3.62(m, 1H), 3.80(s, 3H), 4.12–4.19(m, 1H), 4.37(dd, 1H, J=4 Hz, 9 Hz), 4.58(t, 1H, J=9 Hz), 5.10(d, 1H, J=2 Hz), 6.90(d, 1H, J=9 Hz), 7.15(d, 1H, J=9 Hz), 7.31–7.41(m, 5H), 8.06(d, 1H, J=8 Hz)

IR(KBr, $cm^{-1}$): 3325, 1720, 1626, 1282, 1174

MASS(m/e): 423($M^+$)

Elemental analysis: $C_{25}H_{29}NO_5$

Found (%) C,70.90; H,6.90; N,3.30. Calcd. (%) C,70.90; H,7.04; N,3.34.

EXAMPLE 17

(±)-4-[(3,5-Dichloro-4-pyridyl)aminocarbonyl]-7-methoxy-3-[(4-methylpiperazin-1-yl) carbonylmethyl]-2,3-dihydro-benzofuran.hydrochloride (Compound 17)

Substantially the same procedure as in Example 13 was repeated using Compound 9 (0.354 g) obtained in Example 9 and N-methylpiperazine (0.119 ml) to give (±)-4-[(3,5-Dichloro-4-pyridyl)aminocarbonyl]-7-methoxy-3-[(4-methylpiperazin-1-yl)carbonylmethyl]-2,3-dihydrobenzofuran (0.427 g, 100%) as an oily substance. The obtained free base was dissolved in ethyl acetate (50 ml), and a saturated solution of hydrochloric acid in ethyl acetate (2 ml) was added thereto followed by stirring. The precipitated hydrochloride was collected by filtration and washed with ethyl acetate to give Compound 17 as a white solid.

Melting point: 181–187° C.

NMR(DMSO-$d_6$, δ, ppm): 2.40–3.52(m, 13H), 3.77–4.70 (m, 3H), 3.88(s, 3H), 7.06(d, J=9.6 Hz, 1H), 7.52(d, J=9.6 Hz, 1H), 8.76(s, 2H), 10.55(s, 1H)

IR(KBr, $cm^{-1}$): 1650, 1480, 1280

Elemental analysis: $C_{22}H_{24}Cl_2N_4O_4.HCl.2.5H_2O$

Found (%) C,47.08; H,5.29; N,9.94. Calcd. (%) C,47.11; H,5.39; N,9.99.

EXAMPLE 18

(±)-4-[(3,5-Dichloro-4-pyridyl)aminocarbonyl]-7-methoxy-3-[(3-pyridylmethyl)aminocarbonyl] methyl-2,3-dihydrobenzofuran (Compound 18)

Substantially the same procedure as in Example 13 was repeated using Compound 9 (0.30 g) obtained in Example 9 and 3-pyridylmethylamine to give Compound 18 (0.07 g, 19%) as a white solid.

Melting point: 258–261° C. (decomposed)

NMR($CDCl_3$, δ, ppm): 2.46(dd, 1H, J=10 Hz, 14 Hz), 2.82 (dd, 1H, J=2 Hz, 14 Hz), 3.95(s, 3H), 4.15–4.24(m, 1H), 4.32(dd, 1H, J=6 Hz, 15 Hz), 4.46, 4.32(dd, 1H, J=6 Hz, 15 Hz), 4.67(t, 1H, J=9 Hz), 4.83(dd, 1H, J=3 Hz, 9 Hz), 6.55–6.65(m, 1H), 6.85(d, J=8 Hz, 1H), 7.26–7.21(m, 1H), 7.37(d, J=8 Hz, 1H), 7.55–7.65(m, 1H), 8.38–8.57(m, 2H), 8.56(s, 2H)

IR(KBr, $cm^{-1}$): 3310, 3224, 1662, 1645, 1489, 1284

MASS(m/e): 486($M^+$)

EXAMPLE 19

(±)-4-[(3,5-Dichloro-4-pyridyl)aminocarbonyl]-7-methoxy-3-[(3-pyridyl)aminocarbonyl]methyl-2,3-dihydro-benzofuran (Compound 19)

Substantially the same procedure as in Example 13 was repeated using Compound 9 (0.30 g) obtained in Example 9 and 3-aminopyridine to give Compound 19 (0.18 g, 51%) as a white solid.

Melting point: 267° C. (decomposed)

NMR($CDCl_3$, δ, ppm): 2.55(dd, 1H, J=11 Hz, 15 Hz), 3.01 (dd, 1H, J=2 Hz, 15 Hz), 3.94(s, 3H), 4.21–4.30(m, 1H), 4.67(t, 1H, J=9 Hz), 4.80(dd, 1H, J=3 Hz, 9 Hz), 6.87(d, 1H, J=9 Hz), 7.24(dd, 1H, J=5 Hz, 8 Hz), 7.45(d, 1H, J=9 Hz), 8.10–8.22(m, 2H), 8.50 (d, 1H, J=2 Hz), 8.56(s, 2H)

IR(KBr, $cm^{-1}$): 3300(br), 1668, 1664, 1483, 1278

MASS(m/e): 472($M^+$)

EXAMPLE 20

(±)-4-[(3,5-Dichloro-4-pyridyl)aminocarbonyl]-7-methoxy-3-[(2-pyrimidyl)aminocarbonyl]methyl-2,3-dihydro-benzofuran (Compound 20)

Substantially the same procedure as in Example 13 was repeated using Compound 9 (0.30 g) obtained in Example 9 and 2-aminopyrimidine to give Compound 19 (0.11 g, 31%) as a white solid.

Melting point: 259–261° C.

NMR(DMSO-$d_6$, δ, ppm): 2.82(dd, 1H, J=11 Hz, 18 Hz), 3.10–3.16(m, 1H), 3.87(s, 3H), 4.26–4.30(m, 1H), 4.38(dd, 1H, J=3 Hz, 9 Hz), 4.65(t, 1H, J=9 Hz), 7.05(d, J=9 Hz, 1H), 7.14(t, 1H, J=5 Hz), 7.48(d, J=9 Hz, 1H), 8.61(d, J=5 Hz, 2H), 8.72(s, 2H), 10.49(s, 1H), 10.60(s, 1H)

IR(KBr, $cm^{-1}$): 3200(br), 1668, 1579, 1488, 1278

MASS(m/e): 474($M^+$)

EXAMPLE 21

(±)-4-[(3,5-Dichloro-4-pyridyl)aminocarbonyl]-7-methoxy-3-[(4-phenyl-1-piperazinyl)carbonyl]methyl-2,3-dihydrobenzofuran (Compound 21)

Substantially the same procedure as in Example 13 was repeated using Compound 9 (0.30 g) obtained in Example 9 and 1-phenylpiperazine to give Compound 21 (0.21 g, 51%) as a white solid.

Melting point: 224° C.

NMR($CDCl_3$, δ, ppm): 2.54(dd, 1H, J=11 Hz, 16 Hz), 3.11–3.21(m, 5H), 3.57–3.75(m, 4H), 3.96(s, 3H), 4.36–4.26(m, 1H), 4.66(dd, 1H, J=3 Hz, 9 Hz), 4.79 (t, 1H, J=9 Hz), 6.86–6.92(m, 4H), 7.25–7.31(m, 3H), 7.37(d, J=9 Hz, 1H), 7.68(s, 1H), 8.57(s, 2H)

IR(KBr, $cm^{-1}$): 3232, 1662, 1647, 1486, 1286

MASS(m/e): 542($M^+$+1)

Elemental analysis: $C_{27}H_{26}N_4O_4Cl_2$

Found (%) C,59.83; H,4.82; N,10.20. Calcd. (%) C,59.90; H,4.84; N,10.35.

EXAMPLE 22

(±)-4-[(3,5-Dichloro-4-pyridyl)aminocarbonyl]-7-methoxy-3-[(1,2,3,4-tetrahydroisoquinolinyl)carbonyl]-methyl-2,3-dihydrobenzofuran (Compound 22)

Substantially the same procedure as in Example 13 was repeated using Compound 9 (0.30 g) obtained in Example 9 and 1,2,3,4-tetrahydroisoquinoline to give Compound 22 (0.32 g, 84%) as a white solid.

Melting point: 211–213° C.

NMR($CDCl_3$, δ, ppm): 2.63–2.51(m, 1H), 2.83(dt, 2H, J=6 Hz, 5 Hz), 3.22(d, J=16 Hz, 1H), 3.60–3.92(m, 2H), 3.96(s, 3H), 4.28–4.37(m, 1H), 4.57(s, 1H), 4.61–4.82(m, 3H), 6.86(dd, 1H, J=3 Hz, 9 Hz), 7.10–7.23(m, 4H), 7.38 (dd, 1H, J=2 Hz, 9 Hz), 7.76 (s, 1H), 8.56(s, 2H)

IR(KBr, $cm^{-1}$): 3188, 1659, 1635, 1487, 1282

MASS(m/e): 511($M^+$)

Elemental analysis: $C_{26}H_{23}N_3O_4Cl_2$

Found (%) C,60.95; H,4.52; N,8.20. Calcd. (%) C,60.67; H,4.58; N,8.00.

EXAMPLE 23

(±)-4-[(3,5-Dichloro-4-pyridyl)aminocarbonyl]-7-methoxy-3-phenethyloxycarbonyl)methyl-2,3-dihydrobenzofuran (Compound 23)

Substantially the same procedure as in Example 13 was repeated using Compound 9 (0.30 g) obtained in Example 9 and phenethyl alcohol to give Compound 23 (0.07 g, 57%) as a white solid.

Melting point: 194° C.

NMR($CDCl_3$, δ, ppm): 2.50(dd, 1H, J=11 Hz, 17 Hz), 2.90 (t, 2H, J=7 Hz), 3.03(dd, 1H, J=2 Hz, 17 Hz), 3.95 (s, 3H), 4.27(t, 2H, J=7 Hz), 4.22–4.33(m, 1H), 4.46(dd, 1H, J=3 Hz, 9 Hz), 4.64(t, 1H, J=9 Hz), 6.86(d, 1H, J=9 Hz), 7.17–7.31(m, 5H), 7.34(d, 1H, J=8 Hz), 7.62(s, 1H), 8.57(s, 2H)

IR(KBr, $cm^{-1}$): 3203, 1726, 1660, 1487, 1286

MASS(m/e): 501 ($M^+$+1)

Elemental analysis: $C_{25}H_{22}N_2O_5Cl_2$

Found (%) C,59.89; H,4.42; N,5.59. Calcd. (%) C,59.75; H,4.15; N,5.48.

EXAMPLE 24

(±)-4-[(3,5-Dichloro-4-pyridyl)aminocarbonyl]-7-methoxy-3-[(2-pyridylmethyl)aminocarbonyl]methyl-2,3-dihydrobenzofuran (Compound 24)

Substantially the same procedure as in Example 13 was repeated using Compound 9 (0.30 g) obtained in Example 9 and 2-pyridylmethylamine to give Compound 24 (0.21 g, 56%) as a white solid.

Melting point: 255–258° C.

NMR(DMSO-$d_6$, δ, ppm): 2.35(dd, 1H, J=11 Hz, 15 Hz), 2.79(dd, 1H, J=3 Hz, 15 Hz), 3.86(s, 3H), 4.13–4.24(m, 1H), 4.36(d, 2H, J=6 Hz), 4.29–4.43(m, 1H), 4.56(t, 1H, J=9 Hz), 7.04(d, 1H, J=9 Hz), 7.24–7.28(m, 2H), 7.47(d, 1H, J=9 Hz), 7.75(dt, 1H, J=2 Hz, 8 Hz), 8.43–8.51(m, 2H), 8.75(s, 2H), 10.48(s, 1H)

IR(KBr, $cm^{-1}$): 3350, 3320, 1659, 1635, 1552, 1486, 1282

MASS(m/e): 486($M^+$)

Elemental analysis: $C_{23}H_{20}N_4O_4Cl_2$

Found (%) C,56.69; H,4.14; N,11.50. Calcd. (%) C,56.54; H,4.02; N,11.33.

EXAMPLE 25

(±)-3-(Benzylaminocarbonyl)methyl-4-[(3,5-dichloro-4-pyridyl)aminocarbonyl]-7-methoxy-2,3-dihydrobenzofuran (Compound 25)

Substantially the same procedure as in Example 13 was repeated using Compound 9 (0.10 g) obtained in Example 9 and benzylamine to give Compound 25 (0.08 g, 65%) as a white solid.

Melting point: 284–286° C.

NMR(DMSO-$d_6$, δ, ppm): 2.30(dd, 1H, J=11 Hz, 15 Hz), 2.76(dd, 1H, J=3 Hz, 15 Hz), 3.86(s, 3H), 4.17–4.28(m, 1H), 4.27(d, 2H, J=7 Hz), 4.34(dd, 1H, J=3 Hz, 9 Hz), 4.57(t, 1H, J=9 Hz), 7.04(d, 1H, J=9 Hz), 7.20–7.35(m, 5H), 7.47(d, 1H, J=9 Hz), 8.36(t, 1H, J=6 Hz), 8.75(s, 2H), 10.47(broad s, 1H)

IR(KBr, $cm^{-1}$): 3350, 3230, 1662, 1637, 1552, 1487, 1282

MASS(m/e): 487($M^+$)

Elemental analysis: $C_{24}H_{21}N_3O_4Cl_2$

Found (%) C,59.27; H,4.35; N,8.64. Calcd. (%) C,59.54; H,4.36; N,8.55.

EXAMPLE 26

(±)-4-[(3,5-Dichloro-4-pyridyl)aminocarbonyl]-7-methoxy-3-[(4-pyridylmethyl)aminocarbonyl]methyl-2,3-dihydrobenzofuran (Compound 26)

Substantially the same procedure as in Example 13 was repeated using Compound 9 (0.20 g) obtained in Example 9 and 4-pyridylmethylamine to give Compound 24 (0.04 g, 16%) as a white solid.

Melting point: 259–262° C. (decomposed)

NMR(DMSO-$d_6$, δ, ppm): 2.36(dd, 1H, J=11 Hz, 16 Hz), 2.80(dd, 1H, J=2 Hz, 16 Hz), 3.86(s, 3H), 4.16–4.23(m, 1H), 4.29(d, 2H, J=6 Hz), 4.37(dd, 1H, J=3 Hz, 9 Hz), 4.57(t, 1H, J=9 Hz), 7.22(d, 2H, J=9 Hz), 7.47(d, 1H, J=9 Hz), 8.42–8.50(m, 3H), 8.75(s, 2H), 10.48(s, 1H)

IR(KBr, $cm^{-1}$): 3327, 3205, 1654, 1641, 1551, 1481, 1288

Elemental analysis: $C_{23}H_{20}N_4O_4Cl_2$

Found (%) C,56.69; H,4.14; N,11.50. Calcd. (%) C,56.39; H,4.00; N,11.39.

EXAMPLE 27

(±)-4-[(3,5-Dichloro-4-pyridyl)aminocarbonyl]-7-methoxy-3-(phenylaminocarbonyl)methyl-2,3-dihydrobenzofuran (Compound 27)

Substantially the same procedure as in Example 13 was repeated using Compound 9 (0.20 g) obtained in Example 9 and aniline to give Compound 27 (0.10 g, 42%) as a white solid.

Melting point: 296–300° C. (decomposed)

NMR(DMSO-$d_6$, δ, ppm): 2.50–2.54(m, 1H), 2.93(dd, 1H, J=2 Hz, 14 Hz), 3.87(s, 3H), 4.22–4.29(m, 1H), 4.43(dd, 1H, J=3 Hz, 9 Hz), 4.63(t, 1H, J=9 Hz), 6.98–7.07(m, 2H), 7.27(d, 1H, J=8 Hz), 7.30(d, 1H, J=8 Hz), 7.49(d, 1H, J=8 Hz), 7.55(d, 2H, J=8 Hz), 8.74(s, 2H), 9.90(s, 1H), 10.50(s, 1H)

IR(KBr, $cm^{-1}$): 3350, 3142, 1657, 1651, 1547, 1491, 1290

MASS(m/e): 471($M^+$), 473($M^+$+2)

Elemental analysis: $C_{23}H_{19}N_3O_4Cl_2$

Found (%) C,58.49; H,4.05; N,8.90. Calcd. (%) C,58.14; H,4.14; N,8.62.

EXAMPLE 28

(±)-4-[(3,5-Dichloro-4-pyridyl)aminocarbonyl]-7-methoxy-3-[(4-methoxybenzyl)aminocarbonyl]methyl-2,3-dihydrobenzofuran (Compound 28)

Substantially the same procedure as in Example 13 was repeated using Compound 9 (0.20 g) obtained in Example 9 and 4-methoxybenzylamine to give Compound 28 (0.28 g, 85%) as a white solid.

Melting point: 269–271° C.

NMR(DMSO-$d_6$, δ, ppm): 2.27(dd, 1H, J=15 Hz, 11 Hz), 2.74(dd, 1H, J=3 Hz, 15 Hz), 3.72(s, 3H), 3.86(s, 3H), 4.19(d, 2H, J=5 Hz), 4.12–4.23(m, 1H), 4.33 (dd, 1H, J=3 Hz, 9 Hz), 4.56(t, 1H, J=9 Hz), 6.87(d, 2H, J=9 Hz), 7.03(d, 1H, J=8 Hz), 7.16(d, 1H, J=9 Hz), 7.46(d, 1H, J=8 Hz), 8.27(t, 1H, J=6 Hz), 8.74(s, 2H), 10.47(s, 1H)

IR(KBr, $cm^{-1}$): 3210, 1659, 1643, 1514, 1487, 1290

MASS(m/e): 515($M^+$), 517, 519

Elemental analysis: $C_{25}H_{23}N_3O_5Cl_2$

Found (%) C,58.15; H,4.49; N,8.14. Calcd. (%) C,57.97; H,4.51; N,8.03.

EXAMPLE 29

(±)-4-[(3,5-Dichloro-4-pyridyl)aminocarbonyl]-3-[(4-fluorobenzyl)aminocarbonyl]methyl-7-methoxy-2,3-dihydro-benzofuran (Compound 29)

Substantially the same procedure as in Example 13 was repeated using Compound 9 (0.20 g) obtained in Example 9 and 4-fluorobenzylamine to give Compound 29 (0.13 g, 51%) as a white solid.

Melting point: 287° C.

NMR(DMSO-$d_6$, δ, ppm): 2.28(dd, 1H, J=15 Hz, 11 Hz), 2.80(dd, 1H, J=3 Hz, 15 Hz), 3.85(s, 3H), 4.18–4.25(m, 1H), 4.23(d, 2H, J=6 Hz), 4.33(dd, 1H, J=3 Hz, 9 Hz), 4.55(t, 1H, J=9 Hz), 7.02(d, 1H, J=9 Hz), 7.12(t, 2H, J=9 Hz), 7.23–7.29 (m, 2H), 7.45(d, 1H, J=9 Hz), 8.40(t, 1H, J=6 Hz), 8.73(s, 2H), 10.45(s, 1H)

IR(KBr, $cm^{-1}$): 3368, 3145, 1662, 1647, 1510, 1491, 1286

MASS(m/e): 509 ($M^+$)

Elemental analysis: $C_{24}H_{20}N_3O_4FCl_2$

Found (%) C,57.16; H,4.00; N,8.33. Calcd. (%) C,57.20; H,4.99; N,8.33.

EXAMPLE 30

(±)-3-[(4-Chlorobenzyl)aminocarbonyl]methyl-4-[(3,5-dichloro-4-pyridyl)aminocarbonyl]-7-methoxy-2,3-dihydro-benzofuran (Compound 30)

Substantially the same procedure as in Example 13 was repeated using Compound 9 (0.20 g) obtained in Example 9 and 4-chlorobenzylamine to give Compound 30 (0.15 g, 58%) as a white solid.

Melting point: 283–286° C.

NMR(DMSO-$d_6$, δ, ppm): 2.30(dd, 1H, J=16 Hz, 12 Hz), 2.76(dd, 1H, J=2 Hz, 16 Hz), 3.34(s, 3H), 4.20–4.26(m, 1H), 4.25(d, 2H, J=6 Hz), 4.34(dd, 1H, J=3 Hz, 9 Hz), 4.56(t, 1H, J=9 Hz), 7.04(d, 1H, J=9 Hz), 7.25(d, 2H, J=8 Hz), 7.37(d, 2H, J=8 Hz), 7.47(d, 1H, J=9 Hz), 8.38(t, 1H, J=6 Hz), 8.75(s, 2H), 10.48(s, 1H)

IR(KBr, $cm^{-1}$): 3307, 3296, 1660, 1647, 1489, 1286

MASS(m/e): 520($M^+$)

Elemental analysis: $C_{24}H_{20}N_3O_4Cl_3$

Found (%) C,55.35; H,3.87; N,8.07. Calcd. (%) C,55.22; H,3.77; N,7.98.

EXAMPLE 31

(±)-3-[(2-Chlorobenzyl)aminocarbonyl]methyl-4-[(3,5-dichloro-4-pyridyl)aminocarbonyl]-7-methoxy-2,3-dihydro-benzofuran (Compound 31)

Substantially the same procedure as in Example 13 was repeated using Compound 9 (0.20 g) obtained in Example 9 and 2-chlorobenzylamine to give Compound 31 (0.15 g, 58%) as a white solid.

Melting point: 288–289° C.

NMR(DMSO-$d_6$, δ, ppm): 2.36(dd, 1H, J=15 Hz, 12 Hz), 2.80(dd, 1H, J=3 Hz, 16 Hz), 3.86(s, 3H), 4.22–4.17(m, 1H), 4.30–4.38(m, 3H), 4.57(t, 1H, J=9 Hz), 7.39(d, 1H, J=8 Hz), 7.27–7.31(m, 3H), 7.43–7.42(m, 1H), 7.47(d, 1H, J=8 Hz), 8.35(broad s, 1H), 8.74(s, 2H)

IR(KBr, $cm^{-1}$): 3350, 1660, 1651, 1547, 1493, 1286

MASS(m/e): 519($M^+$), 521(M++2)

Elemental analysis: $C_{24}H_{20}N_3O_4Cl_3$

Found (%) C,55.35; H,3.87; N,8.07. Calcd. (%) C,55.42; H,3.86; N,8.02.

EXAMPLE 32

(±)-4-[(3,5-Dichloro-4-pyridyl)aminocarbonyl]-3-[(3,5-dichloro-4-pyridyl)aminocarbonyl]methyl-7-methoxy-2,3-dihydrobenzofuran (Compound 32)

Substantially the same procedure as in Example 13 was repeated using Compound 9 (0.30 g) obtained in Example 9 and 4-amino-3,5-dichloropyridine to give Compound 32 (0.06 g, 17%) as a white solid.

Melting point: >300° C.

NMR(DMSO-$d_6$, δ, ppm): 2.55–2.61(m, 1H), 3.01–3.07 (m, 1H), 3.87(s, 3H), 4.25–4.28(m, 1H), 4.40(dd, 1H, J=2 Hz, 8 Hz), 4.55(t, 1H, J=8 Hz), 7.07(d, 1H, J=9 Hz), 7.50(d, 1H, J=9 Hz), 8.68(s, 2H), 8.75(s, 2H), 10.32(broad s, 2H), 10.52(broad s, 2H)

IR(KBr, $cm^{-1}$): 3260(br), 1684, 1653, 1487, 1282

MASS(m/e): 542($M^+$)

Elemental analysis: $C_{22}H_{16}N_4O_4Cl_2$

Found (%) C,48.73; H,2.97; N,10.33. Calcd. (%) C,48.53; H,2.91; N,10.12.

EXAMPLE 33

4-[(3,5-Dichloro-4-pyridyl)aminocarbonyl]-7-methoxy-benzofuran (Compound 33)

Substantially the same procedure as in Example 1 was repeated using Compound IIac (0.22 g) obtained in Reference Example 29 to give Compound 33 (0.27 g, 68%) as a white solid.

NMR(DMSO-$d_6$, δ, ppm): 4.05(s, 3H), 7.10(d, J=8.7 Hz, 1H), 7.31(d, J=1.5 Hz, 1H), 7.99(d, J=8.7 Hz, 1H), 8.10(d, J=1.5 Hz, 1H), 8.77(s, 2 H), 10.5(s, 1H)

MASS(m/e): 336($M^+$)

IR(KBr, $cm^{-1}$): 1650, 1490, 1280

Elemental analysis: $C_{15}H_{10}N_2O_3Cl_2$

Found (%) C,53.31; H,2.85; N,8.06. Calcd. (%) C,53.44; H,2.99; N,8.31.

EXAMPLE 34

2-Cyano-4-(3,5-dichloropyridin-4-ylaminocarbonyl)-7-methoxybenzofuran (Compound 34)

Substantially the same procedure as in Example 1 was repeated using Compound IIab (0.26 g) obtained in Reference Example 28 to give Compound 34 (0.10 g, 23.9%) as a white solid.

Melting point: 246–250° C.

NMR(DMSO-$d_6$, δ, ppm): 4.10(s, 3H), 7.40(d, J=8.7 Hz, 1H), 8.15(d, J=8.7 Hz, 1H), 8.32(s, 1H), 8.79(s, 2H), 10.7(s, 1H)

IR(KBr, $cm^{-1}$): 2240, 1650, 1490, 1280

MASS (m/z): 362 ($M^+$)

Elemental analysis: $C_{16}H_9Cl_2N_3O_3$

Found (%) C,53.31; H,2.30; N,11.30. Calcd. (%) C,53.06; H,2.50; N,11.60.

EXAMPLE 35

2-Benzoyl-4-[(3,5-dichloro-4-pyridyl)aminocarbonyl)]-7-methoxybenzofuran (Compound 35)

Compound 34 (0.46 g) obtained in Example 34 was suspended in tetrahydrofuran, 1.0M phenylmagnesium bromide (28.2 g) was dropwise added thereto under stirring at 0° C., and then the temperature of the mixture was slowly raised to room temperature while stirring for 3 hours. Diluted hydrochloric acid was added thereto at 0° C. followed by stirring for one hour. The mixture was extracted with ethyl acetate, the organic layer was washed with a saturated saline and dried over magnesium sulfate, and the solvent was distilled off under reduced pressure. The residue was purified by silica gel column chromatography (toluene:ethyl acetate=4:1) and recrystallized from ethanol to give Compound 35 (0.38 g, 67.3%) as a colorless solid.

Melting point: 217° C.

NMR(DMSO-$d_6$, δ, ppm): 4.11(s, 3H), 7.37(d, 1H, J=8 Hz), 7.61(d, 1H, J=7 Hz), 7.65(s, 1H), 7.72(d, 1H, J=7 Hz), 7.97(s, 3H), 8.01(s, 3H), 8.14(d, 1H, J=8 Hz), 8.76(s, 2H), 10.70(s, 1H)

IR(KBr, $cm^{-1}$): 3307(br), 1647, 1487, 1286, 1271

MASS(m/e): 441($M^+$)

Elemental analysis: $C_{22}H_{14}N_2O_4Cl_2$

Found (%) C,59.88; H,3.20; N,6.35. Calcd. (%) C,59.80; H,3.18; N,6.28.

EXAMPLE 36

2-Butyl-4-(3,5-dichloropyridin-4-ylaminocarbonyl)-7-methoxybenzofuran (Compound 36)

Substantially the same procedure as in Example 1 was repeated using Compound IIad (0.47 g) obtained in Reference Example 30 to give Compound 36 (0.25 g, 34%) as a white solid.

Melting point: 160–164° C.

NMR(DMSO-$d_6$, δ, ppm): 0.92(t, J=8 Hz, 3H), 1.28–1.47 (m, 2H), 1.59–1.78(m, 2H), 2.80 (t, J=7 Hz, 2H), 4.01 (s, 3H), 7.00(s, 1H), 7.04(d, J=8 Hz, 1H), 7.92(d, J=8 Hz, 1H), 8.75(s, 2H), 10.4(s, 1H)

MASS (m/e): 392($M^+$)

IR(KBr, $cm^{-1}$): 1658, 1490, 1285

Elemental analysis: $C_{19}H_{18}Cl_2N_2O_3$

Found (%) C,58.08; H,4.68; N,7.06. Calcd. (%) C,58.03; H,4.61; N,7.12.

EXAMPLE 37

2-Benzyl-4-[(3,5-dichloro-4-pyridyl)aminocarbonyl]-7-methoxybenzofuran (Compound 37)

Substantially the same procedure as in Example 1 was repeated using Compound IIag (0.30 g) obtained in Reference Example 33 to give Compound 37 (0.25 g, 77%).

Melting point: 141–142° C.

NMR($CDCl_3$, δ, ppm): 4.17(s, 2H), 4.41(s, 3H), 6.43(s, 1H), 7.25(d, 1H, J=8 Hz), 7.29–7.64(m, 5H), 8.07 (d, 1H, J=8 Hz), 8.91(s, 2H), 9.97(broad s, 1H)

IR(KBr, $cm^{-1}$): 3298(br), 1674, 1547, 1491, 1477, 1271

MASS(m/e): 306($M^+$)

Elemental analysis: $C_{22}H_{16}N_2O_3Cl_2$

Found (%) C,61.84; H,3.77; N,6.56. Calcd. (%) C,61.79; H,3.75; N,6.48.

EXAMPLE 38

4-[(3,5-Dichloro-4-pyridyl)aminocarbonyl]-7-methoxy-2-(4-pyridyl)benzofuran (Compound 38)

Substantially the same procedure as in Example 1 was repeated using Compound IIae (0.21 g) obtained in Reference Example 31 to give Compound 38 (0.141 g, 50.1%) as a white solid.

Melting point: 289–290° C.

NMR(DMSO-$d_6$, δ, ppm): 4.10(s, 3H), 7.20(d, J=9 Hz, 1H), 7.90(d, J=7 Hz, 2H), 8.07(d, J=9 Hz, 1H), 8.09(s, 1H), 8.69(d, J=7 Hz, 2H), 8.80(s, 2H), 10.58(bs, 1H)

IR(KBr, $cm^{-1}$): 3300(br), 1650, 1490, 1460, 1290

MASS(m/e): 417, 415, 413($M^+$), 253, 252

Elemental analysis: $C_{20}H_{13}N_3O_3Cl_2$

Found (%) C,57.74; H,3.15; N,9.91. Calcd. (%) C,57.97; H,3.16; N,10.15.

EXAMPLE 39

7-Methoxy-2-(4-pyridyl)-4-(4-pyridylaminocarbonyl)-benzofuran.2 hydrochloride (Compound 39)

Substantially the same procedure as in Example 6 was repeated using Compound IIae (3.0 g) obtained in Reference Example 31 to give 7-methoxy-2-(4-pyridyl)-4-(4-pyridylaminocarbonyl)benzofuran (1.45 g, 42.8%) as a white solid. Then, substantially the same procedure as in Example 17 was repeated using the above-obtained product to give Compound 39.

Melting point: 214–217° C.

NMR(DMSO-$d_6$, δ, ppm): 4.11(s, 3H), 7.29(d, J=9 Hz, 1H), 8.39(d, J=9 Hz, 1H), 8.49(d, J=7 Hz, 2H), 8.52(d, J=6 Hz, 2H), 8.55(s, 1H), 8.80(d, J=7 Hz, 2H), 8.96(d, J=6 Hz, 2H), 12.05(bs, 1H)

IR(KBr, $cm^{-1}$): 3400(br), 1685, 1635, 1610, 1505, 1270

MASS(m/e): 345($M^+$), 252

Elemental analysis: $C_{20}H_{15}N_3O_3.2.0HCl.3.0H_2O$

Found (%) C,50.87; H,4.78; N,8.76. Calcd. (%) C,50.86; H,4.91; N,8.90.

EXAMPLE 40

4-[(3,5-Dichloro-4-pyridyl)aminocarbonyl]-7-methoxy-2-(2-pyridyl)benzofuran (Compound 40)

Substantially the same procedure as in Example 1 was repeated using Compound IIaf (0.40 g) obtained in Reference Example 32 to give Compound 40 (0.162 g, 29.9%) as a white solid.

Melting point: 263–264° C.

NMR(DMSO-$d_6$, δ, ppm): 4.12(s, 3H), 7.20(d, J=9 Hz, 1H), 7.44(ddd, J=2 Hz, 5 Hz, 7 Hz, 1H), 7.93(s, 1H), 7.97(dd, J=2 Hz, 8 Hz, 1H), 7.99(dd, J=7 Hz, 8 Hz, 1H), 8.02(d, J=9 Hz, 1H), 8.70(d, J=5 Hz, 1H), 8.78(s, 2H), 10.55(bs, 1H)

IR(KBr, $cm^{-1}$): 3200(br), 1650, 1590, 1500, 1290, 1280

MASS(m/e): 417, 415, 413($M^+$), 252

Elemental analysis: $C_{20}H_{13}N_3O_3Cl_2.0.1H_2O$

Found (%) C,57.66; H,3.06; N,9.91. Calcd. (%) C,57.74; H,3.20; N,10.10.

EXAMPLE 41

7-Methoxy-2-(2-pyridyl)-4-[(4-pyridylamino)carbonyl]-benzofuran.2 hydrochloride (Compound 41)

Substantially the same procedure as in Example 6 was repeated using Compound IIaf (4.87 g) obtained in Reference Example 32 to give 7-methoxy-2-(2-pyridyl)-4-[(4-pyridylamino)carbonyl]benzofuran (4.24 g, 77.1%) as a white solid. Then, substantially the same procedure as in Example 17 was repeated using the above-obtained product to give Compound 41.

Melting point: 251–254° C.

NMR(DMSO-$d_6$/$D_2O$, δ, ppm): 4.17(s, 3H), 7.13(d, J=9 Hz, 1H), 7.58(dd, J=5 Hz, 7 Hz, 1H), 7.9–8.1(m, 2H), 7.98(s, 1H), 8.12(d, J=9 Hz, 1H), 8.29(d, J=7 Hz, 2H), 8.64(d, J=7 Hz, 2H), 8.66(d, J=5 Hz, 1H)

IR(KBr, $cm^{-1}$): 3400(br), 1685, 1625, 1610, 1505, 1280

MASS(m/e): 345($M^+$), 252

Elemental analysis: $C_{20}H_{15}N_3O_3.2.0HCl.1.9H_2O$

Found (%) C,52.99; H,4.30; N,9.10. Calcd. (%) C,53.09; H,4.63; N,9.29.

EXAMPLE 42

4-[(3,5-Dichloro-4-pyridyl)aminocarbonyl]-7-methoxy-3-phenylbenzofuran (Compound 42)

Substantially the same procedure as in Example 1 was repeated using Compound IIah (0.29 g) obtained in Reference Example 34 to give Compound 42 (0.34 g, 76%) as a white solid.

Melting point: 177–179° C.

NMR($CDCl_3$, δ, ppm): 4.12(s, 3H), 6.95(d, J=9 Hz, 1H), 7.17–7.43(m, 5H), 7.76(s, 1H), 7.89(d, J=9 Hz, 1H), 8.44(s, 2H)

IR(KBr, $cm^{-1}$): 1495, 1669, 1402, 1279

MASS(m/e): 412($M^+$)

Elemental analysis: $C_{21}H_{14}N_2O_3Cl_2$

Found (%) C,60.99; H,3.40; N,6.56. Calcd. (%) C,61.03; H,3.41; N,6.78.

EXAMPLE 43

3-Ethoxycarbonylmethyl-4-[(3,5-dichloro-4-pyridyl)-aminocarbonyl]-7-methoxybenzofuran (Compound 43)

Substantially the same procedure as in Example 1 was repeated using Compound IIai (0.80 g) obtained in Reference Example 35 to give Compound 43 (0.47 g, 39%) as a white solid.

Melting point: 216–218° C.

NMR($CDCl_3$, δ, ppm): 1.10(t, J=7 Hz, 3H), 3.91(s, 2H), 4.00(q, J=7 Hz, 2H), 4.08(s, 3H), 6.85(d, J=8 Hz, 1H), 7.66(s, 1H), 7.71(d, J=8 Hz, 1H), 7.75(s, 1H), 8.56(s, 2H)

Elemental analysis: $C_{19}H_{16}Cl_2N_2O_5$

Found (%) C,54.01; H,3.75; N,6.45. Calcd. (%) C,53.92; H,3.81; N,6.62.

EXAMPLE 44

3-Carboxymethyl-4-[(3,5-dichloro-4-pyridyl)aminocarbonyl]-7-methoxybenzofuran (Compound 44)

Substantially the same procedure as in Example 9 was repeated using Compound 43 (0.64 g) obtained in Reference Example 43 to give Compound 44 (0.27 g, 47%) as a white solid.

Melting point: 270–278° C.

NMR(DMSO-$d_6$, δ, ppm): 3.79(s, 2H), 4.02(s, 3H), 7.09 (d, J=9 Hz, 1H), 7.77(d, J=9 Hz, 2H), 7.97(s, 1H), 8.74(s, 2H), 10.6–10.7(broad s, 1H), 12.0–12.1(broad s, 1H)

Elemental analysis: $C_{17}H_{12}C_{12}N_2O_5$

Found (%) C,51.38; H,2.95; N,6.92. Calcd. (%) C,51.67; H,3.06; N,7.09.

EXAMPLE 45

4-[2-(3,5-Dichloro-4-pyridyl)ethyl]-7-methoxy-2,2-dimethyl-2,3-dihydrobenzofuran (Compound 45)

(Step A) (±)-4-[2-(3,5-Dichloro-4-pyridyl)-1-hydroxyethyl]-7-methoxy-2,2-dimethyl-2,3-dihydrobenzofuran (Compound 45a)

Under an argon atmosphere, a solution (20 ml) of 3,5-dichloro-4-methylpyridine (1.4 g) in THF was cooled to −78° C., and then a 1.69M solution of butyl lithium in hexane (6.3 ml) was dropwise added thereto, followed by stirring at the same temperature for one hour. A solution (10 ml) of Compound IIa (2.0 g) obtained in Reference Example 1 in THF was slowly and dropwise added to the mixture, followed by stirring at −78° C. for 2 hours and then at 0° C. for one hour. The reaction solution was poured into water and the mixture was extracted with ether. The organic layer was washed with a saturated saline and dried over anhydrous magnesium sulfate, and the solvent was distilled off under reduced pressure. The residue was purified by silica gel column chromatography (chloroform) to give Compound 45a (3.3 g, 93.4%) as colorless crystals.

Melting point: 100–104° C.

NMR(DMSO-$d_6$, δ, ppm): 1.30(s, 3H), 1.38(s, 3H), 2.77 (d, J=15.8 Hz, 1H), 3.04(d, J=15.8 Hz, 1H), 3.04–3.11(m, 1H), 3.24–3.32(m, 1H), 3.71(s, 3H), 4.82–4.89 (m, 1H), 5.41(d, J=3.96 Hz, 1H), 6.76(s, 2H), 8.55(s, 2H)

MASS(m/e): 369, 367($M^+$), 207

IR(KBr, $cm^{-1}$): 3396(br), 1625, 1507

(Step B) (Compound 45)

Under an argon atmosphere, a solution (80 ml) of Compound 45a (3.0 g) obtained in Step A in methylene chloride was cooled to −78° C., and then boron trifluoride ether complex (2.0 ml) and triethylsilane (3.9 ml) were successively added thereto, followed by stirring at room temperature for 3 hours. The reaction solution was poured into a saturated aqueous solution of sodium bicarbonate and the mixture was extracted with chloroform. The organic layer was washed with a saturated saline and dried over anhydrous magnesium sulfate, and the solvent was distilled off under reduced pressure. The residue was purified by silica gel column chromatography (chloroform/methanol=20/1) to give Compound 45 (1.57 g, 54.7%) as colorless crystals.

Melting point: 128–133° C.

NMR(DMSO-$d_6$, δ, ppm): 1.38(s, 6H), 2.68(t, J=7.25 Hz, 2H), 2.91(s, 2H), 3.07(t, J=7.26 Hz, 2H), 3.71(s, 3H), 6.54(d, J=8.25 Hz, 1H), 6.72(d, J=8.25 Hz, 1H), 8.58(s, 2H).

MASS(m/e): 353, 351($M^+$), 191

IR($cm^{-1}$): 1623, 1593, 1499

Elemental analysis: $C_{18}H_{19}Cl_2NO_2$

Found (%) C,61.37; H,5.41; N,3.92. Calcd. (%) C,61.37; H,5.44; N,3.98.

EXAMPLE 46

7-Methoxy-2,2-dimethyl-4-[2-(4-pyridyl)ethyl]-2,3-dihydrobenzofuran (Compound 46)

(Step A) 4-[1-Hydroxy-2-(4-pyridyl)ethyl]-7-methoxy-2,2-dimethyl-2,3-dihydrobenzofuran (Compound 46a)

Under an argon atmosphere, a solution (35 ml) of 4-methylpyridine (0.78 ml) in THF was cooled to −78° C., and then a 1.69M solution (5.17 ml) of butyl lithium in hexane was dropwise added thereto, followed by stirring at the same temperature for one hour. A solution (35 ml) of Compound IIa (1.5 g) obtained in Reference Example 1 in THF was slowly and dropwise added to the mixture, followed by stirring at −78° C. for 2 hours and then at 0° C. for one hour. The reaction solution was poured into water and the mixture was extracted with ether. The organic layer was washed with a saturated saline and dried over anhydrous magnesium sulfate, and the solvent was distilled off under reduced pressure. The residue was purified by silica gel column chromatography (chloroform/methanol=20/1) to give Compound 46a (1.17 g, 53.8%) as a colorless oily substance.

NMR(DMSO-$d_6$, δ, ppm): 1.29(s, 3H), 1.35(s, 3H), 2.75 (d, J=15.8 Hz, 1H), 2.81–2.94(m, 2H), 2.94(d, J=15.8 Hz, 1H), 3.71(s, 3H), 4.68(m, 1H), 5.27(d, J=4.0 Hz, 1H), 6.76(s, 2H), 7.12(d, J=5.9 Hz, 2H), 8.39(d, J=5.9 Hz, 2H)

MASS(m/z): 299($M^+$), 207

(Step B) (Compound 46)

Under an argon atmosphere, a solution (7 ml) of Compound 46a (0.2 g) obtained in Step A in methylene chloride was cooled to −78° C., and then boron trifluoride ether complex (0.17 ml) and triethylsilane (0.33 ml) were successively added thereto, followed by stirring at 0° C. for 2 hours. The reaction solution was poured into a saturated aqueous solution of sodium bicarbonate and the mixture was extracted with chloroform. The organic layer was washed with a saturated saline and dried over anhydrous magnesium sulfate, and the solvent was distilled off under reduced pressure. The residue was purified by silica gel column chromatography (chloroform/methanol=20/1) to give Compound 46 (0.11 g, 58.1%) as a colorless oily substance.

NMR(DMSO-$d_6$, δ, ppm): 1.35(s, 6H), 2.70–2.82(m, 4H), 2.83(s, 2H), 3.70(s, 3H), 6.58(d, J=8.3 Hz, 1H), 6.71(d, J=8.3 Hz, 1H), 7.19(d, J=5.9 Hz, 2H), 8.43 (d, J=5.9 Hz, 2H)

IR($cm^{-1}$): 1602, 1511, 1505, 1440

MASS(m/z): 283($M^+$), 191

Elemental analysis: $C_{18}H_{21}NO_2.0.3H_2O$

Found (%) C,74.87; H,7.54; N,4.85. Calcd. (%) C,75.03; H,7.44; N,4.89.

EXAMPLE 47

(±) 7-Methoxy-2,2-dimethyl-7-methoxy-4-[1-phenyl-2-(4-pyridyl)ethyl]-2,3-dihydrobenzofuran (Compound 47)

(Step A) (±)-4-[1-Hydroxy-1-phenyl-2-(4-pyridyl)ethyl]-7-methoxy-2,2-dimethyl-2,3-dihydrobenzofuran (Compound 47a)

Under an argon atmosphere, a solution of 4-methylpyridine (0.83 ml) in THF (50 ml) was cooled to −78° C., and then a 1.69M solution (5.0 ml) of butyl lithium in hexane was dropwise added thereto, followed by stirring at the same temperature for one hour. A solution of Compound IIaj (2.0 g) obtained in Reference Example 36 in THF (20 ml) was slowly and dropwise added to the mixture, followed by stirring at 0° C. for 2 hours. The reaction solution was poured into water and the mixture was extracted with ether. The organic layer was washed with a saturated saline and dried over anhydrous magnesium sulfate, and the solvent was distilled off under reduced pressure. The residue was purified by silica gel column chromatography (chloroform/methanol=50/1) to give Compound 47a (0.87 g, 32.5%) as yellowish brown crystals.

Melting point: 78–81° C.

NMR(DMSO-$d_6$; δ, ppm): 1.14(s, 3H), 1.19(s, 3H), 2.39 (d, J=16.1 Hz, 1H), 2.67(d, J=16.1 Hz, 1H), 3.51(s, 2H), 3.72(s, 3H), 5.70(s, 1H), 6.74(d, J=8.6 Hz, 1H), 6.81(d, J=5.9 Hz, 2H), 6.92(d, J=8.6 Hz, 1H), 7.15–7.19(m, 5H), 8.23(d, J=5.6 Hz, 2H)

IR(KBr, $cm^{-1}$): 3500–3000(br), 1606, 1506, 1446, 1427

MASS(m/z): 375($M^+$), 283

(Step B) (Compound 47)

Under an argon atmosphere, a solution of Compound 47a (0.4 g) obtained in Step A in methylene chloride (3 ml) was cooled to −78° C., and then boron trifluoride ether complex (0.3 ml) and triethylsilane (0.52 ml) were successively added thereto, followed by stirring at 0° C. for 2 hours. The reaction solution was poured into a saturated aqueous solution of sodium bicarbonate and the mixture was extracted with chloroform. The organic layer was washed with a saturated saline and dried over anhydrous magnesium sulfate, and the solvent was distilled off under reduced pressure. The residue was purified by silica gel column chromatography (chloroform/methanol=30/1) to give Compound 47 (0.27 g, 56.7%) as a yellowish brown oily substance.

NMR(DMSO-$d_6$; δ, ppm): 1.23(s, 3H), 1.30(s, 3H), 2.75 (s, 2H), 3.30–3.34(m, 2H), 3.68(s, 3H), 4.22(t, J=8.3 Hz, 1H), 6.74(d, J=8.6 Hz, 1H), 6.81(d, J=8.6 Hz, 1H), 7.13(d, J=5.9 Hz, 2H), 7.15–7.26(m, 5H), 8.34(d, J=5.9 Hz, 2H)

IR($cm^{-1}$): 1622, 1598, 1503, 1435

MASS(m/z): 359($M^+$), 267

EXAMPLE 48

7-Methoxy-2,2-dimethyl-4-(4-pyridylthiomethyl)-2,3-dihydrobenzofuran (Compound 48)

(Step A) 4-Hydroxymethyl-2,2-dimethyl-7-methoxy-2,3-dihydrobenzofuran (Compound 48a)

Compound IIa (4.0 g) obtained in Reference Example 1 was added to a suspension of lithium aluminium hydride (0.52 g) in ether (20 ml), followed by stirring at room temperature for one hour. The reaction solution was poured into ice and the reaction mixture was adjusted to pH 3 by adding dropwise 1N hydrochloric acid (10 ml). The ether layer was separated, washed with a saturated saline, and dried over anhydrous magnesium sulfate, and the solvent was distilled off under reduced pressure. The residue was purified by silica gel column chromatography (chloroform/methanol=60/1) to give Compound 48a (0.32 g, 79.2%) as a colorless oily substance.

NMR(DMSO-$d_6$, δ, ppm): 1.40(s, 6H), 2.97(s, 2H), 3.71 (s, 3H), 4.33(d, J=5.6 Hz, 2H), 4.91(t, J=5.6 Hz, 1H), 6.70(d, J=8.3 Hz, 1H), 6.75(d, J=8.2 Hz, 1H)

MASS(m/z): 208($M^+$)

(Step B) (Compound 48)

Compound 48a (2.0 g) obtained in Step A was dissolved in methylene chloride (100 ml), and then diisopropylethylamine (5.0 ml) and methanesulfonyl chloride (0.8 ml) were added thereto, followed by stirring at room temperature for one hour. At the same temperature, 4-mercaptopyridine (1.4 g) was added to the reaction solution, and the mixture was stirred for 30 minutes. Water was added to the reaction solution and the mixture was extracted with methylene chloride. The organic layer was washed with a saturated saline and dried over anhydrous magnesium sulfate, and the solvent was distilled off under reduced pressure. The residue was purified by silica gel column chromatography (chloroform/methanol=30/1) to give Compound 48 (1.4 g, 48.3%) as colorless crystals.

Melting point: 109–113° C.

NMR(DMSO-$d_6$; δ, ppm): 1.41(s, 6H), 3.06(s, 2H), 3.72 (s, 3H), 4.22(s, 2H), 6.74(d, J=8.4 Hz, 1H), 6.80 (d, J=8.4 Hz, 1H), 7.29(d, J=6.4 Hz, 2H), 7.36(d, J=6.4 Hz, 2H)

IR(KBr, $cm^{-1}$): 1572, 1506, 1450, 1439

MASS(m/z): 301($M^+$), 191

Elemental analysis: $C_{17}H_{19}NO_2S.0.1H_2O$

Found (%) C,67.34; H,6.38; N,4.62. Calcd. (%) C,67.30; H,6.45; N,4.93.

EXAMPLE 49

(±)-7-Methoxy-2,2-dimethyl-4-[1-phenyl-1-(4-pyridylthio)methyl]-2,3-dihydrobenzofuran (Compound 49)

Substantially the same procedure as in Step B of Example 48 was repeated using Compound IIaj-a (0.22 g) obtained in Step A of Reference Example 36 to give Compound 49 (0.20 g, 68.2%) as a pale-yellow oily substance.

NMR(DMSO-$d_6$, δ, ppm): 1.35(s, 3H), 1.40(s, 3H), 2.90 (d, J=15.3 Hz, 1H), 3.13(d, J=15.8 Hz, 1H), 3.32(s, 3H), 5.99(s, 1H), 6.77(d, J=8.4 Hz, 1H), 6.83(d, J=8.4 Hz, 1H), 7.18(d, J=7.0 Hz, 2H), 7.26–7.48(m, 5H), 8.30(d, J=6.9 Hz, 2H)

IR($cm^{-1}$): 1600, 1574, 1506, 1439

EXAMPLE 50

4-[2-(3,5-Dichloro-4-pyridyl)ethyl]-2,2-diethyl-7-methoxy-2,3-dihydrobenzofuran.methanesulfonate (Compound 50)

(Step A) (±)-4-[2-(3,5-Dichloro-4-pyridyl)-1-hydroxyethyl]-2,2-diethyl-7-methoxy-2,3-dihydrobenzofuran (Compound 50a)

Substantially the same procedure as in Step A of Example 45 was repeated using Compound IIb (9.0 g) obtained in Reference Example 2 to give Compound 50a (7.8 g, 51.1%) as a pale-yellow oily substance.

NMR(DMSO-$d_6$, δ, ppm): 0.77(t, J=6.9 Hz, 3H), 0.85(t, J=7.4 Hz, 3H), 1.54–1.58 (m, 2H), 1.64(q, J=7.4 Hz, 2H), 2.73(d, J=15.8 Hz, 1H), 3.00(d, J=16.3 Hz, 1H), 3.06–3.13 (m, 1H), 3.25–3.30(m, 1H), 3.72(s, 3H), 4.86–4.91(m, 1H), 5.40 (d, J=4.0 Hz, 1H), 6.73(s, 2H), 8.54(s, 2H)

MASS(m/e): 397, 395($M^+$), 235

(Step B) (Compound 50)

Substantially the same procedure as in Step B of Example 45 was repeated using Compound 50a (4.6 g) obtained in Step A to give 4-[2-(3,5-dichloro-4-pyridyl)ethyl]-2,2-diethyl-7-methoxy-2,3-dihydrobenzofuran (2.6 g, 59.6%) as a colorless oily substance. The obtained colorless oily substance was dissolved in diethyl ether and methane-sulfonic acid was added thereto. The precipitated crystals were collected by filtration, washed with diethyl ether, and dried to give Compound 50.

Melting point: 87–90° C.

NMR(DMSO-$d_6$, δ, ppm): 0.83(t, d=7.4 Hz, 6H), 1.64(q, d=7.4 Hz, 4H), 2.49(s, 3H), 2.70(t, J=8.4 Hz, 2H), 2.87(s, 2H), 3.08(t, J=8.4 Hz, 2H), 3.71(s, 3H), 6.50(d, J=8.4 Hz, 1H), 6.70(d, J=8.4 Hz, 1H), 8.58 (s, 2H)

MASS(m/e): 381, 379($M^+$), 219

IR($cm^{-1}$): 2600–2200(br), 1506

Elemental analysis: $C_{20}H_{23}Cl_2NO_2.CH_3SO_3H$

Found (%) C,46.39; H,5.54; N,2.41. Calcd. (%) C,46.15; H,5.46; N,2.45.

MASS(m/z): 377($M^+$), 267

EXAMPLE 51

2,2-Diethyl-7-methoxy-4-[2-(4-pyridyl)ethyl]-2,3-dihydrobenzofuran.hydrochloride (Compound 51)

(Step A) (±)-2,2-Diethyl-4-[1-hydroxy-2-(4-pyridyl)ethyl]-7-methoxy-2,3-dihydrobenzofuran (Compound 51a)

Substantially the same procedure as in Step A of Example 46 was repeated using Compound IIb (20 g) obtained in Reference Example 2 to give Compound 51a (27.6 g, 98.7%) as a colorless oily substance.

NMR(DMSO-$d_6$, δ, ppm): 0.74–0.86(m, 6H), 1.51–1.66 (m, 4H), 2.71(d, J=15.8 Hz, 1H), 2.79–2.96(m, 3H), 3.72(s, 3H), 4.71(m, 1H), 5.27(d, J=4.45 Hz, 1H), 6.74(s, 2H), 7.12(d, J=5.9 Hz, 2H), 8.39(d, J=5.9 Hz, 2H)

MASS(m/e): 327($M^+$), 235

(Step B) (Compound 51)

Substantially the same procedure as in Step B of Example 46 was repeated using Compound 51a (23 g) obtained in Step A to give 2,2-diethyl-7-methoxy-4-[2-(4-pyridyl)-ethyl]-2,3-dihydrobenzofuran (8.46 g, 38.6%) as a colorless oily substance. The obtained colorless oily substance was dissolved in ethyl acetate and a hydrochloric acid-ethyl acetate solution was added thereto. The precipitated crystals were collected by filtration, washed with ethyl acetate, and dried to give Compound 51.

Melting point: 189–192° C.

NMR(DMSO-$d_6$, δ, ppm): 0.83(t, J=7.4 Hz, 6H), 1.63(q, J=7.4 Hz, 4H), 2.84(t, J=6.9 Hz, 2H), 2.87(s, 2H), 3.13(t, J=6.9 Hz, 2H), 3.71(s, 3H), 6.54(d, J=8.4 Hz, 1H), 6.69(d, J=8.4 Hz, 1H), 7.89(d, J=6.4 Hz, 2H), 8.80(d, J=6.4 Hz, 2H)

MASS(m/e): 312($M^+$), 220

IR($cm^{-1}$): 2970, 1635, 1593, 1508

Elemental analysis: $C_{20}H_{25}NO_2$.HCl

Found (%) C,69.06; H,7.69; N,4.00. Calcd. (%) C,69.05; H,7.53; N,4.03.

EXAMPLE 52

4-[2-(3,5-Dichloro-4-pyridyl)ethyl]-7-methoxy-spiro[2,3-dihydrobenzofuran-2,1'-cyclopentane]. methanesulfonate (Compound 52)

(Step A) (±)-4-[2-(3,5-Dichloro-4-pyridyl)-1-hydroxyethyl]-7-methoxy-spiro[2,3-dihydrobenzofuran-2,1'-cyclopentane] (Compound 52a)

Substantially the same procedure as in Step A of Example 45 was repeated using Compound IIc (8.0 g) obtained in Reference Example 3 to give Compound 52a (7.0 g, 51.4%) as a colorless oily substance.

NMR(DMSO-$d_6$, δ, ppm): 1.57–1.91(m, 8H), 2.93(d, J=16.2 Hz, 1H), 3.06–3.13(m, 1H), 3.20(d, J=16.2 Hz, 1H), 3.24–3.30(m, 1H), 3.32(s, 3H), 4.84–4.90(m, 1H), 5.40(d, J=3.6 Hz, 1H), 6.74(s, 2H), 8.54(s, 2H)

MASS(m/e): 395, 393($M^+$)

(Step B) (Compound 52)

Substantially the same procedure as in Step B of Example 45 was repeated using Compound 52a (2.8 g) obtained in Step A to give 4-[2-(3,5-dichloro-4-pyridyl)ethyl]-7-methoxy-spiro[2,3-dihydrobenzofuran-2,1'-cyclopentane] (1.1 g, 40%) as a pale-yellow oily substance. The obtained colorless oily substance was dissolved in diethyl ether and methanesulfonic acid was added thereto. The precipitated crystals were collected by filtration, washed with diethyl ether, and dried to give Compound 52.

Melting point: 130–133° C.

NMR(DMSO-$d_6$, δ, ppm): 1.67–1.91(m, 8H), 2.42(s, 3H), 2.69(t, J=7.3 Hz, 2H), 3.4–3.09(m, 4H), 3.71(s, 3H), 6.54(d, J=8.3 Hz, 1H), 6.71(d, J=8.3 Hz, 1H), 8.58(s, 2H)

MASS(m/e): 379, 377($M^+$), 217

IR($cm^{-1}$): 2950(br), 1621, 1595, 1506

Elemental analysis: $C_{20}H_{21}Cl_2NO_2$.$CH_3SO_3H$

Found (%) C,53.09; H,5.42; N,2.92. Calcd. (%) C,53.17; H,5.31; N,2.95.

EXAMPLE 53

7-Methoxy-4-[2-(4-pyridyl)ethyl]-spiro[2,3-dihydro-benzofuran-2,1'-cyclopentane].hydrochloride (Compound 53)

(Step A) (±)-4-[1-Hydroxy-2-(4-pyridyl)ethyl-7-methoxy-spiro[2,3-dihydrobenzofuran-2,1'-cyclopentane] (Compound 53a)

Substantially the same procedure as in Step A of Example 46 was repeated using Compound IIc (3.3 g) obtained in Reference Example 3 to give Compound 53a (1.3 g, 29%) as a colorless oily substance.

NMR(DMSO-$d_6$, δ, ppm): 1.59–1.88(m, 8H), 2.78–2.96 (m, 3H), 3.10(d, J=15.8 Hz, 1H), 3.71(s, 3H), 4.70(q, J=4.3 Hz, 1H), 5.26(d, J=4.3 Hz, 1H), 6.75(s, 2H), 7.13(d, J=5.6 Hz, 2H), 8.40(d, J=5.6 Hz, 2H)

MASS(m/z): 325($M^+$), 233

(Step B) (Compound 53)

Substantially the same procedure as in Step B of Example 46 was repeated using Compound 53a (0.5 g) obtained in Step A to give 7-methoxy-4-[2-(4-pyridyl)ethyl]-spiro[2,3-dihydrobenzofuran-2,1'-cyclopentane] (0.037 g, 7.8%) as a colorless oily substance. The obtained colorless oily substance was dissolved in ethyl acetate and a hydrochloric acid-ethyl acetate solution was added thereto. The precipitated crystals were collected by filtration, washed with ethyl acetate, and dried to give Compound 53.

Melting point: 167–169° C.

NMR(DMSO-$d_6$, δ, ppm): 1.68–1.79(m, 6H), 1.84–1.92 (m, 2H), 2.83(t, J=7.9 Hz, 2H), 3.08(s, 2H), 3.11(t, J=7.9 Hz, 2H), 3.70(s, 3H), 6.56(d, J=8.4 Hz, 1H), 6.70(d, J=8.4 Hz, 1H), 7.86(d, J=6.4 Hz, 2H), 8.78(d, J=6.9 Hz, 2H)

MASS(m/e): 309($M^+$), 217

IR($cm^{-1}$): 1635, 1507

Elemental analysis: $C_{20}H_{23}NO_2$.HCl.0.$3H_2O$

Found (%) C,68.48; H,6.97; N,3.91. Calcd. (%) C,68.39; H,7.06; N,3.99.

EXAMPLE 54

4-[2-(3,5-Dichloro-4-pyridyl)ethyl]-7-methoxy-spiro[2,3-dihydrobenzofuran-2,1'-cyclohexane]. methanesulfonate (Compound 54)

(Step A) (±)-4-[2-(3,5-Dichloro-4-pyridyl)-1-hydroxyethyl]-7-methoxy-spiro[2,3-dihydrobenzofuran-2,1'-cyclohexane] (Compound 54a)

Substantially the same procedure as in Step A of Example 45 was repeated using Compound IId (6.0 g) obtained in Reference Example 4 to give Compound 54a (9.3 g, 85%) as a colorless oily substance.

Melting point: 104–108° C.

NMR(DMSO-$d_6$, δ, ppm): 1.41(broad s, 5H), 1.48–1.60 (m, 5H), 2.66(d, J=15.7 Hz, 1H), 2.98(d, J=15.8 Hz, 1H), 3.06–3.13(m, 1H), 3.25–3.30(m, 1H), 3.73(s, 3H), 4.84–4.90(m, 1H), 5.41(d, J=3.9 Hz, 1H), 6.74(s, 2H), 8.54(s, 2H)

MASS(m/e): 409, 407($M^+$), 247

(Step B) (Compound 54)

Substantially the same procedure as in Step B of Example 45 was repeated using Compound 54a (5.5 g) obtained in Step A to give 4-[2-(3,5-dichloro-4-pyridyl)ethyl]-7-methoxy-spiro[2,3-dihydrobenzofuran-2,1'-cyclohexane] (2.7 g, 51%) as a pale-yellow oily substance. The obtained colorless oily substance was dissolved in diethyl ether and methanesulfonic acid was added thereto. The precipitated crystals were collected by filtration, washed with diethyl ether, and dried to give Compound 54.

Melting point: 91–94° C.

NMR(DMSO-$d_6$, δ, ppm): 1.42 (broad s, 4H), 1.53–1.65 (m, 6H), 1.42(s, 3H), 2.70(t, J=8.4 Hz, 1H), 2.84(s, 2H), 3.08(t, J=8.4 Hz, 1H), 3.72(s, 3H), 6.53(d, J=8.4 Hz, 1H), 6.71(d, J=8.4 Hz, 1H), 8.58(s, 2H)

MASS(m/e): 393, 391($M^+$), 231

IR($cm^{-1}$): 2930(br), 1506

Elemental analysis: $C_{21}H_{23}Cl_2NO_2.1.5CH_3SO_3H$

Found (%) C,50.65; H,5.53; N,2.55. Calcd. (%) C,50.37; H,5.45; N,2.61.

EXAMPLE 55

7-Methoxy-4-[2-(4-pyridyl)ethyl]-spiro[2,3-dihydrobenzofuran-2,1'-cyclohexane].hydrochloride (Compound 55)

(Step A) (±)-4-[2-Hydroxy-2-(4-pyridyl)ethyl]-7-methoxy-spiro[2,3-dihydrobenzofuran-2,1'-cyclohexane] (Compound 55a)

Substantially the same procedure as in Step A of Example 46 was repeated using Compound IId (50 g) obtained in Reference Example 4 to give Compound 55a (64.3 g, 93.3%) as a colorless oily substance.

NMR(DMSO-$d_6$, δ, ppm): 1.40–1.76(m, 10H), 2.65(d, J=15.8 Hz, 1H), 2.77–2.96(m, 3H), 3.72(s, 3H), 4.66–4.73 (m, 1H), 5.25(d, J=4.0 Hz, 1H), 6.75(s, 2H), 7.11(dd, J=1.5 Hz, 4.5 Hz, 2H), 8.38(dd, J=1.5 Hz, 4.5 Hz, 2H)

MASS(m/e): 339($M^+$)

(Step B) (Compound 55)

Substantially the same procedure as in Step B of Example 46 was repeated using Compound 55a (30 g) obtained in Step A to give 7-methoxy-4-[2-(4-pyridyl)ethyl]-spiro[2,3-dihydrobenzofuran-2,1'-cyclohexane] (5.6g, 20%) as a colorless oily substance. The obtained colorless oily substance was dissolved in ethyl acetate and a hydrochloric acid-ethyl acetate solution was added thereto. The precipitated crystals were collected by filtration, washed with ethyl acetate, and dried to give Compound 55.

Melting point: 176–179° C.

NMR(DMSO-$d_6$, δ, ppm): 1.43–1.53(m, 4H), 1.58–1.64 (m, 6H), 2.81–2.85(m, 4H), 3.13(t, J=7.9 Hz, 2H), 3.71(s, 3H), 6.55(d, J=8.4 Hz, 1 H), 6.70(d, J=8.4 Hz, 1H), 7.89(d, J=6.4 Hz, 2H), 8.81(d, J=6.9 Hz, 2H)

MASS(m/e): 323($M^+$), 231

IR($cm^{-1}$): 1634, 1506, 1437

Elemental analysis: $C_{21}H_{25}NO_2.HCl$

Found (%) C,69.97; H,7.42; N,3.81. Calcd. (%) C,70.08; H,7.28; N,3.89.

EXAMPLE 56

(±)-4-[2-(3,5-Dichloro-4-pyridyl)ethyl]-7-methoxy-3-methyl-2,3-dihydrobenzofuran (Compound 56)

(Step A) 4-[2-(3,5-Dichloro-4-pyridyl)-1-hydroxyethyl]-7-methoxy-3-methyl-2,3-dihydrobenzofuran (Compound 56a) (a Mixture of Diastereomers)

Under an argon atmosphere, a solution (25 ml) of 3,5-dichloro-4-methylpyridine (1.1 g) in THF was cooled to −78° C., and then a 1.69M solution (4.9 ml) of butyl lithium in hexane was dropwise added to the solution, followed by stirring at the same temperature for one hour. A solution (25 ml) of Compound IIe (1.5 g) obtained in Reference Example 5 in THF was slowly and dropwise added to the mixture, followed by stirring at −78° C. for one hour and then at 0° C. for one hour. The reaction solution was poured into water and the mixture was extracted with ether. The organic layer was washed with a saturated saline and dried over anhydrous magnesium sulfate, and the solvent was distilled off under reduced pressure. The residue was purified by silica gel column chromatography (chloroform/methanol=50/1) to give Compound 56a (2.35 g, 85.0%) as a colorless oily substance.

NMR(DMSO-$d_6$, δ, ppm): (main product) 1.22(d, J=6.93 Hz, 3H), 3.10(d, J=4.95 Hz, 1H), 3.24–3.32(m, 1H), 3.75(s, 3H), 4.13–4.14(m, 1H), 4.34(t, J=8.25 Hz, 1H), 4.99–5.06 (m, 1H), 5.39(d, J=5.28 Hz, 1H), 6.86(d, J=8.35 Hz, 1H), 7.00(d, J=8.58 Hz, 1H), 8.57(s, 2H). (by-product) 1.22(d, J=6.93 Hz, 3H), 3.05(d, J=4.95 Hz, 1H), 3.24–3.32(m, 1H), 3.75(s, 3H), 4.16–4.17(m, 1H), 4.44(t, J=8.25 Hz, 1H), 4.94–4.99(m, 1H), 5.28(d, J=4.29 Hz, 1H), 6.82–6.88(m, 2H), 8.31(s, 2H)

IR($cm^{-1}$): 1625, 1507, 1439

MASS(m/z): 355($M^+$+2), 353, 191

(Step B) (Compound 56)

Under an argon atmosphere, a solution (28 ml) of Compound 56a (1.0 g) obtained in Step A in methylene chloride was cooled to −78° C., and then boron trifluoride ether complex (0.69 ml) and triethylsilane (1.35 ml) were successively added thereto, followed by stirring at 0° C. for 2 hours. The reaction solution was poured into a saturated aqueous solution of sodium bicarbonate and the mixture was extracted with chloroform. The organic layer was washed with a saturated saline and dried over anhydrous magnesium sulfate, and the solvent was distilled off under reduced pressure. The residue was purified by silica gel column chromatography (chloroform/methanol=50/1) to give Compound 56 (0.62 g, 64.9%) as pale-yellow oily crystals.

NMR(DMSO-$d_6$, δ, ppm): 1.23(d, J=6.93 Hz, 3H), 2.69–2.78(m, 2H), 3.08–3.15 (m, 2H), 3.46–3.52(s, 1H), 3.74(s, 3H), 4.15–4.20(m, 1H), 4.48(t, J=8.58 Hz, 1H), 6.63(d, J=8.25 Hz, 1H), 6.78(d, J=8.58 Hz, 1H), 8.61(s, 2H)

IR(KBr, $cm^{-1}$): 1623, 1510, 1451, 1434

MASS(m/z): 339($M^+$+2), 337($M^+$), 177

Elemental analysis: $C_{17}H_{17}Cl_2NO_2$

Found (%) C,60.37; H,5.07; N,4.14. Calcd. (%) C,60.48; H,5.26; N,4.03.

EXAMPLE 57

(±)-7-Methoxy-3-methyl-4-[2-(4-pyridyl)ethyl]-2,3-dihydrobenzofuran (Compound 57)

(Step A) 4-[1-Hydroxy-2-(4-pyridyl)ethyl]-7-methoxy-3-methyl-2,3-dihydrobenzofuran (Compound 57a) (a Mixture of Diastereomers)

Under an argon atmosphere, a solution (25 ml) of 4-methylpyridine (0.66 ml) in THF was cooled to −78° C., and then a 1.69M solution (4.9 ml) of butyl lithium in hexane was dropwise added thereto, followed by stirring at the same temperature for one hour. A solution (25 ml) of Compound IIe (1.5 g) obtained in Reference Example 5 in THF was slowly and dropwise added to the mixture, followed by stirring at −78° C. for one hour and then at 0° C. for one hour. The reaction solution was poured into water and the mixture was extracted with ether. The organic layer was washed with a saturated saline and dried over anhydrous magnesium sulfate, and the solvent was distilled off under reduced pressure. The residue was purified by silica gel column chromatography (chloroform/methanol=50/1) to give Compound 57a (1.64 g, 73.6%) as colorless crystals.

Melting point: 96–100° C.

NMR(DMSO-$d_6$, δ, ppm): (main product) 1.18(d, J=6.93 Hz, 3H), 2.83–2.97(m, 2H), 3.74(s, 3H), 4.10–4.18(m, 1H), 4.31(t, J=8.54 Hz, 1H), 4.73–4.84(m, 1H), 5.25(d, J=4.62 Hz, 1H), 6.81–6.94(m, 2H), 7.16(d, J=4.62 Hz, 2H), 8.41(d, J=4.62 Hz, 2H). (by-product) 1.10(d, J=6.93 Hz, 3H), 2.83–2.97(m, 2H), 3.74(s, 3H), 4.10–4.18(m, 1H), 4.44(t, J=8.25 Hz, 1H), 4.73–4.84(m, 1H), 5.31(d, J=4.62 Hz, 1H), 6.81–6.94(m, 2H), 7.23(d, J=4.61 Hz, 2H), 7.43(d, J=4.61 Hz, 2H)

IR(KBr, $cm^{-1}$): 1609, 1508, 1432

MASS(m/z): 285($M^+$), 193

(Step B) (Compound 57)

Under an argon atmosphere, a solution (17 ml) of Compound 57a (0.6 g) obtained in Step A in methylene chloride was cooled to −78° C., and then boron trifluoride ether complex (0.42 ml) and triethylsilane (0.8 ml) were successively added thereto, followed by stirring at 0° C. for 2 hours. The reaction solution was poured into a saturated aqueous solution of sodium bicarbonate and the mixture was extracted with chloroform. The organic layer was washed with a saturated saline and dried over anhydrous magnesium sulfate, and the solvent was distilled off under reduced pressure. The residue was purified by silica gel column chromatography (chloroform/methanol=30/1) to give Compound 57 (0.042 g, 9.1%) as a pale-yellow oily substance.

NMR(DMSO-$d_6$, δ, ppm): 1.16(d, J=6.93 Hz, 3H), 2.76–2.92(m, 4H), 3.40–3.47(m, 1H), 3.72(s, 3H), 4.11–4.16(m, 1H), 4.44(t, J=8.58 Hz, 1H), 6.66(d, J=8.25 Hz, 1H), 6.76(d, J=8.24 Hz, 1H), 7.26(d, J=4.95 Hz, 2H), 8.46(broad s, 2H)

IR($cm^{-1}$): 1602, 1510, 1435

MASS(m/z): 269($M^+$), 177

EXAMPLE 58

7-Methoxy-3-methyl-4-[1-phenyl-2-(4-pyridyl)ethyl]-2,3-dihydrobenzofuran (Compound 58) (a Mixture of Diastereomers)

(Step A) 4-[1-Hydroxy-1-phenyl-2-(4-pyridyl)ethyl]-7-methoxy-3-methyl-2,3-dihydrobenzofuran (Compound 58a) (a Mixture of Diastereomers)

Under an argon atmosphere, a solution of 4-methylpyridine (0.83 ml) in THF (50 ml) was cooled to −78° C., and then a 1.69M solution (5.0 ml) of butyl lithium in hexane was added thereto, followed by stirring at the same temperature for one hour. A solution of Compound IIak (2.0 g) obtained in Reference Example 37 in THF (20 ml) was slowly and dropwise added to the mixture, followed by stirring at 0° C. for 2 hours. The reaction solution was poured into water and the mixture was extracted with ether. The organic layer was washed with a saturated saline and dried over anhydrous magnesium sulfate, and the solvent was distilled off under reduced pressure to give a crude product of Compound 58a (0.87 g) as yellowish brown crystals. This crude product was subjected to a subsequent step without being purified.

(Step B) (Compound 58)

Under an argon atmosphere, a solution of Compound 58a (0.4 g) obtained in Step A in methylene chloride (3 ml) was cooled to −78° C., and then boron trifluoride ether complex (0.3 ml) and triethylsilane (0.52 ml) were successively added thereto, followed by stirring at 0° C. for 2 hours. The reaction solution was poured into a saturated aqueous solution of sodium bicarbonate and the mixture was extracted with chloroform. The organic layer was washed with a saturated saline and dried over anhydrous magnesium sulfate, and the solvent was distilled off under reduced pressure. The residue was purified by silica gel column chromatography (chloroform/methanol=30/1) to give Compound 58 (a mixture of diastereomers) (0.27 g, 56.7%) as pale-yellow crystals.

NMR(DMSO-$d_6$, δ, ppm): (main product) 0.61(d, J=6.93 Hz, 3H), 3.23–3.33(m, 1H), 3.42(d, J=2.53 Hz, 1H), 3.53(d, J=2.54 Hz, 1H), 3.74(s, 3H), 3.97–3.99(m, 2H), 5.78(m, 1H), 6.77–6.86(m, 4H), 7.15–7.32(m, 5H), 8.24–8.26(m, 2H). (by-product) 0.77(d, J=6.93 Hz, 3H), 3.27–3.55(m, 3H), 3.74(s, 3H), 3.97–3.99(m, 2H), 5.74(m, 1H), 6.77–6.86 (m, 4H), 7.15–7.32(m, 5H), 8.21–8.26(m, 2H)

IR($cm^{-1}$): 1605, 1506, 1447

MASS(m/z): 345($M^+$)

EXAMPLE 59

(±)-7-Methoxy-3-methyl-4-(4-pyridylthiomethyl)-2,3-dihydrobenzofuran (Compound 59)

(Step A) (±)-4-Hydroxymethyl-7-methoxy-3-methyl-2,3-dihydrobenzofuran (Compound 59a)

Substantially the same procedure as in Step A of Example 48 was repeated using Compound IIe (7.0 g) obtained in Reference Example 5 to give Compound 59a (6.0 g, 85.0%) as a colorless oily substance.

NMR(DMSO-$d_6$, δ, ppm): 1.19(d, J=6.93 Hz, 3H), 3.53–3.59(m, 1H), 3.71(s, 3H), 4.14(dd, J=8.75 Hz, 4.29 Hz, 1H), 4.37–4.52(m, 3H), 4.99(t, J=5.61 Hz, 1H), 6.77(s, 2H)

MASS(m/z): 194($M^+$)

(Step B) (Compound 59)

Substantially the same procedure as in Step B of Example 48 was repeated using Compound 59a (1.5 g) obtained in Step A to give Compound 59 (1.5 g, 68%) as a colorless oily substance.

Melting point: 110–112° C.

NMR(DMSO-$d_6$, δ, ppm): 1.25(d, J=6.93 Hz, 3H), 3.62–3.69(m, 1H), 3.74(s, 3H), 4.18(dd, J=3.96 Hz, 8.74 Hz, 1H), 4.30(s, 2H), 4.53(t, J=8.58 Hz, 1H), 6.79(d, J=8.25 Hz, 1H), 6.85(d, J=8.25 Hz, 1H), 7.32(d, J=5.94 Hz, 2H), 8.38(d, J=5.94 Hz, 2H)

IR(KBr, $cm^{-1}$): 1618, 1575, 1506, 1439

MASS(m/z): 287($M^+$), 177

Elemental analysis: $C_{16}H_{17}NO_2S$

Found (%) C,66.87; H,5.96; N,4.87. Calcd. (%) C,66.94; H,5.92; N,5.08.

EXAMPLE 60

(±)-7-Methoxy-3-methyl-4-[1-phenyl-1-(4-pyridylthio)-methyl]-2,3-dihydrobenzofuran (Compound 60A and Compound 60B)

Substantially the same procedure as in Step B of Example 48 was repeated using Compound IIak-a (2.6 g) obtained in Step A of Reference Example 37 to give Compound 60A and Compound 60B [60A (0.11 g, 3.1%) and 60B (0.19 g, 5.4%)] each as colorless crystals.

Compound 60A

Melting point: 59–62° C.

NMR(DMSO-$d_6$, δ, ppm): 1.31(d, J=6.93 Hz, 3H), 3.57–3.63(m, 1H), 3.72(s, 3H), 4.20(dd, J=3.63 Hz, 8.75 Hz, 1H), 4.47(t, J=8.58 Hz, 1H), 5.99(s, 1H), 6.82(d, J=8.58 Hz, 1H), 6.90(d, J=8.24 Hz, 1H), 7.17(d, J=5.94 Hz, 2H), 7.23–7.36 (m, 3H), 7.51–7.54(m, 2H), 8.31(d, J=6.27 Hz, 2H)

IR(KBr, $cm^{-1}$): 1620, 1572, 1504, 1433

MASS (m/z): 363 ($M^+$), 253

Elemental analysis: $C_{22}H_{21}NO_2S.0.5H_2O$

Found (%) C,70.94; H,5.95; N,3.76. Calcd. (%) C,70.85; H,5.84; N,3.85.

Compound 60B

Melting point: 84–85° C.

NMR(DMSO-$d_6$, δ, ppm): 1.02(d, J=6.93 Hz, 3H), 3.65–3.85(m, 1H), 3.73(s, 3H), 4.19(dd, J=2.97 Hz, 8.91 Hz, 1H), 4.52(t, J=8.58 Hz, 1H), 6.09(s, 1H), 6.84(d, J=8.58 Hz, 1H), 6.94(d, J=8.25 Hz, 1H), 7.16(d, J=6.27 Hz, 2H), 7.25–7.39(m, 3H), 7.49–7.52(m, 2H), 8.29(d, J=5.94 Hz, 2H)

IR(KBr, $cm^{-1}$): 1619, 1569, 1506, 1437

MASS (m/z): 363 ($M^+$), 253

Elemental analysis: $C_{22}H_{21}NO_2S.0.2H_2O$

Found (%) C,71.99; H,5.88; N,3.82. Calcd. (%) C,71.95; H,5.79; N,3.90.

EXAMPLE 61

(±)-7-Methoxy-3-methyl-4-(4-pyridylaminomethyl)-2,3-dihydrobenzofuran (Compound 61)

Substantially the same procedure as in Step B of Example 48 was repeated using Compound 59a obtained in Step A of Example 59 and using 4-aminopyridine instead of 4-mercaptopyridine to give Compound 61 (26.5%) as colorless crystals.

Melting point: 138–145° C.

NMR(DMSO-$d_6$, δ, ppm): 1.23(d, J=6.43 Hz, 3H), 3.59–3.79(m, 1H), 3.73(s, 3H), 4.14–4.31(m, 3H), 4.53 (t, J=8.90 Hz, 1H), 6.52(d, J=4.95 Hz, 2H), 6.73(d, J=8.41 Hz, 1H), 6.79(d, J=8.41 Hz, 1H), 6.98(broad s, 1H), 8.01(d, J=5.44 Hz, 2H)

IR(KBr, $cm^{-1}$): 1600, 1523, 1508, 1437

MASS (m/z): 270($M^+$), 177

EXAMPLE 62

(±)-4-[2-(3,5-Dichloro-4-pyridyl)-1-methoxyethyl]-7-methoxy-2,2-dimethyl-2,3-dihydrobenzofuran (Compound 62)

p-Toluenesulfonic acid (1.0 g) was added to a solution (50 ml) of Compound 45a (2.0 g) obtained in Step A of Example 45 in methanol at room temperature, followed by heating under reflux. The reaction solution was cooled and then the solvent was distilled off under reduced pressure. A saturated aqueous solution of sodium bicarbonate was added to the residue, followed by extraction with chloroform. The organic layer was washed with a saturated saline and dried over anhydrous magnesium sulfate, and the solvent was distilled off under reduced pressure. The residue was purified by silica gel column chromatography (chloroform) to give Compound 57 (1.0 g, 48.2%) as a pale-yellow oily substance.

Melting point: 89–93° C.

NMR(DMSO-$d_6$, δ, ppm): 1.31(s, 3H), 1.41(s, 3H), 2.74 (d, J=15.51 Hz, 1H), 3.04 (s, 3H), 3.07–3.15(m, 2H), 3.29–3.42(m, 1H), 3.73(s, 3H), 4.47(dd, J=6.59 Hz, 7.59 Hz, 1H), 6.64(d, J=8.58 Hz, 1H), 6.79(d, J=8.25 Hz, 1H), 8.56(s, 2H)

MASS(m/e): 383, 381($M^+$), 221

IR(KBr, $cm^{-1}$): 1622, 1506, 1436

Elemental analysis: $C_{19}H_{21}Cl_2NO_3$

Found (%) C,59.96; H,5.61; N,3.56. Calcd. (%) C,59.70; H,5.54; N,3.66.

EXAMPLE 63

(±)-4-[1-Cyano-2-(3,5-dichloro-4-pyridyl)ethyl]-2,2-dimethyl-7-methoxy-2,3-dihydrobenzofuran (Compound 63)

A solution (70 ml) obtained in Step A of Example 45 of Compound 45a (2.5 g) in methylene chloride was cooled to 0° C. and then trimethylsilylcyanide (5.4 ml) and boron trifluoride ether complex (2.5 ml) were successively added thereto, followed by stirring at 0° C. for 2 hours. The reaction solution was poured into a saturated aqueous solution of sodium bicarbonate and the mixture was extracted with chloroform. The organic layer was washed with a saturated saline and dried over anhydrous magnesium sulfate, and the solvent was distilled off under reduced pressure. The residue was purified by silica gel column chromatography (chloroform/methanol=30/1) to give Compound 63 (0.61 g, 23.8%) as pale-yellow crystals.

Melting point: 158–162° C.

NMR(DMSO-$d_6$, δ, ppm): 1.34(s, 3H), 1.40(s, 3H), 2.83 (d, J=15.51 Hz, 1H), 3.16(d, J=15.51 Hz, 1H), 3.44–3.53(m, 2H), 3.74(s, 3H), 4.42(t, J=8.25 Hz, 1H), 6.80(d, J=8.25 Hz, 1H), 6.87(d, J=7.92 Hz, 1H), 8.66(s, 2H)

MASS(m/e): 378, 376($M^+$), 216

IR(KBr, $cm^{-1}$): 2248, 1622, 1506, 1437

Elemental analysis: $C_{19}H_{18}Cl_2N_2O_2$

Found (%) C,60.42; H,4.93; N,7.54. Calcd. (%) C,60.49; H,4.81; N,7.43.

EXAMPLE 64

(±)-4-[1-Cyano-2-(4-pyridyl)ethyl]-7-methoxy-spiro[2,3-dihydrobenzofuran-2,1'-cyclopentane].hydrochloride (Compound 64)

Substantially the same procedure as in Example 63 was repeated using Compound 53a (6.6 g) obtained in Step A of Example 53 to give (±)-4-[1-cyano-2-(4-pyridyl)ethyl]-7-methoxy-spiro[2,3-dihydrobenzofuran-2,1'-cyclopentane] (2.2 g, 32%) as a pale-yellow oily substance. Then, substantially the same procedure as in Example 51 was repeated using the obtained oily substance to give Compound 64.

Melting point: 187–189° C.

NMR(DMSO-$d_6$, δ, ppm): 1.73(s, 8H), 3.16(d, J=16.2 Hz, 1H), 3.31(d, J=15.8 Hz, 1H), 3.37–3.56(m, 2H), 3.74(s, 3H), 4.64(t, J=7.6 Hz, 1H), 6.75(d, J=8.2 Hz, 1H), 6.84(d, J=8.3 Hz, 1H), 7.91(d, J=5.6 Hz, 2H), 8.87(d, J=5.6 Hz, 2H)

MASS(m/e): 334($M^+$), 242

IR(KBr, $cm^{-1}$): 2243, 1633, 1508

Elemental analysis: $C_{21}H_{22}N_2O_2.HCl.H_2O$

Found (%) C,67.38; H,6.29; N,7.19. Calcd. (%) C,67.35; H,6.30; N,7.48.

EXAMPLE 65

(±)-4-[1-Cyano-1-methyl-2-(4-pyridyl)ethyl]-7-methoxy-spiro[2,3-dihydrobenzofuran-2,1'-cyclopentane].hydrochloride (Compound 65)

(Step A) (±)-4-[1-Hydroxy-1-methyl-2-(4-pyridyl)ethyl]-7-methoxy-spiro[2,3-dihydrobenzofuran-2,1'-cyclopentane] (Compound 65a)

Substantially the same procedure as in Example 46 was repeated using Compound IIan (2.7 g) obtained in Reference Example 40 to give Compound 65a (2.8 g, 74.7%) as a colorless oily substance.

(Step B) (Compound 65)

Substantially the same procedure as in Example 63 was repeated using Compound 65a (1.8 g) obtained in Step A to give (±)-4-[1-cyano-1-methyl-2-(4-pyridyl)ethyl]-7-methoxy-spiro[2,3-dihydrobenzofuran-2,1'-cyclopentane] (0.35 g, 18.9%) as a pale-yellow oily substance. Then, substantially the same procedure as in Example 51 was repeated using the obtained oily substance to give Compound 65.

Melting point: 142–144° C.

NMR(DMSO-$d_6$, δ, ppm): 1.74–1.94(m, 11H), 3.17(d, J=15.8 Hz, 1H), 3.21(s, 2H), 3.40(d, J=16.3 Hz, 1H), 3.75(s, 3H), 6.70(d, J=8.9 Hz, 1H), 6.82(d, J=8.9 Hz, 1H), 7.04(d, J=5.8 Hz, 2H), 8.46(d, J=5.9 Hz, 2H)

MASS(m/e): 348($M^+$)

EXAMPLE 66

(±)-7-Methoxy-4-[1-phenyl-2-(4-pyridyl)ethyl]-2-(4-pyridyl)benzofuran.hydrochloride (Compound 66)

Substantially the same procedure as in Example 47 was repeated using Compound IIal (0.45 g) obtained in Reference Example 38 to give (±)-7-methoxy-4-[1-phenyl-2-(4-pyridyl)ethyl]-2-(4-pyridyl)benzofuran (0.28 g, 50%) as a pale-yellow solid. Then, substantially the same procedure as in Example 51 was repeated using the obtained crystals to give Compound 66.

Melting point: 183–185° C.

NMR(DMSO-$d_6$, δ, ppm): 3.88(d-like, J=8 Hz, 2H), 3.96(s, 3H), 4.93(t-like, J=8 Hz, 1H), 7.08(d, J=8.5 Hz, 1H), 7.1–7.4(m, 3H), 7.43(d, J=8.5 Hz, 1H), 7.50 (d, J=7 Hz, 2H), 7.94(d, J=6 Hz, 2H), 8.33(d, J=6 Hz, 2H), 8.55(s, 1H), 8.75(d, J=6 Hz, 2H), 8.92(d, J=6 Hz, 2H)

IR(KBr, $cm^{-1}$): 2840, 1630, 1590, 1560, 1200

MASS(m/e): 406($M^+$), 348, 315

Elemental analysis: $C_{27}H_{22}NO_2$.2.0HCl.1.7$H_2O$

Found (%) C,63.63; H,5.33; N,5.23. Calcd. (%) C,63.58; H,5.41; N,5.49.

EXAMPLE 67

(E)-4-[2-(3,5-Dichloro-4-pyridyl)ethenyl]-7-methoxy-2,2-dimethyl-2,3-dihydrobenzofuran (Compound 67)

p-Toluenesulfonic acid (0.8 g) was added to a suspension of Compound 45a (1.0 g) obtained in Step A of Example 45 in toluene (27 ml), followed by heating under reflux for 30 minutes. After being allowed to stand for cooling, a saturated aqueous solution of sodium bicarbonate was added to the reaction solution for neutralization, followed by extraction with ether. The organic layer was washed with a saturated saline and dried over anhydrous magnesium sulfate, and the solvent was distilled off under reduced pressure. The resultant residue was purified by silica gel column chromatography (chloroform/methanol=20/1) to give Compound 67 (0.59 g, 62.2%) as yellow crystals.

Melting point: 114–118° C.

NMR(DMSO-$d_6$, δ, ppm): 1.44(s, 6H), 3.18(s, 2H), 3.80 (s, 3H), 6.91(d, J=8.57 Hz, 1H), 6.92(d, J=16.82 Hz, 1H), 7.16(d, J=8.25 Hz, 1H), 7.36(d, J=16.82 Hz, 1H), 8.64(s, 2H)

MASS(m/e): 351, 349($M^+$)

IR($cm^{-1}$): 1613, 1556, 1508

Elemental analysis: $C_{18}H_{17}Cl_2NO_2$

Found (%) C,61.75; H,4.87; N,4.00. Calcd. (%) C,61.73; H,4.89; N,4.00.

EXAMPLE 68

(E)-7-Methoxy-2,2-dimethyl-4-[2-(4-pyridyl)ethenyl]-2,3-dihydrobenzofuran (Compound 68)

Substantially the same procedure as in Example 67 was repeated using Compound 46a (0.2 g) obtained in Step A of Example 46 to give Compound 68 (0.17 g, 90.2%) as yellow crystals.

Melting point: 145–149° C.

NMR(DMSO-$d_6$, δ, ppm): 1.45(s, 6H), 3.24(s, 2H), 3.78 (s, 3H), 6.88(d, J=8.58 Hz, 1H), 6.97(d, J=16.83 Hz, 1H), 7.15(d, J=8.58 Hz, 1H), 7.39(d, J=16.49 Hz, 1H), 7.54(d, J=5.94 Hz, 2H), 8.51(d, J=5.94 Hz, 2H)

IR(KBr, $cm^{-1}$): 1610, 1589, 1506, 1439

MASS(m/z): 281($M^+$), 266

Elemental analysis: $C_{18}H_{19}NO_2$.0.2$H_2O$

Found (%) C,75.87; H,6.86; N,4.92. Calcd. (%) C,76.10; H,6.86; N,5.10.

EXAMPLE 69

7-Methoxy-2,2-dimethyl-4-[1-methyl-2-(4-pyridyl)-ethenyl]-2,3-dihydrobenzofuran (Compound 69)

(Step A) (±)-4-[1-Hydroxy-1-methyl-2-(4-pyridyl)ethyl]-7-methoxy-2,2-dimethyl-2,3-dihydrobenzofuran (Compound 69a)

Substantially the same procedure as in Step A of Example 65 was repeated using Compound IIan (2.7 g) obtained in Reference Example 39 to give Compound 69a (2.8 g, 74.4%) as a pale-yellow oily substance.

NMR(DMSO-$d_6$, δ, ppm): 1.22(s, 3H), 1.33(s, 3H), 1.45 (s, 3H), 2.83(d, J=16.2 Hz, 1H), 2.91(s, 2H), 3.16 (d, J=16.2 Hz, 1H), 3.70(s, 3H), 6.67(s, 2H), 6.94(d, J=5.9 Hz, 2H), 8.31(d, J=4.3 Hz, 2H)

MASS(m/e): 313($M^+$), 221

(Step B) (Compound 69)

Substantially the same procedure as in Example 67 was repeated using Compound 69a (0.6 g) obtained in Step A to give Compound 69 (0.52 g, 91.5%) as pale-yellow crystals.

Melting point: 85–87° C.

NMR(DMSO-$d_6$, δ, ppm): 1.42(s, 6H), 2.22(s, 3H), 3.15 (s, 2H), 3.77(s, 3H), 6.50(s, 1H), 6.85(s, 2H), 7.37(d, J=5.9 Hz, 2H), 8.56(d, J=5.9 Hz, 2H)

MASS(m/e): 295($M^+$)

IR(KBr, $cm^{-1}$): 1614, 1593, 1504

Elemental analysis: $C_{19}H_{21}NO_2$.0.1$H_2O$

Found (%) C,76.77; H,7.22; N,4.82. Calcd. (%) C,76.79; H,7.19, N,4.71.

EXAMPLE 70

7-Methoxy-2,2-dimethyl-4-[1-phenyl-2-(4-pyridyl)-ethenyl]-2,3-dihydrobenzofuran (Compound 70) (a mixture of E/Z)

Substantially the same procedure as in Example 67 was repeated using Compound 47a (0.3 g) obtained in Step A of Example 47 to give Compound 68 (0.28 g, 98.0%) as pale-yellow crystals.

Melting point: 110–113° C.

NMR(DMSO-$d_6$, δ, ppm): (main product;76%); 1.29(s, 6H), 2.56(s, 2H), 3.76(s, 3H), 6.69(d, J=8.58 Hz, 1H), 6.74(s, 1H), 6.84(d, J=8.58 Hz, 1H), 6.92(d, J=5.93 Hz, 2H), 7.10–7.13(m, 2H), 7.36–7.38(m, 3H), 8.32(d, J=5.94 Hz, 2H). (by-product;22%); 1.21(s, 6H), 2.43(s, 2H), 3.80(s, 3H), 6.54(d, J=8.25 Hz, 1H), 6.87(d, J=8.26 Hz, 1H), 6.96(d, J=5.94 Hz, 2H), 7.06(m, 1H), 7.10–7.13(m, 2H), 7.36–7.38 (m, 3H), 8.37(d, J=5.94 Hz, 2H)

IR(KBr, $cm^{-1}$): 1618, 1592, 1506, 1433

MASS(m/z): 357($M^+$)

Elemental analysis: $C_{24}H_{23}NO_2$

Found (%) C,80.64; H,6.49; N,3.92. Calcd. (%) C,80.56; H,6.61; N,4.00.

EXAMPLE 71

(E)-2,2-Diethyl-7-methoxy-4-[2-(3,5-dichloro-4-pyridyl)ethenyl]-2,3-dihydrobenzofuran.methanesulfonate (Compound 71)

Substantially the same procedure as in Example 67 was repeated using Compound 50a (3.0 g) obtained in Step A of Example 50 to give (E)-2,2-diethyl-7-methoxy-4-[2-(3,5-dichloro-4-pyridyl)ethenyl]-2,3-dihydrobenzofuran (2.5 g, 90.5%) as yellow crystals. Then, substantially the same procedure as in Example 50 was repeated using the obtained crystals to give Compound 71.

Melting point: 137–141° C.

NMR(DMSO-$d_6$, δ, ppm): 0.87(t, d=7.4 Hz, 6H), 1.71(q, d=7.4 Hz, 4H), 2.36(s, 3H), 3.80(s, 3H), 6.84(d, J=8.4 Hz, 1H), 6.94(d, J=16.8 Hz, 1H), 7.14(d, J=8.4 Hz, 1H), 7.37(d, J=16.8 Hz, 1H), 8.64(s, 2H)

MASS(m/e): 379, 377($M^+$)

IR($cm^{-1}$): 1599, 1508

Elemental analysis: $C_{20}H_{21}Cl_2NO_2.CH_3SO_3H$

Found (%) C,52.93; H,5.30; N,2.88. Calcd. (%) C,53.17; H,5.32; N,2.95.

EXAMPLE 72

(E)-2,2-Diethyl-7-methoxy-4-[2-(4-pyridyl)ethenyl]-2,3-dihydrobenzofuran.hydrochloride (Compound 72)

Substantially the same procedure as in Example 67 was repeated using Compound 51a (3.0 g) obtained in Step A of Example 51 to give (E)-2,2-diethyl-7-methoxy-4-[2-(4-pyridyl)ethenyl]-2,3-dihydrobenzofuran (2.6 g, 91%) as pale-yellow crystals. Then, substantially the same procedure as in Example 51 was repeated using the obtained crystals to give Compound 72.

Melting point: 236–239° C.

NMR(DMSO-$d_6$, δ, ppm): 0.90(t, J=7.4 Hz, .6H), 1.72(q, J=7.4 Hz, 4H), 3.27(s, 2H), 3.82(s, 3H), 6.93(d, J=8.9 Hz, 1H), 7.25(d, J=8.4 Hz, 1H), 7.26(d, J=14.8 Hz, 1H), 7.84(d, J=16.3 Hz, 1H), 8.19(d, J=6.9 Hz, 2H), 8.79(d, J=6.4 Hz, 2H)

MASS(m/e): 309($M^+$), 280

IR($cm^{-1}$): 1603, 1571, 1507, 1437

Elemental analysis: $C_{20}H_{23}NO_2.HCl$

Found (%) C,69.17; H,7.08; N,4.00. Calcd. (%) C,69.45; H,6.99; N,4.05.

EXAMPLE 73

(E)-4-[2-(3,5-Dichloro-4-pyridyl)ethenyl]-7-methoxy-spiro[2,3-dihydrobenzofuran-2,1'-cyclopentane].methanesulfonate (Compound 73)

Substantially the same procedure as in Example 67 was repeated using Compound 52a (4.0 g) obtained in Step A of Example 52 to give (E)-4-[2-(3,5-dichloro-4-pyridyl) ethenyl]-7-methoxy-spiro[2,3-dihydrobenzofuran-2,1'-cyclopentane] (1.8 g, 46.1%) as yellow crystals. Then, substantially the same procedure as in Example 50 was repeated using the obtained crystals to give Compound 73.

Melting point: 155–158° C.

NMR(DMSO-$d_6$;δ, ppm): 1.75–1.79(m, 8H), 1.99–2.10 (m, 2H), 2.38(s, 3H), 3.36(s, 2H), 3.80(s, 3H), 6.90(d, J=8.9 Hz, 1H), 6.94(d, J=16.8 Hz, 1H), 7.16(d, J=8.4 Hz, 1H), 7.37(d, J=16.8 Hz, 1H), 8.64(s, 2H)

MASS(m/e): 377, 375($M^+$) 215

IR($cm^{-1}$): 2935(br), 1589, 1566, 1506

Elemental analysis: $C_{20}H_{19}Cl_2NO_2.CH_3SO_3H$

Found (%) C,53.25; H,4.90; N,2.89. Calcd. (%) C,53.40; H,4.91; N,2.97.

EXAMPLE 74

(E)-7-Methoxy-4-[2-(4-pyridyl)ethenyl]-spiro[2,3-dihydrobenzofuran-2,1'-cyclopentane].hydrochloride (Compound 74)

Substantially the same procedure as in Example 67 was repeated using Compound 53a (0.3 g) obtained in Step A of Example 53 to give (E)-7-methoxy-4-[2-(4-pyridyl)-ethenyl]-spiro[2,3-dihydrobenzofuran-2,1'-cyclopentane] (0.2 g, 72%) as pale-yellow crystals. Then, substantially the same procedure as in Example 51 was repeated using the obtained crystals to give Compound 74.

Melting point: 229–231° C.

NMR(DMSO-$d_6$, δ, ppm): 1.65–1.90(m, 6H), 1.90–2.15 (m, 2H), 3.47(s, 2H), 3.82(s, 3H), 6.95(d, J=8.6 Hz, 1H), 7.24(d, J=16.5 Hz, 1H), 7.27(d, J=8.6 Hz, 1H), 7.83(d, J=16.5 Hz, 1H), 8.17(d, J=6.6 Hz, 2H), 8.78(d, J=6.3 Hz, 2H)

MASS(m/z): 307($M^+$)

IR($cm^{-1}$): 1604, 1507

Elemental analysis: $C_{20}H_{21}NO_2.HCl.H_2O$

Found (%) C,66.49; H,6.69; N,3.77. Calcd. (%) C,66.38; H,6.68; N,3.87.

EXAMPLE 75

7-Methoxy-4-[1-methyl-2-(4-pyridyl)ethenyl]-spiro[2,3-dihydrobenzofuran-2,1'-cyclopentane] (Compound 75)

Substantially the same procedure as in Example 67 was repeated using Compound 65a (2.0 g) obtained in Step A of Example 65 to give Compound 75 (1.1 g, 57.3%) as yellow crystals.

Melting point: 85–87° C.

NMR(DMSO-$d_6$, δ, ppm): 1.74–1.90(m, 6H), 1.97–2.05 (m, 2H), 2.36(s, 2H), 3.38(s, 3H), 3.79(s, 3H), 6.79 (s, 1H), 6.89(d, J=8.6 Hz, 1H), 6.96(d, J=8.2 Hz, 1H), 8.02(d, J=6.6 Hz, 2H), 8.84(d, J=6.6 Hz, 2H)

MASS(m/e): 321($M^+$)

IR(KBr, $cm^{-1}$): 1631, 1605, 1601

Elemental analysis: $C_{21}H_{23}NO_2.HCl.0.3H_2O$

Found (%) C,69.45; H,7.05; N,3.91. Calcd. (%) C,69.43; H,6.83; N,3.86.

EXAMPLE 76

(E)-4-[2-(3,5-Dichloro-4-pyridyl)ethenyl]-7-methoxy-spiro[2,3-dihydrobenzofuran-2,1'-cyclohexane].methanesulfonate (Compound 76)

Substantially the same procedure as in Example 67 was repeated using Compound 54a (3.5 g) obtained in Step A of Example 54 to give (E)-4-[2-(3,5-dichloro-4-pyridyl)-ethenyl]-7-methoxy-spiro[2,3-dihydrobenzofuran-2,1'-cyclohexane] (2.7 g, 81%) as pale-yellow crystals. Then, substantially the same procedure as in Example 50 was repeated using the obtained crystals to give Compound 76.

Melting point: 108–109° C.

NMR(DMSO-$d_6$, δ, ppm): 1.44–1.66(m, 4H), 1.70–1.76 (m, 6H), 2.39(s, 3H), 3.14(s, 2H), 3.81(s, 3H), 6.20 (d, J=8.3 Hz, 1H), 6.93(d, J=16.8 Hz, 1H), 7.15(d, J=8.9 Hz, 1H), 7.36(d, J=16.8 Hz, 1H), 8.64(s, 2H)

MASS(m/e): 391, 389($M^+$)

IR($cm^{-1}$): 2932, 1595, 1507

Elemental analysis: $C_{21}H_{21}Cl_2NO_2.CH_3SO_3H.1.2H_2O$

Found (%) C,51.99; H,5.21; N,2.67. Calcd. (%) C,52.01; H,5.44; N,2.76.

EXAMPLE 77

(E)-7-Methoxy-4-[2-(4-pyridyl)ethenyl]-spiro[2,3-dihydrobenzofuran-2,1'-cyclohexane].hydrochloride (Compound 77)

Substantially the same procedure as in Example 67 was repeated using Compound 55a (4 g) obtained in Step A of Example 55 to give (E)-7-methoxy-4-[2-(4-pyridyl) ethenyl]-spiro[2,3-dihydrobenzofuran-2,1'-cyclohexane] (3.1 g, 82%) as pale-yellow crystals. Then, Substantially the same procedure as in Example 51 was repeated using the obtained crystals to give Compound 77.

Melting point: 234–239° C.

NMR(DMSO-$d_6$, δ, ppm): 1.47–1.68(m, 4H), 1.72–1.99 (m, 6H), 3.26(s, 2H), 3.83(s, 3H), 6.94(d, J=8.4 Hz, 1H), 7.26(d, J=15.3 Hz, 1H), 7.27(d, J=8.9 Hz, 1H), 7.83(d, J=16.3 Hz, 1H), 8.19(d, J=6.9 Hz, 2H), 8.78(d, J=6.4 Hz, 2H)

MASS(m/e): 321($M^+$)

IR($cm^{-1}$): 1600, 1511

Elemental analysis: $C_{21}H_{23}NO_2.HCl.0.3H_2O$

Found (%) C,69.51; H,6.90; N,3.84. Calcd. (%) C,69.43; H,6.83; N,3.86.

EXAMPLE 78

(E)-(±)-4-[2-(3,5-Dichloro-4-pyridyl)ethenyl]-7-methoxy-3-methyl-2,3-dihydrobenzofuran (Compound 78)

Substantially the same procedure as in Example 67 was repeated using Compound 56a (1.6 g) obtained in Step A of Example 56 to give Compound 78 (1.4 g, 92%) as yellow crystals.

Melting point: 117–118° C.

NMR(DMSO-$d_6$, δ, ppm): 1.23(s, J=6.93 Hz, 3H), 3.68–3.74(m, 1H), 3.82(s, 3H), 4.26(dd, J=8.62 Hz, 2.97 Hz, 1H), 4.55(d, J=8.58 Hz, 1H), 6.94(d, J=8.58 Hz, 1H), 7.03(d, J=16.50 Hz, 1H), 7.27(d, J=8.58 Hz, 1H), 7.40(d, J=16.82 Hz, 1H), 8.65(s, 2H)

MASS(m/e): 337, 335($M^+$), 300

IR($cm^{-1}$): 1616, 1507

Elemental analysis: $C_{17}H_{15}Cl_2NO_2$

Found (%) C,60.62; H,4.45; N,4.14. Calcd. (%) C,60.73; H,4.50; N,4.17.

EXAMPLE 79

(E)-(±)-7-Methoxy-3-methyl-4-[2-(4-pyridyl) ethenyl]-2,3-dihydrobenzofuran (Compound 79)

Substantially the same procedure as in Example 67 was repeated using Compound 57a (0.25 g) obtained in Step A of Example 57 to give Compound 7 (0.18 g, 95.3%) as yellow crystals.

Melting point: 93–95° C.

NMR(DMSO-$d_6$, δ, ppm): 1.21(d, J=6.93 Hz, 3H), 3.80(s, 3H), 3.80–3.86(m, 1H), 4.26(dd, J=2.97 Hz, 8.58 Hz, 1H), 4.55(t, J=8.58 Hz, 1H), 6.91(d, J=8.57 Hz, 1H), 7.09(d, J=16.49 Hz, 1H), 7.25(d, J=8.58 Hz, 1H), 7.46(d, J=16.50 Hz, 1H), 7.57(d, J=5.94 Hz, 2H), 8.53(d, J=5.92 Hz, 2H)

IR(KBr, $cm^{-1}$): 1612, 1591, 1506, 1459

MASS(m/z): 267($M^+$)

Elemental analysis: $C_{17}H_{17}NO_1$

Found (%) C,76.38; H,6.41; N,5.24. Calcd. (%) C,76.50; H,6.36; N,5.24.

EXAMPLE 80

(±)-7-Methoxy-3-methyl-4-[1-phenyl-2-(4-pyridyl) ethenyl]-2,3-dihydrobenzofuran (Compound 80) (an E/Z mixture)

Substantially the same procedure as in Example 67 was repeated using Compound 58a (1.5 g) obtained in Example 58 to give Compound 80 (1.3 g, 86.8%) as pale-yellow crystals.

Melting point: 103–105.5° C.

NMR(DMSO-$d_6$, δ, ppm): 1.07(d, J=6.60 Hz, 3H), 2.92–3.10(m, 1H), 3.78(s, 3H), 4.08(dd, J=4.29 Hz, 8.75 Hz, 1H), 4.41(t, J=8.75 Hz, 1H), 6.68(d, J=8.25 Hz, 1H), 6.79(s, 1H), 6.86(d, J=8.25 Hz, 1H), 6.95(d, J=5.28 Hz, 2H), 7.13(m, 2H), 7.35(m, 3H), 8.33(d, J=5.61 Hz, 2H)

IR(KBr, $cm^{-1}$): 1591, 1498, 1431

MASS(m/z): 343($M^+$), 251

Elemental analysis: $C_{23}H_{21}NO_2$

Found (%) C,79.66; H,6.26; N,4.07. Calcd. (%) C,79.61; H,6.22; N,4.04.

EXAMPLE 81

(E)-7-Methoxy-2-phenyl-4-[2-(4-pyridyl)ethenyl]-benzofuran.hydrochloride (Compound 81)

(Step A) (±)-4-[1-Hydroxy-2-(4-pyridyl)ethyl]-7-methoxy-2-phenylbenzofuran (Compound 81a)

Substantially the same procedure as in Step A of Example 46 was repeated using Compound IIh (2.6 g) obtained in Reference Example 8 to give Compound 81a (2.33 g, 65.4%) as a yellowish white solid.

NMR($CDCl_3$, δ, ppm): 2.70(brs, 1H), 3.11(dd, J=6 Hz, 14 Hz, 1H), 3.21(dd, J=8 Hz, 14 Hz, 1H), 4.03(s, 3H), 5.15(dd, J=6 Hz, 8 Hz, 1H), 6.69(d, J=8 Hz, 1H), 6.96(d, J=8 Hz, 1H), 7.07(d, J=6 Hz, 2H), 7.18(s, 1H), 7.37(t, J=7 Hz, 1H), 7.44(dd, J=7 Hz, 7 Hz, 2H), 7.90(d, J=7 Hz, 2H), 8.41(d, J=6 Hz, 2H)

MASS(m/e): 345($M^+$), 327, 253

(Step B) (Compound 81)

Substantially the same procedure as in Example 67 was repeated using Compound 81a (2.0 g) obtained in Step A to give (E)-7-methoxy-2-phenyl-4-[2-(4-pyridyl)ethenyl]-benzofuran (1.10 g, 58.0%) as a yellow solid. Then, substantially the same procedure as in Example 51 was repeated using the obtained crystals to give Compound 81.

Melting point: 146–148° C.

NMR(DMSO-$d_6$, δ, ppm): 4.06(s, 3H), 7.11(d, J=9 Hz, 1H), 7.4–7.6(m, 4H), 7.69(d, J=9 Hz, 1H), 8.00(d, J=7 Hz, 2H), 8.16(s, 1H), 8.19(d, J=18 Hz, 1H), 8.30(d, J=7 Hz, 2H), 8.84(d, J=7 Hz, 2H)

IR(KBr, $cm^{-1}$): 1600, 1510, 1290, 1100

MASS(m/e): 328, 327($M^+$)

Elemental analysis: $C_{22}H_{17}NO_2.1.0HCl.1.0OH_2O$

Found (%) C,69.25; H,5.20; N,3.73. Calcd. (%) C,69.20; H,5.28; N,3.67.

EXAMPLE 82

(E)-4-[2-(3,5-Dichloro-4-pyridyl)ethenyl]-7-methoxy-2-(4-pyridyl)benzofuran (Compound 82)

(Step A) (±)-4-[2-(3,5-Dichloro-4-pyridyl)-1-hydroxyethyl]-7-methoxy-2-(4-pyridyl)benzofuran (Compound 82a)

Substantially the same procedure as in Step A of Example 45 was repeated using Compound IIf (4.00 g) obtained in Reference Example 6 to give Compound 82a (3.91 g, 59.6%) as a yellowish white solid.

NMR(DMSO-$d_6$, δ, ppm): 3.23(dd, J=5 Hz, 13 Hz, 1H), 3.45 (dd, J=8 Hz, 13 Hz, 1H), 3.97(s, 3H), 5.22(m, 1H), 5.74(d, J=4 Hz, 1H), 6.95(d, J=8 Hz, 1H), 7.11(d, J=8 Hz, 1H), 7.69(s, 1H), 7.84(d, J=6 Hz, 2H), 8.54(s, 2H), 8.69(d, 6 Hz, 2H)

MASS(m/e): 416, 414($M^+$)

(Step B) (Compound 82)

Substantially the same procedure as in Example 67 was repeated using Compound 82a (1.50 g) obtained in Step A to give Compound 82 (0.847 g, 59.1%) as a yellow solid.

Melting point: 204–206° C.

NMR($CDCl_3$, δ, ppm): 4.10(s, 3H), 6.91(d, J=8 Hz, 1H), 7.16(d, J=17 Hz, 1H), 7.46(d, J=8 Hz, 1H), 7.50(s, 1H), 7.77(d, J=17 Hz, 1H), 7.77(d, J=6 Hz, 2H), 8.52(s, 2H), 8.71(d, J=6 Hz, 2H)

IR(KBr, $cm^{-1}$): 1615, 1550, 1290, 1180

MASS(m/e): 400, 398, 396($M^+$)

Elemental analysis: $C_{21}H_{14}N_2O_2Cl_2$

Found (%) C,63.32; H,3.51; N,6.98. Calcd. (%) C,63.51; H,3.55; N,7.05.

EXAMPLE 83

(E)-7-Methoxy-2-(4-pyridyl)-4-[2-(4-pyridyl) ethenyl]-benzofuran.2 hydrochloride (Compound 83)

(Step A) (±)-4-[1-Hydroxy-2-(4-pyridyl)ethyl]-7-methoxy-2-(4-pyridyl)benzofuran (Compound 83a)

Substantially the same procedure as in Step A of Example 46 was repeated using Compound IIf (1.0 g) obtained in Reference Example 6 to give Compound 83a (1.11 g, 81.4%) as a yellowish white solid.

NMR(DMSO-$d_6$, δ, ppm): 3.15(d, J=7 Hz, 2H), 3.97(s, 3H), 5.17(t, J=7 Hz, 1H), 5.64(bs, 1H), 6.97(d, J=8 Hz, 1H), 7.16(d, J=8 Hz, 1H), 7.52(d, J=6 Hz, 2H), 7.91(d, J=6 Hz, 2H), 8.00(s, 1H), 8.56(d, J=6 Hz, 2H), 8.71(d, J=6 Hz, 2H)

MASS(m/e): 346($M^+$), 328, 254

(Step B) (Compound 83)

Substantially the same procedure as in Example 67 was repeated using Compound 83a (2.8 g) obtained in Step A to give (E)-7-methoxy-2-(4-pyridyl)-4-[2-(4-pyridyl)-ethenyl] benzofuran (1.60 g, 60.4%) as a yellow solid. Then, substantially the same procedure as in Example 51 was repeated using the obtained crystals to give Compound 83.

Melting point: 200–203° C.

NMR(DMSO-$d_6$, δ, ppm): 4.08(s, 3H), 7.27(d, J=8 Hz, 1H), 7.69(d, J=17 Hz, 1H), 7.75(d, J=8 Hz, 1H), 8.25(d, J=17 Hz, 1H), 8.36(d, J=6 Hz, 2H), 8.43(d, J=5 Hz, 2H), 8.88(d, J=6 Hz, 2H), 8.98(d, J=5 Hz, 2H), 9.02(s, 1H)

IR(KBr, $cm^{-1}$): 1640, 1600, 1560, 1500

MASS(m/e): 329($M^+$+1), 313

Elemental analysis: $C_{21}H_{16}N_2O_2$.2.0HCl.1.6$H_2O$

Found (%) C,58.61; H,5.05; N,6.45. Calcd. (%) C,58.64; H,4.97; N,6.51.

EXAMPLE 84

(E)-4-[2-(3,5-Dichloro-4-pyridyl)ethenyl]-7-methoxy-2-(2-pyridyl)benzofuran (Compound 84)

(Step A) (±)-4-[2-(3,5-Dichloro-4-pyridyl)-1-hydroxyethyl]-7-methoxy-2-(2-pyridyl)benzofuran (Compound 84a)

Substantially the same procedure as in Step A of Example 45 was repeated using Compound IIg (3.40 g) obtained in Reference Example 7 to give Compound 84a (4.51 g, 80.9%) as a yellowish white solid.

NMR(DMSO-$d_6$, δ, ppm): 3.22(dd, J=5 Hz, 14 Hz, 1H), 3.45 (dd, J=9 Hz, 14 Hz, 1H), 3.98(s, 3H), 5.21(ddd, J=5 Hz, 5 Hz, 9 Hz, 1H), 5.73(d, J=5 Hz, 1H), 6.91(d, J=10 Hz, 1H), 7.10(d, J=10 Hz, 1H), 7.40(m, 1H), 7.62(s, 1H), 7.9–8.0(m, 2H), 8.55(s, 2H), 8.70 (dd, J=2 Hz, 5 Hz, 1H)

MASS(m/e): 416, 414($M^+$), 254

(Step B) (Compound 84)

Substantially the same procedure as in Example 67 was repeated using Compound 84a (0.60 g) obtained in Step A to give Compound 84 (0.28 g, 49.5%) as a yellow solid.

Melting point: 157–158° C.

NMR($CDCl_3$, δ, ppm): 4.10(s, 3H), 6.90(d, J=8 Hz, 1H), 7.20(d, J=17 Hz, 1H), 7.27(m, 1H), 7.47(d, J=8 Hz, 1H), 7.75(s, 1H), 7.82(m, 1H), 7.82(d, J=17 Hz, 1H), 8.02(d, J=8 Hz, 1H), 8.51(s, 2H), 8.69(dd, J=1 Hz, 4 Hz, 1H).

IR(KBr, $cm^{-1}$): 1610, 1550, 1510, 1290

MASS(m/e): 400, 398, 396($M^+$)

Elemental analysis: $C_{21}H_{14}N_2O_2Cl_2$

Found (%) C,63.81; H,3.57; N,6.91. Calcd. (%) C,63.51; H,3.55; N,7.05.

EXAMPLE 85

(E)-7-Methoxy-2-(2-pyridyl)-4-[2-(4-pyridyl) ethenyl]-benzofuran.2 hydrochloride (Compound 85)

(Step A) (±)-4-[1-Hydroxy-2-(4-pyridyl)ethyl]-7-methoxy-2-(2-pyridyl)benzofuran (Compound 85a)

Substantially the same procedure as in Step A of Example 46 was repeated using Compound IIg (3.0 g) obtained in Reference Example 7 to give Compound 85a (2.10 g, 51.1%) as a yellowish white solid.

NMR(DMSO-$d_6$, δ, ppm): 3.04(d, J=6 Hz, 2H), 3.96(s, 3H), 5.15(dt, J=4 Hz, 6 Hz, 1H), 5.53(d, J=4 Hz, 1H), 6.92(d, J=8 Hz, 1H), 7.12(d, J=8 Hz, 1H), 7.26(d, J=6 Hz, 2H), 7.41(dd, J=5 Hz, 9 Hz, 1H), 7.74(s, 1H), 7.9–8.0(m, 2H), 8.41(d, J=6 Hz, 2H), 8.68(d, J=5 Hz, 1H)

MASS(m/e): 346($M^+$), 253, 252

(Step B) (Compound 85)

Substantially the same procedure as in Example 67 was repeated using Compound 85a (2.1 g) obtained in Step A to give (E)-7-methoxy-2-(2-pyridyl)-4-[2-(4-pyridyl)-ethenyl] benzofuran (0.58 g, 29.2%) as a yellow solid. Then, substantially the same procedure as in Example 51 was repeated using the obtained crystals to give Compound 85.

Melting point: 192–195° C.

NMR($D_2O$, δ, ppm): 4.11(s, 3H), 6.69(d, J=17 Hz, 1H), 6.89(d, J=8 Hz, 1H), 7.25(d, J=8 Hz, 1H), 7.27(d, J=17 Hz, 1H), 7.54(s, 1H), 7.72(dd, J=5 Hz, 7 Hz, 1H), 7.92(d, J=6 Hz, 2H), 7.99(d, J=8 Hz, 1H), 8.31(dd, J=7 Hz, 8 Hz, 1H), 8.55(d, J=5 Hz, 1H), 8.72(d, J=6 Hz, 2H)

IR(KBr, $cm^{-1}$): 1610, 1560, 1280

MASS(m/e): 328($M^+$)

Elemental analysis: $C_{21}H_{16}N_2O_2$.2.0HCl.1.4$H_2O$

Found (%) C,59.12; H,4.73; N,6.51. Calcd. (%) C,59.14; H,4.91; N,6.57.

EXAMPLE 86

(E)-4-[2-Cyano-2-(4-pyridyl)ethenyl]-7-methoxy-2,2-dimethyl-2,3-dihydrobenzofuran (Compound 86)

Compound IIa (2.3 g) obtained in Reference Example 1 was suspended in glacial acetic acid, and sodium acetate (2.3 g) and 4-pyridylacetonitrile (1.6 ml) were successively added thereto, followed by stirring at 110° C. for one hour. The reaction solution was poured into water and the mixture was extracted with ethyl acetate. The collected organic layer was washed with a saturated saline and dried over anhydrous magnesium sulfate. The residue was purified by silica gel column chromatography (ethyl acetate/toluene=1/9) and recrystallized from ethanol to give Compound 88 (1.6 g, 46%) as pale-yellow crystals.

Melting point: 150–163° C.

NMR(DMSO-$d_6$, δ, ppm): 1.44(s, 6H), 3.33(s, 2H), 3.84 (s, 3H), 7.04(d, J=8.57 Hz, 1H), 7.71(d, J=5.94 Hz, 1H), 7.73(d, J=8.25 Hz, 1H), 7.98(s, 1H), 8.67(d, J=6.27 Hz, 1H)

MASS(m/e): 306($M^+$)

IR(KBr, $cm^{-1}$): 2206, 1578, 1508

Elemental analysis: $C_{19}H_{18}N_2O_2$

Found (%) C,74.63; H,5.95; N,9.25. Calcd. (%) C,74.49; H,5.92; N,9.14.

EXAMPLE 87

(E)-4-[2-Ethoxycarbonyl-2-(4-pyridyl)ethenyl]-7-methoxy-2,2-dimethyl-2,3-dihydrobenzofuran (Compound 87)

Substantially the same procedure as in Example 86 was repeated using Compound IIa (2.0 g) obtained in Reference Example 1 and using ethyl ester of 4-pyridine-acetic acid instead of 4-pyridylacetonitrile to give Compound 87 (2.5 g, 73.2%) as dark brown crystals.

Melting point: 98–100° C.

NMR(DMSO-$d_6$, δ, ppm): 1.20(t, J=7.26 Hz, 3H), 1.38(s, 6H), 3.02(s, 2H), 3.68(s, 3H), 4.19(q, J=7.26 Hz, 2H), 6.15(d, J=8.57 Hz, 1H), 6.60(d, J=8.57 Hz, 1H), 7.23(d, J=5.93 Hz, 2H), 7.71(s, 1H), 8.57(d, J=5.93 Hz, 2H)

MASS(m/e): 353($M^+$), 280

IR(KBr, $cm^{-1}$): 1706, 1596, 1508

EXAMPLE 88

4-(2,2-Dicyanoethenyl)-7-methoxy-2,2-dimethyl-2,3-dihydrobenzofuran (Compound 88)

Compound IIa (2.0 g) obtained in Reference Example 1 was suspended in glacial acetic acid, and sodium acetate (1.9 g) and malonitrile (0.8 ml) were successively added thereto, followed by stirring at 110° C. for one hour. The reaction solution was poured into water, and the precipitated crystals were collected by filtration, washed with water, and dried under reduced pressure. The obtained crude crystals were purified by silica gel column chromatography (chloroform) to give Compound 88 (2.4 g, 94.5%) as pale-yellow crystals.

Melting point: 198–200° C.

NMR(DMSO-$d_6$, δ, ppm): 1.43(s, 6H), 3.24(s, 2H), 3.87 (s, 3H), 7.12(d, J=8.6 Hz, 1H), 7.75(d, J=8.6 Hz, 1H), 8.19(s, 1H)

MASS(m/e): 254($M^+$)

IR(KBr, $cm^{-1}$): 2218, 1619, 1589

Elemental analysis: $C_{15}H_{14}N_2O_2$

Found (%) C,70.95; H,5.57; N,10.96. Calcd. (%) C,70.85; H,5.55; N,11.02.

EXAMPLE 89

4-(2-Cyano-2-ethoxycarbonylethenyl)-7-methoxy-2,2-dimethyl-2,3-dihydrobenzofuran (Compound 89)

Substantially the same procedure as in Example 88 was repeated using Compound IIa (2.0 g) obtained in Reference Example 1 and using ethyl cyanoacetate instead of malonitrile to give Compound 89 (2.8 g, 96.5%) as a dark brown oily substance.

Melting point: 112–117° C.

NMR(DMSO-$d_6$, δ, ppm): 1.30(t, J=6.9 Hz, 3H), 1.44(s, 6H), 3.23(s, 2H), 3.86(s, 3H), 4.30(q, J=6.9 Hz, 2H), 7.09(d, J=8.9 Hz, 1H), 7.83(d, J=8.6 Hz, 1H), 8.09(s, 1H)

MASS(m/e): 301($M^+$)

IR(KBr, $cm^{-1}$): 2218, 1718, 1590

Elemental analysis: $C_{17}H_{19}NO_4$

Found (%) C,67.80; H,6.41; N,4.82. Calcd. (%) C,67.76; H,6.35; N,4.65.

EXAMPLE 90

(E)-7-Methoxy-4-[2-(4-pyridylaminocarbonyl)ethenyl]-spiro[2,3-dihydrobenzofuran-2,1'-cyclopentane] (Compound 90)

(Step A) (E)-4-(2-Ethoxycarbonylethenyl)-7-methoxy-spiro[2,3-dihydrobenzofuran-2,1'-cyclopentane] (Compound 90a)

Triethyl phosphonoacetate (10.5 g) was suspended in THF (70 ml), and potassium t-butoxide (3.74 g) was added thereto under ice-cooling, followed by stirring at room temperature for 30 minutes. After cooling the reaction solution with ice again, a solution of Compound IIc (3.1 g) obtained in Reference Example 3 in THF (20 ml) was slowly and dropwise added thereto under ice-cooling, followed by stirring at room temperature for one hour. Water was added to the reaction solution and the mixture was extracted with ether. The collected organic layer was washed with a saturated saline and dried over anhydrous magnesium sulfate. The residue was purified by silica gel column chromatography (chloroform) to give Compound 90a (3.51g, 87.0%) as white crystals.

Melting point: 81–91° C.

NMR(DMSO-$d_6$, δ, ppm): 1.25(t, J=6.4 Hz, 3H), 1.30–2.22 (m, 8H), 3.35(s, 2H), 3.79(s, 3H), 4.17(d, J=7.4 Hz, 2H), 6.28(d, J=16.3 Hz, 1H), 6.83(d, J=8.4 Hz, 1H), 7.18(d, J=8.4 Hz, 1H), 7.53(d, J=16.3 Hz, 1H)

MASS(m/e): 302($M^+$), 229

(Step B) (E)-4-(2-Carboxyethenyl)-7-methoxy-spiro[2,3-dihydrobenzofuran-2,1'-cyclopentane] (Compound 90b)

A mixture of Compound 90a (3.5 g) obtained in Step A, a 4N aqueous solution (35.0 ml) of sodium hydroxide, and ethanol (150 ml) was stirred at room temperature for 15 hours. The solvent was distilled off and the residue was dissolved in water. Concentrated hydrochloric acid was dropwise added to the solution, and a precipitate was collected by filtration, washed with water, and dried to give Compound 90b (2.38 g, 74.9%) as white crystals.

Melting point: 212–215° C.

NMR(DMSO-$d_6$, δ, ppm): 1.75–1.96(m, 8H), 3.33(s, 2H), 3.79(s, 3H), 6.23(d, J=15.8 Hz, 1H), 6.86(d, J=8.4 Hz, 1H), 7.15(d, J=8.4 Hz, 1H), 7.48(d, J=16.3 Hz, 1H), 12.26(broad s, 1H)

MASS(m/e): 274($M^+$)

(Step C) (Compound 90)

Compound 90b (0.3 g) obtained in Step B was suspended in a mixed solvent of methylene chloride (6 ml) and dioxane (1 ml), and dicyclohexylcarbodiimide (DCC) (0.23 g) and 4-aminopyridine (0.11 g) were added thereto after cooling the suspension to 0° C., followed by stirring at room temperature for 6 hours. Water was added to the mixture followed by extraction with chloroform. The collected organic layer was washed with a saturated saline and dried over anhydrous magnesium sulfate. The residue was purified by silica gel column chromatography (chloroform) to give Compound 90 (0.22 g, 64.5%) as pale-yellow crystals.

Melting point: 124–128° C.

NMR(DMSO-$d_6$, δ, ppm): 1.77–1.90(m, 6H), 1.90–2.10 (s, 2H), 3.39(s, 2H), 3.80(s, 3H), 6.60(d, J=15.8 Hz, 1H), 6.91(d, J=8.4 Hz, 1H), 7.09(d, J=8.4 Hz, 1H), 7.55(d, J=15.8 Hz, 1H), 7.57(d, J=5.7 Hz, 2H), 8.45(d, J=5.9 Hz, 1H), 10.47 (s, 1H)

IR(KBr, $cm^{-1}$): 1592, 1506

MASS(m/e): 350($M^+$), 257

Elemental analysis: $C_{21}H_{22}N_2O_3.0.4H_2O$

Found (%) C,70.52; H,6.41; N,7.60. Calcd. (%) C,70.53; H,6.43; N,7.83.

EXAMPLE 91

(E)-7-Methoxy-4-{2-[4-(methoxycarbonyl)phenyl-1-ylaminocarbonyl]ethenyl]-spiro[2,3-dihydrobenzofuran-2,1'-cyclopentane] (Compound 91)

Compound 90b (0.9 g) obtained in Step B of Example 90 was suspended in a mixed solvent of methylene chloride (18 ml) and dioxane (4 ml), and dicyclohexyl-carbodiimide (DCC) (0.69 g) and ethyl 4-aminobenzoate (0.55 g) were added thereto after cooling the suspension to 0° C., followed by stirring at room temperature for 6 hours. Water was added to the mixture followed by extraction with chloroform. The collected organic layer was washed with a saturated saline and dried over anhydrous magnesium sulfate. The residue was purified by silica gel column chromatography (chloroform) to give Compound 91 (0.36 g, 26.9%) as white crystals.

Melting point: 119–123° C.

NMR(DMSO-$d_6$, δ, ppm): 1.77–1.90(m, 6H), 1.90–2.10 (m, 2H), 3.38(s, 2H), 3.80(s, 3H), 3.83(s, 3H), 6.67 (d, J=15.8 Hz, 1H), 6.91(d, J=8.4 Hz, 1H), 7.08(d, J=8.4 Hz, 1H), 7.52(d, J=15.8 Hz, 1H), 7.82(d, J=8.9 Hz, 2H), 7.95(d, J=8.4 Hz, 2H), 10.45(s, 1H)

IR(KBr, $cm^{-1}$): 1699, 1608, 1506

MASS(m/e): 407($M^+$)

Elemental analysis: $C_{24}H_{25}NO_5.0.1H_2O$

Found (%) C,70.43; H,6.37; N,3.44. Calcd. (%) C,70.43; H,6.20; N,3.42.

EXAMPLE 92

(E)-4-{2-[4-(Carboxy)phenyl-1-ylaminocarbonyl]-ethenyl}-7-methoxy-spiro[2,3-dihydrobenzofuran-2, 1'-cyclopentane] (Compound 92)

A mixture of Compound 91 (0.25 g) obtained in Example 91, a 4N aqueous solution (1.6 ml) of sodium hydroxide, and dioxane (2.5 ml) was heated under reflux for 2 hours. The reaction solution was cooled, poured into water, and the mixture was adjusted to pH 3 by 6N hydrochloric acid. The precipitated crystals were collected by filtration, washed with water, and dried to give Compound 92 (0.43 g, 17.8%) as white crystals.

Melting point: 266–269° C.

NMR(DMSO-$d_6$, δ, ppm): 1.65–1.90(s, 6H), 1.90–2.10 (m, 2H), 3.38(s, 2H), 3.80(s, 3H), 6.63(d, J=15.8 Hz, 1H), 6.91(d, J=8.4 Hz, 1H), 7.09(d, J=8.4 Hz, 1H), 7.52(d, J=15.3 Hz, 1H), 7.80(d, J=8.9 Hz, 2H), 7.92(d, J=8.9 Hz, 1H), 10.43(s, 1H).

IR(KBr, $cm^{-1}$): 1682, 1596

MASS(m/e): 394($M^+$+1), 257

Elemental analysis: $C_{23}H_{23}NO_5.0.1H_2O$

Found (%) C,69.85; H,5.92; N,3.54. Calcd. (%) C,69.85; H,6.13; N,3.52.

EXAMPLE 93

(E)-7-Methoxy-4-{2-[3-(methoxycarbony)phenyl-1-ylaminocarbonyl]ethenyl}-spiro[2,3-dihydrobenzofuran-2,1'-cyclopentane] (Compound 93)

Substantially the same procedure as in Example 91 was repeated using Compound 90b (0.9 g) obtained in Step B of Example 90 and methyl 3-aminobenzoate (0.55 g) to give Compound 93 (0.68 g, 50.8%) as white crystals.

Melting point: 88–91° C.

NMR(DMSO-$d_6$, δ, ppm): 1.77–1.90(s, 6H), 1.90–2.10 (m, 2H), 3.39(s, 2H), 3.80(s, 3H), 3.87(s, 3H), 6.60 (d, J=15.8 Hz, 1H), 6.91(d, J=8.6 Hz, 1H), 7.08(d, J=8.3 Hz, 1H), 7.46–7.55(m, 2H), 7.66(d, J=7.9 Hz, 1H), 7.97(d, J=7.9 Hz, 1H), 8.36(s, 1H), 10.37(s, 1H)

IR(KBr, $cm^{-1}$): 1724, 1608

MASS(m/e): 407($M^+$), 257

Elemental analysis: $C_{24}H_{25}NO_5.0.6H_2O$

Found (%) C,68.69; H,6.10; N,3.34. Calcd. (%) C,68.92; H,6.31; N,3.35.

EXAMPLE 94

(E)-4-{2-[4-(Carboxy)phenyl-1-ylaminocarbonyl]-ethenyl}-7-methoxy-spiro[2,3-dihydrobenzofuran-2, 1'-cyclopentane] (Compound 94)

Substantially the same procedure as in Example 92 was repeated using Compound 93 (0.48 g) obtained in Example 93 to give Compound 94 (0.34 g, 73.5%) as white crystals.

Melting point: >290° C.

NMR(DMSO-$d_6$, δ, ppm): 1.77–1.90(m, 6H), 1.90–2.10 (m, 2H), 3.39(s, 2H), 3.80(s, 3H), 6.60(d, J=15.8 Hz, 1H), 6.91(d, J=8.6 Hz, 1H), 7.08(d, J=8.2 Hz, 1H), 7.43–7.63(m, 1H), 7.64(d, J=6.6 Hz, 1H), 7.95(d, J=7.9 Hz, 1H), 8.30(s, 1H), 10.32(s, 1H), 10.32(s, 1H), 12.8–13.1(brs, 1H)

IR(KBr, $cm^{-1}$): 1683, 1610

MASS(m/e): 393($M^+$), 257

Elemental analysis: $C_{23}H_{23}NO_5$

Found (%) C,70.23; H,5.93; N,3.60. Calcd. (%) C,70.21; H,5.89; N,3.56.

EXAMPLE 95

4-[2-(3,5-Dichloro-4-pyridyl)-1-oxoethyl]-7-methoxy-2,2-dimethyl-2,3-dihydrobenzofuran (Compound 95)

Compound 45a (3.0 g) obtained in Step A of Example 45 was dissolved in methylene chloride (80 ml), and a powder of silica gel (15 g) and pyridinium chlorochromate (PCC) (2.1 g) were added thereto, followed by stirring at room temperature for 2 hours. The reaction solution was filtered and the obtained filtrate was concentrated under reduced pressure. The residue was purified by silica gel column chromatography (chloroform/methanol=30/1) to give Compound 95 (1.3 g, 44.9%) as pale-yellow crystals.

Melting point: 127–131° C.

NMR(DMSO-$d_6$, δ, ppm): 1.40(s, 6H), 3.24(s, 2H), 3.87 (s, 3H), 4.71(s, 2H), 7.03(d, J=8.58 Hz, 1H), 7.79(d, J=8.58 Hz, 1H), 8.66(s, 2H)

MASS(m/e): 367, 365($M^+$), 205

IR($cm^{-1}$): 1675, 1613, 1575

Elemental analysis: $C_{18}H_{17}Cl_2NO_3$

Found (%) C,58.91; H,4.60; N,3.73. Calcd. (%) C,59.03; H,4.68; N,3.82.

EXAMPLE 96

7-Methoxy-2,2-dimethyl-4-[1-oxo-2-(4-pyridyl) ethyl]-2,3-dihydrobenzofuran (Compound 96)

Substantially the same procedure as in Example 95 was repeated using Compound 46a (4.5 g) obtained in Step A of Example 46 to give Compound 96 (0.7 g, 15.5%) as pale-yellow crystals.

Melting point: 107–111° C.

NMR(DMSO-$d_6$, δ, ppm): 1.39(s, 6H), 3.26(s, 2H), 3.85 (s, 3H), 4.37(s, 2H), 6.98(d, J=8.58 Hz, 1H), 7.27(d, J=5.61 Hz, 2H), 7.66(d, J=8.57 Hz, 1H), 8.49(d, J=5.61 Hz, 2H)

MASS(m/e): 297($M^+$), 205

IR($cm^{-1}$): 1675, 1608, 1578, 1511

Elemental analysis: $C_{18}H_{19}NO_3.0.1H_2O$

Found (%) C,72.37; H,6.56; N,4.61. Calcd. (%) C,72.27; H,6.47; N,4.68.

EXAMPLE 97

4-[2-(3,5-Dichloro-4-pyridyl)-1-oxoethyl]-2,2-diethyl-7-methoxy-2,3-dihydrobenzofuran (Compound 97)

Under an argon atmosphere, a solution (50 ml) of 3,5-dichloro-4-methylpyridine (7.8 g) in THF was cooled to −78° C., and then a 1.69M solution (29 ml) of butyl lithium in hexane was dropwise added thereto, followed by stirring at the same temperature for one hour. A solution (40 ml) of Compound IIk (4.0 g) obtained in Reference Example 11 in THF was slowly and dropwise added to the mixture, followed by stirring at 0° C. for 2 hours and then at room temperature for 3 hours. The reaction solution was poured into water and the mixture was extracted with ether. The organic layer was washed with a saturated saline and dried over anhydrous magnesium sulfate, and the solvent was distilled off under reduced pressure. The residue was purified by silica gel column chromatography (chloroform) to give Compound 97 (5.0 g, 4.2%) as a white solid.

Melting point: 164–166° C.

NMR(DMSO-$d_6$, δ, ppm): 0.83(t, J=7.4 Hz, 6H), 1.64(q, J=7.4 Hz, 4H), 3.20(s, 2H), 3.88(s, 3H), 4.71(s, 2H), 7.01(d, J=8.4 Hz, 1H), 7.76(d, J=8.9 Hz, 1H), 8.65(s, 2H)

MASS(m/e): 395, 393($M^+$), 233

IR($cm^{-1}$): 2970(br), 1677, 1615, 1574

Elemental analysis: $C_{20}H_{21}Cl_2NO_3$

Found (%) C,60.84; H,5.37; N,3.53. Calcd. (%) C,60.92; H,5.37; N,3.55.

EXAMPLE 98

2,2-Diethyl-7-methoxy-4-[1-oxo-2-(4-pyridyl)ethyl]-2,3-dihydrobenzofuran.hydrochloride (Compound 98)

Under an argon atmosphere, a solution (50 ml) of 4-methylpyridine (4.8 ml) in THF was cooled to −78° C., and then a 1.69M solution (29 ml) of butyl lithium in hexane was dropwise added thereto, followed by stirring at the same temperature for one hour. A solution (40 ml) of Compound IIk (4.0 g) obtained in Reference Example 11 in THF was slowly and dropwise added to the mixture, followed by stirring at 0° C. for 2 hours and then at room temperature for 2 hours. The reaction solution was poured into water and the mixture was extracted with ether. The organic layer was washed with a saturated saline and dried over anhydrous magnesium sulfate, and the solvent was distilled off under reduced pressure. The residue was purified by silica gel column chromatography (chloroform/methanol=20/1) to give 2,2-diethyl-7-methoxy-4-[1-oxo-2-(4-pyridyl)-ethyl]-2,3-dihydrobenzofuran as a colorless oily substance. Then, substantially the same procedure as in Example 51 was repeated using the obtained oily substance to give Compound 98.

Melting point: 185–191° C.

NMR(DMSO-$d_6$, δ, ppm): 0.84(t, J=7.4 Hz, 6H), 1.67(d, J=7.4 Hz, 4H), 3.24(s, 2H), 3.88(s, 3H), 4.78(s, 2H), 7.02(d, J=8.4 Hz, 1H), 7.67(d, J=8.4 Hz, 1H), 7.95(d, J=6.4 Hz, 2H), 8.86(d, J=6.4 Hz, 2H)

MASS(m/e): 325($M^+$), 233

IR($cm^{-1}$): 1671, 1611, 1574, 1505

Elemental analysis: $C_{20}H_{23}NO_3.HCl$

Found (%) C,66.36; H,6.85; N,3.85. Calcd. (%) C,66.38; H,6.69; N,3.87.

EXAMPLE 99

4-[2-(3,5-Dichloro-4-pyridyl)-1-oxoethyl]-7-methoxy-spiro[2,3-dihydrobenzofuran-2,1'-cyclopentane] (Compound 99)

Substantially the same procedure as in Example 97 was repeated using Compound III (1.0 g) obtained in Reference Example 12 to give Compound 99 (0.42 g, 42.0%) as pale-yellow crystals.

Melting point: 159–162° C.

NMR(DMSO-$d_6$, δ, ppm): 1.70–1.78(m, 6H), 1.90–2.09 (m, 2H), 3.42(s, 2H), 3.88(s, 3H), 4.71(s, 3H), 7.03 (d, J=8.9 Hz, 1H), 7.78(d, J=8.4 Hz, 1H), 8.65(s, 2H)

MASS(m/e): 393, 391($M^+$), 231

IR($cm^{-1}$): 1675, 1612, 1576

Elemental analysis: $C_{20}H_{19}Cl_2NO_3.0.3H_2O$

Found (%) C,60.40; H,4.80; N,3.50. Calcd. (%) C,60.40; H,4.97; N,3.52.

EXAMPLE 100

7-Methoxy-4-[1-oxo-2-(4-pyridyl)ethyl]-spiro[2,3-dihydrobenzofuran-2,1'-cyclopentane].hydrochloride (Compound 100)

Substantially the same procedure as in Example 98 was repeated using Compound III (4.0 g) obtained in Reference Example 12 to give 7-methoxy-4-[1-oxo-2-(4-pyridyl) ethyl]-spiro[2,3-dihydrobenzofuran-2,1'-cyclopentane] (2.1 g, 42.6%) as a pale-yellow oily substance. Then, substantially the same procedure as in Example 51 was repeated using the obtained oily substance to give Compound 100.

Melting point: 215–219° C.

NMR(DMSO-$d_6$, δ, ppm): 1.70–1.79(m, 6H), 1.90–1.97 (m, 2H), 3.44(s, 2H), 3.87 (s, 3H), 4.77(s, 2H), 7.03(d, J=6.4 Hz, 2H), 7.68(d, J=6.4 Hz, 2H), 7.94 (d, J=8.4 Hz, 1H), 8.86(d, J=8.9 Hz, 1H)

MASS(m/e): 323($M^+$), 294

IR($cm^{-1}$): 1670, 1610, 1510

Elemental analysis: $C_{20}H_{21}NO_3$.HCl.0.2$H_2O$

Found (%) C,66.21; H,6.26; N,3.79. Calcd. (%) C,66.09; H,6.21; N,3.85.

EXAMPLE 100'

7-Methoxy-4-[1-oxo-2-(4-pyridyl)ethyl]-spiro[2,3-dihydrobenzofuran-2,1'-cyclopentane]hydrochloride (Compound 100)

Under an argon atmosphere, a solution of diisopropylamine (7 ml) in THF (60 ml) was cooled to −78°, and then a 1.57M solution (32 ml) of butyl lithium in hexane was dropwise added thereto, followed by stirring at 0° for 15 minutes. The obtained mixture was cooled to −78° again, and then 4-methylpyridine (4.8 ml) was added thereto, followed by stirring for 2 hours. This solution was dropwise and slowly added to a solution of Compound IIl (4.0g) obtained in Reference Example 12 in THF (54 ml) with cooling at −78°, followed by stirring for 2 hours and then at 0° for one hour. A saturated aqueous solution of ammonium chloride was added to the reaction solution and the mixture was extracted with ether. The organic layer was washed with a saturated saline and dried over anhydrous magnesium sulfate, and the solvent was distilled off. The residue was purified by silica gel column chromatography (chloroform/methanol=50/1). The obtained pale-yellow oily substance was dissolved in ethyl acetate (10 ml) and a hydrochloric acid-ethyl acetate solution was added thereto. The precipitated crystals were collected by filtration, washed with ethyl acetate, and dried to give Compound 100 (2.3 g, 43%) as white crystals. The spectral data of the obtained white crystals were the same as those in Example 100.

EXAMPLE 101

4-[2-(3,5-Dichloro-4-pyridyl)-1-oxoethyl]-7-methoxy-spiro[2,3-dihydrobenzofuran-2,1'-cyclohexane] (Compound 101)

Substantially the same procedure as in Example 97 was repeated using Compound IIm (4.0 g) obtained in Reference Example 13 to give Compound 101 (4.3 g, 72.3%) as pale-yellow crystals.

Melting point: 149–151° C.

NMR(DMSO-$d_6$, δ, ppm): 1.43 (broad s, 4H), 1.62–1.72 (m, 6H), 3.20(s, 2H), 3.89(s, 3H), 4.71(s, 2H), 7.02(d, J=8.4 Hz, 1H), 7.78(d, J=8.9 Hz, 1H), 8.65(s, 2H)

MASS(m/e): 407, 405($M^+$), 245

IR($cm^{-1}$): 2841(br), 1678, 1578

Elemental analysis: $C_{20}H_{19}Cl_2NO_3$.0.2$H_2O$

Found (%) C,60.54; H,4.77; N,3.56. Calcd. (%) C,60.68; H,4.94; N,3.54.

EXAMPLE 102

7-Methoxy-4-[1-oxo-2-(4-pyridyl)ethyl]-spiro[2,3-dihydrobenzofuran-2,1'-cyclohexane].hydrochloride (Compound 102)

Substantially the same procedure as in Example 98 was repeated using Compound IIm (3.0 g) obtained in Reference Example 13 to give 7-methoxy-4-[1-oxo-2-(4-pyridyl)ethyl]-spiro[2,3-dihydrobenzofuran-2,1'-cyclohexane] (2.0 g, 54.9%) as a pale-yellow oily substance. Then, substantially the same procedure as in Example 51 was repeated using the obtained oily substance to give Compound 102.

Melting point: 193–196° C.

NMR(DMSO-$d_6$, δ, ppm): 1.43(broad s, 4H), 1.50–1.72 (m, 6H), 3.23(s, 2H), 3.88(s, 3H), 4.80(s, 2H), 7.03(d, J=8.9 Hz, 1H), 7.68(d, J=8.4 Hz, 1H), 7.97(d, J=6.4 Hz, 2H), 8.88(d, J=6.4 Hz, 2H).

MASS(m/e): 338($M^+$), 245

IR($cm^{-1}$): 1674, 1610, 1510

Elemental analysis: $C_{21}H_{23}NO_3$.HCl.0.1$H_2O$

Found (%) C,66.99; H,6.58; N,3.68. Calcd. (%) C,67.14; H,6.49; N,3.73.

EXAMPLE 103

(±)-4-[2-(3,5-Dichloro-4-pyridyl)-1-oxoethyl]-7-methoxy-3-methyl-2,3-dihydrobenzofuran (Compound 103)

Substantially the same procedure as in Example 95 was repeated using Compound 56a (1.0 g) obtained in Step A in Example 56 to give Compound 103 (0.5 g, 51.3%) as pale-yellow crystals.

Melting point: 99–104° C.

NMR(DMSO-$d_6$, δ, ppm): 1.08(d, J=6.93 Hz, 3H), 3.77–3.90(m, 1H), 3.90(s, 3H), 4.28(dd, J=2.64 Hz, 8.58 Hz, 1H), 4.49(t, J=8.58 Hz, 1H), 4.68(d, J=17.49 Hz, 1H), 4.80(d, J=17.81 Hz, 1H), 7.05(d, J=8.57 Hz, 1H), 7.84(d, J=8.58 Hz, 1H), 8.67(s, 2H)

IR(KBr, $cm^{-1}$): 1684, 1612, 1579, 1506, 1433

MASS(m/z): 353($M^+$+2), 351($M^+$), 191

Elemental analysis: $C_{17}H_{15}Cl_2NO_3$

Found (%) C,57.97; H,4.29; N,3.98. Calcd. (%) C,57.93; H,4.37; N,3.77.

EXAMPLE 104

(±)-7-Methoxy-3-methyl-4-[1-oxo-2-(4-pyridyl)ethyl]-2,3-dihydrobenzofuran (Compound 104)

Substantially the same procedure as in Example 95 was repeated using Compound 57a (0.6 g) obtained in Step A in Example 57 to give Compound 104 (0.03 g, 4,2%) as pale-yellow crystals.

Melting point: 111–117° C.

NMR(DMSO-$d_6$, δ, ppm): 1.08(d, J=6.93 Hz, 3H), 3.77–3.86(m, 1H), 3.86(s, 3H), 4.27(dd, J=2.64 Hz, 8.75 Hz, 1H), 4.40(s, 2H), 4.46(t, J=8.75 Hz, 1H), 7.00(d, J=8.58 Hz, 1H), 7.28(d, J=4.29 Hz, 2H), 7.72(d, J=8.58 Hz, 1H), 8.50(d, J=4.29 Hz, 2H)

IR(KBr, $cm^{-1}$): 1686, 1613, 1579, 1508, 1433

MASS(m/z): 283($M^+$), 191

Elemental analysis: $C_{17}H_{17}NO_3$.0.3$H_2O$

Found (%) C,70.72; H,6.14; N,4.85. Calcd. (%) C,70.54; H,6.10; N,4.46.

EXAMPLE 105

(±)-cis-6-Methoxy-9-[1-oxo-2-(4-pyridyl)ethyl]-1,2,3,4,4a,9b-hexahydrodibenzofuran.hydrochloride (Compound 105)

Substantially the same procedure as in Example 98 was repeated using Compound IIn (0.4 g) obtained in Reference Example 14 to give (±)-cis-6-methoxy-9-[1-oxo-2-(4-pyridyl)ethyl]-1,2,3,4,4a,9b-hexahydrodibenzofuran (0.34 g, 68%) as a pale-yellow oily substance. Then, substantially the same procedure as in Example 51 was repeated using the obtained oily substance to give Compound 105.

Melting point: 225–233° C.

NMR($CDCl_3$, δ, ppm): 0.80–1.00(m, 1H), 1.10–1.36(m, 1H), 1.40–1.85(m, 1H), 1.98–2.12(m, 1H), 2.35–2.52(m, 1H), 3.45–3.64(m, 1H), 3.99(s, 3H), 4.58 (s, 2H), 4.50–4.65 (m, 1H), 6.89(d, J=9 Hz, 1H), 7.51(d, J=9 Hz, 1H), 7.83(d, J=7 Hz, 2H), 8.73(d, J=7 Hz, 2H)

Elemental analysis: $C_{20}H_{21}NO_3$.HCl

Found (%) C,66.59; H,6.15; N,4.02. Calcd. (%) C,66.76; H,6.16; N,3.89.

EXAMPLE 106

2-Cyano-4-[2-(3,5-dichloro-4-pyridyl)-1-oxoethyl]-7-methoxybenzofuran (Compound 106)

(Step A) 2-Cyano-4-[2-(3,5-dichloro-4-pyridyl)-1-hydroxyethyl]-7-methoxybenzofuran (Compound 106a)

Substantially the same procedure as in Step A of Example 45 was repeated using Compound IIi (2.0 g) obtained in Reference Example 9 to give Compound 106a (2.3 g, 63.2%) as pale-yellow crystals.

NMR(DMSO-$d_6$, δ, ppm): 3.15–3.22(m, 1H), 3.30–3.50 (m, 1H), 3.94(s, 3H), 5.13–5.20(m, 1H), 5.83(d, J=4.0 Hz, 1H), 7.10(d, J=8.3 Hz, 1H), 7.16(d, J=7.9 Hz, 1H), 8.12(s, 1H), 8.55(s, 2H)

MASS(m/e): 362($M^+$)

(Step B) (Compound 106)

Substantially the same procedure as in Example 95 was repeated using Compound 106a (1.1 g) obtained in Step A to give Compound 106 (0.27 g, 25.0%) as white crystals.

Melting point: 197–199° C.

NMR(DMSO-$d_6$, δ, ppm): 4.12(s, 3H), 4.88(s, 2H), 7.39 (d, J=8.6 Hz, 1H), 8.41(s, 1H), 8.47(d, J=8.3 Hz, 1H), 8.69(s, 2H).

MASS(m/e): 362, 360($M^+$), 200

IR($cm^{-1}$): 1675, 1557

Elemental analysis: $C_{17}H_{10}Cl_2N_2O_3$

Found (%) C,56.62; H,2.77; N,7.54. Calcd. (%) C,56.53; H,2.79; N,7.76.

EXAMPLE 107

2-Benzoyl-7-methoxy-4-(1-oxo-2-phenylethyl) benzofuran (Compound 107)

Compound IIag-a (1.0 g) obtained in Step A of Reference Example 33 and phenylacetyl chloride (0.79 ml) were dissolved in dry dichloromethane (50 ml), the solution was cooled to 0° C., and titanium tetrachloride (1.3 ml) was dropwise added thereto, followed by stirring at the same temperature. After 5 minutes, the reaction was stopped by adding distilled water, and the reaction solution was extracted with diethylether. Then, the organic layer was washed with a saturated saline and dried over anhydrous magnesium sulfate, and the solvent was distilled off under reduced pressure. The residue was purified by silica gel column chromatography (hexane/ethyl acetate=4/1) to give Compound 107 (0.94 g, 64.0%) as a pale-yellow solid.

NMR($CDCl_3$, δ, ppm): 4.10(s, 3H), 4.37(s, 2H), 6.93(d, J=8.5 Hz, 1H), 7.2–7.4 (m, 5H), 7.51(dd, J=7.5 Hz, 8 Hz, 2H), 7.61(t, J=8 Hz, 1H), 7.91(d, J=8.5 Hz, 1H), 8.01(d, J=7.5 Hz, 2H), 8.26(s, 1H)

MASS(m/e): 370($M^+$), 279, 251

Elemental analysis: $C_{24}H_{18}O_4$

Found (%) C,77.97; H,4.94. Calcd. (%) C,77.82; H,4.91.

EXAMPLE 108

2-Benzoyl-7-methoxy-4-[1-oxo-2-(4-pyridyl)ethyl]-benzofuran (Compound 108)

Substantially the same procedure as in Example 107 was repeated using Compound IIag-a obtained in Step A of Reference Example 33 to give Compound 108 as a pale-yellow solid.

NMR($CDCl_3$, δ, ppm): 4.13(s, 3H), 4.35(s, 2H), 6.98(d, J=8 Hz, 1H), 7.23(d, J=5.5 Hz, 2H), 7.52(dd, J=7 Hz, 8 Hz, 2H), 7.63(t, J=7 Hz, 1H), 7.98(d, J=8 Hz, 2H), 8.03(d, J=8 Hz, 1H), 8.24(s, 1H), 8.57(d, J=5.5 Hz, 2H)

MASS(m/e): 371($M^+$), 279

EXAMPLE 109

2-Butyl-7-methoxy-4-[1-oxo-2-(4-pyridyl)ethyl]-benzofuran.hydrochloride (Compound 109)

Substantially the same procedure as in Example 98 was repeated using Compound IIo (1.3 g) obtained in Reference Example 15 to give 2-butyl-7-methoxy-4-[1-oxo-2-(4-pyridyl)ethyl]benzofuran (0.42 g, 42%) as pale-yellow crystals. Then, substantially the same procedure as in Example 51 was repeated using the obtained crystals to give Compound 109.

Melting point: 212–218° C.

NMR($CDCl_3$, δ, ppm): 0.941(t, J=7 Hz, 3H), 1.30–1.55 (m, 2H), 1.65–1.85(m, 2H), 2.83(t, J=7 Hz, 2H), 4.12 (s, 3H), 4.65(s, 2H), 6.82(d, J=9 Hz, 1H), 7.12(s, 1H), 7.84(d, J=9 Hz, 1H), 7.87(d, J=6 Hz, 2H), 8.72(d, J=6 Hz, 2H)

Elemental analysis: $C_{20}H_{21}NO_3HCl0.2H_2O$

Found (%) C,66.03; H,6.09; N,3.77. Calcd. (%) C,66.09; H,6.21; N,3.85.

EXAMPLE 110

7-Methoxy-2-(2-methylpropyl)-4-[1-oxo-2-(4-pyridyl)-ethyl]benzofuran.hydrochloride (Compound 110)

Substantially the same procedure as in Example 98 was repeated using Compound IIp (1.8 g) obtained in Reference Example 16 to give 7-methoxy-2-(2-methylpropyl)-4-[1-oxo-2-(4-pyridyl)ethyl]benzofuran (1.2 g, 56%) as white crystals. Then, Substantially the same procedure as in Example 51 was repeated using the obtained crystals to give Compound 110.

Melting point: 193–198° C.

NMR($CDCl_3$, δ, ppm): 0.970(d, J=7 Hz, 6H), 2.05–2.20 (m, 1H), 2.70(d, J=7 Hz, 2H), 4.12(s, 3H), 4.64(s, 2H), 6.82(d, J=9 Hz, 1H), 7.13(s, 1H), 7.77–7.88 (m, 3H), 8.71(d, J=7 Hz, 2H)

Elemental analysis: $C_{20}H_{21}NO_3HCl$

Found (%) C,66.64; H,6.16; N,3.90. Calcd. (%) C,66.76; H,6.16; N,3.89.

EXAMPLE 111

7-Methoxy-4-[1-oxo-2-(4-pyridyl)ethyl]-2-phenyl-benzofuran.hydrochloride (Compound 111)

Substantially the same procedure as in Example 98 was repeated using Compound IIs (2.30 g) obtained in Reference Example 19 to give 7-methoxy-4-[1-oxo-2-(4-pyridyl) ethyl]-2-phenylbenzofuran (1.30 g, 26.6%) as a white solid. Then, substantially the same procedure as in Example 51 was repeated using the obtained crystals to give Compound 111.

NMR(DMSO-$d_6$, δ, ppm): 4.12(s, 3H), 4.94(s, 2H), 7.16 (d, J=8.5 Hz, 1H), 7.4–7.6(m, 3H), 7.90(s, 1H), 7.97(d, J=7 Hz, 2H), 8.04(d, J=5.5 Hz, 2H), 8.18(d, J=8.5 Hz, 1H), 8.92(d, J=5.5 Hz, 2H)

MASS(m/e): 343($M^+$), 251, 223

Elemental analysis: $C_{22}H_{17}NO_3$.HCl.0.1$H_2O$

Found (%) C,69.07; H,4.73; N,3.80. Calcd. (%) C,69.24; H,4.81; N,3.67.

EXAMPLE 112

2-(2-Ethylphenyl)-7-methoxy-4-[1-oxo-2-(4-pyridyl)-ethyl]benzofuran.hydrochloride (Compound 112)

Substantially the same procedure as in Example 98 was repeated using Compound IIt (3.0 g) obtained in Reference Example 20 to give 2-(2-ethylphenyl)-7-methoxy-4-[1-oxo-2-(4-pyridyl)ethyl]benzofuran (1.00 g, 27.8%) as a white solid. Then, substantially the same procedure as in Example 51 was repeated using the obtained crystals to give Compound 112.

Melting point: 186–188° C.

NMR(DMSO-$d_6$, δ, ppm): 1.19(t, J=7 Hz, 3H), 2.87(q, J=7 Hz, 2H), 4.11(s, 3H), 4.93(s, 2H), 7.18(d, J=8.5 Hz, 1H), 7.3–7.5(m, 3H), 7.61(s, 1H), 7.75 (d, J=7.5 Hz, 1H), 8.02(d, J=6 Hz, 2H), 8.21(d, J=8.5 Hz, 1H), 8.89(d, J=6 Hz, 2H)

IR(KBr, $cm^{-1}$): 2960, 2920, 1654, 1618, 1573

MASS(m/e): 371($M^+$), 279

Elemental analysis: $C_{24}H_{21}NO_3$.HCl

Found (%) C,70.69; H,5.45; N,3.46. Calcd. (%) C,70.66; H,5.45; N,3.43.

EXAMPLE 113

2-(2-Isopropylphenyl)-7-methoxy-4-[1-oxo-2-(4-pyridyl)ethyl]benzofuran.hydrochloride (Compound 113)

Substantially the same procedure as in Example 98 was repeated using Compound IIu (2.50 g) obtained in Reference Example 21 to give 2-(2-isopropylphenyl)-7-methoxy-4-[1-oxo-2-(4-pyridyl)ethyl]benzofuran (1.10 g, 37.0%) as a white solid. Then, substantially the same procedure as in Example 51 was repeated using the obtained crystals to give Compound 113.

Melting point: 184–185° C.

NMR(DMSO-$d_6$, δ, ppm): 1.23(d, J=6.5 Hz, 6H), 3.44 (sep, J=6.5 Hz, 1H), 4.11(s, 3H), 4.94(s, 2H), 7.17(d, J=8.5 Hz, 1H), 7.37(dd, J=5 Hz, 7 Hz, 1H), 7.4–7.6(m, 2H), 7.53(s, 1H), 7.62(d, J=7 Hz, 1H), 8.02(d, J=6 Hz, 2H), 8.22(d, J=8.5 Hz, 1H), 8.90(d, J=6 Hz, 2H)

IR(KBr, $cm^{-1}$): 2960, 2950, 1653, 1618, 1577

MASS(m/e): 385($M^+$), 293

Elemental analysis: $C_{25}H_{23}NO_3$.HCl

Found (%) C,71.00; H,5.73; N,3.35. Calcd. (%) C,71.16; H,5.74; N,3.32.

EXAMPLE 114

4-[2-(3,5-Dichloro-4-pyridyl)-1-oxoethyl]-7-methoxy-2-(4-pyridyl)benzofuran.2 hydrochloride (Compound 114)

Substantially the same procedure as in Example 97 was repeated using Compound IIq (2.0 g) obtained in Reference Example 17 to give 4-[2-(3,5-dichloro-4-pyridyl)-1-oxoethyl]-7-methoxy-2-(4-pyridyl)benzofuran (0.18 g, 9.1%) as a white solid. Then, substantially the same procedure as in Example 51 was repeated using the obtained crystals to give Compound 114.

Melting point: 263–266° C.

NMR(DMSO-$d_6$, δ, ppm): 4.16(s, 3H), 4.91(s, 2H), 7.34 (d, J=9 Hz, 1H), 8.40(d, J=9 Hz, 1H), 8.50(d, J=6 Hz, 2H), 8.66(s, 1H), 8.70(s, 2H), 8.97(d, J=6 Hz, 2H).

IR(KBr, $cm^{-1}$): 1675, 1630, 1585, 1350

MASS(m/e): 416, 414, 412($M^+$), 253, 252

Elemental analysis: $C_{21}H_{14}N_2O_3Cl_2$.2HCl.0.8$H_2O$

Found (%) C,50.36; H,3.68; N,5.45. Calcd. (%) C,50.38; H,3.54; N,5.59.

EXAMPLE 115

7-Methoxy-4-[1-oxo-2-(4-pyridyl)ethyl]-2-(4-pyridyl)-benzofuran.2 hydrochloride (Compound 115)

Substantially the same procedure as in Example 98 was repeated using Compound IIq (2.6 g) obtained in Reference Example 17 to give 7-methoxy-4-[1-oxo-2-(4-pyridyl) ethyl]-2-(4-pyridyl)benzofuran (1.78 g, 55.9%) as a white solid. Then, substantially the same procedure as in Example 51 was repeated using the obtained crystals to give Compound 115.

Melting point: 225–228° C.

NMR(DMSO-$d_6$, δ, ppm): 4.13(s, 3H), 5.00(s, 2H), 7.32 (d, J=9 Hz, 1H), 8.07(d, J=6 Hz, 2H), 8.25(d, J=9 Hz, 1H), 8.44(d, J=7 Hz, 2H), 8.57(s, 1H), 8.9–9.0(m, 4H)

IR(KBr, $cm^{-1}$): 1665, 1635, 1610, 1520, 1350

MASS(m/e): 344($M^+$), 252

Elemental analysis: $C_{21}H_{16}N_2O_3$.2.0HCl.2.0$H_2O$

Found (%) C,55.74; H,4.82; N,6.10. Calcd. (%) C,55.64; H,4.89; N,6.18.

EXAMPLE 116

4-[2-(3,5-Dichloro-4-pyridyl)-1-oxoethyl]-7-methoxy-2-(2-pyridyl)benzofuran.2 hydrochloride (Compound 116)

Substantially the same procedure as in Example 97 was repeated using Compound IIr (3.0 g) obtained in Reference Example 18 to give 4-[2-(3,5-dichloro-4-pyridyl)-1-oxoethyl]-7-methoxy-2-(2-pyridyl)benzofuran (1.89 g, 63.4%) as a yellowish white solid. Then, substantially the same procedure as in Example 51 was repeated using the obtained crystals to give Compound 116.

Melting point: 226–227° C.

NMR(DMSO-$d_6$, δ, ppm): 4.14(s, 3H), 4.88(s, 2H), 7.24 (d, J=9 Hz, 1H), 7.53(dd, J=5 Hz, 7 Hz, 1H), 8.0–8.1(m, 2H), 8.13(s, 1H), 8.34(d, J=9 Hz, 1H), 8.70(s, 2H), 8.73(d, J=5 Hz, 1H)

IR(KBr, $cm^{-1}$): 1670, 1605, 1580, 1310

MASS[FAB(pos.), m/e]: 417, 415, 413($M^+$), 252

Elemental analysis: $C_{21}H_{14}N_2O_3Cl_2$.2HCl

Found (%) C,51.71; H,3.26; N,5.62. Calcd. (%) C,51.88; H,3.32; N,5.76.

EXAMPLE 117

7-Methoxy-4-[1-oxo-2-(4-pyridyl)ethyl]-2-(2-pyridyl)-benzofuran.2 hydrochloride (Compound 117)

Substantially the same procedure as in Example 98 was repeated using Compound IIr (4.0 g) obtained in Reference Example 18 to give 7-methoxy-4-[1-oxo-2-(4-pyridyl) ethyl]-2-(2-pyridyl)benzofuran (1.30 g, 26.6%) as a white solid. Then, substantially the same procedure as in Example 51 was repeated using the obtained crystals to give Compound 117.

Melting point: 218–220° C.

NMR(DMSO-$d_6$, δ, ppm): 4.13(s, 3H), 4.97(s, 2H), 7.23 (d, J=8 Hz, 1H), 7.49(m, 1H), 8.0–8.1(m, 5H), 8.22(d, J=8 Hz, 1H), 8.72(d, J=4 Hz, 1H), 8.93(d, J=6 Hz, 2H)

IR(KBr, $cm^{-1}$): 1670, 1610, 1470, 1305

MASS(m/e): 344($M^+$), 252

Elemental analysis: $C_{21}H_{16}N_2O_3$.2.0HCl.0.6$H_2O$

Found (%) C,58.86; H,4.54; N,6.47. Calcd. (%) C,58.92; H,4.52; N,6.54.

EXAMPLE 118

7-Methoxy-4-[1-oxo-2-(4-pyridyl)ethyl]-3-phenyl-benzofuran.hydrochloride (Compound 118)

Substantially the same procedure as in Example 98 was repeated using Compound IIv (0.60 g) obtained in Reference Example 22 to give 7-methoxy-4-[1-oxo-2-(4-pyridyl) ethyl]-3-phenylbenzofuran (0.25 g, 35%) as a white solid. Then, substantially the same procedure as in Example 51 was repeated using the obtained crystals to give Compound 118.

Melting point: 176–178° C.

NMR(DMSO-$d_6$, δ, ppm): 4.08(s, 3H), 4.77(s, 2H), 7.13–7.44(m, 6H), 7.80(d, J=6 Hz, 1H), 7.98(d, J=8 Hz, 1H), 8.21(s, 1H), 8.84(d, J=6 Hz, 1H)

IR(KBr, $cm^{-1}$): 1674, 1618, 1402, 1304

MASS(m/e): 343($M^+$)

Elemental analysis: $C_{22}H_{17}NO_3$.HCl.0.5$H_2O$

Found (%) C,67.85; H,4.88; N,3.52. Calcd. (%) C,67.95; H,4.92; N,3.60.

EXAMPLE 119

4-[2-(3,5-Dichloro-4-pyridyl)-1-oxoethyl]-3-ethoxycarbonylmethyl-7-methoxybenzofuran (Compound 119)

(Step A) (±)-4-[2-(3,5-Dichloro-4-pyridyl)-1-hydroxyethyl]-3-ethoxycarbonyl-7-methoxybenzofuran (Compound 119a)

Substantially the same procedure as in Step A of Example 45 was repeated using Compound IIj (0.28 g) obtained in Reference Example 10 to give Compound 119A (0.31 g, 70%) as a pale-yellow solid.

Melting point: 133–135° C.

NMR($CDCl_3$, δ, ppm): 1.22(t, J=7 Hz, 3H), 2.40(d, J=5 Hz, 1H), 3.34(dd, J=4 Hz, 13 Hz, 1H), 3.76(dd, J=10 Hz, 13 Hz, 1H), 3.97(s, 2H), 4.02(s, 3H), 4.07–4.23(m, 2H), 5.30–5.46(m, 1H), 6.82(d, J=8 Hz, 1H), 7.32 (d, J=8 Hz, 1H), 7.64(s, 1H), 8.46 (s, 2H)

(Step B) (Compound 119)

Substantially the same procedure as in Example 95 was repeated using Compound 119A (0.30 g) obtained in Step A to give Compound 119 (0.28 g, 95%) as a white solid.

Melting point: 105–115° C.

NMR($CDCl_3$, δ, ppm): 1.16(t, J=7 Hz, 3H), 3.88(s, 2H), 4.00–4.15(m, 5H), 4.69(s, 2H), 6.87(d, J=8 Hz, 1H), 7.65(s, 1H), 7.95(d, J=8 Hz, 1H), 8.51(s, 2H)

EXAMPLE 120

3-Ethoxycarbonylmethyl-7-methoxy-4-[1-oxo-2-(4-pyridyl)ethyl]benzofuran (Compound 120)

Compound 119 (0.04 g) obtained in Example 119 was dissolved in DMF-methanol (1:1) (1.0 ml), and 10% palladium carbon (0.016 g) was added thereto, followed by hydrogenation at normal temperature and normal pressure for 6 hours. The catalyst was removed and the filtrate was concentrated. Water and a saturated aqueous solution of sodium bicarbonate were added to the residue, and a precipitate was collected by filtration and dried to give Compound 120 (0.02 g, 9%) as a white solid.

Melting point: 111–117° C.

NMR($CDCl_3$, δ, ppm): 1.18(t, J=7 Hz, 3H), 3.92(s, 2H), 4.03(q, J=7 Hz, 2H), 4.07(s, 3H), 4.29(s, 2H), 6.82(d, J=9 Hz, 1H), 7.22(d, J=6 Hz, 2H), 7.69(s, 1H), 7.75(d, J=9 Hz, 1H), 8.56(d, J=6 Hz, 2H)

EXAMPLE 121

5-(3,5-Dichloro-4-pyridylaminocarbonyl)-8-methoxy-2,2-dimethylbenzopyran (Compound 121)

Substantially the same procedure as in Example 1 was repeated using Compound IIao (0.432 g) obtained in Reference Example 41 to give Compound 121 (0.229 g, 33%) as a white solid.

Melting point: 174–178° C.

NMR($CDCl_3$, δ, ppm): 1.51(s, 6H), 3.92(s, 3H), 5.77(d, J=10 Hz, 1H), 6.82(d, J=8.7 Hz, 1H), 6.95(d, J=10 Hz, 1H), 7.29(d, J=8.7 Hz, 1H), 7.41–7.52(broad s, 1H), 8.58(s, 2H)

MASS(m/e): 378($M^+$)

IR(KBr, $cm^{-1}$): 1660, 1480, 1280

Elemental analysis: $C_{18}H_{16}N_2O_3Cl_2$

Found (%) C,57.12; H,4.37; N,7.23. Calcd. (%) C,57.01; H,4.25; N,7.39.

EXAMPLE 122

5-(3,5-Dichloro-4-pyridylaminocarbonyl)-8-methoxy-2,2-dimethyl-3,4-dihydrobenzopyran (Compound 122)

Substantially the same procedure as in Example 1 was repeated using Compound IIap (1.05 g) obtained in Reference Example 42 to give Compound 122 (0.94 g, 56%) as a white solid.

Melting point: 155–156° C.

NMR($CDCl_3$, δ, ppm): 1.42(s, 6H), 1.82(t, J=7.2 Hz, 2H), 3.05(t, J=7.2 Hz, 2H), 3.91(s, 3H), 6.79(d, J=8.3 Hz, 1H), 7.28(d, J=8.3 Hz, 1H), 7.38–7.59 (broad s, 1H), 8.56(s, 2H)

MASS(m/e): 380($M^+$)

IR(KBr, $cm^{-1}$): 1680, 1480, 1280

Elemental analysis: $C_{18}H_{18}N_2O_3Cl_2$

Found (%) C,56.71; H,4.84; N,7.22. Calcd. (%) C,56.71; H,4.76; N,7.35.

EXAMPLE 123

5-(3,5-Dichloro-4-pyridylaminocarbonyl)-8-methoxy-spiro[benzopyran-2,1'-cyclopentane] (Compound 123)

Substantially the same procedure as in Example 1 was repeated using Compound IIaq (1.67 g) obtained in Reference Example 43 to give Compound 123 (1.44 g, 55%) as a white solid.

Melting point: 129–131° C.

NMR($CDCl_3$, δ, ppm): 1.50–2.32(m, 8H), 3.90(s, 3H), 5.82(d, J=9.0 Hz, 1H), 6.80(d, J=8.2 Hz, 1H), 6.99 (d, J=9.0 Hz, 1H), 7.28(d, J=8.2 Hz, 1H), 7.39–7.51(broad s, 1H), 8.55(s, 2H)

MASS (m/e): 404($M^+$)

IR(KBr, $cm^{-1}$): 1670, 1480, 1270

Elemental analysis: $C_{20}H_{18}N_2O_3Cl_2$

Found (%) C,59.13; H,4.54; N,6.66. Calcd. (%) C,59.27; H,4.48; N,6.91.

EXAMPLE 124

8-Methoxy-5-(4-pyridylaminocarbonyl)-spiro[3,4-dihydrobenzopyran-2,1'-cyclopentane] .methanesulfonate (Compound 124)

Substantially the same procedure as in Example 6 was repeated using Compound IIas (0.96 g) obtained in Reference Example 45 to give 8-methoxy-5-(4-pyridylaminocarbonyl)-spiro[3,4-dihydrobenzopyran-2,1'-cyclopentane] (1.14 g, 92%) as a white solid. Then, substantially the same procedure as in Example 50 was repeated using the obtained solid to give Compound 124.

Melting point: 231–233° C.

NMR(DMSO-$d_6$, δ, ppm): 1.45–1.93(m, 10H), 2.30(s, 3H), 2.92(t, J=5 Hz, 2H), 3.80(s, 3H), 6.94(d, J=8 Hz, 1H), 7.21(d, J=8 Hz, 1H), 8.20(d, J=7 Hz, 2H), 8.72(d, J=7 Hz, 2H), 11.4(s, 1H)

IR(KBr, $cm^{-1}$): 1690, 1510, 1270

Elemental analysis: $C_{20}H_{22}N_2O_3.CH_3SO_3H.0.1H_2O$

Found (%) C,57.78; H,6.10; N,6.15. Calcd. (%) C,57.81; H,6.05; N,6.42.

EXAMPLE 125

8-Methoxy-5-[2-(4-pyridyl)ethenyl]-spiro[3,4-dihydrobenzopyran-2,1'-cyclopentane] .hydrochloride (Compound 125)

(Step A) 5-[1-Hydroxy-2-(4-pyridyl)ethyl]-8-methoxy-spiro[3,4-dihydrobenzopyran-2,1'-cyclopentane] (Compound 125a)

Compound 127 (0.78 g) obtained in Example 127 was dissolved in methanol (8 ml) and sodium borohydride (0.18 g) was added thereto under ice-cooling, followed by stirring at room temperature for 2 hours. The mixture was cooled again with ice and dilute hydrochloric acid was dropwise added thereto. After the solvent was distilled off, water was added to the residue, and the mixture was extracted with ethyl acetate and washed with a saturated saline. The resultant was dried over sodium sulfate and the solvent was distilled off to give Compound 125a (0.63 g, 80%) as white crystals.

Melting point: 153–156° C.

NMR($CDCl_3$, δ, ppm): 1.36–2.07(m, 10H), 2.30–2.50(m, 1H), 2.70–3.10(m, 3H), 3.83(s, 3H), 4.99–5.10(m, 1H), 6.78(d, J=8.2 Hz, 1H), 7.02(d, J=8.2 Hz, 1H), 7.08(d, J=6.8 Hz, 2H), 8.46(d, J=6.8 Hz, 2H)

MASS(m/e): 339($M^+$)

(Step B) (Compound 125)

Substantially the same procedure as in Example 67 was repeated using Compound 125a (0.58 g) obtained in Step A to give 8-methoxy-5-[2-(4-pyridyl)ethenyl]-spiro[3,4-dihydrobenzopyran-2,1'-cyclopentane] (0.355 g, 65%) as a yellow solid. Then, substantially the same procedure as in Example 51 was repeated using the obtained solid to give Compound 125.

Melting point: 208–215° C.

NMR($CDCl_3$, δ, ppm): 1.49–1.99(m, 10H), 2.95(t, J=6.8 Hz, 2H), 3.90(s, 3H), 6.80 (d, J=8.5 Hz, 1H), 7.00(d, J=15 Hz, 1H), 7.29(d, J=8.5 Hz, 1H), 7.70–7.90(m, 3H), 8.50–8.67(m, 2H)

IR(KBr, $cm^{-1}$): 1620, 1580, 1500

Elemental analysis: $C_{21}H_{23}NO_3.HCl.0.2H_2O$

Found (%) C,69.75; H,6.74; N,3.82. Calcd. (%) C,69.78; H,6.80; N,3.87.

EXAMPLE 126

8-Methoxy-5-[2-(4-pyridyl)ethenyl]-spiro[3,4-dihydrobenzopyran-2,1'-cyclohexane].hydrochloride (Compound 126)

(Step A) 5-[1-Hydroxy-2-(4-pyridyl)ethyl]-8-methoxy-spiro[3,4-dihydrobenzopyran-2,1'-cyclohexane] (Compound 126a)

Substantially the same procedure as in Step A of Example 125 was repeated using Compound 128 (0.73 g) obtained in Example 128 to give Compound 126a (0.47 g, 64%) as a white solid.

Melting point: 123–133° C.

NMR($CDCl_3$, δ, ppm): 1.20–1.90(m, 12H), 2.29–2.45(m, 1H), 2.68–3.15(m, 3H), 3.86(s, 3H), 4.98–5.12(m, 1H), 6.78(d, J=9 Hz, 1H), 7.01(d, J=9 Hz, 1H), 7.08 (d, J=6 Hz, 2H), 8.47(d, J=6 Hz, 2H)

(Step B) (Compound 126)

Substantially the same procedure as in Example 67 was repeated using Compound 126a (0.48 g) obtained in Step A to give 8-methoxy-5-[2-(4-pyridyl)ethenyl]-spiro[3,4-dihydrobenzopyran-2,1'-cyclohexane] (0.14 g, 31%) as yellow crystals. Then, substantially the same procedure as in Example 51 was repeated using the obtained crystals to give Compound 126.

Melting point: 222–230° C.

NMR($CDCl_3$, δ, ppm): 1.25–2.00(m, 12H), 2.90(t, J=7 Hz, 2H), 3.92(s, 3H), 6.80 (d, J=9 Hz, 1H), 6.97(d, J=16 Hz, 1H), 7.75–7.90(m, 4H), 8.59(d, J=6 Hz, 2H)

Elemental analysis: $C_{22}H_{25}NO_2.HCl.0.1H_2O$

Found (%) C,70.68; H,7.04; N,3.65. Calcd. (%) C,70.71; H,7.07; N,3.75.

EXAMPLE 127

8-Methoxy-5-[1-oxo-2-(4-pyridyl)ethyl]-spiro[3,4-dihydrobenzopyran-2,1'-cyclopentane] .hydrochloride (Compound 127)

Substantially the same procedure as in Example 98 was repeated using Compound IIar (1.83 g) obtained in Reference Example 44 to give 8-methoxy-5-[1-oxo-2-(4-pyridyl)ethyl]-spiro[3,4-dihydrobenzopyran-2,1'-cyclopentane] (1.61 g, 72%) as a pale-yellow solid. Then, substantially the same procedure as in Example 51 was repeated using the obtained solid to give Compound 127.

Melting point: 186–192° C.

NMR($CDCl_3$, δ, ppm): 1.50–2.07(m, 10H), 3.06(t, J=6.8 Hz, 2H), 3.91(s, 3H), 4.59(s, 2H), 6.80(d, J=8.5 Hz, 1H), 7.52(d, J=8.5 Hz, 1H), 7.88(d, J=6.7 Hz, 2H), 8.72(d, J=6.7 Hz, 2H)

IR(KBr, $cm^{-1}$): 1670, 1560, 1280

Elemental analysis: $C_{21}H_{23}NO_3.HCl.0.4H_2O$

Found (%) C,66.19; H,6.75; N,3.72. Calcd. (%) C,66.19; H,6.56; N,3.68.

EXAMPLE 128

8-Methoxy-5-[1-oxo-2-(4-pyridyl)ethyl]-spiro[3,4-dihydrobenzopyran-2,1'-cyclohexane].hydrochloride Substantially the same procedure as in Example 98 was repeated using Compound IIat (2.1 g) obtained in Reference Example 46, to give 8-methoxy-5-[1-oxo-2-(4-pyridyl)ethyl]-spiro[3,4-dihydrobenzopyran-2,1'-cyclohexane] (1.2 g, 48%) as pale-yellow crystals. Then, substantially the same procedure as in Example 51 was repeated using the obtained crystals to give Compound 128.

Melting point: 185–194° C.

NMR($CDCl_3$, δ, ppm): 1.25–1.90(m, 12H), 3.01(t, J=7 Hz, 2H), 3.95(s, 3H), 4.56(s, 2H), 6.82(d, J=9 Hz, 1H), 7.51(d, J=9 Hz, 1H), 7.82(d, J=6 Hz, 2H), 8.71(d, J=6 Hz, 2H)

Elemental analysis: $C_{22}H_{25}NO_3$.HCl.0.6$H_2O$

Found (%) C,66.34; H,6.84; N,3.45. Calcd. (%) C,66.27; H,6.88; N,3.51.

EXAMPLE 129

7-(3,5-Dichloro-4-pyridylaminocarbonyl)-4-methoxy-spiro[2,3-dihydrobenzofuran-2,1'-cyclopentane] (Compound 129)

Substantially the same procedure as in Example 1 was repeated using Compound IIav (1.00 g) obtained in Reference Example 48 to give Compound 129 (1.33 g, 84%) as pale-yellow crystals.

Melting point: 156–158° C.

NMR($CDCl_3$, δ, ppm): 1.80–2.29(m, 8H), 3.20(s, 2H), 3.91(s, 3H), 6.58(d, J=9 Hz, 1H), 7.99(d, J=9 Hz, 1H), 8.54(s, 2H), 9.42(s, 1H)

IR(KBr, $cm^{-1}$): 1690, 1552, 1495, 1271

MASS(m/e): 392($M^+$)

Elemental analysis: $C_{19}H_{18}N_2O_3Cl_2$

Found (%) C,58.06; H,4.56; N,6.94. Calcd. (%) C,58.03; H,4.61; N,7.12.

EXAMPLE 130

4-Methoxy-7-(4-pyridylaminocarbonyl)-spiro(2,3-dihydrobenzofuran-2,1'-cyclopentane) methanesulfonate (Compound 130)

Substantially the same procedure as in Example 6 was repeated using Compound IIav (1.00 g) obtained in Reference Example 48 to give 4-methoxy-7-(4-pyridylaminocarbonyl)-spiro[2,3-dihydrobenzofuran-2,1'-cyclopentane] (0.88 g, 63%) as pale-yellow crystals. Then, substantially the same procedure as in Example 50 was repeated using the obtained crystals to give Compound 130.

Melting point: 164° C. (decomposed)

NMR(DMSO-$d_6$, δ, ppm): 1.75–1.88(m, 6H), 2.10–2.22 (m, 2H), 2.31(s, 3H), 3.18(s, 2H), 3.89(s, 3H), 6.76 (d, J=9 Hz, 1H), 7.72(d, J=9 Hz, 1H), 8.13(d, J=7 Hz, 1H), 8.75(d, J=7 Hz, 1H), 10.5(s, 1H)

IR(KBr, $cm^{-1}$): 1693, 1612, 1512, 1267

MASS(m/e): 324($M^+$)

Elemental analysis: $C_{19}H_{20}N_2O_3$.$CH_3SO_3H$.0.3$H_2O$

Found (%) C,56.45; H,5.78; N,6.52. Calcd. (%) C,58.41; H,5.82; N,6.58.

EXAMPLE 131

7-[2-(3,5-Dichloro-4-pyridyl)ethenyl]-4-methoxy-spiro[2,3-dihydrobenzofuran-2,1'-cyclopentane] (Compound 131)

(Step A) 7-[2-(3,5-Dichloro-4-pyridyl)-1-hydroxyethyl]-4-methoxy-spiro[2,3-dihydrobenzofuran-2,1'-cyclopentane] (Compound 131a)

Substantially the same procedure as in Step A of Example 45 was repeated using Compound IIau (1.00 g) obtained in Reference Example 47 to give Compound 131a (1.32 g, 78%) as pale-yellow crystals.

NMR($CDCl_3$, δ, ppm): 1.70–2.20(m, 8H), 2.91(d, J=9 Hz, 1H), 3.11(s, 2H), 3.25(dd, J=5 Hz, 13 Hz, 1H), 3.61 (dd, J=9 Hz, 13 Hz, 1H), 3.82(s, 3H), 4.94–5.03(m, 1H), 6.35(d, J=9 Hz, 1H), 6.98(d, J=9 Hz, 1H), 8.43(s, 1H)

MASS (m/e): 393($M^+$)

(Step B) (Compound 131)

Substantially the same procedure as in Example 67 was repeated using Compound 131a (0.66 g) obtained in Step A to give Compound 131 (0.55 g, 87%) as yellow crystals.

Melting point: 99–101° C.

NMR($CDCl_3$, δ, ppm): 1.65–2.20(m, 8H), 3.11(s, 2H), 3.82(s, 3H), 6.38(d, J=9 Hz, 1H), 7.13(d, J=9 Hz, 1H), 7.45(d, J=1.7 Hz, 1H), 7.50(d, J=17 Hz, 1H), 8.43(s, 2H)

IR(KBr, $cm^{-1}$): 1612, 1556, 1500, 1232

MASS(m/e): 375($M^+$)

Elemental analysis: $C_{20}H_{19}NO_2Cl_2$

Found (%) C,64.14; H,5.19; N,3.57. Calcd. (%) C,63.84; H,5.09; N,3.72.

EXAMPLE 132

7-[2-(3,5-Dichloro-4-pyridyl)-1-oxoethyl]-4-methoxy-spiro[2,3-dihydrobenzofuran-2,1'-cyclopentane] (Compound 132)

Substantially the same procedure as in Example 95 was repeated using Compound 131a (0.66 g) obtained in Step A in Example 131 to give Compound 132 (0.23 g, 35%) as white crystals.

Melting point: 70–72° C.

NMR($CDCl_3$, δ, ppm): 1.78–2.24(m, 8H), 3.16(s, 2H), 3.90(s, 3H), 4.63(s, 2H), 6.51(d, J=9 Hz, 1H), 7.82(d, J=9 Hz, 1H), 8.49(s, 2H)

IR(KBr, $cm^{-1}$): 1668, 1427, 1297, 1093

MASS(m/e): 391($M^+$)

Elemental analysis: $C_{20}H_{19}NO_3Cl_2$

Found (%) C,61.30; H,4.84; N,3.41. Calcd. (%) C,61.24; H,4.88; N,3.57.

EXAMPLE 133

4-Methoxy-7-[1-oxo-2-(4-pyridyl)ethyl]-spiro[2,3-dihydrobenzofuran-2,1'-cyclopentane] (Compound 133)

Substantially the same procedure as in Example 98 was repeated using Compound IIaw (0.86 g) obtained in Reference Example 49 to give Compound 133 (0.42 g, 40%) as white crystals.

Melting point: 101–103° C.

NMR($CDCl_3$, δ, ppm): 1.73–2.17(m, 8H), 3.11(s, 2H), 3.88(s, 3H), 4.26(s, 2H), 6.49(d, J=9 Hz, 1H), 7.17–7.19(m, 2H), 7.81(d, J=9 Hz, 1H), 8.50–8.53 (m, 2H)

IR(KBr, $cm^{-1}$): 1680, 1612, 1430, 1248

MASS (m/e): 323($M^+$)

Elemental analysis: $C_{20}H_{21}NO_3$

Found (%) C,74.63; H,6.68; N,4.26. Calcd. (%) C,74.28; H,6.54; N,4.33.

EXAMPLE 134

7-(3,5-Dichloro-4-pyridylaminocarbonyl)-4-methoxy-spiro[1,3-benzodioxole-2,1'-cyclopentane] (Compound 134)

Substantially the same procedure as in Example 1 was repeated using Compound IIaz (0.70 g) obtained in Reference Example 52 to give Compound 134 (0.73 g, 66%) as white crystals.

Melting point: 168–170° C.

NMR($CDCl_3$, δ, ppm): 1.84–1.96(m, 4H), 2.24–2.31(m, 4H), 3.97(s, 3H), 6.67(d, J=9 Hz, 1H), 7.60(d, J=9 Hz, 1H), 8.55(s, 2H), 8.78(s, 1H)

IR(KBr, $cm^{-1}$): 1689, 1641, 1490, 1286

MASS (m/e): 394 ($M^+$)

Elemental analysis: $C_{18}H_{16}N_2O_4Cl_2$

Found (%) C,54.57; H,4.05; N,6.95. Calcd. (%) C,54.70; H,4.08; N,7.09.

EXAMPLE 135

4-Methoxy-7-(4-pyridylaminocarbonyl)-spiro[1,3-benzodioxole-2,1'-cyclopentane].methanesulfonate (Compound 135)

Substantially the same procedure as in Example 6 was repeated using Compound IIaz (0.84 g) obtained in Reference Example 52 to give 4-methoxy-7-(4-pyridylaminocarbonyl)-spiro[1,3-benzodioxole-2,1'-cyclopentane] (0.34 g, 31%) as pale-yellow crystals. Then, substantially the same procedure as in Example 50 was repeated using the obtained crystals to give Compound 135.

Melting point: 133–134° C.

NMR(DMSO-$d_6$, δ, ppm): 1.77–1.83(m, 4H), 2.06–2.22 (m, 4H), 2.31(s, 3H), 3.90(s, 3H), 6.84(d, J=9 Hz, 1H), 7.36(d, J=9 Hz, 1H), 8.18(d, J=7 Hz, 2H), 8.73(d, J=7 Hz, 2H), 10.9(s, 1H)

IR(KBr, $cm^{-1}$): 1637, 1508, 1280, 1120

MASS(m/e): 326($M^+$)

Elemental analysis: $C_{18}H_{18}N_2O_4.CH_3SO_3H.0.3H_2O$

Found (%) C,53.34; H,5.20; N,6.58. Calcd. (%) C,53.34; H,5.32; N,6.55.

EXAMPLE 136

4-Methoxy-7-[2-(4-pyridyl)ethyl]-spiro[1,3-benzodioxole-2,1'-cyclopentane].hydrochloride (Compound 136)

Substantially the same procedure as in Example 120 was repeated using Compound 138 (0.86 g) obtained in Example 138 to give 4-methoxy-7-[2-(4-pyridyl)ethyl]-spiro[1,3-benzodioxole-2,1'-cyclopentane] (0.078 g, 99%) as pale-yellow crystals. Then, substantially the same procedure as in Example 51 was repeated using the obtained crystals to give Compound 136.

Melting point: 160–162° C.

NMR(DMSO-$d_6$, δ, ppm): 1.71–2.01(m, 8H), 2.89(t, J=7 Hz, 2H), 3.15(t, J=7 Hz, 2H), 3.75(s, 3H), 6.51(d, J=9 Hz, 1H), 6.61(d, J=9 Hz, 1H), 7.83(d, J=6 Hz, 2H), 8.79(d, J=6 Hz, 2H)

IR(KBr, $cm^{-1}$): 1640, 1508, 1456, 1333

MASS(m/e): 311($M^+$)

Elemental analysis: $C_{19}H_{21}NO_3.HCl.0.2H_2O$

Found (%) C,64.82; H,6.35; N,3.82. Calcd. (%) C,64.93; H,6.42; N,3.99.

EXAMPLE 137

4-Methoxy-7-[1-phenyl-2-(4-pyridyl)ethyl]-spiro[1,3-benzodioxole-2,1'-cyclopentane].hydrochloride (Compound 137)

Substantially the same procedure as in Example 120 was repeated using Compound 139 (0.76 g) obtained in Example 139 to give 4-methoxy-7-[1-phenyl-2-(4-pyridyl)-ethyl]-spiro[1,3-benzodioxole-2,1'-cyclopentane] (0.75 g, 98%) as a pale-yellow oily substance. Then, substantially the same procedure as in Example 51 was repeated using the obtained crystals to give Compound 137.

Melting point: 179–182° C.

NMR(DMSO-$d_6$, δ, ppm): 1.75–2.00(m, 8H), 3.64–3.71 (m, 2H), 3.72(s, 3H), 4.48(t, J=8 Hz, 1H), 6.51(d, J=9 Hz, 1H), 6.76(d, J=9 Hz, 1H), 7.16–7.38(m, 5H), 7.84(d, J=5 Hz, 2H), 8.75(d, J=5 Hz, 2H)

IR(KBr, $cm^{-1}$): 1645, 1633, 1504

MASS(m/e): 387($M^+$)

Elemental analysis: $C_{25}H_{25}NO_3.HCl.0.3H_2O$

Found (%) C,70.07; H,6.23; N,3.17. Calcd. (%) C,69.94; H,6.24; N,3.26.

EXAMPLE 138

7-[2-(3,5-Dichloro-4-pyridyl)ethenyl]-4-methoxy-spiro[1,3-benzodioxole-2,1'-cyclopentane] (Compound 138)

(Step A) 7-[2-(3,5-Dichloro-4-pyridyl)-1-hydroxyethyl]-4-methoxy-spiro[1,3-benzodioxole-2,1'-cyclopentane] (Compound 138a)

Substantially the same procedure as in Step A of Example 45 was repeated using Compound IIax (0.47 g) obtained in Reference Example 50 to give Compound 138a (0.73 g, 92%) as pale-yellow crystals.

NMR($CDCl_3$, δ, ppm): 1.75–2.15(m, 8H), 3.09(d, J=6 Hz, 1H), 3.31(dd, J=6 Hz, 13 Hz, 1H), 3.51(dd, J=9 Hz, 13 Hz, 1H), 3.87(s, 3H), 5.09–5.15(m, 1H), 6.46(d, J=9 Hz, 1H), 1H), 6.79(d, J=9 Hz, 1H), 8.34(s, 1H)

MASS(m/e): 395($M^+$)

(Step B) (Compound 138)

Substantially the same procedure as in Example 67 was repeated using Compound 138a (0.74 g) obtained in Step A to give Compound 138 (0.59 g, 80%) as yellow crystals.

Melting point: 100–101° C.

NMR($CDCl_3$, δ, ppm): 1.82–1.94(m, 4H), 2.14–2.26(m, 4H), 3.91(s, 3H), 6.51(d, J=9 Hz, 1H), 6.87(d, J=9 Hz, 1H), 7.30(d, J=16 Hz, 1H), 7.42(d, J=16 Hz, 1H), 8.45(s, 2H)

IR(KBr, $cm^{-1}$): 1618, 1452, 1288, 1113

MASS(m/e): 377($M^+$)

Elemental analysis: $C_{19}H_{17}NO_3Cl_2$

Found (%) C,60.39; H,4.49; N,3.65. Calcd. (%) C,60.33; H,4.53; N,3.70.

EXAMPLE 139

4-Methoxy-7-[1-phenyl-2-(4-pyridyl)ethenyl]-spiro[1,3-benzodioxole-2,1'-cyclopentane] (Compound 139)

(Step A) 7-[1-Hydroxy-1-phenyl-2-(4-pyridyl)ethyl]-4-methoxy-spiro[1,3-benzodioxole-2,1'-cyclopentane] (Compound 139a)

Substantially the same procedure as in Step A of Example 47 was repeated using Compound IIba (4.90 g) obtained in Reference Example 53 to give Compound 139 (5.34 g, 84%) as pale-yellow crystals.

NMR($CDCl_3$, δ, ppm): 1.69–2.10(m, 8H), 3.10 (s, 1H), 3.46(d, J=12 Hz, 1H), 3.69(d, J=12 Hz, 1H), 3.87(s, 3H), 6.44(d, J=9 Hz, 1H), 6.71(d, J=9 Hz, 1H), 6.93(d, J=6 Hz, 2H), 7.22–7.39(m, 5H), 8.37(d, J=6 Hz, 2H)

MASS(m/e): 403($M^+$)

(Step B) (Compound 139) (an E/Z Mixture)

Substantially the same procedure as in Example 67 was repeated using Compound 139a (2.0 g) obtained in Step A to give Compound 139 (0.76 g, 40%) as pale-yellow crystals.

NMR($CDCl_3$, δ, ppm): 0.83–2.22(m, 8H), 3.88(s, 3H×0.75), 3.92(s, 3H×0.25), 6.39(s, 2H×0.75), 6.49–6.53 (m, 2H×0.25), 6.79(d, J=6 Hz, 2H×0.75), 6.88(s, 1H×0.25), 7.00(d, J=6 Hz, 2H×0.25), 7.20(s, 1H×0.75), 7.15–7.38(m, 5H), 8.31(d, J=6 Hz, 2H×0.75), 8.40(d, J=6 Hz, 2H×0.25)

MASS(m/e): 385($M^+$)

EXAMPLE 140

7-[2-(3,5-Dichloro-4-pyridyl)-1-oxoethyl]-4-methoxy-spiro[1,3-benzodioxole-2,1'-cyclopentane] (Compound 140)

Substantially the same procedure as in Example 95 was repeated using Compound 138a (1.50 g) obtained in Step A of Example 138 to give Compound 140 (0.77 g, 52%) as white crystals.

Melting point: 110–112° C.

NMR($CDCl_3$, δ, ppm): 1.83–1.96(m, 4H), 2.18–2.28(m, 4H), 3.97(s, 3H), 4.59(s, 2H), 6.61(d, J=9 Hz, 1H), 7.47(d, J=9 Hz, 1H), 8.50(s, 2H)

IR(KBr, $cm^{-1}$): 1633, 1448, 1286, 1263

MASS(m/e): 393($M^+$)

Elemental analysis: $C_{19}H_{17}NO_4Cl_2$

Found (%) C,58.05; H,4.32; N,3.52. Calcd. (%) C,57.88; H,4.35; N,3.55.

EXAMPLE 140'

7-[2-(3,5-Dichloro-4-pyridyl)-1-oxoethyl)-4-methoxy-spiro[1,3-benzodioxole-2,1'-cyclopentane] (Compound 140)

(Step A) 7-[2-(3,5-Dichloro-4-pyridyl)-1-hydroxyethyl]-4-methoxy-spiro[1,3-benzodioxole-2,1'-cyclopentane] (Compound 138a)

Under an argon atmosphere, a solution of diisopropylamine (1.78 ml) in THF (10 ml) was cooled to −78° C., and then a 1.63M solution (7.8 ml) of butyl lithium in hexane was dropwise added thereto, followed by stirring at 0° C. for 15 minutes. The obtained mixture was cooled to −78° C. again, and then a solution of 3,5-dichloro-4-methyl-pyridine (2.19 g) dissolved in THF (10 ml) was added thereto, followed by stirring for 2 hours. This solution was dropwise and slowly added to a solution of Compound IIax (1.98 g) obtained in Reference Example 50 in THF (20 ml) with cooling at −78° C., followed by stirring for 2 hours. The mixture was warmed to the room temperature and a saturated aqueous solution of ammonium chloride was added thereto, followed by extraction with ether. The organic layer was washed with a saturated saline and dried over anhydrous magnesium sulfate, and the solvent was distilled off. The residue was purified by silica gel column chromatography (hexane/ethyl acetate=50 to 20/1) to give Compound 138a (3.32 g, 96%) as colorless oil.

The spectral data of the obtained colorless semi-oil were the same as those in Step A of Example 138.

(Step B) (Compound 140)

Compound 138a (2.88 g) obtained in Step A was dissolved in acetone (200 ml) and 2.67M Jones' reagent (3.0 ml) was added thereto, followed by stirring at 0° C. for 15 minutes. The reaction solution was concentrated to about a half by volume, and water was added thereto, followed by extraction with ethyl acetate. The organic layer was washed with water and with saturated saline, and dried over anhydrous magnesium sulfate, and the solvent was distilled off. The residue was purified by silica gel column chromatography (hexane/ethyl acetate=10 to 5/1) to give Compound 140 (2.02 g, 70%) as colorless crystals.

The spectral data of the obtained colorless crystals were the same as those in Example 140.

EXAMPLE 141

4-Methoxy-7-[1-oxo-2-(4-pyridyl)ethyl]-spiro[1,3-benzodioxole-2,1'-cyclopentane].hydrochloride (Compound 141)

Substantially the same procedure as in Example 98 was repeated using Compound IIay (1.0 g) obtained in Reference Example 51 to give 4-methoxy-7-[1-oxo-2-(4-pyridyl) ethyl]-spiro[1,3-benzodioxole-2,1'-cyclopentane] (0.33 g, 27%) as white crystals. Then, substantially the same procedure as in Example 51 was repeated using the obtained crystals to give Compound 141.

Melting point: 110–111° C.

NMR($CDCl_3$, δ, ppm): 1.75–1.88(m, 4H), 2.18–2.28(m, 4H), 3.90(s, 3H), 4.62(s, 2H), 6.82(d, J=9 Hz, 1H), 7.38(d, J=9 Hz, 1H), 7.92(d, J=5 Hz, 2H), 8.84(d, J=5 Hz, 2H)

IR(KBr, $cm^{-1}$): 1668, 1633, 1446, 1119

EXAMPLE 142

7-Methoxy-4-[2-(4-pyridyl)ethynyl]-spiro[2,3-dihydrobenzofuran-2,1'-cyclopentane] (Compound 142)

(Step A) 6-Bromo-4-[1,2-dibromo-2-(4-pyridyl)ethyl]-7-methoxy-spiro[2,3-dihydrobenzofuran-2,1'-cyclopentane] (Compound 142a)

Bromine (0.1 ml) was dropwise added to a solution of (E)-7-methoxy-4-[2-(4-pyridyl)ethenyl]-spiro[2,3-dihydrobenzofuran-2,1'-cyclopentane] (0.18 g) obtained in Example 74 in dichloromethane (15 ml) at 0° C., followed by stirring at the same temperature for 30 minutes. Water was added to the reaction solution and the mixture was extracted with chloroform. The organic layer was washed with a saturated saline and dried over anhydrous magnesium sulfate, and the solvent was distilled off under reduced pressure. The residue was purified by silica gel column chromatography (ethyl acetate/n-hexane=1/2) to give Compound 142a (0.26 g, 81.2%) as pale-yellow crystals.

NMR(DMSO-$d_6$, δ, ppm): 1.50–2.15(m, 8H), 3.24(d, J=15.3 Hz, 1H), 3.65(d, J=15.8 Hz, 1H), 3.82(s, 3H), 5.90(d, J=11.8 Hz, 1H), 6.15(d, J=12.3 Hz, 1H), 7.13(s, 1H), 7.67(d, J=5.9 Hz, 2H), 8.69(d, J=5.4 Hz, 2H)

(Step B) 6-Bromo-7-methoxy-4-[2-(4-pyridyl)ethynyl]-spiro[2,3-dihydrobenzofuran-2,1'-cyclopentane] (Compound 142b)

Potassium tert-butoxide (0.15 g) was added to a solution of Compound 142a (0.25 g) obtained in Step A in THF (9 ml) at 0° C., followed by stirring at room temperature for 5 hours. The reaction solution was poured into water and the mixture was extracted with diethyl ether. The organic layer was washed with a saturated saline and dried over anhydrous magnesium sulfate, and the solvent was distilled off under reduced pressure. The residue was purified by silica gel column chromatography (ethyl acetate/n-hexane=1/1) to give Compound 142b (0.12 g, 68.2%) as pale-yellow crystals.

NMR(DMSO-$d_6$, δ, ppm): 1.70–1.95(m, 6H), 2.05–2.25 (m, 2H), 3.32(s, 2H), 3.88(s, 3H), 6.97(s, 1H), 7.39 (d, J=5.4 Hz, 2H), 8.60(d, J=5.4 Hz, 2H)

MASS(m/e): 383, 385($M^+$)

(Step C) (Compound 142)

Under an argon atmosphere, a solution (2.6 ml) of Compound 142b (0.1 g) obtained in Step B in THF was cooled to −78° C., and then a 1.7M solution (0.2 ml) of n-butyl lithium in hexane was dropwise added thereto, followed by stirring at the same temperature for one hour. The reaction solution was adjusted to pH 7 by adding dropwise 1N hydrochloric acid, followed by stirring at room temperature for one hour. A small amount of water was added to the reaction solution and the mixture was extracted with ether. The organic layer was washed with a saturated saline and dried over anhydrous magnesium sulfate, and the solvent was distilled off under reduced pressure. The residue was purified by silica gel column chromatography (ethyl acetate/n-hexane=1/2) to give Compound 142 (0.014 g, 17.4%) as pale-yellow crystals.

Melting point: 128–131° C.

NMR(DMSO-$d_6$, δ, ppm): 1.42(s, 6H), 3.15(s, 2H), 3.80 (s, 3H), 3.87(s, 3H), 6.94(s, 2H), 7.62(d, J=8.4 Hz, 2H), 7.99(d, J=8.4 Hz, 2H)

IR(KBr, $cm^{-1}$): 2216, 1589, 1506

MASS(m/e): 305($M^+$)

EXAMPLE 143

7-Methoxy-4-[1-oxo-2-(N-oxo-4-pyridyl)ethyl]-spiro[2,3-dihydrobenzofuran-2,1'-cyclopentane] (Compound 143)

m-Chloroperbenzoic acid (0.72 g) was added to a solution of 7-methoxy-4-[1-oxo-2-(4-pyridyl)ethyl]-spiro[2,3-dihydrobenzofuran-2,1'-cyclopentane] (0.27 g) obtained in Example 100 in dichloromethane (8.3 ml) at 0° C., followed by stirring at room temperature for 5 hours. A saturated aqueous solution of sodium bicarbonate was added to the reaction solution and the mixture was extracted with ethyl acetate. The organic layer was washed with a saturated saline and dried over anhydrous magnesium sulfate, and the solvent was distilled off under reduced pressure. The residue was purified by silica gel column chromatography (chloroform/methanol=15/1) to give Compound 143 (0.07 g, 24.8%) as pale-yellow crystals.

NMR(DMSO-$d_6$, δ, ppm): 1.72–1.91(m, 6H), 2.10–2.16 (m, 2H), 3.51(s, 2H), 3.95(s, 3H), 4.24(s, 2H), 6.81 (d, J=8.6 Hz, 2H), 7.18(d, J=6.9 Hz, 2H), 7.45(d, J=8.6 Hz, 1H), 8.20(d, J=6.9 Hz, 2H)

MASS(m/e): 339($M^+$)

EXAMPLE 144

2,2-Dimethyl-7-methoxy-4-[4-(methoxycarbonyl) phenyl]-2,3-dihydrobenzofuran (Compound 144)

(Step A) 2,2-Dimethyl-7-methoxy-4-tributylstannyl-2,3-dihydrobenzofuran (Compound 144a)

Under an argon atmosphere, a solution (80 ml) of Compound IIa-c (2.0 g) obtained in Step C of Reference Example 1 in THF was cooled to −78° C., and then a solution (5.0 ml) of 1.70M butyl lithium in hexane was dropwise added thereto, followed by stirring at the same temperature for one hour. Tributyltin chloride (2.1 ml) was dropwise added to the mixture, followed by stirring at room temperature for 2 hours and then at 60° C. for one hour. The solvent was distilled off and the residue was dried under reduced pressure to give a crude desired product. This product was immediately subjected to a subsequent step without being purified.

(Step B) (Compound 144)

A solution (30 ml) of Compound 144a obtained in Step A in DMF was added to a mixture of methyl 4-bromobenzoate (1.67 g), palladium acetate (0.18 g), sodium carbonate (2.10 g), and dimethylformamide (DMF) (70 ml), followed by stirring at 80° C. for one hour. A small amount of water was added to the reaction solution and the mixture was extracted with ethyl acetate. The organic layer was washed with 1N hydrochloric acid and a saturated saline and dried over anhydrous magnesium sulfate, and the solvent was distilled off under reduced pressure. The residue was purified by silica gel column chromatography (ethyl acetate/hexane=1/20) to give Compound 144 (1.35 g, 55.6%) as colorless crystals.

Melting point: 116–122° C.

NMR(DMSO-$d_6$, δ, ppm): 1.42(s, 6H), 3.15(s, 2H), 3.80 (s, 3H), 3.87(s, 3H), 6.94(s, 2H), 7.62(d, J=8.4 Hz, 2H), 7.99(d, J=8.4 Hz, 2H)

IR(KBr, $cm^{-1}$): 1720, 1606

MASS(m/e): 312($M^+$)

Elemental analysis: $C_{19}H_{20}O_4$

Found (%) C,73.19; H,6.58; N,0.12. Calcd. (%) C,73.06; H,6.45; N,0.00.

EXAMPLE 145

4-(4-Carboxyphenyl)-2,2-dimethyl-7-methoxy-2,3-dihydrobenzofuran (Compound 145)

A mixture of Compound 144 (1.0 g) obtained in Example 144, a 4N aqueous solution (8.0 ml) of sodium hydroxide, and ethanol (40 ml) was stirred at room temperature for 4 hours. The solvent was removed and the residue was dissolved in water. Concentrated hydrochloric acid was dropwise added to the solution, and the generated precipitate was collected by filtration, washed with water, and dried to give Compound 145 (0.82 g, 85.9%) as white crystals.

Melting point: 249–252° C.

NMR(DMSO-$d_6$, δ, ppm): 1.42(s, 6H), 3.15(s, 2H), 3.80 (s, 3H), 6.94(s, 2H), 7.59(d, J=8.4 Hz, 2H), 7.98 (d, J=7.9 Hz, 2H), 12.94(broad s, 1H)

IR(KBr, $cm^{-1}$): 1681, 1606

MASS(m/e): 298($M^+$)

Elemental analysis: $C_{18}H_{18}O_4$

Found (%) C,72.51; H,6.18; N,0.15. Calcd. (%) C,72.47; H,6.08; N,0.00.

EXAMPLE 146

2,2-Dimethyl-7-methoxy-4-[3-(methoxycarbonyl) phenyl]-2,3-dihydrobenzofuran (Compound 146)

A solution (30 ml) of Compound 144a obtained in Step A of Example 144 in DMF was added to a mixture of methyl 3-bromobenzoate (1.67 g), palladium acetate (0.18 g), sodium carbonate (2.10 g), and dimethylformamide (DMF) (70 ml), followed by stirring at 80° C. for one hour. A small amount of water was added to the reaction solution and the mixture was extracted with ethyl acetate. The organic layer was washed with 1N hydrochloric acid and a saturated saline and dried over anhydrous magnesium sulfate, and the solvent was distilled off under reduced pressure. The residue was purified by silica gel column chromatography (ethyl acetate/hexane=1/20) to give Compound 146 (1.69 g, 69.5%) as pale-yellow crystals.

Melting point: 89–91° C.

NMR(DMSO-$d_6$, δ, ppm): 1.42(s, 6H), 3.12(s, 2H), 3.80 (s, 3H), 3.88(s, 3H), 6.90(d, J=8.4 Hz, 1H), 6.95 (d, J=8.4 Hz, 1H), 7.58(dd, J=7.4 Hz, 1H), 7.76(dd, 7.76(dd, J=7.9 Hz, 1.5 Hz, 1H), 7.91(d, J=7.4 Hz, 1H), 7.99(d, J=1.5 Hz, 1H)

IR(KBr, $cm^{-1}$): 1716

MASS(m/e): 312($M^+$)

EXAMPLE 147

4-(3-Carboxyphenyl)-2,2-dimethyl-7-methoxy-2,3-dihydrobenzofuran (Compound 147)

A mixture of Compound 146 (1.3 g) obtained in Example 146, a 4N aqueous solution (10.4 ml) of sodium hydroxide, and ethanol (50 ml) was stirred at room temperature for 3 hours. The solvent was removed and the residue was dissolved in water. Concentrated hydrochloric acid was dropwise added to the solution, and the generated precipitate was collected by filtration, washed with water, and dried to give Compound 147 (1.15 g, 92.7%) as white crystals.

Melting point: 220–225° C.

NMR(DMSO-$d_6$, δ, ppm): 1.42(s, 6H), 3.12(s, 2H), 3.79 (s, 3H), 6.90(d, J=8.4 Hz, 1H), 6.95(d, J=8.4 Hz, 1H), 7.55(dd, J=7.4 Hz, 7.4 Hz, 1H), 7.72(dd, J=6.4 Hz, 1.5 Hz, 1H), 7.89(dd, J=6.4 Hz, 1.5 Hz, 1H), 7.97(d, J=1.5 Hz, 1H), 13.17(broad s, 1H)

IR(KBr, $cm^{-1}$): 1683

MASS(m/e): 298($M^+$)

Elemental analysis: $C_{18}H_{18}O_4$

Found (%) C,72.21; H,6.02; N,0.05. Calcd. (%) C,72.47; H,6.08; N,0.00.

EXAMPLE 148

3-Benzyloxycarbonylmethyl-4-[(2,6-dichlorophenyl) aminocarbonyl]-7-methoxybenzofuran (Compound 148)

Substantially the same procedure as in Example 1 was repeated using Compound IIbb (0.30 g) obtained in Reference Example 54 and 2,6-dichloroaniline (0.7 g) to give Compound 148 (0.13 g, 29%) as white crystals.

Melting point: 202–204 ° C.

NMR(DMSO-$d_6$, δ, ppm): 3.94(s, 2H), 4.02(s, 3H), 5.02 (s, 2H), 7.10(d, 1H, J=8 Hz), 7.15–7.33(m, 5H), 7.40(dd, 1H, J=8 Hz, 8 Hz), 7.59(d, 2H, J=8 Hz), 7.81 (d, 1H, J=8 Hz), 7.99(s, 1H), 10.3(broad s, 1H)

IR($cm^{-1}$): 1718, 1546, 1498, 1197

Elemental analysis: $C_{25}H_{19}C_{12}NO_5$

Found (%) C,61.99; H,4.01; N,2.74. Calcd. (%) C,62.00; H,3.95; N,2.89.

EXAMPLE 149

3-Benzyloxycarbonylmethyl-4-[(2,6-difluorophenyl) aminocarbonyl]-7-methoxybenzofuran (Compound 149)

Substantially the same procedure as in Example 1 was repeated using Compound IIbb (0.20 g) obtained in Reference Example 54 and 2,6-difluoroaniline (0.076 ml) to give Compound 149 (0.18 g, 66%) as white crystals.

Melting point: 223–224 ° C.

NMR(DMSO-$d_6$, δ, ppm): 3.91(s, 2H), 4.02(s, 3H), 4.94 (s, 2H), 7.07((d, 1H, J=8 Hz), 7.10–7.47(m, 8H), 7.69(d, 2H, J=8 Hz), 7.81(d, 1H, J=8 Hz), 7.97(s, 1H), 10.1(broad s, 1H)

IR($cm^{-1}$): 1726, 1668, 1508, 1259

MASS(m/e): 451($M^+$)

Elemental analysis: $C_{25}H_{19}F_2NO_5$

Found (%) C,66.38; H,4.22; N,3.06. Calcd. (%) C,66.52; H,4.24; N,3.10.

EXAMPLE 150

3-Benzyloxycarbonylmethyl-4-[(2,6-dimethylphenyl)aminocarbonyl]-7-methoxybenzofuran (Compound 150)

Substantially the same procedure as in Example 1 was repeated using Compound IIbb (0.30 g) obtained in Reference Example 54 and 2,6-dimethylaniline (0.13 ml) to give Compound 150 (0.27 g, 70%) as white crystals.

Melting point: 202–204° C.

NMR(DMSO-$d_6$, δ, ppm): 2.24(s, 6H), 3.95(s, 2H), 4.01 (s, 3H), 4.95(s, 2H), 7.07(d, 1H, J=8 Hz), 7.11–7.33(m, 8H), 7.77(d, 2H, J=8 Hz), 7.96(s, 1H), 9.68(s, 1H)

IR($cm^{-1}$): 1739, 1647, 1508, 1163

MASS(m/e): 443($M^+$)

Elemental analysis: $C_{27}H_{25}NO_5$

Found (%) C,72.93; H,5.63; N,3.18. Calcd. (%) C,73.12; H,5.68; N,3.16.

EXAMPLE 151

3-Carboxymethyl-4-[2-(3,5-dichloro-4-pyridyl)-1-oxoethyl]-7-methoxybenzofuran (Compound 151)

Substantially the same procedure as in Example 9 was repeated using Compound 119 (0.80 g) obtained in Example 119 to give Compound 151 (0.72 g, 96%) as white crystals.

Melting point: 192–194° C.

NMR($CDCl_3$, δ, ppm): 3.94(s, 2H), 4.10(s, 3H), 4.69(s, 2H), 6.99(d, 1H, J=8 Hz), 7.68(s, 1H), 7.95(d, 1H, J=8 Hz), 8.49(s, 2H)

MASS(m/e): 393($M^+$)

EXAMPLE 152

3-Benzyloxycarbonylmethyl-4-[2-(3,5-dichloro-4-pyridyl)-1-oxoethyl]-7-methoxybenzofuran (Compound 152)

Substantially the same procedure as in Example 13 was repeated using Compound 151 (0.30 g) obtained in Example 151 to give Compound 152 (0.27 g, 72%) as white crystals.

Melting point: 132–133° C.

NMR($CDCl_3$, δ, ppm): 3.94(s, 2H), 4.11(s, 3H), 4.70(s, 2H), 5.05(s, 2H), 6.89(d, 1H, J=9 Hz), 7.15–7.40 (m, 5H), 7.64(s, 1H), 7.96(d, 1H, J=8 Hz), 8.49(s, 2H)

IR($cm^{-1}$): 1720, 1674, 1560, 1240, 1122

MASS(m/e): 483($M^+$)

Elemental analysis: $C_{25}H_{19}C_{12}NO_5$

Found (%) C,61.87; H,3.93; N,2.83. Calcd. (%) C,62.00; H,3.94; N,2.89.

EXAMPLE 153

4-[2-(3,5-Dichloro-4-pyridyl)-1-oxoethyl]-7-methoxy-3-phenethyloxycarbonylmethylbenzofuran (Compound 153)

Substantially the same procedure as in Example 13 was repeated using Compound 151 (0.30 g) obtained in Example 151 and phenethyl alcohol (0.7 ml) to give Compound 153 (0.14 g, 36%) as white crystals.

Melting point: 183–184° C.

NMR(DMSO-$d_6$, δ, ppm): 2.68(t, 2H, J=7 Hz), 3.81(s, 2H), 4.00–4.20(m, 5H), 4.78(s, 2H), 7.00–7.30(m, 6H), 7.15–7.40(m, 5H), 7.99(s, 1H), 8.26(d, 1H, J=9 Hz), 8.61(s, 2H)

IR($cm^{-1}$): 1781, 1672, 1564, 1394, 1238, 1128

MASS(m/e): 497($M^+$)

Elemental analysis: $C_{26}H_{21}Cl_2NO_5$

Found (%) C,62.40; H,4.19; N,2.74. Calcd. (%) C,62.66; H,4.25; N,2.81.

EXAMPLE 154

4-[2-(3,5-Dichloro-4-Pyridyl)-1-oxoethyl]-7-methoxy-3-[(2-nitrobenzyl)oxycarbonylmethyl] benzofuran (Compound 154)

Substantially the same procedure as in Example 13 was repeated using Compound 151 (0.30 g) obtained in Example 151 and 2-nitrobenzyl alcohol (0.12 g) to give Compound 154 (0.15 g, 38%) as white crystals.

Melting point: 200–201° C.

NMR(DMSO-$d_6$, δ, ppm): 3.98(s, 2H), 4.07(s, 3H), 4.75 (s, 2H), 5.33(s, 2H), 7.14(d, 1H, J=9 Hz), 7.40–7.50(m, 1H), 7.50–7.70(m, 2H), 8.06(s, 1H), 8.07–8.17(m, 1H), 8.25(d, 1H, J=9 Hz), 8.54(s, 2H)

IR($cm^{-1}$): 1736, 1672, 1521, 1398, 1334, 1238, 1128

MASS(m/e): 528($M^+$)

Elemental analysis: $C_{25}H_{18}Cl_2N_2O_5$

Found (%) C,56.70; H,3.37; N,5.09. Calcd. (%) C,56.73; H,3.43; N,5.29.

EXAMPLE 155

3-Benzylaminocarbonylmethyl-4-[2-(3,5-dichloro-4-pyridyl)-1-oxoethyl]-7-methoxybenzofuran (Compound 155)

Substantially the same procedure as in Example 13 was repeated using Compound 151 (0.30 g) obtained in Example 151 and benzylamine (0.13 ml) to give Compound 155 (0.11 g, 29%) as white crystals.

Melting point: 244–246° C.

NMR(DMSO-$d_6$, δ, ppm): 3.67(s, 2H), 4.05(s, 3H), 4.18 (d, 2H, J=6 Hz), 4.79(s, 2H), 7.00–7.40(m, 6H),7.93(s, 1H), 8.00–8.30(m, 2H), 8.65(s, 2H)

IR($cm^{-1}$): 1677, 1650, 1567, 1396, 1126

MASS (m/e): 482 ($M^+$)

Elemental analysis: $C_{25}H_{20}Cl_2N_2O_4$

Found (%) C,62.17; H,4.14; N,5.59. Calcd. (%) C,62.12; H,4.17; N,5.80.

EXAMPLE 156

4-[2-(3,5-Dichloro-4-pyridyl)-1-oxoethyl]-7-methoxy-3-[(3-pyridyl)aminocarbonylmethyl] benzofuran (Compound 156)

Substantially the same procedure as in Example 13 was repeated using Compound 151 (0.30 g) obtained in Example 151 and 3-aminopyridine (0.088 g) to give Compound 156 (0.068 g, 19%) as white crystals.

Melting point: 252–255° C.

NMR(DMSO-$d_6$, δ, ppm): 3.91(s, 2H), 4.07(s, 3H), 4.72 (s, 2H), 7.13(d, 1H, J=9 Hz), 7.30(dd, J=5 Hz, 8 Hz, 1H), 7.88–7.93(m, 1H), 8.01(s, 1H), 8.18(d, 1H, J=9 Hz), 8.20–8.30(m, 1H), 8.46(s, 2H), 8.63(d, 1H, J=2 Hz), 10.1(s, 1H)

IR($cm^{-1}$): 1672, 1568, 1398, 1124

MASS(m/e): 471($M^+$)

Elemental analysis: $C_{23}H_{17}Cl_2N_3O_4.0.4H_2O$

Found (%) C,57.83; H,3.64; N,8.62. Calcd. (%) C,57.85; H,3.76; N,8.80.

EXAMPLE 157

4-[2-(3,5-Dichloro-4-pyridyl)-1-oxoethyl]-7-methoxy-3-[(2-pyridylmethyl)aminocarbonylmethyl] benzofuran.2 hydrochloride (Compound 157)

Compound 151 (0.15 g) obtained in Example 151 was dissolved in acetonitrile (3.0 ml), and carbonyldiimidazole (0.086 g) was added thereto under ice-cooling, followed by stirring at 60° C. for 30 minutes. 2-(Aminomethyl)pyridine (0.050 ml) was added to the mixture at room temperature followed by stirring for one hour. Water was added to the mixture and a precipitate was collected by filtration. The obtained crystals were recrystallized from DMF/water to give 4-[2-(3,5-dichloro-4-pyridyl)-1-oxoethyl]-7-methoxy-3-[(2-pyridylmethyl)aminocarbonylmethyl]benzofuran (0.13 g, 68%) as white crystals. Then, substantially the same procedure as in Example 51 was repeated using the obtained crystals to give Compound 157.

Melting point: 237–238° C.

NMR(DMSO-$d_6$, δ, ppm): 3.78(s, 2H), 4.06(s, 3H), 4.59 (d, 2H, J=5 Hz), 4.79(s, 2H), 7.11(d, 1H, J=8 Hz), 7.78(d, 1H, J=8 Hz), 7.87–7.95(m, 1H), 7.99(s, 1H), 8.20(d, 1H, J=9 Hz), 8.37–8.45(m, 1H), 8.50–8.66(m, 2H), 8.67(s, 2H), 8.80(d, 2H, J=5 Hz)

IR($cm^{-1}$): 1674, 1568, 1398, 1296

Elemental analysis $C_{24}H_{19}Cl_2N_3O_4.2HCl.0.1H_2O$

Found (%) C,51.56; H,4.09; N,7.37. Calcd. (%) C,51.56; H,3.82; N,7.52.

EXAMPLE 158

4-[2-(2,6-Dichlorophenyl)-1-oxoethyl]-3-ethoxycarbonylmethyl-7-methoxybenzofuran (Compound 158)

Substantially the same procedure as in Example 107 was repeated using Compound IIbc (0.30 g) obtained in Reference Example 55 and 2,6-dichlorophenylacetyl chloride (1.1 g) to give Compound 158 (0.22 g, 40%) as white crystals.

Melting point: 153–154° C.

NMR($CDCl_3$, δ, ppm): 1.16(t, 3H, J=7 Hz), 3.91(s, 2H), 4.09(s, 3H), 4.08(q, 2H, J=7 Hz), 4.71(s, 2H), 6.87(d, 1H, J=9 Hz), 7.19(dd, 1H, J=8.8 Hz), 7.35(d, 2H, J=8 Hz), 7.65(s, 1H), 7.99(d, 1H, J=9 Hz)

IR($cm^{-1}$): 1730, 1568, 1400, 1236, 1117

Elemental analysis: $C_{21}H_{18}Cl_2O_5$

Found (%) C,59.70; H,4.28; N,0.00. Calcd. (%) C,59.87; H,4.31; N,0.00.

EXAMPLE 159

Ethyl 4-[2-(3,5-dichloro-4-pyridyl)-1-oxoethyl]-7-methoxybenzofuran-3-carboxylate (Compound 159)

(Step A) Ethyl 4-[2-(3,5-dichloro)-4-pyridyl)-1-hydroxyethyl]-7-methoxybenzofuran-3-carboxylate (Compound 159a)

Under an argon atmosphere a solution (3.7 ml) of diisopropylamine (0.34 ml) in THF was cooled to −78° C., and then a 1.69M solution (1.5 ml) of butyl lithium in hexane was dropwise added thereto, followed by stirring at 0° C. for 15 minutes. The obtained mixture was cooled to −78° C. again, and then 3,5-ciichloro-4-methylpyridine (0.42 g) was added thereto, followed by stirring at −78° C. for 2 hours. The obtained solution was slowly and dropwise added to a solution (8.0 ml) of Compound IIbd (0.38 g) obtained in Reference Example 56 in THF, followed by stirring at −78° C. for 2 hours and then at 0° C. for one hour. A saturated aqueous solution of ammonium chloride was added to the reaction solution and the mixture was extracted with ether. The organic layer was washed with a saturated saline and dried over anhydrous magnesium sulfate, and the solvent was distilled off under reduced pressure. The residue was purified by silica gel column chromatography (hexane/ethyl acetate=2/1) to give Compound 159a (0.51 g, 81%) as white crystals.

Melting point: 132–134° C.

NMR($CDCl_3$, δ, ppm): 1.43(t, 3H, J=7 Hz), 3.49(dd, 1H, J=6 Hz, 13 Hz), 3.72(dd, 1H, J=8 Hz, 13 Hz), 3.99(s, 3H), 4.42(q, 2H, J=7 Hz), 5.35–5.48(m, 1H), 6.74(d, 1H, J=8 Hz), 7.08(d, 1H, J=8 Hz), 7.26(s, 1H), 8.40(s, 2H)

(Step B) (Compound 159)

Compound 159a (0.52 g) obtained in Step A was dissolved in acetone (10 ml) and 2.6M Jones' reagent (0.52 ml) was added thereto, followed by stirring at room temperature for 2 hours. The reaction solution was concentrated under reduced pressure. Water was added to the residue and the mixture was extracted with ethyl acetate. The organic layer was washed with a saturated saline and dried over anhydrous magnesium sulfate, and the solvent was distilled off under reduced pressure. The residue was purified by silica gel column chromatography (hexane/ethyl acetate=2/1) to give Compound 159 (0.44 g, 84%) as pale-yellow crystals.

Melting point: 142–143° C.

NMR($CDCl_3$, δ, ppm): 1.28(t, 3H, J=7 Hz), 4.10(s, 3H), 4.30(q, 2H, J=7 Hz), 4.69(s, 2H), 6.92(d, 1H, J=8 Hz), 7.81(d, 1H, J=8 Hz), 8.14(s, 1H), 8.51(s, 2H)

IR($cm^{-1}$): 1708, 1567, 1406, 1290, 1254

MASS(m/e): 312($M^+$)

Elemental analysis: $C_{21}H_{15}Cl_2NO_5$

Found (%) C,55.88; H,3.66; N,3.38. Calcd. (%) C,55.90; H,3.70; N,3.43.

EXAMPLE 160

4-[2-(2,6-Dichlorophenyl)-1-oxoethyl]-7-methoxy-2-(2-pyridylcarbonyl)benzofuran (Compound 160)

Substantially the same procedure as in Example 107 was repeated using Compound IIbe (1.2 g) obtained in Reference Example 57 and 2,6-dichlorophenylacetyl chloride (5.0 g) to give Compound 160 (1.7 g, 83%) as a white solid.

Melting point: 228–229° C.

NMR($CDCl_3$, δ, ppm): 4.15(s, 3H), 4.78(s, 2H), 7.03(d, 1H, J=8 Hz), 7.21(t, 1H, J=7 Hz), 7.36(d, 2H, J=7 Hz), 7.47(dd, 1H, J=5 Hz, 8 Hz), 7.87(ddd, 1H, J=2 Hz, 8 Hz, 8 Hz), 8.11(d, 1H, J=8 Hz), 8.15(d, 1H, J=8 Hz), 8.75(dd, 1H, J=2 Hz, 5 Hz), 9.00(s, 1H)

IR(KBr, $cm^{-1}$): 1654, 1581, 1305, 979

MASS(m/e): 441, 440, 439($M^+$), 282, 281, 280

Elemental analysis: $C_{23}H_{15}Cl_2NO_4$

Found (%) C,62.61; H,3.43; N,3.12. Calcd. (%) C,62.74; H,3.44; N,3.18.

EXAMPLE 161

4-[2-(2,6-Dichlorophenyl)-1-oxoethyl]-2-[(3-fluorophenyl)aminocarbonyl]-7-methoxybenzofuran (Compound 161)

Substantially the same procedure as in Example 107 was repeated using Compound IIbf-a (1.16 g) obtained in Step A of Reference Example 58 and 2,6-dichlorophenylacetyl chloride (5.4 g) to give Compound 161 (0.60 g, 32.5%) as a white solid.

Melting point: 251–252° C.

NMR($CDCl_3$, δ, ppm): 4.13(s, 3H), 4.75(s, 2H), 6.83(m, 1H), 7.01(d, 1H, J=8.5 Hz), 7.15–7.4(m, 5H), 7.65 (ddd, 1H, J=2 Hz, 2 Hz, 11 Hz), 8.08(d, 1H, J=8.5 Hz), 8.31(s, 1H), 8.42(brs, 1H)

IR(KBr, $cm^{-1}$): 3322, 1678, 1654, 1570, 1440, 1180

MASS(m/e): 474, 472($M^+$), 470, 314, 312, 174

Elemental analysis: $C_{24}H_{16}Cl_2FNO_4$

Found (%) C,59.53; H,3.58; N,2.84. Calcd. (%) C,59.66; H,3.58; N,2.89.

EXAMPLE 162

4-[2-(2,6-Dichlorophenyl)-1-oxoethyl]-2-[N-(3-fluorophenyl)-N-methylaminocarbonyl]-7-methoxybenzofuran (Compound 162)

Substantially the same procedure as in Example 107 was repeated using Compound IIbf (1.22 g) obtained in Step B of Reference Example 58 and 2,6-dichlorophenylacetyl chloride (5.4 g) to give Compound 162 (1.00 g, 52.6%) as a white solid.

Melting point: 198–199° C.

NMR($CDCl_3$, δ, ppm): 3.48(s, 3H), 3.95(s, 3H), 4.65(s, 2H), 6.85(d, 1H, J=8 Hz), 6.9–7.0(m, 3H), 7.20(t, 1H, J=5 Hz), 7.2–7.4(m, 3H), 7.56(s, 1H), 7.95(d, 1H, J=8 Hz)

IR(KBr, $cm^{-1}$): 1675, 1654, 1618, 1583

MASS(m/e): 488, 486($M^+$), 328, 327, 326, 174

Elemental analysis: $C_{25}H_{18}Cl_2FNO_4$

Found (%) C,60.31; H,3.64; N,2.76. Calcd. (%) C,60.40; H,3.89; N,2.81.

EXAMPLE 163

2-Benzoyl-4-[2-(2,6-dichlorophenyl)-1-oxoethyl]-7-methoxybenzofuran (Compound 163)

Substantially the same procedure as in Example 107 was repeated using Compound IIag-a (1.7 g) obtained in Step A of Reference Example 33 and 2,6-dichlorophenylacetyl chloride (4.1 g) to give Compound 163 (0.66 g, 22.3%) as a white solid.

Melting point: 223–224° C.

NMR($CDCl_3$, δ, ppm): 4.15(s, 3H), 4.77(s, 2H), 7.05(d, 1H, J=8.5 Hz), 7.21(t, 1H, J=7 Hz), 7.37(d, 2H, J=7 Hz), 7.49(dd, 2H, J=7 Hz, 8 Hz), 7.60(t, 1H, J=7 Hz), 8.00(d, 2H, J=8 Hz), 8.12(d, 1H, J=8.5 Hz), 8.24(s, 1H)

IR(KBr, $cm^{-1}$): 1649, 1579, 1308, 979

MASS(m/e): 440, 438($M^+$), 281, 280, 279

Elemental analysis: $C_{24}H_{16}Cl_2O_4$

Found (%) C,65.62; H,3.62. Calcd. (%) C,65.61; H,3.68.

EXAMPLE 164

2-Benzoyl-4-[2-(3,5-dichloro-4-pyridyl)-1-oxoethyl]-7-methoxybenzofuran (Compound 164)

(Step A) (±)-4-[2-(3,5-Dichloro-4-pyridyl)-1-oxoethyl)-2-(hydroxyphenylmethyl)-7-methoxybenzofuran (Compound 164a)

Under an argon atmosphere, a solution of diisopropylamine (30 ml) in THF (600 ml) was cooled to −78° C., and then a 1.63M solution (120 ml) of butyl lithium in hexane was dropwise added thereto, followed by stirring at 0° C. for 15 minutes. The obtained mixture was cooled to −78° C. again, and then 3,5-dichloro-4-methylpyridine (26.4 g) was added thereto, followed by stirring at 0° C. for 30 minutes. Compound IIbn (17.0 g) obtained in Reference Example 66 was added to this solution at the same temperature, followed by stirring at room temperature for 2 hours. A saturated aqueous solution of ammonium chloride was added to the reaction solution and the mixture was extracted with chloroform. The organic layer was washed with a saturated saline and dried over anhydrous magnesium sulfate, and the solvent was distilled off. The residue was triturated with diethyl ether to give Compound 164a (15.0 g, 62.3%) as a pale yellow solid.

NMR($CDCl_3$, δ, ppm): 2.82(d, 1H, J=4 Hz), 4.09(s, 3H), 4.70(s, 2H), 5.98(d, 1H, J=4 Hz), 6.86(d, 1H, J=8 Hz), 7.24(s, 1H), 7.3–7.4(m, 3H), 7.50(dd, 2H, J=1.5 Hz, 6 Hz), 7.96(d, 1H, J=8 Hz), 8.50(s, 2H)

MASS(m/e): 441($M^+$), 281

Elemental analysis: $C_{23}H_{17}Cl_2NO_4$

Found (%) C,62.45; H,3.88; N,3.17. Calcd. (%) C,62.24; H,3.85; N,3.09.

(Step B) (Compound 164)

Compound 164a (1.0 g) obtained in Step A was dissolved in face tone (200 ml) and 2.67M Jones' reagent (1.0 ml) was added thereto, followed by stirring at room temperature for 10 minutes. A 1N aqueous solution of potassium hydroxide was added to the reaction solution and the mixture was extracted with chloroform. The organic layer was washed with a saturated saline and dried over anhydrous magnesium sulfate, and the solvent was distilled off. The residue was triturated with diethyl ether to give Compound 164 (0.66 g, 66.5%) as a colorless solid.

Melting point: 213–215° C.

NMR($CDCl_3$, δ, ppm): 4.16(s, 3H), 4.76(s, 2H), 7.05(d, 1H, J=8 Hz), 7.50(dd, 2H, J=6 Hz, 6 Hz), 7.58(t, 1H,J=6 Hz), 8.02(d, 2H, J=6 Hz), 8.08(d, 1H, J=8 Hz), 8.19(s, 1H), 8.54(s, 2H)

IR(KBr, $cm^{-1}$): 1660, 1653, 1647, 1577, 1303

MASS(m/e): 441, 439($M^+$), 281, 279

Elemental analysis: $C_{23}H_{15}Cl_2NO_4$

Found (%) C,62.51; H,3.38; N,3.04, Calcd. (%) C,62.74; H,3.44; N,3.18.

EXAMPLE 165

7-Methoxy-4-[1-oxo-2-(4-pyridyl)ethyl]-2-(phenylaminocarbonyl)benzofuran.hydrochloride (Compound 165)

Substantially the same procedure as in Example 107 was repeated using Compound IIbg obtained in Reference Example 59 and 4-pyridylacetyl chloride to give 7-methoxy-4-[1-oxo-2-(4-pyridyl)ethyl]-2-(phenylaminocarbonyl)-benzofuran as a white solid. Then, substantially the same procedure as in Example 51 was repeated using the obtained solid to give Compound 165.

Melting point: 192–193° C.

NMR(DMSO-$d_6$, δ, ppm): 4.12(s, 3H), 4.98(s, 2H), 7.13 (t, 1H, J=7 Hz), 7.30(d, 1H, J=8.5 Hz), 7.37(dd, 2H, J=7 Hz, 7.5 Hz), 7.81(d, 2H, J=7.5 Hz), 8.08(d, 2H, J=6.5 Hz), 8.28(d, 1H, J=8.5 Hz), 8.40(s, 1H), 8.93(d, 2H, J=6.5 Hz), 10.65(s, 1H)

IR(KBr, $cm^{-1}$): 1668, 1650, 1641, 1585, 1292

MASS (m/e): 386($M^+$), 294

Elemental analysis: $C_{23}H_{18}N_2O_4$.HCl.1.8$H_2O$

Found (%): C,60.79; H,4.68; N,5.85. Calcd. (%): C,60.67; H,5.00; N,6.15.

EXAMPLE 166

2-Benzoyl-4-[(3-ethoxycarbonylphenyl)aminocarbonyl]-7-methoxybenzofuran (Compound 166)

Substantially the same procedure as in Example 1 was repeated using Compound IIbh (3.7 g) obtained in Reference Example 60 and ethyl 3-aminobenzoate (2.90 g) to give Compound 166 (4.58 g, 87.8%) as a white solid.

NMR($CDCl_3$, δ, ppm): 1.34(t, 3H, J=7 Hz), 3.94(s, 3H) 4.30(q, 2H, J=7 Hz), 6.75(d, 1H, J=8 Hz), 7.35–7.5(m, 3H), 7.60(dd, 2H, J=6.5 Hz, 7 Hz), 7.78(d, 1H, J=8 Hz), 7.9–8.1 (m, 4H), 8.21(s, 1H), 8.80(bs, 1H)

MASS(m/e): 443($M^+$), 279

Elemental analysis: $C_{26}H_{21}NO_6$.0.6$H_2O$

Found (%) C;68.86; H,4.68; N,3.03. Calcd. (%) C,68.74; H,4.93;N,3.08.

EXAMPLE 167

2-Benzoyl-4-[(3-carboxyphenyl)aminocarbonyl)-7-methoxybenzofuran (Compound 167)

Substantially the same procedure as in Example 9 was repeated using Compound 166 (1.00 g) obtained in Example 166 to give Compound 167 (0.76 g, 81.2%) as a white solid.

Melting point: 262–263° C.

NMR(DMSO-$d_6$, δ, ppm): 4.10(s, 3H), 7.32(d, 1H, J=8.5 Hz), 7.48(t, 1H, J=6.5 Hz), 7.6–7.8(m, 4H), 8.01(d, 2H, J=6 Hz), 8.02(s, 1H), 8.10(d, 1H, J=7 Hz), 8.20 (d, 1H, J=8.5 Hz), 8.48(s, 1H), 10.69(bs, 1H), 12.98(bs, 1H)

IR(KBr, $cm^{-1}$): 3100, 1664, 1650, 1645, 1591, 1542, 1228, 975

MASS(m/e): 415 ($M^+$), 279

Elemental analysis: $C_{24}H_{17}NO_6$0.7$H_2O$

Found (%) C,67.08; H,4.38; N,3.05. Calcd. (%) C,67.34; H,4.33; N,3.27.

EXAMPLE 168

2-Benzoyl-4-[(2,6-dichiorophenyl)aminocarbonyl]-7-methoxybenzofuran (Compound 168)

Substantially the same procedure as in Example 1 was repeated using Compound IIbh (0.59) obtained in Reference Example 60 and 2,6-dichloroaniline (0.34 g) to give Compound 168 (0.05 g, 6.6%) as a white solid.

NMR($CDCl_3$, δ, ppm): 4.13(s, 3H), 7.03(d, 1H, J=8.5 Hz), 7.23(t, 1H, J=8 Hz), 7.41(d, 2H, J=8 Hz), 7.51(dd, 2H, J=8 Hz, 8 Hz), 7.60(t, 1H, J=8 Hz), 7.61(bs, 1H) 7.83(d, 1H, J=8.5 Hz), 8.05(d, 2H, J=8 Hz), 8.14(s, 1H)

IR(KBr, $cm^{-1}$): 3328, 1645, 1515, 1492, 1258, 777

MASS(m/e): 441, 439($M^+$), 406, 404, 279

Elemental analysis: $C_{23}H_{15}Cl_2NO_4$

Found (%) C,62.92; H,3.42; N,3.03. Calcd. (%) C,62.73; H,3.43; N,3.18.

EXAMPLE 169

2-Benzoyl-4-[(2,6-dichlorophenyl)aminocarbonyl)-7-hydroxybenzofuran (Compound 169)

Under a nitrogen atmosphere, Compound 168 (0.04 g) obtained in Example 168 was dissolved in dry dichloromethane (2 ml) and the solution was cooled to −78° C. A 2.4M solution (0.125 ml) of boron tribromide in dichloromethane was slowly and dropwise added to the solution, and then the mixture was warmed to the room temperature and stirred one night. Distilled water (5 ml) was added to the mixture followed by stirring for one hour. The reaction solution was extracted with chloroform, the organic layer was dried over anhydrous magnesium sulfate, and the solvent was distilled off under reduced pressure. The residue was purified by silica gel column chromatography to give Compound 169 (0.02 g, 46.9%) as a pale-yellow solid.

NMR(DMSO-$d_6$, δ, ppm): 7.15(d, 1H, J=9 Hz), 7.40(t, 1H, J=8 Hz), 7.5–7.7(m, 4H), 7.75(t, 1H, J=6.5 Hz), 7.9–8.1 (m, 4H), 10.23 (brs, 1H), 11.31 (bs, 1H)

IR(KBr, $cm^{-1}$): 1660, 1650, 1510, 1290

EXAMPLE 170

7-Methoxy-4-[1-oxo-2-(4-pyridyl)ethyl]-3-[2-oxo-3-(4-pyridyl)propyl]-2,3-dihydrobenzofuran~hydrochloride (Compound 170)

Substantially the same procedure as in Step A of Example 159 was repeated using Compound IIbi (1.0 g) obtained in Reference Example 61 and 4-methylpyridine (0.75 ml) to give 7-methoxy-4-[1-oxo-2-(4-pyridyl)ethyl]-3-[2-oxo-3-(4-pyridyl)propyl]-2,3-dihydrobenzofuran. Then, substantially the same procedure as in Step B of Example 51 was repeated using the above-obtained product to give Compound 170 (0.35 g, 28.1%) as a pale-yellow solid.

Melting point: 214–216° C. (decomposed)

NMR($CDCl_3$, δ, ppm): 2.52–2.62(m, 1H),3.03–3.10(m, 1H) 3.70(s, 2H), 3.72–3.77(m, 1H), 3.95(s, 3H), 4.24(s, 2H), 4.34–4.39(m,3H), 4.59–4.66(m, 1H), 6.83(d, 1H, J=9 Hz), 7.14(dd, 4H, J=5 Hz, 16 Hz), 7.54(d, 1H, J=9 Hz), 8.57(dd, 4H, J=5 Hz, 16 Hz)

IR(KBr, $cm^{-1}$): 1716, 1672, 1292, 1203

MASS(m/e): 402 ($M^+$)

Elemental analysis: $C_{24}H_{22}N_2O_4$.2HCl.1.0$H_2O$

Found (%) C,58.26; H,5.53; N,5.61. Calcd. (%) C,58.42; H,5.31; N,5.67.

EXAMPLE 171

4-[2-(3,5-Dichloro-4-pyridyl)-1-oxoethyl]-3-ethoxycarbonylmethyl-7-methoxy-2,3-dihydrobenzofuran (Compound 171)

(Step A) 4-[2-(3,5-Dichloro-4-pyridyl)-1-hydroxyethyl]-3-ethoxycarbonylmethyl-7-methoxy-2,3-dihydrobenzofuran (Compound 171a) (a mixture of diastereomers)

Substantially the same procedure as in Step A of Example 159 was repeated using Compound IIj (4.00 g) obtained in Reference Example 10 to give Compound 171a (4.22 g, 78.1%) as a colorless solid.

NMR ($CDCl_3$, δ, ppm): 1.24 (t, 3H, J=7 Hz), 2.48–2.62 (m, 1H), 2.74–2.98(m, 1H), 3.02–3.07(m, 1H), 3.15–3.24 (m, 1H), 3.48–3.64(m, 1H), 3.73–3.82(m, 0.75H), 3.88(s, 3H), 3.95–4.04(m, 0.25H), 4.12(q, 2H, J=7 Hz), 4.43–4.62 (m, 2H), 5.07–5.14(m, 1H), 6.75–6.91(m, 1.25H), 7.09(d, 1.75H, J=9 Hz), 8.35(s, 2H)

MASS (m/e): 357($M^+$)

(Step B) (Compound 171)

Substantially the same procedure as in Step B of Example 159 was repeated using Compound 171a (0.1 g) obtained in Step A to give Compound 171 (0.075 g, 75.5%) a colorless solid.

NMR($CDCl_3$, δ, ppm): 1.22(t, 3H, J=7 Hz), 2.37–2.47(m, 1H), 2.81–2.87(m, 1H), 3.98(s, 3H), 4.11(q, 2H, J=7 Hz), 4.27–4.31(m, 3H), 4.56–4.66(m, 1H), 6.90(d, 1H,J=9 Hz), 7.65(d, 1H, J=9 Hz), 8.52(s, 2H)

MASS (m/e): 423($M^+$)

Elemental analysis: $C_{20}H_{19}Cl_2NO_5$

Found (%) C,56.48; H,4.40; N,3.05. Calcd. (%) C,56.61; H,4.51; N,3.30.

EXAMPLE 172

3-Carboxymethyl-4-[2-(3,5-dichloro-4-pyridyl)-1-oxoethyl]-7-methoxy-2,3-dihydrobenzofuran (Compound 172)

Substantially the same procedure as in Example 9 was repeated using Compound 171 (4.60 g) obtained in Example 171 to give Compound 172 (3.80 g, 88.1%) as a colorless solid.

NMR($CDCl_3$, δ, ppm): 2.24–2.38(m, 1H), 2.49–2.55(m, 1H), 3.90(s, 3H), 4.03–4.07(m, 1H), 4.41–4.46(m,1H), 4.53–4.60(m, 1H), 4.74(d, 1H, J=16 Hz), 4.77(d, 1H, J=16 Hz), 7.09(d, 1H, J=9 Hz), 7.89(d, 1H, J=9 Hz), 8.67(s, 2H)

MASS(m/e): 395($M^+$)

EXAMPLE 173

3-Benzyloxycarbonylmethyl-4-[2-(3,5-dichloro-4-pyridyl)-1-oxoethyl]-7-methoxy-2,3-dihydrobenzofuran (Compound 173)

Substantially the same procedure as in Example was repeated using Compound 172 (0.30 g) obtained in Example 170 to give Compound 173 (0.21 9, 58.5%) as a colorless solid.

Melting point: 120–122° C.

NMR ($CDCl_3$,δ, ppm): 2.43–2.53(m, 1H), 2.86–2.93(m, 1H), 3.98(s, 3H), 4.27–4.37(m, 1H), 4.55–4.66(m, 1H), 5.08(d, 1H, J=16 Hz), 5.09(d, 1H, J=16 Hz), 6.89(d, 1H, J=9 Hz), 7.28–7.36(m, 5H), 7.63(d, J=9 Hz, 1H), 8.51(s, 2H)

IR(KBr, $cm^{-1}$): 1668, 1511, 1284, 1182

MASS(m/e): 485($M^+$)

Elemental analysis: $C_{25}H_{21}Cl_2NO_5$

Found (%) C,61.56; H,4.33; N,2.78. Calcd. (%) C,61.74; H,4.35; N,2.87.

EXAMPLE 174

7-[2-(3,5-Dichloro-4-pyridyl)-1-oxoethyl)-4-methoxy-1,3-benzodioxole (Compound 174)

(Step A) 7-[2-(3,5-Dichloro-4-pyridyl)-1-hydroxyethyl]-4-methoxy-1,3-benzbdioxole (Compound 174a)

Substantially the same procedure as in Step A of Example 159 was repeated using Compound IIbj (4.39 g) obtained in Reference Example 62 to give Compound 174a (7.21 g, 87%) as colorless crystals.

NMR($CDCl_3$,δ, ppm): 2.34(d, 1H, J=7 Hz), 3.33(dd, 1H, J=5 Hz, 13 Hz), 3.56(dd, 1H, J=9 Hz, 13 Hz), 3.90(s, 3H), 5.08–5.16(m, 1H), 5.94(s, 1H), 6.00(s, 1H), 6.50(d, 1H, J=9 Hz), 6.78(d, 1H, J=9 Hz), 8.43(s, 2H)

MASS(m/e): 341($M^+$)

(Step B) (Compound 174)

Substantially the same procedure as in Step B of Example 159 was repeated using Compound 174a (3.55 g) obtained in Step A to give Compound 174 (2.42 g, 69%) as pale-yellow crystals.

Melting point: 170–171° C.

NMR($CDCl_3$, δ, ppm): 3.99(s, 3H), 4.60(s, 2H), 6.19(s, 2H), 6.65(d, 1H, J=8 Hz), 7.52(d, 1H, J=8 Hz),8.51(s, 2H)

IR($cm^{-1}$): 1674, 1633, 1439, 1290

MASS(m/e): 339($M^+$)

Elemental analysis: $C_{15}H_{11}Cl_2NO_4$

Found (%) C,52.88; H,3.25; N,4.00. Calcd. (%) C,52.96; H,3.26; N,4.12.

EXAMPLE 175

7-[2-(3,5-Dichloro-4-pyridyl)-1-oxoethyl)-2,2-dimethyl-4-methoxy-1,3-benzodioxole (Compound 175)

(Step A) 7-[2-(3,5-Dichloro-4-pyridyl)-1-hydroxyethyl)-2,2-dimethyl-4-methoxy-1,3-benzodioxole (Compound 175a)

Substantially the same procedure as in Step A of Example 159 was repeated using Compound IIbk (3.3 g) obtained in Reference Example 63 to give Compound 175a (3.89 g, 66%) as colorless crystals.

NMR($CDCl_3$, δ, ppm): 1.59(s, 3H), 1.69(s, 3H), 2.61(d, 1H, J=6 Hz), 3.32(dd, 1H, J=6 Hz, 13 Hz) 3.52(dd, 1H, J=8 Hz, 13 Hz), 3.87(s, 3H), 5.07–5.15(m, 1H), 6.46(d, 1H, J=9 Hz), 6.75(d, 1H, J=9 Hz), 8.39(s, 2H)

MASS (m/e): 369($M^+$)

(Step B) (Compound 175)

Substantially the same procedure as in Step B of was repeated using Compound 175a (3.50 g) obtained in Step A to give Compound 175 (2.3 g, 66%) as Example 159 obtained in pale-yellow crystals.

Melting point: 133–134° C.

NMR($CDCl_3$, δ, ppm): 1.83(s, 6H), 3.97(s, 3H), 4.58(s, 2H), 6.62(d, 1H, J=9 Hz), 7.48(d, 1H, J=9 Hz), 8.50(s, 2H)

IR($cm^{-1}$): 1680, 1633, 1550, 1292

MASS (m/e): 367 ($M^+$)

Elemental analysis: $C_{17}H_{15}Cl_2NO_4$

Found (%) C,55.25; H,4.08; N,3.70. Calcd. (%) C,55.45; H,4.11; N,3.80.

EXAMPLE 176

7-[2-(3,5-Dichloro-4-pyridyl)-1-oxoethyl)-2,2-diphenyl-4-methoxy-1,3-benzodioxole (Compound 176)

(Step A) 7-[2-(3,5-Dichloro-4-pyridyl)-1-hydroxyethyl]-2,2-diphenyl-4-methoxy-1,3-benzodioxole (Compound 176a)

Substantially the same procedure as in Step A of Example 159 was repeated using Compound IIbl (3.46 g) obtained in Reference Example 64 to give Compound 176a (3.09 g, 60%) as colorless crystals.

NMR($CDCl_3$, δ, ppm): 2.19(d, 1H, J=7 Hz), 3.34(dd, 1H, J=5 Hz, 13 Hz), 3.58(dd, 1H, J=9 Hz, 13 Hz), 3.93(s, 3H), 5.18–5.25(m, 1H), 6.51(d, 1H, J=9 Hz), 6.80(d, 1H, J=9 Hz), 7.35–7.39(m, 6H), 7.53–7.64(m, 4H), 8.43(5, 2H)

MASS (m/e): 493($M^+$)

(Step B) (Compound 176)

Substantially the same procedure as in Step B of Example 159 was repeated using Compound 176a (1.9 g) obtained in Step A to give Compound 176 (1.5 g, 79%) as pale-yellow crystals.

Melting point: 156–157° C.

NMR($CDCl_3$, δ, ppm): 3.99(s, 3H), 4.76(s, 2H), 6.63(d, 1H, J=9 Hz), 7.35–7.43(m, 6H), 7.51(d, 1H, J=9 Hz), 7.62–7.68(m, 4H), 8.51(s, 2H) IR($cm^{-1}$): 1508, 1440, 1333, 1294

MASS(m/e): 491($M^+$)

Elemental analysis: $C_{27}H_{19}C_{12}NO_4$

Found (%) C,65.64; H,3.85; N,2.77. Calcd. (%) C,65.87; H,3.89; N,2.84.

EXAMPLE 177

7-[2-(3,5-Dichloro-4-pyridyl)-1-oxoethyl)-4-methoxy-spiro[1,3-benzodioxole-2,1'-cycloheptane] (Compound 177)

(Step A) 7-[2-(3,5-Dichloro-4-pyridyl)-1-hydroxyethyl]-4-methoxy-spiro[1,3-benzodioxole-2,1'-cycloheptane] (Compound 177a)

Substantially the same procedure as in Step A of Example 159 was repeated using Compound IIbm (0.7 g) obtained in Reference Example 65 to give Compound 177a (0.74 g, 65.3%) as colorless crystals.

NMR($CDCl_3$, δ, ppm): 1.58–1.68(m, 8H), 2.00–2.20(m, 4H), 2.32(d, 1H, J=7 Hz), 3.29–3.36(m, 1H), 3.52–3.60(m, 1H), 3.88(s, 3H), 5.07–5.15(m, 1H), 6.46(d, 1H, J=9 Hz), 6.75 (d, 1H, J=9 Hz), 8.43(s,2H)

(Step B) (Compound 177)

Substantially the same procedure as in Step B of Example 159 was repeated using Compound 177a (0.68 g) obtained in Step A to give Compound 177 (0.48 g, 70.9%) as a colorless solid.

NMR($CDCl_3$, δ, ppm): 1.64–1.82(m, 8H), 2.18–2.38(m, 4H), 3.97(s, 3H), 4.61(s, 2H), 6.60(d, 1H, J=9 Hz), 7.45(d, 1H, J=9 Hz), 8.50(s, 2H)

EXAMPLE 178

5-[2-(3,5-dichloro-4-pyridyl)-1-oxoethyl]-2,3-dihydro-8-methoxy-1,4-benzodioxine (Compound 178)

(Step A) (±)-5-[2-(3,5-dichloro-4-pyridyl)-1-hydroxyethyl]-2,3-dihydro-8-methoxy-1,4-benzodioxine (Compound 178a)

Under an argon atmosphere, a solution of diisopropylamine (2.3 ml) in THF (10 ml) was cooled to −78EC., and then, a solution of 1.63 M butyl lithium in hexane (10 ml) was added dropwise to the cooled solution, followed by stirring at OEC for 15 min. The resulting mixture was cooled to −78° C. again, mixed with 3,5-dichloro-4-methylpyridine (2.6 g), and stirred at −78° C. for 2 hours. The thus-obtained solution was slowly added dropwise to a solution of Compound a (2.7 g) in THF (20 ml), which Compound a was obtained in Reference Example 1, followed by stirring for 2 hours at −78° C. and for further 1 hour at 0° C. The reaction solution was mixed with a saturated aqueous ammonium chloride solution and extracted with ether. The organic layer was washed with a saturated aqueous sodium chloride solution, dried over magnesium sulfate anhydride, and evaporated under reduced pressure for removing the solvent to give crude crystals of Compound 178a (5.0 g, quantitative).

NMR($CDCl_3$, δ, ppm): 2.93(d, J=8 Hz, 1H), 3.43(dd, J=6 Hz, 13 Hz, 1H), 3.59(dd, J=9 Hz, 13 Hz, 1H), 3.87(s, 3H), 4.23–4.35(m, 4H), 5.07–5.15(m, 1H), 6.46(d, J=9 Hz, 1H), 6.76(d, J=9 Hz, 1H), 8.41(s, 2H)

MASS (m/e) 355($M^+$)

(Step B) (Compound 178)

Compound 178a (3.0 g) obtained in Step A was dissolved in acetone (30 ml), mixed with Jones reagent (2.6 M) (4.9 ml), and stirred at room temperature for 2 hours. The reaction solution was concentrated under reduced pressure. The resulting residue was mixed with water and extracted with ethyl acetate. The organic layer was washed with a saturated aqueous sodium chloride solution, dried over magnesium sulfate anhydride, and evaporated under reduced pressure for removing the solvent. The residue was purified by silica gel column chromatography (hexane/ethyl acetate=4/1) to give Compound 178 (3.0 g, 75%) as colorless crystals.

Melting point: 158–160° C.

NMR($CDCl_3$, δ, ppm): 3.95(s, 3H), 4.42–4.49(m, 4H), 4.63(s, 2H), 6.61(d, J=9 Hz, 1H), 7.55(d, J=9 Hz, 1H), 8.49(s, 2H)

MASS (m/e): 353($M^+$)

IR (KBr,$cm^{-1}$): 1668, 1660, 1599, 1296, 1122

Elemental analysis: as $C_{16}H_{13}Cl_2NO_4$

Found (%) C,54.21; H,3.68; N,3.77. Calcd. (%) C,54.26; H,3.70; N,3.95.

EXAMPLE 179

2,3-dihydro-8-methoxy-5-[1-oxo-2-(4-pyridyl) ethyl]-1,4-benzodioxine hydrochloride (Compound 179)

Compound 178 (1.1 g) obtained in Example 178 was dissolved in DMF (10 ml), mixed with palladium carbon (containing 50% water) (0.2 g), and stirred at room temperature for 24 hours in a hydrogen atmosphere. The reaction solution was filtered with Celite. The filtrate was mixed with saturated sodium bicarbonate water and extracted with ethyl acetate. The organic layer was washed with a saturated aqueous sodium chloride solution, dried over magnesium sulfate anhydride, and evaporated under reduced pressure for removing the solvent. The residue was purified by silica gel column chromatography (ethyl acetate) to give 2,3-dihydro-5-methoxy-8-[1-oxo-2-(4-pyridyl)ethyl]-1,4-benzodioxine (0.36 g, 41%) as colorless crystals. The thus-obtained compound was dissolved in ethyl acetate and mixed with a saturated hydrochloric acid ethyl acetate solution. The precipitated crystals were filtered and washed with ethyl acetate to give Compound 179 as colorless crystals.

Melting point: 226–228° C.

NMR(DMSO-$d_6$, δ, ppm): 3.84(s, 3H), 4.29–4.41(m, 4H), 4.66(s, 2H), 6.76(d, J=9 Hz, 1H), 7.39(d, J=9 Hz, 1H), 7.96(d, J=6 Hz, 2H), 8.87(d, J=6 Hz, 2H)

MASS (m/e): 285($M^+$)

IR (KBr,$cm^{-1}$): 1606, 1596, 1294, 1119

Elemental analysis: $C_{16}H_{15}NO_4$.HCl.0.2$H_2O$

Found (%) C,59.06; H,5.08; N,4.30. Calcd. (%) C,59.07; H,5.03; N,4.28.

EXAMPLE 180

5-[2-(2,6-dichlorophenyl)-1-oxoethyl]-2,3-dihydro-8-methoxy-1,4-benzodioxine (Compound 180)

Compound IIbq (1.0 g) obtained in Reference Example 69 was dissolved in methylene chloride (100 ml) and mixed with 2,6-dichlorophenylacetyl chloride (6.73 g) at room temperature. Under ice-cold conditions, titanium tetrachloride (5.3 ml) was added to the resultant and stirred for 15 hours. The reaction solution was added to an aqueous hydrochloric acid solution under ice-cold conditions, and extracted with ethyl acetate. The organic layer was washed with a saturated aqueous sodium chloride solution, dried over magnesium sulfate anhydride, and evaporated under reduced pressure for removing the solvent. The residue was purified by silica gel column chromatography (hexane/ethyl acetate=3/1) to give Compound 180 (1.5 g, 72%) as colorless crystals.

Melting Point: 154–155° C.

NMR($CDCl_3$, δ,ppm): 3.94(s, 3H), 4.07–4.23(m, 2H), 4.45–4.48(m, 2H), 4.64(s, 2H), 6.59(d, J=9 Hz, 1H), 7.15(d, J=8 Hz, 1H), 7.32(d, J=8 Hz, 1H), 7.54(d, J=9 Hz, 1H)

MASS (m/e): 352($M^+$)

Elemental analysis: $C_{17}H_{14}Cl_2O_4$

Found (%) C,57.59; H,3.94; N,0.05. Calcd. (%) C,57.81; H,3.99; N,0.00.

EXAMPLE 181

(E)-5-[2-(3,5-dichloro-4-pyridyl)ethenyl)]-2,3-dihydro-8-methoxy-1,4-benzodioxine (Compound 181)

To a suspension of Compound 178a (1.6 g) in toluene (20 ml), which Compound 178a was obtained in Step A of Example 178, was added p-toluenesulfonic acid (0.8 g), followed by heat-refluxing for 30 min. The reaction solution was allowed to stand for cooling, neutralized by adding a saturated aqueous sodium hydrogencarbonate solution, and extracted with ether. The organic layer was washed with a saturated aqueous sodium chloride solution, dried over magnesium sulfate anhydride, and evaporated under reduced pressure for removing the solvent. The residue was purified by silica gel column chromatography (hexane/ethyl acetate=3/1) to give Compound 181 (1.4 g, 95%) as yellow crystals.

Melting point: 94–95° C.

NMR($CDCl_3$, δ,ppm): 3.92(s, 3H), 4.37(s, 4H), 6.57(d, J=9 Hz, 1H), 7.10(d, J=17 Hz, 1H), 7.16(d, J=9 Hz, 1H), 7.69(d, J=17 Hz, 1H), 8.47(s, 2H)

MASS (m/e): 337($M^+$)

IR (KBr,$cm^{-1}$): 1603, 1500, 1290, 1120

Elemental analysis: $C_{16}H_{13}Cl_2NO_3$

Found (%) C,56.78; H,3.85; N,4.01. Calcd. (%) C,56.82; H,3.87; N,4.14.

EXAMPLE 182

2,3-dihydro-8-methoxy-5-[2-(4-pyridyl)ethyl)]-1,4-benzodioxine.hydrochloride (Compound 182)

Using Compound 180 (0.8 g) obtained in Example 180, 2,3-dihydro-8-methoxy-5-[2-(4-pyridyl)ethyl)]-1,4-benzodioxine (0.55 g, 86%) was obtained as colorless crystals according to substantially the same procedure as in Example 179. Furthermore, the resultant was rendered to a hydrochloride according to substantially the same procedure as in Example 179 to give Compound 182 as colorless crystals.

Melting point: 199–201° C.

NMR(DMSO-$d_6$, δ, ppm): 2.86(t, J=7 Hz, 3H), 3.11(t, J=7 Hz, 3H), 3.69(s, 3H), 4.18(s, 4H), 4.66(s, 2H), 6.45(d, J=8 Hz, 1H), 6.56(d, J=8 Hz, 1H), 7.84(d, J=6 Hz, 2H), 8.78(d, J=6 Hz, 2H)

MASS (m/e): 271($M^+$)

IR (KBr,$cm^{-1}$): 1633, 1504, 1282, 1116

Elemental analysis: $C_{16}H_{17}NO_3$.HCl

Found (%) C,62.12; H,5.91; N,4.47. Calcd. (%) C,62.44; H,5.89; N,4.55.

EXAMPLE 183

5-(3,5-dichloro-4-pyridylaminocarbonyl)-2,3-dihydro-8-methoxy-1,4-benzodioxine (Compound 183)

A mixture of Compound IIbp (0.30 g) obtained in Reference Example 68, thionyl chloride (1.5 ml), and dichloromethane (3.0 ml) was heat-refluxed for 1 hour. The mixture was allowed to stand for cooling and evaporated for removing the solvent. The residue was dissolved in dry toluene. The residual thionyl chloride was evaporated away under reduced pressure to give a crude acid chloride. After dissolving 4-amino-3,5-dichloropyridine (0.28 g) in THF (8.0 ml), sodium hydride (140 mg) was added to the resulting solution under ice-cold conditions, stirred for 15 min. at room temperature, and then, the resulting mixture was again cooled with ice. A solution of the above crude acid chloride in THF (5 ml) was added dropwise to the mixture under ice-cold conditions, followed by stirring for 1 hour under ice-cold conditions. The reaction mixture was extracted with ethyl acetate; the organic layer was washed with a saturated aqueous sodium chloride solution, dried over magnesium sulfate anhydride, and evaporated under reduced pressure for removing the solvent. The residue was recrystallized from ethanol to give Compound 183 (0.22 g, 35%) as colorless crystals.

Melting point: 143–145° C.

NMR($CDCl_3$, δ,ppm): 3.96(s, 3H), 4.47–4.44(m, 2H), 4.56–4.53(m, 2H), 6.69(d, J=9 Hz, 1H),7.87(d, J=9 Hz, 1H), 8.55(s, 2H), 9.49(broad s, 1H)

MASS (m/e): 355($M^+$)

IR (KBr,$cm^{-1}$): 1689, 1492, 1297, 1116

Elemental analysis: $C_{15}H_{12}Cl_2N_2O_4$

Found (%) C,50.86; H,3.46; N,7.74. Calcd. (%) C,50.73; H,3.41; N,7.89.

EXAMPLE 184

5-(2,6-dichlorophenylaminocarbonyl)-2,3-dihydro-8-methoxy-1,4-benzodioxine (Compound 184)

Using Compound IIbp (0.60 g) obtained in Reference Example 68 and 2,6-dichloroaniline (0.55 g), Compound 184 (0.41 g, 41%) was obtained as colorless crystals according to substantially the same procedure as in Example 183.

Melting point: 176–177° C.

NMR($CDCl_3$, δ,ppm): 3.92(s, 3H), 4.38–4.41(m, 2H), 4.48–4.51(m, 2H), 6.64(d, J=9 Hz, 1H), 7.15(d, J=9 Hz, 1H), 7.38(d, J=9 Hz, 1H), 7.85(d, J=9 Hz, 1H), 9.23(s, 1H)

MASS(m/e) 353($M^+$)

Elemental analysis: $C_{16}H_{13}Cl_2NO_4$

Found (%) C,54.14; H,3.67; N,3.83. Calcd. (%) C,54.25; H,3.69; N,3.94.

EXAMPLE 185

5-(3-ethoxycarbonylphenylaminocarbonyl)-2,3-dihydro-8-methoxy-1,4-benzodioxine (Compound 185)

Using Compound IIbp (0.30 g) obtained in Reference Example 68 and ethyl 3-aminobenzoate (0.28 g), Compound 185 (0.39 g, 77%) was obtained as colorless crystals according to substantially the same procedure as in Example 183.

Melting point: 174–175° C.

NMR($CDCl_3$, δ,ppm): 1.41(t, J=7 Hz, 3H), 3.92(s, 3H), 4.40(q, J=7 Hz, 2H), 4.45–4.46(m, 2H), 4.54–4.57(m, 2H), 6.68(d, J=9 Hz, 1H), 7.44(t, J=8 Hz, 1H), 7.80(d, J=8 Hz, 1H), 7.88(d, J=9 Hz, 1H), 8.06(s, 1H), 8.15(d, J=8 Hz, 1H), 9.54(s, 1H)

MASS (m/e): 357($M^+$)

Elemental analysis: $C_{19}H_{19}NO_6$

Found (%) C,63.64; H,5.34; N,3.83. Calcd. (%) C,63.85; H,5.35; N,3.91.

EXAMPLE 186

5-(3-carboxyphenylaminocarbonyl)-2,3-dihydro-8-methoxy-1,4-benzodioxine (Compound 186)

Compound 185 (0.19 g) obtained in Example 185 was suspended in ethanol (1 ml), mixed with a 24% aqueous sodium hydroxide solution (1.3 ml), and heat-refluxed for 2 hours. The resultant was allowed to stand for cooling, mixed with water, and adjusted to PH 2 by adding 2N hydrochloric acid water. The precipitated solid was collected by filtration to give Compound 186(0.14 g, 80%) as colorless crystals.

Melting point: 283–284° C.

NMR($CDCl_3$, δ,ppm): 3.96(s, 3H), 4.44–4.46(m, 2H), 4.56–4.59(m, 2H), 6.71(d, J=9 Hz, 1H), 7.46(t, J=8 Hz, 1H), 7.79(d, J=9 Hz, 1H), 7.83(d, J=8 Hz, 1H), 8.06(d, J=8 Hz, 1H), 8.10(s, 1H)

MASS (m/e) 329($M^+$)

Elemental analysis: $C_{17}H_{15}NO_6$

Found (%) C,62.22; H,4.58; N,4.20. Calcd. (%) C,62.00; H,4.59; N,4.25.

EXAMPLE 187

5-(4-ethoxycarbonylphenyl)-2,3-dihydro-8-methoxy-1,4-benzodioxine (Compound 187)

(Step A) 2,3-dihydro-8-methoxy-5-tributylstannyl-1,4-benzodioxine (Compound 187a)

Under an argon atmosphere, a solution of Compound aa (0.5 g) in THF (5 ml), which Compound aa was obtained in Reference Example 1 (Step A), was cooled to −78° C., and then, a solution of 1.66 M butyl lithium in hexane (1.48 ml) was added dropwise to the cooled solution. The resultant was stirred at the same temperature for 30 min, mixed with tributyltin chloride (0.67 ml), and stirred for 5 min. The resultant was heated to room temperature and the organic layer was extracted by adding an aqueous ammonium chloride solution and ether. The organic layer was washed with a saturated aqueous sodium chloride solution, dried over magnesium sulfate anhydride, and evaporated under reduced pressure for removing the solvent to give the target compound as a crude product. The crude product was subjected to the subsequent step without being purified.

(Step B) (Compound 187)

Compound 187a (0.93 g) obtained in Step A, ethyl 4-iodobenzoate (0.34 ml), palladium acetate (0.05 g), and sodium carbonate (0.54 g) were dissolved in DMF (10 ml), followed by stirring for 6 hours at 60° C. The reaction solution was mixed with an aqueous ammonium fluoride solution and diethyl ether, and then, filtered with Celite. The organic layer was extracted from the resultant, washed with a saturated aqueous sodium chloride solution, dried over magnesium sulfate anhydride, and evaporated under reduced pressure for removing the solvent. The residue was purified by silica gel column chromatography (hexane/ethyl acetate=4/1) to give Compound 187 (0.30 g, 50%) as colorless crystals.

Melting point: 141–141.5° C.

NMR($CDCl_3$, δ, ppm): 0.92(t, J=7 Hz, 3H), 3.93(s, 3H), 4.27–4.30(m, 2H), 4.35–4.38(m, 2H), 4.39(q, J=7 Hz, 2H), 6.60(d, J=9 Hz, 1H), 6.89(d, J=9 Hz, 1H), 7.59(d, J=9 Hz, 1H), 8.06(d, J=9 Hz, 1H)

MASS (m/e): 314($M^+$)

Elemental analysis: $C_{18}H_{18}O_5$

Found (%) C,68.68; H,5.93; N,0.00. Calcd. (%) C,68.77; H,5.77; N,0.00.

EXAMPLE 188

5-(4-carboxyphenyl)-2,3-dihydro-8-methoxy-1,4-benzodioxine (Compound 188)

Using Compound 187 (1.0 g) obtained in Example 187, Compound 188 (0.57 g, 63%) was obtained as colorless crystals according to substantially the same procedure as in Example 186.

Melting point: 281–284° C.

NMR(DMSO-$d_6$, δ, ppm): 3.83(s, 3H), 4.22–4.38(m, 4H), 6.74(d, J=9 Hz, 1H), 6.93(d, J=9 Hz, 1H), 7.64(d, J=8 Hz, 2H), 8.00(d, J=8 Hz, 2H)

MASS (m/e): 286($M^+$)

IR(KBr, $cm^{-1}$): 1670, 1450, 1284, 1122

Elemental analysis: $C_{16}H_{14}O_5.0.3H_2O$

Found (%) C,65.70; H,4.97; N,0.05. Calcd. (%) C,65.88; H,5.04; N,0 00.

EXAMPLE 189

6-[2-(3,5-dichloro-4-pyridyl)-1-oxoethyl]-3,4-dihydro-9-methoxy-2H-1,5-benzodioxepin (Compound 189)

(Step A) (±)-6-[2-(3,5-dichloro-4-pyridyl)-1-hydroxyethyl]-3,4-dihydro-9-methoxy-2H-1,5-benzodioxepin (Compound 189a)

Using Compound IIbr (3.2 g) obtained in Reference Example 70, Compound 189a (4.6 g, 81%) was obtained as colorless crystals according to substantially the same procedure as in Step A of Example 178.

NMR($CDCl_3$, δ, ppm): 2.22–2.30(m, 2H), 2.93(d, J=8 Hz, 1H), 3.26(dd, J=6 Hz, 13 Hz, 1H), 3.56(dd, J=9 Hz, 13 Hz, 1H), 3.86(s, 3H), 4.25–4.35(m, 4H), 5.08–5.14(m, 1H), 6.46(d, J=9 Hz, 1H), 6.76(d, J=9 Hz, 1H), 8.41(s, 2H)

MASS (m/e): 369($M^+$)

(Step B) (Compound 189)

Using Compound 189a (3.0 g) obtained in Step A, Compound 189(2.2 g, 74%) was obtained as colorless crystals according to substantially the same procedure as in Step B of Example 178.

Melting point: 150–151° C.

NMR($CDCl_3$, δ, ppm): 2.30–2.36(m, 2H), 3.93(s, 3H), 4.36(t, J=6 Hz, 2H), 4.46(t, J=6 Hz, 2H), 4.65(s, 2H), 6.69(d, J=9 Hz, 1H), 7.55(d, J=9 Hz, 1H), 8.50(s, 2H)

MASS (m/e): 367($M^+$)

IR(EBr, $cm^{-1}$): 1670, 1583, 1286, 1105

Elemental analysis: $C_{17}H_{15}Cl_2NO_4$

Found (%) C,55.33; H,4.06; N,3.58. Calcd. (%) C,55.45; H,4.11; N,3.80.

EXAMPLE 190

3,4-dihydro-6-methoxy-9-[1-oxo-2-(4-pyridyl)ethyl]-2H-1,5-benzodioxepin hydrochloride (Compound 190)

Using Compound 189 (1.2 g) obtained in Example 189, 3,4-dihydro-6-methoxy-9-[1-oxo-2-(4-pyridyl)ethyl]-2H-1,5-benzodioxepin (0.13 g, 13%) was obtained as colorless crystals according to substantially the same procedure as in Example 179. Furthermore, the resultant was rendered to a hydrochloride according to substantially the same procedure as in Example 179 to give Compound 190 as colorless crystals.

Melting point: 205–208° C.

NMR(DMSO-$d_6$, δ, ppm): 2.12–2.20(m, 2H), 3.84(s, 3H), 4.12(t, J=6 Hz, 2H), 4.31(t, J=6 Hz, 2H), 4.67(s, 2H), 6.89(d, J=9 Hz, 1H), 7.45(d, J=9 Hz, 1H), 7.93(d, J=6 Hz, 2H), 8.85(d, J=6 Hz, 2H)

MASS (m/e): 299($M^+$)

IR(Kbr, $cm^{-1}$): 1657, 1587, 1298, 1108

Elemental analysis: $C_{17}H_{17}NO_4.HCl.H_2O$

Found (%) C,57.69; H,5.83; N,3.75. Calcd. (%) C,57.71; H,5.70; N,3.96.

EXAMPLE 191

(E)-6-[2-(3,5-dichloro-4-pyridyl)ethenyl]-3,4-dihydro-9-methoxy-2H-1,5-benzodioxepin (Compound 191)

Using Compound 189a (1.4 g) obtained in Step A of Example 189, Compound 191 (1.1 g, 79%) was obtained as yellow crystals according to substantially the same procedure as in Example 181.

Melting point: 118–120° C.

NMR ($CDCl_3$, δ,ppm): 2.22–2.29(m, 2H), 3.90(s, 3H), 4.31–4.35(m, 4H), 6.65(d, J=9 Hz, 1H), 7.05(d, J=17 Hz, 1H), 7.26(d, J=9 Hz, 1H), 7.76(d, J=17 Hz, 1H), 8.47(s, 2H)

MASS(m/e): 351 ($M^+$)

IR(KBr, $cm^{-1}$): 1593, 1502, 1297, 1101

Elemental analysis: $C_{17}H_{15}Cl_2NO_3$

Found (%) C,57.99; H,4.28; N,3.87. Calcd. (%) C,57.97; H,4.29; N,3.98.

EXAMPLE 192

3,4-dihydro-6-methoxy-9-[2-(4-pyridyl)ethyl]-2H-1,5-benzodioxepin hydrochloride (Compound 192)

Using Compound 191 (0.57 g) obtained in Example 191, 3,4-dihydro-6-methoxy-9-[2-(4-pyridyl)ethyl]-2H-1,5-benzodioxepin (0.33 g, 71%) was obtained as colorless crystals according to substantially the same procedure as in Example 179. Furthermore, the resultant was rendered to a hydrochloride according to substantially the same procedure as in Example 179 to give Compound 192 as colorless crystals.

Melting point: 185–187° C.

NMR (DMSO-$d_6$, δ, ppm): 2.06–2.11(m, 2H), 2.88(t, J=7 Hz, 3H), 3.08(t, J=7 Hz, 3H), 3.70(s, 3H), 4.02–4.08(m, 4H), 6.59(d, J=8 Hz, 1H), 6.73(d, J=8 Hz, 1H), 7.84(d, J=6 Hz, 2H), 8.77(d, J=6 Hz, 2H)

MASS(m/e): 285 ($M^+$)

IR(KBr, $cm^{-1}$): 1633, 1497, 1257, 1101

Elemental analysis: $C_{17}H_{19}NO_3.HCl$

Found (%) C,63.12; H,6.29; N,4.25. Calcd. (%) C,63.45; H,6.26; N,4.35.

EXAMPLE 193

6-(3,5-dichloro-4-pyridylaminocarbonyl)-3,4-dihydro-9-methoxy-2H-1,5-benzodioxepin (Compound 193)

Using Compound IIbs (0.70 g) obtained in Example 71, Compound 193 (0.66 g, 56%) was obtained as colorless crystals according to substantially the same procedure as in Example 183.

Melting point: 149–150° C.

NMR ($CDCl_3$, δ, ppm): 2.38–2.34(m, 2H), 3.94(s, 3H), 4.36(t, J=6 Hz, 2H), 4.54(t, J=6 Hz, 2H), 6.77(d, J=9 Hz, 1H), 7.95(d, J=9 Hz, 1H), 8.55(s, 2H), 9.92(broad s, 1H)

MASS(m/e): 369 ($M^+$)

IR(KBr, $cm^{-1}$): 1689, 1486, 1270, 1091

Elemental analysis: $C_{16}H_{14}Cl_2N_2O_4.0.4H_2O$

Found (%) C,51.04; H,3.79; N,7.39. Calcd. (%) C,51.06; H,3.96; N,7.44.

EXAMPLE 194

7-[2-(3,5-dichloro-4-pyridyl)-1-oxoethyl]-10-methoxy-2,3,4,5-tetrahydro-1,6-benzodioxocin (Compound 194)

Compound IIbt (1.0 g) obtained in Reference Example 72 was dissolved in DMF (10 ml), mixed with 1,4-dibromobutane (0.45 ml) and potassium carbonate (0.95 g), and stirred at 60° C. for 1 hour. The mixture was allowed to stand for cooling, mixed with water, and extracted with ether. The organic layer was washed with a saturated aqueous sodium chloride solution, dried over sodium sulfate anhydride, and evaporated under reduced pressure for removing the solvent. The residue was purified by silica gel column chromatography (hexane/ethyl acetate=3/1) and recrystallized from ethanol to give Compound 194 (0.36 g, 30%) as white crystals.

Melting point: 142–143° C.

NMR($CDCl_3$, δ, ppm): 1.87–2.13(m, 4H), 3.92(s, 3H), 4.27–4.40(m, 2H), 4.55–4.72(m, 4H), 6.67(d, J=9 Hz, 1H), 7.58(d, J=9 Hz, 1H), 8.49(s, 2H)

MASS (m/e): 381 ($M^+$)

Elemental analysis: $C_{18}H_{17}Cl_2NO_4$

Found (%) C,56.63; H,4.49; N,3.5. Calcd. (%) C,56.56; H,4.48; N,3.66.

EXAMPLE 195

7-[2-(3,5-dichloro-N-oxo-4-pyridyl)-1-oxoethyl]-10-methoxy-2,3,4,5-tetrahydro-1,6-benzodioxocin (Compound 195)

Compound 194 (1.4 g) obtained in Example 194 was dissolved in dichloromethane (14 ml), mixed with metachloroperbenzoic acid (1.2 g), and stirred at room temperature for 1 hour. Metachloroperbenzoic acid (1.2 g) was further added to the mixture and stirred for 5 hours. The resultant was mixed with an aqueous sodium hydrogen sulfite solution and saturated sodium bicarbonate water, and then, extracted with ethyl acetate. The organic layer was washed with a saturated aqueous sodium chloride solution, dried over sodium sulfate anhydride, and evaporated under reduced pressure for removing the solvent. The residue was purified by silica gel column chromatography (chloroform/methanol=30/1) and recrystallized from ethanol to give Compound 195 (0.85 g, 59%) as white crystals.

Melting point: 188–189° C.

NMR(DMSO-$d_6$, δ, ppm): 1.65–2.00(m, 4H), 3.85(s, 3H), 4.05–4.23(m, 2H), 4.44–4.55(m, 4H), 6.86(d, J=9 Hz, 1H), 7.48(d, J=9 Hz, 1H), 8.64(s, 2H)

MASS (m/e): 397($M^+$)

IR (KBr,$cm^{-1}$): 1664, 1581, 1433, 1290, 1105

Elemental analysis: $C_{18}H_{17}Cl_2NO_5$

Found (%) C,54.24; H,4.43; N,3.35. Calcd. (%) C,54.29; H,4.30; N,3.52.

EXAMPLE 196

7-(3,5-dichloro-4-pyridylaminocarbonyl)-10-methoxy-2,3,4,5-tetrahydro-1,6-benzodioxocin (Compound 196)

Using Compound g (1.1 g) obtained in Reference Example 7, Compound 196 (1.0 g, 56%) was obtained as white crystals according to substantially the same procedure as in Example 182.

Melting point: 115–117° C.

NMR(DMSO-$d_6$, δ, ppm): 1.64–1.96(m, 4H), 3.84(s, 3H), 4.08–4.23(m, 2H), 4.45–4.59(m, 2H), 6.89(d, J=9 Hz, 1H), 7.59(d, J=9 Hz, 1H), 8.72(s, 2H), 10.1(s, 1H)

MASS (m/e): 382 ($M^+$)

Elemental analysis: $C_{17}H_{16}Cl_2N_2O_4$

Found (%) C,53.33; H,4.28; N,7.22. Calcd. (%) C,53.28; H,4.21; N,7.31.

EXAMPLE 197

5-(3,5-dichloro-4-pyridylaminocarbonyl)-8-methoxy-2,2-dimethylbenzopyran (Compound 197)

A mixture of Compound IIao (0.43 g) obtained in Reference Example 41, thionyl chloride (2.0 ml), and dichloromethane (5.0 ml) was heat-refluxed for 40min. The mixture was allowed to stand for cooling, evaporated for removing the solvent, and the residue was dissolved in dry toluene. The residual thionyl chloride was evaporated away under reduced pressure to give a crude acid chloride. After dissolving 4-amino-3,5-dichloropyridine (0.36 g) in THF (4 ml), sodium hydride (0.18 g) was added to the resulting solution under ice-cold conditions, stirred at room temperature for 15 min., and cooled again with ice. A solution of the above crude acid chloride in THF (4 ml) was added dropwise to the mixture under ice-cold conditions, followed by stirring for 1 hour under ice-cold conditions. The resultant was mixed with diluted hydrochloric acid. The thus-precipitated crystals were collected by filtration and washed with water and hexane. The thus-obtained crystals were recrystallized from ethanol/water to give Compound 197 (0.23 g, 33%) as colorless crystals.

Melting point: 174–178° C.

NMR($CDCl_3$, δ, ppm): 1.51(s, 6H), 3.92(s, 3H), 5.77(d, J=10 Hz, 1H), 6.82(d, J=9 Hz, 1H), 6.95(d, J=10 Hz, 1H), 7.29(d, J=9 Hz, 1H), 7.41–7.52(broad s, 1H), 8.58(s, 2H)

MASS (m/e): 378($M^+$).

IR (KBr,$cm^{-1}$): 1660, 1480, 1280.

Elemental analysis: $C_{18}H_{16}Cl_2N_2O_3$

Found (%) C,57.12; H,4.37; N,7.23. Calcd. (%) C,57.01; H,4.25; N,7.39.

EXAMPLE 198

5-(3,5-dichloro-4-pyridylaminocarbonyl)-8-methoxy-2,2-dimethyl-3,4-dihydrobenzopyran (Compound 198)

Using Compound IIap (1.1 g) obtained in Reference Example 42, Compound 198 (0.94 g, 56%) was obtained as colorless crystals according to substantially the same procedure as in Example 197.

Melting point: 155–156° C.

NMR($CDCl_3$, δ, ppm): 1.42(s, 6H), 1.82(t, J=7 Hz, 2H), 3.05(t, J=7 Hz, 2H), 3.91(s, 3H), 6.79(d, J=8 Hz, 1H), 7.28(d, J=8 Hz, 1H), 7.38–7.59(broad s, 1H), 8.56(s, 2H).

MASS (m/e): 380($M^+$)

IR (KBr,$cm^{-1}$): 1680, 1480, 1280

Elemental analysis: $C_{18}H_{18}Cl_2N_2O_3$

Found (%) C,56.71; H,4.84; N,7.22. Calcd. (%) C,56.71; H,4.76; N,7.35.

EXAMPLE 199

7-(3,5-dichloro-4-pyridylaminocarbonyl)-4-methoxy-2,2-dimethyl-3,4-benzodioxole (Compound 199)

Using Compound IIbv (0.50 g) obtained in Reference Example 74, Compound 199 (0.63 g, 77%) was obtained as colorless crystals according to substantially the same procedure as in Example 197.

Melting point: 162–163° C.

NMR($CDCl_3$, δ,ppm): 1.84(s, 6H), 3.97(s,3H), 6.68(d, J=9 Hz, 1H), 7.64(d, J=9 Hz, 1H), 8.56(s, 2H), 8.72(broad s, 1H)

MASS (m/e): 368($M^+$)

IR (KBr,$cm^{-1}$): 1704, 1490, 1446, 1276

Elemental analysis: $C_{16}H_{14}Cl_2N_2O_4$

Found (%) C,52.01; H,3.82; N,7.48. Calcd. (%) C,52.05; H,3.82; N,7.59.

EXAMPLE 200

4-methoxy-2,2-dimethyl-7-(4-pyridylaminocarbonyl)-1,3-benzodioxole (Compound 200)

Using Compound IIbv (0.30 g) obtained in Reference Example 74 and 4-aminopyridine (0.19 mg), Compound 200 (0.32 g, 77%) was obtained as colorless crystals according to substantially the same procedure as in Example 197.

Melting point: 180–181° C.

NMR($CDCl_3$, δ, ppm): 1.85(s, 6H), 3.97(s, 3H), 6.67(d, J=9 Hz, 1H), 7.64–7.57(m, 3H), 8.54–8.52(m, 2H), 8.80 (broad s, 1H)

MASS (m/e): 300 ($M^+$)

IR (KBr,$cm^{-1}$): 1592, 1446, 1280, 1112

EXAMPLE 201

4-(3,5-dichloro-4-pyridyl)aminocarbonyl-7-methoxy-2-(4-methyl-1-piperazinyl)carbonylbenzofuran (Compound 201)

Compound IIbw (0.75 g) obtained in Reference Example 75 was dissolved in DMF (80 ml), and mixed with 1-hydroxybenzotriazole monohydrate (1.06 g), N-ethyl-N=-3-dimethylaminopropylcarbodiimide monohydrochloride (1.51 g), and 1-methylpiperazine (1.09 ml), followed by stirring at room temperature for 8 hours. The resultant was concentrated under reduced pressure and the residue was extracted with chloroform (200 ml). The resultant was washed with a saturated aqueous sodium chloride solution, dried over sodium sulfate, and evaporated under reduced pressure for removing the solvent. The thus-obtained residue was purified by silica gel column chromatography (chloroform/methanol=9/1) to give Compound 201 (0.75 g, 82%) as colorless crystals.

Melting point: 224–225° C.

NMR(DMSO-$d_6$, δ,ppm): 2.12(s, 3H), 2.20–2.37(m, 4H), 3.57–3.70(m, 4H), 4.07(s, 3H), 7.25(d, J=8 Hz, 1H), 7.63(s, 1H), 8.07(d, J=8 Hz, 1H), 8.77(s, 2H), 10.6(s, 1H).

MASS (m/e); 462 ($M^+$)

IR (KBr, $cm^{-1}$): 1294, 1486, 1625, 1652, 3178

Elemental analysis: $C_{21}H_{20}Cl_2N_4O_4.0.2H_2O$

Found (%) C,54.07; H,4.39; N,11.85. Calcd. (%) C,54.02; H,4.40; N,12.00.

EXAMPLE 202

4-(3,5-dichloro-4-pyridyl)aminocarbonyl-7-methoxy-2-[4-(2-hydroxyethyl)-1-piperazinyl]carbonylbenzofuran (Compound 202)

Using Compound IIbw (0.30 g) obtained in Reference Example 75, Compound 202 (0.24 g, 62%) was obtained as colorless crystals according to substantially the same procedure as in Example 197.

Melting point: 164–165° C.

NMR($CDCl_3$, δ, ppm): 2.58–2.62(m, 6H), 3.66(t, J=5 Hz, 3H), 3.83–3.87(m, 4H), 4.09(s, 3H), 6.94(d, J=8 Hz, 1H), 7.75(s, 1H), 7.81(d, J=8 Hz, 1H), 8.58(s, 2H)

MASS (m/e): 492 ($M^+$)

IR(KBr,$cm^{-1}$): 1284, 1490, 1631, 1646, 3318

Elemental analysis: $C_{22}H_{22}Cl_2N_4O_5$

Found (%) C,53.13; H,4.49; N,11.08. Calcd. (%) C,53.17; H,4.54; N,11.27.

EXAMPLE 203

7-(4-carboxy-4-pyridyl)-4-methoxy-spiro[1,3-benzodioxole-2,1=-cyclopentane] (Compound 203)

Compound IIbx (0.28 g) obtained in Reference Example 76 was dissolved in THF (3.0 ml), mixed with a 6 mol/L aqueous NaOH solution (1.4 ml), and stirred at room temperature for 1 hour. The resultant was mixed with water and ethyl acetate to extract the water layer. The water layer was rendered to weakly acidic by adding diluted hydrochloric acid dropwise. The precipitated crystals were collected by filtration and washed with water to give Compound 203 (0.2 g, 76%) as colorless crystals.

Melting point: 187–188° C.

NMR(DMSO-$d_6$, δ, ppm): 1.78–1.83(m, 4H), 2.04–2.11 (m, 4H), 3.86(s, 3H), 6.80(d, J=9 Hz, 1H), 7.25(d, J=9 Hz, 1H), 8.09(d, J=8 Hz, 1H), 8.23(dd, J=2 Hz, 8 Hz, 1H), 9.02(d, J=2 Hz, 1H)

MASS (m/e): 327 ($M^+$)

IR(KBr, $cm^{-1}$): 2933, 1697, 1448, 1284, 1115

Elemental analysis: $C_{18}H_{17}NO_5$

Found (%) C,66.11; H,5.29; N,4.05. Calcd. (%) C,66.05; H,5.23; N,4.28.

EXAMPLE 204

7-(4-carboxyphenyl)-2,2-dimethyl-4-methoxy-1,3-benzodioxole (Compound 204)

Using Compound IIby (0.5 g) obtained in Reference Example 77, Compound 204 (0.25 g, 50%) was obtained as colorless crystals according to substantially the same procedure as in Example 203.

Melting point: 237–239° C.

NMR(DMSO-$d_6$, δ, ppm): 1.70(s, 6H), 3.84(s, 3H), 6.75 (d, J=9 Hz, 1H), 7.13(d, J=9 Hz, 1H), 7.77(d, J=9 Hz, 2H), 7.98(d, J=9 Hz, 2H)

MASS (m/e): 300 ($M^+$)

IR(KBr, $cm^{-1}$): 2940, 1684, 1452, 1290, 1103

Elemental analysis: $C_{17}H_{16}O_5.0.5H_2O$

Found (%) C,65.87; H,5.32; N,0.04. Calcd. (%) C,66.01; H,5.54; N,0.00.

EXAMPLE 205

4-methoxy-7-(4-methyl-3-pyridyl)-spiro[1,3-benzodioxole-2,1'-cyclopentane] (Compound 205)

Compound IIbx (6.9 g) obtained in Reference Example 76, 6-methyl-3-pyridyltrifluoromethanesulfonate (2.3 g), and dichlorobistriphenylphosphine palladium (0.33 g) were dissolved in DMF (23 ml), followed by stirring at 120 EC. for 1 hour. The reaction solution was mixed with an aqueous ammonium fluoride solution and diethyl ether, and then, filtered with Celite. The organic layer was extracted from the resultant, washed with a saturated aqueous sodium chloride solution, dried over magnesium sulfate anhydride, and evaporated under reduced pressure for removing the solvent. The residue was purified by silica gel column chromatography (ethyl acetate/hexane=1/3) to give Compound 205 (1.1 g, 39%) as colorless crystals.

NMR($CDCl_3$, δ, ppm): 1.76–1.97(m, 4H), 2.03–2.25(m, 4H), 2.58(s, 3H), 3.93(s, 3H), 6.60(d, J=9 Hz, 1H), 6.96(d, J=9 Hz, 1H), 7.19(d, J=8 Hz, 1H), 7.85(dd, J=2 Hz ,8 Hz, 1H), 8.82(d, J=2 Hz, 1H)

MASS (m/e): 297 ($M^+$)

EXAMPLE 206

4-[2-(3,5-Dichloro-4-pyridyl)-1-oxoethyl]-2-(4-methyl-1-piperazinylcarbonyl)-7-methoxybenzene (Compound 206)

Compound IIbz (5.8 g) obtained in Reference Example 78 was dissolved in DMF (700 ml), to which were added 1-hydroxybenzotriazole monohydrate (8.4 g), N-ethyl-N'-3-dimethylaminopropylcarbodiimide monohydrochloride (11.6 g) and 1-methylpiperazine (6.8 ml), and stirred at room temperature for 5 hours. The solvent was evaporated under reduced pressure, and the residue was extracted with chloroform, and the organic layer was washed with a saturated saline solution. This was dried over magnesium sulfate, and subjected to distillation under reduced pressure. The resulting residue was purified by silica gel column chromatography (chloroform:methanol=80:1 to 20:1), and then recrystallized from ethanol to obtain Compound 206 (5.5 g, 79%) as colorless crystals.

Melting point: 160–161° C.

NMR ($CDCl_3$, δ, ppm): 2.33(m, 3H), 2.45–2.49(m, 4H), 3.81–3.85(m, 4H), 4.12 (s, 3H), 4.74 (s, 2H), 6.96 (d, J=8.5 Hz, 1H), 7.88 (s, 1H), 8.03 (d, J=8.5 Hz, 1H), 8.54 (s, 2H)

MASS (m/e): 461 ($M^+$)

IR (KBr, $cm^{-1}$): 1207, 1297, 1405, 1583, 1618, 1666

Elemental analysis: $C_{22}H_{21}N_3O_4Cl_2$

Found (%) C,57.16; H,4.65; N,9.03. Calcd. (%) C,57.15; H,4.58; N,9.09.

EXAMPLE 207

4-[2-(3,5-Dichloro-4-pyridyl)-1-oxoethyl]-2-[4-(2-hydroxyethyl)-1-piperazinylcarbonyl]-7-methoxybenzofuran (Compound 207)

Substantially the same procedure as in Example 206 was repeated using Compound IIbz (3.0 g) obtained in Reference Example 78 to give Compound 207 (2.68 g, 69%) as colorless crystals.

Melting point: 155–156° C.

NMR ($CDCl_3$, δ, ppm): 2.58–2.62 (m, 6H), 3.66 (broad, 2H), 3.84 (broad, 4H), 4.12 (s, 3H), 4.74 (s, 2H), 6.96 (d, J=8.5 Hz, 1H), 7.89 (s, 1H), 8.03 (d, J=8.5 Hz, 1H), 8.54 (s, 2H)

MASS(m/e): 491 ($M^+$)

IR (KBr, $cm^{-1}$): 1211, 1284, 1305, 1402, 1577, 1629, 1662

Elemental analysis: $C_{23}H_{23}N_3O_5Cl_2.0.4H_2O$

Found (%) C,55.37; H,4.76; N,8.27. Calcd. (%) C,55.30; H,4.80; N,8.41.

EXAMPLE 208

2-(4-Ethyl-1-piperazinylcarbonyl)-4-[2-(3,5-dichloro-4-pyridyl)-1-oxoethyl]-7-methoxybenzofuran monofumarate (Compound 208)

Substantially the same procedure as in Example 206 was repeated using Compound IIbz (1.5 g) obtained in Reference Example 78 to give Compound 208 (1.5 g, 65%) as colorless crystals.

Melting point: 196–197° C.

NMR ($CDCl_3$, δ, ppm): 1.02 (t, J=7 Hz, 3H), 2.42 (q, J=7 Hz, 2H), 2.47–2.51 (m, 4H), 3.70–3.83 (m, 4H), 4.10 (s, 3H), 4.86 (s, 2H), 6.62 (s, 2H), 7.25 (d, J=8 Hz, 1H), 7.70 (s, 1H), 8.36 (d, J=8 Hz, 1H), 8.68 (s, 2H)

MASS (m/e): 476 ($M^+$)

IR (KBr, $cm^{-1}$): 1216, 1299, 1307, 1403, 1579, 1635, 1654

Elemental analysis: $C_{27}H_{27}N_3O_8Cl_2.0.6H_2O$

Found (%) C,53.80; H,4.71; N,6.88. Calcd. (%) C,53.76; H,4.71; N,6.96.

EXAMPLE 209

2-(4-Isopropyl-1-piperazinylcarbonyl)-4-[2-(3,5-dichloro-4-pyridyl)-1-oxoethyl]-7-methoxybenzofuran monofumarate (Compound 209)

Compound IIcb (0.80 g) obtained in Reference Example 80 was dissolved in anhydrous DMF (40 ml), to which were added 2-bromopropane (1.67 ml), triethylamine (2.48 ml) and potassium iodide (0.80 mg), and stirred at 100° C. for 2 hours. The solvent was evaporated under reduced pressure, and the residue was extracted with chloroform, washed with a saturated saline solution and then dried over sodium sulfate. The solvent was evaporated. The resulting residue was purified by silica gel column chromatography (3% triethylamine-ethyl acetate), and then dissolved in chloroform, to which was added a methanol solution of fumaric acid (0.3 g) and stirred. The solvent was again evaporated. The resulting solid was recrystallized from ethanol to obtain Compound 209 (0.50 g, 37%) as colorless crystals.

Melting point: 195–196° C.

NMR (DMSO-$d_6$, δ, ppm): 0.97(d, J=6.5 Hz, 6H), 2.49–2.50(m, 4H), 2.67–2.75(m, 1H), 3.60–3.70(m, 4H), 4.09(s, 3H), 4.85(s, 2H), 6.60(s, 2H), 7.23(d, J=8.5 Hz, 1H), 7.68(s, 1H), 8.35(d, J=8.5 Hz, 1H), 8.67(s, 2H)

MASS(m/e): 489 ($M^+$)

IR (KBr, $cm^{-1}$): 1180, 1294, 1305, 1405, 1579, 1633, 1656

Elemental analysis: $C_{28}H_{29}N_3O_8Cl_2.0.4H_2O$

Found (%) C,54.79; H,4.92; N,6.81. Calcd. (%) C,54.80; H,4.89; N,6.84.

EXAMPLE 210

2-(4-Ethoxyethyl-1-piperazinylcarbonyl)-4-[2-(3,5-dichloro-4-pyridyl)-1-oxoethyl]-7-methoxybenzofuran monofumarate (Compound 210)

Substantially the same procedure as in Example 209 was repeated using Compound IIcb (0.70 g) obtained in Reference Example 80 to give Compound 210 (0.34 g, 34%) as colorless crystals.

Melting point: 184–185° C.

NMR (DMSO-$d_6$, δ, ppm): 1.07(t, J=7 Hz, 3H), 3.35–3.65 (m, 12H), 4.08(s, 3H), 4.84(s, 2H), 6.60(s, 2H), 7.23(d, J=8.5 Hz, 1H), 7.67(s, 1H), 8.34(d, 1H, J=8.5 Hz), 8.66(s, 2H)

MASS(m/e): 519 ($M^+$)

IR (KBr, $cm^{-1}$): 1176, 1267, 1403, 1581, 1629, 1668

Elemental analysis: $C_{29}H_{31}N_3O_9Cl_2$

Found (%) C,54.98; H,4.89; N,6.62. Calcd. (%) C,54.73; H,4.91; N,6.60.

EXAMPLE 211

4-[2-(3,5-Dichloro-4-pyridyl)ethyl]-2-(4-methyl-1-piperazinylcarbonyl)-7-methoxybenzofuran monofumarate (Compound 211)

Substantially the same procedure as in Example 206 was repeated using Compound IIca (1.0 g) obtained in Reference Example 79 to give Compound 211 (1.38 g, 90%) as colorless crystals.

Melting point: 186–187° C.

NMR (DMSO-$d_6$, δ, ppm): 2.24(s, 3H), 2.42–2.49(m, 4H), 3.04–3.08(m, 2H), 3.15–3.19(m, 2H), 3.64–3.70(m, 4H), 3.91(s, 3H), 6.61(s, 2H), 6.94(d, J=8 Hz, 1H), 6.99(d, J=8 Hz, 1H), 7.32(s, 1H), 8.57(s, 2H)

MASS(m/e): 447 ($M^+$)

IR (KBr, $cm^{-1}$): 977, 1172, 1272, 1295, 1438, 1560, 1575, 1640

Elemental analysis: $C_{26}H_{27}N_3O_7Cl_2.0.3H_2O$

Found (%) C,54.86; H,4.85; N,7.23. Calcd. (%) C,54.80; H,4.88; N,7.37.

EXAMPLE 212

4-[2-(3,5-Dichloro-4-pyridyl)ethyl]-2-[4-(2-hydroxyethyl)-1-piperazinylcarbonyl]-7-methoxybenzofuran 0.5 fumarate (Compound 212)

Substantially the same procedure as in Example 206 was repeated using Compound IIca (0.72 g) obtained in Reference Example 79 to give Compound 212 (0.89 g, 84%) as colorless crystals.

Melting point: 184–185° C.

NMR (DMSO-$d_6$, δ, ppm): 2.42–2.49(m, 2H), 3.03–3.07 (m, 2H), 3.14–3.18(m, 2H), 3.40–3.67(m, 10H), 3.91(s, 3H), 6.60(s, 2H), 6.94(d, J=8 Hz, 1H), 6.99(d, J=8 Hz, 1H), 7.31(s, 1H), 8.56(s, 2H)

MASS(m/e): 477 ($M^+$)

IR (KBr, $cm^{-1}$): 1091, 1292, 1508, 1652

Elemental analysis: $C_{25}H_{27}N_3O_6Cl_2$

Found (%) C,56.09; H,5.14; N,7.78. Calcd. (%) C,55.98; H,5.07; N,7.83.

EXAMPLE 213

N-(3,5-Dichloropyridin-4-yl)-2-(4-morpholino) butyryl-7methoxybenzofuran-4-carboxamide (Compound 213)

Step A: N-(3,5-dichloropyridin-4-yl)-2-[4-(methylsulfonyloxy)]butyryl-7-methoxybenzofuran-4-carboxamide (Compound 213a)

Compound 215 (1.34 g) obtained in Example 215 was dissolved in anhydrous pyridine (10 ml), to which was dropwise added methanesulfonyl chloride (0.30 ml) at 0° C., and stirred at room temperature for 3 hours. Water was added to the reaction mixture, which was then extracted with ethyl acetate. The organic layer was washed with an aqueous dilute hydrochloric acid solution and a saturated saline solution, and dried over anhydrous magnesium sulfate, and the solvent was evaporated under reduced pressure to obtain crude crystals (1.59 g, quantitative) of Compound 213a.

NMR (DMSO-$d_6$, δ, ppm): 1.99–2.10(m, 2H), 3.13–3.18 (m, 2H), 3.18(s, 3H), 4.09(s, 3H), 4.28(t, J=6 Hz, 2H), 7.34(d, J=8 Hz, 1H), 8.11(s, 1H), 8.12(d, J=8 Hz, 1i), 8.78(s, 2H), 10.69(broad s, 1H)

MASS(m/e): 500 ($M^+$)

Step B: Compound 213

Compound 213a obtained in Step A was dissolved in DMF (15 ml), to which was added morpholine (0.41 ml) at room temperature, and heated at 80° C. for 4 hours. After being allowed to stand for cooling to the room temperature, water was added thereto, which was then extracted with ethyl acetate. The organic layer was washed with a saturated saline solution, and dried over anhydrous magnesium sulfate, and the solvent was evaporated under reduced pressure. The residue was purified by silica gel column chromatography (chloroform:methanol=30:1) to obtain Compound 213(0.91 g, 58%) as colorless crystals.

Melting point: 176.5–177.5° C.

NMR (DMSO-$d_6$, δ, ppm): 1.84(t, J=7 Hz, 2H), 2.28–2.34 (m, 6H), 2.97(t, J=7 Hz, 2H), 3.33–3.40(m, 4H), 4.08(s, 3H), 7.32(d, J=9 Hz, 1H), 8.07(s, 1H), 8.10(d, J=9 Hz, 1H), 8.78(s, 2H), 10.67(broad s, 1H)

MASS (m/e): 491 ($M^+$)

IR (KBr, $cm^{-1}$): 1283, 1483, 1670, 1683

Elemental analysis: $C_{23}H_{23}Cl_2N_3O_5$

Found (%) C,56.03; H,4.75; N,8.38. Calcd. (%) C,56.11; H,4.71; N,8.53.

EXAMPLE 214

N-(3,5-dichloropyridin-4-yl)-2-[4-(4-methyl-1-piperazinyl)]-butyryl-7-methoxybenzofuran-4-carboxamide (Compound 214)

Substantially the same procedure as in Example 213 was repeated using Compound 215 (1.36 g) obtained in Example 215 to give Compound 214 (0.84 g, 51%) as colorless crystals.

Melting point: 155.0–156.5° C.

NMR (DMSO-$d_6$, δ, ppm): 1.80–1.84(m, 2H), 2.03(s, 3H), 2.03–2.12(m, 2H), 2.27–2.32(m, 4H), 2.49–2.50(m, 4H), 2.91–2.95(m, 2H), 4.08(s, 3H), 7.30(d, J=8 Hz, 1H), 8.03(s, 1H), 8.08(d, J=8 Hz, 1H), 8.76(s, 2H), 10.62(broad s, 1H)

MASS(m/e): 504 ($M^+$)

IR (KBr, $cm^{-1}$): 1285, 1484, 1664, 1681

Elemental analysis: $C_{24}H_{26}Cl_2N_4O_4.0.3H_2O$

Found (%) C,56.51; H,5.22; N,10.69. Calcd. (%) C,56.43; H,5.24; N,10.96.

EXAMPLE 215

N-(3,5-dichloropyridin-4-yl)-2-(4-hydroxy)butyryl-7-methoxybenzofuran-4-carboxamide (Compound 215)

A THF solution (500 ml) of N-(3,5-dichloropyridin-4-yl)-7-methoxybenzofuran-4-carboxamide (10.0 g) was cooled to −78° C. in an argon atmosphere, to which were dropwise added N,N,N',N'-tetramethylethylenediamine (13.43 ml) and n-butyl lithium (1.57 M hexane solution, 56.67 ml), and stirred for 1.5 hours at the same temperature. To the reaction mixture was dropwise added γ-butyrolactone (Compound IV, 11.40 ml), and stirred at the same temperature for 2 hours. This was heated to be at 0° C., and an aqueous solution of ammonium chloride was added thereto to stop the reaction, which was then extracted with ethyl acetate. The organic layer was washed with a saturated saline solution, and dried over anhydrous magnesium sulfate, and the solvent was evaporated under reduced pressure. The residue was purified by silica gel column chromatography (hexane:ethyl acetate=1:2) to obtain Compound 215 (6.34 g, 51%) as colorless crystals.

Melting point: 210.0–211.0° C.

NMR (DMSO-$d_6$, δ, ppm): 1.78(tt, J=7, 7 Hz, 2H), 3.03(t, J=7 Hz, 2H), 3.45(dt, J=5, 7 Hz, 2H), 4.08(s, 3H), 4.57(t, J=5 Hz, 1H), 7.32(d, J=8 Hz, 1H), 8.09(s, 1H), 8.10(d, J=8 Hz, 1H), 8.79(s, 2H), 10.68(broad s, 1H)

MASS(m/e): 422 ($M^+$)

IR (KBr, $cm^{-1}$): 1282, 1486, 1678

Elemental analysis: $C_{19}H_{16}Cl_2N_2O_5$

Found (%) C,53.91; H,3.83; N,6.54. Calcd. (%) C,53.91; H,3.81; N,6.61.

EXAMPLE 216

N-(2-morpholinoethyl)-4-[2-(3,5-dichloropyridin-4-yl)-1-oxo]ethyl-7-methoxybenzofuran-2-carboxamide (Compound 216)

N,N-diisopropylamine (0.70 ml) was dissolved in anhydrous THF (15 ml), to which was dropwise added n-butyl lithium (1.63 M hexane solution, 2.8 ml) at −78° C., and stirred for 5 minutes at 0° C. This was again cooled to −78° C., to which was added 3,5-dichloropicoline (0.56 g, see Step 1–2 in Reference Example 81), and stirred for 20 minutes at 0° C. Then, a THF (5 ml) solution of Compound IIcd (0.40 g) obtained in Reference Example 82 was dropwise added to this, and directly stirred for 30 minutes at 0° C. A saturated saline solution was added to this to stop the reaction, which was then extracted with methylene chloride. The extract was washed with a saturated saline solution, and dried over potassium carbonate, and the solvent was evaporated under reduced pressure. The residue was purified by silica gel column chromatography (chloroform:methanol=50:1), then suspended in ethyl ether, and taken out through filtration to obtain Compound 216 (300 mg, 53%) as colorless crystals.

Melting point: 183–184° C.

NMR ($CDCl_3$, δ, ppm): 2.50–2.54(m, 4H), 2.61(t, J=6 Hz, 2H), 3.58(q, J=6 Hz, 2H), 3.73–3.77(m, 4H), 4.14(s, 3H), 4.73(s, 2H), 7.00(d, J=8 Hz, 1H), 7.13(broad s, 1H), 8.03(d, J=8 Hz, 1H), 8.12(s, 1H), 8.54(s, 2H)

MASS(m/e): 491 ($M^+$)

IR (KBr, $cm^{-1}$): 1203, 1303, 1402, 1575, 1660, 1677

Elemental analysis: $C_{23}H_{23}N_3O_5Cl_2$

Found (%) C,56.01; H,4.71; N,8.31. Calcd. (%) C,56.11; H,4.71; N,8.53.

EXAMPLE 217

N-(2-piperidinoethyl)-4-[2-(3,5-dichloropyridin-4-yl)-1-oxo]ethyl-7-methoxybenzofuran-2-carboxamide (Compound 217)

Compound Icc (0.30 g) obtained in Reference Example 81 was dissolved in DMF (50 ml), to which were added 1-hydroxybenzotriazole monohydrate (0.48 g), N-ethyl-N'-3-dimethylaminopropylcarbodiimide monohydrochloride (0.68 g) and 1-(2-hydroxyethyl)piperidine (0.87 ml) were added, and stirred for 18 hours at room temperature. The solvent was evaporated under reduced pressure, and the residue was extracted with chloroform. The extract was washed with a saturated saline solution, and dried over sodium sulfate. The solvent was evaporated under reduced pressure, and the residue was purified through partitioning TLC (chloroform:methanol=9:1), and recrystallized from chloroform-hexane to obtain Compound 217 (0.14 g, 16%) as colorless crystals.

Melting point: 168–169° C.

NMR ($CDCl_3$, δ, ppm): 1.47–1.74(m, 6H), 2.47(broad s, 4H), 2.58(t, J=6 Hz, 2H), 3.57(q, J=6 Hz, 2H), 4.14(s, 3H), 4.73(s, 2H), 6.98(d, J=8.5 Hz, 1H), 7.30(broad, 1H), 8.02(d, J=8.5 Hz, 1H), 8.11(s, 1H), 8.54(s, 2H)

MASS(m/e): 489 ($M^+$)

IR (KBr, $cm^{-1}$): 1201, 1301, 1575, 1660, 1677

Elemental analysis: $C_{24}H_{25}N_3O_4Cl_2.0.3H_2O$

Found (%) C,58.07; H,5.18; N,8.40. Calcd. (%) C,58.14; H,5.20; N,8.48.

EXAMPLE 218

N-[3-(4-methyl-1-piperazinyl)propyl]-4-[2-(3,5-dichloropyridin-4-yl)-1-oxo]ethyl-7-methoxybenzofuran-2-carboxamide dihydrochloride (Compound 218)

Substantially the same procedure as in Example 217 was repeated using Compound IIcc (0.30 g) obtained in Reference Example 81 to give Compound 218 (0.18 g, 39%) as colorless crystals.

Melting point: 199–200° C.

NMR (DMSO-$d_6$, δ, ppm): 1.63(m, 2H), 2.17(s, 3H), 2.84–3.30(m, 12H), 3.77(s, 3H), 4.53(s, 2H), 6.94(d, J=8 Hz, 1H), 7.68(s, 1H), 8.03(d, J=8.5 Hz, 1H)

MASS(m/e): 518 ($M^+$)

IR (KBr, $cm^{-1}$): 1207, 1307, 1407, 1573, 1618, 1658

Elemental analysis: $C_{25}H_{30}N_4O_4Cl_4.2.0H_2O$

Found (%) C,47.85; H,5.46; N,8.67. Calcd. (%) C,47.79; H,5.43; N,8.92.

EXAMPLE 219

N-Cyclohexyl-7-methoxy-4-morpholino-methylbenzofuran-2-carboxamide (Compound 219)

A mixture of the starting material, 7-Methoxybenzofuran-2-carboxylic Acid (5.0 g), oxalyl chloride (3.4 ml) and dichloromethane (75 ml) was stirred at room temperature for 3 hours. The solvent was distilled off under reduced pressure to give a crude acid chloride.

A mixture of this crude acid chloride, triethylamine (5.44 ml) and cyclohexylamine (3.57 ml) was stirred at room temperature for 1 hour. Silica Gel (3 g) was added and the mixture was stirred for 3 hours, then it was filtered off. The solvent was distilled off under reduced pressure to give compound 219a (6.51 g, 92%) as a white solid.

NMR($CDCl_3$, δ, ppm): 1.17–1.44 (m, 6H), 1.69–1.81(m, 4H), 2.01–2.05(m,1H), 4.02(s, 3H), 6.59(m, 1H), 6.90(dd, J=1.5 Hz, 8 Hz, 1H), 7.20(t, J=8 Hz, 1H), 7.25(dd, J=1 Hz, 8 Hz, 1H), 7.45(s, 1H)

MASS(m/e): 273($M^+$)

A mixture of compound 219a (200 mg), dichloromethyl methyl Ether (132 ml) and titanium tetrachloride (241 ml) was stirred at room temperature for 5 hours. Sodium sulfate hydrate was added to quench, then the reaction mixture was filtered by silica gel short column and eluted with dicholomethane. The solvent was distilled off under pressure to give compound 219b (219 mg) as a white solid.

NMR($CDCl_3$, δ, ppm): 1.22–1.46 (m, 6H), 1.65–1.81(m, 4H), 2.02–2.07(m,1H), 4.12(s, 3H), 6.54(m, 1H), 7.01(d, J=8 Hz, 1H), 7.74(t, J=8 Hz, 1H), 8.15(s, 1H), 10.07(s, 1H)

MASS(m/e): 301($M^+$)

A mixture of compound 219b (110 mg), morpholine (64 ml), acetic acid (10 ml) and sodium triacetoxyborohydride (232 mg) was stirred at room temperature for 24 hours. 1 mol/L NaOH solution was added to quench the reaction, then the organic layer was washed with 1 mol/L NaOH solution and brine. After drying over sodium sulfate dehydrate, the solvent was distilled off under reduced pressure to give compound 219 (85 mg, 63%) as a white solid.

NMR($CDCl_3$, δ, ppm): 1.23–1.46 (m, 6H), 1.65–1.81(m, 4H), 2.02–2.09(m,1H), 2.41–2.44(m, 4H), 3.65(s, 2H), 3.66–3.72(m, 4H), 4.01(s, 3H), 6.55(m, 1H), 6.81(d, J=8 Hz, 1H), 7.09(t, J=8 Hz, 1H), 7.69(s, 1H)

MASS(m/e): 372($M^+$)

EXAMPLE 220

N-Cyclohexyl-4-methylaminomethyl-7-methoxybenzofuran-2-carboxamide (Compound 220)

Substantially the same procedure as in Example 219 was repeated using compound 219b obtained in Example 219 and methylamine hydrochloride to give compound 220 as a white solid.

Rf($CHCl_3$:MeOH=9:1); 0.14

EXAMPLE 221

4-Ethylaminomethyl-N-cyclohexyl-7-methoxybenzofuran-2-carboxamide (Compound 221)

Substantially the same procedure as in Example 219 was repeated using compound 219b obtained in Example 219 and ethylamine hydrochloride to give compound 221 as a white solid.

Rf($CHCl_3$:MeOH=9:1); 0.20

EXAMPLE 222

N-Cyclohexyl-4-propylaminomethyl-7-methoxybenzofuran-2-carboxamide (Compound 222)

Substantially the same procedure as in Example 219 was repeated using compound 219b obtained in Example 219 and n-propylamine to give compound 222 as a white solid.

Rf($CHCl_3$:MeOH=9:1); 0.26

EXAMPLE 223

N-Cyclohexyl-4-(2-propylaminomethyl)-7-methoxybenzofuran-2-carboxamide (Compound 223)

Substantially the same procedure as in Example 219 was repeated using compound 219b obtained in Example 219 and 2-propylamine to give compound 223 as a white solid.

Rf($CHCl_3$:MeOH=9:1); 0.26

EXAMPLE 224

N-Cyclohexyl-4-butylaminomethyl-7-methoxybenzofuran-2-carboxamide (Compound 224)

Substantially the same procedure as in Example 219 was repeated using compound 219b obtained in Example 219 and n-butylamine to give compound 224 as a white solid.

Rf($CHCl_3$:MeOH=9:1); 0.34

EXAMPLE 225

N-Cyclohexyl-4-cyclobutylaminomethyl-7-methoxybenzofuran-2-carboxamide (Compound 225)

Substantially the same procedure as in Example 219 was repeated using compound 219b obtained in Example 219 and cyclobutylamine to give compound 225 as a white solid.

Rf($CHCl_3$:MeOH=9:1); 0.17

EXAMPLE 226

N-Cyclohexyl-4-cyclopentylaminomethyl-7-methoxybenzofuran-2-carboxamide (Compound 226)

Substantially the same procedure as in Example 219 was repeated using compound 219b obtained in Example 219 and cyclopentylamine to give compound 226 as a white solid.

Rf($CHCl_3$:MeOH=9:1); 0.34

EXAMPLE 227

N-Cyclohexyl-4-cyclohexylaminomethyl-7-methoxybenzofuran-2-carboxamide (Compound 227)

Substantially the same procedure as in Example 219 was repeated using compound 219b obtained in Example 219 and cyclohexylamine to give compound 227 as a white solid.

Rf($CHCl_3$:MeOH=9:1); 0.45

EXAMPLE 228

4-Cyclooctylaminomethyl-N-cyclohexyl-7-methoxybenzofuran-2-carboxamide (Compound 228)

Substantially the same procedure as in Example 219 was repeated using compound 219b obtained in Example 219 and cyclooctylamine to give compound 228 as a white solid.

Rf($CHCl_3$:MeOH=9:1); 0.29

EXAMPLE 229

N-Cyclohexyl-4-(2,3-dimethylcyclohexyl-aminomethyl)-7-methoxybenzofuran-2-carboxamide (Compound 229)

Substantially the same procedure as in Example 219 was repeated using compound 219b obtained in Example 219 and 2,3-dimethylcyclohexylamine to give compound 229 as a white solid.

Rf($CHCl_3$:MeOH=9:1); 0.31

EXAMPLE 230

N-Cyclohexyl-4-benzylaminomethyl-7-methoxybenzofuran-2-carboxamide (Compound 230)

Substantially the same procedure as in Example 219 was repeated using compound 219b obtained in Example 219 and benzylamine to give compound 230 as a white solid.

Rf($CHCl_3$:MeOH=9:1); 0.63

EXAMPLE 231

N-Cyclohexyl-4-piperidinomethyl-7-methoxybenzofuran-2-carboxamide (Compound 231)

Substantially the same procedure as in Example 219 was repeated using compound 219b obtained in Example 219 and piperidine to give compound 231 as a white solid.

Rf($CHCl_3$:MeOH=9:1); 0.57

EXAMPLE 232

N-Cyclohexyl-4-(1-pyrrolidinylmethyl)-7-methoxybenzofuran-2-carboxamide (Compound 232)

Substantially the same procedure as in Example 219 was repeated using compound 219b obtained in Example 219 and pyrrolidine to give compound 232 as a white solid.

Rf($CHCl_3$:MeOH=9:1); 0.23

EXAMPLE 233

N-Cyclohexyl-4-(4-methyl-1-piperazinylmethyl)-7-methoxybenzofuran-2-carboxamide (Compound 233)

Substantially the same procedure as in Example 219 was repeated using compound 219b obtained in Example 219 and 1-methylpiperazine to give compound 233 as a white solid.

Rf($CHCl_3$:MeOH=9:1); 0.23

EXAMPLE 234

N-Cyclohexyl-4-(2-phenylethylaminomethyl)-7-methoxybenzofuran-2-carboxamide (Compound 234)

Substantially the same procedure as in Example 219 was repeated using compound 219b obtained in Example 219 and 2-phenethylamine to give compound 234 as a white solid.

Rf($CHCl_3$:MeOH=9:1); 0.51

EXAMPLE 235

N-Cyclohexyl-4-[1-(S)-phenylethylamino-methyl]-7-methoxybenzofuran-2-carboxamide (Compound 235)

Substantially the same procedure as in Example 219 was repeated using compound 219b obtained in Example 219 and 1-(S)-phenethylamine to give compound 235 as a white solid.

Rf($CHCl_3$:MeOH=9:1); 0.57

EXAMPLE 236

N-Cyclohexyl-4-(3-pheylpropylaminomethyl)-7-methoxybenzofuran-2-carboxamide (Compound 236)

Substantially the same procedure as in Example 219 was repeated using compound 219b obtained in Example 219 and 3-phenylpropylamine to give compound 236 as a white solid.

Rf($CHCl_3$:MeOH=9:1); 0.54

EXAMPLE 237

N-Cyclohexyl-4-[2-(2-pyridyl)ethylaminomethyl]-7-methoxybenzofuran-2-carboxamide (Compound 237)

Substantially the same procedure as in Example 219 was repeated using compound 219b obtained in Example 219 and 2-(2-pyridyl)amine to give compound 237 as a white solid.

Rf($CHCl_3$:MeOH=9:1); 0.29

EXAMPLE 238

N-Cyclohexyl-7-methoxy-4-(2-morpholinoethylaminomethyl)-benzofuran-2-carboxamide (Compound 238)

Substantially the same procedure as in Example 219 was repeated using compound 219b obtained in Example 219 and 2-morpholinoethylamine to give compound 238 as a white solid.

Rf($CHCl_3$:MeOH=9:1); 0.34

EXAMPLE 239

4-Cyclobutylaminomethyl-N-(3-phenylpropyl)-7-methoxybenzofuran-2-carboxamide (Compound 239)

Substantially the same procedure as in Example 219 was repeated using a starting material, 7-methoxybenzofuran-2-carboxylic acid, and 3-phenylpropylamine to give N-(3-phenylpropyl)-7-methoxybenzofuran-2-carboxamide (Compound 239a). Successively, it was formylated to give N-(3-phenylpropyl)-4-formyl-7-methoxybenzofuran-2-carboxamide (Compound 239b), then compound 239b was reacted with cyclobutylamine to give compound 239 as a white solid.

Rf($CHCl_3$:MeOH=9:1); 0.25

EXAMPLE 240

4-Cyclooctylaminomethyl-N-(3-phenylpropyl)-7-methoxybenzofuran-2-carboxamide (Compound 240)

Substantially the same procedure as in Example 239 was repeated using compound 239b obtained in Example 239 and cyclooctylamine to give compound 240 as a white solid.

Rf($CHCl_3$:MeOH=9:1); 0.33

EXAMPLE 241

4-(2,3-dimethylcyclohexylaminomethyl)-N-(3-phenylpropyl)-7-methoxybenzofuran-2-carboxamide (Compound 241)

Substantially the same procedure as in Example 239 was repeated using compound 239b obtained in Example 239 and 2,3-dimethylcyclohexylamine to give compound 241 as a white solid.

Rf($CHCl_3$:MeOH=9:1); 0.33

EXAMPLE 242

N-(3-Phenylpropyl)-4-(4-methyl-1-piperazinyl)-7-methoxybenzofuran-2-carboxamide (Compound 242)

Substantially the same procedure as in Example 239 was repeated using compound 239b obtained in Example 239 and 1-methylpiperazine to give compound 242 as a white solid.

Rf($CHCl_3$:MeOH=9:1); 0.50

EXAMPLE 243

4-(1-pyrrolidinylmethyl)-N-(3-phenylpropyl)-7-methoxybenzofuran-2-carboxamide (Compound 243)

Substantially the same procedure as in Example 239 was repeated using compound 239b obtained in Example 239 and pyrrolidine to give compound 243 as a white solid.

Rf($CHCl_3$:MeOH=9:1); 0.19

EXAMPLE 244

4-(2-Phenylethylaminomethyl)-N-(3-phenylpropyl)-7-methoxybenzofuran-2-carboxamide (Compound 244)

Substantially the same procedure as in Example 239 was repeated using compound 239b obtained in Example 239 and 2-phenetylamine to give compound 244 as a white solid.

Rf($CHCl_3$:MeOH=9:1); 0.56

EXAMPLE 245

4-[1-(S)-Phenylethyiaminomethyl]-N-(3-phenylpropyl)-7-methoxybenzofuran-2-carboxamide (Compound 245)

Substantially the same procedure as in Example 239 was repeated using compound 239b obtained in Example 239 and 1-(S)-phenetylamine to give compound 245 as a white solid.

Rf($CHCl_3$:MeOH=9:1); 0.61

EXAMPLE 246

N-(3-Phenylpropyl)-4-(3-phenylpropylaminomethyl)-7-methoxybenzofuran-2-carboxamide (Compound 246)

Substantially the same procedure as in Example 239 was repeated using compound 239b obtained in Example 239 and 3-phenylpropylamine to give compound 246 as a white solid.

Rf($CHCl_3$:MeOH=9:1); 0.53

EXAMPLE 247

4-[2-(2-Pyridyl)ethylaminomethyl]-N-(3-phenylpropyl)-7-methoxybenzofuran-2-carboxamide (Compound 247)

Substantially the same procedure as in Example 239 was repeated using compound 239b obtained in Example 239 and 2-(2-pyridyl)ethylamine to give compound 247 as a white solid.

Rf($CHCl_3$:MeOH=9:1); 0.42

EXAMPLE 248

7-methoxy-N-(3-phenylpropyl)-4-(2-morpholinoethylaminomethyl)benzofuran-2-carboxamide (Compound 248)

Substantially the same procedure as in Example 239 was repeated using compound 239b obtained in Example 239 and 2-morpholinoethylamine to give compound 248 as a white solid.

Rf($CHCl_3$:MeOH=9:1); 0.39

EXAMPLE 249

N-Phenyl-4-methylaminomethyl-7-methoxybenzofuran-2-carboxamide (Compound 249)

Substantially the same procedure as in Example 219 was repeated using a starting material, 7-methoxybenzofuran-2-carboxylic acid, and aniline to give N-phenyl-7-methoxybenzofuran-2-carboxamide (Compound 249a). Successively, it was formylated to give N-phenyl-4-formyl-7-methoxybenzofuran-2-carboxamide (Compound 249b), then compound 249b was reacted with methylamine hydrochloride to give compound 249 as a white solid.

Rf($CHCl_3$:MeOH=9:1); 0.18

EXAMPLE 250

4-Ethylaminomethyl-N-phenyl-7-methoxybenzofuran-2-carboxamide (Compound 250)

Substantially the same procedure as in Example 249 was repeated using compound 249b obtained in Example 249 and ethylamine hydrochloride to give compound 250 as a white solid.

Rf($CHCl_3$:MeOH=9:1); 0.21

EXAMPLE 251

N-Phenyl-4-propylaminomethyl-7-methoxybenzofuran-2-carboxamide (Compound 251)

Substantially the same procedure as in Example 249 was repeated using compound 249b obtained in Example 249 and n-propylamine to give compound 251 as a white solid.

Rf($CHCl_3$:MeOH=9:1); 0.29

EXAMPLE 252

N-Phenyl-4-(2-propylaminomethyl)-7-methoxybenzofuran-2-carboxamide (Compound 252)

Substantially the same procedure as in Example 249 was repeated using compound 249b obtained in Example 249 and 2-propylamine to give compound 252 as a white solid.

Rf($CHCl_3$:MeOH=9:1); 0.26

EXAMPLE 253

N-Phenyl-4-butylaminomethyl-7-methoxybenzofuran-2-carboxamide (Compound 253)

Substantially the same procedure as in Example 249 was repeated using compound 249b obtained in Example 249 and n-butylamine to give compound 253 as a white solid.

Rf($CHCl_3$:MeOH=9:1); 0.44

EXAMPLE 254

4-Cyclobutylaminomethyl-N-phenyl-7-methoxybenzofuran-2-carboxamide (Compound 254)

Substantially the same procedure as in Example 249 was repeated using compound 249b obtained in Example 249 and cyclobutylamine to give compound 254 as a white solid.

Rf($CHCl_3$:MeOH=9:1); 0.28

EXAMPLE 255

4-Cyclopentylaminomethyl-N-phenyl-7-methoxybenzofuran-2-carboxamide (Compound 255)

Substantially the same procedure as in Example 249 was repeated using compound 249b obtained in Example 249 and cyclopentylamine to give compound 255 as a white solid.

Rf($CHCl_3$:MeOH=9:1); 0.44

EXAMPLE 256

4-Cyclohexylaminomethyl-N-phenyl-7-methoxybenzofuran-2-carboxamide (Compound 256)

Substantially the same procedure as in Example 249 was repeated using compound 249b obtained in Example 249 and cyclohexylamine to give compound 256 as a white solid.

Rf($CHCl_3$:MeOH=9:1); 0.50

EXAMPLE 257

4-Cyclooctylaminomethyl-N-phenyl-7-methoxybenzofuran-2-carboxamide (Compound 257)

Substantially the same procedure as in Example 249 was repeated using compound 249b obtained in Example 249 and cyclooctylamine to give compound 257 as a white solid.

Rf($CHCl_3$:MeOH=9:1); 0.28

EXAMPLE 258

4-(2,3-Dimethylcyclohexylaminomethyl)-N-phenyl-7-methoxybenzofuran-2-carboxamide (Compound 258)

Substantially the same procedure as in Example 249 was repeated using compound 249b obtained in Example 249 and 2,3-dimethylcyclohexylamine to give compound 258 as a white solid.

Rf($CHCl_3$:MeOH=9:1); 0.41

EXAMPLE 259

N-Phenyl-4-benzylaminomethyl-7-methoxybenzofuran-2-carboxamide (Compound 259)

Substantially the same procedure as in Example 249 was repeated using compound 249b obtained in Example 249 and benzylamine to give compound 259 as a white solid.

Rf($CHCl_3$:MeOH=9:1); 0.64

EXAMPLE 260

4-Piperidinomethyl-N-phenyl-7-methoxybenzofuran-2-carboxamide (Compound 260)

Substantially the same procedure as in Example 249 was repeated using compound 249b obtained in Example 249 and piperidine to give compound 260 as a white solid.

Rf($CHCl_3$:MeOH=9:1); 0.61

EXAMPLE 261

N-Phenyl-7-methoxy-4-morpholinomethyl-benzofuran-2-carboxamide monohydrochloride (Compound 261)

Substantially the same procedure as in Example 249 was repeated using compound 249b obtained in Example 249 and morpholine to give compound 261 as a white solid.

NMR(DMSO-$d_6$, δ, ppm): 2.85–2.95 (m, 2H), 3.30–3.35 (m, 2H), 3.90–3.95(m,2H), 4.08(s, 3H), 4.26–4.38 (m, 4H), 7.06(d, J=8 Hz, 1H), 7.21(t, J=7.6 Hz, 1H), 7.41(t-like, J=7.6, 8 Hz, 2H), 7.71(d, J=7.5 Hz, 2H), 7.97(d, J=8 Hz, 1H), 8.43(s, 1)

MASS(m/e): 366($M^+$)

Rf($CHCl_3$:MeOH=9:1); 0.39

Elemental analysis: $C_{21}H_{23}N_2O_4Cl.1.2H_2O$

Found (%) C,59.44; H,6.13; N,6.42. Calcd. (%) C,59.42; H,6.03; N,6.60.

EXAMPLE 262

4-(1-Pyrrolidinylmethyl)-N-phenyl-7-methoxybenzofuran-2-carboxamide (Compound 262)

Substantially the same procedure as in Example 249 was repeated using compound 249b obtained in Example 249 and pyrrolidine to give compound 262 as a white solid.

Rf($CHCl_3$:MeOH=9:1); 0.14

EXAMPLE 263

N-Phenyl-4-(4-methyl-1-piperazinylmethyl)-7-methoxybenzofuran-2-carboxamide (Compound 263)

Substantially the same procedure as in Example 249 was repeated using compound 249b obtained in Example 249 and 1-methylpiperazine to give compound 263 as a white solid.

Rf($CHCl_3$:MeOH=9:1); 0.61

EXAMPLE 264

N-Phenyl-4-(2-phenylethylaminomethyl)-7-methoxybenzofuran-2-carboxamide (Compound 264)

Substantially the same procedure as in Example 249 was repeated using compound 249b obtained in Example 249 and 2-phenetylamine to give compound 264 as a white solid.

Rf($CHCl_3$:MeOH=9:1); 0.57

EXAMPLE 265

N-Phenyl-4-[1-(S)-phenylethylaminomethyl)-7-methoxybenzofuran-2-carboxamide (Compound 265)

Substantially the same procedure as in Example 249 was repeated using compound 249b obtained in Example 249 and 1-(S)-phenetylamine to give compound 265 as a white solid.

Rf($CHCl_3$:MeOH=9:1); 0.69

EXAMPLE 266

N-Phenyl-4-(3-phenylpropylaminomethyl)-7-methoxybenzofuran-2-carboxamide (Compound 266)

Substantially the same procedure as in Example 249 was repeated using compound 249b obtained in Example 249 and 3-phenylpropylamine to give compound 266 as a white solid.

Rf($CHCl_3$:MeOH=9:1); 0.63

EXAMPLE 267

4-[2-(2-pyridyl)ethylaminomethyl]-N-phenyl-7-methoxybenzofuran-2-carboxamide (Compound 267)

Substantially the same procedure as in Example 249 was repeated using compound 249b obtained in Example 249 and 2-(2-pyridyl)ethylamine to give compound 267 as a white solid.

Rf($CHCl_3$:MeOH=9:1); 0.35

EXAMPLE 268

N-Phenyl-7-methoxy-4-(2-morpholinoethyl-aminomethyl)benzofuran-2-carboxamide (Compound 268)

Substantially the same procedure as in Example 249 was repeated using compound 249b obtained in Example 249 and 2-morpholinoethylamine to give compound 268 as a white solid.

Rf($CHCl_3$:MeOH=9:1); 0.44

EXAMPLE 269

N-Benzyl-4-methylaminomethyl-7-methoxybenzofuran-2-carboxamide (Compound 269)

Substantially the same procedure as in Example 219 was repeated using a starting material, 7-methoxybenzofuran-2-carboxylic acid, and benzylamine to give N-benzyl-7- methoxybenzofuran-2-carboxamide (Compound 269a). Successively, it was formylated to give N-benzyl-4-formyl-7-methoxybenzofuran-2-carboxamide (Compound 269b), then compound 269b was reacted with methylamine hydrochloride to give compound 269 as a white solid.

Rf($CHCl_3$:MeOH=9:1); 0.15

EXAMPLE 270

4-Ethylaminomethyl-N-benzyl-7-methoxybenzofuran-2-carboxamide (Compound 270)

Substantially the same procedure as in Example 269 was repeated using compound 269b obtained in Example 269 and ethylamine hydrochloride to give compound 270 as a white solid.

Rf($CHCl_3$:MeOH=9:1); 0.26

EXAMPLE 271

4-Propylaminomethyl-N-benzyl-7-methoxybenzofuran-2-carboxamide (Compound 271)

Substantially the same procedure as in Example 269 was repeated using compound 269b obtained in Example 269 and n-propylamine to give compound 271 as a white solid.

Rf($CHCl_3$:MeOH=9:1); 0.37

EXAMPLE 272

4-(2-Propylaminomethyl)-N-benzyl-7-methoxybenzofuran-2-carboxamide (Compound 272)

Substantially the same procedure as in Example 269 was repeated using compound 269b obtained in Example 269 and 2-propylamine to give compound 272 as a white solid.

Rf($CHCl_3$:MeOH=9:1); 0.35

EXAMPLE 273

4-Butylaminomethyl-N-benzyl-7-methoxybenzofuran-2-carboxamide (Compound 273)

Substantially the same procedure as in Example 269 was repeated using compound 269b obtained in Example 269 and n-butylamine to give compound 273 as a white solid.

Rf($CHCl_3$:MeOH=9:1); 0.50

EXAMPLE 274

4-Cyclobutylaminomethyl-N-benzyl-7-methoxybenzofuran-2-carboxamide (Compound 274)

Substantially the same procedure as in Example 269 was repeated using compound 269b obtained in Example 269 and cyclobutylamine to give compound 274 as a white solid.

Rf($CHCl_3$:MeOH=9:1); 0.21

EXAMPLE 275

4-Cyclopentylaminomethyl-N-benzyl-7-methoxybenzofuran-2-carboxamide (Compound 275)

Substantially the same procedure as in Example 269 was repeated using compound 269b obtained in Example 269 and cyclopentylamine to give compound 275 as a white solid.

Rf($CHCl_3$:MeOH=9:1); 0.50

EXAMPLE 276

4-Cyclohexylaminomethyl-N-benzyl-7-methoxybenzofuran-2-carboxamide (Compound 276)

Substantially the same procedure as in Example 269 was repeated using compound 269b obtained in Example 269 and cyclohexylamine to give compound 276 as a white solid.

Rf($CHCl_3$:MeOH=9:1); 0.56

EXAMPLE 277

4-Cyclooctylaminomethyl-N-benzyl-7-methoxybenzofuran-2-carboxamide (Compound 277)

Substantially the same procedure as in Example 269 was repeated using compound 269b obtained in Example 269 and cyclooctylamine to give compound 277 as a white solid.

Rf($CHCl_3$:MeOH=9:1); 0.31

EXAMPLE 278

4-(2,3-Dimethylcyclohexylaminomethyl)-N-benzyl-7-methoxybenzofuran-2-carboxamide (Compound 278)

Substantially the same procedure as in Example 269 was repeated using compound 269b obtained in Example 269 and 2,3-dimethylcyclohexylamine to give compound 278 as a white solid.

Rf($CHCl_3$:MeOH=9:1); 0.33

EXAMPLE 279

N-Benzyl-4-benzylaminomethyl-7-methoxybenzofuran-2-carboxamide (Compound 279)

Substantially the same procedure as in Example 269 was repeated using compound 269b obtained in Example 269 and benzylamine to give compound 279 as a white solid.

Rf($CHCl_3$:MeOH=9:1); 0.59

EXAMPLE 280

4-Piperidinomethyl-N-benzyl-7-methoxybenzofuran-2-carboxamide (Compound 280)

Substantially the same procedure as in Example 269 was repeated using compound 269b obtained in Example 269 and piperidine to give compound 280 as a white solid.

Rf($CHCl_3$:MeOH=9:1); 0.56

EXAMPLE 281

N-Benzyl-7-methoxy-4-morpholinomethyl-benzofuran-2-carboxamide (Compound 281)

Substantially the same procedure as in Example 269 was repeated using compound 269b obtained in Example 269 and morpholine to give compound 281 as a white solid.

Rf($CHCl_3$:MeOH=9:1); 0.79

EXAMPLE 282

4-(1-Pyrrolidinylmethyl)-N-benzyl-7-methoxybenzofuran-2-carboxamide (Compound 282)

Substantially the same procedure as in Example 269 was repeated using compound 269b obtained in Example 269 and pyrrolidine to give compound 282 as a white solid.

Rf($CHCl_3$:MeOH=9:1); 0.17

EXAMPLE 283

N-Benzyl-4-(4-methyl-1-piperazinylaminomethyl)-7-methoxy-benzofuran-2-carboxamide (Compound 283)

Substantially the same procedure as in Example 269 was repeated using compound 269b obtained in Example 269 and 1-methylpiperazine to give compound 283 as a white solid.

Rf($CHCl_3$:MeOH=9:1); 0.21

EXAMPLE 284

4-(2-Phenylethylaminoethyl)-N-benzyl-7-methoxybenzofuran-2-carboxamide (Compound 284)

Substantially the same procedure as in Example 269 was repeated using compound 269b obtained in Example 269 and 2-phenetylamine to give compound 284 as a white solid.

Rf($CHCl_3$:MeOH=9:1); 0.54

EXAMPLE 285

4-[1-(S)-Phenylethylaminomethyl)-N-benzyl-7-methoxybenzofuran-2-carboxamide (Compound 285)

Substantially the same procedure as in Example 269 was repeated using compound 269b obtained in Example 269 and 1-(S)-phenetylamine to give compound 285 as a white solid.

Rf($CHCl_3$:MeOH=9:1); 0.66

EXAMPLE 286

4-(3-Phenylpropylaminomethyl)-N-benzyl-7-methoxybenzofuran-2-carboxamide (Compound 286)

Substantially the same procedure as in Example 269 was repeated using compound 269b obtained in Example 269 and 3-phenylpropylamine to give compound 286 as a white solid.

Rf($CHCl_3$:MeOH=9:1); 0.46

EXAMPLE 287

4-[2-(2-Pyridyl)ethylaminomethyl]-N-benzyl-7-methoxybenzofuran-2-carboxamide (Compound 287)

Substantially the same procedure as in Example 269 was repeated using compound 269b obtained in Example 269 and 2-(2-pyridyl)ethylamine to give compound 287 as a white solid.

Rf($CHCl_3$:MeOH=9:1); 0.37

EXAMPLE 288

N-Benzyl-7-methoxy-4-(2-morpholinoethylaminomethyl)benzofuran-2-carboxamide dihydrochloride (Compound 288)

Substantially the same procedure as in Example 269 was repeated using compound 269b obtained in Example 269 and 2-morpholinoethylamine to give compound 288 as a white solid.

NMR(DMSO-$d_6$, δ, ppm):3.12–3.18 (m, 2H),3.41–3.51 (m, 8H), 4.00(s, 3H), 4.43 (br. s, 2H), 4.48(d, J=6 Hz, 2H), 7.17(t, J=8 Hz, 1H), 7.24–7.34(m, 5H), 7.53(d, J=8 Hz, 1H), 7.93(s, 1H), 9.32–9.36(m, 1H), 9.50(br., 1H), 11.2(br., 1H)

MASS(m/e): 432($M^+$)

Rf($CHCl_3$:MeOH=9:1); 0.28

Elemental analysis: $C_{24}H_{31}N_3O_4Cl_2$.0.3$H_2O$

Found (%) C,57.50; H,6.46; N,8.20. Calcd. (%) C,57.44; H,6.35; N,8.37.

EXAMPLE 289

N-Cyclobutyl-4-methylaminomethyl-7-methoxybenzofuran-2-carboxamide (Compound 289)

Substantially the same procedure as in Example 219 was repeated using a starting material, 7-methoxybenzofuran-2-carboxylic acid, and cyclobutylamine to give N-Cyclobutyl-7-methoxybenzofuran-2-carboxamide (Compound 289a). Successively, it was formylated to give N-cyclobutyl-4-formyl-7-methoxybenzofuran-2-carboxamide (Compound 289b), then compound 289b was reacted with methylamine hydrochloride to give Compound 289 as a white solid.

Rf($CHCl_3$:MeOH=9:1); 0.14

EXAMPLE 290

4-Ethylaminomethyl-N-cyclobutyl-7-methoxybenzofuran-2-carboxamide (Compound 290)

Substantially the same procedure as in Example 289 was repeated using compound 289b obtained in Example 289 and ethylamine hydrochloride to give compound 290 as a white solid.

Rf($CHCl_3$:MeOH=9:1); 0.21

EXAMPLE 291

N-cyclobutyl-4-propylaminomethyl-7-methoxybenzofuran-2-carboxamide (Compound 291)

Substantially the same procedure as in Example 289 was repeated using compound 289b obtained in Example 289 and n-propylamine to give compound 291 as a white solid.

Rf($CHCl_3$:MeOH=9:1); 0.31

EXAMPLE 292

N-cyclobutyl-4-(2-propylaminomethyl)-7-methoxybenzofuran-2-carboxamide (Compound 292)

Substantially the same procedure as in Example 289 was repeated using compound 289b obtained in Example 289 and 2-propylamine to give compound 292 as a white solid.

Rf($CHCl_3$:MeOH=9:1); 0.28

EXAMPLE 293

N-cyclobutyl-4-butylaminomethyl-7-methoxybenzofuran-2-carboxamide (Compound 293)

Substantially the same procedure as in Example 289 was repeated using compound 289b obtained in Example 289 and n-butylamine to give compound 293 as a white solid.

Rf($CHCl_3$:MeOH=9:1); 0.28

EXAMPLE 294

N-cyclobutyl-4-cyclopentylaminomethyl-7-methoxybenzofuran-2-carboxamide (Compound 294)

Substantially the same procedure as in Example 289 was repeated using compound 289b obtained in Example 289 and cyclopentylamine to give compound 294 as a white solid.

Rf($CHCl_3$:MeOH=9:1); 0.36

EXAMPLE 295

N-cyclobutyl-4-cyclohexylaminomethyl-7-methoxybenzofuran-2-carboxamide (Compound 295)

Substantially the same procedure as in Example 289 was repeated using compound 289b obtained in Example 289 and cyclohexylamine to give compound 295 as a white solid.

Rf($CHCl_3$:MeOH=9:1); 0.42

EXAMPLE 296

N-cyclobutyl-4-benzylaminomethyl-7-methoxybenzofuran-2-carboxamide (Compound 296)

Substantially the same procedure as in Example 289 was repeated using compound 289b obtained in Example 289 and benzylamine to give compound 296 as a white solid.

Rf($CHCl_3$:MeOH=9:1); 0.53

EXAMPLE 297

N-cyclobutyl-4-piperidinomethyl-7-methoxybenzofuran-2-carboxamide (Compound 297)

Substantially the same procedure as in Example 289 was repeated using compound 289b obtained in Example 289 and piperidine to give compound 297 as a white solid.

Rf($CHCl_3$:MeOH=9:1); 0.56

EXAMPLE 298

N-cyclobutyl-7-methoxy-4-morpholinomethyl-benzofuran-2-carboxamide (Compound 298)

Substantially the same procedure as in Example 289 was repeated using compound 289b obtained in Example 289 and morpholine to give compound 298 as a white solid.

Rf($CHCl_3$:MeOH=9:1); 0.75

EXAMPLE 299

N-Cyclopentyl-4-methylaminomethyl-7-methoxybenzofuran-2-carboxamide (Compound 299)

Substantially the same procedure as in Example 219 was repeated using a starting material, 7-Methoxybenzofuran-2-carboxylic acid, and cyclopentylamine to give N-cyclopentyl-7-methoxybenzofuran-2-carboxamide (Compound 299a). Successively, it was formylated to give N-cyclopentyl-4-formyl-7-methoxybenzofuran-2-carboxamide (Compound 299b), then compound 299b was reacted with methylamine hydrochloride to give compound 299 as a white solid.

Rf($CHCl_3$:MeOH=9:1); 0.28

Rf($CHCl_3$:MeOH=9:1); 0.17

EXAMPLE 300

4-Ethylaminomethyl-N-cyclopentyl-7-methoxy-benzofuran-2-carboxamide (Compound 300)

Substantially the same procedure as in Example 299 was repeated using compound 299b obtained in Example 299 and ethylamine hydrochloride to give compound 300 as a white solid.

Rf($CHCl_3$:MeOH=9:1); 0.21

EXAMPLE 301

N-Cyclopentyl-4-propylaminomethyl$^{-7}$-methoxy-benzofuran-2-carboxamide (Compound 301)

Substantially the same procedure as in Example 299 was repeated using compound 299b obtained in Example 299 and n-propylamine to give compound 301 as a white solid.

Rf($CHCl_3$:MeOH=9:1); 0.39

EXAMPLE 302

N-Cyclopentyl-4-(2-propylaminomethyl)-7-methoxy-benzofuran-2-carboxamide (Compound 302)

Substantially the same procedure as in Example 299 was repeated using compound 299b obtained in Example 299 and 2-propylamine to give compound 302 as a white solid.

Rf($CHCl_3$:MeOH=9:1); 0.33

EXAMPLE 303

N-Cyclopentyl-4-butylaminomethyl-7-methoxy-benzofuran-2-carboxamide (Compound 303)

Substantially the same procedure as in Example 299 was repeated using compound 299b obtained in Example 299 and n-butylamine to give compound 303 as a white solid.

Rf($CHCl_3$:MeOH=9:1); 0.33

EXAMPLE 304

N-Cyclopentyl-4-cyclopentylaminomethyl-7-methoxy-benzofuran-2-carboxamide (Compound 304)

Substantially the same procedure as in Example 299 was repeated using compound 299b obtained in Example 299 and cyclopentylamine to give compound 304 as a white solid.

Rf($CHCl_3$:MeOH=9:1); 0.39

EXAMPLE 305

4-Cyclohexylaminomethyl-N-cyclopentyl-7-methoxy benzofuran-2-carboxamide (Compound 305)

Substantially the same procedure as in Example 299 was repeated using compound 299b obtained in Example 299 and cyclohexylamine to give compound 305 as a white solid.

Rf($CHCl_3$:MeOH=9:1); 0.42

EXAMPLE 306

N-Cyclopentyl-4-benzylaminomethyl$^{-7}$-methoxy benzofuran-2-carboxamide (Compound 306)

Substantially the same procedure as in Example 299 was repeated using compound 299b obtained in Example 299 and benzylamine to give compound 306 as a white solid.

Rf($CHCl_3$:MeOH=9:1); 0.56

EXAMPLE 307

N-Cyclopentyl-4-piperidinomethyl$^{-7}$-methoxy benzofuran-2-carboxamide (Compound 307)

Substantially the same procedure as in Example 299 was repeated using compound 299b obtained in Example 299 and piperidine to give compound 307 as a white solid.

Rf($CHCl_3$:MeOH=9:1); 0.56

EXAMPLE 308

N-Cyclopentyl-7-methoxy-4-morpholinomethylbenzofuran-2-carboxamide (Compound 308)

Substantially the same procedure as in Example 299 was repeated using compound 299b obtained in Example 299 and morpholine to give compound 308 as a white solid.

Rf($CHCl_3$:MeOH=9:1); 0.77

EXAMPLE 309

2-Pyrrolidinylcarbonyl-4-methylaminomethyl-7-methoxybenzofuran (Compound 309)

Substantially the same procedure as in Example 219 was repeated using a starting material, 7-methoxybenzofuran-2-carboxylic acid, and pyrrolidine to give 2-Pyrrolidinylcarbonyl-7-methoxybenzofuran (Compound 309a). Successively, it was formylated to give 2-pyrrolidinylcarbonyl-4-formyl-7-methoxybenzofuran (Compound 309b), then compound 309b was reacted with methylamine hydrochloride to give compound 309 as a white solid.

Rf($CHCl_3$:MeOH=9:1); 0.11

EXAMPLE 310

4-Ethylaminomethyl-2-pyrrolidinylcarbonyl-7-methoxybenzofuran (Compound 310)

Substantially the same procedure as in Example 309 was repeated using compound 309b obtained in Example 309 and ethylamine hydrochloride to give compound 310 as a white solid.

Rf($CHCl_3$:MeOH=9:1); 0.19

EXAMPLE 311

2-Pyrrolidinylcarbonyl-4-propylaminomethyl-7-methoxybenzofuran (Compound 311)

Substantially the same procedure as in Example 309 was repeated using compound 309b obtained in Example 309 and n-propylamine to give compound 311 as a white solid.

Rf($CHCl_3$:MeOH=9:1); 0.28

EXAMPLE 312

2-Pyrrolidinylcarbonyl-4-(2-propylamino-methyl)-7-methoxybenzofuran (Compound 312)

Substantially the same procedure as in Example 309 was repeated using compound 309b obtained in Example 309 and 2-propylamine to give compound 312 as a white solid.

Rf($CHCl_3$:MeOH=9:1); 0.28

EXAMPLE 313

2-Pyrrolidinylcarbonyl-4-butylaminomethyl-7-methoxybenzofuran (Compound 313)

Substantially the same procedure as in Example 309 was repeated using compound 309b obtained in Example 309 and n-butylamine to give compound 313 as a white solid.

Rf($CHCl_3$:MeOH=9:1); 0.34

EXAMPLE 314

4-Cyclopentylaminomethyl-2-pyrrolidinyl-carbonyl-7-methoxybenzofuran (Compound 314)

Substantially the same procedure as in Example 309 was repeated using compound 309b obtained in Example 309 and cyclopentylamine to give compound 314 as a white solid.

Rf($CHCl_3$:MeOH=9:1); 0.33

EXAMPLE 315

4-Cyclohexylaminomethyl-2-pyrrolidinyl-carbonyl-7 methoxybenzofuran (Compound 315)

Substantially the same procedure as in Example 309 was repeated using-compound 309b obtained in Example 309 and cyclohexylamine to give compound 315 as a white solid.

Rf($CHCl_3$:MeOH=9:1); 0.34

EXAMPLE 316

2-Pyrrolidinylcarbonyl-4-benzylaminomethyl-7-methoxybenzofuran (Compound 316)

Substantially the same procedure as in Example 309 was repeated using compound 309b obtained in Example 309 and benzylamine to give compound 316 as a white solid.

Rf($CHCl_3$:MeOH=9:1); 0.61

EXAMPLE 317

4-Piperidinomethyl-2-pyrrolidinylcarbonyl-7-methoxybenzofuran (Compound 317)

Substantially the same procedure as in Example 309 was repeated using compound 309b obtained in Example 309 and piperidine to give compound 317 as a white solid.

Rf($CHCl_3$:MeOH=9:1); 0.55

EXAMPLE 318

2-Pyrrolidinylcarbonyl-7-methoxy-4-morpholinomethylbenzofuran (Compound 318)

Substantially the same procedure as in Example 309 was repeated using compound 309b obtained in Example 309 and morpholine to give compound 318 as a white solid.

Rf($CHCl_3$:MeOH=9:1); 0.58

EXAMPLE 319

2-Piperidinocarbonyl-4-methylaminomethyl-7-methoxybenzofuran (Compound 319)

Substantially the same procedure as in Example 219 was repeated using a starting material, 7-Methoxybenzofuran-2-carboxylic acid, and piperidine to give 2-piperidinocarbonyl-7-methoxybenzofuran (Compound 319a). Successively, it was formylated to give 2-piperidinocarbonyl-4-formyl-7-methoxybenzofuran (Compound 319b), then compound 319b was reacted with methylamine hydrochloride to give compound 319 as a white solid.

Rf($CHCl_3$:MeOH=9:1); 0.14

EXAMPLE 320

4-Ethylaminomethyl-2-piperidinocarbonyl-7-methoxybenzofuran (Compound 320)

Substantially the same procedure as in Example 319 was repeated using compound 319b obtained in Example 319 and ethylamine hydrochloride to give compound 320 as a white solid.

Rf($CHCl_3$:MeOH=9:1); 0.17

EXAMPLE 321

2-Piperidinocarbonyl-4-propylaminomethyl-7-methoxybenzofuran (Compound 321)

Substantially the same procedure as in Example 319 was repeated using compound 319b obtained in Example 319 and n-propylamine to give compound 321 as a white solid.

Rf($CHCl_3$:MeOH=9:1); 0.17

EXAMPLE 322

2-Piperidinocarbonyl-4-(2-propylamino-methyl)-7-methoxybenzofuran (Compound 322)

Substantially the same procedure as in Example 319 was repeated using compound 319b obtained in Example 319 and 2-propylamine to give compound 322 as a white solid.

Rf($CHCl_3$:MeOH=9:1); 0.22

EXAMPLE 323

2-Piperidinocarbonyl-4-butylaminomethyl-7-methoxybenzofuran (Compound 323)

Substantially the same procedure as in Example 319 was repeated using compound 319b obtained in Example 319 and n-butylamine to give compound 323 as a white solid.

Rf($CHCl_3$:MeOH=9:1); 0.22

EXAMPLE 324

4-Cyclopentylaminomethyl-2-piperidinocarbonyl-7-methoxybenzofuran (Compound 324)

Substantially the same procedure as in Example 319 was repeated using compound 319b obtained in Example 319 and cyclopentylamine to give compound 324 as a white solid.

Rf($CHCl_3$:MeOH=9:1); 0.28

EXAMPLE 325

4-Cyclohexylaminomethyl-2-piperidinocarbonyl-7-methoxybenzofuran (Compound 325)

Substantially the same procedure as in Example 319 was repeated using compound 319b obtained in Example 319 and cyclohexylamine to give compound 325 as a white solid.

Rf($CHCl_3$:MeOH=9:1); 0.28

EXAMPLE 326

2-Piperidinocarbonyl-4-benzylaminomethyl-7-methoxybenzofuran (Compound 326)

Substantially the same procedure as in Example 319 was repeated using compound 319b obtained in Example 319 and benzylamine to give compound 326 as a white solid.

Rf($CHCl_3$:MeOH=9:1); 0.50

EXAMPLE 327

2-Piperidinocarbonyl-4-piperidinomethyl-7-methoxybenzofuran (Compound 327)

Substantially the same procedure as in Example 319 was repeated using compound 319b obtained in Example 319 and piperidine to give compound 327 as a white solid.

Rf($CHCl_3$:MeOH=9:1); 0.47

EXAMPLE 328

2-Piperidinocarbonyl-7-methoxy-4-morpholinomethylbenzofuran (Compound 328)

Substantially the same procedure as in Example 319 was repeated using compound 319b obtained in Example 319 and morpholine to give compound 328 as a white solid.

Rf($CHCl_3$:MeOH=9:1); 0.67

EXAMPLE 329

4-Methylaminomethyl-7-methoxy-2-morpholinocarbonylbenzofuran (Compound 329)

Substantially the same procedure as in Example 219 was repeated using a starting material, 7-methoxybenzofuran-2-carboxylic acid, and morpholine to give 7-methoxy-2-morpholinocarbonylbenzofuran (Compound 329a). Successively, it was formylated to give 4-formyl-7-methoxy-2-morpholinocarbonylbenzofuran (Compound 329b), then compound 329b was reacted with methylamine hydrochloride to give compound 329 as a white solid.

Rf($CHCl_3$:MeOH=9:1); 0.17

EXAMPLE 330

4-Ethylaminomethyl-7-methoxy -2morpholinocarbonylbenzofuran (Compound 330)

Substantially the same procedure as in Example 329 was repeated using compound 329b obtained in Example 329 and ethylamine hydrochloride to give compound 330 as a white solid.

Rf($CHCl_3$:MeOH=9:1); 0.20

EXAMPLE 331

4-Propylaminomethyl-7-methoxy-2-morpholinocarbonylbenzofuran (Compound 331)

Substantially the same procedure as in Example 329 was repeated using compound 329b obtained in Example 329 and n-propylamine to give compound 331 as a white solid.

Rf($CHCl_3$:MeOH=9:1); 0.25

EXAMPLE 332

4-(2-Propylaminomethyl)-7-methoxy-2-morpholinocarbonylbenzofuran (Compound 332)

Substantially the same procedure as in Example 329 was repeated using compound 329b obtained in Example 329 and 2-propylamine to give compound 332 as a white solid.

Rf($CHCl_3$:MeOH=9:1); 0.29

EXAMPLE 333

4-Butylaminomethyl-7-methoxy-2-morpholinocarbonylbenzofuran (Compound 333)

Substantially the same procedure as in Example 329 was repeated using compound 329b obtained in Example 329 and n-butylamine to give compound 333 as a white solid.

Rf($CHCl_3$:MeOH=9:1); 0.29

EXAMPLE 334

4-Cyclopentylaminomethyl-7-methoxy-2-morpholinocarbonylbenzofuran (Compound 334)

Substantially the same procedure as in Example 329 was repeated using compound 329b obtained in Example 329 and cyclopentylamine to give compound 334 as a white solid.

Rf($CHCl_3$:MeOH=9:1); 0.29

EXAMPLE 335

4-Cyclohexylaminomethyl-7-methoxy-2-morpholiocarbonylbenzofuran monohydrochloride (Compound 335)

Substantially the same procedure as in Example 329 was repeated using compound 329b obtained in Example 329 and cyclohexylamine to give compound 335 as a white solid.

NMR(DMSO-$d_6$, δ, ppm):1.08–1.64(m, 6H), 1.76–1.81 (m, 2H), 2.13–2.17(m, 2H), 3.00–3.09(m, 1H),3.66–3.74(m, 8H), 3.98(s, 3H), 4.36 (br. s, 2H),7.13(d, J=8 Hz, 1H), 7.50(d, J=8 Hz, 1H), 7.79(s, 1H),9.08(br.s, 1H)

MASS(m/e): 372($M^+$)

Rf($CHCl_3$:MeOH=9:1); 0.35

Elemental analysis: $C_{21}H_{29}N_2O_4Cl.0.6H_2O$

Found (%) C,60.06; H,7.49; N,6.46. Calcd. (%) C,60.09; H,7.25; N,6.67.

EXAMPLE 336

4-Benzylaminomethyl-7-methoxy-2-morpholinocarbonylbenzofuran (Compound 336)

Substantially the same procedure as in Example 329 was repeated using compound 329b obtained in Example 329 and benzylamine to give compound 336 as a white solid.

Rf($CHCl_3$:MeOH=9:1); 0.50

EXAMPLE 337

4-Piperidinomethyl-7-methoxy-2-morpholinocarbonylbenzofuran (Compound 337)

Substantially the same procedure as in Example 329 was repeated using compound 329b obtained in Example 329 and piperidine to give compound 337 as a white solid.

Rf($CHCl_3$:MeOH=9:1); 0.46

EXAMPLE 338

7-Methoxy-2-morpholinocarbonyl-4-morpholinomethylbenzofuran (Compound 338)

Substantially the same procedure as in Example 329 was repeated using compound 329b obtained in Example 329 and morpholine to give compound 338 as a white solid.

Rf($CHCl_3$:MeOH=9:1); 0.69

EXAMPLE 339

N-(2-Phenylethyl)4-methylaminomethyl-7-methoxybenzofuran-2-carboxamide (Compound 339)

Substantially the same procedure as in Example 219 was repeated using a starting material, 7-methoxybenzofuran-2-carboxylic acid, and 2-phenetylamine to give N-(2-phenylethyl)-7-methoxybenzofuran-2-carboxamide (Compound 339a). Successively, it was formylated to give N-(2-phenylethyl)-4-formyl-7-methoxybenzofuran-2-carboxamide (Compound 339b), then compound 339b was reacted with methylamine hydrochloride to give compound 339 as a white solid.

Rf($CHCl_3$:MeOH=9:1); 0.14

EXAMPLE 340

4-Ethylaminomethyl-N-(2-phenylethyl)-7-methoxybenzofuran-2-carboxamide (Compound 340)

Substantially the same procedure as in Example 339 was repeated using compound 339b obtained in Example 339 and ethylamine hydrochloride to give compound 340 as a white solid.

Rf($CHCl_3$:MeOH=9:1); 0.21

EXAMPLE 341

N-(2-Phenylethyl)-4-propylaminomethyl-7-methoxybenzofuran-2-carboxamide (Compound 341)

Substantially the same procedure as in Example 339 was repeated using compound 339b obtained in Example 339 and n-propylamine to give compound 341 as a white solid.

Rf($CHCl_3$:MeOH=9:1); 0.29

EXAMPLE 342

N-(2-Phenylethyl)-4-(2-propylaminomethyl)-7-methoxybenzofuran-2-carboxamide (Compound 342)

Substantially the same procedure as in Example 339 was repeated using compound 339b obtained in Example 339 and 2-propylamine to give compound 342 as a white solid.

Rf($CHCl_3$:MeOH=9:1); 0.34

EXAMPLE 343

N-(2-Phenylethyl)-4-butylaminomethyl-7-methoxybenzofuran-2-carboxamide (Compound 343)

Substantially the same procedure as in Example 339 was repeated using compound 339b obtained in Example 339 and n-butylamine to give compound 343 as a white solid.

Rf($CHCl_3$:MeOH=9:1); 0.37

EXAMPLE 344

4-Cyclobutylaminomethyl-N-(2-phenylethyl)-7-methoxybenzofuran-2-carboxamide (Compound 344)

Substantially the same procedure as in Example 339 was repeated using compound 339b obtained in Example 339 and cyclobutylamine to give compound 344 as a white solid.

Rf($CHCl_3$:MeOH=9:1); 0.26

EXAMPLE 345

4-Cyclopentylaminomethyl-N-(2-phenylethyl)-7-methoxybenzofuran-2-carboxamide (Compound 345)

Substantially the same procedure as in Example 339 was repeated using compound 339b obtained in Example 339 and cyclopentylamine to give compound 345 as a white solid.

Rf($CHCl_3$:MeOH=9:1); 0.37

EXAMPLE 346

4-Cyclohexylaminomethyl-N-(2-phenylethyl)-7-methoxybenzofuran-2-carboxamide (Compound 346)

Substantially the same procedure as in Example 339 was repeated using compound 339b obtained in Example 339 and cyclohexylamine to give compound 346 as a white solid.

Rf($CHCl_3$:MeOH=9:1); 0.63

EXAMPLE 347

4-Cyclooctylaminomethyl-N-(2-phenylethyl)-7-methoxybenzofuran-2-carboxamide (Compound 347)

Substantially the same procedure as in Example 339 was repeated using compound 339b obtained in Example 339 and cyclooctylamine to give compound 347 as a white solid.

Rf($CHCl_3$:MeOH=9:1); 0.26

EXAMPLE 348

4-(2,3-Dimethylcyclohexylaminomethyl)-N-(2-phenylethyl)-7-methoxybenzofuran-2-carboxamide (Compound 348)

Substantially the same procedure as in Example 339 was repeated using compound 339b obtained in Example 339 and 2,3-dimethylcyclohexylamine to give compound 348 as a white solid.

Rf($CHCl_3$:MeOH=9:1); 0.38

EXAMPLE 349

N-(2-Phenylethyl)-4-benzylaminomethyl-7-methoxybenzofuran-2-carboxamide (Compound 349)

Substantially the same procedure as in Example 339 was repeated using compound 339b obtained in Example 339 and benzylamine to give compound 349 as a white solid.

Rf($CHCl_3$:MeOH=9:1); 0.64

EXAMPLE 350

4-Piperidinomethyl-N-(2-phenylethyl)-7-methoxybenzofuran-2-carboxamide (Compound 350)

Substantially the same procedure as in Example 339 was repeated using compound 339b obtained in Example 339 and piperidine to give compound 350 as a white solid.

Rf($CHCl_3$:MeOH=9:1); 0.60

EXAMPLE 351

N-(2-Phenylethyl)-7-methoxy-4-morpholinomethylbenzofuran-2-carboxamide monohydrochloride (Compound 351)

Substantially the same procedure as in Example 339 was repeated using compound 339b obtained in Example 339 and morpholine to give compound 351 as a white solid.

Rf($CHCl_3$:MeOH=9:1); 0.83

EXAMPLE 352

4-(1-Pyrrolidinylmethyl)-N-(2-phenylethyl)-7-methoxybenzofuran-2-carboxamide (Compound 352)

Substantially the same procedure as in Example 339 was repeated using compound 339b obtained in Example 339 and pyrrolidine to give compound 352 as a white solid.

Rf($CHCl_3$:MeOH=9:1); 0.21

EXAMPLE 353

N-(2-Phenyethyl)-4-(4-methyl-1-piperazinylmethyl)-7-methoxybenzofuran-2-carboxamide (Compound 353)

Substantially the same procedure as in Example 339 was repeated using compound 339b obtained in Example 339 and 1-methylpiperazine to give compound 353 as a white solid.

Rf($CHCl_3$:MeOH=9:1); 0.23

EXAMPLE 354

N-(2-Phenylethyl)-4-(2-phenylethylamino-methyl)-7-methoxybenzofuran-2-carboxamide (Compound 354)

Substantially the same procedure as in Example 339 was repeated using compound 339b obtained in Example 339 and 2-phenetylamine to give compound 354 as a white solid.

NMR(DMSO-$d_6$, δ, ppm):2.87 (t, J=8 Hz, 2H),2.97–3.01 (m, 2H), 3.19–3.24(m, 2H), 3.52(dt, J=8, 6 Hz, 2H),3.99(s, 3H), 4.39 (br. s, 2H), 7.14–7.37(m,11H), 7.49(d, J=8 Hz, 1H), 7.89(s, 1H), 8.81–8.85(m, 1H), 9.92(br., 1H)

MASS(m/e): 429($M^+$)

Rf($CHCl_3$:MeOH=9:1); 0.28

Elemental analysis: $C_{27}H_{29}N_2O_3Cl$

Found (%) C,69.95; H,6.26; N,5.83. Calcd. (%) C,69.74; H,6.28; N,5.83.

EXAMPLE 355

N-(2-Phenylethyl)-4-[1-(S)-phenylethylamino-methyl]-7-methoxybenzofuran-2-carboxamide (Compound 355)

Substantially the same procedure as in Example 339 was repeated using compound 339b obtained in Example 339 and 1-(S)-phenetylamine to give compound 355 as a white solid.

Rf($CHCl_3$:MeOH=9:1); 0.54

EXAMPLE 356

N-(2-Phenylethyl)-4-(3-phenylpropylamino-methyl)-7-methoxybenzofuran-2-carboxamide (Compound 356)

Substantially the same procedure as in Example 339 was repeated using compound 339b obtained in Example 339 and 3-phenylpropylamine to give compound 356 as a white solid.

Rf($CHCl_3$:MeOH=9:1); 0.46

EXAMPLE 357

4-[2-(2-pyridyl)ethylaminomethyl]-N-(2-phenylethyl)-7-methoxybenzofuran-2-carboxamide (Compound 357)

Substantially the same procedure as in Example 339 was repeated using compound 339b obtained in Example 339 and 2-(2-pyridyl)ethylamine to give compound 357 as a white solid.

Rf($CHCl_3$:MeOH=9:1); 0.29

EXAMPLE 358

N-(2-Phenylethyl)-7-methoxy-4-(2-morpholinoethylaminomethyl)-benzofuran-2-carboxamide (Compound 358)

Substantially the same procedure as in Example 339 was repeated using compound 339b obtained in Example 339 and 2-morpholinoethylamine to give compound 358 as a white solid.

Rf($CHCl_3$:MeOH=9:1); 0.29

EXAMPLE 359

N-[1-(S)-Phenylethyl)-4-methylaminomethyl-7-methoxybenzofuran-2-carboxamide (Compound 339)

Substantially the same procedure as in Example 219 was repeated using a starting material, 7-methoxybenzofuran-2- carboxylic acid, and 1-(S)-phenylethylamine to give N-[1-(S)-phenylethyl]-7-methoxybenzofuran-2-carboxamide (Compound 359a). Successively, it was formylated to give N-[1-(S)-phenylethyl]-4-formyl-7-methoxybenzofuran-2-carboxamide (Compound 359b), then compound 359b was reacted with methylamine hydrochloride to give compound 359 as a white solid.

Rf($CHCl_3$:MeOH=9:1); 0.11

EXAMPLE 360

4-Ethylaminomethyl-N-[1-(S)-phenylethyl]-7-methoxybenzofuran-2-carboxamide (Compound 360)

Substantially the same procedure as in Example 359 was repeated using compound 359b obtained in Example 359 and ethylamine hydrochloride to give compound 360 as a white solid.

Rf($CHCl_3$:MeOH=9:1); 0.17

EXAMPLE 361

N-[1-(S)-Phenylethyl]-4-propylaminomethyl-7-methoxybenzofuran-2-carboxamide (Compound 361)

Substantially the same procedure as in Example 359 was repeated using compound 359b obtained in Example 359 and n-propylamine to give compound 361 as a white solid.

Rf($CHCl_3$:MeOH=9:1); 0.34

EXAMPLE 362

N-[1-(S)-Phenylethyl]-4-(2-propylamino-methyl)-7-methoxybenzofuran-2-carboxamide (Compound 362)

Substantially the same procedure as in Example 359 was repeated using compound 359b obtained in Example 359 and 2-propylamine to give compound 362 as a white solid.

Rf($CHCl_3$:MeOH=9:1); 0.31

EXAMPLE 363

N-[1-(S)-Phenylethyl]-4-butylaminomethyl-7-methoxybenzofuran-2-carboxamide (Compound 363)

Substantially the same procedure as in Example 359 was repeated using compound 359b obtained in Example 359 and n-butylamine to give compound 363 as a white solid.

Rf($CHCl_3$:MeOH=9:1); 0.31

EXAMPLE 364

4-Cyclobutylaminomethyl-N-[1-(S)-phenylethyl]-7-methoxybenzofuran-2-carboxamide (Compound 364)

Substantially the same procedure as in Example 359 was repeated using compound 359b obtained in Example 359 and cyclobutylamine to give compound 364 as a white solid.

Rf($CHCl_3$:MeOH=9:1); 0.23

EXAMPLE 365

4-Cyclopentylaminomethyl-N-[1-(S)-phenylethyl)-7-methoxybenzofuran-2-carboxamide (Compound 365)

Substantially the same procedure as in Example 359 was repeated using compound 359b obtained in Example 359 and cyclopentylamine to give compound 365 as a white solid.

EXAMPLE 366

4-Cyclohexylaminomethyl-N-[1-(S)-phenylethyl]-7-methoxybenzofuran-2-carboxamide (Compound 366)

Substantially the same procedure as in Example 359 was repeated using compound 359b obtained in Example 359 and cyclohexylamine to give compound 366 as a white solid.

Rf($CHCl_3$:MeOH=9:1); 0.43

EXAMPLE 367

4-Cyclooctylaminomethyl-N-[1-(S)-phenylethyl]-7-methoxybenzofuran-2-carboxamide (Compound 367)

Substantially the same procedure as in Example 359 was repeated using compound 359b obtained in Example 359 and cyclooctylamine to give compound 367 as a white solid.

Rf($CHCl_3$:MeOH=9:1); 0.26

EXAMPLE 368

4-(2,3-Dimethylcyclohexylaminomethyl)-N-(1-(S)-phenylethyl]-7-methoxybenzofuran-2-carboxamide (Compound 368)

Substantially the same procedure as in Example 359 was repeated using compound 359b obtained in Example 359 and 2,3-dimethylcyclohexylamine to give compound 368 as a white solid.

Rf($CHCl_3$:MeOH=9:1); 0.38

EXAMPLE 369

N-[1-(S)-phenylethyl]-4-benzylaminomethyl-7-methoxybenzofuran-2-carboxamide (Compound 369)

Substantially the same procedure as in Example 359 was repeated using compound 359b obtained in Example 359 and benzylamine to give compound 369 as a white solid.

Rf($CHCl_3$:MeOH=9:1); 0.54

EXAMPLE 370

4-Piperidinomethyl-N-[1-(S)-phenylethyl]-7-methoxybenzofuran-2-carboxamide (Compound 370)

Substantially the same procedure as in Example 359 was repeated using compound 359b obtained in Example 359 and piperidine to give compound 370 as a white solid.

Rf($CHCl_3$:MeOH=9:1); 0.57

EXAMPLE 371

N-[1-(S)-phenylethyl]-7-methoxy-4-morpholinomethylbenzofuran-2-carboxamide monohydrochloride (Compound 371)

Substantially the same procedure as in Example 359 was repeated using compound 359b obtained in Example 359 and morpholine to give compound 371 as a white solid.

Rf($CHCl_3$:MeOH=9:1); 0.68

EXAMPLE 372

4-(1-Pyrrolidinylmethyl)-N-[1-(S)-phenylethyl]-7-methoxybenzofuran-2-carboxamide (Compound 372)

Substantially the same procedure as in Example 359 was repeated using compound 359b obtained in Example 359 and pyrrolidine to give compound 372 as a white solid.

Rf($CHCl_3$:MeOH=9:1); 0.43

Rf($CHCl_3$:MeOH=9:1); 0.15

EXAMPLE 373

N-[1-(S)-Phenylethyl]-4-(4-methyl-1-piperazinylmethyl)-7-methoxybenzofuran-2-carboxamide (Compound 373)

Substantially the same procedure as in Example 359 was repeated using compound 359b obtained in Example 359 and 1-methylpiperazine to give compound 373 as a white solid.

Rf($CHCl_3$:MeOH=9:1); 0.23

EXAMPLE 374

N-[1-(S)-Phenylethyl]-4-(2-phenylethylamino-methyl)-7-methoxybenzofuran-2-carboxamide (Compound 374)

Substantially the same procedure as in Example 359 was repeated using compound 359b obtained in Example 359 and 2-phenetylamine to give compound 374 as a white solid.

Rf($CHCl_3$:MeOH=9:1); 0.42

EXAMPLE 375

N-[1-(S)-Phenylethyl]-4-[1-(S)-phenylethylaminomethyl]-7-methoxybenzofuran-2-carboxamide (Compound 375)

Substantially the same procedure as in Example 359 was repeated using compound 339b obtained in Example 359 and 1-(S)-phenetylamine to give compound 375 as a white solid.

Rf($CHCl_3$:MeOH=9:1); 0.47

EXAMPLE 376

N-[1-(S)-Phenylethyl]-4-(3-phenylpropyl-aminomethyl)-7-methoxybenzofuran-2-carboxamide (Compound 376)

Substantially the same procedure as in Example 359 was repeated using compound 359b obtained in Example 359 and 3-phenylpropylamine to give compound 376 as a white solid.

Rf($CHCl_3$:MeOH=9:1); 0.42

EXAMPLE 377

4-[2-(2-pyridyl)ethylaminomethyl]-N-[1-(S)-phenylethyl]-7-methoxybenzofuran-2-carboxamide (Compound 377)

Substantially the same procedure as in Example 359 was repeated using compound 359b obtained in Example 359 and 2-(2-pyridyl)ethylamine to give compound 377 as a white solid.

Rf($CHCl_3$:MeOH=9:1); 0.33

EXAMPLE 378

N-[1-(S)-Phenylethyl]-7-methoxy-4-(2-morpholinoethylaminomethyl)-benzofuran-2-carboxamide (Compound 378)

Substantially the same procedure as in Example 359 was repeated using compound 359b obtained in Example 359 and 2-morpholinoethylamine to give compound 378 as a white solid.

Rf($CHCl_3$:MeOH=9:1); 0.33

EXAMPLE 379

N-(4-Chlorophenyl)-4-cyclobutylaminomethyl-7-methoxybenzofuran-2-carboxamide (Compound 379)

Substantially the same procedure as in Example 219 was repeated using a starting material, 7-methoxybenzofuran-2-carboxylic acid, and 4-chloroaniline to give N-(4-chlorophenyl)-7-methoxybenzofuran-2-carboxamide (Compound 379a). Successively, it was formylated to give N-(4-chloropheny)-4-formyl-7-methoxybenzofuran-2-carboxamide (Compound 379b), then compound 379b was reacted with cyclobutylamine to give compound 379 as a white solid.

Rf($CHCl_3$:MeOH=9:1); 0.28

EXAMPLE 380

N-(4-Chlorophenyl)-4-cyclooctylaminomethyl-7-methoxy benzofuran-2-carboxamide (Compound 380)

Substantially the same procedure as in Example 379 was repeated using compound 379b obtained in Example 379 and cyclooctylamine to give compound 380 as a white solid.

Rf($CHCl_3$:MeOH=9:1); 0.28

EXAMPLE 381

N-(4-Chlorophenyl)-4-(2,3-dimethylcyclohexylaminomethyl)-7-methoxybenzofuran-2-carboxamide (Compound 381)

Substantially the same procedure as in Example 379 was repeated using compound 379b obtained in Example 379 and 2,3-dimethylcyclohexylamine to give compound 381 as a white solid.

Rf($CHCl_3$:MeOH=9:1); 0.31

EXAMPLE 382

N-(4-Chlorophenyl)-4-(4-methyl-1-piperazinylmethyl)-7-methoxybenzofuran-2-carboxamide (Compound 382)

Substantially the same procedure as in Example 379 was repeated using compound 379b obtained in Example 379 and 1-methylpiperazine to give compound 382 as a white solid.

Rf($CHCl_3$:MeOH=9:1); 0.50

EXAMPLE 383

N-(4-Chlorophenyl)-4-(1-pyrrolidinylmethyl)-7-methoxybenzofuran-2-carboxamide (Compound 383)

Substantially the same procedure as in Example 379 was repeated using compound 379b obtained in Example 379 and pyrrolidine to give compound 383 as a white solid.

Rf($CHCl_3$:MeOH=9:1); 0.19

EXAMPLE 384

N-(4-Chlorophenyl)-4-(2-phenylethylamino-methyl)-7-methoxybenzofuran-2-carboxamide (Compound 384)

Substantially the same procedure as in Example 379 was repeated using compound 379b obtained in Example 379 and 2-phenetylamine to give compound 384 as a white solid.

Rf($CHCl_3$:MeOH=9:1); 0.42

EXAMPLE 385

N-(4-Chlorophenyl)-4-[1-(S)-phenylethyl-aminomethyl]-7-methoxybenzofuran-2-carboxamide (Compound 385)

Substantially the same procedure as in Example 379 was repeated using compound 379b obtained in Example 379 and 1-(S)-phenetylamine to give compound 385 as a white solid.

Rf($CHCl_3$:MeOH=9:1); 0.56

EXAMPLE 386

N-(4-Chlorophenyl)-4-(3-phenylpropyl-aminomethyl)-7-methoxybenzofuran-2-carboxamide (Compound 386)

Substantially the same procedure as in Example 379 was repeated using compound 379b obtained in Example 379 and 3-phenylpropylamine to give compound 386 as a white solid.

Rf($CHCl_3$:MeOH=9:1); 0.56

EXAMPLE 387

N-(4-Chlorophenyl)-4-[2-(2-pyridyl)ethyl-amino]-7-methoxybenzofuran-2-carboxamide (Compound 387)

Substantially the same procedure as in Example 379 was repeated using compound 379b obtained in Example 379 and 2-(2-pyridyl)ethylamine to give compound 387 as a white solid.

Rf($CHCl_3$:MeOH=9:1); 0.28

EXAMPLE 388

N-(4-Chlorophenyl)-7-methoxy-4-(2-morpholinoethyl)aminomethylbenzofuran-2-carboxamide (Compound 388)

Substantially the same procedure as in Example 379 was repeated using compound 379b obtained in Example 379 and 2-morpholinoethylamine to give compound 388 as a white solid.

Rf($CHCl_3$:MeOH=9:1); 0.25

EXAMPLE 389

4-Cyclobutylaminomethyl-N-(4-t-butylphenyl)-7-methoxybenzofuran-2-carboxamide (Compound 389)

Substantially the same procedure as in Example 219 was repeated using a starting material, 7-methoxybenzofuran-2-carboxylic acid, and 4-t-butylaniline to give N-(4-t-butylphenyl)-7-methoxybenzofuran-2-carboxamide (Compound 389a). Successively, it was formylated to give N-(4-t-butylphenyl)-4-formyl-7-methoxybenzofuran-2-carboxamide (Compound 389b), then compound 389b was reacted with cyclobutylamine to give compound 389 as a white solid.

Rf($CHCl_3$:MeOH=9:1); 0.25

EXAMPLE 390

4-Cyclooctylaminomethyl-N-(4-t-butylphenyl)-7-methoxy benzofuran-2-carboxamide (Compound 390)

Substantially the same procedure as in Example 389 was repeated using compound 389b obtained in Example 389 and cyclooctylamine to give compound 390 as a white solid.

Rf($CHCl_3$:MeOH=9:1); 0.33

EXAMPLE 391

4-(2,3-Dimethylcyclohexylaminomethyl)-N-(4-t-butylphenyl)-7-methoxybenzofuran-2-carboxamide (Compound 391)

Substantially the same procedure as in Example 389 was repeated using compound 379b obtained in Example 389 and 2,3-dimethylcyclohexylamine to give compound 391 as a white solid.

Rf($CHCl_3$:MeOH=9:1); 0.36

EXAMPLE 392

N-(4-t-Butylphenyl)-4-(4-methyl-1-piperazinylmethyl)-7-methoxybenzofuran-2-carboxamide (Compound 392)

Substantially the same procedure as in Example 389 was repeated using compound 389b obtained in Example 389 and 1-methylpiperazine to give compound 392 as a white solid.

Rf($CHCl_3$:MeOH=9:1); 0.51

EXAMPLE 393

4-(1-Pyrrolidinylmethyl)-N-(4-t-butylphenyl)-7-methoxybenzofuran-2-carboxamide (Compound 393)

Substantially the same procedure as in Example 389 was repeated using compound 389b obtained in Example 389 and pyrrolidine to give compound 393 as a white solid.

Rf($CHCl_3$:MeOH=9:1); 0.23

EXAMPLE 394

4-(2-Phenylethylaminomethyl)-N-(4-t-butylphenyl)-7-methoxybenzofuran-2-carboxamide (Compound 394)

Substantially the same procedure as in Example 389 was repeated using compound 389b obtained in Example 389 and 2-phenetylamine to give compound 394 as a white solid.

Rf($CHCl_3$:MeOH=9:1); 0.50

EXAMPLE 395

4-[1-(S)-Phenylethylaminomethyl]-N-(4-t-butylphenyl)-7-methoxybenzofuran-2-carboxamide (Compound 395)

Substantially the same procedure as in Example 389 was repeated using compound 389b obtained in Example 389 and 1-(S)-phenetylamine to give compound 395 as a white solid.

Rf($CHCl_3$:MeOH=9:1); 0.64

EXAMPLE 396

4-(3-Phenylpropylaminomethyl)-N-(4-t-butylphenyl)-7-methoxybenzofuran-2-carboxamide (Compound 396)

Substantially the same procedure as in Example 389 was repeated using compound 389b obtained in Example 389 and 3-phenylpropylamine to give compound 396 as a white solid.

Rf($CHCl_3$:MeOH=9:1); 0.61

EXAMPLE 397

4-[2-(2-Pyridyl)ethylamine]-N-(4-t-butylphenyl)-7-methoxybenzofuran-2-carboxamide (Compound 397)

Substantially the same procedure as in Example 389 was repeated using compound 389b obtained in Example 389 and 2-(2-pyridyl)ethylamine to give compound 397 as a white solid.

Rf($CHCl_3$:MeOH=9:1); 0.39

EXAMPLE 398

N-(4-t-Butylphenyl)-7-methoxy-4-(2-morpholinoethyl)aminomethylbenzofuran-2-carboxamide (Compound 398)

Substantially the same procedure as in Example 389 was repeated using compound 389b obtained in Example 389 and 2-morpholinoethylamine to give compound 398 as a white solid.

Rf($CHCl_3$:MeOH=9:1); 0.39

EXAMPLE 399

4-Cyclobutylaminomethyl-7-methoxy-N-(4-methoxyphenyl)benzofuran-2-carboxamide (Compound 399)

Substantially the same procedure as in Example 219 was repeated using a starting material, 7-methoxybenzofuran-2-carboxylic acid, and p-anisidineto give N-(4-methoxyphenyl)-7-methoxybenzofuran-2-carboxamide (Compound 399a). Successively, it was formylated to give N-(4-methoxyphenyl)-4-formyl-7-methoxybenzofuran-2-carboxamide (Compound 399b), then compound 399b was reacted with cyclobutylamine to give compound 399 as a white solid.

Rf($CHCl_3$:MeOH=9:1); 0.23

EXAMPLE 400

4-Cyclooctylaminomethyl-7-methoxy-N-(4-methoxyphenyl)benzofuran-2-carboxamide (Compound 400)

Substantially the same procedure as in Example 399 was repeated using compound 399b obtained in Example 399 and cyclooctylamine to give compound 400 as a white solid.

Rf($CHCl_3$:MeOH=9:1); 0.31

EXAMPLE 401

4-(2,3-Dimethylcyclohexylaminomethyl)-7-methoxy-N-(4-methoxyphenyl)benzofuran-2-carboxamide (Compound 401)

Substantially the same procedure as in Example 399 was repeated using compound 399b obtained in Example 399 and 2,3-dimethylcyclohexylamine to give compound 401 as a white solid.

Rf($CHCl_3$:MeOH=9:1); 0.34

EXAMPLE 402

4-(4-Methyl-1-piperazinylmethyl)-7-methoxy-N-(4-methoxyphenyl)benzofuran-2-carboxamide (Comound 402)

Substantially the same procedure as in Example 399 was repeated using compound 399b obtained in Example 399 and 1-methylpiperazine to give compound 402 as a white solid.

Rf($CHCl_3$:MeOH=9:1); 0.21

EXAMPLE 403

4-(1-Pyrrolidinylmethyl)-7-methoxy-N-(4-methoxyphenyl)benzofuran-2-carboxamide (Compound 403)

Substantially the same procedure as in Example 399 was repeated using compound 399b obtained in Example 399 and pyrrolidine to give compound 403 as a white solid.

Rf($CHCl_3$:MeOH=9:1); 0.14

EXAMPLE 404

4-(2-Phenylethylaminomethyl)-7-methoxy-N-(4-methoxyphenyl)benzofuran-2-carboxamide (Compound 404)

Substantially the same procedure as in Example 399 was repeated using compound 399b obtained in Example 399 and 2-phenetylamine to give compound 404 as a white solid.

Rf($CHCl_3$:MeOH=9:1); 0.54

EXAMPLE 405

4-[1-(S)-Phenylethylaminomethyl]-7-methoxy-N-(4-methoxyphenyl)benzofuran-2-carboxamide (Compound 405)

Substantially the same procedure as in Example 399 was repeated using compound 399b obtained in Example 399 and 1-(S)-phenetylamine to give compound 404 as a white solid.

Rf($CHCl_3$:MeOH=9:1); 0.63

EXAMPLE 406

4-(3-Phenylpropylaminomethyl)-7-methoxy-N-(4-methoxyphenyl)benzofuran-2-carboxamide (Compound 406)

Substantially the same procedure as in Example 399 was repeated using compound 399b obtained in Example 399 and 3-phenylpropylamine to give compound 406 as a white solid.

Rf($CHCl_3$:MeOH=9:1); 0.41

EXAMPLE 407

4-[2-(2-Pyridyl)ethylamine)-7-methoxy-N-(4-methoxyphenyl)benzofuran-2-carboxamide (Compound 407)

Substantially the same procedure as in Example 399 was repeated using compound 399b obtained in Example 399 and 2-(2-pyridyl)ethylamine to give compound 407 as a white solid.

Rf($CHCl_3$:MeOH=9:1); 0.24

EXAMPLE 408

7-Methoxy-N-(4-methoxyphenyl)-4-(2-morpholinoethyl)aminomethylbenzofuran-2-carboxamide (Compound 408)

Substantially the same procedure as in Example 399 was repeated using compound 399b obtained in Example 399 and 2-morpholinoethylamine to give compound 408 as a white solid.

Rf($CHCl_3$:MeOH=9:1); 0.24

EXAMPLE 409

4-Cyclobutylaminomethyl-7-methoxy-N-(2-methoxyphenyl)benzofuran-2-carboxamide (Compound 409)

Substantially the same procedure as in Example 219 was repeated using a starting material, 7-methoxybenzofuran-2-carboxylic acid, and o-anisidineto give N-(2-methoxyphenyl)-7-methoxybenzofuran-2-carboxamide (Compound 409a). Successively, it was formylated to give N-(2-methoxyphenyl)-4-formyl-7-methoxybenzofuran-2-carboxamide (Compound 409b), then compound 409b was reacted with cyclobutylamine to give compound 409 as a white solid.

Rf($CHCl_3$:MeOH=9:1); 0.24

EXAMPLE 410

4-Cyclooctylaminomethyl-7-methoxy-N-(2-methoxyphenyl)benzofuran-2-carboxamide (Compound 410)

Substantially the same procedure as in Example 409 was repeated using compound 409b obtained in Example 409 and cyclooctylamine to give compound 410 as a white solid.

Rf($CHCl_3$:MeOH=9:1); 0.24

EXAMPLE 411

4-(2,3-Dimethylcyclohexylaminomethyl)-7-methoxy-N-(2-methoxyphenyl)benzofuran-2-carboxamide (Compound 411)

Substantially the same procedure as in Example 409 was repeated using compound 409b obtained in Example 409 and 2,3-dimethylcyclohexylamine to give compound 411 as a white solid.

Rf($CHCl_3$:MeOH=9:1); 0.31

EXAMPLE 412

4-(4-Methyl-1-piperazinylmethyl)-7-methoxy-N-(2-methoxyphenyl)benzofuran-2-carboxamide (Compound 412)

Substantially the same procedure as in Example 409 was repeated using compound 409b obtained in Example 409 and 1-methylpiperazine to give compound 412 as a white solid.

Rf($CHCl_3$:MeOH=9:1); 0.19

EXAMPLE 413

4-(1-Pyrrolidinylmethyl)-7-methoxy-N-(2-methoxyphenyl)benzofuran-2-carboxamide (Compound 413)

Substantially the same procedure as in Example 409 was repeated using compound 399b obtained in Example 409 and pyrrolidine to give compound 413 as a white solid.

Rf($CHCl_3$: MeOH=9:1); 0.12

EXAMPLE 414

4-(2-Phenylethylaminomethyl)-7-methoxy-N-(2-methoxyphenyl)benzofuran-2-carboxamide (Compound 414)

Substantially the same procedure as in Example 409 was repeated using compound 409b obtained in Example 409 and 2-phenetylamine to give compound 414 as a white solid.

Rf($CHCl_3$:MeOH=9:1); 0.50

EXAMPLE 415

4-[1-(S)-Phenylethylaminomethyl)-7-methoxy-N-(2-methoxyphenyl)benzofuran-2-carboxamide (Compound 415)

Substantially the same procedure as in Example 409 was repeated using compound 409b obtained in Example 409 and 1-(S)-phenetylamine to give compound 415 as a white solid.

Rf($CHCl_3$:MeOH=9:1); 0.58

EXAMPLE 416

4-(3-Phenylpropylaminomethyl)-7-methoxy-N-(2-methoxyphenyl)benzofuran-2-carboxamide (Compound 416)

Substantially the same procedure as in Example 409 was repeated using compound 409b obtained in Example 409 and 3-phenylpropylamine to give compound 416 as a white solid.

Rf($CHCl_3$: MeOH=9:1); 0.55

EXAMPLE 417

4-[2-(2-Pyridyl)ethylamine]-7-methoxy-N-(2-methoxyphenyl)benzofuran-2-carboxamide (Compound 417)

Substantially the same procedure as in Example 409 was repeated using compound 409b obtained in Example 409 and 2-(2-pyridyl)ethylamine to give compound 417 as a white solid.

Rf($CHCl_3$:MeOH=9:1); 0.29

EXAMPLE 418

7-Methoxy-N-(2-methoxyphenyl)-4-(2-morpholinoethyl)aminomethylbenzofuran-2-carboxamide (Compound 418)

Substantially the same procedure as in Example 409 was repeated using compound 409b obtained in Example 409 and 2-morpholinoethylamine to give compound 418 as a white solid.

Rf($CHCl_3$:MeOH=9:1); 0.33

Reference Example 1

7-Methoxy-2,2-dimethyl-2,3-dihydrobenzofuran-4-carbaldehyde] (Compound IIa)

(Step A) 2-(2-Methyl-2-propen-1-yloxy)-4-bromoanisole (Compound IIa-a)

A mixture of 5-bromo-2-methoxyphenol (17.8 g), 3-chloro-2-methyl-1-propene (13.0 ml), potassium carbonate (18.2 g), and DMF (150 ml) was stirred at 80° C. for 2 hours. The mixture was diluted with toluene, washed with a saturated saline and dried over anhydrous magnesium sulfate, and the solvent was distilled off to give Compound IIa-a (22.2 g, 98.4%) as a colorless oily substance.

NMR(DMSO-$d_6$, δ, ppm): 1.76(s, 3H), 3.76(s, 3H), 4.48 (s, 2H), 4.96(s, 1H), 5.05(s, 1H), 6.92(d, J=8.41 Hz, 1H), 7.04–7.11(m, 2H)

(Step B) 3-Bromo-6-methoxy-2-(2-methyl-2-propen-1-yl) phenol (Compound IIa-b)

Compound IIa-a (22.2 g) obtained in Step A was dissolved in 1-methylpyrrolidinone (50 ml) followed by stirring at 180° C. for 5 hours. The mixture was extracted with ethyl acetate, washed with a saturated saline and dried over anhydrous magnesium sulfate, and the solvent was distilled off. The residue was purified by silica gel column chromatography (chloroform) to give Compound IIa-b (19.6 g, 88.5%) as a colorless oily substance.

NMR(DMSO-$d_6$, δ, ppm): 1.74(s, 3H), 3.37(s, 2H), 3.79 (s, 3H), 4.31(s, 1H), 4.68(s, 1H), 6.81(d, J=8.58 Hz, 1H), 7.00(d, J=8.91 Hz, 1H)

(Step C) 4-Bromo-7-methoxy-2,2-dimethyl-2,3-dihydrobenzofuran (Compound IIa-c)

Compound IIa-b (19.6 g) obtained in Step B was dissolved in 88% formic acid (80 ml) followed by stirring at room temperature for 24 hours. The mixture was neutralized with an aqueous solution of sodium bicarbonate and extracted with toluene. The organic layer was washed with a saturated saline and dried over anhydrous magnesium sulfate, and the solvent was distilled off. The residue was purified by silica gel column chromatography (chloroform) to give Compound IIa-c (16.3 g, 83.3%) as an oily substance.

NMR(DMSO-$d_6$, δ, ppm): 1.43(s, 6H), 2.99(s, 2H), 3.74 (s, 3H), 6.79(d, J=8.58 Hz, 1H), 6.93(d, J=8.57 Hz, 1H)

MASS(m/z): 258, 256($M^+$)

(Step D) (Compound IIa)

Under an argon atmosphere, a solution (300 ml) of Compound IIa-c (20.0 g) obtained in Step C in THF was cooled to −78° C., and then a 1.69M solution (50.6 ml) of butyl lithium in hexane was dropwise added thereto. The reaction solution was gradually warmed and stirred at −20° C. for one hour, and then DMF (200 ml) was dropwise added thereto, followed by stirring at room temperature for 2 hours. A small amount of water was added to the reaction solution and the mixture was extracted with ether. The organic layer was washed with a saturated saline and dried over anhydrous magnesium sulfate, and the solvent was distilled off under reduced pressure. The residue was purified by silica gel column chromatography (chloroform/hexane=9/1) to give Compound IIa (7.11 g, 44.3%) as colorless crystals.

NMR(DMSO-$d_6$, δ, ppm): 1.41(s, 6H), 3.28(s, 2H), 3.84 (s, 3H), 7.04(d, J=8.25 Hz, 1H), 7.39(d, J=8.24 Hz, 1H), 9.85(s, 1H)

MASS (m/z): 206, 191

Reference Example 2

2,2-Diethyl-7-methoxy-2,3-dihydrobenzofuran-4-carbaldehyde] (Compound IIb)

(Step A) 4-Bromo-2-(3-oxopentan-2-yloxy)anisole (Compound IIb-a)

A mixture of 5-bromo-2-methoxyphenol (50.0 g), 2-bromo-3-pentanone (68.1 g), potassium carbonate (52.8 g), and DMF (500 ml) was stirred at 70° C. for 2 hours. After being allowed to stand for cooling, water was added to the mixture followed by extraction with ether. The organic layer was washed with a saturated saline and dried over anhydrous magnesium sulfate, and the solvent was distilled off. The residue was purified by silica gel column chromatography (hexane:chloroform=1:1) to give Compound IIb-a (86.8 g, 94.0%) as a pale-yellow oily substance.

NMR(DMSO-$d_6$, δ, ppm): 0.93(t, J=7.4 Hz, 3H), 1.39(d, J=6.9 Hz, 3H), 2.47–2.75(m, 2H), 3.77(s, 3H), 4.92(q, J=6.9 Hz, 1H), 6.96(d, J=8.9 Hz, 1H), 7.00 (d, J=2.7 Hz, 1H), 7.10(dd, J=8.9 Hz, 2.5 Hz, 1H)

MASS(m/e): 287($M^+$), 285

(Step B) 4-Bromo-2-(3-methylenepentan-2-yloxy)anisole (Compound IIb-b)

Methyltriphenylphosphonium bromide (308.1 g) was suspended in THF (1 l), and potassium t-butoxide (92.4 g) was added thereto under ice-cooling, followed by stirring for one hour under ice-cooling. A solution of Compound IIb-a (86.0 g) obtained in Step A in THF (500 ml) was dropwise added to the suspension under ice-cooling, followed by stirring for 2 hours. Water was added to the mixture and the resultant was extracted with ethyl acetate. The organic layer was washed with a saturated saline and and dried over anhydrous magnesium sulfate. The residue was purified by silica gel column chromatography (hexane:chloroform=1:1) to give Compound IIb-b (74.8 g, 87.9%) as a pale-yellow oily substance.

NMR(DMSO-$d_6$, δ, ppm): 1.00(t, J=7.4 Hz, 3H), 1.37(d, J=6.4 Hz, 3H), 2.04(m, 2H), 3.32(s, 3H), 4.84–4.91(m, 1H), 4.86(s, 1H), 5.05(s, 1H), 6.90(d, J=7.4 Hz, 1H), 7.02–7.05 (m, 2H)

MASS(m/e): 286, 284($M^+$)

(Step C) 3-Bromo-2-(2-ethyl-2-buten-1-yl)-6-methoxyphenol (Compound IIb-c)

Compound IIb-b (62.0 g) obtained in Step B was dissolved in 1-methylpyrrolidinone (68 ml) followed by stirring at 170° C. for 2 hours. After being allowed to stand for cooling, a saturated saline was added to the mixture followed by extraction with ethyl acetate. The organic layer was dried over anhydrous magnesium sulfate and the solvent was distilled off to give Compound IIb-c (73.9 g) as a crude pale-yellow oily substance.

NMR(DMSO-$d_6$, δ, ppm): 0.99(t, J=7.4 Hz, 3H), 1.48(d, J=6.9 Hz, 3H), 2.04(q, J=7.4 Hz, 2H), 3.37(s, 2H), 4.71(q, J=6.9 Hz, 1H), 6.79(d, J=8.9 Hz, 1H), 6.98 (d, J=8.91 Hz, 1H), 8.86(broad s, 1H)

MASS(m/e): 286, 284($M^+$)

(Step D) 4-Bromo-2,2-diethyl-7-methoxy-2,3-dihydrobenzofuran (Compound IIb-d)

Compound IIb-c (73.9 g) obtained in Step C was dissolved in methanol (740 ml), and sulfuric acid (74 ml) was dropwise added thereto under ice-cooling, followed by heating under reflux for 3 hours. After being allowed to stand for cooling, the mixture was concentrated and water was added thereto, followed by extraction with ethyl acetate. The organic layer was washed with a saturated saline and dried over-anhydrous magnesium sulfate, and the solvent was distilled off. The residue was purified by silica gel column chromatography (hexane:ethyl acetate=8:1) to give Compound IIb-d (70.9 g, 83.0% from Compound IIb-b) as a pale-yellow oily substance.

NMR(DMSO-$d_6$, δ, ppm): 0.86(t, J=7.4 Hz, 6H), 1.69(q, J=7.4 Hz, 4H), 2.95(s, 2H), 3.73(s, 3H), 6.77(d, J=8.9 Hz, 1H), 6.90(d, J=8.4 Hz, 1H)

(Step E) 2,2-Diethyl-7-methoxy-2,3-dihydrobenzofuran-4-carbaldehyde (Compound IIb)

Under an argon atmosphere, a solution (600 ml) of Compound IIb-d (61.6 g) obtained in Step D in THF was cooled to −78° C., and then a 1.69M solution (197 ml) of n-butyl lithium in hexane was dropwise added, followed by stirring at the same temperature for 2 hours. DMF (37 ml) was added to the reaction solution and the mixture was stirred at room temperature for 2 hours. A small amount of water was added to the reaction solution and the mixture was extracted with ethyl acetate. The organic layer was washed with a saturated saline and dried over anhydrous magnesium sulfate, and the solvent was distilled off. The residue was purified by silica gel column chromatography (ethyl acetate/hexane=1/5) to give Compound IIb (43.6 g, 86.0%) as colorless crystals.

NMR(DMSO-$d_6$, δ, ppm): 0.85(t, J=7.4 Hz, 6H), 1.70(q, J=7.4 Hz, 4H), 3.26(s, 2H), 3.87(s, 3H), 7.03(d, J=8.4 Hz, 1H), 7.38(d, J=8.4 Hz, 1H), 9.88(s, 1H)

MASS(m/e): 234($M^+$), 205

Reference Example 3

7-Methoxy-spiro[2,3-dihydrobenzofuran-2,1'-cyclopentane]-4-carbaldehyde (Compound IIc)
(Step A) 4-Bromo-2-(2-oxocyclopentyloxy)anisole (Compound IIc-a)

A mixture of 5-bromo-2-methoxyphenol (120.0 g), 2-chloro-1-cyclopentanone (100.0 g), potassium carbonate (163.3 g), and DMF (1.2 l) was stirred at 70° C. for 3 hours. After being allowed to stand for cooling, water was added to the mixture followed by extraction with ethyl acetate. The organic layer was washed with a saturated saline and dried over anhydrous magnesium sulfate, and the solvent was distilled off. The residue was purified by silica gel column chromatography (hexane:ethyl acetate=9:1) to give Compound IIc-a (141.43 g, 83.9%) as a pale-yellow oily substance.

NMR(DMSO-$d_6$, δ, ppm): 1.78–1.99(m, 3H), 2.21–2.40 (m, 3H), 3.74(s, 3H), 4.95(t, J=7.9 Hz, 1H), 6.92(d, J=9.4 Hz, 1H), 7.09(dd, J=2.0 Hz, 9.4 Hz, 1H), 7.22 (d, J=2.0 Hz, 1H)

MASS(m/z): 286, 284($M^+$)

(Step B) 4-Bromo-2-(2-methylenecyclopentyloxy)anisole (Compound IIc-b)

Methyltriphenylphosphonium bromide (510.3 g) was suspended in THF (2.5 l), and potassium t-butoxide (153.1 g) was added thereto under ice-cooling, followed by stirring for 3 hours under ice-cooling. A solution of Compound IId-a (141.43 g) obtained in Step A in THF (1.0 l) was dropwise added to the suspension under ice-cooling, followed by stirring for one hour. Water was added to the mixture followed by extraction with ether. The organic layer was washed with a saturated saline and and dried over anhydrous magnesium sulfate. The residue was purified by silica gel column chromatography (hexane:chloroform=1:1) to give Compound IIc-b (108.4 g, 70.7%) as a pale-yellow oily substance.

NMR(DMSO-$d_6$, δ, ppm): 1.66–1.98(m, 4H), 2.21–2.42 (m, 2H), 3.74(s, 3H), 5.01–5.05(m, 3H), 6.92(d, J=8.6 Hz, 1H), 7.08(dd, J=1.0 Hz, 8.6 Hz, 1H), 7.22 (d, J=1.0 Hz, 1H)

MASS(m/e): 284, 282($M^+$)

(Step C) 3-Bromo-2-[(2-cyclopenten-1-yl)methyl]-6-methoxyphenol (Compound IIc-c)

Compound IIc-b (108.4 g) obtained in Step B was dissolved in 1-methylpyrrolidinone (110 ml) followed by stirring at 170° C for 3 hours. After being allowed to stand for cooling, a saturated saline was added to the mixture followed by extraction with ethyl acetate. The organic layer was dried over anhydrous magnesium sulfate and the solvent was distilled off to give Compound IIc-c (129.7 g) as a crude pale-yellow oily substance.

NMR(DMSO-$d_6$, δ, ppm): 1.78(m, 2H), 2.19–2.25(m, 4H), 3.43(s, 2H), 3.78(s, 3H), 5.06(t, J=2.0 Hz, 1H), 6.79(d, J=8.9 Hz, 1H), 6.99(d, J=8.9 Hz, 1H), 8.92(s, 1H)

MASS(m/e): 285, 283($M^+$)

(Step D) 4-Bromo-7-methoxy-spiro[2,3-dihydrobenzofuran-2,1'-cyclopentane] (Compound IIc-d)

Compound IIc-c (129.7 g) obtained in Step C was dissolved in methanol (1.3 l), and sulfuric acid (130 ml) was dropwise added thereto under ice-cooling, followed by heating under reflux for 3 hours. After being allowed to stand for cooling, water was added followed by extraction with ethyl acetate. The organic layer was successively washed with a saturated aqueous solution of sodium bicarbonate and a saturated saline and dried over anhydrous magnesium sulfate, and the solvent was distilled off. The residue was purified by silica gel column chromatography (hexane:ethyl acetate=9:1) to give Compound IIc-d (102.7 g, 94.7% yield from Compound IId-b) as pale-yellow crystals.

Melting point: 45–47° C.

NMR(DMSO-$d_6$, δ, ppm): 1.71–1.80(m, 6H), 1.96–2.01 (m, 2H), 3.16(s, 2H), 3.74(s, 3H), 6.78(d, J=8.4 Hz, 1H), 6.92(d, J=8.4 Hz, 1H)

MASS(m/e): 285, 283($M^+$)

(Step E) (Compound IIc)

Under an argon atmosphere, a solution (700 ml) of Compound IIc-d (102.7 g) obtained in Step D in THF was cooled to −78° C., and then a 1.56M solution (360 ml) of n-butyl lithium in hexane was dropwise added thereto, followed by stirring at the same temperature for one hour. DMF (62 ml) was added to the reaction solution and the mixture was stirred at the same temperature for 2 hours. A small amount of water was added to the reaction solution and the mixture was extracted with ethyl acetate. The organic layer was washed with a saturated saline and dried over anhydrous magnesium sulfate, and the solvent was distilled off. The residue was purified by silica gel column chromatography (chloroform) to give Compound IIc (77.4 g, 91.9%) as colorless crystals.

Melting point: 50–52° C.

NMR(DMSO-$d_6$, δ, ppm): 1.75–1.86(m, 6H), 1.92–2.02 (m, 2H), 3.46(s, 2H), 3.86(s, 3H), 7.04(d, J=8.4 Hz, 1H), 7.40(d, J=8.4 Hz, 1H), 9.88(s, 1H)

MASS(m/e): 232($M^+$)

Reference Example 4

7-Methoxy-spiro[2,3-dihydrobenzofuran-2,1'-cyclohexane]-4-carbaldehyde (Compound IId) (Step A) 4-Bromo-2-(2-oxocyclohexyloxy)anisole (Compound IId-a)

A mixture of 5-bromo-2-methoxyphenol (120.0 g), 2-chloro-1-cyclohexanone (108.0 g), potassium carbonate (163.3 g), and DMF (1.2 l) was stirred at 70° C. for 3 hours. After being allowed to stand for cooling, water was added to the mixture followed by extraction with ethyl acetate. The organic layer was washed with a saturated saline and dried over anhydrous magnesium sulfate, and the solvent was distilled off. The residue was purified by silica gel column chromatography (hexane:ethyl acetate=9:1) to give Compound IId-a (138.5 g, 78.3%) as pale-yellow crystals.

Melting point: 71–73° C.

NMR(DMSO-$d_6$, δ, ppm): 1.54–2.02(m, 5H), 2.28–2.33 (m, 2H), 2.50–2.73(m, 1H), 3.75(s, 3H), 5.03(m, 1H), 6.91 (d, J=8.4 Hz, 1H), 6.98(d, J=2.5 Hz, 1H), 7.04 (dd, J=8.4 Hz, 2.0 Hz, 1H)

MASS(m/e): 300, 298($M^+$), 204, 202

(Step B) 4-Bromo-2-(2-methylenecyclohexyloxy)anisole (Compound IId-b)

Methyltriphenylphosphonium bromide (476.0 g) was suspended in THF (1.3 l), and potassium t-butoxide (143.0 g) was added thereto under ice-cooling, followed by stirring for 3 hours under ice-cooling. A solution of Compound IId-a (138.5 g) obtained in Step A in THF (1.0 l) was dropwise added to the suspension under ice-cooling, followed by stirring at room temperature for one hour. Water was added to the mixture followed by extraction with ether. The organic layer was washed with a saturated saline and dried over anhydrous magnesium sulfate. The residue was purified by silica gel column chromatography (hexane:chloroform=1:1) to give Compound IId-b (133.7 g, 97.3%) as a pale-yellow oily substance.

NMR(DMSO-$d_6$, δ, ppm): 1.44–1.89(m, 6H), 2.06–2.11 (m, 1H), 2.26–2.30(m, 1H), 3.76(s, 3H), 4.76(t, J=4.0 Hz, 1H), 4.79(s, 2H), 6.90(d, J=8.4 Hz, 1H), 7.05(dd, J=2.5 Hz, 8.4 Hz, 1H), 7.08(d, J=2.5 Hz, 1H)

MASS(m/e): 298, 296($M^+$), 204, 202

(Step C) 3-Bromo-2-[(2-cyclohexen-1-yl)methyl]-6-methoxyphenol (Compound IId-c)

Compound IId-b (133.7 g) obtained in Step B was dissolved in 1-methylpyrrolidinone (160 ml) followed by stirring at 170° C. for 2 hours. After being allowed to stand for cooling, a saturated saline was added to the mixture followed by extraction with ethyl acetate. The organic layer was dried over anhydrous magnesium sulfate and the solvent was distilled off to give Compound IId-c (169.5 g) as a crude pale-yellow oily substance.

NMR(DMSO-$d_6$, δ.ppm): 1.44–1.59(m, 4H), 1.87–1.99 (m, 4H), 3.31(s, 2H), 3.79(s, 3H), 5.05(t, J.=1.5 Hz, 1H), 6.78(d, J=8.9 Hz, 1H), 6.98(d, J=8.9 Hz, 1H), 8.85(s, 1H)

MASS(m/e): 298, 296($M^+$), 217, 215

(Step D) 4-Bromo-7-methoxy-spiro[2,3-dihydrobenzofuran-2,1'-cyclohexane] (Compound IId-d)

Compound IId-c (169.5 g) obtained in Step C was dissolved in methanol (1.4 l), and sulfuric acid (170 ml) was dropwise added thereto under ice-cooling, followed by heating under reflux for 2 hours. After being allowed to stand for cooling, the mixture was concentrated, and water was added thereto, followed by extraction with ethyl acetate. The organic layer was successively washed with a saturated aqueous solution of sodium bicarbonate and a saturated saline and dried over anhydrous magnesium sulfate, and the solvent was distilled off. The residue was purified by silica gel column chromatography (hexane:ethyl acetate=9:1) to give Compound IId-d (127.8 g, 95.6% from Compound IId-b) as orange-yellow crystals.

NMR(DMSO-$d_6$, δ, ppm): 1.43–1.50(m, 4H), 1.65–1.77 (m, 6H), 2.94(s, 2H), 3.74(s, 3H), 6.78(d, J=8.4 Hz, 1H), 6.92(d, J=8.4 Hz, 1H)

MASS(m/e): 298, 296($M^+$), 217, 215

(Step E) (Compound IId)

Under an argon atmosphere, a solution (1.0 l) of Compound IId-d (100.0 g) obtained in Step D in THF was cooled to −78° C., and a 1.70M solution (307 ml) of n-butyl lithium in hexane was dropwise added thereto, followed by stirring at the same temperature for one hour. DMF (60 ml) was added to the reaction solution and the mixture was stirred at the same temperature for 2 hours. A small amount of water was added to the reaction solution followed by extraction with ethyl acetate. The organic layer was washed with a saturated saline and dried over anhydrous magnesium sulfate, and the solvent was distilled off. The residue was purified by silica gel column chromatography (hexane/ethyl acetate=6/1) to give Compound IId (78.9 g, 95.1%) as colorless crystals.

NMR(DMSO-$d_6$, δ, ppm): 1.30–1.61(m, 4H), 1.66–1.76 (m, 6H), 3.25(s, 2H), 3.87(s, 3H), 7.04(d, J=8.4 Hz, 1H), 7.39(d, J=8.4 Hz, 1H), 9.87(s, 1H)

MASS(m/e): 246($M^+$)

Reference Example 5

(±)-7-Methoxy-3-methyl-2,3-dihydrobenzofuran-4-carbaldehyde (Compound IIe)

(Step A) 3-Allyloxy-2-bromo-4-methoxybenzaldehyde (Compound IIe-a)

2-Bromo-3-hydroxy-4-methoxybenzaldehyde (1.68 g) was dissolved in DMF (17 ml), and sodium hydride (0.209 g) was added thereto under ice-cooling, followed by stirring for 30 minutes. Allyl bromide (0.944 ml) was added to the mixture, followed by stirring at 60° C. for one hour. After being allowed to stand for cooling, water was added to the mixture and the precipitated solid was collected by filtration. The obtained crude crystals were recrystallized from isopropanol to give Compound IIe-a (1.30 g, 66%).

Melting point: 75–78° C.

NMR($CDCl_3$, δ, ppm): 3.96(s, 3H), 4.57(d, J=8.3 Hz, 2H), 5.19–5.50(m, 2H), 6.02–6.27(m, 1H), 6.95(d, J=9.3 Hz, 1H), 7.75(d, J=9.3 Hz, 1H), 10.27(s, 1H)

(Step B) (Compound IIe)

A mixture of Compound IIe-a (0.436 g) obtained in Step A, tributyltin hydride (0.519 ml), and azobisiso-butyronitrile (AIBN) (26.4 mg) was heated under reflux for 5 hours. Further, tributyltin hydride (1.3 ml) and AIBN (52 mg) were added to the mixture followed by heating under reflux one night. After being allowed to stand for cooling, ether and a 50% aqueous solution of KF were added to the mixture, followed by stirring at room temperature for 5 hours. The insoluble matters were filtered off and the filtrate was extracted with ether. The organic layer was dried over anhydrous magnesium sulfate and concentrated. The residue was purified by silica gel column chromatography (toluene/ethyl acetate=20/1) to give Compound IIe (0.184 g, 60%) as an oily substance.

NMR($CDCl_3$, δ, ppm): 1.31(d, J=7.2 Hz, 3H), 3.86–4.07 (m, 1H), 3.97(s, 3H), 4.40(dd, J=8.8 Hz, 4.5 Hz, 1H), 4.60–4.72(m, 1H), 6.89(d, J=9.0 Hz, 1H), 7.36(d, J=9.0 Hz, 1H), 9.91(s, 1H)

Reference Example 6

7-Methoxy-2-(4-pyridyl)benzofuran-4-carbaldehyde (Compound IIf)

(Step A) 7-Methoxy-2-(4-pyridyl)benzofuran (Compound IIf-a)

Ortho-vanillin (93.0 g) and 4-picolyl chloride hydrochloride (100 g) as starting materials were dissolved in DMF (1200 ml), and potassium carbonate (337 g) and potassium iodide (30 g) were added thereto, followed by heating under reflux for 24 hours while stirring. The reaction solution was filtered using celite, the solvent was distilled off under reduced pressure, and the residue was extracted with ethyl acetate. The organic layer was washed with a saturated saline and dried over anhydrous magnesium sulfate, and the solvent was distilled off under reduced pressure. The residue was purified by silica gel column chromatography (hexane:ethyl acetate=1:2) and further washed with diethyl ether to give Compound IIf-a (26.7 g, 19.4%) as pale-yellow needles.

NMR($CDCl_3$, δ, ppm): 4.04(s, 3H), 6.84(dd, J=2 Hz, 7 Hz, 1H), 7.1–7.2(m, 3H), 7.70(d, J=6 Hz, 2H), 8.65(d, J=6 Hz, 2H)

MASS(m/e): 225($M^+$)

(Step B) (Compound IIf)

Under a nitrogen stream, Compound IIf-a (3.70 g) obtained in Step A was dissolved in dichloromethane (60 ml) followed by stirring at −10° C., and titanium tetrachloride (4.00 ml) dissolved in dichloromethane (10 ml) was dropwise added thereto over 5 minutes at the same temperature. Then, dichloromethyl methyl ether (1.60 ml) was added to the mixture at the same temperature, and the mixture was warmed to room temperature followed by stirring for 20 minutes. The reaction solution was poured into ice-water containing potassium hydroxide (about 10 g) followed by stirring for some time, and the mixture was filtered using celite. The filtrate was extracted with ethyl acetate, the organic layer was washed with a saturated saline and dried over anhydrous magnesium sulfate, and the solvent was distilled off under reduced pressure. The residue was purified by silica gel column chromatography (hexane:ethyl acetate=1:2) to give Compound IIf (2.60 g, 62.9%) as a white solid.

Melting point: 178–179° C.

NMR($CDCl_3$, δ, ppm): 4.15(s, 3H), 6.96(d, J=8 Hz, 1H), 7.72(d, J=8 Hz, 1H), 7.78(d, J=6 Hz, 2H), 8.01(s, 1H), 8.72(d, J=6 Hz, 2H), 10.06(s, 1H)

MASS(m/e): 254($M^+$+1), 224

IR(KBr, $cm^{-1}$): 1670, 1606, 1573

Reference Example 7

7-Methoxy-2-(2-pyridyl)benzofuran-4-carbaldehyde (Compound IIg)

(Step A) 7-Methoxy-2-(2-pyridyl)benzofuran (Compound IIg-a)

Substantially the same procedure as in Step A of Reference Example 6 was repeated using ortho-vanillin (10.0 g) and using 2-picolyl chloride hydrochloride (11.0 g) instead of 4-picolyl chloride hydrochloride to give Compound IIg-a (4.23 g, 26.5%) as colorless needles.

NMR($CDCl_3$, δ, ppm): 4.03(s, 3H), 6.84(dd, J=1 Hz, 8 Hz, 1H), 7.18(dd, J=8 Hz, 8 Hz, 1H), 7.23(ddd, J=1 Hz, 5 Hz, 8 Hz, 1H), 7.25(dd, J=1 Hz, 8 Hz, 1H), 7.45(s, 1H), 7.76(ddd, J=2 Hz, 8 Hz, 8 Hz, 1H), 7.98(ddd, J=1 Hz, 1 Hz, 8 Hz, 1H), 8.65(ddd, J=1 Hz, 2 Hz, 5 Hz, 1H)

MASS(m/e): 225($M^+$)

(Step B) (Compound IIg)

Substantially the same procedure as in Step B of Reference Example 6 was repeated using Compound IIg-a (5.00 g) obtained in Step A to give Compound IIg (3.81 g, 67.8%) as a white solid.

Melting point: 143–144° C.

NMR($CDCl_3$, δ, ppm): 4.11(s, 3H), 6.92(d, J=9 Hz, 1H), 7.27(dd, J=6 Hz, 8 Hz, 1H), 7.72(d, J=9 Hz, 1H), 7.79(ddd, J=2 Hz, 8 Hz, 8 Hz, 1H), 7.95(d, J=8 Hz, 1H), 8.12(s, 1H), 8.72(dd, J=2 Hz, 6 Hz, 1H), 10.09(s, 1H)

MASS (m/e): 253 ($M^+$), 252

IR(KBr.$cm^{-1}$): 1670, 1575, 1475, 1309

Reference Example 8

7-Methoxy-2-phenylbenzofuran-4-carbaldehyde (Compound IIh)

(Step A) 7-Methoxy-2-(4-nitrophenyl)benzofuran (Compound IIh-a)

Substantially the same procedure as in Step A of Reference Example 6 was repeated using ortho-vanillin (50.0 g) and using 4-nitrobenzyl chloride (59.0 g) instead of 4-picolyl chloride hydrochloride to give Compound IIh-a (53.0 g, 59.8%) as a yellow solid.

NMR($CDCl_3$, δ, ppm): 4.03(s, 3H), 6.89(dd, J=2 Hz, 8 Hz, 1H), 7.1–7.3(m, 3H), 8.00(d, J=9 Hz, 2H), 8.29(d, J=9 Hz, 2H)

MASS(m/e): 269($M^+$), 239, 223

(Step B) 7-Methoxy-2-phenylbenzofuran (Compound IIh-b)

Compound IIh-a (26.0 g) obtained in Step A was dissolved in ethanol (400 ml)/distilled water (40 ml), and reduced iron (26.0 g) and iron (III) chloride (1.56 g) were added thereto, followed by heating under reflux for 2 hours. The reaction solution was filtered using celite, the filtrate was concentrated under reduced pressure, and the residue was extracted with ethyl acetate. The organic layer was dried over magnesium sulfate and the solvent was distilled off under reduced pressure. The residue was dissolved in tetrahydrofuran (400 ml), and sodium nitrite (10 g) and phosphinic acid (a 32–36% aqueous solution, 400 ml) were added thereto with stirring at 0° C., followed by stirring for 7 hours. The reaction solution was adjusted to alkaline by slowly adding a 1N aqueous solution of potassium hydroxide, and then the organic layer was extracted with dichloromethane. The organic layer was dried over magnesium sulfate and the solvent was distilled off under reduced pressure. The residue was purified by silica gel column chromatography (hexane:ethyl acetate=8:1) to give Compound IIh-b (16.6 g, 77.1%) as a white solid.

NMR($CDCl_3$, δ, ppm): 4.06(s, 3H), 6.81(dd, J=2 Hz, 7 Hz, 1H), 7.02(s, 1H), 7.15(dd, J=7 Hz, 7 Hz, 1H), 7.17 (t, J=7 Hz, 1H), 7.36(dd, J=2 Hz, 7 Hz, 1H), 7.44 (dd, J=7 Hz, 8 Hz, 2H), 7.89(d, J=8 Hz, 2H)

MASS(m/e): 224($M^+$)

(Step C) (Compound IIh)

Substantially the same procedure as in Step B of Reference Example 6 was repeated using Compound IIh-b (16.0 g) obtained in Step B to give Compound IIh (6.86 g, 38.0%) as a white solid.

Melting point: 110–111° C.

NMR($CDCl_3$, δ, ppm): 4.12(s, 3H), 6.87(d, J=9 Hz, 1H), 7.3–7.5(m, 3H), 7.62(d, J=9 Hz, 1H), 7.78(s, 1H), 7.91(d, J=8 Hz, 2H), 10.05(s, 1H)

MASS(m/e): 252($M^+$), 251

IR(KBr, $cm^{-1}$): 1683, 1621, 1581, 1396, 1265, 1174

Reference Example 9

2-Cyano-7-methoxybenzofuran-4-carbaldehyde (Compound IIi)

A mixture of 2-cyano-7-methoxybenzofuran (4.17 g), hexamethylenetetramine (3.38 g), and trifluoroacetic acid (62 ml) was stirred at 60 to 70° C. for one hour. The mixture was concentrated and the residue was purified by silica gel column chromatography (toluene/ethyl acetate=20/1) to give Compound IIi (1.02 g, 21%) as colorless crystals.

Melting point: 170–178° C.

NMR($CDCl_3$, δ, ppm): 4.14(s, 3H), 7.10(d, J=8.1 Hz, 1H), 7.82(d, J=8.1 Hz, 1H), 8.21(s, 1H), 10.05(s, 1H)

Reference Example 10

3-Ethoxycarbonylmethyl-7-methoxybenzofuran-4-carbaldehyde (Compound IIj)

(Step A) 3-[(E)-3-Ethoxycarbonyl-2-propen-1-oxy]-2-iodo-4-methoxybenzaldehyde (Compound IIj-a)

Substantially the same procedure as in Step A of Reference Example 1 was repeated using 3-hydroxy-2-iodo-4-methoxybenzaldehyde (13 g) to give Compound IIj-a (18 g, 100%) as a dark brown oily substance.

NMR($CDCl_3$, δ, ppm): 1.32(t, J=7 Hz, 3H), 3.95(s, 3H), 4.24(q, J=7 Hz, 2H), 4.68(dd, J=2 Hz, 4 Hz, 2H), 6.35(dt, J=2 Hz, 16 Hz, 1H), 7.00(d, J=9 Hz, 1H), 7.13(dt, J=4 Hz, 16 Hz, 1H), 7.75(d, J=9 Hz, 1H), 10.0(s, 1H)

MASS(m/e): 390($M^+$)

(Step B) (Compound IIj)

A mixture of Compound IIj-a (18 g) obtained in Step A, THF-acetonitrile (1:1) (18 ml), triethylamine (7.8 ml), and palladium acetate (0.73 g) was heated under reflux for 3 hours. The catalyst was removed and the filtrate was concentrated. Ethyl acetate was added to the residue, and the mixture was washed with dilute hydrochloric acid and a saturated saline and dried over sodium sulfate. The solvent was distilled off and the residue was purified by silica gel column chromatography (hexane:ethyl acetate=2:1) to give Compound IIj (11 g, 87%) as pale-yellow crystals.

Melting point: 45–50° C.

NMR($CDCl_3$, δ, ppm): 1.27(t, J=7 Hz, 3H), 4.05(s, 2H), 4.09(s, 3H), 4.18(q, J=7 Hz, 2H), 6.91(d, J=9 Hz, 1H), 7.70(d, J=9 Hz, 1H), 9.93(s, 1H)

Reference Example 11

Methyl 2,2-diethyl-7-methoxy-2,3-dihydrobenzofuran-4-carboxylate (Compound IIk)

(Step A) Methyl 4-methoxy-3-(1-methyl-2-oxobutan-1-yloxy)benzoate (Compound IIk-a)

A mixture of methyl 3-hydroxy-4-methoxy benzoate (19.3 g), 2-bromo-3-pentanone (19.2 ml), potassium carbonate (29.3 g), and DMF (193 ml) was stirred at 90° C. for 2 hours. After being allowed to stand for cooling, water was added to the mixture followed by extraction with toluene. The organic layer was washed with a saturated saline and dried over sodium sulfate, and the solvent was distilled off. The residue was purified by column chromatography (silica gel, hexane:ethyl acetate=3:1) to give Compound IIk-a (25.8 g, 91.5%) as a colorless oily substance.

NMR($CDCl_3$, δ, ppm): 1.08(t, J=5.8 Hz, 3H), 1.52(d, J=7.0 Hz, 3H), 2.47–2.90(m, 2H), 3.88(s, 3H), 3.93(s, 3H), 4.71(q, J=7.0 Hz, 1H), 6.92(d, J=8.6 Hz, 1H), 7.47(d, J=1.0 Hz, 1H), 7.74(dd, J=1.0 Hz, 8.6 Hz, 1H)

MASS(m/e): 266($M^+$)

(Step B) Methyl 4-methoxy-3-(1-methyl-2-methylenebutan-1-yloxy)benzoate (Compound IIk-b)

Methyltriphenylphosphonium bromide (48.5 g) was suspended in ether (485 ml), and a 1.7N solution (78.8 ml) of n-butyl lithium in hexane was dropwise added thereto under ice-cooling. The mixture was stirred at room temperature for 30 minutes and then cooled with ice again. Compound IIb-a (25.8 g) obtained in Step A was dissolved in ether (120 ml). The solution was dropwise added to the mixture, followed by stirring for 30 minutes under ice-cooling. Water was added to the mixture followed by extraction with ethyl acetate. The organic layer was washed with a saturated saline and dried over sodium sulfate, and the solvent was distilled off. The residue was purified by column chromatography (silica gel, hexane:ethyl acetate=10:1) to give Compound IIk-b (20.5 g, 80%) as a colorless oily substance.

NMR($CDCl_3$, δ, ppm): 1.10(t, J=7.6 Hz, 3H), 1.51(d, J=7.0 Hz, 3H), 2.02–2.20(m, 2H), 3.88(s, 3H), 3.91(s, 3H), 4.81(q, J=7.0 Hz, 1H), 4.90(s, 1H), 5.10(s, 1H), 6.88(d, J=8.4 Hz, 1H), 7.53(d, J=1.1 Hz, 1H), 7.65(dd, J=1.1 Hz, 8.4 Hz, 1H)

MASS(m/e): 264($M^+$)

(Step C) Methyl 3-hydroxy-4-methoxy-2-(2-ethyl-2-buten-1-yl)benzoate (Compound IIk-c)

Compound IIk-b (20.3 g) obtained in Step B was dissolved in 1-methylpiperidone (22 ml) followed by stirring at 120° C. one night and then at 180° C. for 2 hours. After being allowed to stand for cooling, a saturated saline was added to the mixture followed by extraction with ethyl acetate. The organic layer was dried over sodium sulfate and the solvent was distilled off. The residue was purified by column chromatography (silica gel, hexane:ethyl acetate=10:1) to give an oily Compound IIk-c (17.0 g, 84%) as a mixture of isomers (5:1).

NMR($CDCl_3$, δ, ppm): 0.89(t, J=7.6 Hz, 0.2H), 1.06(t, J=7.6 Hz, 0.8H), 1.52(d, J=7.7 Hz, 0.8H), 1.75(d, J=7.7 Hz, 0.2H), 2.10 and 2.12(each q, J=7.6 Hz, total 2H), 3.77 and 3.78(each s, total 2H), 3.81 and 3.82(each s, total 3H), 3.91 and 3.92 (each s, total 3H), 4.80(q, J=7.7 Hz, 0.8 Hz), 5.31(q, J=7.7 Hz, 0.2H), 5.79(s, 0.8H), 5.87(s, 0.2H), 6.74 and 6.76(each d, J=8.4 Hz, total 1H), 7.40 (d, J=8.4 Hz, 0.2H), 7.49(d, J=8.4 Hz, 0.8H)

MASS(m/e): 264($M^+$)

(Step D) Methyl 2,2-diethyl-7-methoxy-2,3-dihydrobenzofuran-4-carboxylate (Compound IIk)

Compound IIk-c (16.8 g) obtained in Step C was dissolved in methanol (170 ml), and sulfuric acid (20 ml) was dropwise added thereto under ice-cooling, followed by heating under refluxone night. After being allowed to stand for cooling, the mixture was concentrated and poured into a 1N aqueous solution of sodium hydroxide under ice-cooling. The mixture was extracted with ethyl acetate, and the organic layer was washed with a saturated saline and dried over sodium sulfate. The solvent was distilled off, and the residue was purified by column chromatography (silica gel, hexane:ethyl acetate=10:1 and 3:1) to give Compound IIk (12.0 g, 73%) as a pale-yellow oily substance.

NMR($CDCl_3$, δ, ppm): 0.95(t, J=8.0 Hz, 6H), 1.80(q, J=8.0 Hz, 4H), 3.34(s, 2H), 3.88(s, 3H), 3.92(s, 3H), 6.77(d, J=8.4 Hz, 1H), 7.52(d, J=8.4 Hz, 1H)

MASS(m/e): 264($M^+$)

Reference Example 12

Methyl 7-methoxy-spiro[2,3-dihydrobenzofuran-2,1'-cyclopentane]-4-carboxylate (Compound IIl)

(Step A) 4-Bromo-2-(2-oxocyclopentyloxy)anisole (Compound IIl-a)

A mixture of 5-bromo-2-methoxyphenol (6.31 g), α-chlorocyclopentanone (6.9 ml), potassium carbonate (9.57 g), and DMF (63 ml) was stirred at 90° C. for 2 hours. α-Chlorocyclopentanone (14 ml) was further added to the mixture, followed by stirring at 90° C. for one hour. After being allowed to stand for cooling, water was added to the mixture followed by extraction with ether. The organic layer was washed with a 1N aqueous solution of sodium hydroxide and then with a saturated saline, and dried over sodium sulfate. The solvent was distilled off, and the residue was purified by column chromatography (silica gel, hexane:ethyl acetate=2:1) to give Compound IIl-a (11.8 g, 99%) as an oily substance.

NMR($CDCl_3$, δ, ppm): 1.80–2.60(m, 6H), 3.89(s, 3H), 3.90(s, 3H), 4.65–4.77(m, 1H), 6.90(d, J=8.4 Hz, 1H), 7.62(d, J=2.0 Hz, 1H), 7.72(dd, J=8.4 Hz, 2.0 Hz, 1H)

MASS(m/z): 264($M^+$)

(Step B) 4-Bromo-2-(2-methylenecyclopentyloxy)anisole (Compound IIl-b)

Methyltriphenylphosphonium bromide Compound 1 (66.2 g) was suspended in THF (600 ml), and a 1M solution (185 ml) of potassium t-butoxide in THF was dropwise added thereto under ice-cooling, followed by stirring for 30 minutes under ice-cooling. Compound IIl-a (35.0 g) obtained in Step A was dissolved in THF (150 ml). The solution was dropwise added to the mixture under ice-cooling followed by stirring for 15 minutes. Water was added to the mixture followed by extraction with ethyl acetate. The organic layer was washed with a saturated saline and dried over sodium sulfate. The residue was purified by column chromatography (silica gel, hexane:ethyl acetate=10:1) to give Compound IIl-b (24.5 g, 71%) as an oily substance.

NMR($CDCl_3$, δ, ppm): 1.60–2.65(m, 6H), 3.90(s, 3H), 3.91(s, 3H), 4.95–5.05(m, 1H), 5.09–5.20(m, 2H), 6.90(d, J=8.4 Hz, 1H), 7.62(d, J=2.2 Hz, 1H), 7.70 (dd, J=8.4 Hz, 2.2 Hz, 1H)

MASS(m/e): 262($M^+$)

(Step C) 3-Bromo-2-[(2-cyclopenten-1-yl)methyl]-4-methoxyphenol (Compound IIl-c)

Compound IIl-b (29.4 g) obtained in Step B was dissolved in 1-methylpiperidinone (32 ml) followed by stirring at 140° C. for 3 hours. After being allowed to stand for cooling, a saturated saline was added to the mixture followed by extraction with ethyl acetate. The organic layer was dried over sodium sulfate and the solvent was distilled off. The residue was purified by column chromatography (silica gel, hexane:ethyl acetate=7:1) to give Compound IIl-c (26.4 g, 90%) as an oily substance.

NMR($CDCl_3$, δ, ppm): 1.76–1.93(m, 2H), 2.16–2.38(m, 4H), 3.82(s, 2H), 3.82(s, 3H), 3.94(s, 3H), 5.01–5.11(m, 1H), 5.78(s, 1H), 6.75(d, J=8.5 Hz, 1H), 7.50(d, J=8.5 Hz, 1H)

MASS(m/e): 262($M^+$)

(Step D) (Compound IIl)

Compound IIl-c (0.274 g) obtained in Step C was dissolved in methanol (10 ml), and sulfuric acid (1 ml) was dropwise added thereto under ice-cooling, followed by heating under reflux one night. After being allowed to stand for cooling, the mixture was concentrated and poured into a 1N aqueous solution of sodium hydroxide under ice-cooling. The mixture was extracted with ethyl acetate, and the organic layer was washed with a saturated saline and dried over sodium sulfate.

The solvent was distilled off, and the residue was purified by column chromatography (silica gel, hexane:ethyl acetate=10:1) to give Compound IIl (0.223 g, 82%) as an oily substance.

NMR($CDCl_3$, δ, ppm): 1.66–2.25(m, 8H), 3.51(s, 2H), 3.89(s, 3H), 3.92(s, 3H), 6.78(d, J=8.7 Hz, 1H), 7.53(d, J=8.7 Hz, 1H)

Reference Example 13

Methyl 7-methoxy-spiro[2,3-dihydrobenzofuran-2,1'-cyclohexane]-4-carboxylate (Compound IIm)

(Step A) Methyl 4-methoxy-3-(2-oxocyclohexyloxy) benzoate (Compound IIm-a)

A mixture of methyl 3-hydroxy-4-methoxybenzoate (2.47 g), α-chlorocyclohexanone (2.33 ml), potassium carbonate (3.76 g), and DMF (25 ml) was stirred at 90° C. for 2 hours. α-Chlorocyclohexanone (2.0 ml) was further added to the mixture, followed by stirring at 90° C. for one hour. After being allowed to stand for cooling, water was added to the mixture followed by extraction with ether. The organic layer was washed with a 1N aqueous solution of sodium hydroxide and then with a saturated saline, and dried over sodium sulfate. The solvent was distilled off, and the residue was purified by column chromatography (silica gel, hexane:ethyl acetate=2:1) to give Compound IIm-a (3.16 g, 83%) as an oily substance.

Melting point: 66–69° C.

NMR($CDCl_3$, δ, ppm): 1.65–1.90(m, 2H), 1.96–2.14(m, 3H), 2.32–2.72(m, 3H), 3.87(s, 3H), 3.92(s, 3H), 4.69–4.82 (m, 1H), 6.90(d, J=8.0 Hz, 1H), 7.43(d, J=1.5 Hz, 1H), 7.70(dd, J=8.0 Hz, 1.5 Hz, 1H)

MASS(m/e): 278($M^+$)

(Step B) Methyl 3-(2-methylenecyclohexyloxy)-4-methoxybenzoate (Compound IIm-b)

Methyltriphenylphosphonium bromide (40.4 g) was suspended in ether (400 ml), and a 1.7N solution (64.8 ml) of n-butyl lithium in hexane was dropwise added thereto under ice-cooling, followed by stirring at room temperature for 10 minutes and then cooling with ice again. Compound IIm-a (15.7 g) obtained in Step A was dissolved in ether (16 ml). The solution was dropwise added to the mixture followed by stirring at room temperature for one hour. Water was added to the mixture under ice-cooling followed by extraction with ethyl acetate. The organic layer was washed with a saturated saline and dried over sodium sulfate. The solvent was distilled off, and the residue was purified by column chromatography (silica gel, hexane:ethyl acetate=10:1) to give Compound IIm-b (9.15 g, 59%) as an oily substance.

NMR($CDCl_3$, δ, ppm): 1.45–2.18(m, 7H), 2.37–2.52(m, 1H), 3.88(s, 3H), 3.91(s, 3H), 4.62–4.75(m, 1H), 4.82(s, 1H), 4.90(s, 1H), 6.90(d, J=8.2 Hz, 1H), 7.55(d, J=1.3 Hz, 1H), 7.67(dd, J=8.2 Hz, 1.3 Hz, 1H)

MASS(m/e): 276($M^+$)

(Step C) Methyl 2-[(2-cyclohexen-1-yl)methyl]-3-hydroxy-4-methoxybenzoate (Compound IIm-c)

Compound IIm-b (9.0 g) obtained in Step B was dissolved in 1-methylpiperidinone (10 ml) followed by stirring at 140° C. for 3 hours and then at 150° C. for 2 hours. After being allowed to stand for cooling, a saturated saline was added to the mixture followed by extraction with ethyl acetate, and the organic layer was dried over sodium sulfate. The solvent was distilled off, and the residue was purified by column chromatography (silica gel, hexane:ethyl acetate=10:1) to give Compound IIm-c (7.63 g, 85%) as an oily substance.

NMR($CDCl_3$, δ, ppm): 1.44–1.70(m, 4H), 1.85–2.07(m, 4H), 3.70(s, 2H), 3.82(s, 3H), 3.95(s, 3H), 5.07–5.18(m, 1H), 5.79(s, 1H), 6.77(d, J=8.0 Hz, 1H), 7.48(d, J=8.0 Hz, 1H)

MASS(m/e): 276($M^+$)

(Step D) (Compound IIm)

Compound IIm-c (7.6 g) obtained in Step C was dissolved in methanol (100 ml), and sulfuric acid (10 ml) was dropwise added thereto under ice-cooling, followed by heating under reflux one night. After being allowed to stand for cooling, the mixture was concentrated, and the residue was poured into a saturated aqueous solution of sodium bicarbonate under ice-cooling. The mixture was extracted with ethyl acetate, the organic layer was washed with a saturated saline, and the solvent was distilled off. The residue was purified by column chromatography (silica gel, hexane:ethyl acetate=10:1) to give Compound IIm (3.42 g, 45%) as an oily substance.

Melting point: 81–83° C.

NMR($CDCl_3$, δ, ppm): 1.25–1.95(m, 10H), 3.32(s, 2H), 3.87(s, 3H), 3.92(s, 3H), 6.77(d, J=8.2 Hz, 1H), 7.51(d, J=8.2 Hz, 1H)

MASS(m/e): 276($M^+$)

Reference Example 14

Methyl (±)-cis-6-methoxy-1,2,3,4,4a,9b-hexahydrodibenzofuran-9-carboxylate (Compound IIn)

(Step A) 2-Bromo-3-(cyclohexan-2-en-1-oxy)-4-methoxy-benzaldehyde (Compound IIn-a)

Diethyl azodicarboxylate (2.7 ml) was dropwise added to a mixture of 2-bromo-3-hydroxy-4-methoxy-benzaldehyde (4.0 g), THF (80 ml), 2-cyclohexen-1-ol (1.2 ml), and triphenylphosphine (4.5 g) under ice-cooling, followed by stirring at room temperature for 2 hours. The mixture was poured into water followed by extraction with ether. The organic layer was washed with a 1N aqueous solution of sodium hydroxide and with a saturated saline, and dried over sodium sulfate. The solvent was distilled off, and the residue was purified by column chromatography (hexane:ethyl acetate=10:1 and 5:1) to give Compound IIn-a (1.8 g, 47%) as a pale-yellow oily substance.

NMR($CDCl_3$, δ, ppm): 1.50–2.25(m, 6H), 3.94(s, 3H), 4.70–4.85(m, 1H), 5.20–6.02(m, 2H), 6.96(d, J=8 Hz, 1H), 7.72(d, J=8 Hz, 1H), 10.3(s, 1H)

MASS(m/e): 311($M^+$)

(Step B) (±)-cis-6-Methoxy-1,2,3,4,4a,9b-hexahydrodibenzofuran-9-carbaldehyde (Compound IIn-b)

Substantially the same procedure as in Step B of Reference Example 5 was repeated using Compound IIn-a (1.1 g) obtained in Step A to give Compound IIn-b (0.45 g, 56%) as colorless crystals.

NMR($CDCl_3$, δ, ppm): 0.90–1.10(m, 1H), 1.15–1.42(m, 1H), 1.46–1.84(m, 4H), 2.00–2.20(m, 1H), 2.35–2.55(m, 1H), 3.54–3.70(m, 1H), 3.97(s, 3H), 4.60–4.71(m, 1H), 6.88(d, J=8 Hz, 1H), 7.35(d, J=8 Hz, 1H), 9.90(s, 1H)

MASS(m/e): 232($M^+$)

(Step C) (Compound IIn)

Compound IIn-b (0.42 g) obtained in Step B was dissolved in a mixed solvent of dichloromethane (5 ml) and methanol (5 ml) followed by stirring at 0° C., and potassium hydroxide (1.6 g) was added thereto. The mixture was warmed to the room temperature and stirred for 8 hours, while iodine (0.93 g) dissolved in methanol (3 ml) was slowly and dropwise added thereto. Water was added to the reaction solution followed by extraction with dichloromethane. The organic layer was dried over magnesium sulfate and the solvent was distilled off under reduced pressure. The residue was purified by silica gel column chromatography (ethyl acetate/n-hexane=1/5) to give Compound IIn (0.41 g, 88%) as pale-yellow crystals.

NMR($CDCl_3$, δ, ppm): 0.90–1.10(m, 1H), 1.15 –1.35(m, 1H), 1.45–1.85(m, 4H), 2.05–2.22(m, 1H), 2.35–2.45(m, 1H), 3.50–3.65(m, 1H), 3.87(s, 3H), 3.94 (s, 3H), 4.58–4.66 (m, 1H), 6.77(d, J=9 Hz, 1H), 7.56(d, J=9 Hz, 1H)

MASS(m/e): 262($M^+$)

Reference Example 15

Methyl 2-butyl-7-methoxybenzofuran-4-carboxylate (Compound IIo)

Compound IIad (1.3 g) obtained in Reference Example 30 was dissolved in methanol (16 ml), and concentrated sulfuric acid (5 ml) was dropwise added thereto under ice-cooling, followed by heating under reflux for one hour. After being allowed to stand for cooling, the solvent was distilled off, and the residue was poured into a 1N aqueous solution of sodium hydroxide. The precipitate was collected by filtration and dried to give Compound IIo (0.82 g, 56%) as a pale-yellow oily substance.

NMR($CDCl_3$, δ, ppm): 0.954(t, J=8 Hz, 3H), 1.30–1.56 (m, 2H), 1.64–1.89(m, 2H), 2.82(t, J=8 Hz, 2H), 3.94 (s, 3H), 4.06(s, 3H), 6.76(d, J=9 Hz, 1H), 6.98(s, 1H), 7.91(d, J=9 Hz, 1H)

MASS(m/e): 262($M^+$)

Reference Example 16

Methyl 7-methoxy-2-(2-methylpropyl)benzofuran-4-carboxylate (Compound IIp)

(Step A) 7-Methoxy-2-(2-methyl-1-propen-1-yl)benzofuran (Compound IIp-a)

Substantially the same procedure as in Step B of Reference Example 2 was repeated using Compound IIad-a (6.2 g) obtained in Step A of Reference Example 30, 2-propyltriphenylphosphonium iodide (20 g), and potassium tert-butoxide (5.1 g) to give Compound IIp-a (5.7 g, 81%) as a pale-yellow oily substance.

NMR($CDCl_3$, δ, ppm): 1.96(s, 3H), 2.09(s, 3H), 4.01(s, 3H), 6.20–6.23(broad s, 1H), 6.51(s, 1H), 6.75(dd, J=4 Hz, 6 Hz, 1H), 7.05–7.15(m, 2H)

(Step B) 7-Methoxy-2-(2-methylpropyl)benzofuran (Compound IIp-b)

Substantially the same procedure as in Step C of Reference Example 30 was repeated using Compound IIp-a (0.4 g) obtained in Step A to give Compound IIp-b (0.8 g, 93%) as a pale-yellow oily substance.

NMR($CDCl_3$, δ, ppm): 0.980(d, J=7 Hz, 6H), 2.05–2.22 (m, 1H), 2.65(d, J=7 Hz, 2H), 4.00(s, 3H), 6.37(s, 1H), 6.68–6.80(m, 1H), 7.05–7.15(m, 2H)

(Step C) 7-Methoxy-2-(2-methylpropyl)benzofuran-4-carbaldehyde (Compound IIp-c)

Substantially the same procedure as in Step D of Reference Example 30 was repeated using Compound IIp-b (0.38 g) obtained in Step B to give Compound IIp-c (0.29 g, 66%) as a pale-yellow oily substance.

NMR($CDCl_3$, δ, ppm): 0.999(d, J=8 Hz, 6H), 2.05–2.23 (m, 1H), 2.70(d, J=8 Hz, 2H), 4.10(s, 3H), 6.84(d, J=8 Hz, 1H), 7.17(s, 1H), 7.63(d, J=8 Hz, 1H), 10.0(s, 1H)

(Step D) (Compound IIp)

Substantially the same procedure as in Step C of Reference Example 14 was repeated using Compound IIp-c (2.7 g) obtained in Step C to give Compound IIp (3.0 g, 100%) as pale-yellow crystals.

NMR($CDCl_3$, δ, ppm): 1.00(d, J=7 Hz, 6H), 2.05–2.25(m, 1H), 2.69(d, J=7 Hz, 2H), 3.94(s, 3H), 4.06(s, 3H), 6.76(d, J=8 Hz, 1H), 6.99(s, 1H), 7.91(d, J=8 Hz, 1H)

Reference Example 17

Methyl 7-methoxy-2-(4-pyridyl)benzofuran-4-carboxylate (Compound IIq)

Compound IIf (1.80 g) obtained in Reference Example 6 was dissolved in a mixed solvent of dichloromethane (40 ml) and methanol (80 ml) followed by stirring at 0° C., and potassium hydroxide (8.0 g) was added thereto. The mixture was warmed to the room temperature and stirred for 12 hours, while iodine (13.5 g) dissolved in methanol (30 ml) was slowly and dropwise added thereto. The reaction solution was extracted with dichloromethane, the organic layer was dried over magnesium sulfate, and the solvent was distilled off under reduced pressure. The residue was purified by silica gel column chromatography (hexane:ethyl acetate=1:3) to give Compound IIq (1.50 g, 74.5%) as a white solid.

NMR($CDCl_3$, δ, ppm): 4.00(s, 3H), 4.10(s, 3H), 6.87(d, J=9 Hz, 1H), 7.78(d, J=7 Hz, 2H), 7.85(s, 1H), 7.99(d, J=9 Hz, 1H), 8.70(d, J=7 Hz, 2H)

Reference Example 18

Methyl 7-methoxy-2-(2-pyridyl)benzofuran-4-carboxylate (Compound IIr)

Substantially the same procedure as in Reference Example 17 was repeated using Compound IIg (5.50 g) obtained in Reference Example 7 to give Compound IIr (4.05 g, 65.9%) as a white solid.

Melting point: 148–149° C.

NMR($CDCl_3$, δ, ppm): 3.99(s, 3H), 4.10(s, 3H), 6.87(d, J=8 Hz, 1H), 7.27(dd, J=6 Hz, 8 Hz, 1H), 7.78(ddd, J=2 Hz, 8 Hz, 8 Hz, 1H), 7.95(s, 1H), 7.97(d, J=8 Hz, 1H), 7.97(d, J=8 Hz, 1H), 8.71(dd, J=2 Hz, 6 Hz, 1H)

MASS(m/e): 283($M^+$), 252

IR(KBr, $cm^{-1}$): 1712, 1585, 1274, 1265, 1193, 1147

Reference Example 19

Methyl 7-methoxy-2-phenylbenzofuran-4-carboxylate (Compound IIs)

Substantially the same procedure as in Reference Example 17 was repeated using Compound IIh (3.00 g) obtained in Reference Example 8 to give Compound IIs (2.72 g, 85.8%) as a white solid.

Melting point: 117–118° C.

NMR($CDCl_3$, δ, ppm): 3.97(s, 3H), 4.09(s, 3H), 6.81(d, J=9 Hz, 1H), 7.3–7.5(m, 3H), 7.62(s, 1H), 7.93(d, J=9 Hz, 1H), 7.94(d, J=9 Hz.2H)

MASS(m/e): 282 ($M^+$), 251

IR(KBr, $cm^{-1}$): 1701, 1620, 1292, 1220, 1095

Reference Example 20

Methyl 2-(2-ethylphenyl)-7-methoxybenzofuran-4-carboxylate (Compound IIt)

(Step A) 2-(2-Cyanophenyl)-7-methoxybenzofuran (Compound IIt-a)

Substantially the same procedure as in Step A of Reference Example 17 was repeated using ortho-vanillin (38.8 g) and using α-bromoorthotolunitrile (50.0 g) instead of 4-picolyl chloride hydrochloride to give Compound IIt-a (39.6 g, 62.3%) as colorless needles.

NMR($CDCl_3$, δ, ppm): 4.05(s, 3H), 6.87(d, J=8 Hz, 1H), 7.1–7.3(m, 2H), 7.41(dd, J=7 Hz, 7 Hz, 1H), 7.70 (dd, J=8 Hz, 8 Hz, 1H), 7.74(s, 1H), 7.77(d, J=8 Hz, 1H), 8.17(d, J=7 Hz, 1H)

(Step B) 2-(2-Formylphenyl)-7-methoxybenzofuran (Compound IIt-b)

Compound IIt-a (26.0 g) obtained in Step A was dissolved in dry dichloromethane (500 ml), and the solution was cooled to −78° C. followed by stirring. A 1.0M solution (156 ml) of diisobutylaluminium hydride in toluene was dropwise added to the mixture followed by stirring for one hour while warming the solution to the room temperature. A saturated aqueous solution of ammonium chloride was added to the reaction solution, and ethyl acetate and a 5% aqueous solution of sulfuric acid were added thereto, followed by stirring at room temperature for 30 minutes. The mixture was extracted with ethyl acetate, the organic layer was washed with a saturated saline and dried over anhydrous magnesium sulfate, and the solvent was distilled off under reduced pressure. The residue was washed with diethyl ether to give Compound IIt-b (20.0 g, 76.0%) as a pale-yellow solid.

NMR($CDCl_3$, δ, ppm): 4.03(s, 3H), 6.86(dd, J=2 Hz, 7 Hz, 1H), 6.95(s, 1H), 7.2–7.3(m, 2H), 7.53(dd, J=7.5 Hz, 7.5 Hz, 1H), 7.67(dd, J=2 Hz, 6 Hz, 1H), 7.87(d, J=8 Hz, 1H), 8.04(d, J=7.5 Hz, 1H), 10.47 (s, 1H)

(Step C) 2-(2-Ethenylphenyl)-7-methoxybenzofuran (Compound IIt-c)

Methyltriphenylphosphonium bromide (33.1 g) was dissolved in dry tetrahydrofuran (300 ml) followed by stirring at 0° C., and potassium tert-butoxide (10.0 g) was added thereto, followed by stirring at the same temperature for 30 minutes. Compound IIt-b (9.0 g) obtained in Step B was added to the reaction solution followed by stirring at room temperature for 10 minutes. Then, distilled water was added to the mixture followed by extraction with diethyl ether. The organic layer was washed with a saturated saline and dried over anhydrous magnesium sulfate, and the solvent was distilled off under reduced pressure. The residue was purified by silica gel column chromatography (hexane:ethyl acetate=3:1) to give Compound IIt-c (7.71 g, 86.3%) as a pale-yellow oily substance.

NMR($CDCl_3$, δ, ppm): 4.04(s, 3H), 5.36(d, J=11 Hz, 1H), 5.73(d, J=17 Hz, 1H), 6.83(dd, J=1 Hz, 8 Hz, 1H), 6.86(s, 1H), 7.1–7.25(m, 3H), 7.3–7.4(m, 2H), 7.58(m, 1H), 7.85 (m, 1H)

MASS(m/e): 250 ($M^+$), 207, 165

(Step D) 2-(2-Ethylphenyl)-7-methoxybenzofuran (Compound IIt-d)

Compound IIt-c (7.7 g) obtained in Step C and palladium-carbon (1.9 g) were added to diethyl ether (200 ml) and the mixture was subjected to hydrogenation while stirring at room temperature. After one hour, the reaction solution was filtered with celite; and the solvent was distilled off under reduced pressure from the filtrate to give Compound IIt-d as a pale-yellow oily substance.

NMR($CDCl_3$, δ, ppm): 1.30(t, J=7.5 Hz, 3H), 2.93(q, J=7.5 Hz, 2H), 4.03(s, 3H), 6.80(dd, J=1.5 Hz, 7 Hz, 1H), 6.84(s, 1H), 7.1–7.4(m, 5H), 7.75(d, J=7 Hz, 1H)

MASS(m/e): 252 ($M^+$), 237, 194

(Step E) 2-(2-Ethylphenyl)-7-methoxybenzofuran-4-carbaldehyde (Compound IIt-e)

Substantially the same procedure as in Step B of Reference Example 6 was repeated using Compound IIt-d (7.50 g) obtained in Step D to give Compound IIt-e (5.17 g, 62.1%) as a white solid.

NMR($CDCl_3$, δ, ppm): 1.29(t, J=7.5 Hz, 3H), 2.96(q, J=7.5 Hz, 2H), 4.13(s, 3H), 6.91(d, J=8 Hz, 1H.), 7.2–7.4(m, 3H), 7.64(s, 1H), 7.69(d, J=8 Hz, 1H), 7.80(d, J=7 Hz, 1H), 10.07(s, 1H)

MASS(m/e): 280 ($M^+$), 265, 247

(Step F) (Compound IIt)

Substantially the same procedure as in Step C of Reference Example 14 was repeated using Compound IIt-d (5.00 g) obtained in Step D to give Compound IIt (4.43 g, 80.0%) as a white solid.

NMR($CDCl_3$, δ, ppm): 1.29(t, J=6.5 Hz, 3H), 2.94(q, J=7.5 Hz, 2H), 3.96(s, 3H), 4.08(s, 3H), 6.82(d, J=8.5 Hz, 1H), 7.2–7.4(m, 3H), 7.47(s, 1H), 7.77 (d, J=7 Hz, 1H), 7.96(d, J=8.5 Hz, 1H)

MASS(m/e): 311 ($M^+$), 279

Reference Example 21

Methyl 2-[2-(2-propyl)phenyl]-7-methoxybenzofuran-4-carboxylate (Compound IIu)

(Step A) 2-(2-Acetylphenyl)-7-methoxybenzofuran (Compound IIu-a)

Compound IIt-b (18.4 g) obtained in Step B of Reference Example 20 was dissolved in dry tetrahydrofuran (500 ml), and the solution was cooled to −78° C. followed by stirring. A 3.0M solution (36.4 ml) of methyl magnesium bromide in diethyl ether was dropwise added to the mixture and the reaction solution was slowly warmed to the room temperature. Distilled water was added to the mixture to cease the reaction and the solution was extracted with ethyl acetate. The organic layer was washed with a saturated saline and dried over anhydrous magnesium sulfate, and the solvent was distilled off under reduced pressure. The residue was purified by silica gel column chromatography (hexane:ethyl acetate=3:1) to give 2-[2-(1-hydroxyethyl)phenyl]-7-methoxybenzofuran (17.8 g, 91.0%) as a colorless solid. Then, the solid was dissolved in dry dichloromethane (400 ml), and pyridinium chlorochromate (PCC, 27.0 g) and molecular sieve (3 Å, 30.0 g) were added thereto, followed by stirring at room temperature for one hour. Then, dichloromethane and 5% sulfuric acid were added to the reaction solution, the mixture was filtered with celite, and the filtrate was extracted with dichloromethane. The organic layer was washed with a saturated saline and dried over anhydrous magnesium sulfate, and the solvent was distilled off under reduced pressure. The residue was purified by silica gel column chromatography (hexane:ethyl acetate=3:1) to give Compound IIu-a (16.6 g, 98.4%) as a pale-yellow oily substance.

NMR($CDCl_3$, δ, ppm): 2.37(s, 3H), 4.01(s, 3H), 6.82(dd, J=2 Hz, 6.5 Hz, 1H), 6.89(s, 1H), 7.1–7.2(m, 2H), 7.4–7.6 (m, 3H), 7.78(d, J=6 Hz, 1H)

MASS(m/e): 266 ($M^+$), 207

(Step B) 2-[2-(1-Methylethenyl)-7-methoxybenzofuran (Compound IIu-b)

Substantially the same procedure as in Step C of Reference Example 20 was repeated using Compound IIu-a (16.0 g) obtained in Step A to give Compound 21 (15.6 g, 98.0%) as a pale-yellow oily substance.

NMR($CDCl_3$, δ, ppm): 1.98(bs, 3H), 4.02(s, 3H), 5.07 (bs, 1H), 5.22(bs, 1H), 6.78(dd, J=1.5 Hz, 7 Hz, 1H), 7.05(s, 1H), 7.1–7.4(m, 5H), 7.91(dd, J=1.5 Hz, 5 Hz, 1H)

MASS(m/e): 264 ($M^+$)

(Step C) 2-(2-Isopropylphenyl)-7-methoxybenzofuran (Compound IIu-c)

Substantially the same procedure as in Step D of Reference Example 20 was repeated using Compound IIu-b (15.3 g) obtained in Step B to give Compound IIu-c (14.0 g, 91.1%) as a colorless oily substance.

NMR($CDCl_3$, δ, ppm): 1.26(d, J=7 Hz, 6H), 3.45(sep, J=7 Hz, 1H), 4.00(s, 3H), 6.77(s, 1H), 6.78(dd, J=1.5 Hz, 7.5 Hz, 1H), 7.1–7.3(m, 3H), 7.3–7.5(m, 2H), 7.61(d, J=7.5 Hz, 1H)

MASS(m/e): 266($M^+$), 219

(Step D) 2-(2-Isopropylphenyl)-7-methoxybenzofuran-4-carbaldehyde (Compound IIu-d)

Substantially the same procedure as in Step B of Reference Example 6 was repeated using Compound IIu-c (1.00 g) obtained in Step C to give Compound IIu-d (0.67 g, 60.7%) as a pale-yellow oily substance.

NMR($CDCl_3$, δ, ppm): 1.29(d, J=7 Hz, 6H), 3.45(sep, J=7 Hz, 1H), 4.12(s, 3H), 6.91(d, J=8 Hz, 1H), 7.25(m, 1H), 7.35–7.5(m, 2H), 7.57(s, 1H), 7.63 (d, J=7.5 Hz, 1H), 7.68(d, J=8 Hz, 1H), 10.08(s, 1H)

MASS(m/e): 294($M^+$), 280, 261

(Step E) (Compound IIu)

Substantially the same procedure as in Step C of Reference Example 14 was repeated using Compound IIu-d (5.40 g) obtained in Step D to give Compound IIu (5.00 g, 84.0%) as a white solid.

NMR($CDCl_3$, δ, ppm): 1.29(d, J=7 Hz, 6H), 3.47(sep, J=7 Hz, 1H), 3.97(s, 3H), 4.09(s, 3H), 6.83(d, J=8 Hz, 1H), 7.25(m, 1H), 7.41(s, 1H), 7.4–7.5(m, 2H), 7.63(dd, J=1 Hz, 8.5 Hz, 1H), 7.97(d, J=8 Hz, 1H)

MASS(m/e): 324($M^+$), 277

Reference Example 22

Methyl 7-methoxy-3-phenylbenzofuran-4-carboxylate (Compound IIv)

Substantially the same procedure as in Reference Example 15 was repeated using Compound IIah (1.32 g) obtained in Reference Example 34 to give Compound IIv (1.26 g, 91%) as a colorless oily substance.

NMR($CDCl_3$, δ, ppm): 3.16(s, 3H), 4.07(s, 3H), 6.87(d, J=9 Hz, 1H), 7.31–7.44 (m, 5H), 7.68(s, 1H), 7.81 (d, J=9 Hz, 1H)

MASS(m/e): 282($M^+$)

Reference Example 23

7-Methoxy-2,3-dihydrobenzofuran-4-carboxylic acid (Compound IIw)

(Step A) Methyl 7-methoxybenzofuran-4-carboxylate (Compound IIw-a)

7-Methoxybenzofuran-4-carboxylic acid (0.50 g) was dissolved in methanol (10 ml), and sulfuric acid (0.6 ml) was dropwise added thereto under ice-cooling, followed by heating under reflux for one hour. Sulfuric acid (0.2 ml) was further added to the mixture followed by heating under reflux for 30 minutes. After being allowed to stand for cooling, the solvent was distilled off, and the residue was poured into a 1N aqueous solution of sodium hydroxide. The precipitate was collected by filtration and dried to give Compound IIw-a (0.53 g, 99%) as a white solid.

Melting point: 87–89° C.

NMR($CDCl_3$, δ, ppm): 3.96(s, 3H), 4.09(s, 3H), 6.83(d, J=9 Hz, 1H), 7.36(d, J=1 Hz, 1H), 7.70(d, J=1 Hz, 1H), 7.98(d, J=9 Hz, 1H)

MASS(m/e): 206($M^+$)

(Step B) Methyl 7-methoxy-2,3-dihydrobenzofuran-4-carboxylate (Compound IIw-b)

Compound IIw-a (0.84 g) obtained in Step A was dissolved in ethanol (16 ml), and 5% rhodium carbon (0.17 g) was added thereto, followed by hydrogenation at normal temperature and normal pressure for 10 hours. The catalyst was removed, and then the filtrate was concentrated to give Compound IIw-b (0.80 g, 95%) a white solid.

Melting point: 68–78° C.

NMR($CDCl_3$, δ, ppm): 3.56(t, J=9 Hz, 2H), 3.89(s, 3H), 3.93(s, 3H), 4.67(t, J=9 Hz, 2H), 6.77(d, J=8 Hz, 1H), 7.59(d, J=8 Hz, 1H)

(Step C) (Compound IIw)

A mixture of Compound IIw-b (0.76 g) obtained in Step B, ethanol (3 ml), and a 2N solution of sodium hydroxide (3 ml) was heated under reflux for 3 hours. The mixture was adjusted to pH 1 by adding dilute hydrochloric acid under ice-cooling. The precipitate was collected by filtration and dried to give Compound IIw (0.64 g, 90%) as a white solid.

Melting point: 202–207° C.

NMR($CDCl_3$, δ, ppm): 3.61(t, J=9 Hz, 2H), 3.95(s, 3H), 4.70(t, J=9 Hz, 2H), 6.80(d, J=8 Hz, 1H), 7.65(d, J=8 Hz, 1H)

MASS(m/e): 194($M^+$)

Reference Example 24

(±)-7-Methoxy-3-methyl-2,3-dihydrobenzofuran-4-carboxylic acid (Compound IIx)

Compound IIe (0.184 g) obtained in Reference Example 5 was dissolved in acetone (2 ml), and an aqueous solution of potassium permanganate (0.182 g) was slowly added thereto with stirring at room temperature. The insoluble matters were filtered off, and concentrated hydrochloric acid was added to the filtrate. The precipitated solid was collected by filtration and dried to give Compound IIx (0.116 g, 58.3%) as colorless crystals.

Melting point: 194–197° C.

NMR($CDCl_3$, δ, ppm): 1.36(d, J=8.0 Hz, 3H), 3.89–4.09 (m, 1H), 3.96(s, 3H), 4.40(dd, J=9.3 Hz, 3.0 Hz, 1H), 4.56–4.70 (m, 1H), 6.82 (d, J=8.9 Hz, 1H), 7.69 (d, J=8.9 Hz, 1H)

Reference Example 25

(±)-3-Ethyl-7-methoxy-2,3-dihydrobenzofuran-4-carboxylic acid (Compound IIy)

Substantially the same procedures as in Reference Example 5 and then as in Reference Example 24 were repeated using 2-bromo-3-hydroxy-4-methoxybenzaldehyde (0.64 g) and 1-bromo-2-butene to give Compound IIy (0.37 g) as colorless crystals.

Melting point: 174–177° C.

NMR($CDCl_3$, δ, ppm): 0.92(t, J=8.1 Hz, 3H), 1.51–1.89 (m, 2H), 3.78–4.02(m, 1H), 3.95(s, 3H), 4.50–4.66(m, 2H), 6.82(d, J=9.0 Hz, 1H), 7.70(d, J=9.0 Hz, 1H)

Reference Example 26

(±)-7-Methoxy-3-(2-propyl)-2,3-dihydrobenzofuran-4-carboxylic acid (Compound IIz)

Substantially the same procedures as in Reference Example 5 and then as in Reference Example 24 were repeated using 2-bromo-3-hydroxy-4-methoxybenzaldehyde (0.21 g) and 1-bromo-3-methyl-2-butene to give Compound IIz (0.163 g) as colorless crystals.

Melting point: 179–183° C.

NMR($CDCl_3$, δ, ppm): 0.67(d, J=8.7 Hz, 3H), 1.01(d, J=8.7 Hz, 3H), 2.14–2.32(m, 1H), 3.82–4.01(m, 1H), 3.95(s, 3H), 4.41–4.51(m, 1H), 4.68(dd, J=9.2 Hz, 3.0 Hz, 1H), 6.82(d, J=9.0 Hz, 1H), 7.69(d, J=9.0 Hz, 1H)

Reference Example 27

(±)-3-Ethoxycarbonylmethyl-7-methoxy-2,3-dihydrobenzofuran-4-carboxylic acid (Compound IIaa)

Substantially the same procedures as in Reference Example 5 and then as in Reference Example 24 were repeated using 2-bromo-3-hydroxy-4-methoxybenzaldehyde (2.14 g) and ethyl bromocrotonate to give Compound IIaa (2.45 g) as white crystals.

NMR($CDCl_3$, δ, ppm): 1.27(t, J=5.7 Hz, 3H), 2.52(dd, J=17.2 Hz, 12.3 Hz, 1H), 2.98(dd, J=17.2 Hz, 4.1 Hz, 1H), 3.95(s, 3H), 4.17(q, J=5.7 Hz, 2H), 4.23–4.37 (m, 1H), 4.50–4.77(m, 2H), 6.85(d, J=8.2 Hz, 1H), 7.70(d, J=8.2 Hz, 1H)

Reference Example 28

2-Cyano-7-methoxybenzofuran-4-carboxylic acid (Compound IIab)

A mixture of Compound IIi (0.2 g) obtained in Reference Example 9, a 80% aqueous solution (2 ml) of acetic acid, sulfamic acid (0.145 g), and a 80% aqueous solution (0.084 g) of sodium chlorite was stirred at room temperature one night. The mixture was diluted with water, and then the precipitated solid was collected by filtration and dried to give Compound IIab (0.259 g, 83%) as white crystals.

NMR(DMSO-$d_6$, δ, ppm): 4.05(s, 3H), 7.30(d, J=9.1 Hz, 1H), 8.00(d, J=9.1 Hz, 1H), 8.30(s, 1H), 12.98–13.22(br, 1H)

Reference Example 29

7-Methoxybenzofuran-4-carboxylic acid (Compound IIac)

Compound IIac was synthesized according to the method described in Org. Prep. Proced. Int., 763 (1989).

Melting point: 224–226° C.

NMR(DMSO-$d_6$, δ, ppm): 4.00(s, 3H), 7.02(d, J=9 Hz, 1H), 7.30(d, J=3 Hz, 1H), 7.88(d, J=9 Hz, 1H), 8.10(d, J=3 Hz, 1H), 12.7–12.8(broad s, 1H)

MASS(m/e): 192($M^+$)

Reference Example 30

2-Butyl-7-methoxybenzofuran-4-carboxylic acid (Compound IIad)

(Step A) 7-Methoxybenzofuran-2-carbaldehyde (Compound IIad-a)

2-Cyano-7-methoxybenzofuran (0.736 g) was dissolved in dichloromethane (10 ml), and a 1.02N DIBAL solution (5.4 ml) in toluene was added thereto at −4 to −30° C., followed by stirring for one hour. Methanol and dilute hydrochloric acid were added to the mixture, and the solvent was distilled off. The obtained residue was purified by column chromatography (hexane/ethyl acetate=10/1) to give Compound IIad-a (0.371 g, 50%) as an oily substance.

NMR($CDCl_3$, δ, ppm): 4.04(s, 3H), 6.92–7.03(m, 1H), 7.17–7.40(m, 2H), 7.54(s, 1H), 9.90(s, 1H)

(Step B) (E/Z)-2-(1-Buten-1-yl)-7-methoxybenzofuran (Compound IIad-b)

1-Propyltriphenylphosphonium bromide (0.907 g) was suspended in ether (10 ml), and a 1.7N solution (1.42 ml) of butyl lithium in hexane was added thereto under ice-cooling, followed by stirring for one hour. A solution of Compound IIad-a (0.319 g) dissolved in ether (3.2 ml) was dropwise added to the mixture, followed by stirring for 10 minutes. Water was added to the mixture followed by extraction with ethyl acetate. The organic layer was washed with a saturated saline and dried over sodium sulfate, and the solvent was distilled off. The residue was purified by silica gel column chromatography (hexane/ethyl acetate=30/1) to give Compound IIad-b (0.28 g, 78%) as a colorless oily mixture of isomers (2:5).

NMR($CDCl_3$, δ, ppm): 1.11 and 1.14(each t, J=7 Hz, total 3H), 2.16–2.33(m, 0.3H), 2.48–2.67(m, 0.7H), 4.01 and 4.02(each s, total 3H), 5.80(dt, J=8, 10 Hz, 0.7H), 6.23–6.39 (m, 1H), 6.48(s, 0.3H), 6.60(dt, J=8, 14 Hz, 0.3H), 6.61(s, 0.7H), 6.70–6.83(m, 1H), 7.04–7.20(m, 2H)

(Step C) 2-Butyl-7-methoxybenzofuran (Compound IIad-c)

Compound IIad-b (0.27 g) was dissolved in methanol (5.4 ml), and 10% palladium carbon (27 mg) was added thereto, followed by hydrogenation at normal temperature and normal pressure for 3 hours. The catalyst was removed, and then the filtrate was concentrated to give Compound IIad-c (0.248 g, 91%) as an oily substance.

NMR($CDCl_3$, δ, ppm): 0.94(t, J=8 Hz, 3H), 1.30–1.51(m, 2H), 1.64–1.82(m, 2H), 2.79(t, J=7 Hz, 2H), 4.00 (s, 3H), 6.38(s, 1H), 6.68–6.80(m, 1H), 7.02–7.17(m, 2H)

(Step D) 2-Butyl-4-carbaldehyde-7-methoxybenzofuran (Compound IIad-d)

Compound IIad-c (1.70 g) was dissolved in DMF (17 ml), and phosphorus oxychloride (2.3 ml) was added thereto under ice-cooling, followed by stirring at 80° C. for one hour. Phosphorus oxychloride (2.3 ml) was further added to the mixture under ice-cooling, followed by stirring at 80° C. for 2 hours. After being allowed to stand for cooling, the mixture was poured into ice-water followed by extraction with ether. The organic layer was washed with a saturated saline and dried over sodium sulfate, and the solvent was distilled off. The residue was purified by silica gel column chromatography (hexane/ethyl acetate=10/1) to give Compound IIad-d (1.19 g, 62%) as an oily substance.

NMR($CDCl_3$, δ, ppm): 0.97(t, J=7 Hz, 3H), 1.31–1.52(m, 2H), 1.67–1.88(m, 2H), 2.83(t, J=8 Hz, 2H), 4.09 (s, 3H), 6.83(d, J=9 Hz, 1H), 7.14(s, 1H), 7.61(d, J=9 Hz, 1H), 10.0(s, 1H)

MASS(m/e): 232($M^+$)

(Step E) (Compound IIad)

Substantially the same procedure as in Reference Example 24 was repeated using Compound IIad-d (0.500 g) to give Compound IIad (0.467 g, 88%) as a white solid.

Melting point: 114–120° C.

NMR($CDCl_3$, δ, ppm): 0.97(t, J=8 Hz, 3H), 1.31–1.54(m, 2H), 1.68–1.87(m, 2H), 2.85(t, J=8 Hz, 2H), 4.09 (s, 3H), 6.80(d, J=9 Hz, 1H), 7.07(s, 1H), 8.00(d, J=9 Hz, 1H)

MASS(m/e): 248($M^+$)

Reference Example 31

7-Methoxy-2-(4-pyridyl)benzofuran-4-carboxylic acid-hydrochloride (Compound IIae)

Distilled water (350 ml) and sodium hydroxide (544 mg) were added to Compound IIq (3.50 g) obtained in Reference Example 17, followed by heating under reflux for 2 hours. The solvent was distilled off from the reaction solution under reduced pressure, and the residue was dissolved in hot ethanol (500 ml). The mixture was cooled to 0° C. followed by stirring. A hydrochloric acid-ethanol solution was dropwise added to the mixture followed by stirring for 20 minutes. The precipitated crystals were collected by filtration to give Compound IIae (1.83 g, 48.2%) as a white solid.

NMR($D_2O$, δ, ppm): 3.61(s, 3H), 6.44(d, J=9 Hz, 1H), 7.00(s, 1H), 7.12(d, J=9 Hz, 1H), 7.58(d, J=7 Hz, 2H), 8.30(d, J=7 Hz, 2H)

Reference Example 32

7-Methoxy-2-(2-pyridyl)benzofuran-4-carboxylic acid hydrochloride (Compound IIaf)

Substantially the same procedure as in Reference Example 31 was repeated using Compound IIr (5.00 g) obtained in Reference Example 18 to give Compound IIaf (5.04 g, 93.3%) as a white solid.

NMR(DMSO-$d_6$, δ, ppm): 4.07(s, 3H), 7.14(d, J=8 Hz, 1H), 7.53(dd, J=6 Hz, 8 Hz, 1H), 7.91(d, J=8 Hz, 1H), 8.02(s, 1H), 8.05–8.15(m, 2H), 8.73(d, J=6 Hz, 1H)

Reference Example 33

2-Benzyl-7-methoxybenzofuran-4-carboxylic acid (Compound IIag)

(Step A) 2-Benzoyl-7-methoxybenzofuran (Compound IIag-a)

Substantially the same procedure as in Step A of Reference Example 6 was repeated using ortho-vanillin (7.8 g) and using phenyl chloride (9.5 g) instead of 4-picolyl chloride hydrochloride to give Compound IIag-a (13.9 g, quant.) as a pale-yellow solid.

NMR($CDCl_3$, δ, ppm): 4.01(s, 3H), 6.94(dd, J=1 Hz, 8 Hz, 1H), 7.21–7.29(m, 2H), 7.48–7.63(m, 4H), 8.06(dd, J=1 Hz, 8 Hz, 2H)

MASS(m/e): 252($M^+$)

(Step B) 2-Benzyl-7-methoxybenzofuran (Compound IIag-b)

Compound IIag-a (10.00 g) obtained in Step A was suspended in diethylene glycol (100 ml), and potassium hydroxide (7.57 g) and hydrazinemonohydrate (5.77 ml) were added thereto with stirring at room temperature, followed by heating under reflux for 2 hours with stirring. The reaction solution was poured into ice-water, and the mixture was adjusted to weak acidic with dilute hydrochloric acid, followed by extraction with ether. The organic layer was washed with a saturated saline and dried over anhydrous magnesium sulfate, and the solvent was distilled off under reduced pressure. The residue was purified by silica gel column chromatography (hexane:ethyl acetate=30:1) to give Compound IIag-b (7.35 g, 77.8%) as a yellow oily substance.

NMR($CDCl_3$, δ, ppm): 3.98(s, 3H), 4.12(s, 2H), 6.31(s, 1H), 6.73(dd, J=1 Hz, 7 Hz, 2H), 7.03–7.12(m, 2H), 7.22–7.35(m, 5H)

MASS(m/e): 238($M^+$)

(Step C) 2-Benzyl-7-methoxybenzofuran-4-carbaldehyde (Compound IIag-c)

Substantially the same procedure as in Step B of Reference Example 6 was repeated using Compound IIag-b (7.35 g) obtained in Step B to give Compound IIag-c (2.70 g, 32.9%) as a white solid.

(Step D) Methyl 2-benzyl-7-methoxybenzofuran-4-carboxylate (Compound IIag-d)

Substantially the same procedure as in Reference Example 17 was repeated using Compound IIag-c (2.70 g) obtained in Step C to give Compound IIag-d (1.20 g, 39.9%) as a white solid.

(Step E) 2-Benzyl-7-methoxybenzofuran-4-carboxylic acid (Compound IIag)

Substantially the same procedure as in Reference Example 31 was repeated using Compound IIag-d (1.20 g) obtained in Step D to give Compound IIag (0.39 g, 34.1%) as a white solid.

NMR(DMSO-$d_6$, δ, ppm): 4.01(s, 3H), 4.20(s, 2H), 6.65 (s, 1H), 7.26(d, 1H, J=8 Hz), 7.28–7.39(m, 5H), 7.53(d, 1H, J=8 Hz)

MASS(m/e): 282($M^+$)

Reference Example 34

7-Methoxy-3-phenylbenzofuran-4-carboxylic acid (Compound IIah)

(Step A) 4-Bromo-2-phenacyloxyanisole (Compound IIah-a)

Substantially the same procedure as in Step A of Reference Example 6 was repeated using 4-bromo-2-methoxyphenol (7.0 g) and phenyl bromide (10.6 g) to give Compound IIah-a (9.8 g, 74%) as a pale-yellow oily substance.

NMR($CDCl_3$, δ, ppm): 3.83(s, 3H), 5.33(s, 2H), 6.76(d, J=8 Hz, 1H), 6.95(d, J=2 Hz, 1H), 6.76(d, J=8 Hz, 1H), 7.06(dd, J=2 Hz, 8 Hz, 1H), 7.45–7.63(m, 3H), 7.96–7.99 (m, 2H)

MASS(m/e): 320($M^+$)

(Step B) 4-Bromo-7-methoxy-3-phenylbenzofuran (Compound IIah-b)

Polyphosphoric acid (50 ml) was added to Compound IIah-a (10.8 g) obtained in Step A followed by heating at 60° C. for 4 hours. After being allowed to stand for cooling, the reaction solution was poured into ice followed by extraction with ether. The organic layer was washed with a saturated saline and dried over magnesium sulfate. The solvent was distilled off and the residue was purified by silica gel column chromatography (hexane:ethyl acetate=30:1) to give Compound IIah-b (5.9 g, 58%) as a pale-yellow oily substance.

NMR($CDCl_3$, δ, ppm): 4.02(s, 3H), 6.72(d, J=9 Hz, 1H), 7.32(d, J=9 Hz, 1H), 7.40–7.51(m, 5H), 7.62(s, 1H)

MASS(m/e): 302($M^+$)

(Step C) (Compound IIah)

Substantially the same procedure as in Step D of Reference Example 1 was repeated using Compound IIah-b (4.0 g) obtained in Step B and using dry ice instead of DMF to give Compound IIah (1.5 g, 42%) as white crystals.

NMR($CDCl_3$, δ, ppm): 4.10(s, 3H), 6.88(d, J=9 Hz, 1H), 7.31–7.35(m, 5H), 7.71(s, 1H), 7.88(d, J=9 Hz, 1H)

MASS(m/e): 268($M^+$)

Reference Example 35

3-Ethoxycarbonylmethyl-7-methoxybenzofuran-4-carboxylic acid (Compound IIai)

Substantially the same procedure as in Reference Example 24 was repeated using Compound IIj (4.9 g) obtained in Reference Example 10 to give Compound IIai (4.4 g, 85%) as white crystals.

Melting point: 170–177° C.

NMR($CDCl_3$, δ, ppm): 1.26(t, J=7 Hz, 3H), 3.98(s, 2H), 4.08(s, 3H), 4.17(q, J=7 Hz, 2H), 6.85(d, J=9 Hz, 1H), 7.65(s, 1H), 8.06(d, J=9 Hz, 1H)

Reference Example 36

4-Benzoyl-7-methoxy-2,2-dimethyl-2,3-dihydrobenzofuran (Compound IIaj)

(Step A) 4-(1-Hydroxy-1-phenylmethyl)-7-methoxy-2,2-dimethyl-2,3-dihydrobenzofuran (Compound IIaj-a)

Under an argon atmosphere, a solution of Compound IIa (4.6 g) obtained in Reference Example 1 in THF (25 ml) was cooled to −78° C., and a 1.0M solution (26 ml) of phenylmagnesium bromide in THF was slowly and dropwise added thereto, followed by stirring at 0° C. for one hour. A saturated aqueous solution of ammonium chloride was added to the reaction solution followed by extraction with methylene chloride. The organic layer was washed with a saturated saline and dried over anhydrous magnesium sulfate, and the solvent was distilled off under reduced pressure. The residue was purified by silica gel column chromatography (chloroform/methanol=50/1) to give Compound IIaj-a (4.6 g, 72.2%) as a pale-yellow oily substance.

NMR(DMSO-$d_6$, δ, ppm): 1.32(s, 3H), 1.34(s, 3H), 2.84 (s, 2H), 3.71(s, 3H), 6.74–6.81(m, 2H), 7.28–7.30(m, 5H)

(Step B) (Compound IIaj)

Compound IIaj-a (4.0 g) obtained in Step A was dissolved in methylene chloride (140 ml), and manganese dioxide (4.0 g) was added thereto, followed by stirring at room temperature for 5 hours. The reaction solution was filtered and the obtained filtrate was concentrated under reduced pressure. The residue was purified by silica gel column chromatography (chloroform/hexane=1/2) to give Compound IIaj (2.0 g, 67.4%) as colorless crystals.

Melting point: 65–69° C.

NMR(DMSO-$d_6$, δ, ppm): 1.43(s, 6H), 3.34(s, 2H), 3.85 (s, 3H), 6.94(d, J=8.25 Hz, 1H), 7.04(d, J=8.25 Hz, 1H), 7.39–7.69(m, 5H)

IR(KBr, $cm^{-1}$): 1637, 1608, 1576, 1506, 1446

MASS(m/z): 282($M^+$)

Reference Example 37

(±)-4-Benzoyl-7-methoxy-3-methyl-2,3-dihydrobenzofuran (Compound IIak)

(Step A) 4-(1-Hydroxy-1-phenylmethyl)-7-methoxy-3-methyl-2,3-dihydrobenzofuran (Compound IIak-a)

Under an argon atmosphere, a solution of Compound IIe (7.0 g) obtained in Reference Example 5 in THF (70 ml) was cooled to −78° C., and a 1.0M solution (41 ml) of phenylmagnesium bromide in THF was slowly and dropwise added thereto, followed by stirring at 0° C. for one hour. A saturated aqueous solution of ammonium chloride was added to the reaction solution followed by extraction with methylene chloride. The organic layer was washed with a saturated saline and dried over anhydrous magnesium sulfate, and the solvent was distilled off under reduced pressure. The residue was purified by silica gel column chromatography (chloroform/methanol=50/1) to give Compound IIaj-a (7.8 g, 79.4%) as a pale-yellow oily substance.

NMR(DMSO-$d_6$, δ, ppm): 1.18(d, J=6.93 Hz, 3H), 3.25–3.40(m, 1H), 3.72(s, 3H), 4.13(dd, J=8.75 Hz, 3.30 Hz, 1H), 4.39(t, J=8.58 Hz, 1H), 6.80(d, J=8.58 Hz, 1H), 6.87(d, J=8.58 Hz, 1H), 7.20–7.31 (m, 5H)

(Step B) Compound IIak

Compound IIaj-a (5.0 g) obtained in Step A was dissolved in methylene chloride (240 ml), and manganese dioxide (5.0 g) was added thereto, followed by stirring at room temperature for 5 hours. The reaction solution was filtered and the obtained filtrate was concentrated under reduced pressure. The residue was purified by silica gel column chromatography (chloroform/hexane=1/2) to give Compound IIak (4.62 g, 93.1%) as a yellowish brown oily substance.

NMR(DMSO-$d_6$, δ, ppm): 1.10(d, J=6.93 Hz, 3H), 3.79–3.86(m, 1H), 3.86(s, 3H), 4.24(dd, J=4.29 Hz, 8.91 Hz, 1H), 4.62(t, J=8.91 Hz, 1H), 6.96(d, J=8.25 Hz, 1H), 7.02(d, J=8.25 Hz, 1H), 7.52–7.57 (m, 2H), 7.64–7.71(m, 3H)

Reference Example 38

4-Benzoyl-7-methoxy-2-(4-pyridyl)benzofuran (Compound IIal)

Substantially the same procedure as in Reference Example 36 was repeated using Compound IIaf (6.0 g) obtained in Reference Example 6 to give Compound IIal (5.6 g, 75%) as a pale-yellow oily substance.

NMR($CDCl_3$, δ, ppm): 4.12(s, 3H), 6.83(d, J=8 Hz, 1H), 7.4–7.6(m, 4H), 7.7–7.9(m, 5H), 8.69(d, J=5.5 Hz, 2H)

Reference Example 39

4-Acetyl-7-methoxy-2,2-dimethyl-2,3-dihydrobenzofuran (Compound IIam)

(Step A) 4-(1-Hydroxyethyl)-7-methoxy-2,2-dimethyl-2,3-dihydrobenzofuran (Compound IIam-a)

Under an argon atmosphere, a solution of Compound IIa (21 g) obtained in Reference Example 1 in THF (100 ml) was cooled to −78° C., and a 1.0M solution (122 ml) of methylmagnesiumbromide in THF was slowly and dropwise added thereto, followed by stirring at 0° C. for one hour. A saturated aqueous solution of ammonium chloride was added to the reaction solution followed by extraction with methylene chloride. The organic layer was washed with a saturated saline and dried over anhydrous magnesium sulfate, and the solvent was distilled off under reduced pressure. The residue was purified by silica gel column chromatography (chloroform/methanol=50/1) to give Compound IIam-a (24.4 g, quant.) as a pale-yellow oily substance.

NMR(DMSO-$d_6$, δ, ppm): 1.26(d, J=6.3 Hz, 3H), 1.39(s, 3H), 1.41(s, 3H), 3.00(s, 2H), 3.71(s, 3H), 4.60–4.64(m, 1H), 4.94(d, J=4.0 Hz, 1H), 6.75(s, 2H)

MASS(m/z): 282($M^+$)

(Step B) (Compound IIam)

Compound IIam-a (20.9 g) obtained in Step A was dissolved in methylene chloride (200 ml), and manganese dioxide (31 g) was added thereto, followed by stirring at room temperature for 5 hours. The reaction solution was filtered off and the obtained filtrate was concentrated under reduced pressure. The residue was purified by silica gel column chromatography (chloroform/hexane=1/2) to give Compound IIam (12.2 g, 59.0%) as colorless crystals.

NMR(DMSO-$d_6$, δ, ppm): 1.40(s, 6H), 2.49(s, 3H), 3.27 (s, 2H), 3.83(s, 3H), 6.94(d, J=8.6 Hz, 1H), 7.49 (d, J=8.6 Hz, 1H)

MASS(m/e): 220($M^+$)

Reference Example 40

4-Acetyl-7-methoxy-spiro[2,3-dihydrobenzofuran-2, 1'-cyclopentane] (Compound IIan)

(Step A) 4-(1-Hydroxyethyl)-7-methoxy-spiro[2,3-dihydrobenzofuran-2,1'-cyclopentane] (Compound IIan-a)

Under an argon atmosphere, a solution of Compound IIc (5.5 g) obtained in Reference Example 3 in THF (20 ml) was cooled to −78° C., and a 0.95M solution (30 ml) of methylmagnesiumbromide in THF was slowly and dropwise added thereto, followed by stirring at 0° C. for one hour. A saturated aqueous solution of ammonium chloride was added to the reaction solution followed by extraction with methylene chloride. The organic layer was washed with a saturated saline and dried over anhydrous magnesium sulfate, and the solvent was distilled off under reduced pressure. The residue was purified by silica gel column chromatography (chloroform/methanol=50/1) to give Compound IIan-a (6.7 g, quant.) as a pale-yellow oily substance.

NMR(DMSO-$d_6$, δ, ppm): 1.25(d, J=6.6 Hz, 3H), 1.71–1.86 (m, 8H), 3.17(s, 2H), 3.71(s, 3H), 4.60–4.65(m, 1H), 4.96(d, J=4.0 Hz, 1H), 6.74(s, 2H)

(Step B) (Compound IIan)

Compound IIan-a (6.5 g) obtained in Step A was dissolved in methylene chloride (260 ml), and pyridinium chlorochromate (6.8 g) was added thereto, followed by stirring at room temperature for 2 hours. The reaction solution was filtered and the obtained filtrate was concentrated under reduced pressure. The residue was purified by silica gel column chromatography (ethyl acetate/hexane=1/9) to give Compound IIan (2.98 g, 52.8%) as colorless crystals.

NMR(DMSO-$d_6$, δ, ppm): 1.71–1.99(m, 8H), 2.49(s, 3H), 3.44(s, 2H), 3.83(s, 3H), 6.93(d, J=8.6 Hz, 1H), 7.48(d, J=8.6 Hz, 1H)

Reference Example 41

8-Methoxy-2,2-dimethylbenzopyran-5-carboxylic acid (Compound IIao)

(Step A) Methyl 3-(1,1-dimethyl-2-propyn-1-yloxy)-4-methoxybenzoate (Compound IIao-a)

A mixture of methyl 3-hydroxy-4-methoxybenzoate (5.41 g), 3-chloro-3-methyl-1-butyne (10 ml), cesium carbonate (19.4 g), and DMF (54 ml) was stirred at 80° C. for one hour. 3-Chloro-3-methyl-1-butyne (5 ml) was further added to the mixture followed by stirring at 90° C. for 3 hours. After being allowed to stand for cooling, water was added to the mixture followed by extraction with ether. The organic layer was washed with a 1N aqueous solution of sodium hydroxide and with a saturated saline and dried over sodium sulfate, and the solvent was distilled off. The residue was purified by silica gel column chromatography (hexane/ethyl acetate=10/1 and 7/1) to give Compound IIao-a (2.31 g, 31%) as a brown oily substance.

NMR($CDCl_3$, δ, ppm): 1.68(s, 6H), 2.54(s, 1H), 3.87(s, 3H), 3.88(s, 3H), 6.90(d, J=8 Hz, 1H), 7.79(dd, J=1 Hz, 8 Hz, 1H), 8.09(d, J=1 Hz, 1H)

(Step B) Methyl 8-methoxy-2,2-dimethylbenzopyran-5-carboxylate (Compound IIao-b)

Compound IIao-a (2.30 g) obtained in Step A was dissolved in diethylaniline (14 ml) followed by stirring at 160° C. for 5 hours. After being allowed to stand for cooling, dilute hydrochloric acid was added to the mixture followed by extraction with ether. The organic layer was washed with a saturated saline and dried over sodium sulfate, and the solvent was distilled off. The residue was purified by silica gel column chromatography (hexane/ethyl acetate=10/1 and 7/1) to give Compound IIao-b (2.12 g, 92%) as a pale-yellow oily substance.

NMR($CDCl_3$, δ, ppm): 1.48(s, 6H), 3.86(s, 3H), 3.90(s, 3H), 5.78(d, J=9 Hz, 1H), 6.78(d, J=8 Hz, 1H), 7.33(d, J=9 Hz, 1H), 7.56(d, J=8 Hz, 1H)

(Step C) (Compound IIao)

Substantially the same procedure as in Reference Example 31 was repeated using Compound IIao-b (0.38 g) obtained in Step B to give Compound IIao (0.34 g, 96%) as a white solid.

Melting point: 159–166° C.

NMR($CDCl_3$, δ, ppm): 1.50(s, 6H), 3.92(s, 3H), 5.80(d, J=9 Hz, 1H), 6.80(d, J=9 Hz, 1H), 7.41(d, J=9 Hz, 1H), 7.69(d, J=9 Hz, 1H)

MASS(m/e): 234($M^+$)

Reference Example 42

8-Methoxy-2,2-dimethyl-3,4-dihydrobenzopyran-5-carboxylic acid (Compound IIap)

(Step A) Methyl 8-methoxy-2,2-dimethyl-3,4-dihydrobenzopyran-5-carboxylate (Compound IIap-a)

Substantially the same procedure as in Step C of Reference Example 30 was repeated using Compound IIao-b (1.78 g) obtained in Step B of Reference Example 41 and 10% palladium carbon (0.36 g) to give Compound IIap-a (1.31 g, 73%) as a white solid.

NMR($CDCl_3$, δ, ppm): 1.40(s, 6H), 1.70–1.87(m, 2H), 3.03–3.20(m, 2H), 3.85(s, 3H), 3.90(s, 3H), 6.73 (d, J=8 Hz, 1H), 7.57(d, J=8 Hz, 1H)

MASS(m/e): 250($M^+$)

(Step B) (Compound IIap)

Substantially the same procedure as in Reference Example 31 was repeated using Compound IIap-a (1.27 g) obtained in Step A to give Compound IIap (1.3 g, 96%) as a white solid.

NMR($CDCl_3$, δ, ppm): 1.40(s, 6H), 1.75–1.90(m, 2H), 3.11–3.26(m, 2H), 3.91(s, 3H), 6.78(d, J=9 Hz, 1H), 7.73(d, J=9 Hz, 1H)

MASS(m/e): 236($M^+$)

Reference Example 43

5-Carboxy-8-methoxy-spiro(benzopyran-2,1'-cyclopentane] (Compound IIaq)

(Step A) 8-Methoxy-4-oxo-spiro[3,4-dihydrobenzopyran-2, 1'-cyclopentane] (Compound IIaq-a)

A mixture of methyl 2-hydroxy-3-methoxyacetophenone (16 g), cyclopentanone (33 ml), pyrrolidine (15 ml), and toluene (200 ml) was heated under reflux for 3 hours. Cyclopentanone (6 ml) was further added to the mixture followed by heating under reflux for 2 hours. After being allowed to stand for cooling, ether was added to the mixture followed by washing with dilute hydrochloric acid and with a saturated saline. The mixture was dried over sodium sulfate and the solvent was distilled off to give Compound IIaq-a (20 g, 90%) as a brown oily substance.

NMR($CDCl_3$, δ, ppm): 1.54–2.00(m, 6H), 2.02–2.26(m, 2H), 2.85(s, 2H), 3.88(s, 3H), 6.90(dd, J=9 Hz, 9 Hz, 1H), 7.02(d, J=9 Hz, 1H), 7.48(d, J=9 Hz, 1H)

MASS(m/e): 232($M^+$)

(Step B) 4-Hydroxy-8-methoxy-spiro[3,4-dihydrobenzopyran-2,1'-cyclopentane] (Compound IIaq-b)

Compound IIaq-a (39 g) obtained in Step A was dissolved in methanol (300 ml), and sodium borohydride (7.5 g) was added thereto under ice-cooling, followed by stirring at room temperature for one hour. The mixture was cooled with ice again, dilute hydrochloric acid was added thereto, and the solvent was distilled off. Water was added to the residue followed by extraction with ethyl acetate. The organic layer was washed with a saturated saline and dried over sodium sulfate, and the solvent was distilled off. The residue was purified by silica gel column chromatography (hexane/ethyl acetate=6/1 and 2/1) to give Compound IIaq-b (29 g, 74%) as a pale-yellow oily substance.

NMR($CDCl_3$, δ, ppm): 1.46–2.18(m, 9H), 2.25(dd, J=8 Hz, 12 Hz, 1H), 3.82(s, 3H), 4.78–4.92(m, 1H), 6.80 (dd, J=2 Hz, 8 Hz, 1H), 6.88(dd, J=8 Hz, 9 Hz, 1H), 7.07(dd, J=2 Hz, 8 Hz, 1H)

MASS(m/e): 234($M^+$)

(Step C) 8-Methoxy-spiro[benzopyran-2,1'-cyclopentane] (Compound IIaq-c)

Methanesulfonyl chloride (4.9 ml) was dropwise added to a mixture of Compound IIaq-b (11 g) obtained in Step B, triethylamine (8.8 ml), and dichloromethane (114 ml) under ice-cooling, followed by stirring at room temperature for 30 minutes. DBU (9.5 ml) was added to the mixture followed by heating under reflux for 7 hours. After being allowed to stand for cooling, water was added to the mixture followed by extraction with hexane. The organic layer was washed with a saturated saline and dried over sodium sulfate, and the solvent was distilled off to give Compound IIaq-c (11 g, 99%) as a brown oily substance.

NMR($CDCl_3$, δ, ppm): 1.50–1.79(m, 4H), 1.82–2.08(m, 2H), 2.11–2.32(m, 2H), 3.84(s, 3H), 5.79(d, J=10 Hz, 1H), 6.35(d, J=10 Hz, 1H), 6.61(dd, J=4 Hz, 6 Hz, 1H), 6.71–6.87 (m, 2H)

(Step D) 8-Methoxy-spiro[benzopyran-2,1'-cyclopentane]-5-carbaldehyde (Compound IIaq-d)

Phosphorus oxychloride (18 ml) was dropwise added to a mixture of Compound IIaq-c (11 g) obtained in Step C, N-methylformanilide (24 ml), and dichloroethane (53 ml) under ice-cooling, followed by stirring at 90° C. for 2 hours. After being allowed to stand for cooling, the reaction solution was poured into ice-water followed by extraction with ethyl acetate. The organic layer was washed with a saturated saline and dried over sodium sulfate. The solvent was distilled off and the residue was purified by silica gel column chromatography (hexane/ethyl acetate=8/1) to give Compound IIaq-d (7.8 g, 65%) as an oily mixture of isomers (1:3).

NMR($CDCl_3$, δ, ppm): 1.50–1.80(m, total 4H), 1.81–2.08 (m, total 2H), 2.10–2.32(m, total 2H), 3.90 and 3.91(each s, total 3H), 5.71(d, J=9 Hz, 0.75H), 5.90(d, J=9 Hz, 0.25H), 6.39(d, J=9 Hz, 0.75H), 6.85(d, J=8 Hz, 0.25H), 7.15(d, J=1 Hz, 0.75H), 7.29(d, J=1 Hz, 0.75H), 7.30(d, J=8 Hz, 0.25H), 7.48(d, J=9 Hz, 0.25H), 9.80(s, 0.75H), 10.0(s, 0.25H)

(Step E) 8-Methoxy-5-methoxycarbonyl-spiro[benzopyran-2,1'-cyclopentane] (Compound IIaq-e)

Compound IIaq-d (21 g) obtained in Step D was dissolved in a 5% solution (400 ml) of potassium hydroxide in methanol, and iodine (45 g) was portionwise added thereto under ice-cooling, followed by stirring at room temperature for 6 hours. The mixture was cooled again with ice, the mixture was adjusted to pH 3 by adding dilute hydrochloric acid, and the solvent was distilled off. Water was added to the mixture followed by extraction with ethyl acetate. The organic layer was washed with a saturated saline and dried over sodium sulfate, and the solvent was distilled off. The residue was purified twice by silica gel column chromatography (hexane/ethyl acetate=10/1 and toluene/ether=80/1) to give Compound IIaq-e (5.5 g, 23%) as a pale-yellow solid.

Melting point: 48–50° C.

NMR($CDCl_3$, δ, ppm): 1.45–2.30(m, 8H), 3.85(s, 3H), 3.86(s, 3H), 5.82(d, J=9 Hz, 1H), 6.76(d, J=8 Hz, 1H), 7.37(d, J=9 Hz, 1H), 7.53(d, J=8 Hz, 1H)

MASS(m/e): 274($M^+$)

(Step F) 5-Carboxy-8-methoxy-spiro[benzopyran-2,1'-cyclopentane] (Compound IIaq)

Substantially the same procedure as in Reference Example 31 was repeated using Compound IIaq-e (1.9 g) obtained in Step E to give Compound IIaq (1.7 g, 95%) as a white solid.

Melting point: 177–189° C.

NMR($CDCl_3$, δ, ppm): 1.52–2.32(m, 8H), 3.90(s, 3H), 5.88(d, J=9 Hz, 1H), 6.80(d, J=9 Hz, 1H), 7.45(d, J=9 Hz, 1H), 7.70(d, J=9 Hz, 1H)

MASS(m/e): 260($M^+$)

Reference Example 44

Methyl 8-methoxy-spiro[(3,4-dihydrobenzopyran-2, 1'-cyclopentane]-5-carboxylate (Compound IIar)

Substantially the same procedure as in Step A of Reference Example 42 was repeated using Compound (2.0 g) obtained in Step E of Reference Example 43 to give Compound IIar (2.0 g, 100%) as an oily substance.

NMR($CDCl_3$, δ, ppm): 1.47–2.08(m, 10H), 3.17(t, J=7 Hz, 2H), 3.83(s, 3H), 3.88(s, 3H), 6.70(d, J=9 Hz, 1H), 7.56(d, J=9 Hz, 1H)

Reference Example 45

8-Methoxy-spiro[3,4-dihydrobenzopyran-2,1'-cyclopentane]-5-carboxylic acid (Compound IIas)

Substantially the same procedure as in Reference Example 31 was repeated using Compound IIar (2.0 g) obtained in Reference Example 44 to give Compound IIas (1.8 g, 96%) as white crystals.

Melting point: 182–189° C.

NMR($CDCl_3$, δ, ppm): 1.50–2.10(m, 10H), 3.22(t, J=6 Hz, 2H), 3.90(s, 3H), 6.75(d, J=8 Hz, 1H),7.70(d, J=8 Hz, 1H)

MASS(m/e): 262($M^+$)

Reference Example 46

Methyl 8-methoxy-spiro[3,4-dihydrobenzopyran-2, 1'-cyclohexane]-5-carboxylate (Compound IIat)

(Step A) 8-Methoxy-4-oxo-spiro[3,4-dihydrobenzopyran-2, 1'-cyclohexane] (Compound IIat-a)

Substantially the same procedure as in Step A of Reference Example 43 was repeated using 2-hydroxy-3-methoxyacetophenone (40 g), cyclohexanone (100 ml), and pyrrolidine (40 ml) to give Compound at-a (59 g, 100%) as a brown oily substance.

NMR($CDCl_3$, δ, ppm): 1.20–2.10(m, 10H), 2.74(s, 2H), 3.90(s, 3H), 6.90(dd, J=8 Hz, 8 Hz, 1H), 7.05(dd, J=1 Hz, 8 Hz, 1H), 7.46(d, J=1, 8 Hz, 1H)

MASS(m/e): 246($M^+$)

(Step B) 4-Hydroxy-8-methoxy-spiro[3,4-dihydrobenzopyran-2,1'-cyclohexane] (Compound IIat-b)

Substantially the same procedure as in Step B of Reference Example 43 was repeated using Compound at-a (59 g) obtained in Step A and sodium borohydride (18 g) to give Compound (51 g, 80%) as a pale-yellow oily substance.

NMR($CDCl_3$, δ, ppm): 1.20–2.05(m, 11H), 2.26(dd, J=6 Hz, 13 Hz, 1H), 3.85(s, 3H), 4.75–4.90(m, 1H), 6.80 (dd, J=1 Hz, 8 Hz, 1H), 6.88(dd, J=8 Hz, 8 Hz, 1H), 7.03(dd, J=1 Hz, 8 Hz, 1H)

MASS(m/e): 248($M^+$)

(Step C) 8-Methoxy-spiro[benzopyran-2,1'-cyclohexane] (Compound IIat-c)

Substantially the same procedure as in Step C of Reference Example 43 was repeated using Compound at-b (50 g) obtained in Step B, triethylamine (54 ml), methane-sulfonyl chloride (33 ml), and DBU (58 ml) to give Compound at-c (46 g, 100%) as a brown oily substance.

NMR($CDCl_3$, δ, ppm): 1.20–2.08(m, 10H),3.85(s, 3H), 5.70(d, J=9 Hz, 1H), 6.33(d, J=9 Hz, 1H), 6.57–6.85(m, 3H)

MASS(m/e): 230($M^+$)

(Step D) 8-Methoxy-spiro[benzopyran-2,1'-cyclohexane]-5-carbaldehyde (Compound IIat-d)

Substantially the same procedure as in Step D of Reference Example 43 was repeated using Compound at-c (46 g) obtained in Step C, N-methylformanilide (100 ml), and phosphorus oxychloride (76 ml) to give Compound at-d (36 g, 69%) as an oily mixture of isomers (1:3).

NMR($CDCl_3$, δ, ppm): 1.25–2.10(m, total 10H), 3.91 and 3.94(each s, total 3H), 5.80(d, J=9 Hz, 0.75H), 5.90(d, J=9 Hz, 0.25H), 6.39(d, J=9 Hz, 0.75H), 6.90(d, J=8 Hz, 0.25H), 7.16(d, J=1 Hz, 0.75H), 7.28(d, J=1 Hz, 0.75H), 7.32(d, J=8 Hz, 0.25H), 7.45(d, J=9 Hz, 0.25H), 9.80(s, 0.75H), 10.0(s, 0.25H)

(Step E) Methyl 8-methoxy-spiro[benzopyran-2,1'-cyclohexane]-5-carboxylate (Compound IIat-e)

Substantially the same procedure as in Step E of Reference Example 43 was repeated using Compound at-d (36 g) obtained in Step D and iodide (71 g) to give Compound at-e (4.8 g, 12%) as a pale-yellow solid.

Melting point: 70–75° C.

NMR($CDCl_3$, δ, ppm): 1.20–2.03(m, 10H), 3.85(s, 3H), 3.90(s, 3H), 5.83(d, J=9 Hz, 1H), 6.77(d, J=8 Hz, 1H), 7.32(d, J=9 Hz, 1H), 7.55(d, J=8 Hz, 1H)

MASS(m/e): 288($M^+$)

(Step F) Methyl 8-methoxy-spiro[3,4-dihydrobenzopyran-2,1'-cyclohexane]-5-carboxylate (Compound IIat)

Substantially the same procedure as in Step A of Reference Example 42 was repeated using Compound at-e (2.1 g) obtained in Step E to give Compound IIat (2.1 g, 100%) as a pale-yellow oily substance.

NMR($CDCl_3$, δ, ppm): 1.25–1.94(m, 12H), 3.10(t, 7 Hz, 2H), 3.84(s, 3H), 3.89(s, 3H), 6.73(d, J=9 Hz, 1H), 7.55(d, J=9 Hz, 1H)

Reference Example 47

4-Methoxy-spiro[2,3-dihydrobenzofuran-2,1'-cyclopentane]-7-carbaldehyde (Compound IIau)

(Step A) 4-Bromo-3-(2-oxocyclopentyloxy)anisole (Compound IIau-a)

Substantially the same procedure as in Step A of Reference Example 3 was repeated using 2-bromo-5-methoxyphenol [Journal of Medicinal Chemistry, 1263, (1985)] (13.0 g) to give Compound IIau-a (15.1 g, 83%) as a pale-yellow oily substance.

NMR($CDCl_3$, δ, ppm): 1.85–2.50(m, 6H), 3.78(s, 3H), 4.53–4.59(m, 1H), 6.45(dd, J=9 Hz, 3 Hz, 1H), 6.67(d, J=3 Hz, 1H), 7.39(d, J=9 Hz, 1H)

MASS(m/z): 284 ($M^+$)

(Step B) 2-Bromo-4-(2-methylenecyclopentyloxy)anisole (Compound IIau-b)

Substantially the same procedure as in Step B of Reference Example 3 was repeated using Compound IIau-a (10.5 g) obtained in Step A to give Compound IIau-b (8.2 g, 79%) as a pale-yellow oily substance.

NMR($CDCl_3$, δ, ppm): 1.66–2.62(m, 6H), 3.77(s, 3H), 4.89–5.92(m, 1H), 5.11–5.12(m, 1H), 5.22–5.23(m, 1H), 6.40(dd, J=9 Hz, 3 Hz, 1H), 6.57(d, J=3 Hz, 1H), 7.40(d, J=9 Hz, 1H)

MASS(m/e): 282($M^+$)

(Step C) 6-Bromo-2-[(2-cyclopenten-1-yl)methyl]-3-methoxyphenol (Compound IIau-c)

Substantially the same procedure as in Step C of Reference Example 3 was repeated using Compound IIau-b (8.2 g) obtained in Step B to give Compound IIau-c (7.6 g, 93%) as a brown oily substance.

NMR($CDCl_3$, δ, ppm): 1.80–1.91(m, 2H), 2.24–2.30(m, 4H), 3.47(s, 2H), 3.78(s, 3H), 5.25(s, 1H), 5.62 (s, 1H), 6.41(d, J=9 Hz, 1H), 7.27(d, J=9 Hz, 1H)

MASS(m/e): 282($M^+$)

(Step D) 7-Bromo-4-methoxy-spiro[2,3-dihydrobenzofuran-2,1'-cyclopentane] (Compound IIau-d)

Substantially the same procedure as in Step D of Reference Example 3 was repeated using Compound IIau-c (5.7 g) obtained in Step C to give Compound IIau-d (5.5 g, 96%) as a brown oily substance.

NMR($CDCl_3$, δ, ppm): 1.65–2.20(m, 8H), 3.17(s, 2H), 3.79(s, 3H), 6.28(d, J=9 Hz, 1H), 7.18(d, J=9 Hz, 1H)

MASS(m/e): 282($M^+$)

(Step E) 4-Methoxy-spiro[2,3-dihydrobenzofuran-2,1'-cyclopentane]-7-carbaldehyde (Compound IIau)

Substantially the same procedure as in Step E of Reference Example 3 was repeated using Compound IIau-d (5.5 g) obtained in Step D to give Compound IIau (4.3 g, 95%) as colorless crystals.

NMR($CDCl_3$, δ, ppm): 1.70–2.19(m, 8H), 3.09(s, 2H), 3.88(s, 3H), 6.47(d, J=9 Hz, 1H), 7.63(d, J=9 Hz, 1H), 10.08(s, 1H)

MASS(m/e): 232($M^+$)

Reference Example 48

4-Methoxy-spiro[2,3-dihydrobenzofuran-2,1'-cyclopentane]-7-carboxylic acid (Compound IIav)

Substantially the same procedure as in Step E of Reference Example 47 was repeated using Compound (6.9 g) obtained in Step D of Reference Example 47 and using dry ice instead of DMF to give Compound IIav (3.5 g, 58%) as white crystals.

NMR($CDCl_3$, δ, ppm): 1.68–2.23(m, 8H), 3.17(s, 2H), 3.90(s, 3H),6.55(d, J=9 Hz, 1H), 7.83(d, J=9 Hz, 1H), 9.63(broad s, 1H)

MASS(m/e): 248($M^+$)

Reference Example 49

Methyl 4-methoxy-spiro[2,3-dihydrobenzofuran-2,1'-cyclopentane]-7-carboxylate (Compound IIaw)

Substantially the same procedure as in Reference Example 15 was repeated using Compound IIav (1.0 g) obtained in Reference Example 48 to give Compound (0.86 g, 81%) as colorless crystals.

NMR($CDCl_3$, δ, ppm): 1.70–2.22(m, 8H), 3.06(s, 2H), 3.85(s, 3H), 3.87(s, 3H), 6.42(d, J=9 Hz, 1H), 7.75(d, J=9 Hz, 1H)

MASS(m/e): 262($M^+$)

Reference Example 50

7-Methoxy-spiro[1,3-benzodioxole-2,1'-cyclopentane]-4-carbaldehyde (Compound IIax)

(Step A) 7-Methoxy-spiro[1,3-benzodioxole-2,1'-cyclopentane] (Compound IIax-a)

A mixture of 3-methoxycatechol (22.6 g), cyclopentanone (27.1 g), methyl orthoformate (34.2 g), p-toluenesulfonic acid.monohydrate (0.2 g), and benzene (300 ml) was heated under reflux for 24 hours. After being allowed to stand for cooling, a dilute solution of sodium hydroxide was added to the mixture followed by extraction with ether. The organic layer was washed with a saturated saline and dried over anhydrous potassium carbonate. The solvent was distilled off under reduced pressure to give Compound IIax-a (30 g, 90%) as a colorless oily substance.

NMR($CDCl_3$, δ, ppm): 1.79–1.89(m, 4H), 2.06–2.21(m, 4H), 3.89(s, 3H), 6.44–6.50(m, 2H), 6.74(t, J=8 Hz, 1H)

MASS(m/e): 206($M^+$)

(Step B) (Compound IIax)

Compound IIax-a (17.0 g) obtained in Step A was dissolved in dimethylformamide (100 ml), and phosphorus oxychloride (23.1 ml) was added thereto, followed by heating at 60° C. for 6 hours. After being allowed to stand for cooling, the reaction solution was poured into ice followed by extraction with ether. The organic layer was washed with a saturated saline and dried over anhydrous potassium carbonate. The solvent was distilled off and the residue was purified by silica gel column chromatography (hexane:ethyl acetate=20:1) to give Compound IIax (2.1 g, 11%) as colorless crystals.

NMR($CDCl_3$, δ, ppm): 1.83–1.91(m, 4H), 2.14–2.24(m, 4H), 3.97(s, 3H), 6.58 (d, J=9 Hz, 1H), 7.27(d, J=9 Hz, 1H), 9.99(s, 1H)

MASS(m/e): 234($M^+$)

Reference Example 51

Methyl 7-methoxy-spiro[1,3-benzodioxole-2,1'-cyclopentane]-4-carboxylate (Compound IIay)

Substantially the same procedure as in Step C of Reference Example 14 was repeated using Compound IIay (3.7 g) obtained in Reference Example 50 to give Compound IIay (2.7 g, 64%) as a colorless oily substance.

NMR($CDCl_3$, δ, ppm): 1.84–1.90(m, 4H), 2.11–2.25(m, 4H), 3.88(s, 3H), 3.94(s, 3H), 6.52(d, J=9 Hz, 1H), 7.40(d, J=9 Hz, 1H)

MASS(m/e): 264($M^+$)

Reference Example 52

7-Methoxy-spiro[1,3-benzodioxole-2,1'-cyclopentane]-4-carboxylic acid (Compound IIaz)

Substantially the same procedure as in Reference Example 31 was repeated using Compound IIay (1.70 g) obtained in Reference Example 51 to give Compound IIaz (1.54 g, 96%) as colorless crystals.

NMR($CDCl_3$, δ, ppm): 1.83–1.91(m, 4H), 2.14–2.24(m, 4H), 3.97(s, 3H), 6.58(d, J=9 Hz, 1H), 7.27(d, J=9 Hz, 1H), 9.63(broad s, 1H)

MASS(m/e): 250($M^+$)

Reference Example 53

7-Benzoyl-4-methoxy-spiro[1,3-benzodioxole-2,1'-cyclopentane] (Compound IIba)

(Step A) 7-(1-Hydroxy-1-phenyl)methyl-4-methoxy-spiro[1,3-benzodioxole-2,1'-cyclopentane] (Compound IIba-a)

Substantially the same procedure as in Step A of Reference Example 36 was repeated using Compound IIax (4.4 g) obtained in Reference Example 50 to give Compound IIba-a (5.6 g, 95%) as a pale-yellow oily substance.

NMR($CDCl_3$, δ, ppm): 1.77–1.87(m, 4H), 2.03–2.18(m, 4H), 2.48(d, J=4 Hz, 1H), 3.85(s, 3H), 5.92(d, J=4 Hz, 1H), 6.43(d, J=9 Hz, 1H), 7.15(d, J=9 Hz, 1H), 7.22–7.43(m, 5H)

MASS(m/e): 312($M^+$)

(Step B) (Compound IIba)

Substantially the same procedure as in Step B of Reference Example 36 was repeated using Compound IIba-a (5.6 g) obtained in Step A to give Compound IIba (4.9 g, 88%) as a colorless oily substance.

NMR($CDCl_3$, δ, ppm): 1.72–1.83(m, 4H), 2.04–2.18(m, 4H), 3.94(s, 3H), 6.56(d, J=9 Hz, 1H), 6.68(d, J=9 Hz, 1H), 7.40–7.57(m, 3H), 7.77–7.81(m, 2H)

MASS(m/e): 310($M^+$)

Reference Example 54

3-Benzyloycarhonylmethyl-7-methoxybenzofuran-4-carboxylic acid (Compound IIbb)

(Step A) 3-Carboxymethyl-7-methoxybenzofuran-4-carbaldehyde (Compound IIbb-a)

Substantially the same procedure as in Example 9 was repeated using Compound IIj (5.0 g) obtained in Reference Example 10 to give Compound IIbb-a (4.1 g, 91%) as white crystals.

Melting point: 185–188° C.

NMR(DMSO-$d_6$, δ, ppm): 3.96(s, 2H), 4.05(s, 3H), 7.17 (d, J=8 Hz, 1H), 7.86(d, J=8 Hz, 1H), 8.03(s, 1H), 9.96(s, 1H), 12.5(broad s, 1H)

(Step B) 3-Benzyloxycarbonylmethyl-7-methoxybenzofuran-4-carbaldehyde (Compound IIbb-b)

Substantially the same procedure as in Example 13 was repeated using Compound IIbb-a (4.1 g) obtained in Step A to give Compound IIbb-b (4.3 g, 77%) as white crystals.

Melting point: 98–100° C.

NMR(DMSO-$d_6$, δ, ppm): 4.05(s, 3H), 4.10(s, 2H), 5.09 (s, 1H), 7.18(d, J=8 Hz, 1H), 7.25–7.43(m, 5H), 7.87(d, J=8 Hz, 2H), 8.06(s, 1H), 9.90(s, 1H)

MASS(m/e): 324($M^+$)

(Step C) (Compound IIbb)

Substantially the same procedure as in Reference Example 28 was repeated using Compound IIbb-b (4.3 g) obtained in Step B to give Compound IIbb (4.3 g, 95%) as white crystals.

Melting point: 168–171° C.

NMR(DMSO-$d_6$, δ, ppm): 4.00(s, 3H), 4.03(s, 2H), 5.06 (s, 1H), 7.02(d, J=9 Hz, 1H), 7.20–7.42(m, 5H), 7.84(d, J=8 Hz, 2H), 7.99(s, 1H)

MASS(m/e): 340($M^+$)

Reference Example 55

3-Ethoxycarbonylmethyl-7-methoxybenzofuran (Compound IIbc)

(Step A) Ethyl 4-(6-iodo-2-methoxyphenoxy)crotonate (Compound IIbc-a)

Substantially the same procedure as in Step A of Reference Example 1 was repeated using 6-iodo-2-methoxyphenol [Heterocyclic Communications, 289 (1995)] (0.4 g) and ethyl 4-bromocrotonate (0.29 ml) to give Compound IIbc-a (0.52 g, 90%) as a pale-yellow oily substance.

NMR($CDCl_3$, δ, ppm): 1.31(t, J=7 Hz, 3H), 3.84(s, 3H), 4.23(q, 2H, J=7 Hz), 4.65(dd, 2H, J=2 Hz, 5 Hz), 6.32 (dt, J=2 Hz, 16 Hz, 1H), 6.82(dd, J=8 Hz, 8 Hz, 1H), 6.89(dd, J=2 Hz, 8 Hz, 1H), 7.12(dt, 1H, J=5 Hz, 16 Hz), 7.36(dd, J=2 Hz, 8 Hz, 1H)

MASS(m/e): 362($M^+$)

(Step B) (Compound IIbc)

Substantially the same procedure as in Step B of Reference Example 10 was repeated using Compound IIbc-a (0.52 g) obtained in Step A to give Compound IIbc (0.32 g, 94%) as a pale-yellow oily substance.

NMR($CDCl_3$, δ, ppm): 1.27(t, J=7 Hz, 3H), 3.68(s, 2H), 4.01(s, 3H), 4.19(q, J=7 Hz, 2H), 6.82(dd, J=3 Hz, 7 Hz, 1H), 7.10–7.22(m, 2H), 7.64(s, 1H)

MASS(m/e): 234($M^+$)

Reference Example 56

Ethyl 4-formyl-7-Tnethoxybenzofuran-3-carboxylate (Compound IIbd)

(Step A) Ethyl 2-methoxyphenoxyacetate (Compound IIbd-a)

A mixture of 2-methoxyphenol (11.3 g), potassium carbonate (25 g), ethyl bromoacetate (12 ml), and acetone (113 ml) was heated under reflux for 4 hours. After cooling to the room temperature, the mixture was filtered and the solvent was distilled off under reduced pressure from the filtrate. The residue was purified by silica gel column chromatography (hexane/ethyl acetate=4/1) to give Compound IIbd-a (17 g, 91%) as a pale-yellow oily substance.

NMR($CDCl_3$, δ, ppm) 1.29(t, J=7 Hz, 3H), 3.88(s, 3H), 4.26(q, J=7 Hz, 2H), 4.68(s, 2H), 6.78–7.03(m, 4H)

MASS(m/e): 210($M^+$)

(Step B) Diethyl 3-(2-methoxyphenoxy)-2-oxosuccinate (Compound IIbd-b)

Ethanol (34 ml) was dropwise added to a suspension of 60% sodium hydride (25 g) and ether (400 ml) with stirring under ice-cooling, followed by stirring at room temperature for 15 minutes. The mixture was again cooled with ice and diethyl oxalate (78 ml) was added thereto. After 10 minutes, a solution of Compound IIbd-a (80 g) obtained in Step A dissolved in ether (300 ml) was dropwise added to the mixture, followed by stirring at room temperature for 5 hours. The reaction solution was poured into ice-water, and the aqueous layer was adjusted to acidic with hydrochloric acid, followed by extraction with ether. The organic layer was washed with a saturated saline and dried over sodium sulfate, and the solvent was distilled off under reduced pressure. The residue was purified by silica gel column chromatography (hexane/ethyl acetate=1/1) to give Compound IIbd-b (73 g, 62%) as a pale-yellow oily substance.

NMR($CDCl_3$, δ, ppm): 1.29(t, J=7 Hz, 3H), 3.88(s, 3H), 4.26(q, J=7 Hz, 2H), 4.68(s, 2H), 6.78–7.03(m, 4H)

MASS(m/e): 310($M^+$)

(Step C) Diethyl 7-methoxybenzofuran-2,3-dicarboxylate (Compound IIbd-c)

Polyphospholic acid (460 g) was stirred at 60° C., and Compound IIbd-b (30 g) obtained in Step B was slowly and dropwise added thereto, followed by stirring for 30 minutes. After being allowed to stand for cooling, the mixture was poured into water under ice-cooling, followed by extraction with ethyl acetate. The organic layer was washed with a saturated saline and dried over sodium sulfate, and the solvent was distilled off under reduced pressure. Substantially the same procedure was repeated twice and the residue was combined. The combined residue was purified by silica gel column chromatography (hexane/ethyl acetate=5/1) to give Compound IIbd-c (32 g, 56%) as pale-yellow crystals.

Melting point: 50–52° C.

NMR($CDCl_3$, δ, ppm): 1.38–1.52(m, 6H), 4.02(s, 3H), 4.40–4.55(m, 4H), 6.95(dd, J=1 Hz, 8 Hz, 1H), 7.29 (dd, J=8 Hz, 8 Hz, 1H), 7.48(dd, J=1 Hz, 8 Hz, 1H)

MASS(m/e): 292 ($M^+$)

(Step D) Ethyl 7-methoxybenzofuran-3-carboxylate (Compound IIbd-d)

A mixture of Compound IIbd-c (1.5 g) obtained in Step C, sodium chloride (1.5 g), dimethylsulfoxide (15 ml), and water (1.5 ml) was stirred at 160° C. for 6 hours. After being allowed to stand for cooling, the mixture was filtered, and the solvent was distilled off under reduced pressure from the filtrate. Water was added to the residue and the mixture was extracted with ether. The organic layer was washed with a saturated saline and dried over sodium sulfate, and the solvent was distilled off under reduced pressure to give a crude product of Compound IIbd-d (0.77 g, 68%) as a pale-yellow solid. This crude product was subjected to a subsequent step without being purified.

Melting point: 39–41° C.

NMR($CDCl_3$, δ, ppm): 1.42(t, J=7 Hz, 3H), 4.02(s, 3H), 4.40(q, J=7 Hz, 2H), 6.87(dd, J=1 Hz, 8 Hz, 1H), 7.28 (dd, J=8 Hz, 8 Hz, 1H), 7.65(dd, J=1 Hz, 8 Hz, 1H), 8.26 (s, 1H)

(Step E) (Compound IIbd)

Substantially the same procedure as in Step B of Reference Example 6 was repeated using Compound IIbd-d (0.77 g) obtained in Step D to give Compound IIbd (0.61 g, 70%) as white crystals.

Melting point: 144–145° C.

NMR($CDCl_3$, δ, ppm): 1.43(t, J=7 Hz, 3H), 4.09(s, 3H), 4.41(q, J=7 Hz, 2H), 6.99(d, J=9 Hz, 1H), 8.06(d, J=9 Hz, 1H), 8.41(s, 1H), 11.1(s, 1H)

MASS(m/e): 248($M^+$)

Reference Example 57

7-Methoxy-2-(2-pyridylcarbonyl)benzofuran (Compound IIbe)

Substantially the same procedure as in Step A of Reference Example 6 was repeated using ortho-vanillin (5.1 g) and using α-bromoacetyl-2-pyridine hydrochloride (11.8 g) instead of 4-picolyl chloride hydrochloride to give Compound IIbe (3.06 g, 36.3%) as a colorless solid.

NMR($CDCl_3$, δ, ppm): 4.04(s, 3H), 6.98(d, J=8 Hz, 1H), 7.23(dd, J=8 Hz, 8 Hz, 1H), 7.33(d, J=8 Hz, 1H), 7.53 (ddd, J=1 Hz, 4.5 Hz, 10 Hz, 1H), 7.92(ddd, J=1 Hz, 8 Hz, 10 Hz, 1H), 8.23(dd, J=1 Hz, 8 Hz, 1H), 8.43(s, 1H), 8.77 (dd, J=1 Hz, 4.5 Hz, 1H)

MASS(m/e): 312($M^+$)

Reference Example 58

2-[N-(3-Fluorophenyl)-N-methylaminocarbonyl]-7-methoxybenzofuran (Compound IIbf)

(Step A) 2-(3-Fluorophenylaminocarbonyl)-7-methoxybenzofuran (Compound IIbf-a)

Under a nitrogen atmosphere, 3-fluoroaniline (6.2 ml) was dissolved in dry THF (150 ml), and the solution was stirred at 0° C. Sodium hydride (3.4 g) was slowly added to the mixture followed by stirring at 0° C. for 20 minutes. After the generation of hydrogen ceased, 7-methoxybenzofuran-2-carbonyl chloride (9.0 g) was added to the mixture, followed by stirring at room temperature for 3 hours. The reaction was stopped with 1N hydrochloric acid and the mixture was extracted with ethyl acetate. The organic layer was washed with a 1N aqueous solution of hydrochloric acid and with a saturated saline, and dried over anhydrous magnesium sulfate, and the solvent was distilled off under reduced pressure. The residue was triturated with diethyl ether to give Compound IIbf-a (7.82 g, 64.2%) as a white solid.

NMR($CDCl_3$, δ, ppm): 4.05(s, 3H), 6.88(m, 1H), 6.95(dd, J=2 Hz, 7 Hz, 1H), 7.2–7.4(m, 4H), 7.61(s, 1H), 7.68 (ddd, J=2 Hz, 3 Hz, 11 Hz, 1H), 8.48(bs, 1H)

(Step B) (Compound IIbf)

Under a nitrogen atmosphere, Compound IIbf-a (5.50 g) was dissolved in dry THF (200 ml), and the solution was stirred at 0° C. Sodium hydride (1.16 g) was slowly added to the mixture followed by stirring at 0° C. for 10 minutes. After the generation of hydrogen ceased, methyl iodide (2.4 ml) was added to the mixture, followed by stirring at room temperature for 2 hours. The reaction was stopped with a saturated saline and the mixture was extracted with ethyl acetate. The organic layer was washed with a saturated saline and dried over anhydrous magnesium sulfate, and the solvent was distilled off under reduced pressure. The residue was triturated with diethyl ether to give Compound IIbf (4.23 g, 73.3%) as a white solid.

NMR($CDCl_3$, δ, ppm): 3.49(s, 3H), 3.84(s, 3H), 6.75(s, 1H), 6.80(dd, J=3 Hz, 6 Hz, 1H), 7.0–7.2(m, 5H), 7.30(m, 1H)

Reference Example 59

2-Phenylaminocarbonyl-7-methoxybenzofuran (Compound IIbg)

Substantially the same procedure as in Step A of Reference Example 58 was repeated using 7-methoxybenzofuran-2-carbonyl chloride and aniline to give Compound IIbg (13.0 g, 68.2%) as a yellowish white solid.

NMR($CDCl_3$, δ, ppm): 3.97(s, 3H), 6.88(dd, J=2 Hz, 7 Hz, 1H), 7.1–7.3(m, 3H), 7,35(dd, J=7 Hz, 9 Hz, 2H), 7.55(s, 1H), 7.71(d, J=9 Hz, 2H), 8.51(bs, 1H)

MASS(m/e): 267($M^+$), 175

Reference Example 60

2-Benzoyl-7-methoxybenzofuran-4-carboxylic acid (Compound IIbh)

(Step A) 2-Benzoyl-7-methoxybenzofuran-4-carbaldehyde (Compound IIbh-a)

Substantially the same procedure as in Step B of Reference Example 6 was repeated using Compound IIag-a (20.0 g) obtained in Step A of Reference Example 33 to give Compound IIbh-a (19.9 g, 90.0%) as a white solid.

NMR($CDCl_3$, δ, ppm): 4.14(s, 3H), 7.07(d, J=8 Hz, 1H), 7.55(dd, J=7 Hz, 7.5 Hz, 2H), 7.63(t, J=7 Hz, 1H), 7.77(d, J=8 Hz, 1H), 8.06(d, J=7.5 Hz, 2H), 8.20(s, 1H), 10.06(s, 1H)

MASS(m/e): 280($M^+$)

(Step B) (Compound IIbh)

Substantially the same procedure as in Example 9 was repeated using Compound IIbh-a (6.65 g) obtained in Step A to give Compound IIbh (4.70 g, 66.9%) as a white solid.

NMR(DMSO-$d_6$, δ, ppm): 4.07(s, 3H), 7.27(d, J=8.5 Hz, 1H), 7.64(dd, J=5.5 Hz, 7 Hz, 2H), 7.73(d, J=5.5 Hz, 1H), 7.91(s, 1H), 7.95–8.05(m, 3H), 13.07(bs, 1H)

MASS(m/e): 296($M^+$), 219

Reference Example 61

3-Ethoxycarbonylmethyl-7-methoxy-4-(N-methoxy-N-methylaminocarbonyl)-2,3-dihydrobenzofuran (Compound IIbi)

Substantially the same procedure as in Example 1 was repeated using Compound IIaa (1.0 g) obtained in Reference Example 27 to give a crude acid chloride, which was dissolved in THF (10 ml). N,O-Dimethylhydroxylamine.hydrochloride (523 mg) was added to the solution under ice-cooling, followed by stirring at room temperature for 2.5 hours. A 1N aqueous solution of hydrochloric acid was added to the mixture under ice-cooling, followed by extraction with ethyl acetate. The organic layer was washed with a saturated saline and dried over anhydrous magnesium sulfate, and the solvent was distilled off under reduced pressure. The residue was purified by silica gel column chromatography (hexane/ethyl acetate=1/1) to give Compound IIbi (1.05 g, 91.1%) as a colorless solid.

NMR($CDCl_3$, δ, ppm): 1.25(t, J=7 Hz, 3H), 2.45–2.55(m, 1H), 2.85–2.92(m, 1H), 3.33(s, 3H), 3.57(s, 3H), 3.90(s, 3H), 4.09–4.17 (m, 3H), 4.41–4.48(m, 1H), 4.76–4.83(m, 1H), 6.77(d, J=9 Hz, 1H), 7.04(d, J=9 Hz, 1H)

MASS(m/e): 323($M^+$)

Reference Example 62

7-Methoxy-1,3-benzodioxole-4-carbaldehyde (Compound IIbj)

(Step A) 4-Bromo-7-methoxy-1,3-benzodioxole (Compound IIbj-a)

3-Bromo-6-methoxycatechol (23.4 g) was dissolved in DMF (150 ml), and dibromomethane (15.4 ml) and potassium fluoride (31.1 g) were added thereto, followed by heating at 110° C. for 6 hours with stirring. After being allowed to stand for cooling, water was added to the mixture followed by extraction with ether. The organic layer was washed with an aqueous solution of sodium hydroxide, with water, and with a saturated saline, and dried over anhydrous magnesium sulfate, and the solvent was distilled off under reduced pressure. The residue was purified by silica gel column chromatography (hexane/ethyl acetate=50/1) to give Compound IIbj-a (5.6 g, 40%) as a white solid.

NMR($CDCl_3$, δ, ppm): 3.89(s, 3H), 6.04(m, 4H), 6.42(d, J=9 Hz, 1H), 7.04(d, J=9 Hz, 1H)

MASS(m/e): 232($M^+$), 230

(Step B) (Compound IIbj)

Substantially the same procedure as in Step E of Reference Example 3 was repeated using Compound IIbj-a (6.7 g) obtained in Step A to give Compound IIbj (4.44 g, 85%) as colorless crystals.

NMR($CDCl_3$, δ, ppm): 3.99(s, 3H), 6.15(s, 2H), 6.63(d, J=9 Hz, 1H), 7.31(d, J=9 Hz, 1H), 9.98(s, 1H)

MASS(m/e): 180($M^+$)

Reference Example 63

7-Methoxy-2,2-dimethyl-1,3-benzodioxole-4-carbaldehyde (Compound IIbk)

(Step A) 4-Methoxy-2,2-dimethyl-1,3-benzodioxole (Compound IIbk-a)

3-Methoxycatechol (25 g) was dissolved in benzene, and dimethoxyacetal (35 ml) and a catalytic amount of p-toluenesulfonic acid were added thereto, followed by heating at reflux for 6 hours. After being allowed to stand for cooling, the mixture was adjusted to alkaline with an aqueous solution of sodium hydroxide, followed by extraction with ether. The organic layer was washed with a saturated saline and dried over magnesium sulfate, and the solvent was distilled off under reduced pressure. The residue was purified by silica gel column chromatography (hexane/ethyl acetate=99/1) to give Compound IIbk-a (19.4 g, 60.5%) as a white solid.

NMR($CDCl_3$, δ, ppm): 1.68(s, 6H), 3.86(s, 3H), 6.42–6.49(m, 2H), 6.69–6.75(m, 1H)

MASS(m/e): 180($M^+$)

(Step B) (Compound IIbk)

Substantially the same procedure as in Step B of Reference Example 50 was repeated using Compound IIbk-a (20 g) obtained in Step A to give Compound IIbk (4.05 g, 17.7%) as a white solid.

NMR($CDCl_3$, δ, ppm): 1.68(s, 6H), 3.87(s, 3H), 6.50(d, J=9 Hz, 1H), 7.18(d, J=9 Hz, 1H), 9.88(s, 1H)

MASS(m/e): 208($M^+$)

Reference Example 64

7-Methoxy-2,2-diphenyl-1,3-benzodioxole-4-carbaldehyde (Compound IIbl)

(Step A) 4-Bromo-7-methoxy-2,2-diphenyl-1,3-benzodioxole (Compound IIbl-a)

3-Bromo-6-methoxycatechol (3.87 g) and diphenyldichloromethane (4.61 g) were heated at 170° C. with stirring without a solvent. After being allowed to stand for cooling, a saturated aqueous solution of sodium bicarbonate was added to the mixture, followed by extraction with ether. The organic layer was washed with a saturated saline and dried over anhydrous magnesium sulfate, and the solvent was distilled off under reduced pressure. The residue was triturated with methanol to give Compound IIbl-a (4.7 g, 69%) as a white solid.

NMR($CDCl_3$, δ, ppm): 3.89(s, 3H), 6.42(d, J=9 Hz, 1H), 6.89(d, J=9 Hz, 1H), 7.34–7.39(m, 6H), 7.58–7.63(m, 4H)

MASS(m/e): 384($M^+$), 382

(Step B) (Compound IIbl)

Substantially the same procedure as in Step E of Reference Example 3 was repeated using Compound IIbl-a (4.8 g) obtained in Step A to give Compound IIbl (3.64 g, 87%) as colorless crystals.

NMR($CDCl_3$, δ, ppm): 4.00(s, 3H), 6.60(d, J=9 Hz, 1H), 7.33(d, J=9 Hz, 1H), 7.35–7.41(m, 6H), 7.59–7.63(m, 4H), 10.14(s, 1H)

MASS(m/e): 332($M^+$)

Reference Example 65

4-Methoxy-spiro[1,3-benzodioxole-2,1'-cycloheptane)-4-carbaldehyde (Compound IIbm)

(Step A) 4-Methoxy-spiro[1,3-benzodioxole-2,1'-cycloheptane] (Compound IIbm-a)

Substantially the same procedure as in Reference Example 63 was repeated using 3-methoxycatechol (18 g) and dimethoxycycloheptane (24.35 g) to give Compound IIbm-a (28.0 g, 93.5%) as a colorless solid.

NMR($CDCl_3$, δ, ppm): 1.60–1.83(m, 8H), 2.15–2.20(m, 4H), 3.88(s, 3H), 6.45(t, J=9 Hz, 1H), 6.71(d, J=9 Hz, 1H), 6.74(d, J=9 Hz, 1H)

MASS(m/e): 234($M^+$)

(Step B) (Compound IIbm)

Substantially the same procedure as in Step B of Reference Example 50 was repeated using Compound IIbm-a (12.2 g) obtained in Step A to give Compound IIbm (0.85 g, 6.2%) as a yellow oily substance.

NMR($CDCl_3$, δ, ppm): 1.60–1.75(m, 8H), 2.07–2.25(m, 4H), 3.96(s, 3H), 6.56(d, J=9 Hz, 1H), 7.26(d, J=9 Hz, 1H), 10.00(s, 1H)

Reference Example 66

Methyl (±)-2-(hydroxyphenylmethyl)-7-methoxybenzofuran-4-carboxylate (Compound IIbn)

(Step A) Methyl 2-benzoyl-7-methoxybenzofuran-4-carboxylate (Compound IIbn-a)

Substantially the same procedure as in Step C of Reference Example 14 was repeated using Compound IIag-a (10.0 g) obtained in Step A of Reference Example 33 to give Compound IIbn-a (6.7 g, 60.6%) as a colorless solid.

NMR(DMSO-$d_6$, δ, ppm): 3.95(s, 3H), 4.11(s, 3H), 7.06 (d, J=8 Hz, 1H), 7.59(dd, J=7 Hz, 7 Hz, 2H), 7.69(t, 1H, J=7 Hz), 8.0–8.1(m, 4H)

(Step B) (Compound IIbn)

Compound IIbn-a (22.7 g) obtained in Step A was dissolved in dichloromethane (900 ml) and methanol (500 ml), and the mixture was stirred at 0° C. Sodium borohydride (3.04 g) was slowly added to the mixture followed by stirring at room temperature for one hour. The mixture was cooled to 0° C., and distilled water was added thereto to cease the reaction, followed by extraction with dichloromethane. The organic layer was washed with a saturated saline and dried over anhydrous magnesium sulfate, and the solvent was distilled off. The residue was triturated with diethyl ether to give Compound IIbn (17.6 g, 77.0%) as a colorless solid.

NMR($CDCl_3$, δ, ppm): 2.74(d, J=5 Hz, 1H), 3.90(s, 3H), 4.02(s, 3H), 5.99(d, J=5 Hz, 1H), 6.78(d, J=8 Hz, 1H), 7.12(s, 1H), 7.3–7.4(m, 3H), 7.50(dd, J=1.5 Hz, 6 Hz, 2H), 7.91(d, J=8 Hz, 1H)

MASS(m/e): 312($M^+$), 207

Reference Example 67

2,3-dihydro-8-methoxy-1,4-benzodioxine-5-carboaldehyde (Compound IIbo)

(Step A) 5-bromo-2,3-dihydro-8-methoxy-1,4-benzodioxine (Compound IIbo-a)

3-bromo-6-methoxycatechol (16 g) was dissolved in DMF (50 ml), mixed with 1,2-dibromoethane (15 ml) and potassium fluoride (21 g), stirred for 6 hours while heating at 110 EC. The resultant was allowed to stand for cooling, mixed with water, and extracted with ether. The organic layer was washed with an aqueous sodium hydroxide solution, water, and a saturated aqueous sodium chloride solution in that order, dried over manganese sulfate anhydride, and then, evaporated under reduced pressure for removing the solvent. The residue was purified by silica gel column chromatography (hexane/ethyl acetate=4/1) to give Compound IIbo-a (5.9 g, 34%) as a white solid.

NMR($CDCl_3$, δ, ppm): 3.87(s, 3H), 4.32–4.38(m, 4H), 6.42(d, J=9 Hz, 1H), 7.04(d, J=9 Hz, 1H), MASS (m/e): 244 ($M^+$)

(Step B) (Compound IIbo)

Under an argon atmosphere, a solution of Compound aa (6.1 g) in THF 60 ml), which Compound IIbo-a was obtained in Step A of Reference Example 67, was cooled to −78 EC., and then, a solution of 1.63 M butyl lithium in hexane (17 ml) was added dropwise to the cooled solution, followed by stirring at the same temperature. Dimethylformamide (3.9 ml) was slowly added dropwise to the reaction solution, followed by stirring at −78 EC. for 15 min. and then at room temperature for 1 hour. The reaction solution was mixed with saturated ammonium chloride water and extracted with ether. The organic layer was washed with a saturated aqueous sodium chloride solution, dried over magnesium sulfate anhydride, and evaporated under reduced pressure for removing the solvent. The residue was purified by silica gel column chromatography (hexane/ethyl acetate=3/1) to give Compound IIbo (2.8 g, 57%) as colorless crystals.

NMR($CDCl_3$, δ, ppm): 3.95(s, 3H), 4.39(s, 4H), 6.60(d, J=9 Hz, 1H), 7.44(d, J=9 Hz, 1H), 10.21(s, 1H)

MASS (m/e) 194($M^+$)

Reference Example 68

2,3-dihydro-8-methoxy-1,4-benzodioxine-5-carboxylic acid (Compound IIbp)

Under an argon atmosphere, a solution of Compound aa (1.3 g) in THF (30 ml), which Compound IIbo-a was obtained in Step A of Reference Example 67, was cooled to −78 EC., and then, a solution of 1.69 M butyl lithium in hexane (8.2 ml) was added dropwise to the cooled solution, followed by stirring at the same temperature for 30 min. The reaction solution was mixed with dry ice, stirred at room temperature for 1 hour, mixed with water, and washed with ether. The water layer was mixed with a 6 N aqueous hydrochloric acid solution, and the thus-precipitated solid was collected by filtration to give Compound IIbp (0.63 g, 57%) as a colorless solid.

NMR($CDCl_3$, δ, ppm): 3.95(s, 3H), 4.41–4.44(m, 2H), 4.50–4.53(m, 2H), 6.65(d, J=9 Hz, 1H), 7.75(d, J=9 Hz, 1H)

MASS (m/e) 210($M^+$)

Reference Example 69

2,3-dihydro-8-methoxy-1,4-benzodioxine (Compound IIbq)

Using 3-methoxycatechol (3.0 g), Compound IIbq (2.28 g, 64.2%) was obtained as a white oily substance according to substantially the same procedure as in Step A of Reference Example 67.

NMR($CDCl_3$, δ, ppm): 3.86(s, 3H), 4.23–4.26(m, 2H), 4.29–4.32(m, 2H), 6.50(d, J=8 Hz, 1H), 6.52(d, J=8 Hz, 1H), 6.76(t, J=8 Hz, 1H)

MASS (m/e) 166($M^+$)

Reference Example 70

3,4-dihydro-9-methoxy-2H-1,5-benzodioxepin-6-carboaldehyde (Compound IIbr)

(Step A) 6-bromo-3,4-dihydro-9-methoxy-2H-1,5-benzodioxepin (Compound IIbr-a)

3-bromo-6-methoxycatechol (31 g) was dissolved in DMF (50 ml), mixed with 1,3-dibromopropane (36 ml) and potassium fluoride (42 g), stirred for 12 hours while heating at 110° C. The resultant was allowed to stand for cooling, mixed with water, and extracted with ether. The organic layer was washed with an aqueous sodium hydroxide solution, water, and a saturated aqueous sodium chloride solution in that order, dried over manganese sulfate, and evaporated under reduced pressure for removing the solvent. The residue was purified by silica gel column chromatography (hexane/ethyl acetate=7/1) to give Compound IIbr-a (6.7 g, 18%) as a white solid.

NMR($CDCl_3$, δ, ppm): 2.37–2.41(m, 2H), 3.98(s, 3H), 4.34–4.45(m, 4H), 6.64(d, J=9 Hz, 1H), 7.26(d, J=9 Hz, 1H), MASS (m/e) 258($M^+$)

(Step B) Compound IIbr

Using Compound IIbr-a (6.5 g) obtained in Step A of Reference Example 70, Compound IIbr (3.3 g, 63%) was obtained as colorless crystals according to substantially the same procedure as in Step B of Reference Example 67.

NMR($CDCl_3$, δ, ppm): 2.26–2.35(m, 2H), 3.93(s, 3H), 4.35(t, J=6 Hz, 2H), 4.41(t, J=6 Hz, 2H), 6.67(d, J=9 Hz, 1H), 7.53(d, J=9 Hz, 1H), 10.28(s, 1H)

MASS (m/e) 208 ($M^+$)

Reference Example 71

3,4-dihydro-9-methoxy-2H-1,5-benzodioxepin-6-carboxylic acid (Compound IIbs)

Using Compound IIbr-a (3.0 g) obtained in Step A of Reference Example 70, Compound IIbs (0.80 g, 31%) was obtained as white crystals according to substantially the same procedure as in Reference Example 68.

NMR($CDCl_{13}$, δ, ppm): 2.32–2.40(m, 2H), 3.93(s, 3H), 4.35(t, J=6 Hz, 2H), 4.53(t, J=6 Hz, 2H), 6.75(d, J=9 Hz, 1H), 7.85(d, J=9 Hz, 1H)

MASS (m/e) 224 ($M^+$)

Reference Example 72

[2-(3,5-dichloro-4-pyridyl)-1-oxoethyl]-2,3-dihydroxy-4-methoxybenzene (Compound IIbt)

(Step A) methyl 2,3,4-trimethoxybenzoate (Compound IIbt-a)

2,3,4-trimethoxybenzoic acid (7.3 g) was dissolved in methanol (73 ml), mixed with sulfuric acid (15 ml), and stirred for 3 hours while heating at 80° C. The resultant was allowed to stand for cooling, evaporated under reduced pressure for removing the solvent, and the residue was added to cold water, followed by extraction with ethyl acetate. The organic layer was washed with saturated sodium bicarbonate water and then with a saturated aqueous sodium chloride solution, dried over sodium sulfate anhydride, and evaporated under reduced pressure for removing the solvent to give Compound IIbt-a (6.8 g, 87%) as a colorless oily substance.

NMR($CDCl_3$, δ, ppm): 3.88(s, 3H), 3.89(s, 3H), 3.91(s, 3H), 3.94(s, 3H), 6.70(d, J=9 Hz, 1H), 7.61(d, J=9 Hz, 1H)

MASS (m/e) 226($M^+$)

(Step B) [2-(3,5-dichloro-4-pyridyl)-1-oxoethyl]-2,3,4-trimethoxybenzene (Compound IIbt-b)

Under an argon atmosphere, a solution of diisopropylamine (9.9 ml) in THF (30 ml) was cooled to −78° C. and then a solution of 1.66 M butyl lithium in hexane (46 ml) was added dropwise to the cooled solution, followed by stirring at 0° C. for 15 min. The resultant was cooled to −78° C. again, mixed with 3,5-dichloro-4-methylpyridine (12 g), and stirred at −78° C. for 2 hours. The thus-obtained solution was slowly added dropwise to a solution of Compound IIbt-b (5.7 g) in THF (40 ml), which Compound IIbt-b was obtained in Step A, followed by stirring at −78° C. for 2 hours and then at 0° C. for 1 hour. The reaction solution was mixed with a saturated aqueous ammonium chloride solution and extracted with ether. The organic layer was washed with a saturated aqueous sodium chloride solution, dried over sodium sulfate anhydride, and evaporated under reduced pressure for removing the solvent. The residue was recrystallized from ethyl acetate/diisopropyl ether to give Compound IIbt-b (7.0 g, 78%) as pale yellow crystals.

Melting point: 125–128° C.

NMR($CDCl_3$, δ, ppm): 3.92(s, 3H), 3.94(s, 3H), 4.13(s, 3H), 4.69(s, 2H), 6.77(d, J=9 Hz, 1H), 7.63 (d, J=9 Hz, 1H), 8.50(s, 2H)

MASS (m/e) 355($M^+$)

(Step C) [2-(3,5-dichloro-4-pyridyl)-1-oxoethyl]-2,3-dihydroxy-4-methoxybenzene (Compound IIbt)

Compound IIbt-b (4.0 g) obtained in Step B was dissolved in dichloromethane (60 ml), mixed with 1.0 M boron trichloride dichloromethane solution (23 ml) at room temperature, and stirred for 10 min. To the resultant, was added 1.0 M boron trichloride dichloromethane solution (23 ml) again, followed by stirring for one day and night. The reaction solution was added to a 5% aqueous sodium hydroxide solution, adjusted to pH 2 by adding sulfuric acid, and extracted with ethyl acetate. The organic layer was washed with a saturated aqueous sodium chloride solution, dried over sodium sulfate anhydride, and evaporated under reduced pressure for removing the solvent to give Compound IIbt (3.2 g, 86%) as a pale yellow solid.

Melting point: 180–183° C.

NMR($CDCl_3$, δ, ppm): 4.01(s, 3H), 4.68(s, 2H), 6.61(d, J=9 Hz, 1H), 7.51(d, J=9 Hz, 1H), 8.55(s, 2H), 11.9(s, 1H)

Reference Example 73

10-methoxy-2, 3,4,5-tetrahydro-1,6-benzodioxocin-7-carboxylic acid (Compound IIbu)

(Step A) 7-bromo-10-methoxy-2,3,4,5-tetrahydro-1,6-benzodioxocin (Compound IIbu-a)

Using 3-bromo-6-methoxycatechol (5.4 g), Compound IIbu-a (2.9 g, 44%) was obtained as a colorless oily substance according to substantially the same procedure as in Example 194.

NMR(DMSO-$d_6$, δ, ppm): 1.65–1.85(m, 4H), 3.76(s, 3H), 4.07–4.17(m, 2H), 4.18–4.28(m, 2H), 6.72(d, J=9 Hz, 1H), 7.24(d, J=9 Hz, 1H)

MASS (m/e) 273($M^+$)

(Step B) 10-methoxy-2,3,4,5-tetrahydro-1,6-benzodioxocin-7-carboxylic acid (Compound IIbu)

Using Compound IIbu-a (3.3 g) obtained in Step A, Compound bu (1.3 g, 45%) was obtained as a white solid according to substantially the same procedure as in Reference Example 68.

NMR(DMSO-$d_6$, δ, ppm): 1.63–1.84(m, 4H), 3.82(s, 3H), 4.05–4.15(m, 2H), 4.15–4.31(m, 2H), 6.83 (d, J=9 Hz, 1H), 7.50(d, J=9 Hz, 1H), 12.4(s, 1H)

MASS (m/e) 238($M^+$)

Reference Example 74

7-methoxy-2,2-dimethyl-1,3-benzodioxole-4-carboxylic acid (Compound IIbv)

(Step A) 4-methoxy-2,2-dimethyl-1,3-benzodioxole (Compound IIbv-a)

3-methoxycatechol (25 g) was dissolved in benzene, mixed with dimethoxyacetal (35 ml) and a catalytic amount of tosylic acid, and then, heat-refluxed for 6 hours. The resultant was allowed to stand for cooling, alkalified by adding an aqueous sodium hydroxide solution, and extracted with ether. The organic layer was washed with a saturated aqueous sodium chloride solution, dried over manganese sulfate, and evaporated under reduced pressure for removing the solvent. The residue was purified by silica gel column chromatography (hexane/ethyl acetate=99/1) to give Compound IIbv-a (19.4 g, 60.5%) as a white solid.

NMR($CDCl_3$, δ, ppm): 1.68(s, 6H), 3.86(s, 3H), 6.42–6.49(m, 2H), 6.69–6.75(m, 1H)

MASS (m/e) 180($M^+$)

(Step B) 7-methoxy-2,2-dimethyl-1,3-benzodioxole-4-carboaldehyde (Compound IIbv-b)

Compound IIbv-a (20 g) obtained in Step A was dissolved in DMF (140 ml), and phosphorus oxychloride (41.4 ml) was added dropwise to the resulting solution under ice-cold conditions, followed by stirring for 10 hours while heating at 60° C. The reaction solution was poured into ice water and extracted with ether. The organic layer was washed with a saturated aqueous sodium chloride solution, dried over manganese sulfate, and evaporated under reduced pressure for removing the solvent. The residue was purified by silica gel column chromatography (hexane/ethyl acetate=24/1) to give Compound IIbv-b (4.05 g, 17.7%) as a white solid.

NMR($CDCl_3$, δ, ppm): 1.68(s, 6H), 3.87(s, 3H), 6.50(d, J=9 Hz, 1H), 7.18(d, J=9 Hz, 1H), 9.88(s, 1H)

MASS (m/e) 208($M^+$)

(Step C) Compound IIbv

Compound IIbv-b (3.8 g) obtained in Step B was dissolved in a 80% aqueous acetic acid solution (60 ml), mixed with sulfamic acid (2.5 g), and stirred for 30 min. Then, a 80% aqueous sodium chlorite solution (1.82 g, 9.1 ml) was added dropwise to the resulting mixture, followed by stirring at room temperature for 2 hours. The reaction solution was mixed with water, and the thus-precipitated solid was collected by filtration to give Compound IIbv (1.91 g, 46.9%) as a white solid.

NMR($CDCl_3$, δ, ppm): 1.78(s, 6H), 3.94(s, 3H), 6.56(d, J=9 Hz, 1H), 7.48(d, J=9 Hz, 1H)

MASS (m/e) 224 ($M^+$)

Reference Example 75 ethyl ester of 4-[(3,5-dichloro-4-pyridyl) aminocarbonyl]-7-methoxybenzofuran-2-carboxylic acid (Compound IIbw)

(Step 1) ethyl ester of 4-formyl-7-methoxybenzofuran-2-carboxylic acid (Compound IIbw-a)

Ethyl ester of 7-methoxybenzofuran-2-carboxylic acid (10 g) was dissolved in anhydrous methylene chloride (200 ml), and then, dichloromethyl methyl ether (8.2 ml) and titanium tetrachloride (10 ml) were added dropwise to the resulting solution under ice-cold conditions, followed by stirring for 30 min. The mixture was heated to room temperature, stirred for 1.5 hours, and then, a 1 mol/L aqueous HCl solution was added dropwise to the mixture so as to decompose the residual titanium tetrachloride, followed by extraction with chloroform. The resultant was washed with 1 mol/L aqueous NaOH solution and a saturated aqueous sodium chloride solution, dried over sodium sulfate, and evaporated under reduced pressure for removing the solvent. The residue was suspended in ether and filtered to give Compound IIbw-a (8.9 g, 79%) as colorless crystals.

NMR($CDCl_3$, δ, ppm): 1.43(t, J=7 Hz, 3H), 4.12(s, 3H), 4.46(q, J=7 Hz, 2H), 7.01(d, J=8 Hz, 1H), 7.75(d, J=8 Hz, 1H), 8.22(s, 1H), 10.0(s, 1H)

MASS (m/e) 248 ($M^+$)

(Step 2) 2-ethoxycarbonyl-7-methoxybenzofuran-4-carboxylic acid (Compound IIbw-b)

Compound IIbw-a (9.5 g) obtained in Step 1 was dissolved in acetic acid (800 ml) /water (200 ml), mixed with sulfamic acid (19 g) and sodium chlorite (14 g), and then, stirred at room temperature for 7 hours. The resultant was mixed with water (1 l). The precipitated crystals were collected by filtration and washed with water to give Compound IIbw-b (9.4 g, 93%) as colorless crystals.

NMR($CDCl_3$, δ, ppm): 1.36(t, J=7 Hz, 3H), 4.05(s, 3H), 4.38(q, J=7 Hz, 2H), 7.23(d, J=9 Hz, 1H), 7.93(s, 1H), 7.95(d, J=9 Hz, 1H)

MASS (m/e) 264 ($M^+$)

(Step 3) ethyl ester of 4-[(3,5-dichloro-4-pyridyl) aminocarbonyl]-7-methoxybenzofuran-2-carboxylic acid (Compound IIbw-c)

Compound IIbw-b (4.5 g) was suspended in anhydrous methylene chloride (70 ml), mixed with thionyl chloride (60 ml), and refluxed for 3 hours. The resultant was concentrated under reduced pressure. The thus-obtained acid chloride was dried and subjected to the subsequent reaction as it was.

4-amino-2,6-dichloropyridine (V, 5.5 g) was dissolved in anhydrous THF (200 ml), mixed with sodium hydride (60% oil suspension, 1.7 g) under ice-cold conditions, and stirred for 50 min. The mixture was cooled to −78° C., and then, a solution of the above acid chloride in anhydrous THF (200 ml) was added dropwise thereto over 30 min. After stirring the mixture at −78° C. for 2 hours, the reaction was stopped by adding 1 mol/L HCl dropwise under ice cold conditions, and then, the resulting mixture was extracted with chloroform (800 ml). The resultant was washed with 1 mol/L HCl and a saturated aqueous sodium chloride solution, dried over sodium sulfate, and evaporated under reduced pressure for removing the solvent. The residue was suspended in ether and filtered to give Compound IIbw-c (6.1 g, 88%) as colorless crystals.

NMR($CDCl_3$, δ, ppm): 1.41(t, J=7 Hz, 3H), 4.12(s, 3H), 4.4(q, J=7 Hz, 2H), 7.00(d, J=8 Hz, 1H), 7.82(d, J=8 Hz, 1H), 8.09(s, 1H), 8.59(s, 2H)

MASS (m/e) 409 ($M^+$)

(Step 4) Synthesis of Compound IIbw

Compound IIbw-c (6.1 g) was dissolved in methanol (80 ml), mixed with a 1 mol/L aqueous NaOH solution (40 ml) under ice-cold conditions, heated to room temperature, and stirred for 2 hours. Under ice-cold conditions, the reaction solution was acidified by adding concentrated hydrochloric acid and 1 mol/L HCl dropwise. The precipitated crystals were collected by filtration and washed with water to give Compound IIbw (5.6 g, 98%).

NMR(DMSO-$d_6$, δ, ppm): 4.07(s, 3H), 7.29(d, J=8.5 Hz, 1H), 7.90(s, 1H), 8.08(d, J=8.5 Hz, 1H), 8.77(s, 2H), 10.6(s, 1H), 13.8(broad s, 1H)

MASS (m/e) 380 ($M^+$)

Reference Example 76

7-(4-methylcarbonyl-3-pyridyl)-4-methoxy-spiro[1, 3-benzodioxole-2,1=-cyclopentane] (Compound IIbx)

(Step A) Production of 4-methoxy-7-tributylstannyl-spiro[1, 3-benzodioxole-2,1=-cyclopentane] (Compound IIbx-a)

Under an argon atmosphere, a solution of 7-bromo-4-methoxy-7-spiro[1,3-benzodioxole-2,1'-cyclopentane] (5.5 g) in THF (100 ml) was cooled to −78° C., and then, a solution of butyl lithium in hexane (1.6 M) (15 ml) was added dropwise to the cooled solution. The resultant was stirred at the same temperature for 1 hour, mixed with tributyltin chloride (6.3 ml), and stirred for 1 hour. The organic layer was extracted from the resultant by adding an aqueous ammonium chloride solution and ether, washed with a saturated aqueous sodium chloride solution, dried over magnesium sulfate, and evaporated under reduced pressure for removing the solvent to give the target compound as a crude product. The crude product was subjected to the subsequent step without being purified.

(Step B) Production of Compound IIbx

Using Compound IIbx-a (3.4 g) obtained in Step A, methyl 5-iodopyridine-2-carboxylate (1.2 g) and diphenylphosophinoferrocene palladium (0.2 g), Compound IIbx (0.78 g, 50%) was obtained as colorless crystals according to substantially the same procedure as in Reference Example 205.

NMR($CDCl_3$, δ, ppm): 1.86–1.89(m, 4H), 2.17–2.19(m, 4H), 3.95(s, 3H), 4.03(s, 3H), 6.63(d, J=9 Hz, 1H), 7.06 (d, J=9 Hz, 1H), 8.12(dd, J=2 Hz, 8 Hz, 1H), 8.18(d, J=8 Hz, 1H), 9.09(d, J=2 Hz, 1H)

MASS (m/e) 341($M^+$)

Reference Example 77

7-(4-ethoxycarbonylphenyl)-2,2-dimethyl-4-methoxy-1,3-benzodioxole (Compound IIby)

(Step A) Synthesis of 2,2-dimethyl-4-methoxy-7-tributylstannyl-1,3-benzodioxole (Compound IIby-a)

Using 7-bromo-2,2-dimethyl-4-methoxy-1,3-benzodioxole (0.7 g), a crude product of the target compound was obtained according to substantially the same procedure as in Step A of Reference Example 76. The crude product was directly subjected to the subsequent step without being purified.

(Step B) Synthesis of Compound IIby

Using Compound IIby-a obtained in Step A of Reference Example 77, ethyl 4-iodobenzoate (0.9 g), palladium acetate (0.037 g), and silver oxide (0.038 g), Compound IIby (0.51 g, 57%) was obtained as colorless crystals according to substantially the same procedure as in Step B of Reference Example 76.

NMR($CDCl_3$, δ, ppm): 1.40(t, J=7 Hz, 3H), 1.70(s, 6H), 3.84(s, 3H), 4.39(q, J=7 Hz, 2H), 6.75(d, J=9 Hz, 1H), 7.13(d, J=9 Hz, 1H), 7.77(d, J=9 Hz, 2H), 7.98(d, J=9 Hz, 2H)

MASS (m/e) 300 ($M^+$)

Reference Example 78

4-[2-(3,5-Dichloro-4-pyridyl)-1-oxoethyl]-7-methoxybenzofuran-2-carboxylic acid (Compound IIbz)

Step 1: Ethyl 4-formyl-7-methoxybenzofuran-2-carboxylate (Compound IIbz-a)

Ethyl 7-methoxybenzofuran-2-carboxylate (10 g) was dissolved in anhydrous methylene chloride (200 ml), to which were dropwise added dichloromethyl methyl ether (8.2 ml) and titanium tetrachloride (10 ml) with cooling with ice, and directly stirred for 30 minutes. After having been restored to be at room temperature, the mixture was stirred for further 1.5 hours. Then, an aqueous HCl (1 mol/liter) solution was dropwise added thereto to decompose the remaining titanium tetrachloride, and thereafter the mixture was extracted with chloroform. The extract was washed with an aqueous NaOH (1 mol/liter) solution and a saturated saline solution, and dried over sodium sulfate, and the solvent was thereafter evaporated. The residue was suspended in ether, and taken out therefrom through filtration to obtain Compound IIbz-s (8.9 g, 79%) as colorless crystals.

NMR ($CDCl_3$, δ, ppm): 1.43(t, J=7 Hz, 3H), 4.12(s, 3H), 4.46(q, J=7 Hz, 2H), 7.01(d, J=8 Hz, 1H), 7.75(d, J=8 Hz, 1H), 8.22(s, 1H), 10.0(s, 1H)

MASS(m/e): 248 ($M^+$)

Step 2: Ethyl 4-[2-(3,5-dichloro-4-pyridyl)-1-hydroxyethyl]-7-methodxybenzofuran-2-carboxylate (Compound IIbz-c)

N,N-diisopropylamine (65.6 ml) was dissolved in anhydrous THF (150 ml), to which was dropwise added n-butyl lithium (1.54 mols/liter hexane solution, 300 ml) in an argon atmosphere at −78° C., and directly stirred for 5 minutes. An anhydrous THF (600 ml) solution of 3,5-dichloropyridine (63 g) was dropwise added thereto and stirred for 1 hours, and thereafter methyl iodide (29.2 ml) was dropwise added thereto and further stirred for 1.5 hours. Water was added to the reaction mixture to stop the reaction, which was then extracted with ethyl acetate. The extract was washed with a saturated saline solution, then dried over magnesium sulfate, and distilled under reduced pressure. This was purified by silica gel column chromatography (hexane:ethyl acetate=10:1), and the resulting residue was suspended in ether, and taken out therefrom through filtration to obtain 3,5-dichloropicoline (Compound IIbz-b, 62.8 g, 91%) as colorless crystals.

N,N-diisopropylamine (8.5 ml) was dissolved in anhydrous THF (150 ml), to which was dropwise added n-butyl lithium (1.65 mols/liter hexane solution, 32 ml) in an argon atmosphere at −78° C., and directly stirred for 5 minutes. The reaction mixture was further stirred at room temperature for 3 minutes, and then again cooled to −78° C. 3,5-dichloropicoline (IIbz-b, 7.2 g) was added thereto, and directly stirred for 30 minutes. This was dropwise added to an anhydrous THF (500 ml) solution of Compound IIbz-a (10 g) in an argon atmosphere at −78° C. over a period of 1 hour. The resulting mixture was stirred for further 2.5 hours still at −78° C., and then restored to be at room temperature. Water was added to this to stop the reaction, which was then diluted with ethyl acetate. This was washed with a saturated saline solution, then dried over sodium sulfate, and distilled under reduced pressure. The resulting residue was suspended in isopropanol, and taken out therefrom through filtration to obtain Compound IIbz-c (14.3 g, 87%) as colorless crystals.

NMR ($CDCl_3$, δ, ppm): 1.43(t, J=7 Hz, 3H), 3.32(dd, J=13 Hz, 5 Hz, 1H), 3.60(dd, J=13 Hz, 8.5 Hz, 1H), 4.01(s, 3H), 4.45(q, J=7 Hz, 2H), 5.34(m, 1H), 6.83(d, J=8 Hz, 1H), 7.11(d, J=8 Hz, 1H), 7.80(s, 1H), 8.41(s, 2H)

MASS(m/e): 409 ($M^+$)

Step 3: Ethyl 4-(2-(3,5-dichloro-4-pyridyl)-1-oxoethyl)-7-methoxybenzofuran-2-carboxylate (Compound IIbz-d)

Compound IIbz-c (10 g) was dissolved in acetone (200 ml), to which was dropwise added Jones reagent (2.76 M solution, 9.7 ml) with cooling with ice, and directly stirred for 20 minutes. Isopropanol was added thereto and stirred at room temperature for 30 minutes to stop the reaction. Then, the solvent was evaporated under reduced pressure. The resulting concentrate was extracted with chloroform, and the extract was washed with a saturated saline solution, then dried over magnesium sulfate, and distilled under reduced pressure. The residue was suspended in isopropanol, and taken out therefrom through filtration to obtain Compound IIbz-d (8.34 g, 84%) as colorless crystals.

NMR ($CDCl_3$, δ, ppm): 1.39(t, J=7 Hz, 3H), 4.13(s, 3H), 4.42 (q, J=7 Hz, 2H), 4.73(s, 2H), 6.99(d, J=8 Hz, 1H), 8.04 (d, J=8 Hz, 1H), 8.21(s, 1H), 8.54(s, 2H)

MASS(m/e): 407 ($(M+1)^+$)

Step 4: Compound IIbz

Compound IIbz-d (6.0 g) was dissolved in methanol (60 ml), to which was added an aqueous solution of NaOH (5 mols/liter) (15 ml) with cooling with ice. After having been restored to be at room temperature, this was stirred for 1 hour. HCl (1 mol/liter) was dropwise added to the reaction mixture with cooling with ice to thereby make the mixture acidic, and the crystals thus precipitated were taken out through filtration, and washed with water to obtain Compound IIbz (5.4 g, 96%) as colorless crystals.

NMR (DMSO-$d_6$, δ, ppm): 4.09(s, 3H), 4.86(s, 2H), 7.29(d, J=8.5 Hz, 1H), 8.38(d, J=8.5 Hz, 1H), 8.68(s, 2H)

MASS(m/e): 379 ($M^+$)

Reference Example 79

4-[2-(3,5-Dichloro-4-pyridyl)ethyl]-7-methoxybenzofuran-2-carboxylic acid (Compound IIca)

Step 1: Ethyl 4-[2-(3,5-dichloro-4-pyridyl)ethyl]-7-methoxybenzofuran-2-carboxylate (Compound IIca-a)

Compound IIbzc (3.0 g) was dissolved in anhydrous methylene chloride (150 ml), to which were added boron trifluoride-ethyl ether complex (4.5 ml) and triethylsilane (8.8 ml) at −78° C. Then, After being allowed to stand for heating to the room temperature, the mixture was stirred overnight. An aqueous solution of HCl (1 mol/liter) was added thereto to stop the reaction. Then, the reaction mixture was extracted with chloroform. The extract was washed with an aqueous solution of HCl (1 mol/liter) and a saturated saline solution, and dried over sodium sulfate, and the solvent was evaporated under reduced pressure. The residue was purified by silica gel column chromatography (hexane:ethyl acetate=3:2), and then recrystallized from ethanol to obtain Compound IIca-a (2.0 g, 69%) as colorless crystals.

NMR ($CDCl_3$, δ, ppm): 1.43(t, J=7 Hz, 3H), 3.02–3.08(m, 2H), 3.21–3.27(m, 2H), 4.01(s, 3H), 4.45(q, J=7 Hz, 2H), 6.84(d, J=8 Hz, 1H), 7.01(d, J=8 Hz, 1H), 7.60(s, 1H), 8.45(s, 2H)

MASS(m/e): 393 ($M^+$)

Step 2: Compound IIca

Compound IIca-a (1.9 g) was dissolved in dioxane (20 ml)-methanol (5 ml), to which was added an aqueous solution of NaOH (1 mol/liter). Then, After being allowed to stand for cooling to the room temperature, the mixture was stirred for 30 minutes. HCl (1 mol/liter) was dropwise added to the reaction mixture with cooling with ice to thereby make the mixture acidic. Then, the crystals thus precipitated were taken out through filtration, and washed with water to obtain Compound IIca (1.72 g, 97%) as colorless crystals.

NMR (DMSO-$d_6$, δ, ppm): 3.17–3.25(m, 4H), 3.91(s, 3H), 6.97(s, 2H), 7.58(s, 1H), 8.56(s, 2H)

MASS(m/e): 365 ($M^+$)

Reference Example 80

4-(2-(3,5-Dichloro-4-pyridyl)-1-oxoethyl-2-(1-piperazinylcarbonyl)-7-methoxybenzofuran (Compound IIcb)

Step 1: Compound IIcb

Compound IIbz (4.12 g) was dissolved in DMF (150 ml), to which were added 1-hydroxybenzotriazole monohydrate (5.8 g) and N-ethyl-N'-3-dimethylaminopropylcarbodiimide monohydrochloride (8.2 g), and stirred at room temperature for 10 minutes. This was dropped into a DMF solution (300 ml) of piperazine (18.6 g), and directly stirred at room temperature for 12 hours. The solvent was evaporated under reduced pressure, and the residue was extracted with chloroform. The extract was washed with a saturated saline solution, and dried over sodium sulfate. The solvent was vaporized out, and the residue was suspended in ethanol to obtain Compound IIcb (3.54 g, 73%) as colorless crystals.

NMR ($CDCl_3$, δ, ppm): 2.88–2.96(m, 4H), 3.73–3.81(m, 4H), 4.12(s, 3H), 4.73(s, 2H), 6.95(d, 1H, J=8 Hz), 7.86(s, 1H), 8.02(d, 1H, J=8 Hz), 8.53(s, 1H)

MASS(m/e): 447 ($M^+$)

Reference Example 81

4-[2-(3,5-Dichloropyridin-4-yl)-1-oxo]ethyl-7-methoxybenzofuran-2-carboxylic acid (Compound IIcc)

Step 1-1: Ethyl 4-formyl-7-methoxybenzofuran-2-carboxylate (Compound IIcc-a)

Ethyl 7-methoxybenzofuran-2-carboxylate (10 g) was dissolved in anhydrous methylene chloride (200 ml), to which were dropwise added dichloromethyl methyl ether (8.2 ml) and titanium tetrachloride (10 ml) with cooling with ice, and directly stirred for 30 minutes. After being allowed to stand for heating to the room temperature, the mixture was stirred for 1.5 hours, to which was dropwise added an aqueous HCl (1 mol/liter) solution to decompose the remaining titanium tetrachloride. Then, this was extracted with chloroform. The organic layer was washed with an aqueous NaOH (1 mol/liter) solution and a saturated saline solution, and dried over sodium sulfate, and the solvent was evaporated. The residue was suspended in ether and taken out through filtration to obtain Compound IIcc-a (8.9 g, 79%) as colorless crystals.

NMR ($CDCl_3$, δ, ppm): 1.43(t, J=7 Hz, 3H), 4.12(s, 3H), 4.46(q, J=7 Hz, 2H), 7.01(d, J=8 Hz, 1H), 7.75(d, J=8 Hz, 1H), 8.22(s, 1H), 10.0(s, 1H)

MASS(m/e): 248 ($M^+$)

Step 1-2: Ethyl 4-[2-(3,5-dichloropyridin-4-yl)-1-hydroxy]-7-methoxybenzofuran-2-carboxylate (Compound IIcc-b)

N,N-diisopropylamine (65.6 ml) was dissolved in anhydrous THF (150 ml), to which was dropwise added n-butyl lithium (1.54 mols/liter hexane solution, 300 ml) in an argon atmosphere at −78° C., and directly stirred for 5 minutes. An anhydrous THF (600 ml) solution of 3,5-dichloropyridine (63 g) was dropwise added to this, and stirred for 1 hour, and then methyl iodide (29.2 ml) was dropwise added thereto, and stirred for further 1.5 hours. Water was added to this to stop the reaction, which was then extracted with ethyl acetate. The organic layer was washed with a saturated saline solution, then dried over magnesium sulfate, and the solvent was distilled under reduced pressure. The residue was purified by silica gel column chromatography (hexane:ethyl acetate=10:1), then suspended in hexane, and taken out through filtration to obtain 3,5-dichloropicoline (62.8 g, 91%) as colorless crystals.

N,N-diisopropylamine (8.5 ml) was dissolved in anhydrous THF (150 ml), to which was dropwise added n-butyl lithium (1.65 mols/liter hexane solution, 32 ml) in an argon atmosphere at −78° C., and directly stirred for 5 minutes. The reaction mixture was further stirred at room temperature for 3 minutes, and then again cooled to −78° C. 3,5-dichloropicoline (7.2 g) was added thereto, and directly stirred for 30 minutes. This was dropwise added to an anhydrous THF (500 ml) solution of Compound IIcc-a (10 g) in an argon atmosphere at −78° C. over a period of 1 hour. The resulting mixture was stirred for further 2.5 hours still at −78° C., and then restored to be at room temperature. Water was added to this to stop the reaction, which was then diluted with ethyl acetate. The organic layer was washed with a saturated saline solution, then dried over sodium sulfate, and the solvent was distilled under reduced pressure. The resulting residue was suspended in isopropanol, and taken out therefrom through filtration to obtain Compound IIcc-b (14.3 g, 87%) as colorless crystals.

NMR ($CDCl_3$, δ, ppm): 1.43(t, J=7 Hz, 3H), 3.32(dd, J=13 Hz, 5 Hz, 1H), 3.60(dd, J=13 Hz, 8.5 Hz, 1H), 4.01(s, 3H), 4.45(q, J=7 Hz, 2H), 5.34(m, 1H), 6.83(d, J=8 Hz, 1H), 7.11(d, J=8 Hz, 1H), 7.80(s, 1H), 8.41(s, 2H)

MASS(m/e): 409 ($M^+$)

Step 1-3: Ethyl 4-[2-(3,5-dichloropyridin-4-yl)-1-oxo]ethyl-7-methoxybenzofuran-2-carboxylate (Compound IIcc-c)

Compound IIcc-b (10 g) was dissolved in acetone (200 ml), to which was dropwise added Jones reagent (2.76 M solution, 9.7 ml) with cooling with ice, and directly stirred for 20 minutes. Isopropanol was added thereto and stirred at room temperature for 30 minutes to stop the reaction. Then, the solvent was evaporated under reduced pressure. The resulting concentrate was extracted with chloroform, and the organic layer was washed with a saturated saline solution, then dried over magnesium sulfate, and the solvent was distilled under reduced pressure. The residue was suspended in isopropanol, and taken out therefrom through filtration to obtain Compound IIcc-c (8.34 g, 84%) as colorless crystals.

NMR ($CDCl_3$, δ, ppm): 1.39(t, J=7 Hz, 3H), 4.13(s, 3H), 4.42(q, J=7 Hz, 2H), 4.73(s, 2H), 6.99(d, J=8 Hz, 1H), 8.04(d, J=8 Hz, 1H), 8.21(s, 1H), 8.54(s, 2H)

MASS(m/e): 407 ($(M+1)^+$)

Step 1-4: Compound IIcc

Compound IIcc-c (6.0 g) was dissolved in methanol (60 ml), to which was added an aqueous solution of NaOH (5 mols/liter) (15 ml) with cooling with ice. After having been restored to be at room temperature, this was stirred for 1 hour. HCl (1 mol/liter) was dropwise added to the reaction mixture with cooling with ice to thereby make the mixture acidic, and the crystals thus precipitated were taken out through filtration, and washed with water to obtain Compound IIcc (5.4 g, 96%) as colorless crystals.

NMR (DMSO-$d_6$, δ, ppm): 4.09(s, 3H), 4.86(s, 2H), 7.29(d, J=8.5 Hz, 1H), 8.38(d, J=8.5 Hz, 1H), 8.68(s, 2H)

MASS(m/e): 379 ($M^+$)

Reference Example 82

Methyl 2-(2-morpholinoethyl)carbamoyl-7-methoxybenzofuran-4-carboxylate (Compound IIcd)

:

Step 2-1: N-(2-morpholinoethyl)-7-methoxybenzofuran-2-carboxamide (Compound IIcd-a)

7-Methoxybenzofuran-2-carboxylic acid (10 g) as obtained according to a known method (J. Med. Chem., 30, 62–67, 1987) was suspended in anhydrous methylene chloride (150 ml), to which was added oxalyl chloride (6.8 ml), and stirred at room temperature for 22 hours. This was distilled under reduced pressure, and the resulting residue was dried in vacuum, and dissolved in anhydrous methylene chloride (40 ml), to which were added triethylamine (1.9 ml) and 2-morpholinoethylamine (0.91 ml), and stirred at room temperature for 6 hours. An aqueous KOH (1 mol/liter) solution was added to this to stop the reaction, which was then extracted with methylene chloride, and the organic layer was washed with a saturated saline solution, then dried over potassium carbonate, and the solvent was distilled under reduced pressure. The residue was suspended in ethyl ether, and taken out through filtration to obtain Compound IIcd-a (1.0 g, 71%) as colorless crystals.

NMR ($CDCl_3$, δ, ppm): 2.5–2.6(m, 4H), 2.6–2.7(m, 2H), 3.55–3.65(m, 2H), 3.7–3.8(m, 4H), 4.03(s, 3H), 6.92(dd, J=7 Hz, 2 Hz, 1H), 7.20(broad s, 1H), 7.22(dd, J=7 Hz, 7 Hz, 1H), 7.25(dd, J=7 Hz, 2 Hz, 1H), 7.46(s, 1H)

Step 2-2: 4-Formyl-N-(2-morpholinoethyl)-7-methoxybenzofuran-2-carboxamide (Compound IIcd-b)

Compound IIcd-a (0.90 g) was dissolved in anhydrous methylene chloride (50 ml), to which were added dichloromethyl methyl ether (0.40 ml) and titanium tetrachloride (0.97 ml), and stirred for 12 hours at room temperature. This was poured into ice-water containing an aqueous potassium hydroxide solution, and then extracted with chloroform. The organic layer was washed with a saturated saline, dried over potassium carbonate, and the solvent was distilled under reduced pressure. The residue was suspended in ethyl ether, and taken out through filtration to obtain Compound IIcd-b (0.55 mg, 58%) as colorless crystals.

NMR ($CDCl_3$, δ, ppm): 2.5–2.6(m, 4H), 2.6–2.7(m, 2H), 3.55–3.65(m, 2H), 3.7–3.8(m, 4H), 4.12(s, 3H), 7.01(d, J=8 Hz, 1H), 7.20(broad s, 1H), 7.74(d, J=8 Hz, 1H), 8.15(s, 1H), 10.07(s, 1H)

Step 2-3: Compound IIcd

Compound IIcd-b (0.35 g) was dissolved in methylene chloride (10 ml)-methanol (10 ml), to which were added potassium hydroxide (0.35 g) and iodine (0.4 g), and stirred for 5 hours. This was diluted with methylene chloride, washed with a saturated saline solution, dried over potassium carbonate, and then the solvent was distilled under reduced pressure. The residue was purified by silica gel column chromatography (chloroform:methanol=50:1) to obtain Compound IIcd (0.46 g, 85%) as colorless oil.

NMR ($CDCl_3$, δ, ppm): 2.5–2.6(m, 4H), 2.6–2.7(m, 2H), 3.55–3.65(m, 2H), 3.7–3.8(m, 4H), 3.96(s, 3H), 4.05(s, 3H), 6.89(d, J=8 Hz, 1H), 7.35(broad s, 1H), 7.94(s, 1H), 7.97(d, J=8 Hz, 1H)

MASS (m/e): 362 ($M^+$)

Preparation Example 1

Tablet

Tablets having the following composition are prepared according to a conventional method.

| | |
|---|---|
| Compound 68 | 50 mg |
| Lactose | 60 mg |
| Potato starch | 50 mg |
| Polyvinyl alcohol | 2 mg |
| Magnesium stearate | 1 mg |
| Tar dye | a trace amount |

Preparation Example 2

Tablet

Powder having the following composition is prepared according to a conventional method.

| | |
|---|---|
| Compound 68 | 50 mg |
| Lactose | 250 mg |

Preparation Example 3

Nasal Inhalation

A nasal inhalation having the following composition is prepared according to a conventional method.

| | |
|---|---|
| Compound 68 | 1 mg |
| Lactose | 20 mg |

Preparation Example 4

Opthalmic Preparation

An ophthalmic preparation having the following composition is prepared according to a conventional method.

| | |
|---|---|
| Compound 68 | 10 mg |
| Sodium chloride | 20 mg |

-continued

| | |
|---|---|
| Methylparaben | 0.1 mg |
| Propylparaben | 0.1 mg |
| Injectable water | q.s. 1.0 ml |

Preparation Example 5

Transdermal Therapeutic System

A transdermal therapeutic system having the following composition is prepared according to a conventional method.

| | |
|---|---|
| Compound 68 | 10 g |
| White beeswax | 80 g |
| Stearyl alcohol | 30 g |
| Cholesterol | 30 g |
| White vaseline | q.s. 1,000 g |

Preparation Example 6

Suppository

A suppository having the following composition is prepared according to a conventional method.

| | |
|---|---|
| Compound 68 | 10 mg |
| Witepsol W-15 | 1.79 g |

Preparation Example 7

Injectable Preparation

An injectable preparation having the following composition is prepared according to a conventional method.

| | |
|---|---|
| Compound 68 | 10 mg |
| Injectable water | q.s. 1.0 ml |

Preparation Example 8

Syrup

A syrup having the following composition is prepared according to a conventional method.

| | |
|---|---|
| Compound 68 | 10 mg |
| Sucrose | 300 mg |
| Methylparaben | 0.5 mg |
| Sodium benzoate | 0.5 mg |
| Lemon flavor | as necessary |
| Dye | as necessary |
| Purified water | q.s. 1.0 ml |

Preparation Example 9

Nasal spray

A nasal spray having the following composition is prepared according to a conventional method.

| | |
|---|---|
| Compound 68 | 10 mg |
| Sodium chloride | 8 mg |
| Benzalkonium chloride | 0.1 mg |
| Carbopol | 10 mg |
| Purified water | q.s. 1.0 ml |

Preparation Example 10

Tablet

Tablets having the following composition are prepared according to a conventional method.

| | |
|---|---|
| Compound 68 | 10 mg |
| Lactose | 140 mg |
| Corn starch | 45 mg |
| Sodium croscarmellose | 10 mg |
| Hydroxypropyl cellulose L | 4 mg |
| Magnesium stearate | 1 mg |

Preparation Example 11

Capsule

Capsules having the following composition are prepared according to a conventional method.

| | |
|---|---|
| Compound 68 | 10 mg |
| Lactose | 185 mg |
| Sodium croscarmellose | 10 mg |
| Hydroxypropyl cellulose L | 4 mg |
| Magnesium stearate | 1 mg |

Preparation Example 12

Dry syrup

A dry syrup having the following composition is prepared according to a conventional method.

| | |
|---|---|
| Compound 68 | 10 mg |
| Sucrose | 0.7 g |
| D-mannitol | 0.28 g |
| Pullulan | 20 mg |

Preparation Example 13

Granules

Granules having the following composition are prepared according to a conventional method.

| | |
|---|---|
| Compound 68 | 10 mg |
| Lactose | 0.8 g |
| Corn starch | 0.17 g |
| Hydroxypropyl cellulose L | 30 mg |

INDUSTRIAL APPLICABILITY

The present invention can provide oxygen-containing heterocyclic compounds which exhibit PDE IV inhibitory activity and which are useful as therapeutic agents for asthma, allergy, rheumatoid arthritis, psoriasis, myocardial infarction, depression, amnesia, multiple sclerosis, Crohn's disease, systemic lupus erythematosus, diabetes, wounds, AIDS, and the like.

What is claimed is:

1. An oxygen-containing heterocyclic compound represented by Formula (I):

(I)

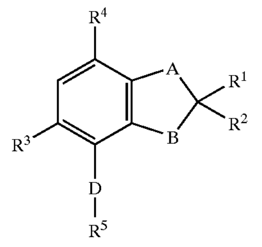

wherein $R^1$ represents hydrogen, substituted or unsubstituted lower alkyl, C3–10 cycloalkyl, C4–12 polycycloalkyl, lower alkenyl, C4–10 cycloalkenyl, substituted or unsubstituted aryl, a substituted or unsubstituted aromatic heterocyclic group, aralkyl, cyano, or $—(CH_2)_n—E^1—CO—G^1$ (wherein n is an integer of 0 to 4; $E^1$ represents a bond, O, or NH: and $G^1$ represents hydrogen, substituted or unsubstituted lower alkyl, C3–10 cyclo-alkyl, C4–12 polycycloalkyl, substituted or unsubstituted aryl, a substituted or unsubstituted aromatic heterocyclic group, aralkyl, $OR^6$ (wherein $R^6$ represents hydrogen, lower alkyl, C3–10 cycloalkyl, C4–12 polycycloalkyl, substituted or unsubstituted aryl, a substituted or unsubstituted aromatic heterocyclic group, or aralkyl), or $NR^7R^8$ (wherein $R^7$ represents hydrogen, substituted or unsubstituted lower alkyl, C3–10 cycloalkyl, C4–12 polycycloalkyl, substituted or unsubstituted aryl, a substituted or unsubstituted aromatic heterocyclic group, substituted or unsubstituted aralkyl, or substituted or unsubstituted heteroarylalkyl; and $R^8$ represents substituted or unsubstituted lower alkyl, C3–10 cycloalkyl, C4–12 polycycloalkyl, substituted or unsubstituted aryl, a substituted or unsubstituted aromatic heterocyclic group, substituted or unsubstituted aralkyl, or substituted or unsubstituted heteroarylalkyl; or $R^7$ and $R^8$ are combined to represent a substituted or unsubstituted heterocyclic group containing at least one nitrogen atom)):

$R^2$ represents hydrogen, substituted or unsubstituted lower alkyl, C3–10 cycloalkyl, C4–12 polycycloalkyl, lower alkenyl, C4–10 cycloalkenyl, substituted or unsubstituted aryl, a substituted or unsubstituted aromatic heterocyclic group, aralkyl, cyano, or $—(CH_2)_n—E^1—CO—G^1$ (wherein n is an integer of 0 to 4; $E^1$ represents a bond, O, or NH: and $G^1$ represents hydrogen, substituted or unsubstituted lower alkyl, C3–10 cycloalkyl, C4–12 polycycloalkyl, substituted or unsubstituted aryl, a substituted or unsubstituted aromatic heterocyclic group, aralkyl, $OR^6$ (wherein $R^6$ represents hydrogen, lower alkyl, C3–10 cycloalkyl, C4–12 polycycloalkyl, substituted or unsubstituted aryl, a substituted or unsubstituted aromatic heterocyclic group, or aralkyl), or $NR^7R^8$ (wherein $R^7$ represents hydrogen, substituted or unsubstituted lower alkyl, C3–10 cycloalkyl, C4–12 polycycloalkyl, substituted or unsubstituted aryl, a substituted or unsubstituted aromatic heterocyclic group, substituted or unsubstituted aralkyl, or substituted or unsubstituted heteroarylalkyl; and $R^8$ represents substituted or unsubstituted lower alkyl, C3–10 cycloalkyl, C4–12 polycycloalkyl, substituted or unsubstituted aryl, a substituted or unsubstituted aromatic heterocyclic group, substituted or unsubstituted aralkyl, or substituted or unsubstituted heteroarylalkyl; or $R^7$ and $R^8$ are combined to represent a substituted or unsubstituted heterocyclic group containing at least one nitrogen atom)); or $R^1$ and $R^2$ are combined to represent a saturated carbon ring together with a carbon atom adjacent thereto;

$R^3$ represents hydrogen, phenyl, or halogen;

$R^4$ represents hydroxy or substituted or unsubstituted lower alkoxy;

A represents $—C(R^9)(R^{10})—$ (wherein $R^9$ and $R^{10}$ independently represent hydrogen, substituted or unsubstituted lower alkyl, C3–10 cycloalkyl, or C4–12 polycycloalkyl);

B represents O;

D represents (i) $—C(R^{18})(R^{19})—X—$ (wherein $R^{18}$ represents hydrogen, substituted or unsubstituted lower alkyl, C3–10 cycloalkyl, C4–12 polycycloalkyl, lower alkenyl, C4–10 cycloalkenyl, substituted or unsubstituted aryl, a substituted or unsubstituted aromatic heterocyclic group, hydroxy, substituted or unsubstituted lower alkoxy, or lower alkanoyloxy; and $R^{19}$ represents hydrogen, substituted or unsubstituted lower alkyl, C3–10 cycloalkyl, C4–12 polycyclooalkyl, lower alkenyl, C4–10 cycloalkenyl, substituted or unsubstituted aryl, a substituted or unsubstituted aromatic heterocyclic group, hydroxy, substituted or unsubstituted lower alkoxy, lower alkanoyloxy, lower alkanoyl, cycloalkylcarbonyl, lower alkoxycarbonyl, or cyano; or $R^{18}$ and $R^{19}$ are combined to form O, S, or $NR^{20}$ (wherein $R^{20}$ represents hydrogen, substituted or unsubstituted lower alkyl, C3–10 cycloalkyl, C4–12 polycycloalkyl, lower alkenyl, C4–10 cycloalkenyl, substituted or unsubstituted aryl, a substituted or unsubstituted aromatic heterocyclic group, hydroxy, substituted or unsubstituted lower alkoxy, or lower alkanoyloxy); and X represents S, $—C(R21)(R^{22})—$ (wherein $R^{21}$ and $R^{22}$ independently represent hydrogen, substituted or unsubstituted lower alkyl, C3–10 cycloalkyl, C4–12 polycycloalkyl, lower alkenyl, C4–10 cycloalkenyl, substituted or unsubstituted aryl, a substituted or unsubstituted aromatic heterocyclic group, lower alkanoyl, cycloalkylcarbonyl, lower alkoxycarbonyl, or cyano, with the proviso that when $R^4$ is hydroxy and $R^{18}$ and $R^{19}$ are combined to form O, $R^{21}$ and $R^{22}$ do not simultaneously represent hydrogen), or $NR^{23}$ (wherein $R^{23}$ represents hydrogen, substituted or unsubstituted lower alkyl, C3–10 cycloalkyl, substituted or unsubstituted aryl, a substituted or unsubstituted aromatic heterocyclic group, or substituted or unsubstituted aralkyl, or $R^{23}$ and $R^5$ are combined to form a substituted or unsubstituted heterocyclic group containing at least one nitrogen atom)), (ii) $—C(R^{19a})=Y—$ (wherein $R^{19a}$ represents hydrogen, substituted or unsubstituted lower alkyl, C3–10 cycloalkyl, C4–12 polycycloalkyl, lower alkenyl, C4–10 cycloalkenyl, substituted or unsubstituted aryl, a substituted or unsubstituted aromatic heterocyclic group, hydroxy, substituted or unsubstituted lower alkoxy, lower alkanoyloxy, lower alkanoyl, cycloalkylcarbonyl, lower alkoxycarbonyl, or cyano; and Y represents N or $—C(R^{24})—Z—$ (wherein $R^{24}$ represents hydrogen, substituted or unsubstituted lower alkyl, C3–10 cycloalkyl, C4–12 polycycloalkyl, lower alkenyl, C4–10 cycloalkenyl, substituted or unsubstituted aryl a substituted or unsubstituted aromatic heterocyclic group, lower alkanoyl, cycloalkylcarbonyl, lower alkoxycarbonyl, or cyano; or $R^{24}$ and $R^{19a}$ are combined to form a single bond; and Z represents CONH, $CONHCH_2$, or a bond)), or (iii) a bond; and $R^5$ represents substituted or unsubstituted aryl, a substituted or unsubstituted aromatic heterocyclic group, or pyridine-N-oxide;

or a pharmaceutically acceptable salt thereof.

2. The oxygen-containing heterocyclic compound according to claim 1, wherein $R^1$ and $R^2$ are combined to represent a saturated carbon ring together with a carbon atom adjacent thereto, or a pharmaceutically acceptable salt thereof.

3. The oxygen-containing heterocyclic compound according to claim 1 or 2, wherein D is $CH_2CH_2$, CH═CH, $CH(C_6H_5)CH_2$, or $C(C_6H_5)$═CH, or a pharmaceutically acceptable salt thereof.

4. The oxygen-containing heterocyclic compound according to claim 1 or 2, wherein $R^5$ is a substituted or unsubstituted aromatic heterocyclic group, or a pharmaceutically acceptable salt thereof.

5. The oxygen-containing heterocyclic compound according to claim 3, wherein $R^5$ is a substituted or unsubstituted aromatic heterocyclic group, or a pharmaceutically acceptable salt thereof.

6. The oxygen-containing heterocyclic compound according to claim 4, wherein the aromatic heterocyclic group is pyridyl, or a pharmaceutically acceptable salt thereof.

7. The oxygen-containing heterocyclic compound according to claim 5, wherein the aromatic heterocyclic group is pyridyl, or a pharmaceutically acceptable salt thereof.

* * * * *

UNITED STATES PATENT AND TRADEMARK OFFICE

CERTIFICATE OF CORRECTION

PATENT NO. : 6,716,987 B1 
DATED : April 6, 2004
INVENTOR(S) : Etsuo Ohshima et al.

It is certified that error appears in the above-identified patent and that said Letters Patent is hereby corrected as shown below:

Title page,
Item [56], References Cited, OTHER PUBLICATIONS,
"Guiotto et al.," reference "trifoliate", should read -- Trifoliata", --;
"Miyano et al.," reference "11961)," should read -- (1961), --;
"Dallacker," reference "Derivative : Bar.," should read -- Ber., --;
"Seshadri et al.," reference "guava"," should read -- Guava", --;
"Kaufman et al.," reference "11995)," should read -- (1995), --;
"Dallacker et al.," reference "al., (CA" should read -- al., CA --;
"Wade et al.," should read -- Wada et al., --;
"Crich et al.," reference "Reararrangments" should read -- Rearrangements --; and
"Dallacker et al., (CA" should read -- Dallacker et al., CA --.

Column 1,
Line 7, "19971" should read -- 1997 --.

Column 2,
Line 1, "TNFa" should read -- TNFα --.

Column 7,
Line 66, "Can" should read -- can --.

Column 8,
Line 17, "dilsopro-" should read -- diisopro --.

Column 14,
Line 39, "Kagakb-Kai," should read -- Kagaku-Kai, --.

Column 17,
Line 2, "Ga-H." should read -- $G^a$-H. --.

Column 20,
Line 30, "(Iae)" should read -- (Iae); --; and
Lines 36 and 37, "(lad)," should read -- (lad), --.

Column 21,
Line 55, "an" (first occurrence) should read -- of an --; and
Line 67, "iS" should read -- is --.

UNITED STATES PATENT AND TRADEMARK OFFICE
CERTIFICATE OF CORRECTION

PATENT NO. : 6,716,987 B1
DATED : April 6, 2004
INVENTOR(S) : Etsuo Ohshima et al.

It is certified that error appears in the above-identified patent and that said Letters Patent is hereby corrected as shown below:

<u>Column 22,</u>
Line 1, "alkoyy," should read -- alkoxy, --.

<u>Column 26,</u>
Line 30, "solvent." should read -- solvent --;
Line 36, "catalytic" should read -- catalyst --; and
Line 60, "ire" should read -- are --.

<u>Column 33,</u>
Compound 27, "H H 14" should read -- H H H --.

<u>Column 67,</u>
Table 8,

| Compd. No. | W |
|---|---|

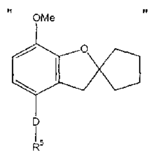

should read

Table 8-1

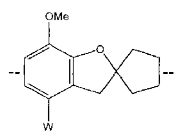

<u>Column 68,</u>
Line 1, "Table 8 - continued" should read -- Table 8-2 --.

<u>Column 111,</u>
Line 36, "[$^3$]cAMP" should read -- [$^3$H]cAMP --.

<u>Column 113,</u>
Lines 40 and 41, "CDNA" should read -- cDNA --;
Line 59, "separeted" should read -- separated --; and
Line 60, "Radioacitivity" should read -- Radioactivity --.

<u>Column 114,</u>
Line 33, "Muscle." should read -- Muscle --; and
Line 62, "Rossler'" should read -- Rossler --.

UNITED STATES PATENT AND TRADEMARK OFFICE

CERTIFICATE OF CORRECTION

PATENT NO. : 6,716,987 B1
DATED : April 6, 2004

INVENTOR(S) : Etsuo Ohshima et al.

It is certified that error appears in the above-identified patent and that said Letters Patent is hereby corrected as shown below:

Column 115,
Line 32, "Rossler" should read -- Rossler --;
Line 62, "TNFa" should read -- TNFα --; and
Line 65, "a" (first occurrence) should read -- α --.

Column 117,
Line 51, "suspened" should read -- suspended --.

Column 120,
Line 26, "sovent" should read -- solvent --.

Column 129,
Line 58, "2,3-dihydro-benzofuran" should read -- 2,3-dihydrobenzofuran --.

Column 130,
Lines 19 and 39, "2,3-dihydro-benzofuran" should read -- 2,3-dihydrobenzofuran --; and
Line 56, "521 (M++2)" should read -- 521 ($M^+$+2) --.

Column 131,
Line 16, "methoxy-benzofuran" should read -- methoxybenzofuran --.

Column 135,
Line 1, "$C_{17}$ $H_{12}$ $C_{12}$ $N_2$ $O_5$" should read -- $C_{17}$ $H_{12}$ $Cl_{12}$ $N_2$ $O_5$--

Column 149,
Line 49, ".6H)," should read -- 6H), --.

Column 151,
Line 24, "Substantially" should read -- substantially --.

Column 164,
Line 37, "Substantially" should read -- substantially --.

Column 172,
Line 16, "7.45(d, J=1.7 Hz, 1H)," should read -- 7.45(d, J=17 Hz, 1H), --.

Column 178,
Line 62, "7.76 (dd," (first occurrence) should be deleted.

UNITED STATES PATENT AND TRADEMARK OFFICE

CERTIFICATE OF CORRECTION

PATENT NO. : 6,716,987 B1
DATED : April 6, 2004
INVENTOR(S) : Etsuo Ohshima et al.

It is certified that error appears in the above-identified patent and that said Letters Patent is hereby corrected as shown below:

Column 179,
Line 22, "H, 6.08; N, 0.00." should read -- H, 6.08; N, 0.00. ¶
MASS (m/e): 325($M^+$)
Elemental analysis: $C_{19}H_{19}NO_4$•HC1•0 . $1H_2O$
Found (%) C:62.62, H:5.72, N:3.91
Calcd. (%) C:62.76, H:5.60, N:3.85 --.

Column 185,
Line 12, "face tone" should read -- acetone --.

Column 187,
Line 49, "a" should read -- as a --.

Column 188,
Line 12, "as in Example" should be deleted; and
Line 33, "benzbdioxole" should read -- benzodioxole --.

Column 189,
Line 7, "Step B of" add -- Example 159 --.

Column 194,
Line 66, "N, 0 00." should read -- N, 0.00. --.

Column 195,
Line 27, "IR(EBr," should read -- IR (KBr, --.

Column 197,
Line 12, "N, 3.5." should read -- N, 3.57. --.

Column 203,
Line 56, "1i)," should read -- 1H), --.

Column 209,
Line 29, "(3-pheylpropylaminomethyl)" should read -- (3-phenypropylaminomethyl) --.

Column 211,
Line 2, "[1-(s)-Phenylethyiaminomethyl]" should read -- [1-(s)-Phenylethylaminomethyl] --.

UNITED STATES PATENT AND TRADEMARK OFFICE

CERTIFICATE OF CORRECTION

PATENT NO. : 6,716,987 B1 
DATED : April 6, 2004
INVENTOR(S) : Etsuo Ohshima et al.

It is certified that error appears in the above-identified patent and that said Letters Patent is hereby corrected as shown below:

Column 220,
Line 1, should be deleted;
Line 14, "-propylaminoethyl$^{-7}$-" should read -- -propylaminoethyl-7- --; and
Line 51, "-benzylaminoethyl$^{-7}$-" should read -- -benzylaminoethyl-7- --.

Column 221,
Line 2, "-piperidinomethyl$^{-7}$-" should read -- -pipendinomethyl-7- --.

Column 222,
Line 15, "using - compound" should read -- using compound --.

Column 224,
Line 22, "-2morpholinocarbonylbenzofuran" should read
-- -2-morpholinocarbonylbenzofuran --.

Column 225,
Line 6, "morpholiocarbonylbenzofuran" should read -- morpholinocarbonylbenzofuran --.

Column 227,
Line 59, "(2-Phenyethyl)" should read -- (2-Phenylethyl) --.

Column 229,
Line 66, "solid." should read -- solid. ¶
Rf ($CHCl_3$:MeOH=9:1); 0.43 --.

Column 230,
Line 66, should be deleted.

Column 232,
Line 11, "(4-chloropheny)" should read -- (4-chlorophenyl) --; and
Line 19, "methoxy benzofuran" should read -- methoxybenzofuran --.

Column 233,
Line 61, "methoxy benzofuran" should read -- methoxybenzofuran --.

Column 240,
Line 44, "over-anhydrous" should read -- over anhydrous --.

UNITED STATES PATENT AND TRADEMARK OFFICE

CERTIFICATE OF CORRECTION

PATENT NO. : 6,716,987 B1
DATED : April 6, 2004
INVENTOR(S) : Etsuo Ohshima et al.

It is certified that error appears in the above-identified patent and that said Letters Patent is hereby corrected as shown below:

Column 241,
Line 37, "and" (first occurrence) should be deleted.

Column 248,
Line 15, "refluxone" should read -- reflux one --.

Column 253,
Line 15, "Hz. 2H)" should read -- Hz, 2H) --.

Column 254,
Line 31, "1H.)," should read -- 1H), --.

Column 256,
Line 27, "a" should read -- as a --.

Column 272,
Line 3, "dimethylsulfoxide" should read -- dimethyl sulfoxide --.

Column 273,
Line 28, "7, 35" should read -- 7.35 --.

Column 276,
Line 55, "60 ml)," should read -- (60 ml), --.

Column 278,
Line 13, "NMR ($CDCL_{13}$," should read -- NNR($CDCL_3$, --.

Column 282,
Line 52, "methodxy benzofuran" should read -- methoxybenzofuran --; and
Line 59, "hours," should read -- hour, --.

Column 284,
Lines 2 and 22, "After" should read -- after --.

Column 291,
Line 49, "polycycloloalkyl," should read -- polycycloalkyl, --.

UNITED STATES PATENT AND TRADEMARK OFFICE

CERTIFICATE OF CORRECTION

PATENT NO. : 6,716,987 B1
DATED : April 6, 2004
INVENTOR(S) : Etsuo Ohshima et al.

It is certified that error appears in the above-identified patent and that said Letters Patent is hereby corrected as shown below:

Column 292,
Line 29, "aryl a" should read -- aryl, a --.

Signed and Sealed this

Twenty-first Day of September, 2004

JON W. DUDAS
*Director of the United States Patent and Trademark Office*